(12) United States Patent
Alam et al.

(10) Patent No.: US 11,084,798 B1
(45) Date of Patent: Aug. 10, 2021

(54) 2-OXOQUINAZOLINE DERIVATIVES AS METHIONINE ADENOSYLTRANSFERASE 2A INHIBITORS

(71) Applicant: IDEAYA BIOSCIENCES, INC., South San Francisco, CA (US)

(72) Inventors: Muzaffar Alam, South San Francisco, CA (US); Leah Cleary, South San Francisco, CA (US); Melissa Fleury, South San Francisco, CA (US); Zhonghua Pei, South San Francisco, CA (US); Richard Steel, South San Francisco, CA (US); James Sutton, South San Francisco, CA (US); John E. Knox, South San Francisco, CA (US); Zachary E. R. Newby, South San Francisco, CA (US)

(73) Assignee: IDEAYA BIOSCIENCES, INC., South San Francisco, CA (US)

( * ) Notice: Subject to any disclaimer, the term of this patent is extended or adjusted under 35 U.S.C. 154(b) by 0 days.

(21) Appl. No.: 17/175,579

(22) Filed: Feb. 12, 2021

Related U.S. Application Data

(63) Continuation of application No. PCT/US2019/065260, filed on Dec. 9, 2019.

(60) Provisional application No. 62/883,945, filed on Aug. 7, 2019, provisional application No. 62/835,853, filed on Apr. 18, 2019, provisional application No. 62/777,715, filed on Dec. 10, 2018.

(51) Int. Cl.
| | |
|---|---|
| *C07D 239/95* | (2006.01) |
| *C07D 401/12* | (2006.01) |
| *C07D 471/04* | (2006.01) |
| *C07D 473/04* | (2006.01) |
| *C07D 403/12* | (2006.01) |
| *C07D 417/04* | (2006.01) |
| *C07D 403/06* | (2006.01) |
| *C07D 401/02* | (2006.01) |
| *C07D 239/80* | (2006.01) |

(52) U.S. Cl.
CPC .......... *C07D 401/02* (2013.01); *C07D 239/80* (2013.01)

(58) Field of Classification Search
CPC .. C07D 239/95; C07D 401/12; C07D 471/04; C07D 473/04; C07D 403/12; C07D 417/04; C07D 403/06
See application file for complete search history.

(56) References Cited

U.S. PATENT DOCUMENTS

| | | |
|---|---|---|
| 10,329,298 B2 | 6/2019 | Konteatis et al. |
| 10,519,146 B2 | 12/2019 | Lanman et al. |
| 10,532,042 B2 | 1/2020 | Lanman et al. |
| 10,800,782 B2 | 10/2020 | Konteatis et al. |
| 2018/0079753 A1 | 3/2018 | Konteatis et al. |
| 2018/0177767 A1 | 6/2018 | Lanman et al. |
| 2018/0334454 A1 | 11/2018 | Lanman et al. |
| 2018/0371551 A1 | 12/2018 | Marion et al. |
| 2019/0077801 A1 | 3/2019 | Lanman et al. |
| 2019/0343838 A1 | 11/2019 | Allen et al. |
| 2019/0374542 A1 | 12/2019 | Allen et al. |
| 2020/0022984 A1 | 1/2020 | Wang et al. |

FOREIGN PATENT DOCUMENTS

| | | |
|---|---|---|
| EP | 2266984 A1 | 12/2010 |
| JP | 50105694 A | 8/1975 |
| WO | WO-1995031469 A1 | 11/1995 |
| WO | WO-1995031495 A1 | 11/1995 |
| WO | WO-2008154221 A2 | 12/2008 |
| WO | WO-2010149786 A1 | 12/2010 |
| WO | WO-2013049352 A2 | 4/2013 |
| WO | WO-2017096165 A1 | 6/2017 |
| WO | WO-2018045071 A1 | 3/2018 |
| WO | WO-2018119183 A2 | 6/2018 |
| WO | WO-2018221433 A1 | 12/2018 |
| WO | WO-2019191470 A1 | 10/2019 |
| WO | WO-2019213516 A1 | 11/2019 |
| WO | WO-2020113071 A1 | 6/2020 |
| WO | WO-2020139991 A1 | 7/2020 |
| WO | WO-2020139992 A1 | 7/2020 |

OTHER PUBLICATIONS

Botros et al., Synthesis of Pyrido [2,3-d] Pyrimidines from 2-Amino-3-Cyanopyridines, Egypt J. Chem, 1986, vol. 29, No. 3, pp. 275-281.

European Patent Office, International Search Report and Written Opinion for International Application No. PCT/US2019/065260, dated Apr. 8, 2020, 14 pages.

(Continued)

*Primary Examiner* — Bruck Kifle
(74) *Attorney, Agent, or Firm* — Mintz, Levin Cohn, Ferris, Glovsky & Popeo, P.C.

(57) ABSTRACT

Disclosed herein are certain 2-oxoquinazoline derivatives of Formula (IA):

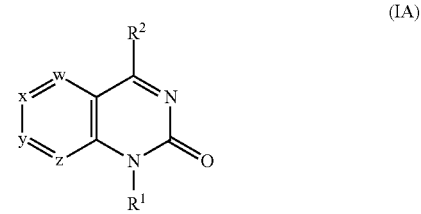

that are methionine adenosyltransferase 2A (MAT2A) inhibitors. Also disclosed are pharmaceutical compositions comprising such compounds and methods of treating diseases treatable by inhibition of MAT2A such as cancer, including cancers characterized by reduced or absence of methylthioadenosine phosphorylase (MTAP) activity.

26 Claims, No Drawings

(56) References Cited

OTHER PUBLICATIONS

Kamal et al., Efficient Enzymatic Cyclization of 2-(Carbmoyloxy)- and 2-(Sulfamoyloxy)-Benzonitriles by Ultrasonically Stimulated Baker's Yeast, Heterocycles, 1990, vol. 31, No. 4, pp. 577-579.
Zhao et al., Synthesis of a Complete Janus-type Guanosine-Cystosine Base and Its 2'-Deoxyribonucleoside, Chem Lett., 2011, vol. 40, pp. 684-686.

2-OXOQUINAZOLINE DERIVATIVES AS METHIONINE ADENOSYLTRANSFERASE 2A INHIBITORS

CROSS-REFERENCES TO RELATED APPLICATIONS

This is application is a continuation of International Patent Application No. PCT/US2019/065260, filed Dec. 9, 2019, which claims priority benefit of U.S. Provisional Application No. 62/777,715 filed Dec. 10, 2018, U.S. Provisional Application No. 62/835,853 filed Apr. 18, 2019, and U.S. Provisional Application No. 62/883,945 filed Aug. 7, 2019, which applications are incorporated herein by reference in their entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Cancer is a leading cause of death throughout the world. A limitation of prevailing therapeutic approaches, e.g. chemotherapy and immunotherapy is that their cytotoxic effects are not restricted to cancer cells and adverse side effects can occur within normal tissues. Consequently, novel strategies are needed to better target cancer cells.

Synthetic lethality arises when a combination of deficiencies in the expression of two or more genes leads to cell death, whereas a deficiency in only one of these genes does not. The concept of synthetic lethality originates from studies in *drosophila* model systems in which a combination of mutations in two or more separate genes leads to cell death (in contrast to viability, which occurs when only one of the genes is mutated or deleted). More recently, a multitude of studies have explored maladaptive genetic changes in cancer cells that render them vulnerable to synthetic-lethality approaches. These tumor-specific genetic defects lead to the use of targeted agents that induce the death of tumor cells while sparing normal cells.

Methionine adenosyltransferase 2A (MAT2A) is an enzyme that utilizes methionine (Met) and adenosine triphosphate (ATP) to generate s-adenosyl methionine (SAM). SAM is a primary methyl donor in cells used to methylate several substrates including DNA, RNA and proteins. One methylase that utilizes SAM as a methyl donor, is protein arginine N-methyltransferase 5 (PRMT5). While SAM is required for PRMT5 activity, PRMT5 is competitively inhibited by 5'methylthioadenosine (MTA). Since MTA is part of the methionine salvage pathway, cellular MTA levels stay low in a process initiated by methylthioadenosine phosphorylase (MTAP).

MTAP is in a locus on chromosome 9 that is often deleted in cells of patients with cancers from several tissues of origin including central nervous system, pancreas, esophageal, bladder and lung (cBioPortal database). Loss of MTAP results in the accumulation of MTA making MTAP-deleted cells more dependent on SAM production, and thus MAT2A activity, compared to cells that express MTAP. In an shRNA cell-line screen across approximately 400 cancer cell lines, MAT2A knockdown resulted in the loss of viability in a larger percentage of MTAP-deleted cells compare to MTAP WT cells (see McDonald et. al. 2017 *Cell* 170, 577-592). Furthermore, inducible knockdown of MAT2A protein decreased tumor growth in vivo (see Marjon et. al., 2016 *Cell Reports* 15(3), 574-587). These results indicate that MAT2A inhibitors may provide a novel therapy for cancer patients including those with MTAP-deleted tumors.

SUMMARY

Disclosed herein are certain 2-oxoquinazoline derivatives that are methionine adenosyltransferase 2A (MAT2A) inhibitors. Also disclosed are pharmaceutical compositions comprising such compounds and methods of treating diseases treatable by inhibition of MAT2A such as cancer, including cancers characterized by reduced or absence of methylthioadenosine phosphorylase (MTAP) activity.

In a first aspect, provided is a compound of Formula (IA'):

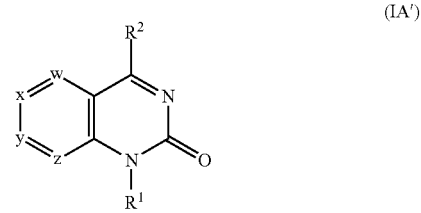

where:
w is $CR^3$ or N; x is $CR^4$ or N; y is CR or N; and z is $CR^6$ or N, wherein:
$R^3$ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;
$R^5$ is hydrogen, alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ and $R^6$ are independently hydrogen, alkyl, alkenyl, alkynyl, alkoxy, alkylthio, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^1$ is alkyl, alkenyl, haloalkyl, hydroxyalkyl, alkoxyalkyl, aminoalkyl, aminocarbonylalkyl, aminosulfonylalkyl, or —$X^a$—$R^7$ wherein $X^a$ is a bond or alkylene and $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is hydrogen, alkyl, halo, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl, deuteroalkyl, or cycloalkyl; and $R^{10}$ is hydrogen, alkyl, deuteroalkyl, haloalkyl, hydroxyalkyl, alkoxyalkyl, haloalkoxyalkyl, aminoalkyl, aminosulfonylalkyl, thioureidoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, alkylamino, cycloalkylsulfonylamino, cyano, cyanoalkyl, alkoxycarbonylalkyl, carboxyalkyl, aminocarbonylalkyl, or —$X^c$—$R^{12}$ where $X^c$ is bond, alkylene, or heteroalkylene and $R^{12}$ is optionally substituted aryl, optionally substituted heteroaryl, and optionally substituted heterocyclyl, provided that when $R^l$ is heterocyclyl and one $R^d$ and $R^e$ is hydroxy, then $R^f$ is not hydroxy; or a pharmaceutically acceptable salt thereof; provided that:
(1) when

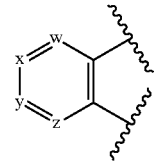

is

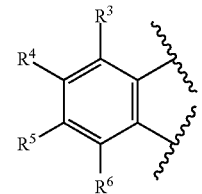

where: (a) when $R^2$ is chloro, piperazin-1-yl, 2-methylpiperazin-1-yl, or 1H-benzo[d][1,2,3]triazol-1-yl, $R^3$ and $R^6$ are hydrogen, $R^4$ is chloro and $R^5$ is bromo or 5-methylindazol-4-yl, then $R^1$ is not 2-isopropylphenyl; (b) when $R^2$ is furan-2-yl, thien-2-yl, methyl, or butyl, $R^3$, $R^4$, and $R^6$ are hydrogen, and $R^5$ is methyl, then $R^1$ is not isopropyl; (c) when $R^2$ is hydrogen, $R^3$, $R^5$, and $R^6$ are hydrogen, and $R^4$ is chloro, then $R^1$ is not benzyl; (d) when $R^2$ is hydrogen, $R^3$, $R^5$, and $R^6$ are hydrogen, and $R^4$ is bromo, then $R^1$ is not 2-morpholin-4-ylethyl; (e) when $R^2$ is cyclopropyl, methyl, difluoromethyl, or pentafluoroethyl, $R^3$, $R^5$, and $R^6$ are hydrogen, and $R^4$ is chloro or fluoro, then $R^1$ is not 4-methoxybenzyl; (f) when $R^2$ is cyclohexyl, pyridin-2-yl, or furan-2-yl, $R^3$, $R^5$, and $R^6$ are hydrogen, and $R^4$ is chloro, then $R^1$ is not cyclopropylmethyl; (g) when $R^2$ is hydrogen or thien-2-yl, $R^3$, $R^5$, and $R^6$ are hydrogen, and $R^4$ is methoxy; or $R^2$ is thien-2-yl, $R^3$, $R^4$, and $R^6$ are hydrogen, and $R^5$ is methyl, then $R^1$ is not cyclopropylmethyl or 2,2,2-trifluoroethyl; (h) when $R^2$ and $R^6$ are methyl and $R^3$, $R^4$, and $R^5$ are hydrogen; or $R^2$ and $R^3$ are methyl and $R^4$, $R^5$, and $R^6$ are hydrogen, then $R^1$ is not 2,5-, 2,6- or 2,8-dimethylquinolin-4-yl or 2-methyl-5-methoxy-, 2-methyl-6-methoxy- or 2-methyl-8-methoxyquinolin-4-yl; (i) when $R^2$ is trifluoromethyl, $R^3$ is methoxy or methyl, and $R^4$, $R^5$, and $R^6$ are hydrogen; or $R^2$ is trifluoromethyl, $R^3$ is fluoro or hydrogen, $R^4$ is halo, methyl, methoxy, isopropyl, or trifluoromethyl, and $R^5$ and $R^6$ are hydrogen, then $R^1$ is not 4-methoxybenzyl or napth-1-ylmethyl; (j) when $R^2$ and $R^3$ are chloro and $R^4$, $R^5$, and $R^6$ are hydrogen; or $R^2$ is trifluoromethyl, $R^3$ is chloro, and $R^4$, $R^5$, and $R^6$ are hydrogen; or $R^4$ is amino, $R^3$, R and $R^6$ are hydrogen, and $R^2$ is 1-methyl-1-pyrimidin-2-ylethylamino, 1-cyclopropylethylamino, 1-pyrimidin-2-ylethylamino, 2-hydroxy-1-methylethylamino, or 3-hydroxy-1-methylpropylamino; or $R^3$ is methoxy, $R^4$, $R^5$ and $R^6$ are hydrogen, $R^2$ is 2-methyl-2-phenylpropylamino; or $R^4$ is chloro, $R^3$, $R^5$ and $R^6$ are H, and $R^2$ is 1-napth-2-ylmethylpiperidin-4-ylamino, 1-ethoxycarbonylpiperidin-4-ylamino, or 1-quinoline-6-ylmethylpiperidin-4-ylamino, then $R^1$ is not methyl; (k) when $R^2$ is methyl, $R^3$ and $R^6$ are hydrogen, and $R^4$ and $R^5$ are methoxy, then $R^1$ is not methyl, 2-pyridin-2-ylethyl or 3-phenylpropyl; (1) when $R^2$ is trifluoromethyl, $R^3$, $R^5$, and $R^6$ are hydrogen, and $R^4$ is chloro, methoxy, or fluoro, then $R^1$ is not benzyl, 4-methylbenzyl or 3,5-dimethylbenzyl; (m) when $R^2$ is methyl, $R^3$, $R^5$, and $R^6$ are hydrogen, and $R^4$ is bromo, then $R^1$ is not ethyl; (n) when $R^2$ is 4-methoxycyclohexylamino, $R^3$, $R^5$, and $R^6$ are hydrogen, and $R^4$ is iodo; or $R^2$ is methyl, $R^3$ and $R^4$ are methoxy, and $R^5$ and $R^6$ are hydrogen; then $R^1$ is not methyl; (o) when $R^2$ is amino or acetylamino, $R^4$ is dimethylamino, and $R^3$, $R^5$, and $R^6$ are hydrogen, then $R^1$ is not 4-hydroxy-5-hydroxymethyl-tetrahydrofuran-2-yl; (p) when $R^4$ is chloro, $R^3$, $R^5$ and $R^6$ are hydrogen, and $R^1$ is 2,2,2-trifluoroethyl, then $R^2$ is not 1-ethoxycarbonylpiperidin-4-ylamino or 8-azabicyclo[3.2.1]ocy-3ylamino; (q) when $R^5$ is fluoro, $R^3$, $R^4$ and $R^6$ are hydrogen, and $R^2$ is -4-aminocarbonylmethyl-2-methylphenylamino, then $R^1$ is not 4-fluoro-2-(2-thiazol-2-yl-methoxy)phenyl, 4-fluoro-2-(2-pyridin-2-ylmethoxy)phenyl, or 4-chloro-2-methoxyphenyl; (r) when $R^6$ is fluoro, $R^3$, $R^4$ and $R^5$ are hydrogen, and $R^2$ is 4-aminocarbonylmethyl-2-methylphenylamino, then $R^1$ is not 4-fluoro-2-methoxyphenyl; (s) when $R^1$ is 4-chloro-2-ethoxyphenyl, $R^5$ is fluoro, and $R^3$, $R^4$ and $R^6$ are hydrogen, then $R^2$ is not 3-(2-oxoimidazolidin-1-yl)-2-methylphenylamino; and (t) when $R^4$ is chloro, $R^3$, $R^5$ and $R^6$ are hydrogen, and $R^1$ is pentyl, then $R^2$ is not 1-napth-1-ylmethylpiperidin-4-ylamino, 1-napth-2-ylmethylpiperidin-4-ylamino, or 1-ethoxycarbonylpiperidin-4-ylamino.

(2) when

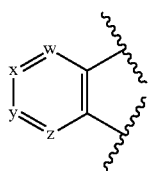

is

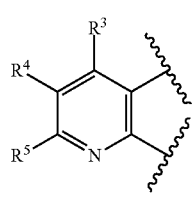

then (a) when $R^2$ is hydrogen, $R^3$ and $R^5$ are methyl, and $R^4$ is hydrogen, then $R^1$ is not 2-dimethylaminoethyl or 2-diisopropylaminoethyl; (b) when $R^2$ is chloro, $R^3$ is 3-pentyloxy, $R^4$ is hydrogen, and $R^5$ is methyl, then $R^1$ is not 2,4,6-trimethylphenyl; (c) when $R^2$ is cyclohexyl, 3-hydroxy- or 4-hydroxycyclohexyl, or 3-methylcyclohexyl, $R^3$ and $R^4$ are hydrogen, and $R^5$ is methyl, hydroxymethyl, or ethyl, then $R^1$ is not ethyl; (d) when $R^2$ and $R^3$ are hydrogen, $R^4$ is cyano, and $R^5$ is amino, then $R^1$ is not allyl, benzyl, methyl, or ethyl;

(3) when

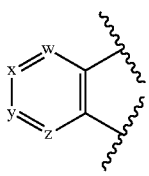

is

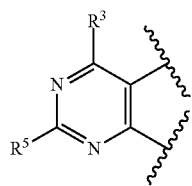

then (a) when $R^2$ is hydrogen, $R^3$ is chloro, and $R^5$ is 1,3-dihydroxyprop-2-ylamino, 3-diethylaminopropylamino, or 4-(4-methylpiperidin-1-yl)piperidin-1-yl, then $R^1$ is not 2,4-difluorophenyl, 2,6-difluorophenyl or 4-trifluoromethylphenyl; (b) when $R^2$ and $R^3$ are hydrogen and $R^5$ is pyridin-4-ylamino, then $R^1$ is not cyclopentyl; (c) when $R^1$ is 4-hydroxy-5-hydroxymethylfuran-1-yl, $R^5$ is amino, and $R^3$ is methoxy; or when $R^1$ is 4-methoxybenzyl, $R^3$ is methoxy, and $R^5$ is amino; then $R^2$ is not amino;

(4) when

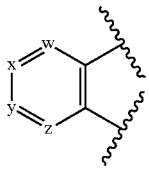

is

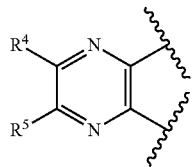

then (a) when $R^2$ and $R^5$ are methoxy and $R^4$ is hydrogen; or when $R^2$ is hydrogen, amino or dimethylamino and one of $R^4$ and $R^5$ is hydrogen, and the other of $R^4$ and $R^5$ is methyl or $R^4$ and $R^5$ are methyl; then $R^1$ is not methyl; (b) when $R^1$ is 4-hydroxy-5-hydroxymethylfuran-1-yl, one of $R^4$ and $R^5$ is hydrogen, and the other of $R^4$ and $R^5$ is methyl or both of $R^4$ and $R^5$ are methyl, then $R^2$ is not amino;

(5) when

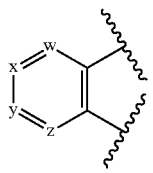

is

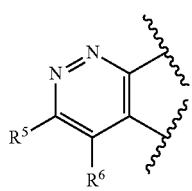

then (a) when R² is 4-hydroxycyclohexylamino, dimethylaminocarbonylmethylamino, or 4-(2-hydroxyethyl)piperazin-1-yl, R⁵ is chloro or 6-methoxypyridin-3-yl, and R⁶ is hydrogen, then R¹ is not 2-ethoxyethyl and (b) when R² is 4-hydroxycyclohexylamino, 4-(2-hydroxyethyl)-piperazin-1-yl, 4-hydroxypiperidin-1-yl, 2-hydroxyethylamino, piperidin-4-ylamino, dimethylaminocarbonylmethylamino, or 2-morpholin-4-ylethylamino, R⁵ is chloro or 6-methoxypyridin-3-yl, and R⁶ is hydrogen, then R¹ is not 2-propyloxyethyl;

(6) when

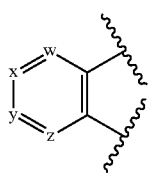

is

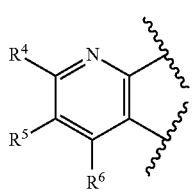

then when R² is 4-(2-hydroxyethyl)piperazin-1-yl or 4-hydroxycyclohexylamino, R⁴ and R⁶ are hydrogen, and R⁵ is chloro or 6-methoxypyridin-3-yl, then, R¹ is not 2-propoxyethyl; and (7) when

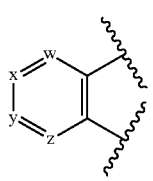

is

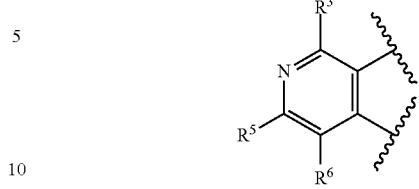

then when R² is 2-isopropyloxyethylamino, 4-hydroxy-cyclohexylamino, 4-(2-hydroxyethyl)piperazin-1-yl, 2-(morpholin-4-yl)ethylamino, R³ and R⁶ are hydrogen, and R⁵ is 6-methoxypyridin-3-yl, then R¹ is not 2-propoxyethyl.

In one embodiment of the first aspect, provided is a compound of Formula (IA):

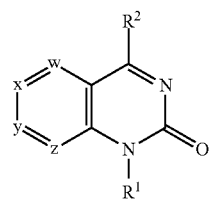

(IA)

where:

w is CR³ or N; x is CR⁴ or N; y is CR⁵ or N; and z is CR⁶ or N, wherein:

R³ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocyclyloxyalkoxy, or heterocyclyloxyalkylamino, wherein heterocyclyl or heteroaryl, by itself or as part of another group, is unsubstituted or substituted with Rᵃ, Rᵇ, and/or Rᶜ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;

R⁵ is hydrogen, alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with Rᵃ, Rᵇ, and/or Rᶜ independently selected from alkyl, cycloalkyl, haloalkyl, haloalkoxy, alkoxy, hydroxy, halo, cyano, hydroxyalkyl, alkoxyalkyl, or aminoalkyl;

R⁴ and R⁶ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^1$ is alkyl, alkenyl, haloalkyl, hydroxyalkyl, alkoxyalkyl, aminoalkyl, aminocarbonylalkyl, aminosulfonylalkyl, or —$X^a$—$R^7$ wherein $X^a$ is a bond or alkylene and $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is hydrogen, alkyl, halo, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl, deuteroalkyl, or cycloalkyl; and $R^{10}$ is hydrogen, alkyl, deuteroalkyl, haloalkyl, hydroxyalkyl, alkoxyalkyl, aminoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, cycloalkylsulfonylamino, cyano, cyanoalkyl, alkoxycarbonylalkyl, carboxyalkyl, aminocarbonylalkyl, or —$X^c$—$R^{12}$ where $X^c$ is bond, alkylene, or heteroalkylene and $R^{12}$ is optionally substituted aryl, optionally substituted heteroaryl, and optionally substituted heterocyclyl, provided that when $R^1$ is heterocyclyl and one $R^d$ and $R^e$ is hydroxy, then $R^f$ is not hydroxy; or a pharmaceutically acceptable salt thereof.

In another embodiment of the first aspect, provided is a compound of Formula (I):

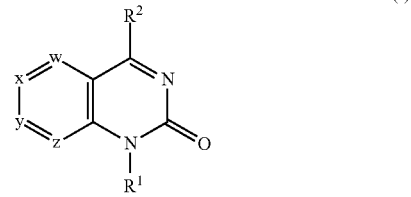

(I)

where:

w is $CR^3$ or N; x is $CR^4$ or N; y is CR or N; and z is $CR^6$ or N, wherein:

$R^3$ and $R^5$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^1$ is alkyl, alkenyl, haloalkyl, hydroxyalkyl, alkoxyalkyl, aminoalkyl, aminocarbonylalkyl, aminosulfonylalkyl, or —$X^a$—$R^7$ wherein $X^a$ is a bond or alkylene and $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is hydrogen, alkyl, halo, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl or cycloalkyl; and $R^{10}$ is hydrogen, alkyl, haloalkyl, hydroxyalkyl, alkoxyalkyl, aminoalkyl, alkylcarbonyl, alkoxycarbonyl, alkylaminocarbonyl, dialkylaminocarbonyl, aminocarbonylalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, haloalkyl, haloalkoxy, alkoxy, hydroxy, halo, cyano, or —$X^c$—$R^{12}$ where $X^c$ is bond, alkylene, or heteroalkylene and $R^{12}$ is optionally substituted aryl, optionally substituted heteroaryl, and optionally substituted heterocyclyl; or a pharmaceutically acceptable salt thereof.

In a second aspect, provided is a pharmaceutical composition comprising:

(a) is a compound of Formula (IIA'):

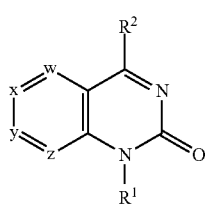

(IIA')

where:

w is $CR^3$ or N; x is $CR^4$ or N; y is CR or N; and z is $CR^6$ or N, wherein:

$R^3$ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;

$R^5$ is hydrogen, alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ and $R^6$ are independently hydrogen, alkyl, alkenyl, alkynyl, alkoxy, alkylthio, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^1$ is alkyl, alkenyl, haloalkyl, hydroxyalkyl, alkoxyalkyl, aminoalkyl, aminocarbonylalkyl, aminosulfonylalkyl, or —$X^a$—$R^7$ wherein $X^a$ is a bond or alkylene and $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is hydrogen, alkyl, halo, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl, deuteroalkyl, or cycloalkyl; and $R^{10}$ is hydrogen, alkyl, deuteroalkyl, haloalkyl, hydroxyalkyl, alkoxyalkyl, haloalkoxyalkyl, aminoalkyl, aminosulfonylalkyl, thioureidoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, alkylamino, cycloalkylsulfonylamino, cyano, cyanoalkyl, alkoxycarbonylalkyl, carboxyalkyl, aminocarbonylalkyl, or —$X^c$—$R^{12}$ where $X^c$ is bond, alkylene, or heteroalkylene and $R^{12}$ is optionally substituted aryl, optionally substituted heteroaryl, and optionally substituted heterocyclyl, provided that when $R^1$ is heterocyclyl and one $R^d$ and $R^e$ is hydroxy, then $R^f$ is not hydroxy; or (b) a compound of Formula (IIA):

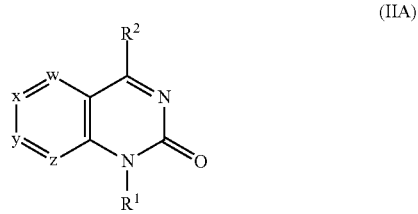

(IIA)

where:

w is $CR^3$ or N; x is $CR^4$ or N; y is CR or N; and z is $CR^6$ or N, wherein:

$R^3$ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;

$R^5$ is hydrogen, alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^1$ is alkyl, alkenyl, haloalkyl, hydroxyalkyl, alkoxyalkyl, aminoalkyl, aminocarbonylalkyl, aminosulfonylalkyl, or —$X^a$—$R^7$ wherein $X^a$ is a bond or alkylene and $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is hydrogen, alkyl, halo, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl, deuteroalkyl, or cycloalkyl; and $R^{10}$ is hydrogen, alkyl, deuteroalkyl, haloalkyl, hydroxyalkyl, alkoxyalkyl, aminoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, cycloalkylsulfonylamino, cyano, cyanoalkyl, alkoxycarbonylalkyl, carboxyalkyl, aminocarbonylalkyl, or —$X^c$—$R^{12}$ where $X^c$ is bond, alkylene, or heteroalkylene and $R^{12}$ is optionally substituted aryl, optionally substituted heteroaryl, and optionally substituted heterocyclyl;

(c) a compound of Formula (II):

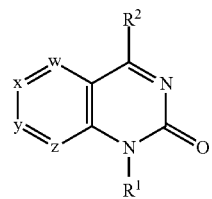

where:
w is $CR^3$ or N; x is $CR^4$ or N; y is CR or N; and z is $CR^6$ or N, wherein:

$R^3$ and $R^5$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^1$ is alkyl, alkenyl, haloalkyl, hydroxyalkyl, alkoxyalkyl, aminoalkyl, aminocarbonylalkyl, aminosulfonylalkyl, or —$X^a$—$R^7$ wherein $X^a$ is a bond or alkylene and $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^C$, and/or R;

$R^2$ is hydrogen, alkyl, halo, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl or cycloalkyl; and $R^{10}$ is hydrogen, alkyl, haloalkyl, hydroxyalkyl, alkoxyalkyl, aminoalkyl, alkylcarbonyl, alkoxycarbonyl, alkylaminocarbonyl, dialkylaminocarbonyl, aminocarbonylalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, haloalkyl, haloalkoxy, alkoxy, hydroxy, halo, cyano, or —$X^c$—$R^{12}$ where $X^c$ is bond, alkylene, or heteroalkylene and $R^{12}$ is optionally substituted aryl, optionally substituted heteroaryl, and optionally substituted heterocyclyl;

(d) a compound of Formula (IVA):

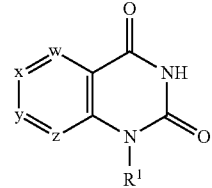

wherein:
w is $CR^3$ or N; x is $CR^4$ or N; y is CR or N; and z is $CR^6$ or N, wherein:

$R^3$ and $R^5$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$, and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen and (iii) at least one of $R^3$, $R^4$, $R^5$, and $R^6$ is hydrogen;

$R^1$ is five to 8 membered cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, heterocyclyl, bridged heterocyclyl, fused heterocyclyl, and spiroheterocyclyl are unsubstituted or substituted with $R^d$, $R^e$, and/or $R^f$ wherein $R^d$ and $R^e$ are independently selected from alkyl, haloalkyl, haloalkoxy, alkoxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido, and $R^f$ is alkyl, haloalkyl, haloalkoxy, alkoxy, hydroxy, halo, cyano, or —$X^e$—$R^{12}$ where $X^e$ is bond, alkylene, or heteroalkylene and $R^{12}$ is optionally substituted aryl, optionally substituted heteroaryl, or optionally substituted heterocyclyl; or a tautomeric form thereof; or
(e) a compound of Formula (IA'), (IA), (I), or (IV);
(or any embodiments thereof disclosed herein), or a pharmaceutically acceptable salt thereof;
and at least one pharmaceutically acceptable excipient.

In a third aspect, provided is a method for treating a disease mediated by MAT2A in a patient comprising administering to the patient a therapeutically effective amount of a compound of Formula (IA'), (IA), (I), (IIA), (II), (IVA), or (IV) (or an embodiment thereof disclosed herein), or a pharmaceutically acceptable salt thereof. In first embodiment of the third aspect, the patient is in recognized need of such treatment. In second embodiment of the third aspect and first embodiment contained therein, the compound of Formula (IA'), (IA), (I), (IIA), (II), (IVA), or (IV) (or an embodiment thereof disclosed herein), or a pharmaceutically acceptable salt thereof is administered in a pharmaceutical composition. In a third embodiment of the third aspect and first and second embodiments contained therein, the disease is mediated by overexpression of MAT2A. In fourth embodiment of the third aspect and first, second, and third embodiments contained therein, the disease is cancer.

In a fourth aspect, provided is a method of treating a MTAP null cancer in a patient comprising administering to the patient a therapeutically effective amount of a compound of Formula (IA'), (IA), (I), (IIA), (II), (IVA), or (IV) (or an embodiment thereof disclosed herein), or a pharmaceutically acceptable salt thereof. In first embodiment of the fourth aspect, the patient is in recognized need of such treatment. In second embodiment of the fourth aspect and first embodiment contained therein, the compound of Formula (IA'), (IA), (I), (IIA), (II), (IVA), or (IV) (or an embodiment thereof disclosed herein), or a pharmaceutically acceptable salt thereof is administered in a pharmaceutical composition.

In a fifth aspect, provided is a method for inhibiting the synthesis of S-adenosyl methionine (SAM) from methionine and ATP by MAT2A in a cell comprising contacting the cell with an effective amount of a compound of Formula (IA'), (IA), (I), (IIA), (II), (IVA), or (IV) (or an embodiment thereof disclosed herein), or a pharmaceutically acceptable salt thereof.

In a sixth aspect, provided is a method for treating a cancer in a patient, wherein the cancer is characterized by a reduction or absence of methylthioadenosine phosphorylase (MTAP) gene expression, the absence of the MTAP gene, or reduced function of MTAP protein, comprising administering to the subject a therapeutically effective amount of a compound of Formula (IA'), (IA), (I), (IIA), (II), (IVA), or (IV) (or an embodiment thereof disclosed herein), or a pharmaceutically acceptable salt thereof optionally in a pharmaceutical composition.

In a seventh aspect, provided is a compound of Formula (IA'), (IA), (I), (IIA), (II), (IVA), or (IV) (or an embodiment thereof disclosed herein), or a pharmaceutically acceptable salt thereof for inhibiting the synthesis of S-adenosyl methionine (SAM) from methionine and ATP by MAT2A in a cell.

In an eighth aspect, provided a compound of Formula (IA'), (IA), (I), (IIA), (II), (IVA), or (IV) (or an embodiment thereof disclosed herein), or a pharmaceutically acceptable salt thereof for use in the treatment of a disease in a patient, wherein the disease is mediated by the overexpression of MAT2A.

In a ninth aspect, provided a compound of Formula (IA'), (IA), (I), (IIA), (II), (IVA), or (IV) (or an embodiment thereof disclosed herein), or a pharmaceutically acceptable salt thereof for use in the treatment a cancer in a patient, wherein the cancer is characterized by a reduction or absence of methylthioadenosine phosphorylase (MTAP) gene expression, the absence of the MTAP gene, or reduced function of MTAP protein.

In a tenth aspect provided are compounds of Formula (IV):

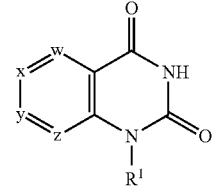

wherein:
w is $CR^3$ or N; x is $CR^4$ or N; y is CR or N; and z is $CR^6$ or N, wherein:
$R^3$ and $R^5$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;
$R^4$ and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen and (iii) at least one of $R^3$, $R^4$, $R^5$, and $R^6$ is hydrogen;
$R^1$ is five to 8 membered cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, heterocyclyl, bridged heterocyclyl, fused heterocyclyl, and spiroheterocyclyl are unsubstituted or substituted with $R^d$, $R^e$, and/or $R^f$ wherein $R^d$ and $R^e$ are independently selected from alkyl, haloalkyl, haloalkoxy, alkoxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido, and $R^f$ is alkyl, haloalkyl, haloalkoxy, alkoxy, hydroxy, halo, cyano, or $—X^c—R^{12}$ where $X^c$ is bond, alkylene, or heteroalkylene and $R^{12}$ is optionally substituted aryl, optionally substituted heteroaryl, or optionally substituted heterocyclyl; or a tautomeric form thereof; or a pharmaceutically acceptable salt thereof; provided that the compound of Formula (IV) is not wherein:

(1) $R^1$ is not (a) 5-hydroxymethyltetrahydrofuran-2-yl or 5-hydroxymethyltetrahydro-furan-2-yl substituted with hydroxy or fluoro; (b) 3-hydroxy-4-hydroxymethylcyclopentyl; and (c) 5-aminomethyltetrahydrofuran-2-yl substituted with fluoro or hydroxy;

(2) when

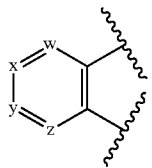

is

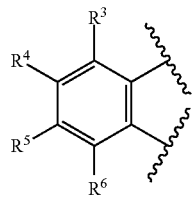

where: (a) when $R^3$ and $R^5$ are fluoro and $R^4$ and $R^6$ are hydrogen; or $R^4$ and $R^5$ are fluoro and $R^3$ and $R^6$ are hydrogen; or $R^5$ is fluoro and $R^3$, $R^4$ and $R^6$ are hydrogen, then $R^1$ is not cyclopentyl or tetrahydrofuran-3-yl; (b) when $R^5$ is chloro and $R^3$, $R^4$ and $R^6$ are hydrogen, then $R^1$ is not phenyl, 2-methoxyphenyl, 3,4-dimethylphenyl, 2,4-dimethylphenyl, 3-methoxyphenyl, 3-trifluoromethylphenyl, 3-chlorophenyl, 4-methoxyphenyl, 3-methylphenyl, 2-ethoxyphenyl, or 4-ethoxyphenyl; (c) when $R^3$ is fluoro and $R^4$, $R^5$ and $R^6$ are hydrogen, then $R^1$ is not 4-chlorophenyl; (d) when $R^4$ is bromo and $R^3$, $R^5$ and $R^6$ are hydrogen, then $R^1$ is not 2,4-dibromophenyl or 2-bromo-4-methylphenyl; (e) when $R^4$ is chloro, $R^5$ is bromo and $R^3$ and $R^6$ are hydrogen, then $R^1$ is not 3-cyanophenyl, 2-isopropylphenyl, 1-methylpropylphenyl, or 3-cyclopropylpyridin-4-yl; (f) when $R^4$ is trifluoromethyl and $R^3$, $R^5$ and $R^6$ are hydrogen, then $R^1$ is not 5-chloro-2-hydroxyphenyl or 5-chloro-2-methoxyphenyl; (g) when $R^4$ is 2,2-difluoroethoxy and $R^3$, $R^5$ and $R^6$ are hydrogen, then $R^1$ is not piperidin-4-yl; and (h) when $R^5$ is methoxy and $R^3$, $R^4$ and $R^6$ are hydrogen; or $R^4$ and $R^5$ are fluoro, $R^3$ is hydrogen and $R^6$ is methyl, then $R^1$ is not phenyl;

(3) when

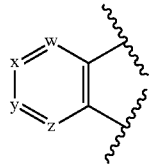

is

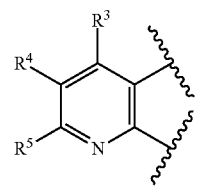

then (a) when $R^1$ and $R^5$ are methyl and $R^4$ is hydrogen, then $R^1$ is not 4-ethoxyphenyl; (b) when $R^3$ is 3-pentyloxy, $R^5$ is methyl and $R^4$ is hydrogen, then $R^1$ is not 2,4,6-trimethylphenyl; (c) when $R^4$ and $R^5$ are chloro and $R^3$ is hydrogen, then $R^1$ is not 2-isopropyl-6-methylphenyl; (d) when $R^5$ is trifluoromethyl and $R^3$ and $R^4$ are hydrogen, then $R^1$ is not phenyl, 4,6-dimethoxypyrimidin-2-yl or 4-hydroxy-6-methoxypyrimidin-2-yl; (e) when $R^4$ is amino and $R^3$ and $R^5$ are hydrogen, then $R^1$ is not phenyl, 2-methylphenyl, 4-methylphenyl, 4-fluorophenyl, 2-, 3- or 4-chlorophenyl, 4-ethylphenyl, cyclopentyl, cyclohexyl, 2,4-dimethylphenyl, 3,5-dimethylphenyl, 3,4-dimethylphenyl, or 2- or 4-methoxyphenyl; (f) when $R^4$ is bromo and $R^3$ and $R^5$ are hydrogen; or $R^4$ is hydrogen and one of $R^3$ and $R^5$ is methyl and the other of $R^3$ and $R^5$ is hydrogen; or $R^4$ is hydrogen and $R^3$ and $R^5$ are methyl; or $R^5$ is amino, $R^3$ and $R^4$ are hydrogen; $R^5$ is amino, $R^3$ is hydrogen, and $R^4$ is cyano; or $R^4$ is 2-hydroxyethyl, $R^3$ is hydrogen, and $R^5$ is methyl, then $R^1$ is not phenyl; and (g) $R^3$ is furan-2-yl, $R^4$ and $R^5$ are hydrogen, then $R^1$ is not cyclohexyl;

(4) when

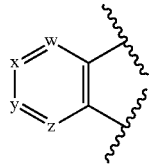

is

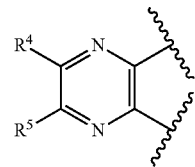

then, (a) when $R^4$ and $R^5$ are methyl, then $R^1$ is not phenyl, 2-chlorophenyl, 3-chlorophenyl, 2-methoxyphenyl, 4-methylphenyl, or 4-methoxyphenyl; and

21

(5) when

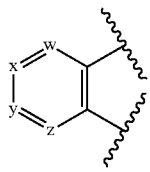

is

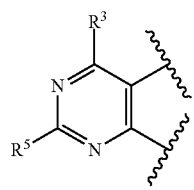

then, when $R^3$ and $R^5$ are ethylamino or chloro, then $R^1$ is not phenyl.

In one embodiment of the tenth aspect, w, x, y, z, $R^1$, $R^3$, $R^4$, $R^5$, and $R^6$ in Formula (IV) are as defined in Embodiments 5, 21, 22, 23, 27 to 34 and subembodiments contained therein below.

Compounds of Formula (IV) are useful as intermediates for the synthesis of compounds of Formula (IA), (I), (IIA), and (II) and also inhibit MAT2A.

DETAILED DESCRIPTION

Before the present invention is further described, it is to be understood that the invention is not limited to the particular embodiments set forth herein, and it is also to be understood that the terminology used herein is for the purpose of describing particular embodiments only, and is not intended to be limiting.

The singular forms "a," "an," and "the" as used herein and in the appended claims include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

When needed, any definition herein may be used in combination with any other definition to describe a composite structural group. By convention, the trailing element of any such definition is that which attaches to the parent moiety. For example, the composite group alkoxyalkyl means that an alkoxy group is attached to the parent molecule through an alkyl group.

The publications discussed herein are provided solely for their disclosure prior to the filing date of the present application. Further, the dates of publication provided may be different from the actual publication dates, which may need to be independently confirmed.

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenyl" means a linear monovalent hydrocarbon radical of two to six carbon atoms or a branched monovalent hydrocarbon radical of three to six carbon atoms containing a double bond, e.g., propenyl, butenyl, and the like.

"Alkynyl" means a linear monovalent hydrocarbon radical of two to six carbon atoms or a branched monovalent hydrocarbon radical of three to six carbon atoms containing a triple bond, e.g., ethynyl, propynyl, butynyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with one alkoxy group, as defined above, e.g., 2-methoxyethyl, 1-, 2-, or 3-methoxypropyl, 2-ethoxyethyl, and the like.

"Alkoxyalkoxy" means a —OR radical where R is alkoxyalkyl as defined above e.g., methoxyethyloxy, ethyloxypropyloxy, and the like.

"Alkoxyalkylamino" means a —NRR' radical where R is hydrogen or alkyl and R' is alkoxyalkyl, each as defined above e.g., methoxyethylamino, methoxypropylamino, and the like.

"Alkylcarbonyl" means a —C(O)R radical where R is alkyl as defined herein, e.g., methylcarbonyl, ethylcarbonyl, and the like.

"Alkoxycarbonyl" means a —C(O)OR radical where R is alkyl as defined above, e.g., methoxycarbonyl, ethoxycarbonyl, and the like.

"Alkoxycarboxyalkyl" means an alkyl radical as defined above, that is substituted with an alkoxycarboxy group e.g., methylcarboxymethyl, ethylcarboxyethyl, and the like.

"Alkylthio" means a —SR radical where R is alkyl as defined above, e.g., methylthio, ethylthio, and the like.

"Alkylsulfonyl" means a —$SO_2$R radical where R is alkyl as defined above, e.g., methylsulfonyl, ethylsulfonyl, and the like.

"Alkylsulfonylalkyl" means a -(alkylene)-$SO_2$R radical where R is alkyl as defined above, e.g., methylsulfonylethyl, ethylsulfonylmethyl, and the like.

"Amino" means a —NH$_2$.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen, alkyl, haloalkyl, hydroxyalkyl, alkoxyalkyl, or alkylcarbonyl, each as defined herein, e.g., aminomethyl, aminoethyl, methylaminomethyl, and the like.

"Aminoalkoxy" means a —OR radical where R is aminoalkyl as defined above e.g., aminoethyloxy, methylaminopropyloxy, dimethylaminoethyloxy, diethylaminopropyloxy, and the like.

"Aminoalkylamino" means a —NRR' radical where R is hydrogen or alkyl and R' is aminoalkyl, each as defined above e.g., aminoethylamino, methylaminopropylamino, dimethylaminoethylamino, diethylaminopropylamino, and the like.

"Aminocarbonyl" means a —CONH$_2$ radical.

"Alkylaminocarbonyl" means a —CONHR radical where R is alkyl as defined above, e.g., methylaminocarbonyl, ethylaminocarbonyl and the like.

"Aminosulfonyl" means a —SO$_2$NH$_2$ radical.

"Aminosulfonylalkyl" means a -(alkylene)SO$_2$NRR' radical where R is hydrogen or alkyl and R' is hydrogen, alkyl, or cycloalkyl, or R and R' together with the nitrogen atom to which they are attached form heterocyclyl, as defined above, e.g., methylaminosulfonylethyl, dimethylsulfonylethyl, and the like.

"Alkylaminosulfonyl" means a —SO$_2$NHR radical where R is alkyl as defined above, e.g., methylaminosulfonyl, ethylaminosulfonyl and the like.

"Aminocarbonylalkyl" means a -(alkylene)-CONRR' radical where R' and R" are independently hydrogen, alkyl, haloalkyl, hydroxyalkyl, or alkoxyalkyl, each as defined herein, e.g., aminocarbonylethyl, methylaminocarbonylethyl, dimethylaminocarbonylethyl, and the like.

"Aminosulfonylalkyl" means a -(alkylene)-SO$_2$NRR' radical where R' and R" are independently hydrogen, alkyl, haloalkyl, hydroxyalkyl, or alkoxyalkyl, each as defined herein, e.g., aminosulfonylethyl, methylaminosulfonylethyl, dimethylaminosulfonylethyl, and the like.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above e.g., benzyl, phenethyl, and the like.

"Bridged cycloalkyl" means a saturated monocyclic 5- to 7-membered hydrocarbon radical in which two non-adjacent ring atoms are linked by a (CRR')n group where n is 1 to 3 and each R is independently H or methyl (also referred to herein as the bridging group). The bridged cycloalkyl is optionally substituted with one or two substituents independently selected from alkyl, halo, alkoxy, hydroxy, or cyano. Examples of bridged cycloalkyl include but are not limited to bicyclo[2.2.1]heptane, bicyclo[2.2.2]octane, etc.

"Bridged cycloalkylalkyl" means -(alkylnene)-R radical where R is bridged cycloalkyl as defined above. Examples include, but are not limited to, bicyclo[2.2.1]heptylmethyl, and the like.

"Bridged heterocyclyl" means a saturated monocyclic ring having 5 to 7 ring carbon atoms in which two non-adjacent ring atoms are linked by a (CRR')n group where n is 1 to 3 and each R is independently H or methyl (also may be referred to herein as "bridging" group) and further wherein one or two ring carbon atoms, including an atom in the bridging group, is replaced by a heteroatom selected from N, O, or S(O)n, where n is an integer from 0 to 2. Bridged heterocyclyl is optionally substituted with one or two substituents independently selected from alkyl, halo, alkoxy, hydroxy, or cyano. Examples include, but are not limited to, 2-azabicyclo[2.2.2]octane, quinuclidine, 7-oxabicyclo[2.2.1]heptane, and the like.

"Bridged heterocyclylalkyl" means -(alkylene)-R radical where R is bridged heterocyclyl (including specific bridged heterocyclyl rings) as defined above.

"Cycloalkyl" means a monocyclic monovalent hydrocarbon radical of three to six carbon atoms which may be saturated or contains one double bond. Cycloalkyl may be unsubstituted or substituted with one or two substituents independently selected from alkyl, halo, alkoxy, hydroxy, or cyano. Examples include, but are not limited to, cyclopropyl, cyclobutyl, cyclopentyl, cyclohexyl, 1-cyanocycloprop-1-yl, 1-cyanomethylcycloprop-1-yl, 3-fluorocyclohexyl, and the like. When cycloalkyl contains a double bond, it may be referred to herein as cycloalkenyl.

"Cycloalkylalkyl" means -(alkylene)-R radical where R is cycloalkyl as defined above. Examples include, but are not limited to, cyclopropylmethyl, cyclobutylmethyl, and the like.

"Cycloalkylalkyloxy" means —O—R radical where R is cycloalkylalkyl as defined above. Examples include, but are not limited to, cyclopropylmethyloxy, cyclobutylmethyloxy, and the like.

"Cycloalkyloxyalkyl" means -(alkylene)-OR radical where R is cycloalkyl as defined above. Examples include, but are not limited to, cyclopropyloxymethyl, cyclopropyloxyethyl, cyclobutyloxyethyl, and the like.

"Cycloalkylsulfonylamino" means —NRSO$_2$—R' radical where R is hydrogen or alkyl and R' is cycloalkyl, each as defined above. Examples include, but are not limited to, cyclopropylsulfonylamino, N-cyclopropylsulfonylN(CH$_3$), and the like.

"Cyanoalkyl" means an alkyl radical as defined above, that is substituted with a cyano group, e.g., cyanomethyl, cyanoethyl, and the like.

"Carboxy" means —COOH radical.

"Carboxyalkyl" means an alkyl radical as defined above, that is substituted with a carboxy group e.g., carboxymethyl, carboxyethyl, and the like.

"Deuteroalkyl" means alkyl radical, as defined above, wherein one to six hydrogen atoms in alkyl chain are replaced by deuterium atoms. Examples include, but are not limited to, —CD$_3$, —CH$_2$CHD$_2$, and the like.

"Dialkylamino" means a —NRR' radical where R and R' are alkyl as defined above, e.g., dimethylamino, methylethylamino, and the like.

"Dialkylaminocarbonyl" means a —CONRR' radical where R and R' are alkyl as defined above, e.g., dimethylaminocarbonyl, diethylaminocarbonyl and the like.

"Dialkylaminosulfonyl" means a —SO$_2$NRR' radical where R and R' are alkyl as defined above, e.g., dimethylaminosulfonyl, diethylaminosulfonyl and the like.

"Fused cycloalkyl" means a saturated monovalent hydrocarbon radical of three to six carbon atoms that is fused to phenyl or a five- or six-membered heteroaryl ring, as defined herein, and is optionally substituted with one, two, or three substituents independently selected from alkyl, halo, alkoxy, haloalkyl, haloalkoxy, hydroxy, and cyano. Examples include, but are not limited to, tetrahydronaphthyl, 4,5,6,7-tetrahydro-1H-indolyl, 4,5,6,7-tetrahydrobenzoxazolyl, and the like.

"Fused heterocyclyl" means heterocyclyl as defined herein that is fused to cycloalkyl, phenyl or a five- or six-membered heteroaryl ring, as defined herein. Fused heterocyclyl is optionally substituted with one or two substituents independently selected from alkyl, halo, alkoxy, hydroxy, or cyano. Examples include, but are not limited to, 4,5,6,7-tetrahydro-1H-pyrrolo[2,3-b]pyridinyl, 1,2,3,4-tetrahydroquinolinyl, 3,4-dihydroquinolin-2(1H)-one, and the like.

"Fused heterocyclylalkyl" means -(alkylene)-R radical where R is fused heterocyclyloxy (including specific fused heterocyclyl rings) as defined above.

"Halo" means fluoro, chloro, bromo, or iodo, preferably fluoro or chloro.

"Haloalkyl" means alkyl radical as defined above, which is substituted with one to five halogen atoms, such as fluorine or chlorine, including those substituted with different halogens, e.g., —$CH_2Cl$, —$CF_3$, —$CHF_2$, —$CH_2CF_3$, —$CF_2CF_3$, —$CF(CH_3)_2$, and the like. When the alkyl is substituted with only fluoro, it can be referred to in this Application as fluoroalkyl.

"Haloalkoxy" means a —OR radical where R is haloalkyl as defined above e.g., —$OCF_3$, —$OCHF_2$, and the like. When R is haloalkyl where the alkyl is substituted with only fluoro, it is referred to in this Application as fluoroalkoxy.

"Haloalkoxyalkyl" means an alkyl radical that is substituted with haloalkoxy, each as defined above, e.g., trifluoromethoxyethyl, and the like.

"Heteroalkylene" means a linear saturated divalent hydrocarbon radical of two to six carbon atoms or a branched saturated divalent hydrocarbon radical of three to six carbon atoms wherein one carbon atom are replaced with —O—, —NR—, —NR'CO—, —CONR'—, $SO_2NR'$—, or —NR'$SO_2$—, where R and R' are independently H or alkyl as defined herein, unless stated otherwise, e.g., —$CH_2O$—, —$OCH_2$—, —$(CH_2)_2O$—, —$O(CH_2)_2$—, —$(CH_2)_2NH$—, —$NH(CH_2)_2$—, and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkoxy" means a —OR radical where R is hydroxyalkyl as defined above e.g., hydroxyethyloxy, hydroxypropyloxy, and the like.

"Hydroxyalkylamino" means a —NRR' radical where R is hydrogen or alkyl and R' is hydroxyalkyl, each as defined above e.g., hydroxyethylamino, hydroxypropylamino, and the like.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Non-limiting examples of heteroaryl groups include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroaralkyl" means a -(alkylene)-R radical where R is heteroaryl (including specific rings) as defined above.

"Heteroaryloxy" means —OR where R is heteroaryl (including specific rings) as defined above.

"Heteroaralkyloxy" means a —O-(alkylene)-R radical where R is heteroaryl (including specific rings) as defined above.

"Heteroarylcarbonyl" means —COR where R is heteroaryl (including specific rings) as defined above.

"Heteroarylamino" means —NRR' where R is hydrogen or alkyl and R' is heteroaryl (including specific rings) as defined above.

"Heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, azetidinyl, oxetanyl, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When heterocyclyl contains at least one nitrogen atom, it may be referred to herein as heterocycloamino.

"Heterocyclylalkyl" means -(alkylene)-R radical where R is heterocyclyl (including specific heterocyclyl rings) as defined above. For example, oxetanylethyl, piperidinylethyl, and the like.

"Heterocyclyloxy" means —OR radical where R is heterocyclyl (including specific heterocyclyl rings) as defined above.

"Heterocyclylalkyloxy" means —O-(alkylene)-R radical where R is heterocyclyl (including specific heterocyclyl rings) as defined above. For example, oxetanylethyloxy, piperidinylethyloxy, and the like.

"Heterocyclylcarbonyl" means —COR where R is heterocyclyl (including specific rings) as defined above.

"Heterocyclylamino" means —NRR' radical where R is hydrogen or alkyl and R' is heterocyclyl (including specific heterocyclyl rings) as defined above.

"Heterocyclyloxyalkyl" means -(alkylene)-OR radical where R is heterocyclyl (including specific heterocyclyl rings) as defined above. For example, oxetanyloxyethyl, piperidinyloxyethyl, and the like.

"Heterocyclyloxyalkoxy" means —O-(alkylene)-R radical where R is heterocyclyloxy (including specific heterocyclyl rings) as defined above. For example, oxetanyloxyethyloxy, piperidinyloxyethyloxy, and the like.

"Heterocyclyloxyalkylamino" means —NR-(alkylene)-R' radical where R is hydrogen or alkyl and R' is heterocyclyloxy (including specific heterocyclyl rings) as defined above. For example, oxetanyloxyethylamino, piperidinyloxyethylamino, and the like.

"Oxo," as used herein, alone or in combination, refers to =(O).

"Pharmaceutically acceptable salts" as used herein is meant to include salts of the active compounds which are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen carbonic, phosphoric, monohydrogen phosphoric, dihydrogen phosphoric, sulfuric, monohydrogen sulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The present disclosure also includes protected derivatives of compounds of the present disclosure. For example, when compounds of the present disclosure contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, 5$^{th}$ Ed., John Wiley & Sons, Inc. (2014), the disclosure of which is incorporated herein by reference in its entirety. The protected derivatives of compounds of the present disclosure can be prepared by methods well known in the art.

The present disclosure also includes prodrugs of the compound of Formula (I) (IA), (II), (IIA) and (IVA) and (IV), or a pharmaceutically acceptable salt thereof. Prodrugs of the compounds described herein are those compounds that readily undergo chemical changes under physiological conditions to provide the compounds of the present invention. An example, without limitation, of a prodrug would be a compound which is administered as an ester (the "prodrug"), but then is metabolically hydrolyzed to the carboxylic acid, the active entity. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of Formulae (I) (IA), (II), (IIA) and (IVA) and (IV) can exist in unsolvated forms as well as solvated forms, including hydrated forms. In general, the solvated forms are equivalent to unsolvated forms and are intended to be encompassed within the scope of the present invention. Certain compounds of Formulae (I) (IA), (II), (IIA) and (IVA) and (IV) may exist in multiple crystalline or amorphous forms. In general, all physical forms are equivalent for the uses contemplated by the present disclosure and are intended to be within the scope of the present disclosure.

Certain compounds of Formulae (I) (IA), (II), (IIA) and (IVA) and (IV) possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of Formulae (I) (IA), (II), (IIA) and (IVA) and (IV) may also contain unnatural amounts of isotopes at one or more of the atoms that constitute such compounds. Unnatural amounts of an isotope may be defined as ranging from the amount found in nature to an amount 100% of the atom in question. that differ only in the presence of one or more isotopically enriched atoms. Exemplary isotopes that can be incorporated into compounds of the present invention, such as a compound of Formula (I) (IA), (II), (IIA) and (IVA) and (IV) (and any embodiment thereof disclosed herein including specific compounds) include isotopes of hydrogen, carbon, nitrogen, oxygen, phosphorus, sulfur, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{32}$P, $^{33}$P, 35S, $^{18}$F, $^{36}$Cl, $^{123}$I, and $^{125}$I, respectively. Isotopically-labeled compounds (e.g., those labeled with $^{3}$H and $^{14}$C) can be useful in compound or substrate tissue distribution assays. Tritiated (i.e., $^{3}$H) and carbon-14 (i.e., $^{14}$C) isotopes can be useful for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^{2}$H or $^{3}$H, or one or more carbon atoms are replaced by $^{13}$C- or $^{14}$C-enriched carbon. Positron emitting isotopes such as $^{15}$O, $^{13}$N, $^{11}$C, and $^{15}$F are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

"Optionally substituted aryl" means aryl that is optionally substituted with one, two, or three substituents independently selected from alkyl, cycloalkyl, carboxy, alkoxycarbonyl, hydroxy, hydroxyalkyl, alkoxy, alkylsulfonyl, amino, alkylamino, dialkylamino, halo, haloalkyl, haloalkoxy, and cyano.

"Optionally substituted heteroaryl" means heteroaryl as defined above that is optionally substituted with one, two, or three substituents independently selected from alkyl, alkylsulfonyl, cycloalkyl, carboxy, alkoxycarbonyl, hydroxy, alkoxy, halo, haloalkyl, haloalkoxy, amino, alkylamino, dialkylamino, and cyano.

"Optionally substituted heterocyclyl" means heterocyclyl as defined above that is optionally substituted with one, two, or three substituents independently selected from alkyl, alkylsulfonyl, cycloalkyl, carboxy, alkoxycarbonyl, hydroxy, hydroxyalkyl, alkoxy, alkoxyalkyl, aminoalkyl, halo, haloalkyl, haloalkoxy, and cyano, unless stated otherwise.

"Pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Spirocycloalkyl" means a saturated bicyclic ring having 6 to 10 ring carbon atoms wherein the rings are connected through only one atom, the connecting atom is also called the spiroatom, most often a quaternary carbon ("spiro carbon"). The spirocycloalkyl ring is optionally substituted with one or two substituents independently selected from alkyl, halo, alkoxy, hydroxy, and cyano. Representative examples include, but are not limited to, spiro[3.3]heptane, spiro[3.4]octane, spiro[3.5]nonane, spiro[4.4]nonane (1:2:1:1), and the like.

"Spirocycloalkylalkyl" means -(alkylene)-R radical where R is spirocycloalkyl (including specific spirocycloalkyl) as defined above.

"Spiroheterocyclyl" means a saturated bicyclic ring having 6 to 10 ring atoms in which one, two, or three ring atoms are heteroatom selected from N, O, or S(O), where n is an integer from 0 to 2, the remaining ring atoms being C and the rings are connected through only one atom, the connecting atom is also called the spiroatom, most often a quaternary carbon ("spiro carbon"). Spiroheterocyclyl is optionally substituted with one or two substituents independently selected from alkyl, halo, alkoxy, hydroxy, or cyano. Examples include, but are not limited to, Representative examples include, but are not limited to, 2,6-diazaspiro[3.3]heptane, 2,6-diazaspiro[3.4]octane, 2-azaspiro[3.4]octane, 2-azaspiro[3.5]-nonane, 2,7-diazaspiro[4.4]nonane, and the like.

"Spiroheterocyclylalkyl" means -(alkylene)-R radical where R is spiroheterocyclyl (including specific spiroheterocyclyl) as defined above.

"Sulfonylamino" means a —NRSO$_2$R' radical where R is hydrogen or alkyl, and R' is alkyl, optionally substituted aryl, optionally substituted heteroaryl, or optionally substituted heterocyclyl, each group as defined herein.

"Substituted cycloalkyl" means a saturated monocyclic monovalent hydrocarbon radical of three to six carbon atoms that is substituted with one, two or three substituents where two of the three substitutents are independently selected from alkyl, halo, alkoxy, hydroxy, haloalkyl, or haloalkoxy and the third substituent is alkyl, halo, hydroxyalkyl, haloalkyl, haloalkoxy, or cyano. Examples include, but are not limited to, 3-hydroxy-3-trifluorocyclobutyl, 2,2-dimethyl-3-hydroxycyclobutyl, and the like.

"Substituted cycloalkylalkyl" means -(alkylene)-substituted cycloalkyl, each term is defined herein. Examples include, but are not limited to, 1-hydroxymethylcycloprop-1-ylmethyl, and the like.

"About," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

"Disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

"Patient" is generally synonymous with the term "subject" and as used herein includes all mammals including humans. Examples of patients include humans, livestock such as cows, goats, sheep, pigs, and rabbits, and companion animals such as dogs, cats, rabbits, and horses. Preferably, the patient is a human.

"In need of treatment" as used herein refers to a judgment made by a physician or other caregiver that a subject requires or will benefit from treatment. This judgment is made based on a variety of factors that are in the realm of the physician's or caregiver's expertise.

"Administration", "administer" and the like, as they apply to, for example, a patient, cell, tissue, organ, or biological fluid, refer to contact of, for example, a compound of Formula (I), a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

"Therapeutically effective amount" as used herein means the amount of a compound of Formula (I), (IA), (IA'), (II), (IIA), (IIA') or a subembodiment described herein and/or a pharmaceutically acceptable salt thereof that, when administered to a patient for treating a disease either alone or as part of a pharmaceutical composition and either in a single dose or as part of a series of doses, is sufficient to affect such treatment for the disease. The "therapeutically effective amount" will vary depending on the compound, the disease and its severity and the age, weight, etc., of the mammal to be treated. The therapeutically effective amount can be ascertained by measuring relevant physiological effects, and it can be adjusted in connection with the dosing regimen and diagnostic analysis of the subject's condition, and the like. By way of example, measurement of the serum level of a compound of Formula (I) (or, e.g., a metabolite thereof) at a particular time post-administration may be indicative of whether a therapeutically effective amount has been used.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

"Inhibiting", "reducing," or any variation of these terms in relation of MAT2A, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of MAT2A activity compared to its normal activity.

"Ureido" means a —NHCONRR' radical where R and R' are independently hydrogen or alkyl, as defined above, e.g., —NHCONHmethyl, —NHCON(CH$_3$)$_2$, and the like. "Thioureidoalkyl" means a -(alkylene)-NHSO$_2$NRR' radical where R and R' are independently hydrogen or alkyl, as defined above, e.g., -ethylene-NHSO$_2$NHmethyl, -propylene-NHSO$_2$NH$_2$, and the like.

Representative compound of Formula (I) are listed in Table 1 below:

TABLE 1

| Cpd. No. | Structure | Name | Mass Spec. |
|---|---|---|---|
| 1 | 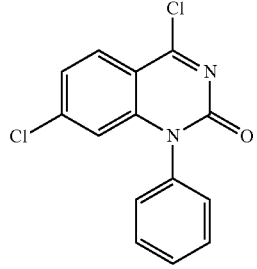 [SMILES: O=c1nc(Cl)c2ccc(Cl)cc2n1-c1ccccc1] | 4,7-dichloro-1-phenylquinazolin-2(1H)-one | |
| 2 | 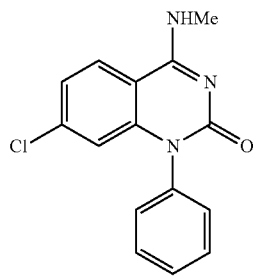 [SMILES: CNc1nc(=O)n(-c2ccccc2)c2cc(Cl)ccc12] | 7-chloro-4-(methylamino)-1-phenyl-quinazolin-2(1H)-one | |
| 3 | 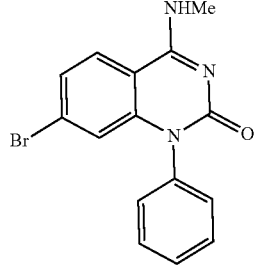 | 7-bromo-4-(methylamino)-1-phenyl-quinazolin-2(1H)-one | |
| 4 | 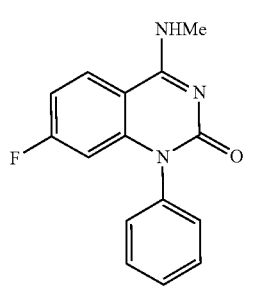 | 7-fluoro-1-phenylquinazolin-2(1H)-one | |

TABLE 1-continued

| Cpd. No. | Structure | Name | Mass Spec. |
|---|---|---|---|
| 5 | 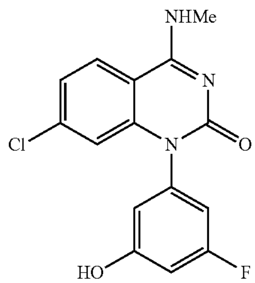 | 7-Chloro-1-(5-fluoro-3-hydroxy-phenyl)-4-(methylamino)-hydroquinazolin-2-one | |
| 6 | 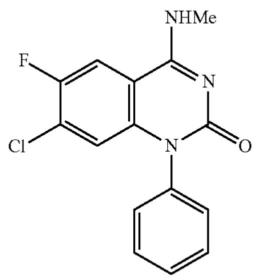 [SMILES: CNc1nc(=O)n(-c2ccccc2)c2cc(Cl)c(F)cc12] | 7-chloro-6-fluoro-4-(methylamino)-1-phenyl-quinazolin-2(1H)-one | |
| 7 | 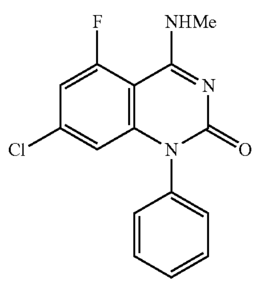 [SMILES: CNc1nc(=O)n(-c2ccccc2)c2cc(Cl)cc(F)c12] | 7-chloro-5-fluoro-4-(methylamino)-1-phenyl-quinazolin-2(1H)-one | |
| 8 | 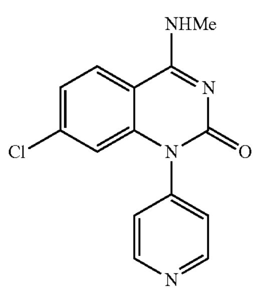 [SMILES: CNc1nc(=O)n(-c2ccncc2)c2cc(Cl)ccc12] | 7-chloro-4-(methylamino)-1-(pyridin-4-yl)-quinazolin-2(1H)-one | |
| 9 | 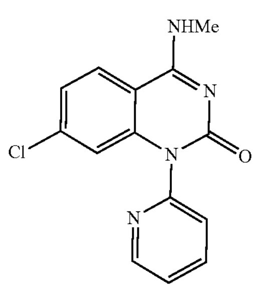 [SMILES: CNc1nc(=O)n(-c2ccccn2)c2cc(Cl)ccc12] | 7-chloro-4-(methylamino)-1-(pyridin-3-yl)-quinazolin-2(1H)-one | |

TABLE 1-continued

| Cpd. No. | Structure | Name | Mass Spec. |
|---|---|---|---|
| 10 | 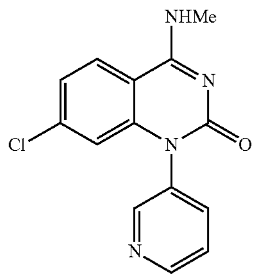 | 7-chloro-4-(methylamino)-1-(pyridin-2-yl)-quinazolin-2(1H)-one | |
| 11 | 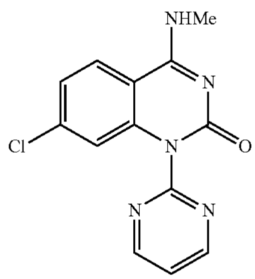 [SMILES: CNc1nc(=O)n(-c2ncccn2)c2cc(Cl)ccc12] | 7-chloro-4-(methylamino)-1-pyrimidin-2-yl-quinazolin-2(1H)-one | |
| 12 | 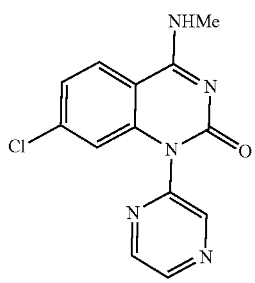 [SMILES: CNc1nc(=O)n(-c2cnccn2)c2cc(Cl)ccc12] | 7-chloro-4-(methylamino)-1-(pyrazin-2-yl)-quinazolin-2(1H)-one | |
| 13 | 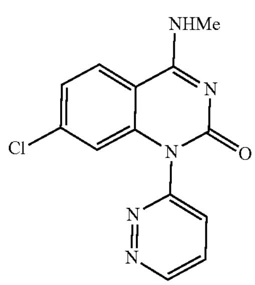 [SMILES: CNc1nc(=O)n(-c2cccnn2)c2cc(Cl)ccc12] | 7-chloro-4-(methylamino)-1-(pyridazin-3-yl)-quinazolin-2(1H)-one | |
| 14 | 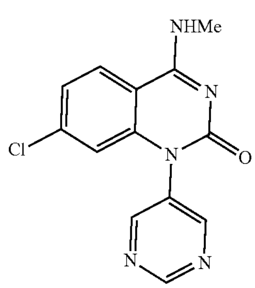 [SMILES: CNc1nc(=O)n(-c2cncnc2)c2cc(Cl)ccc12] | 7-chloro-4-(methylamino)-1-(pyrimidin-5-yl)-quinazolin-2(1H)-one | |

TABLE 1-continued
| Cpd. No. | Structure | Name | Mass Spec. |
|---|---|---|---|
| 15 | 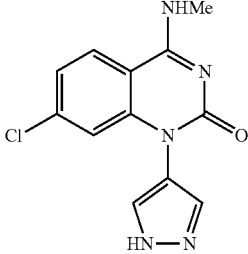 [SMILES: CNc1nc(=O)n(-c2cn[nH]c2)c2cc(Cl)ccc12] | 7-chloro-4-(methylamino)-1-(1H-pyrazol-4-yl)-quinazolin-2(1H)-one | |
| 16 | 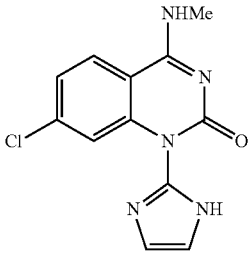 [SMILES: CNc1nc(=O)n(-c2ncc[nH]2)c2cc(Cl)ccc12] | 7-chloro-1-(1H-imidazol-2-yl)-4-(methylamino)-quinazolin-2(1H)-one | |
| 17 | 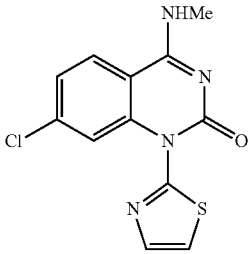 [SMILES: CNc1nc(=O)n(-c2nccs2)c2cc(Cl)ccc12] | 7-chloro-4-(methylamino)-1-(thiazol-2-yl)-quinazolin-2(1H)-one | |
| 18 | 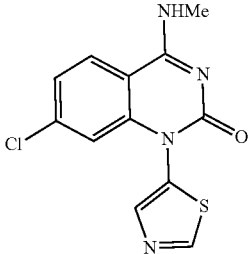 [SMILES: CNc1nc(=O)n(-c2cncs2)c2cc(Cl)ccc12] | 7-chloro-4-(methylamino)-1-(thiazol-5-yl)-quinazolin-2(1H)-one | |
| 19 | 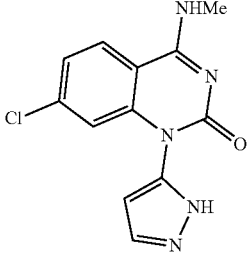 [SMILES: CNc1nc(=O)n(-c2ccn[nH]2)c2cc(Cl)ccc12] | 7-chloro-4-(methylamino)-1-(1H-pyrazol-5-yl)-quinazolin-2(1H)-one | |

TABLE 1-continued

| Cpd. No. | Structure | Name | Mass Spec. |
|---|---|---|---|
| 20 | 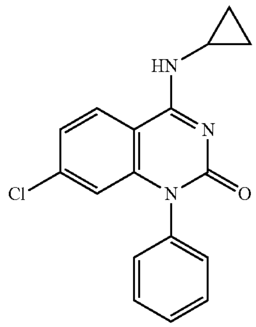 [SMILES: O=c1nc(NC2CC2)c2ccc(Cl)cc2n1-c1ccccc1] | 7-chloro-4-(cyclopropylamino)-1-phenylquinazolin-2(1H)-one | |
| 21 | 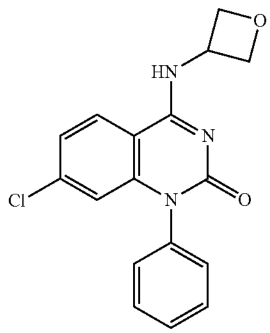 [SMILES: O=c1nc(NC2COC2)c2ccc(Cl)cc2n1-c1ccccc1] | 7-Chloro-4-(oxetan-3-ylamino)-1-phenylquinazolin-2(1H)-one | |
| 22 | 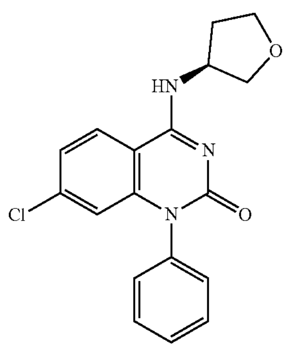 [SMILES: O=c1nc(N[C@H]2CCOC2)c2ccc(Cl)cc2n1-c1ccccc1] | (S)-7-chloro-1-phenyl-4-((tetrahydrofuran-3-yl)amino)-quinazolin-2(1H)-one | |
| 23 | 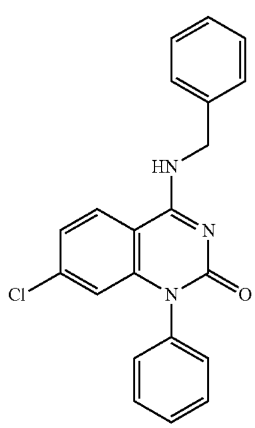 [SMILES: O=c1nc(NCc2ccccc2)c2ccc(Cl)cc2n1-c1ccccc1] | 4-(benzylamino)-7-chloro-1-phenyl-quinazolin-2(1H)-one | |

TABLE 1-continued

| Cpd. No. | Structure | Name | Mass Spec. |
|---|---|---|---|
| 24 | 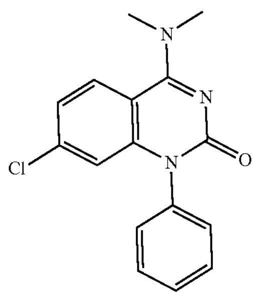 [SMILES: CN(C)c1nc(=O)n(-c2ccccc2)c2cc(Cl)ccc12] | 7-chloro-4-(dimethylamino)-1-phenyl-quinazolin-2(1H)-one | |
| 25 | 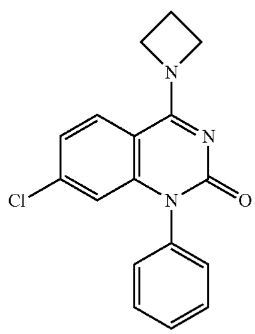 [SMILES: O=c1nc(N2CCC2)c2ccc(Cl)cc2n1-c1ccccc1] | 4-(azetidin-1-yl)-7-chloro-1-phenyl-quinazolin-2(1H)-one | |
| 26 | 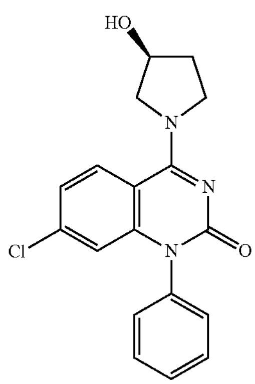 [SMILES: O=c1nc(N2CC[C@H](O)C2)c2ccc(Cl)cc2n1-c1ccccc1] | (S)-7-chloro-4-(3-hydroxypyrrolidin-1-yl)-1-phenylquinazolin-2(1H)-one | |
| 27 | 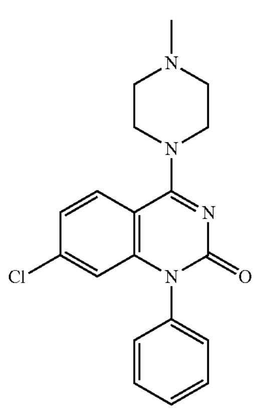 [SMILES: CN1CCN(c2nc(=O)n(-c3ccccc3)c3cc(Cl)ccc23)CC1] | 7-chloro-4-(4-methylpiperazin-1-yl)-1-phenyl-quinazolin-2(1H)-one | |

TABLE 1-continued

| Cpd. No. | Structure | Name | Mass Spec. |
|---|---|---|---|
| 28 | 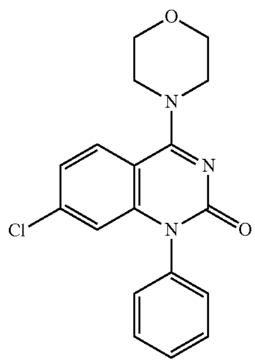 [SMILES: O=c1nc(N2CCOCC2)c2ccc(Cl)cc2n1-c1ccccc1] | 7-chloro-4-morpholino-1-phenyl-quinazolin-2(1H)-one | |
| 29 | 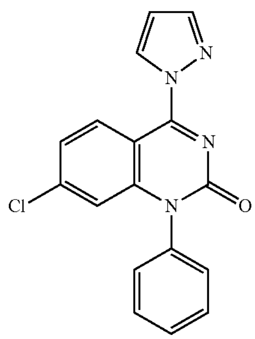 [SMILES: O=c1nc(-n2cccn2)c2ccc(Cl)cc2n1-c1ccccc1] | 7-chloro-1-phenyl-4-(1H-pyrazol-1-yl)quinazolin-2(1H)-one | |
| 30 | 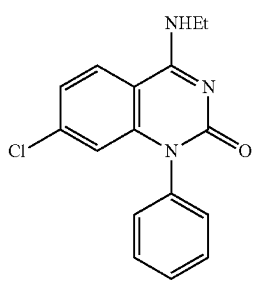 | 7-chloro-4-(ethylamino)-1-phenyl-quinazolin-2(1H)-one | |
| 31 | 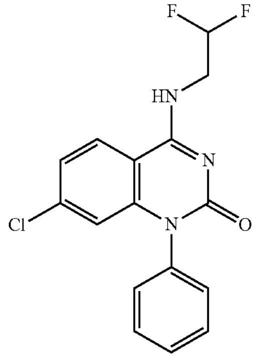 [SMILES: O=c1nc(NCC(F)F)c2ccc(Cl)cc2n1-c1ccccc1] | 7-chloro-4((2,2-difluoroethyl)amino)-1-phenyl-quinazolin-2(1H)-one | |

TABLE 1-continued
| Cpd. No. | Structure | Name | Mass Spec. |
|---|---|---|---|
| 32 | 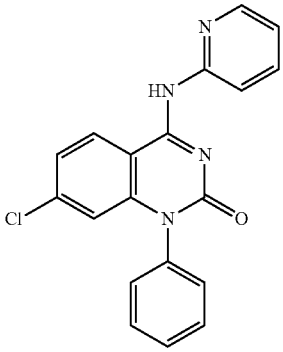 [SMILES: O=c1nc(Nc2ccccn2)c2ccc(Cl)cc2n1-c1ccccc1] | 7-chloro-1-phenyl-4-(pyridin-2-yl-amino)quinazolin-2(1H)-one | |
| 33 | 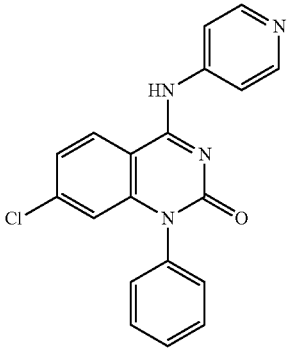 [SMILES: O=c1nc(Nc2ccncc2)c2ccc(Cl)cc2n1-c1ccccc1] | 7-chloro-1-phenyl-4-(pyridin-4-yl-amino)quinazolin-2(1H)-one | |
| 34 | 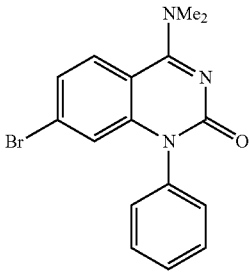 | 7-bromo-4-(dimethyl amino)-1-phenyl-quinazolin-2(1H)-one | |
| 35 | 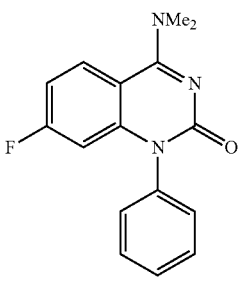 [SMILES: CN(C)c1nc(=O)n(-c2ccccc2)c2cc(F)ccc12] | 4-(dimethylamino)-7-fluoro-1-phenyl-quinazolin-2(1H)-one | |

TABLE 1-continued

| Cpd. No. | Structure | Name | Mass Spec. |
|---|---|---|---|
| 36 | 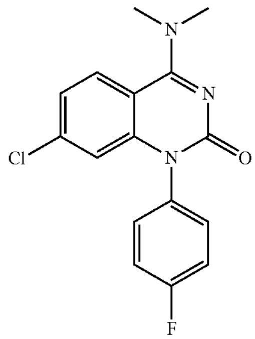 [SMILES: CN(C)c1nc(=O)n(-c2ccc(F)cc2)c2cc(Cl)ccc12] | 4-(dimethylamino)-7-chloro-1-(4-fluorophenyl)-hydroquinazolin-2-one | |
| 37 | 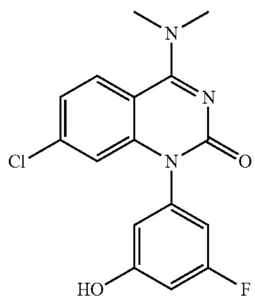 [SMILES: CN(C)c1nc(=O)n(-c2cc(O)cc(F)c2)c2cc(Cl)ccc12] | 4-(dimethylamino)-7-chloro-1-(5-fluoro-3-hydroxyphenyl)hydroquinazolin-2-one | |
| 38 | 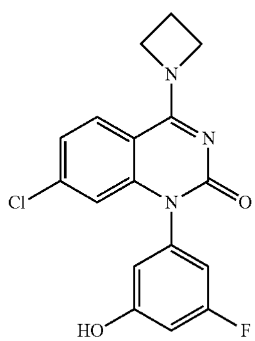 [SMILES: O=c1nc(N2CCC2)c2ccc(Cl)cc2n1-c1cc(O)cc(F)c1] | 4-azetidinyl-7-chloro-1-(5-fluoro-3-hydroxy-phenyl)hydroquinazolin-2-one | |
| 39 | 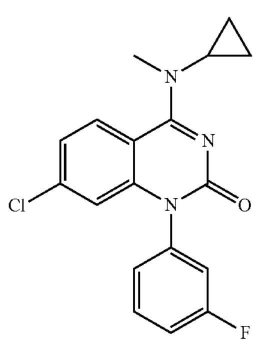 [SMILES: CN(c1nc(=O)n(-c2cccc(F)c2)c2cc(Cl)ccc12)C1CC1] | 7-chloro-4-(cyclopropylmethylamino)-1-(3-fluorophenyl)hydroquinazolin-2-one | |

TABLE 1-continued

| Cpd. No. | Structure | Name | Mass Spec. |
|---|---|---|---|
| 40 | 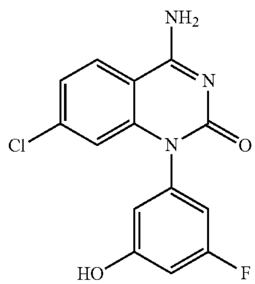 [SMILES: Nc1nc(=O)n(-c2cc(O)cc(F)c2)c2cc(Cl)ccc12] | 4-amino-7-chloro-1-(5-fluoro-3-hydroxyphenyl)-hydroquinazolin-2-one | |
| 41 | 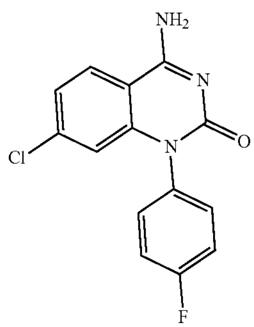 [SMILES: Nc1nc(=O)n(-c2ccc(F)cc2)c2cc(Cl)ccc12] | 4-amino-7-chloro-1-(4-fluorophenyl)-hydro-quinazolin-2-one | |
| 42 | 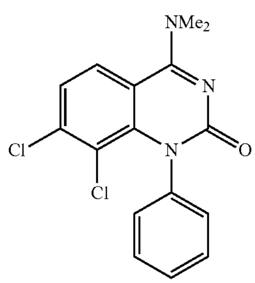 [SMILES: CN(C)c1nc(=O)n(-c2ccccc2)c2c(Cl)c(Cl)ccc12] | 7,8-dichloro-4-(dimethylamino)-1-phenylquinazolin-2(1H)-one | |
| 43 | 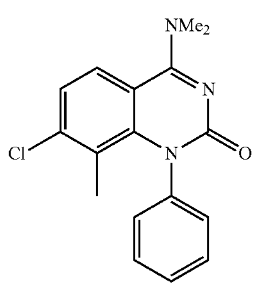 [SMILES: Cc1c(Cl)ccc2c(N(C)C)nc(=O)n(-c3ccccc3)c12] | 7-chloro-4-(dimethylamino)-8-methyl-1-phenyl-quinazolin-2(1H)-one | |
| 44 | 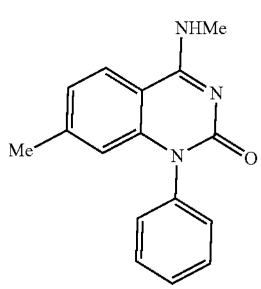 [SMILES: CNc1nc(=O)n(-c2ccccc2)c2cc(C)ccc12] | 7-methyl-4-(methylamino)-1-phenyl-quinazolin-2(1H)-one | |

TABLE 1-continued

| Cpd. No. | Structure | Name | Mass Spec. |
|---|---|---|---|
| 45 | 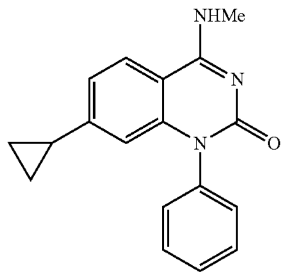 [SMILES: CNc1nc(=O)n(-c2ccccc2)c2cc(C3CC3)ccc12] | 7-cyclopropyl-4-(methylamino)-1-phenylquinazolin-2(1H)-one | |
| 46 | 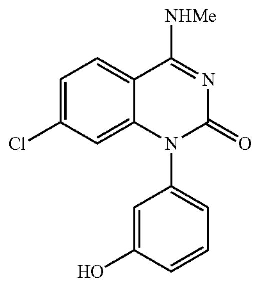 [SMILES: CNc1nc(=O)n(-c2cccc(O)c2)c2cc(Cl)ccc12] | 7-chloro-1-(3-hydroxyphenyl)-4-(methylamino)-hydroquinazolin-2-one | |
| 47 | 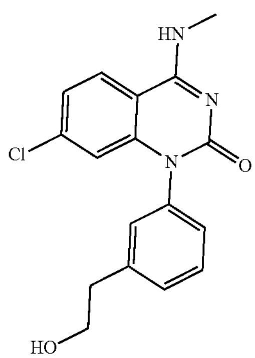 [SMILES: CNc1nc(=O)n(-c2cccc(CCO)c2)c2cc(Cl)ccc12] | 7-chloro-1-[3-(2-hydroxyethyl)phenyl]-4-(methylamino)-hydroquinazolin-2-one | |
| 48 | 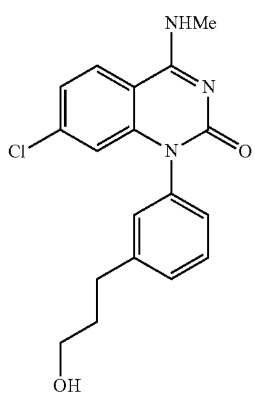 [SMILES: CNc1nc(=O)n(-c2cccc(CCCO)c2)c2cc(Cl)ccc12] | 7-chloro-1-[3-(3-hydroxypropyl)-phenyl]-4-(methylamino)hydro-quinazolin-2-one | |
| 49 | 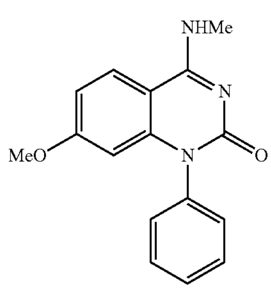 [SMILES: CNc1nc(=O)n(-c2ccccc2)c2cc(OC)ccc12] | 7-methoxy-4-(methylamino)-1-phenyl-quinazolin-2(1H)-one | |

TABLE 1-continued

| Cpd. No. | Structure | Name | Mass Spec. |
|---|---|---|---|
| 50 | 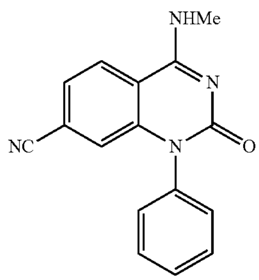 [SMILES: CNc1nc(=O)n(-c2ccccc2)c2cc(C#N)ccc12] | 4-(methylamino)-2-oxo-1-phenyl-1,2-dihydro-quinazoline-7-carbonitrile | |
| 51 | 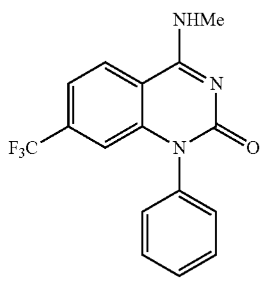 [SMILES: CNc1nc(=O)n(-c2ccccc2)c2cc(C(F)(F)F)ccc12] | 4-(methylamino)-1-phenyl-7-(trifluoromethyl)-quinazolin-2(1H)-one | |
| 52 | 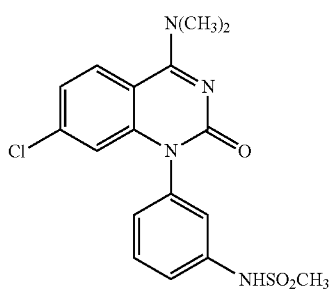 | N-(3-(7-chloro-4-(dimethylamino)-2-oxoquinazolin-1(2H)-yl)phenyl)-methanesulfonamide | |
| 54 | 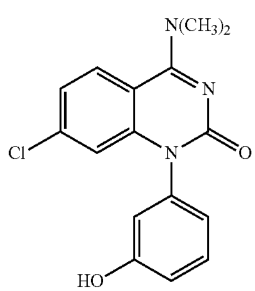 [SMILES: CN(C)c1nc(=O)n(-c2cccc(O)c2)c2cc(Cl)ccc12] | 4-(dimethylamino)-7-chloro-1-(3-hydroxyphenyhydroquinazolin-2-one | |
| 55 | 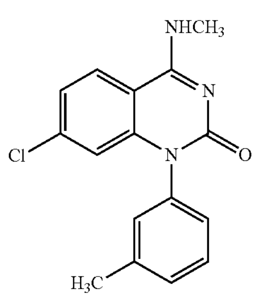 [SMILES: CNc1nc(=O)n(-c2cccc(C)c2)c2cc(Cl)ccc12] | 7-Chloro-4-(methylamino)-1-(3-methylphenyhydroquinazolin-2-one | |

TABLE 1-continued

| Cpd. No. | Structure | Name | Mass Spec. |
|---|---|---|---|
| 56 | 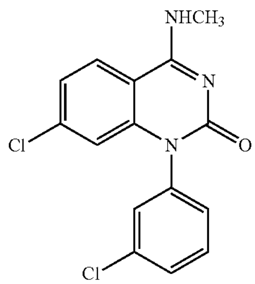 [SMILES: CNc1nc(=O)n(-c2cccc(Cl)c2)c2cc(Cl)ccc12] | 7-Chloro-1-(3-chlorophenyl)-4-(methylamino)hydroquinazolin-2-one | |
| 57 | 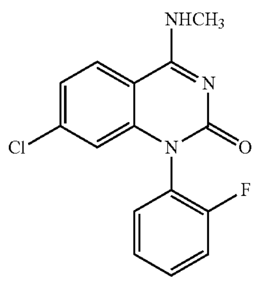 [SMILES: CNc1nc(=O)n(-c2ccccc2F)c2cc(Cl)ccc12] | 7-chloro-1-(2-fluorophenyl)-4-(methylamino)quinazolin-2(1H)-one | |
| 58 | 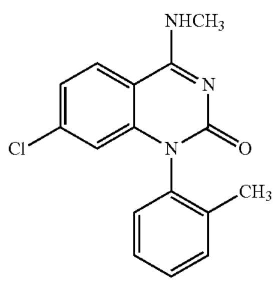 [SMILES: CNc1nc(=O)n(-c2ccccc2C)c2cc(Cl)ccc12] | 7-Chloro-4-(methylamino)-1-(2-methylphenyphydroquinazolin-2-one | |
| 59 | 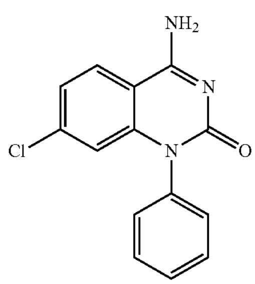 [SMILES: Nc1nc(=O)n(-c2ccccc2)c2cc(Cl)ccc12] | 4-amino-7-chloro-1-phenylquinazolin-2(1H)-one | |
| 60 | 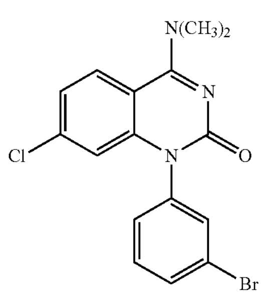 [SMILES: CN(C)c1nc(=O)n(-c2cccc(Br)c2)c2cc(Cl)ccc12] | 1-(3-bromophenyl)-7-chloro-4-(dimethylamino)quinazolin-2(1H)-one | |

TABLE 1-continued
| Cpd. No. | Structure | Name | Mass Spec. |
|---|---|---|---|
| 61 | 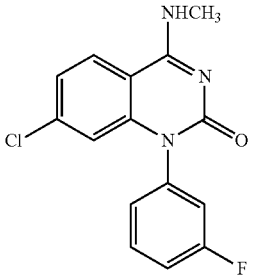 [SMILES: CNc1nc(=O)n(-c2cccc(F)c2)c2cc(Cl)ccc12] | 7-chloro-1-(3-fluorophenyl)-4-(methylamino)quinazolin-2(1H)-one | |
| 62 | 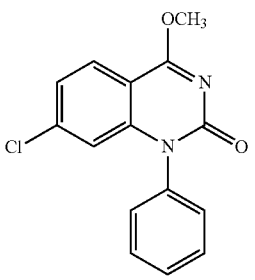 [SMILES: COc1nc(=O)n(-c2ccccc2)c2cc(Cl)ccc12] | 7-chloro-4-methoxy-1-phenyl-quinazolin-2(1H)-one | |
| 63 | 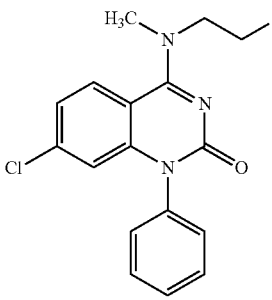 | 7-chloro-4-((2-(dimethylamino)ethyl)-(methyl)-amino)-1-phenylquinazolin-2(1H)-one | |
| 64 | 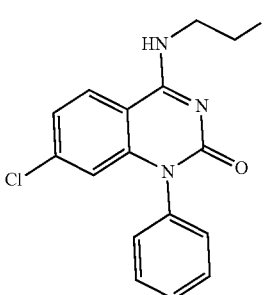 | 7-chloro-4-((2-(dimethylamino)ethyl)-amino)-1-phenylquinazolin-2(1H)-one | |
| 65 | 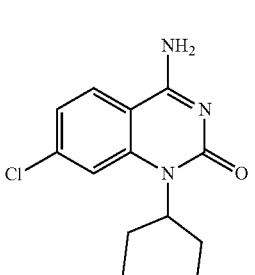 | 4-amino-7-chloro-1-cyclohexyl-quinazolin-2(1H)-one | |

TABLE 1-continued

| Cpd. No. | Structure | Name | Mass Spec. |
|---|---|---|---|
| 66 | 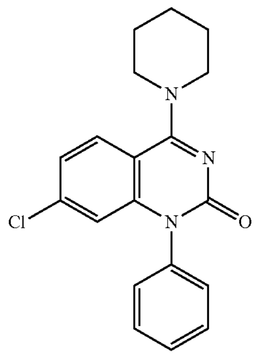 [SMILES: O=c1nc(N2CCCCC2)c2ccc(Cl)cc2n1-c1ccccc1] | 7-chloro-1-phenyl-4-(piperidin-1-yl)-quinazolin-2(1H)-one | |
| 67 | 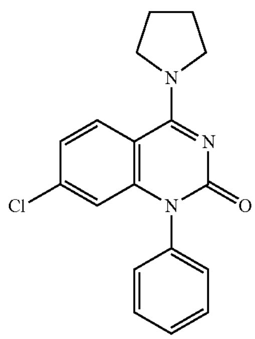 [SMILES: O=c1nc(N2CCCC2)c2ccc(Cl)cc2n1-c1ccccc1] | 7-chloro-1-phenyl-4-(pyrrolidin-1-yl)-quinazolin-2(1H)-one | |
| 68 | 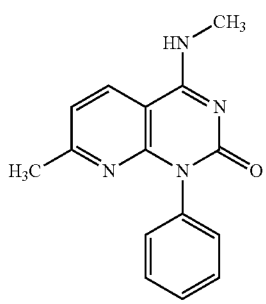 [SMILES: CNc1nc(=O)n(-c2ccccc2)c2nc(C)ccc12] | 7-methyl-4-(methylamino)-1-phenyl-pyrido[2,3-d]pyrimidin-2(1H)-one | |
| 69 | 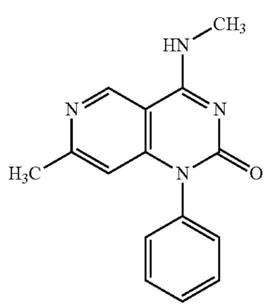 [SMILES: CNc1nc(=O)n(-c2ccccc2)c2cc(C)ncc12] | 7-methyl-4-(methylamino)-1-phenyl-pyrido[4,3-d]pyrimidin-2(1H)-one | |

TABLE 1-continued

| Cpd. No. | Structure | Name | Mass Spec. |
|---|---|---|---|
| 70 | 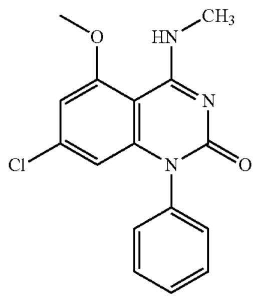 [SMILES: CNc1nc(=O)n(-c2ccccc2)c2cc(Cl)cc(OC)c12] | 7-chloro-5-methoxy-4-(methylamino)-1-phenylquinazolin-2(1H)-one | |
| 71 | 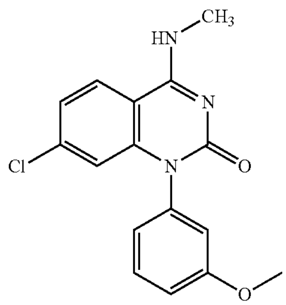 [SMILES: CNc1nc(=O)n(-c2cccc(OC)c2)c2cc(Cl)ccc12] | 7-chloro-1-(3-methoxyphenyl)-4-(methylamino)quinazolin-2(1H)-one | |
| 73 | 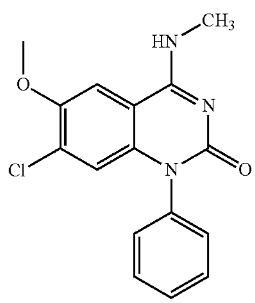 [SMILES: CNc1nc(=O)n(-c2ccccc2)c2cc(Cl)c(OC)cc12] | 7-chloro-6-methoxy-4-(methylamino)-1-phenylquinazolin-2(1H)-one | |
| 74 | 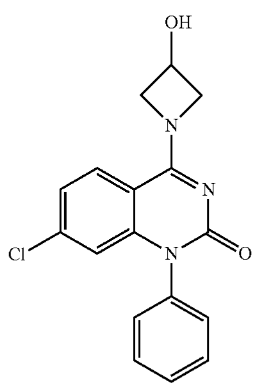 [SMILES: O=c1nc(N2CC(O)C2)c2ccc(Cl)cc2n1-c1ccccc1] | 7-chloro-4-(3-hydroxyazetidin-1-yl)-1-phenylquinazolin-2(1H)-one | |
| 75 | 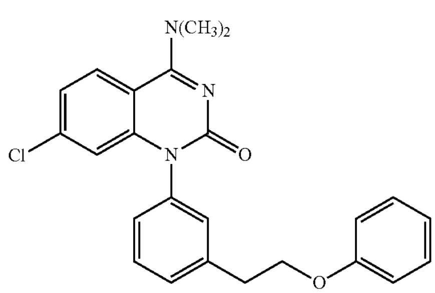 [SMILES: CN(C)c1nc(=O)n(-c2cccc(CCOc3ccccc3)c2)c2cc(Cl)ccc12] | 7-chloro-4-(dimethylamino)-1-(3-(2-phenoxyethyl)phenyl)quinazolin-2(1H)-one | |

TABLE 1-continued

| Cpd. No. | Structure | Name | Mass Spec. |
|---|---|---|---|
| 76 | 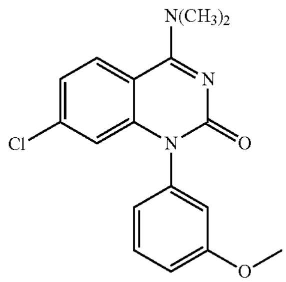 [SMILES: COc1cccc(-n2c(=O)nc(N(C)C)c3ccc(Cl)cc32)c1] | 4-(dimethylamino)-7-chloro-1-(3-methoxyphenyphydroquinazolin-2-one | |
| 77 | 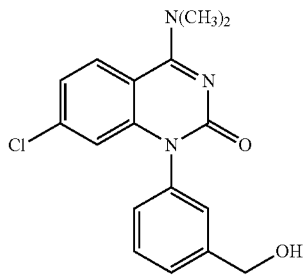 [SMILES: CN(C)c1nc(=O)n(-c2cccc(CO)c2)c2cc(Cl)ccc12] | 4-(dimethylamino)-7-chloro-1-[3-(hydroxymethyl)phenyl]hydroquinazolin-2-one | |
| 78 | 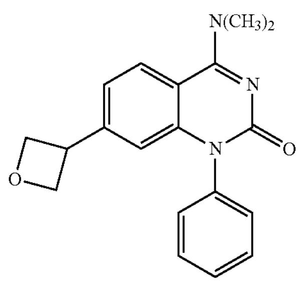 [SMILES: CN(C)c1nc(=O)n(-c2ccccc2)c2cc(C3COC3)ccc12] | 4-(dimethylamino)-7-(oxetan-3-yl)-1-phenylquinazolin-2(1H)-one | |
| 79 | 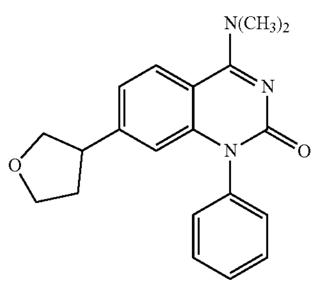 [SMILES: CN(C)c1nc(=O)n(-c2ccccc2)c2cc(C3CCOC3)ccc12] | 4-(dimethylamino)-1-phenyl-7-(tetrahydrofuran-3-yl)quinazolin-2(1H)-one | |
| 80 | 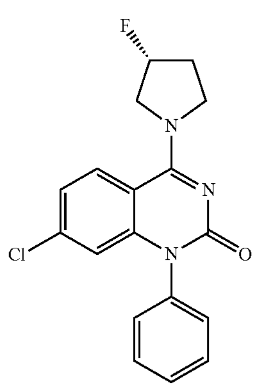 [SMILES: O=c1nc(N2CC[C@@H](F)C2)c2ccc(Cl)cc2n1-c1ccccc1] | (R)-7-chloro-4-(3-fluoropyrrolidin-1-yl)-1-phenylquinazolin-2(1H)-one | |

TABLE 1-continued

| Cpd. No. | Structure | Name | Mass Spec. |
|---|---|---|---|
| 81 | 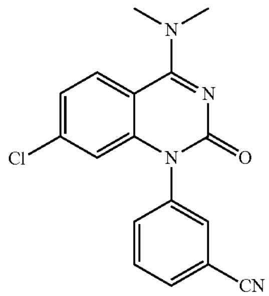 [SMILES: CN(C)c1nc(=O)n(-c2cccc(C#N)c2)c2cc(Cl)ccc12] | 3-[4-(dimethylamino)-7-chloro-2-oxohydroquinazolinyl]benzenecarbonitrile | |
| 82 | 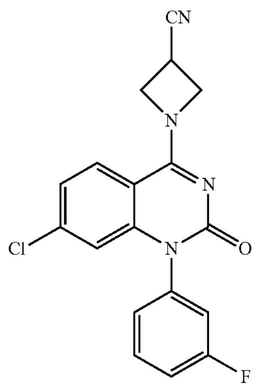 [SMILES: N#CC1CN(c2nc(=O)n(-c3cccc(F)c3)c3cc(Cl)ccc23)C1] | 1-(7-chloro-1-(3-fluorophenyl)-2-oxo-1,2-dihydroquinazolin-4-yl)azetidine-3-carbonitrile | |
| 83 | 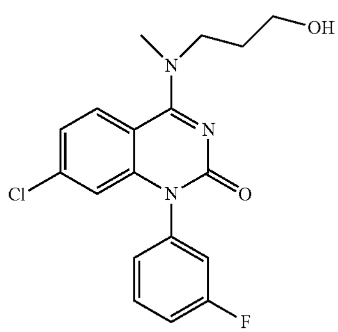 [SMILES: CN(CCCO)c1nc(=O)n(-c2cccc(F)c2)c2cc(Cl)ccc12] | 7-chloro-1-(3-fluorophenyl)-4-((3-hydroxypropyl)(methyl)amino)quinazolin-2(1H)-one | |
| 85 | 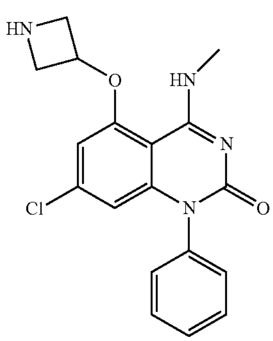 [SMILES: CNc1nc(=O)n(-c2ccccc2)c2cc(Cl)cc(OC3CNC3)c12] | 5-azetidin-3-yloxy-7-chloro-4-(methylamino)-1-phenylhydroquinazolin-2-one | m/z [M + H]+ 357.1 |

TABLE 1-continued

| Cpd. No. | Structure | Name | Mass Spec. |
|---|---|---|---|
| 86 | 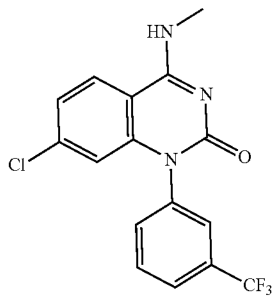 [SMILES: CNc1nc(=O)n(-c2cccc(C(F)(F)F)c2)c2cc(Cl)ccc12] | 7-chloro-4-(methylamino)-1-[3-(trifluoromethyl)phenyl]hydroquinazolin-2-one | m/z [M + H]+ 354.04 |
| 87 | 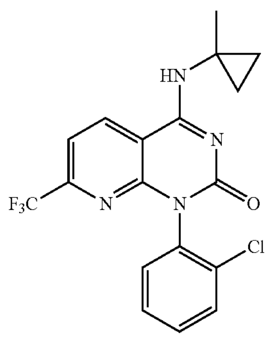 | 4-((3R)-3-hydroxypyrrolidin-1-yl)-1-(2-bromophenyl)-7-chlorohydroquinazolin-2-one | m/z [M + H]+ 420.04 |
| 88 | 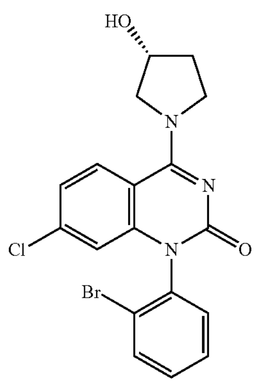 [SMILES: O=c1nc(N2CC[C@@H](O)C2)c2ccc(Cl)cc2n1-c1ccccc1Br] | 1-(2-chlorophenyl)-4((1-methylcyclopropyl)amino)-7-(trifluoromethyl)-pyrido[2,3-d]pyrimidin-2(1H)-one | m/z [M + H]+ 395.05 |
| 89 | 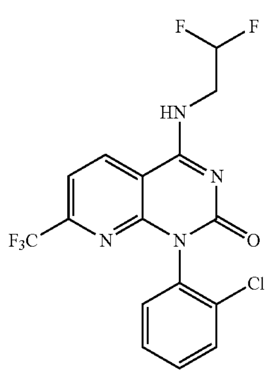 [SMILES: O=c1nc(NCC(F)F)c2ccc(C(F)(F)F)nc2n1-c1ccccc1Cl] | 1-(2-chlorophenyl)-4-[(2,2-difluoroethyl)amino]-7-(trifluoromethyl)-pyrido[2,3-d]-pyrimidin-2(1H)-one | m/z [M + H]+ 405.1 |

TABLE 1-continued

| Cpd. No. | Structure | Name | Mass Spec. |
|---|---|---|---|
| 90 | 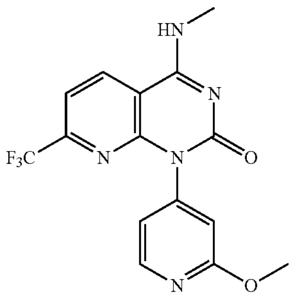 [SMILES: CNc1nc(=O)n(-c2ccnc(OC)c2)c2nc(C(F)(F)F)ccc12] | 1-(2-methoxypyridin-4-yl)-4-(methyl-amino)-7-(trifluoromethyl)pyrido[2,3-d]-pyrimidin-2(1H)-one | m/z [M + H]+ 352.0 |
| 91 | 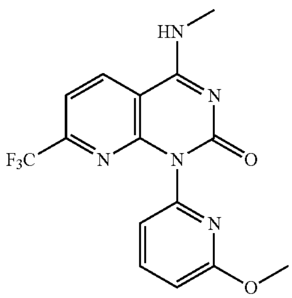 [SMILES: CNc1nc(=O)n(-c2cccc(OC)n2)c2nc(C(F)(F)F)ccc12] | 1-(6-methoxypyridin-2-yl)-4-(methylamino)-7-(trifluoromethyl)-pyrido[2,3-d]pyrimidin-2(1H)-one | m/z [M + H]+ 352.0 |
| 92 | 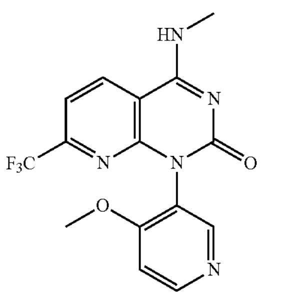 [SMILES: CNc1nc(=O)n(-c2cnccc2OC)c2nc(C(F)(F)F)ccc12] | 1-(4-methoxypyridin-3-yl)-4-(methyl-amino)-7-(trifluoromethyl)pyrido[2,3-d]pyrimidin-2(1H)-one | m/z [M + H]+ 352.0 |
| 93 | 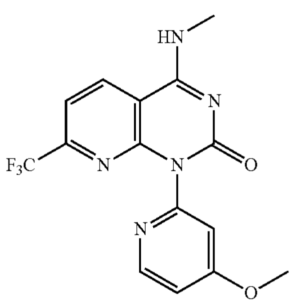 [SMILES: CNc1nc(=O)n(-c2cc(OC)ccn2)c2nc(C(F)(F)F)ccc12] | 1-(4-methoxypyridin-2-yl)-4-(methyl-amino)-7-(trifluoromethyl)pyrido[2,3-d]pyrimidin-2(1H)-one | m/z [M + H]+ 352.0 |
| 94 | 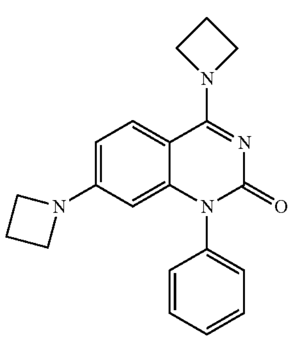 [SMILES: O=c1nc(N2CCC2)c2ccc(N3CCC3)cc2n1-c1ccccc1] | 4,7-bis(dimethylamino)-1-phenylhydro-quinazolin-2-one | m/z [M + H]+ 333.2 |

TABLE 1-continued

| Cpd. No. | Structure | Name | Mass Spec. |
|---|---|---|---|
| 94 | 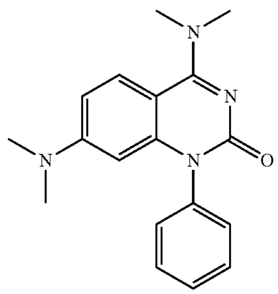 [SMILES: CN(C)c1ccc2c(N(C)C)nc(=O)n(-c3ccccc3)c2c1] | 4,7-bis(dimethylamino)-1-phenylhydroquinazolin-2-one | m/z [M + H]+ 309.2 |
| 96 | 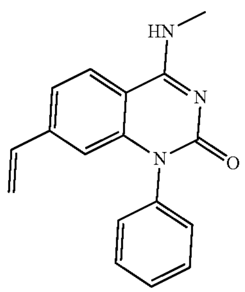 [SMILES: C=Cc1ccc2c(NC)nc(=O)n(-c3ccccc3)c2c1] | 4-(methylamino)-1-phenyl-7-vinylhydro-quinazolin-2-one | m/z [M + H]+ 278.15 |
| 97 | 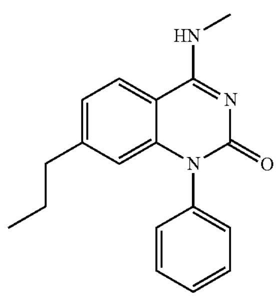 [SMILES: CCCc1ccc2c(NC)nc(=O)n(-c3ccccc3)c2c1] | 4-(methylamino)-1-phenyl-7-propylhydroquinazolin-2-one | m/z [M + H]+ 294.2 |
| 99 | 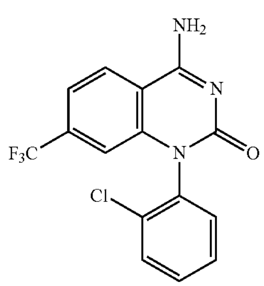 [SMILES: Nc1nc(=O)n(-c2ccccc2Cl)c2cc(C(F)(F)F)ccc12] | 4-amino-1-(2-chlorophenyl)-7-(trifluoromethyl)hydroquinazolin-2-one | m/z [M + H]+ 340.0 |
| 100 | 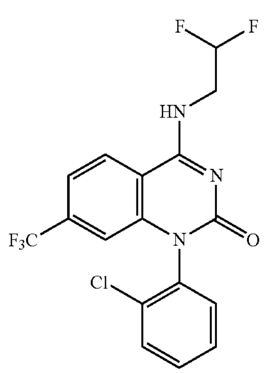 [SMILES: O=c1nc(NCC(F)F)c2ccc(C(F)(F)F)cc2n1-c1ccccc1Cl] | 1-(2-chlorophenyl)-4-[(2,2-difluoroethyl)amino]-7-(trifluoromethyl)hydroquinazolin-2-one | m/z [M + H]+ 404.0 |

TABLE 1-continued

| Cpd. No. | Structure | Name | Mass Spec. |
|---|---|---|---|
| 101 | 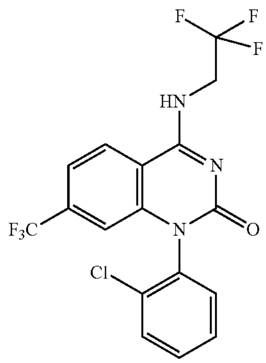 | 1-(2-chlorophenyl)-4-[(2,2,2-trifluoro-ethyl)amino]-7-(trifluoromethyl)hydro-quinazolin-2-one | m/z [M + H]+ 422.0 |
| 102 | 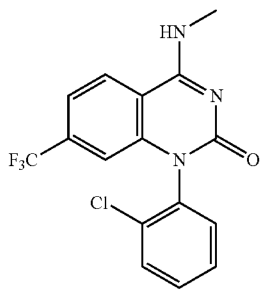 [SMILES: CNc1nc(=O)n(-c2ccccc2Cl)c2cc(C(F)(F)F)ccc12] | 1-(2-chlorophenyl)-4-(methylamino)-7-(trifluoromethyl)hydroquinazolin-2-one | m/z [M + H]+ 354.1 |
| 103 | 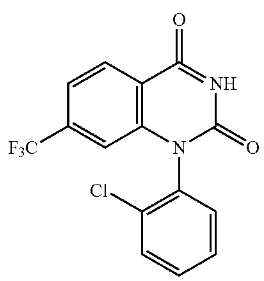 | 1-(2-chlorophenyl)-7-(trifluoromethyl)-1,3-dihydroquinazoline-2,4-dione | m/z [M + H]+ 341.0 |
| 104 | 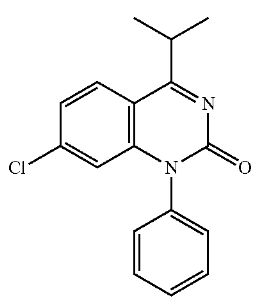 [SMILES: CC(C)c1nc(=O)n(-c2ccccc2)c2cc(Cl)ccc12] | 7-chloro-4-(methylethyl)-1-phenylhydro-quinazolin-2-one | m/z [M + H]+ 299.19 |
| 105 | 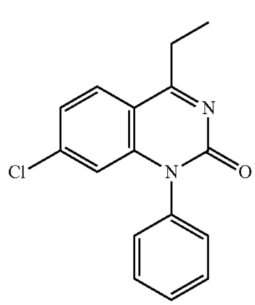 [SMILES: CCc1nc(=O)n(-c2ccccc2)c2cc(Cl)ccc12] | 7-chloro-4-ethyl-1-phenylhydro-quinazolin-2-one | m/z [M + H]+ 285.21 |

TABLE 1-continued

| Cpd. No. | Structure | Name | Mass Spec. |
|---|---|---|---|
| 106 | 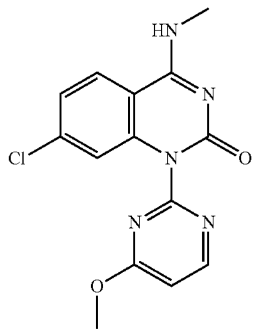 [SMILES: CNc1nc(=O)n(-c2nccc(OC)n2)c2cc(Cl)ccc12] | 7-chloro-1-(4-methoxypyrimidin-2-yl)-4-(methylamino)hydroquinazolin-2-one | m/z [M + H]+ 318.12 |
| 107 | 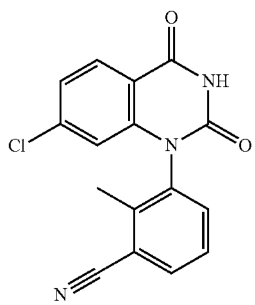 [SMILES: Cc1c(C#N)cccc1-n1c(=O)[nH]c(=O)c2ccc(Cl)cc21] | 3-(7-chloro-2,4-dioxo-3,4-dihydro-quinazolin-1(2H)-yl)-2-methyl-benzonitrile | m/z [M + H]+ 310.13 |
| 108 | 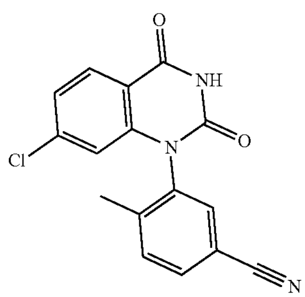 [SMILES: Cc1ccc(C#N)cc1-n1c(=O)[nH]c(=O)c2ccc(Cl)cc21] | 3-(7-chloro-2,4-dioxo-3,4-dihydro-quinazolin-1(2H)-yl)-4-methyl-benzonitrile | m/z [M + H]+ 310.06 |
| 109 | 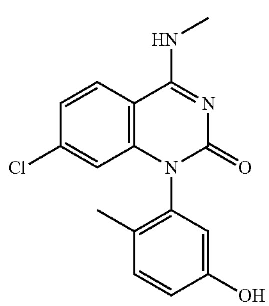 [SMILES: CNc1nc(=O)n(-c2cc(O)ccc2C)c2cc(Cl)ccc12] | 7-chloro-1-(3-hydroxy-6-methylphenyl)-4-(methylamino)hydroquinazolin-2-one | m/z [M + H]+ 316.18 |
| 110 | 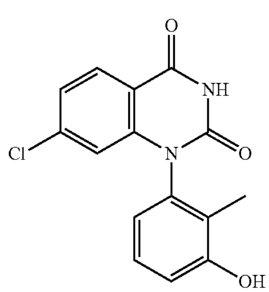 [SMILES: Cc1c(O)cccc1-n1c(=O)[nH]c(=O)c2ccc(Cl)cc21] | 7-chloro-1-(3-hydroxy-2-methylphenyl)-1,3-dihydroquinazoline-2,4-dione | m/z [M + H]+ 303.13 |

TABLE 1-continued

| Cpd. No. | Structure | Name | Mass Spec. |
|---|---|---|---|
| 112 | 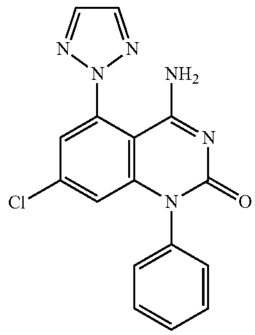 [SMILES: Nc1nc(=O)n(-c2ccccc2)c2cc(Cl)cc(-n3nccn3)c12] | 4-amino-7-chloro-1-phenyl-5-(1,2,3-triazol-2-yl)hydroquinazolin-2-one | m/z [M + H]+ 339.11 |
| 113 | 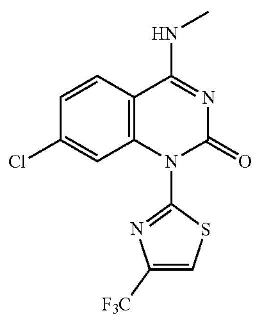 [SMILES: CNc1nc(=O)n(-c2nc(C(F)(F)F)cs2)c2cc(Cl)ccc12] | 7-chloro-4-(methylamino)-1-[4-(trifluoromethyl)(1,3-thiazol-2-yl)]hydroquinazolin-2-one | m/z [M + H]+ 361.0 |
| 114 | 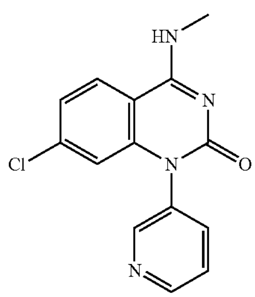 [SMILES: CNc1nc(=O)n(-c2cccnc2)c2cc(Cl)ccc12] | 7-chloro-4-(methylamino)-1-(3-pyridyl)-hydroquinazolin-2-one | m/z [M + H]+ 287.1 |
| 115 | 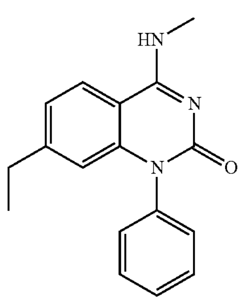 [SMILES: CCc1ccc2c(NC)nc(=O)n(-c3ccccc3)c2c1] | 7-ethyl-4-(methylamino)-1-phenylhydro-quinazolin-2-one | m/z [M + H]+ 280.1 |
| 116 | 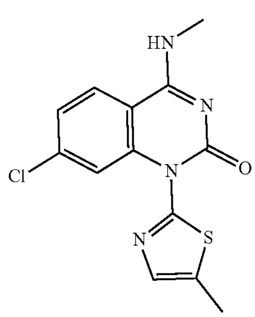 [SMILES: CNc1nc(=O)n(-c2ncc(C)s2)c2cc(Cl)ccc12] | 7-chloro-1-(5-methyl(1,3-thiazol-2-yl))-4-(methylamino)hydroquinazolin-2-one | m/z [M + H]+ 307.0 |

TABLE 1-continued

| Cpd. No. | Structure | Name | Mass Spec. |
|---|---|---|---|
| 117 | 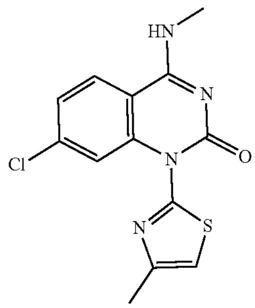 [SMILES: CNc1nc(=O)n(-c2nc(C)cs2)c2cc(Cl)ccc12] | 7-chloro-1-(4-methyl(1,3-thiazol-2-yl))-4-(methylamino)hydroquinazolin-2-one | m/z [M + H]+ 307.0 |
| 118 | 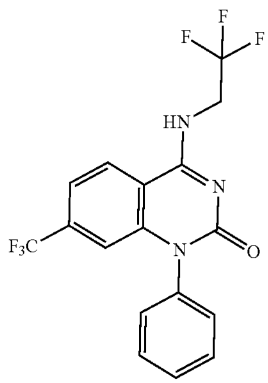 [SMILES: O=c1nc(NCC(F)(F)F)c2ccc(C(F)(F)F)cc2n1-c1ccccc1] | 1-phenyl-4-[(2,2,2-trifluoroethyl)amino]-7-(trifluoromethyphydroquinazolin-2-one | m/z [M + H]+ 388.0 |
| 119 | 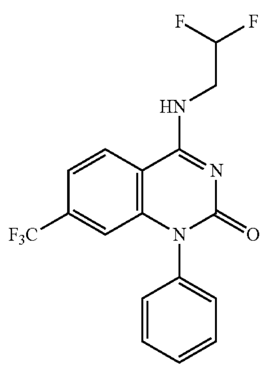 [SMILES: O=c1nc(NCC(F)F)c2ccc(C(F)(F)F)cc2n1-c1ccccc1] | 4-[(2,2-difluoroethyl)amino]-1-phenyl-7-(trifluoromethyl)hydroquinazolin-2-one | m/z [M + H]+ 370.0 |
| 120 | 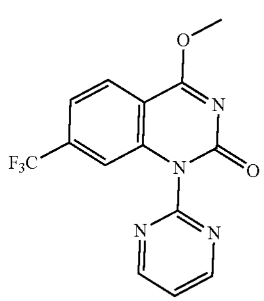 [SMILES: COc1nc(=O)n(-c2ncccn2)c2cc(C(F)(F)F)ccc12] | 4-methoxy-1-pyrimidin-2-yl-7-(trifluoro-methyphydroquinazolin-2- | m/z [M + H]+ 323.0 |

TABLE 1-continued

| Cpd. No. | Structure | Name | Mass Spec. |
|---|---|---|---|
| 121 | 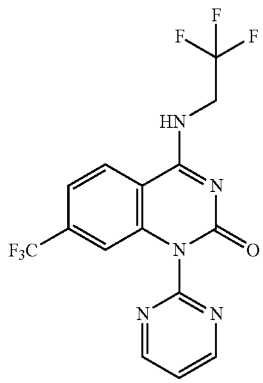 [SMILES: O=c1nc(NCC(F)(F)F)c2ccc(C(F)(F)F)cc2n1-c1ncccn1] | 1-pyrimidin-2-yl-4-[(2,2,2-trifluoro-ethyparnino]-7-(trifluoromethyphydro-quinazolin-2-one | m/z [M + H]+ 390.0 |
| 122 | 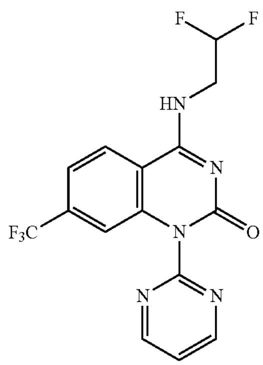 [SMILES: O=c1nc(NCC(F)F)c2ccc(C(F)(F)F)cc2n1-c1ncccn1] | 4-[(2,2-difluoroethyl)amino]-1-pyrimidin-2-yl-7-(trifluoromethyl)hydro-quinazolin-2-one | m/z [M + H]+ 372.0 |
| 123 | 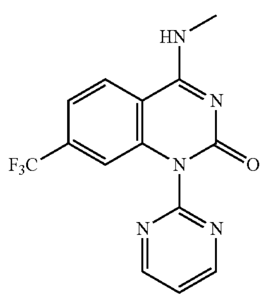 [SMILES: CNc1nc(=O)n(-c2ncccn2)c2cc(C(F)(F)F)ccc12] | 4-(methylamino)-1-pyrimidin-2-yl-7-(trifluoromethyl)hydroquinazolin-2-one | m/z [M + H]+ 322.0 |
| 124 | 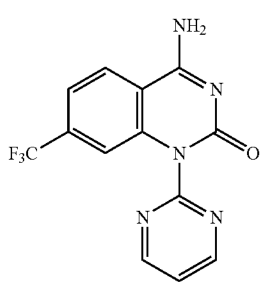 [SMILES: Nc1nc(=O)n(-c2ncccn2)c2cc(C(F)(F)F)ccc12] | 4-amino-1-pyrimidin-2-yl-7-(trifluoro-methyl)hydroquinazolin-2-one | m/z [M + H]+ 308.0 |
| 125 | 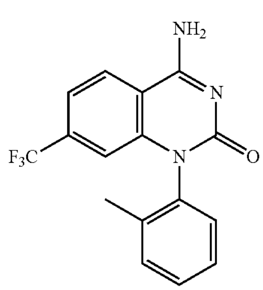 [SMILES: Cc1ccccc1-n1c(=O)nc(N)c2ccc(C(F)(F)F)cc21] | 4-amino-1-(2-methylphenyl)-7-(trifluoromethyl)hydroquinazolin-2-one | m/z [M + H]+ 320.0 |

TABLE 1-continued

| Cpd. No. | Structure | Name | Mass Spec. |
|---|---|---|---|
| 126 | 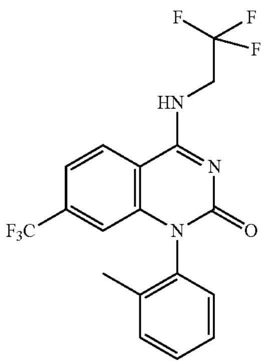 [SMILES: Cc1ccccc1-n1c(=O)nc(NCC(F)(F)F)c2ccc(C(F)(F)F)cc21] | 1-(2-methylphenyl)-4-[(2,2,2-trifluoroethyl)amino]-7-(trifluoromethyl)hydroquinazolin-2-one | m/z [M + H]+ 402.0 |
| 127 | 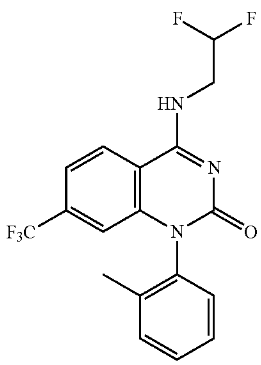 [SMILES: Cc1ccccc1-n1c(=O)nc(NCC(F)F)c2ccc(C(F)(F)F)cc21] | 4-[(2,2-difluoroethyl)amino]-1-(2-methylphenyl)-7-(trifluoromethyl)hydro-quinazolin-2-one | m/z [M + H]+ 384.0 |
| 128 | 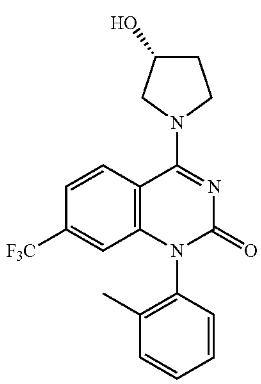 [SMILES: Cc1ccccc1-n1c(=O)nc(N2CC[C@@H](O)C2)c2ccc(C(F)(F)F)cc21] | 4-((3R)-3-hydroxypyrrolidin-1-yl)-1-(2-methylphenyl)-7-(trifluoromethyl)hydro-quinazolin-2-one | m/z [M + H]+ 390.0 |
| 129 | 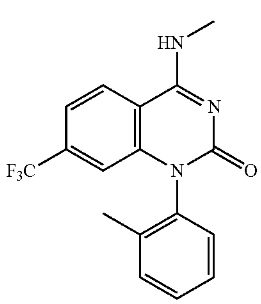 [SMILES: CNc1nc(=O)n(-c2ccccc2C)c2cc(C(F)(F)F)ccc12] | 4-(methylamino)-1-(2-methylphenyl)-7-(trifluoromethyl)hydroquinazolin-2-one | m/z [M + H]+ 334.0 |

TABLE 1-continued

| Cpd. No. | Structure | Name | Mass Spec. |
|---|---|---|---|
| 130 | 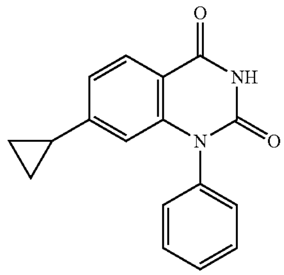 [SMILES: O=c1[nH]c(=O)n(-c2ccccc2)c2cc(C3CC3)ccc12] | 7-cyclopropyl-1-phenyl-1,3-dihydro-quinazoline-2,4-dione | m/z [M + H]+ 279.21 |
| 132 | 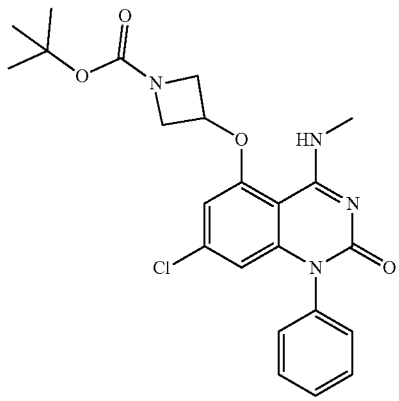 [SMILES: CNc1nc(=O)n(-c2ccccc2)c2cc(Cl)cc(OC3CN(C(=O)OC(C)(C)C)C3)c12] | tert-butyl 3-[7-chloro-4-(methylamino)-2-oxo-1-phenylhydroquinazolin-5-yl-oxy]azetidinecarboxylate | m/z [M + H]+ 457.13 |
| 133 | 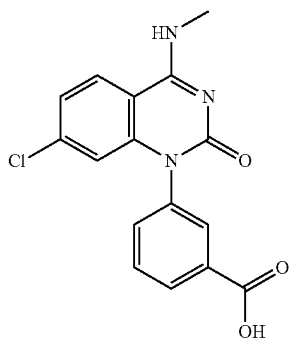 [SMILES: CNc1nc(=O)n(-c2cccc(C(=O)O)c2)c2cc(Cl)ccc12] | 3-[7-chloro-4-(methylamino)-2-oxo-hydroquinazolin-1-yl]benzoic acid | m/z [M + H]+ 330.11 |
| 134 | 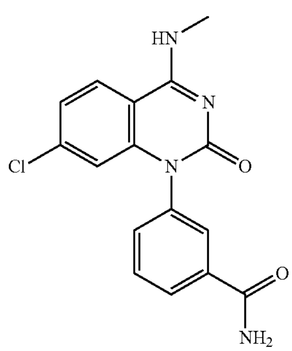 [SMILES: CNc1nc(=O)n(-c2cccc(C(N)=O)c2)c2cc(Cl)ccc12] | 3-[7-chloro-4-(methylamino)-2-oxo-hydroquinazolin-1-yl]benzamide | m/z [M + H]+ 329.11 |

TABLE 1-continued

| Cpd. No. | Structure | Name | Mass Spec. |
|---|---|---|---|
| 135 | 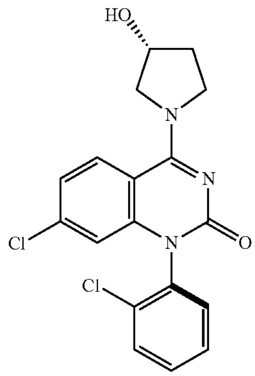 | 4-((3R)-3-hydroxypyrrolidin-1-yl)-7-chloro-1-(2-chlorophenyl)hydroquinazolin-2-one | m/z [M + H]+ 376.10 |
| 136 | 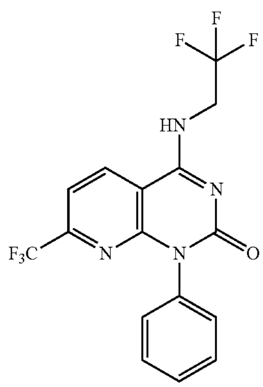 [SMILES: O=c1nc(NCC(F)(F)F)c2ccc(C(F)(F)F)nc2n1-c1ccccc1] | 1-phenyl-4-((2,2,2-trifluoroethyl)amino)-7-(trifluoromethyl)pyrido[2,3-d]pyrimidin-2(1H)-one | m/z [M + H]+ 389.0 |
| 137 | 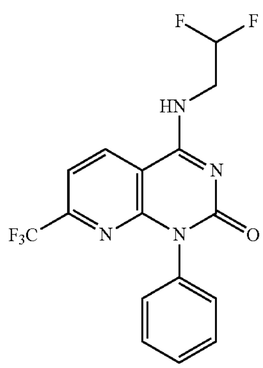 [SMILES: O=c1nc(NCC(F)F)c2ccc(C(F)(F)F)nc2n1-c1ccccc1] | 4-((2,2-difluoroethyl)amino)-1-phenyl-7-(trifluoromethyl)pyrido[2,3-d]pyrimidin-2(1H)-one | m/z [M + H]+ 371.0 |
| 138 | 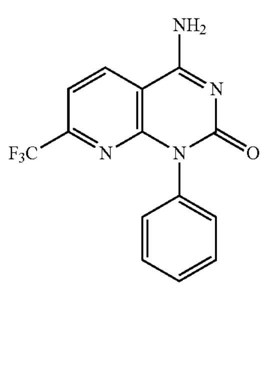 [SMILES: Nc1nc(=O)n(-c2ccccc2)c2nc(C(F)(F)F)ccc12] | 4-amino-1-phenyl-7-(trifluoromethyl)-hydropyridino[2,3-d]pyrimidin-2-one | m/z [M + H]+ 307.0 |

TABLE 1-continued

| Cpd. No. | Structure | Name | Mass Spec. |
|---|---|---|---|
| 139 | 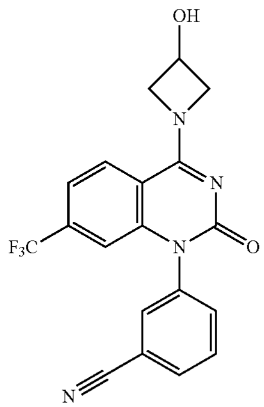 [SMILES: N#Cc1cccc(-n2c(=O)nc(N3CC(O)C3)c3ccc(C(F)(F)F)cc32)c1] | 3[4-(3-hydroxyazetidinyl)-2-oxo-7-(trifluoromethyl)hydroquinazolinyl]-benzenecarbonitrile | m/z [M + H]+ 387.0 |
| 140 | 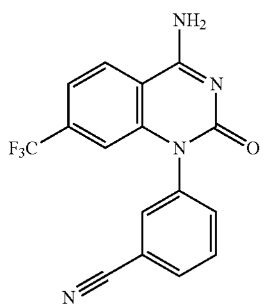 [SMILES: N#Cc1cccc(-n2c(=O)nc(N)c3ccc(C(F)(F)F)cc32)c1] | 3-[4-amino-2-oxo-7-(trifluoromethyl)-hydroquinazolinyl]benzenecarbonitrile | m/z [M + H]+ 331.0 |
| 141 | 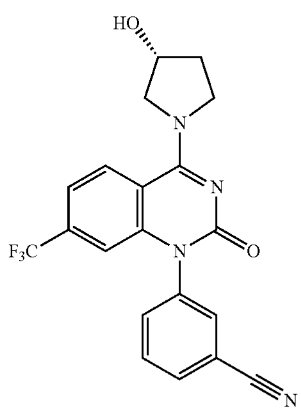 [SMILES: N#Cc1cccc(-n2c(=O)nc(N3CC[C@@H](O)C3)c3ccc(C(F)(F)F)cc32)c1] | 3[4-((3R)-3-hydroxypyrrolidinyl)-2-oxo-7-(trifluoromethyl)hydro-quinazolinyl]-benzenecarbonitrile | m/z [M + H]+ 401.1 |
| 142 | 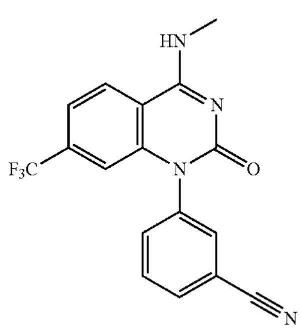 [SMILES: CNc1nc(=O)n(-c2cccc(C#N)c2)c2cc(C(F)(F)F)ccc12] | 3[4-(methylamino)-2-oxo-7-(trifluoromethyl)hydroquinazolinyl]benzene-carbonitrile | m/z [M + H]+ 345.1 |

TABLE 1-continued

| Cpd. No. | Structure | Name | Mass Spec. |
|---|---|---|---|
| 143 | 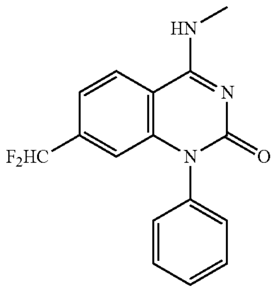 [SMILES: CNc1nc(=O)n(-c2ccccc2)c2cc(C(F)F)ccc12] | 7-(difluoromethyl)-4-(methylamino)-1-phenylhydroquinazolin-2-one | m/z [M + H]⁺ 302.0 |
| 144 | 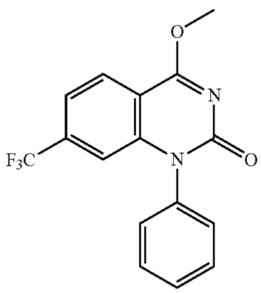 [SMILES: COc1nc(=O)n(-c2ccccc2)c2cc(C(F)(F)F)ccc12] | 4-methoxy-1-phenyl-7-(trifluoromethyl)-hydroquinazolin-2-one | m/z [M + H]⁺ 321.0 |
| 145 | 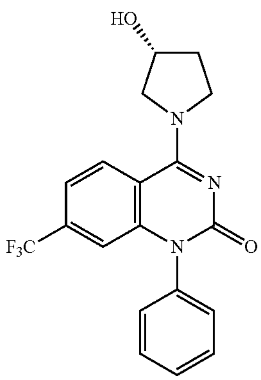 [SMILES: O=c1nc(N2CC[C@@H](O)C2)c2ccc(C(F)(F)F)cc2n1-c1ccccc1] | 4-((3R)-3-hydroxypyrrolidinyl)-1-phenyl-7-(trifluoromethyphydro-quinazolin-2-one | m/z [M + H]⁺ 376.0 |
| 146 | 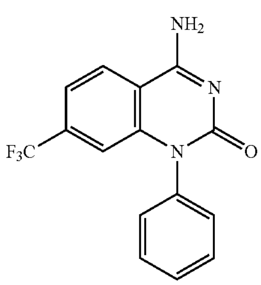 [SMILES: Nc1nc(=O)n(-c2ccccc2)c2cc(C(F)(F)F)ccc12] | 4-amino-1-phenyl-7-(trifluoromethyl)-hydroquinazolin-2-one | m/z [M + H]⁺ 306.0 |
| 147 | 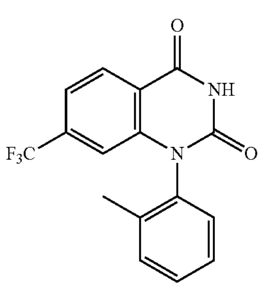 [SMILES: Cc1ccccc1-n1c(=O)[nH]c(=O)c2ccc(C(F)(F)F)cc21] | 1-(2-methylphenyl)-7-(trifluoromethyl)-1,3-dihydroquinazoline-2,4-dione | m/z [M + H]⁺ 321.0 |

TABLE 1-continued

| Cpd. No. | Structure | Name | Mass Spec. |
|---|---|---|---|
| 148 | 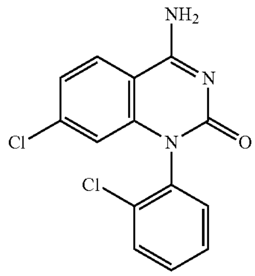 [SMILES: Nc1nc(=O)n(-c2ccccc2Cl)c2cc(Cl)ccc12] | 4-amino-7-chloro-1-(2-chlorophenyl)-hydroquinazolin-2-one | m/z [M + H]+ 307.06 |
| 149 | 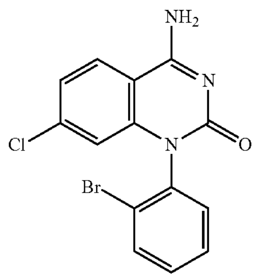 [SMILES: Nc1nc(=O)n(-c2ccccc2Br)c2cc(Cl)ccc12] | 4-amino-1-(2-bromophenyl)-7-chloro-hydroquinazolin-2-one | m/z [M + H]+ 349.98 |
| 150 | 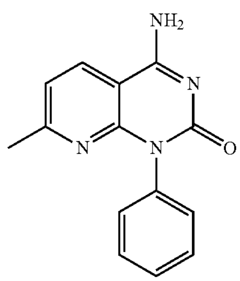 | 4-amino-7-methyl-1-phenylhydro-pyridino[2,3-d]pyrimidin-2-one | m/z [M + H]+ 353.24 |
| 151 | 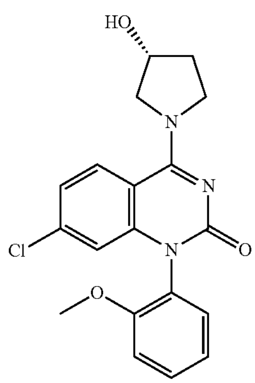 [SMILES: COc1ccccc1-n1c(=O)nc(N2CC[C@@H](O)C2)c2ccc(Cl)cc21] | 4-((3R)-3-hydroxypyrrolidin-1-yl)-7-chloro-1-(2-methoxyphenyl)hydro-quinazolin-2-one | m/z [M + H]+ 372.10 |
| 153 | 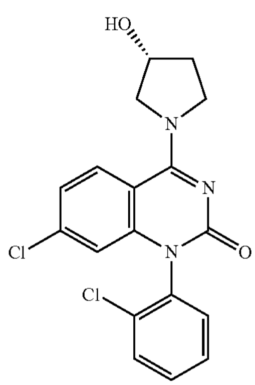 [SMILES: O=c1nc(N2CC[C@@H](O)C2)c2ccc(Cl)cc2n1-c1ccccc1Cl] | 4-((3R)-3-hydroxypyrrolidin-1-yl)-7-chloro-1-(2-chlorophenyhydro-quinazolin-2-one | m/z [M + H]+ 376.04 |

TABLE 1-continued

| Cpd. No. | Structure | Name | Mass Spec. |
|---|---|---|---|
| 154 | 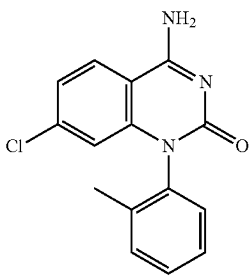 | 4-amino-7-chloro-1-(2-methylphenyl)-hydroquinazolin-2-one | m/z [M + H]+ 386.0 |
| 155 | 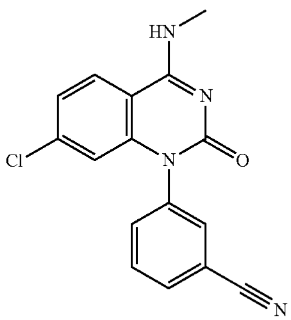 [SMILES: CNc1nc(=O)n(-c2cccc(C#N)c2)c2cc(Cl)ccc12] | 3-[7-chloro-4-(methylamino)-2-oxo-hydroquinazolinyl]benzenecarbonitrile | m/z [M + H]+ 311.12 |
| 156 | 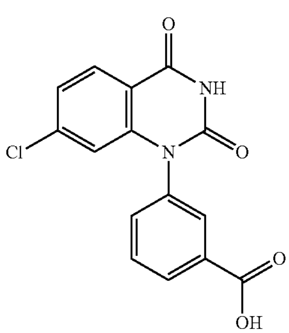 [SMILES: O=C(O)c1cccc(-n2c(=O)[nH]c(=O)c3ccc(Cl)cc32)c1] | 3-(7-chloro-4-hydroxy-2-oxohydro-quinazolinyl)benzoic acid | m/z [M + H]+ 317.06 |
| 157 | 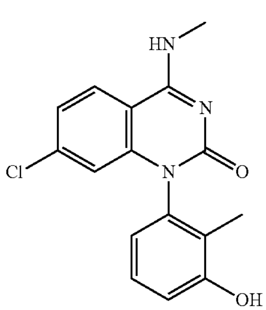 [SMILES: CNc1nc(=O)n(-c2cccc(O)c2C)c2cc(Cl)ccc12] | 7-chloro-1-(3-hydroxy-2-methylphenyl)-4-(methylamino)hydroquinazolin-2-one | m/z [M + H]+ 316.12 |

TABLE 1-continued

| Cpd. No. | Structure | Name | Mass Spec. |
|---|---|---|---|
| 159 | 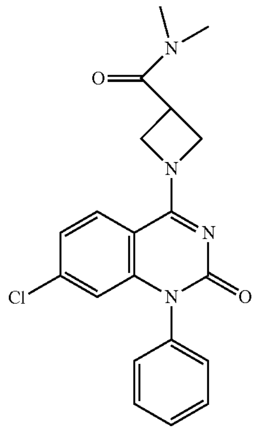 [SMILES: CN(C)C(=O)C1CN(c2nc(=O)n(-c3ccccc3)c3cc(Cl)ccc23)C1] | [1-(7-chloro-2-oxo-1-phenylhydro-quinazolin-4-yl)azetidin-3-yl]-N,N-dimethylcarboxamide | m/z [M + H]+ 383.1 |
| 160 | 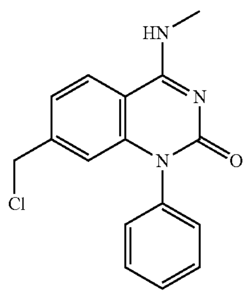 [SMILES: CNc1nc(=O)n(-c2ccccc2)c2cc(CCl)ccc12] | 7-(chloromethyl)-4-(methylamino)-1-phenylhydroquinazolin-2-one | m/z [M + H]+ 300.0 |
| 161 | 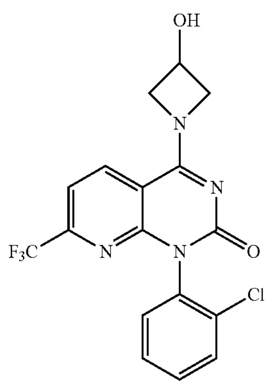 [SMILES: O=c1nc(N2CC(O)C2)c2ccc(C(F)(F)F)nc2n1-c1ccccc1Cl] | 1-(2-chlorophenyl)-4-(3-hydroxy-azetidinyl)-7-(trifluoromethyl)pyrido-[2,3-d]pyrimidin-2(1H)-one | m/z [M + H]+ 397.1 |
| 162 | 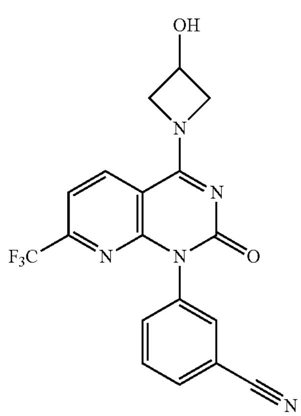 [SMILES: N#Cc1cccc(-n2c(=O)nc(N3CC(O)C3)c3ccc(C(F)(F)F)nc32)c1] | 3-(4-(3-hydroxyazetidin-1-yl)-2-oxo-7-(trifluoromethyl)pyrido[2,3-d]pyrimidin-1(2H)-yl)benzonitrile | m/z [M + H]+ 388.1 |

TABLE 1-continued

| Cpd. No. | Structure | Name | Mass Spec. |
|---|---|---|---|
| 163 | 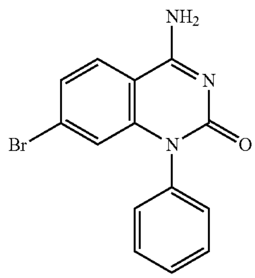 [SMILES: Nc1nc(=O)n(-c2ccccc2)c2cc(Br)ccc12] | 4-amino-7-bromo-1-phenylhydroquinazolin-2-one | m/z [M + H]+ 316.0 |
| 164 | 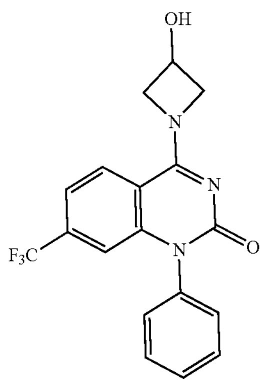 [SMILES: O=c1nc(N2CC(O)C2)c2ccc(C(F)(F)F)cc2n1-c1ccccc1] | 4-(3-hydroxyazetidin-1-yl)-1-phenyl-7-(trifluoromethyl)pyrido[2,3-d]pyrimidin-2(1H)-one | m/z [M + H]+ 362.0 |
| 165 | 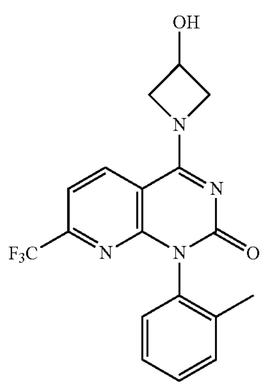 [SMILES: Cc1ccccc1-n1c(=O)nc(N2CC(O)C2)c2ccc(C(F)(F)F)nc21] | 4-(3-hydroxyazetidinyl)-1-(2-methylphenyl)-7-(trifluoromethyl)pyrido[2,3-d]pyrimidin-2(1H)-one | m/z [M + H]+ 377.24 |
| 166 | 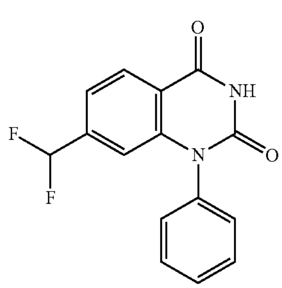 [SMILES: O=c1[nH]c(=O)n(-c2ccccc2)c2cc(C(F)F)ccc12] | 7-(difluoromethyl)-1-phenyl-1,3-dihydroquinazoline-2,4-dione | m/z [M + H]+ 289.0 |

TABLE 1-continued

| Cpd. No. | Structure | Name | Mass Spec. |
|---|---|---|---|
| 167 | 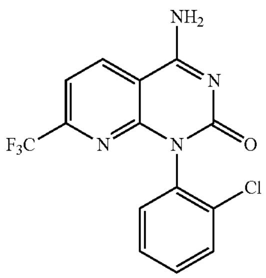 [SMILES: Nc1nc(=O)n(-c2ccccc2Cl)c2nc(C(F)(F)F)ccc12] | 4-amino-1-(2-chlorophenyl)-7-(trifluoro-methyl)pyrido[2,3-d]pyrimidin-2(1H)-one | m/z [M + H]+ 341.10 |
| 168 | 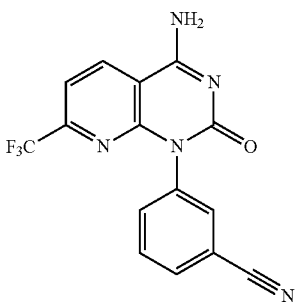 [SMILES: N#Cc1cccc(-n2c(=O)nc(N)c3ccc(C(F)(F)F)nc32)c1] | 3-(4-amino-2-oxo-7-(trifluoromethyl)-pyrido[2,3-d]pyrimidin-1(2H)-yl)-benzonitrile | m/z [M + H]+ 332.10 |
| 169 | 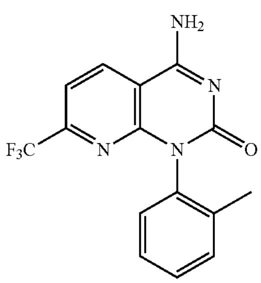 [SMILES: Cc1ccccc1-n1c(=O)nc(N)c2ccc(C(F)(F)F)nc21] | 4-amino-1-(2-methylphenyl)-7-(trifluoromethyl)pyrido[2,3-d]pyrimidin-2(1H)-one | m/z [M + H]+ 321.1 |
| 170 | 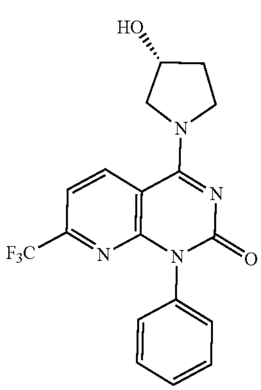 [SMILES: O=c1nc(N2CC[C@@H](O)C2)c2ccc(C(F)(F)F)nc2n1-c1ccccc1] | (R)-4-(3-hydroxypyrrolidin-1-yl)-1-phenyl-7-(trifluoromethyl)pyrido[2,3-d]-pyrimidin-2(1H)-one | m/z [M + H]+ 377.15 |

TABLE 1-continued

| Cpd. No. | Structure | Name | Mass Spec. |
|---|---|---|---|
| 171 | 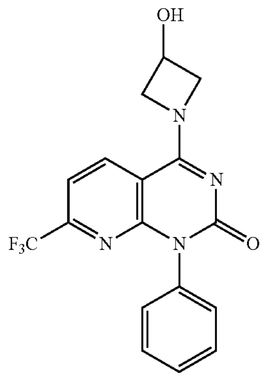 [SMILES: O=c1nc(N2CC(O)C2)c2ccc(C(F)(F)F)nc2n1-c1ccccc1] | 4-(3-hydroxyazetidin-1-yl)-1-phenyl-7-(trifluoromethyl)pyrido[2,3-d]pyrimidin-2(1H)-one | m/z [M + H]+ 363.0 |
| 172 | 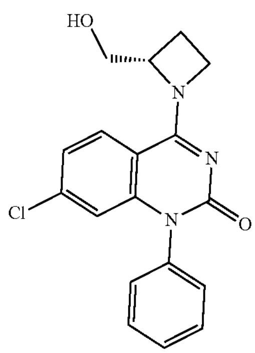 [SMILES: O=c1nc(N2CC[C@H]2CO)c2ccc(Cl)cc2n1-c1ccccc1] | (S)-7-chloro-4-(2-(hydroxymethyl)-azetidin-1-yl)-1-phenylquinazolin-2(1H)-one | m/z [M + H]+ 342.1 |
| 173 | 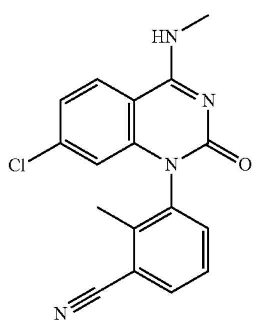 [SMILES: CNc1nc(=O)n(-c2cccc(C#N)c2C)c2cc(Cl)ccc12] | 3-[7-chloro-4-(methylamino)-2-oxo-hydroquinazolinyl]-2-methylbenzene-carbonitrile | m/z [M + H]+ 325.11 |
| 174 | 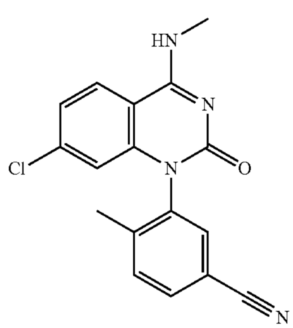 [SMILES: CNc1nc(=O)n(-c2cc(C#N)ccc2C)c2cc(Cl)ccc12] | 3-(7-chloro-4-(methylamino)-2-oxo-quinazolin-1(2H)-yl)-2-methyl-benzonitrile | m/z [M + H]+ 325.11 |

TABLE 1-continued

| Cpd. No. | Structure | Name | Mass Spec. |
|---|---|---|---|
| 175 | 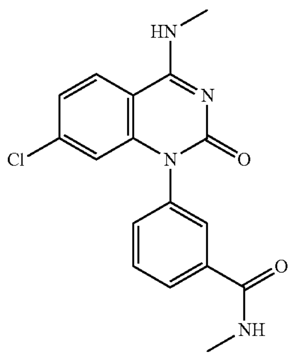 [SMILES: CNC(=O)c1cccc(-n2c(=O)nc(NC)c3ccc(Cl)cc32)c1] | 3-(7-chloro-4-(methylamino)-2-oxo-quinazolin-1(2H)-yl)benzamide | m/z [M + H]+ 343.1 |
| 176 | 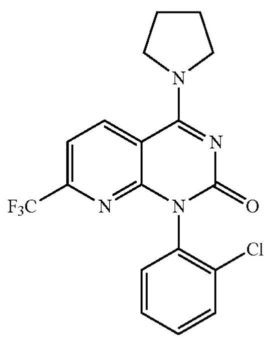 [SMILES: O=c1nc(N2CCCC2)c2ccc(C(F)(F)F)nc2n1-c1ccccc1Cl] | 1-(2-chlorophenyl)-4-(pyrrolictin-1-yl)-7-(trifluoromethyl)pyrido[2,3-d]pyrimidin-2(1H)-one | m/z [M + H]+ 395.10 |
| 177 | 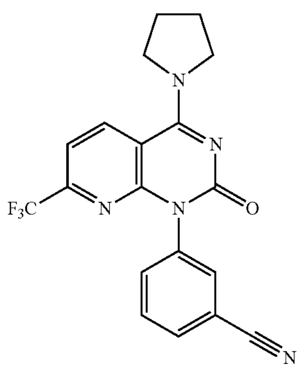 [SMILES: N#Cc1cccc(-n2c(=O)nc(N3CCCC3)c3ccc(C(F)(F)F)nc32)c1] | 3-(2-oxo-4-(pyrrolidin-1-yl)-7-(trifluoro-methyl)pyrido[2,3-d]pyrimidin-1(2H)-yl)benzonitrile | m/z [M + H]+ 385.15 |
| 178 | 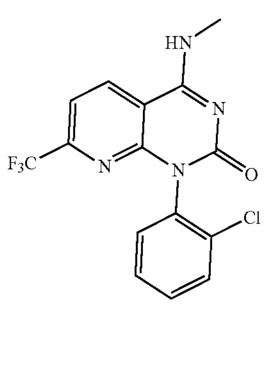 [SMILES: CNc1nc(=O)n(-c2ccccc2Cl)c2nc(C(F)(F)F)ccc12] | 1-(2-chlorophenyl)-4-(methylamino)-7-(trifluoromethyl)pyrido[2,3-d]pyrimidin-2(1H)-one | m/z [M + H]+ 355.10 |

TABLE 1-continued

| Cpd. No. | Structure | Name | Mass Spec. |
|---|---|---|---|
| 179 | 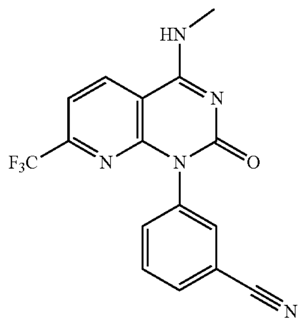 [SMILES: CNc1nc(=O)n(-c2cccc(C#N)c2)c2nc(C(F)(F)F)ccc12] | 3-[4-(methylamino)-2-oxo-7-(trifluoromethyl)pyrido[2,3-d]pyrimidin-1(2H)-yl)benzonitrile | m/z [M + H]+ 346.1 |
| 180 | 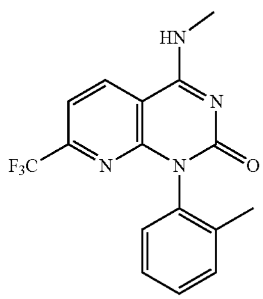 [SMILES: CNc1nc(=O)n(-c2ccccc2C)c2nc(C(F)(F)F)ccc12] | 4-(methylamino)-1-(2-methylphenyl)-7-(trifluoromethyl)pyrido[2,3-d]pyrimidin-2(1H)-one | m/z [M + H]+ 335.10 |
| 181 | 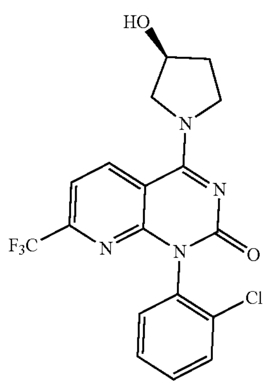 [SMILES: O=c1nc(N2CC[C@H](O)C2)c2ccc(C(F)(F)F)nc2n1-c1ccccc1Cl] | (S)-1-(2-chlorophenyl)-4-(3-hydroxy-pyrrolidin-1-yl)-7-(trifluoromethyl)-pyrido[2,3-d]pyrimidin-2(1H)-one | m/z [M + H]+ 411.10 |
| 182 | 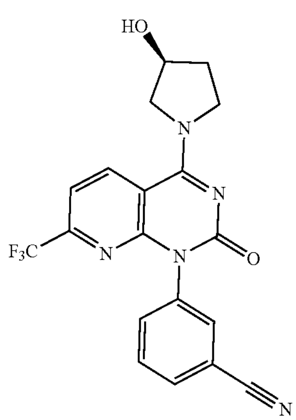 [SMILES: N#Cc1cccc(-n2c(=O)nc(N3CC[C@H](O)C3)c3ccc(C(F)(F)F)nc32)c1] | (S)-3-(4-(3-hydroxypyrrolidin-1-yl)-2-oxo-7-(trifluoromethyl)pyrido[2,3-d]pyrimidin-1(2H)-yl)benzonitrile | m/z [M + H]+ 402.1 |

TABLE 1-continued

| Cpd. No. | Structure | Name | Mass Spec. |
|---|---|---|---|
| 183 | 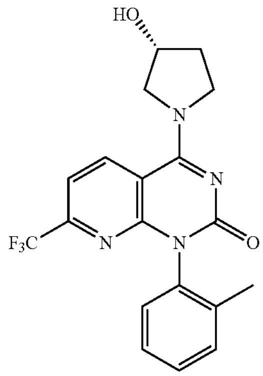 [SMILES: Cc1ccccc1-n1c(=O)nc(N2CC[C@@H](O)C2)c2ccc(C(F)(F)F)nc21] | (R)-4-(3-hydroxypyrrolidin-1-yl)-1-(o-tolyl)-7-(trifluoromethyl)pyrido[2,3-d]-pyrimidin-2(1H)-one | m/z [M + H]+ 391.2 |
| 184 | 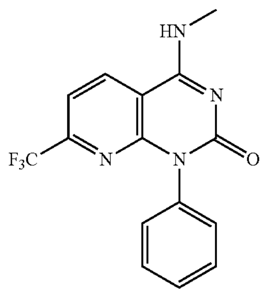 [SMILES: CNc1nc(=O)n(-c2ccccc2)c2nc(C(F)(F)F)ccc12] | 4-(methylamino)-1-phenyl-7-(trifluoromethyl)pyrido[2,3-d]-pyrimidin-2(1H)-one | m/z [M + H]+ 321.1 |
| 185 | 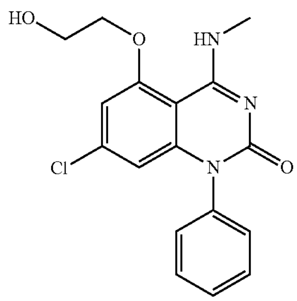 [SMILES: CNc1nc(=O)n(-c2ccccc2)c2cc(Cl)cc(OCCO)c12] | 7-chloro-5-(2-hydroxyethoxy)-4-(methylamino)-1-phenylhydro-quinazolin-2-one | m/z [M + H]+ 346.17 |
| 186 | 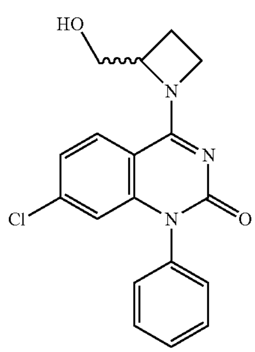 [SMILES: O=c1nc(N2CCC2CO)c2ccc(Cl)cc2n1-c1ccccc1] | 7-chloro-4-[2-(hydroxymethyl)azetidin-1-yl]-1-phenylhydroquinazolin-2-one | m/z [M + H]+ 342.17 |

TABLE 1-continued

| Cpd. No. | Structure | Name | Mass Spec. |
|---|---|---|---|
| 187 | 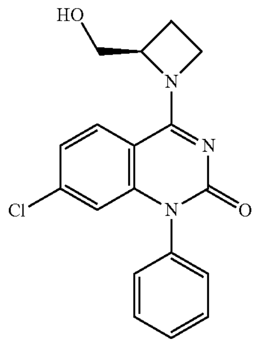 [SMILES: O=c1nc(N2CC[C@@H]2CO)c2ccc(Cl)cc2n1-c1ccccc1] | (R)-7-chloro-4-(2-(hydroxymethyl)-azetidin-1-yl)-1-phenylquinazolin-2(1H)-one | m/z [M + H]$^+$ 342.17 |
| 188 | 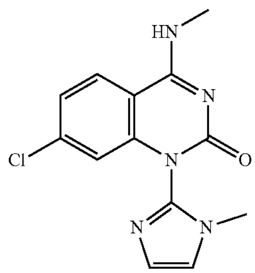 [SMILES: CNc1nc(=O)n(-c2nccn2C)c2cc(Cl)ccc12] | 7-chloro-4-(methylamino)-1-(1-methyl-imidazol-2-yphydroquinazolin-2-one | m/z [M + H]$^+$ 290.0 |
| 189 | 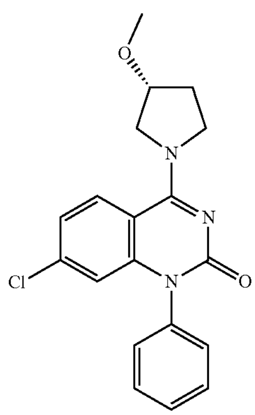 [SMILES: CO[C@@H]1CCN(c2nc(=O)n(-c3ccccc3)c3cc(Cl)ccc23)C1] | (R)-7-chloro-4-(3-methoxypyrrolidin-1-yl)-1-phenylquinazolin-2(1H)-one | m/z [M + H]$^+$ 356.24 |
| 190 | 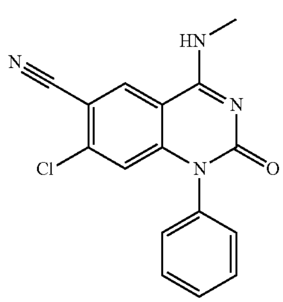 [SMILES: CNc1nc(=O)n(-c2ccccc2)c2cc(Cl)c(C#N)cc12] | 7-chloro-4-(methylamino)-2-oxo-1-phenylhydroquinazoline-6-carbonitrile | m/z [M + H]$^+$ 311.18 |
| 191 | 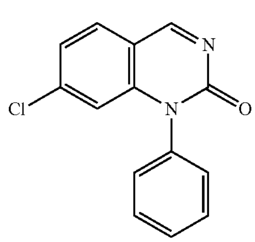 [SMILES: O=c1ncc2ccc(Cl)cc2n1-c1ccccc1] | 7-chloro-1-phenylhydroquinazolin-2-one | m/z [M + H]$^+$ 257.26 |

TABLE 1-continued

| Cpd. No. | Structure | Name | Mass Spec. |
|---|---|---|---|
| 192 | 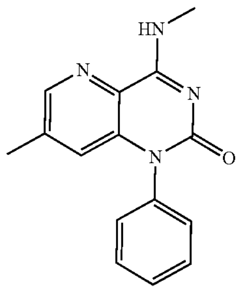 [SMILES: CNc1nc(=O)n(-c2ccccc2)c2cc(C)cnc12] | 7-methyl-4-(methylamino)-1-phenyl-pyrido[3,2-d]pyrimidin-2(1H)-one | m/z [M + H]+ 267.29 |
| 193 | 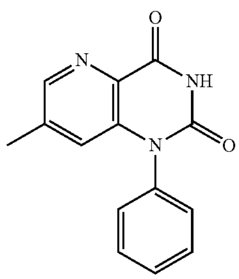 [SMILES: Cc1cnc2c(=O)[nH]c(=O)n(-c3ccccc3)c2c1] | 7-methyl-1-phenylpyrido[3,2-d]-pyrimidine-2,4(1H,3H)-dione | m/z [M + H]+ 254.24 |
| 194 | 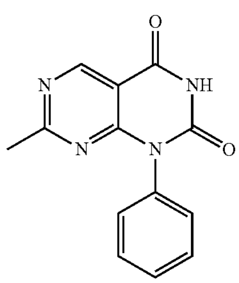 [SMILES: Cc1ncc2c(=O)[nH]c(=O)n(-c3ccccc3)c2n1] | 7-methyl-1-phenylpyrimido[4,5-d]-pyrimidine-2,4(1H,3H)-dione | m/z [M + H]+ 254.26 |
| 195 | 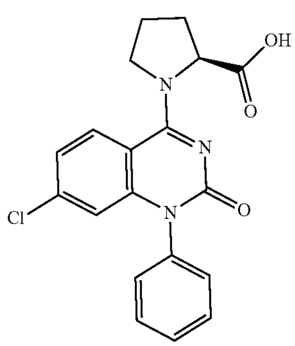 [SMILES: O=C(O)[C@@H]1CCCN1c1nc(=O)n(-c2ccccc2)c2cc(Cl)ccc12] | (2S)-1-(7-chloro-2-oxo-1-phenylhydro-quinazolin-4-yl)pyrrolidine-2-carboxylic acid | m/z [M + H]+ 370.12 |

TABLE 1-continued

| Cpd. No. | Structure | Name | Mass Spec. |
|---|---|---|---|
| 196 | 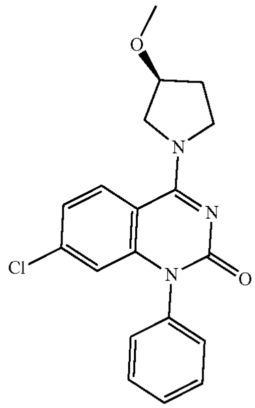 [SMILES: CO[C@H]1CCN(c2nc(=O)n(-c3ccccc3)c3cc(Cl)ccc23)C1] | (S)-7-chloro-4-(3-methoxypyrrolidin-1-yl)-1-phenylquinazolin-2(1H)-one | m/z [M + H]+ 356.24 |
| 197 | 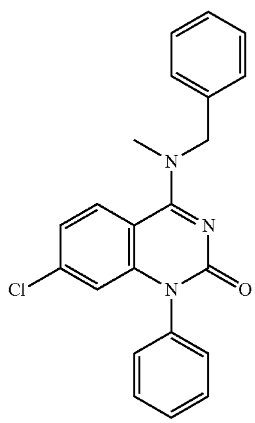 [SMILES: CN(Cc1ccccc1)c1nc(=O)n(-c2ccccc2)c2cc(Cl)ccc12] | 7-chloro-4-[methylbenzylamino]-1-phenylhydroquinazolin-2-one | m/z [M + H]+ 376.24 |
| 198 | 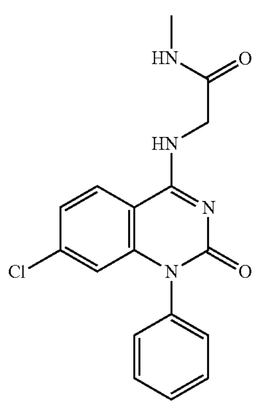 [SMILES: CNC(=O)CNc1nc(=O)n(-c2ccccc2)c2cc(Cl)ccc12] | 2-((7-chloro-2-oxo-1-phenyl-1,2-dihydroquinazolin-4-yl)(methyl)amino)-N-methylacetamide | m/z [M + H]+ 343.10 |

TABLE 1-continued

| Cpd. No. | Structure | Name | Mass Spec. |
|---|---|---|---|
| 199 | 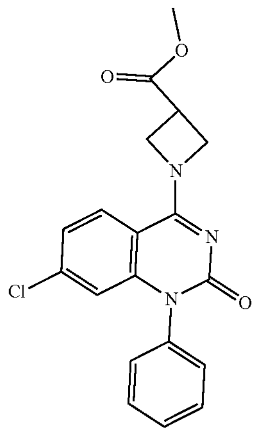 [SMILES: COC(=O)C1CN(c2nc(=O)n(-c3ccccc3)c3cc(Cl)ccc23)C1] | methyl 1-(7-chloro-2-oxo-1-phenyl-1,2-dihydroquinazolin-4-yl)azetidine-3-carboxylate | m/z [M + H]+ 370.10 |
| 200 | 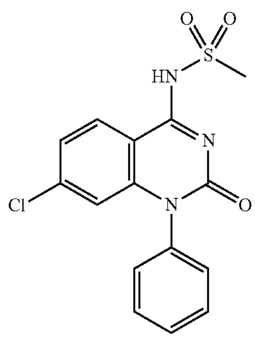 [SMILES: CS(=O)(=O)Nc1nc(=O)n(-c2ccccc2)c2cc(Cl)ccc12] | N-(7-chloro-2-oxo-1-phenyl-1,2-dihydroquinazolin-4-yl)methane-sulfonamide | m/z [M + H]+ 350.04 |
| 201 | 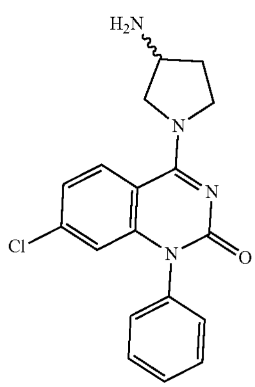 [SMILES: NC1CCN(c2nc(=O)n(-c3ccccc3)c3cc(Cl)ccc23)C1] | 4-(3-aminopyrrolidin-1-yl)-7-chloro-1-phenylquinazolin-2(1H)-one | m/z [M + H]+ 341.11 |
| 202 | 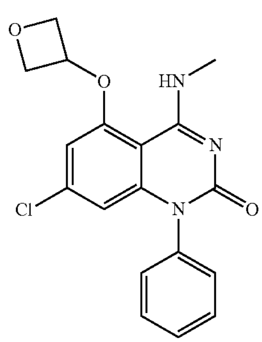 [SMILES: CNc1nc(=O)n(-c2ccccc2)c2cc(Cl)cc(OC3COC3)c12] | 7-chloro-4-(methylamino)-5-oxetan-3-yloxy-1-phenylhydroquinazolin-2-one | m/z [M + H]+ 358.10 |

TABLE 1-continued

| Cpd. No. | Structure | Name | Mass Spec. |
|---|---|---|---|
| 203 | 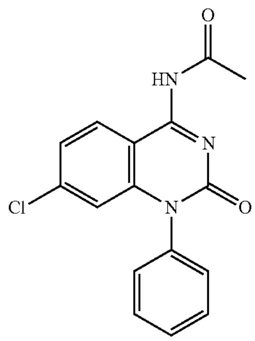 [SMILES: CC(=O)Nc1nc(=O)n(-c2ccccc2)c2cc(Cl)ccc12] | N-(7-chloro-2-oxo-1-phenyl-1,2-dihydroquinazolin-4-yl)acetamide | m/z [M + H]+ 314.12 |
| 204 | 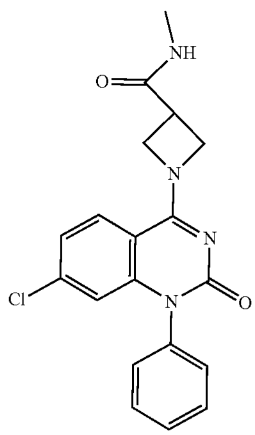 [SMILES: CNC(=O)C1CN(c2nc(=O)n(-c3ccccc3)c3cc(Cl)ccc23)C1] | 1-(7-chloro-2-oxo-1-phenyl-1,2-dihydroquinazolin-4-yl)-N-methyl-azetidine-3-carboxamide | m/z [M + H]+ 369.22 |
| 205 | 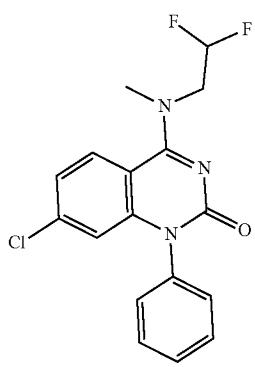 [SMILES: CN(CC(F)F)c1nc(=O)n(-c2ccccc2)c2cc(Cl)ccc12] | 4-[(2,2-difluoroethyl)methylamino]-7-chloro-1-phenylhydroquinazolin-2-one | m/z [M + H]+ 350.10 |
| 206 | 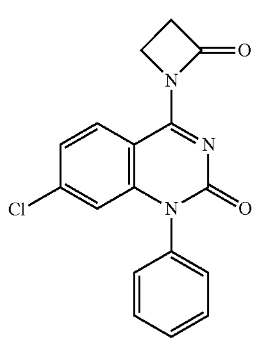 [SMILES: O=C1CCN1c1nc(=O)n(-c2ccccc2)c2cc(Cl)ccc12] | 7-chloro-4-(2-oxoazetidin-1-yl)-1-phenylhydroquinazolin-2-one | m/z [M + H]+ 326.17 |

TABLE 1-continued

| Cpd. No. | Structure | Name | Mass Spec. |
|---|---|---|---|
| 207 | 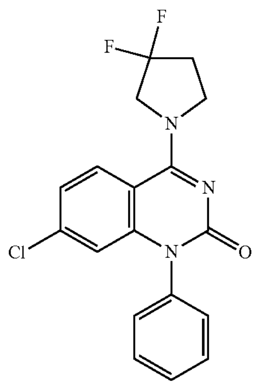 [SMILES: O=c1nc(N2CCC(F)(F)C2)c2ccc(Cl)cc2n1-c1ccccc1] | 4-(3,3-difluoropyrrolidin-1-yl)-7-chloro-1-phenylhydroquinazolin-2-one | m/z [M + H]+ 328.17 |
| 208 | 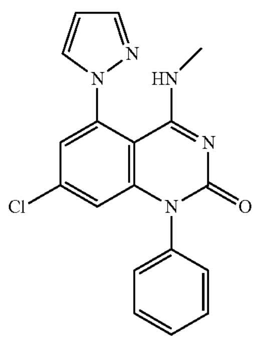 [SMILES: CNc1nc(=O)n(-c2ccccc2)c2cc(Cl)cc(-n3cccn3)c12] | 7-chloro-4-(methylamino)-1-phenyl-5-(1H-pyrazol-1-yl)quinazolin-2(1H)-one | m/z [M + H]+ 352.18 |
| 209 | 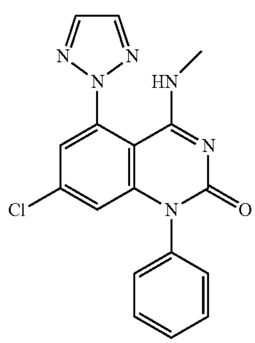 [SMILES: CNc1nc(=O)n(-c2ccccc2)c2cc(Cl)cc(-n3nccn3)c12] | 7-chloro-4-(methylamino)-1-phenyl-5-(1,2,3-triazol-2-yl)quinazolin-2(1H)-one | m/z [M + H]+ 353.1 |
| 210 | 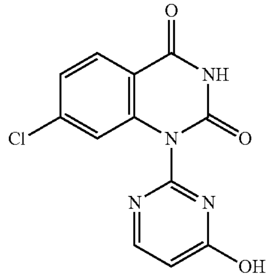 [SMILES: O=c1[nH]c(=O)n(-c2nccc(O)n2)c2cc(Cl)ccc12] | 7-chloro-1-(4-hydroxypyrimidin-2-yl)-1,3-dihydroquinazoline-2,4-dione | m/z [M + H]+ 291.0 |

TABLE 1-continued

| Cpd. No. | Structure | Name | Mass Spec. |
|---|---|---|---|
| 211 | 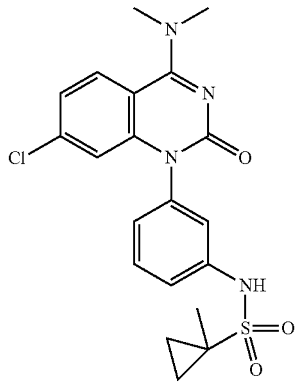 [SMILES: CN(C)c1nc(=O)n(-c2cccc(NS(=O)(=O)C3(C)CC3)c2)c2cc(Cl)ccc12] | 4-(dimethylamino)-7-chloro-1-(3-{[(methylcyclopropyl)sulfonyl]amino}phenyl)-hydroquinazolin-2-one | m/z [M + H]+ 433.1 |
| 212 | 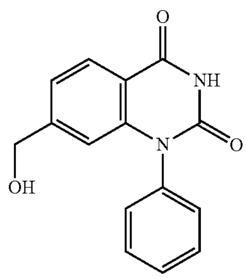 [SMILES: O=c1[nH]c(=O)n(-c2ccccc2)c2cc(CO)ccc12] | 7-(hydroxymethyl)-1-phenyl-1,3-dihydroquinazoline-2,4-dione | m/z [M + H]+ 269.0 |
| 213 | 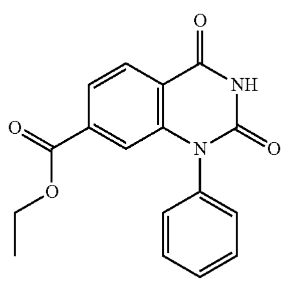 [SMILES: CCOC(=O)c1ccc2c(=O)[nH]c(=O)n(-c3ccccc3)c2c1] | ethyl 2,4-dioxo-1-phenyl-1,3-dihydroquinazoline-7-carboxylate | m/z [M + H]+ 311.0 |
| 214 | 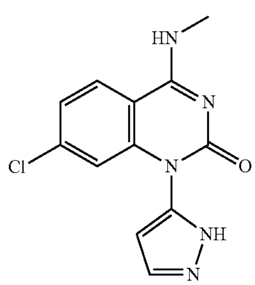 [SMILES: CNc1nc(=O)n(-c2ccn[nH]2)c2cc(Cl)ccc12] | 7-chloro-4-(methylamino)-1-pyrazol-5-ylhydroquinazolin-2-one | m/z [M + H]+ 276.1 |
| 215 | 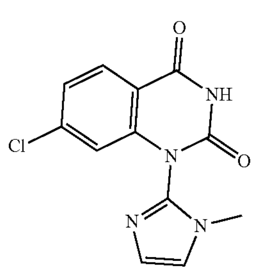 [SMILES: Cn1ccnc1-n1c(=O)[nH]c(=O)c2ccc(Cl)cc21] | 7-chloro-1-(1-methylimidazol-2-yl)-1,3-dihydroquinazoline-2,4-dione | m/z [M + H]+ 277.1 |

TABLE 1-continued

| Cpd. No. | Structure | Name | Mass Spec. |
|---|---|---|---|
| 216 | 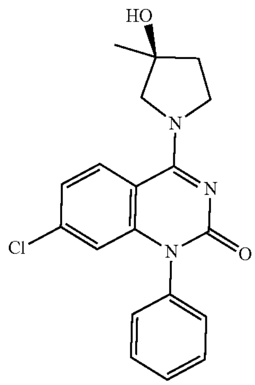 [SMILES: C[C@]1(O)CCN(c2nc(=O)n(-c3ccccc3)c3cc(Cl)ccc23)C1] | 4-((3S)-3-hydroxy-3-methylpyrrolidin-1-yl)-7-chloro-1-phenylhydroquinazolin-2-one | m/z [M + H]+ 256.12 |
| 217 | 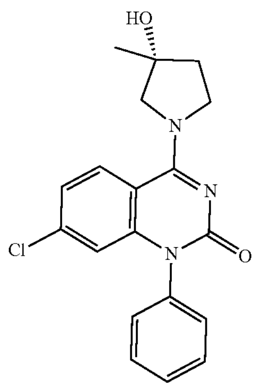 [SMILES: C[C@@]1(O)CCN(c2nc(=O)n(-c3ccccc3)c3cc(Cl)ccc23)C1] | 4-((3R)-3-hydroxy-3-methylpyrrolidin-1-yl)-7-chloro-1-phenylhydroquinazolin-2-one | m/z [M + H]+ 256.12 |
| 218 | 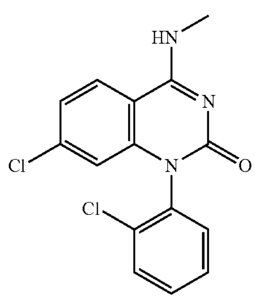 [SMILES: CNc1nc(=O)n(-c2ccccc2Cl)c2cc(Cl)ccc12] | 7-chloro-1-(2-chlorophenyl)-4-(methylamino)quinazolin-2(1H)-one | m/z [M + H]+ 320.0 |
| 219 | 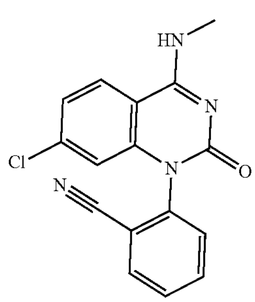 [SMILES: CNc1nc(=O)n(-c2ccccc2C#N)c2cc(Cl)ccc12] | 2-(7-chloro-4-(methylamino)-2-oxo-quinazolin-1(2H)-yl)benzonitrile | m/z [M + H]+ 311.0 |

TABLE 1-continued

| Cpd. No. | Structure | Name | Mass Spec. |
|---|---|---|---|
| 220 | 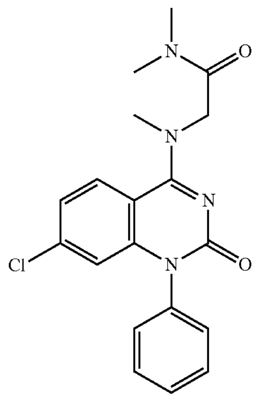 [SMILES: CN(C)C(=O)CN(C)c1nc(=O)n(-c2ccccc2)c2cc(Cl)ccc12] | 2-((7-chloro-2-oxo-1-phenyl-1,2-dihydroquinazolin-4-yl)(methyl)amino)-N,N-dimethylacetamide | m/z [M + H]$^+$ 371.18 |
| 221 | 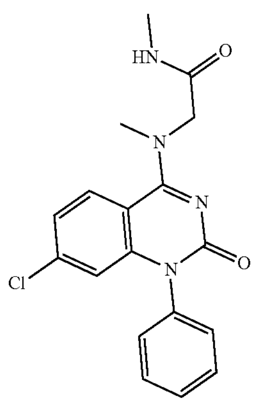 [SMILES: CNC(=O)CN(C)c1nc(=O)n(-c2ccccc2)c2cc(Cl)ccc12] | 2-((7-chloro-2-oxo-1-phenyl-1,2-dihydroquinazolin-4-yl)(methyl)amino)-,N-methylacetamide | m/z [M + H]$^+$ 357.12 |
| 222 | 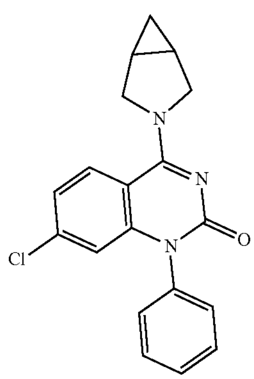 [SMILES: O=c1nc(N2CC3CC3C2)c2ccc(Cl)cc2n1-c1ccccc1] | 4-(3-azabicyclo[3.1.0]hex-3-yl)-7-chloro-1-phenylhydroquinazolin-2-one | m/z [M + H]$^+$ 338.13 |
| 223 | 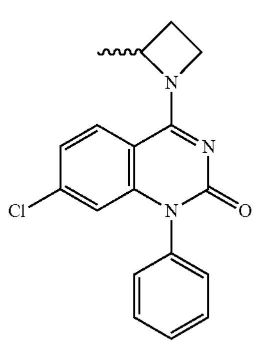 [SMILES: CC1CCN1c1nc(=O)n(-c2ccccc2)c2cc(Cl)ccc12] | 7-chloro-4-(2-methylazetidin-1-yl)-1-phenylhydroquinazolin-2-one | m/z [M + H]$^+$ 326.13 |

TABLE 1-continued

| Cpd. No. | Structure | Name | Mass Spec. |
|---|---|---|---|
| 224 | 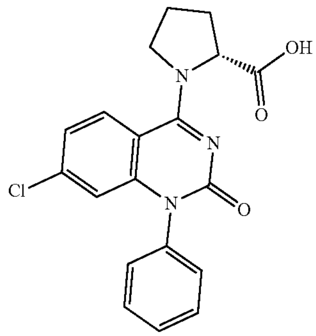 [SMILES: O=C(O)[C@H]1CCCN1c1nc(=O)n(-c2ccccc2)c2cc(Cl)ccc12] | (2R)-1-(7-chloro-2-oxo-1-phenylhydroquinazolin-4-yl)pyrrolidine-2-carboxylic acid | m/z [M + H]+ 370.12 |
| 225 | 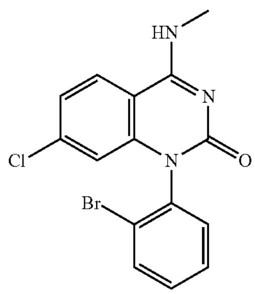 [SMILES: CNc1nc(=O)n(-c2ccccc2Br)c2cc(Cl)ccc12] | 1-(2-bromophenyl)-7-chloro-4-(methylamino)quinazolin-2-one | m/z [M + H]+ 364.0 |
| 226 | 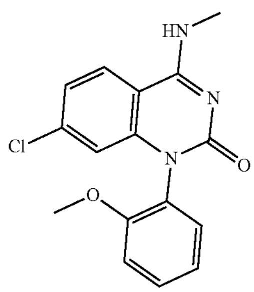 [SMILES: CNc1nc(=O)n(-c2ccccc2OC)c2cc(Cl)ccc12] | 7-chloro-1-(2-methoxyphenyl)-4-(methylamino)hydroquinazolin-2-one | m/z [M + H]+ 316.0 |
| 227 | 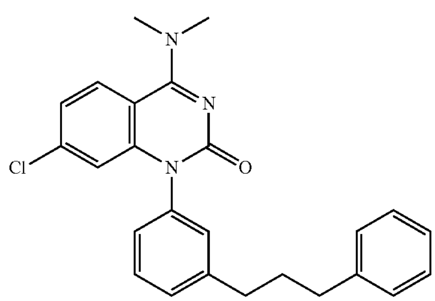 [SMILES: CN(C)c1nc(=O)n(-c2cccc(CCCc3ccccc3)c2)c2cc(Cl)ccc12] | 4-(dimethylamino)-7-chloro-1-[3-(3-phenylpropyl)phenyl]hydroquinazolin-2-one | m/z [M + H]+ 418.2 |
| 228 | 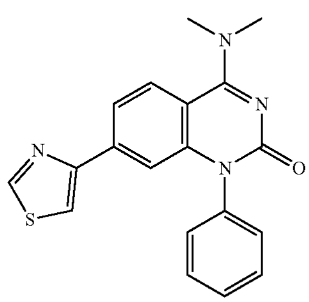 [SMILES: CN(C)c1nc(=O)n(-c2ccccc2)c2cc(-c3cscn3)ccc12] | 4-(dimethylamino)-1-phenyl-7-(1,3-thiazol-4-yl)hydroquinazolin-2-one | m/z [M + H]+ 349.0 |

TABLE 1-continued

| Cpd. No. | Structure | Name | Mass Spec. |
|---|---|---|---|
| 229 | 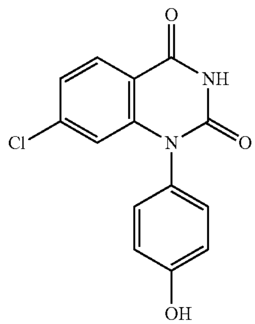 [SMILES: O=c1[nH]c(=O)n(-c2ccc(O)cc2)c2cc(Cl)ccc12] | 7-chloro-1-(4-hydroxyphenyl)-1,3-dihydroquinazoline-2,4-dione | m/z [M + H]+ 289.1 |
| 230 | 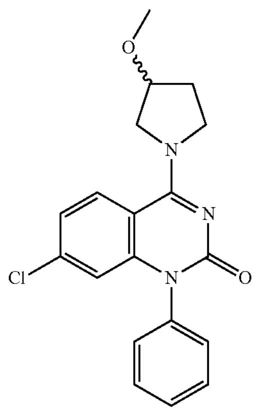 [SMILES: COC1CCN(c2nc(=O)n(-c3ccccc3)c3cc(Cl)ccc23)C1] | 7-chloro-4-(3-methoxypyrrolidin-1-yl)-1-phenylquinazolin-2(1H)-one | m/z [M + H]+ 356.12 |
| 231 | 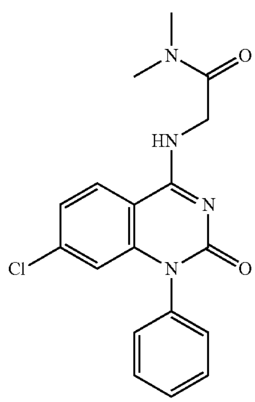 | 2-[(7-chloro-2-oxo-1-phenyl-1,2-dihydroquinazolin-4-yl)amino]-N,N-dimethylacetamide | m/z [M + H]+ 357.12 |
| 232 | 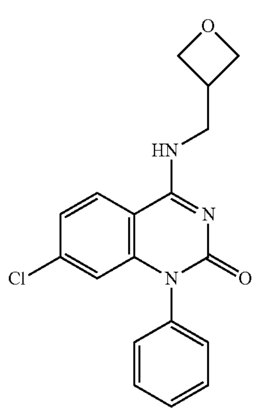 [SMILES: O=c1nc(NCC2COC2)c2ccc(Cl)cc2n1-c1ccccc1] | 7-chloro-4-[(oxetan-3-ylmethyl)amino]-1-phenylhydroquinazolin-2-one | m/z [M + H]+ 342.23 |

TABLE 1-continued

| Cpd. No. | Structure | Name | Mass Spec. |
|---|---|---|---|
| 233 | 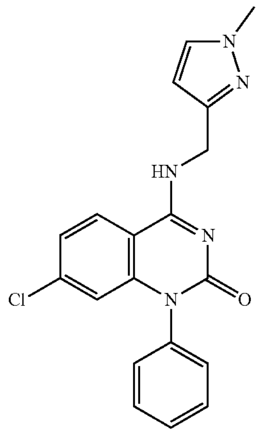 [SMILES: Cn1ccc(CNc2nc(=O)n(-c3ccccc3)c3cc(Cl)ccc23)n1] | 7-chloro-4-1{[(1-methylpyrazol-3-yl)-methyl]amino}-1-phenylhydroquinazolin-2-one | m/z [M + H]+ 366.24 |
| 234 | 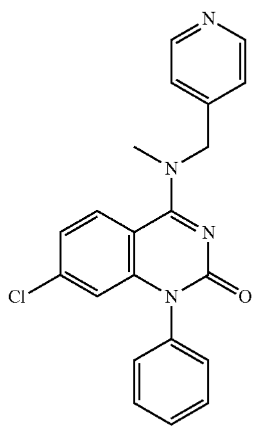 [SMILES: CN(Cc1ccncc1)c1nc(=O)n(-c2ccccc2)c2cc(Cl)ccc12] | 7-chloro-4-[methyl(pyridin-4-ylmethyl)-amino]-1-phenylhydroquinazolin-2-one | m/z [M + H]+ 377.1 |
| 235 | 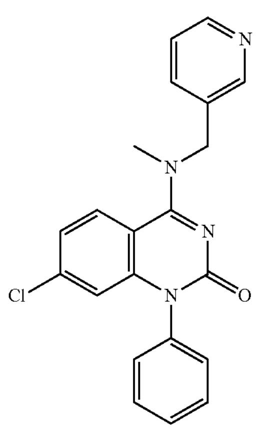 [SMILES: CN(Cc1cccnc1)c1nc(=O)n(-c2ccccc2)c2cc(Cl)ccc12] | 7-chloro-4-[methyl(pyridin-3-ylmethyl)-amino]-1-phenylhydroquinazolin-2-one | m/z [M + H]+ 377.24 |

TABLE 1-continued

| Cpd. No. | Structure | Name | Mass Spec. |
|---|---|---|---|
| 236 | 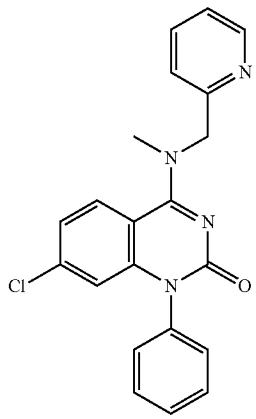 [SMILES: CN(Cc1ccccn1)c1nc(=O)n(-c2ccccc2)c2cc(Cl)ccc12] | 7-chloro-4-[methyl(pyridin-2-ylmethyl)-amino]-1-phenylhydroquinazolin-2-one | m/z [M + H]+ 377.12 |
| 237 | 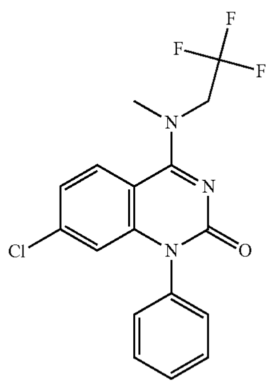 [SMILES: CN(CC(F)(F)F)c1nc(=O)n(-c2ccccc2)c2cc(Cl)ccc12] | 7-chloro-4-[methyl(2,2,2-trifluoroethyl)-amino]-1-phenylhydroquinazolin-2-one | m/z [M + H]+ 368.18 |
| 238 | 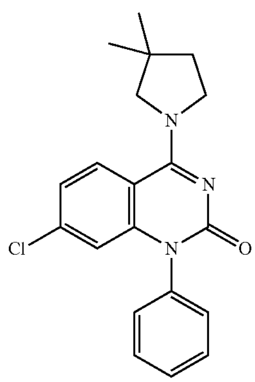 [SMILES: CC1(C)CCN(c2nc(=O)n(-c3ccccc3)c3cc(Cl)ccc23)C1] | 4-(3,3-dimethylpyrrolidin-1-yl)-7-chloro-1-phenylhydroquinazolin-2-one | m/z [M + H]+ 354.12 |
| 239 | 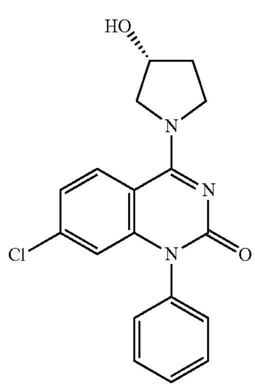 [SMILES: O=c1nc(N2CC[C@@H](O)C2)c2ccc(Cl)cc2n1-c1ccccc1] | 4-((3R)-3-hydroxypyrrolidinyl)-7-chloro-1-phenylhydroquinazolin-2-one | m/z [M + H]+ 342.19 |

TABLE 1-continued

| Cpd. No. | Structure | Name | Mass Spec. |
|---|---|---|---|
| 240 | 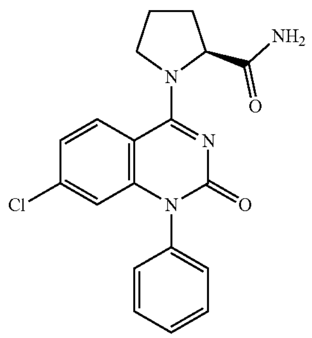 [SMILES: NC(=O)[C@@H]1CCCN1c1nc(=O)n(-c2ccccc2)c2cc(Cl)ccc12] | (2S)-1-(7-chloro-2-oxo-1-phenylhydro-quinazolin-4-yl)pyrrolidine-2-carboxamide | m/z [M + H]+ 369.18 |
| 241 | 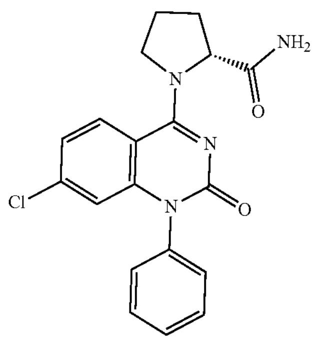 [SMILES: NC(=O)[C@H]1CCCN1c1nc(=O)n(-c2ccccc2)c2cc(Cl)ccc12] | (2R)-1-(7-chloro-2-oxo-1-phenylhydro-quinazolin-4-yl)pyrrolidine-2-carboxamide | m/z [M + H]+ 369.19 |
| 242 | 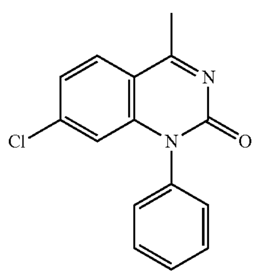 [SMILES: Cc1nc(=O)n(-c2ccccc2)c2cc(Cl)ccc12] | 7-chloro-4-methyl-1-phenylhydro-quinazolin-2-one | m/z [M + H]+ 271.1 |
| 243 | 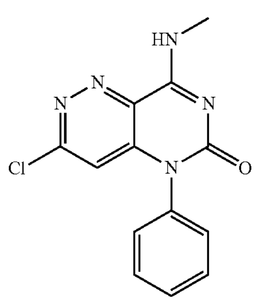 [SMILES: CNc1nc(=O)n(-c2ccccc2)c2cc(Cl)nnc12] | 3-chloro-8-(methylamino)-5-phenyl-5-hydropyrimidino[5,4-c]pyridazin-6-one | m/z [M + H]+ 288.16 |
| 244 | 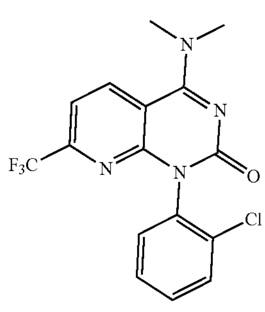 [SMILES: CN(C)c1nc(=O)n(-c2ccccc2Cl)c2nc(C(F)(F)F)ccc12] | 1-(2-chlorophenyl)-4-(dimethylamino)-7-(trifluoromethyl)pyrido[2,3-d]-pyrimidin-2(1H)-one | m/z [M + H]+ 369.05 |

TABLE 1-continued

| Cpd. No. | Structure | Name | Mass Spec. |
|---|---|---|---|
| 245 | 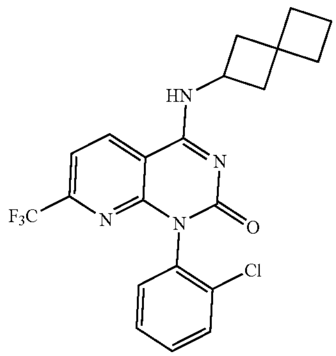 [SMILES: O=c1nc(NC2CC3(CCC3)C2)c2ccc(C(F)(F)F)nc2n1-c1ccccc1Cl] | 1-(2-chlorophenyl)-4-(spiro[3.3]heptan-2-ylamino)-7-(trifluoromethyl)pyrido[2,3-d]pyrimidin-2(1H)-one | m/z [M + H]⁺ 435.10 |
| 246 | 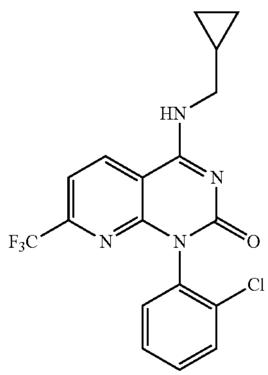 [SMILES: O=c1nc(NCC2CC2)c2ccc(C(F)(F)F)nc2n1-c1ccccc1Cl] | 1-(2-chlorophenyl)-4-((cyclopropylmethyl)amino)-7-(trifluoromethyl)-pyrido[2,3-d]pyrimidin-2(1H)-one | m/z [M + H]⁺ 395.05 |
| 247 | 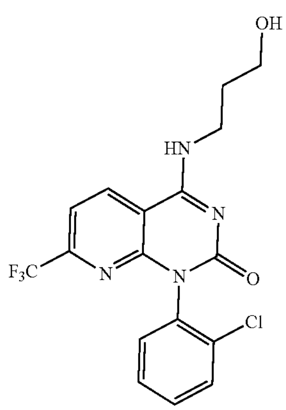 [SMILES: O=c1nc(NCCCO)c2ccc(C(F)(F)F)nc2n1-c1ccccc1Cl] | 1-(2-chlorophenyl)-4-[(3-hydroxypropyl)amino]-7-(trifluoromethyl)-pyrido[2,3-d]pyrimidin-2(1H)-one | m/z [M + H]⁺ 399.05 |
| 248 | 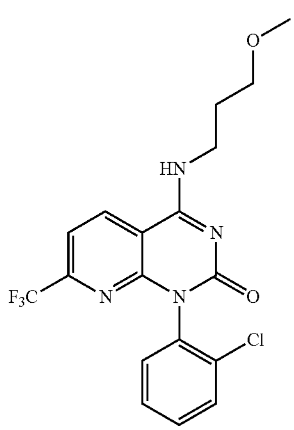 [SMILES: COCCCNc1nc(=O)n(-c2ccccc2Cl)c2nc(C(F)(F)F)ccc12] | 1-(2-chlorophenyl)-4-[(3-methoxypropyl)amino]-7-(trifluoromethyl)-pyrido[2,3-d]pyrimidin-2(1H)-one | m/z [M + H]⁺ 413.10 |

TABLE 1-continued

| Cpd. No. | Structure | Name | Mass Spec. |
|---|---|---|---|
| 249 | 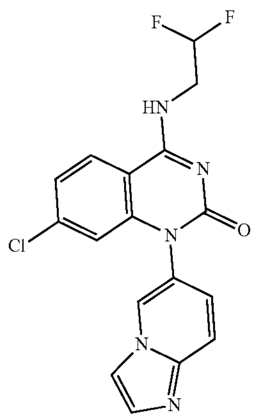 [SMILES: O=c1nc(NCC(F)F)c2ccc(Cl)cc2n1-c1ccc2nccn2c1] | 4-[(2,2-difluoroethyl)amino]-7-chloro-1-(4-hydroimidazo[1,2-a]pyridin-6-yl)-hydroquinazolin-2-one | m/z [M + H]+ 376.0 |
| 250 | 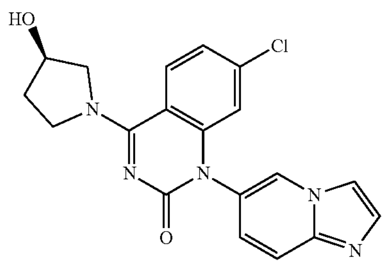 [SMILES: O=c1nc(N2CC[C@@H](O)C2)c2ccc(Cl)cc2n1-c1ccc2nccn2c1] | 4-((3R)-3-hydroxypyrrolidin-1-yl)-7-chloro-1-(4-hydroimidazo[1,2-a]pyridin-6-yl)-hydroquinazolin-2-one | m/z [M + H]+ 382.00 |
| 251 | 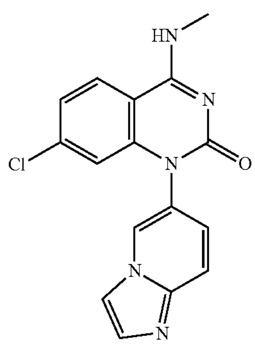 [SMILES: CNc1nc(=O)n(-c2ccc3nccn3c2)c2cc(Cl)ccc12] | 7-chloro-1-(4-hydroimidazo[1,2-a]-pyridin-6-yl)-4-(methylamino)hydro-quinazolin-2-one | m/z [M + H]+ 326.00 |
| 252 | 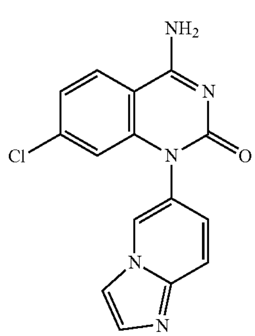 [SMILES: Nc1nc(=O)n(-c2ccc3nccn3c2)c2cc(Cl)ccc12] | 4-amino-7-chloro-1-(4-hydroimidazo-[1,2-a]pyridin-6-yl)hydroquinazolin-2-one | m/z [M + H]+ 312.00 |

TABLE 1-continued

| Cpd. No. | Structure | Name | Mass Spec. |
|---|---|---|---|
| 253 | 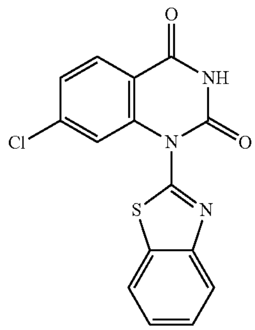 [SMILES: O=c1[nH]c(=O)n(-c2nc3ccccc3s2)c2cc(Cl)ccc12] | 1-benzothiazol-2-yl-7-chloro-1,3-dihydroquinazoline-2,4-dione | m/z [M + H]+ 330.0 |
| 254 | 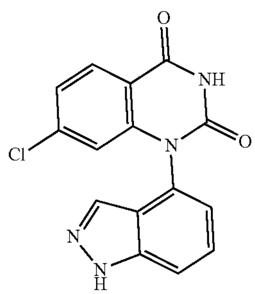 [SMILES: O=c1[nH]c(=O)n(-c2cccc3[nH]ncc23)c2cc(Cl)ccc12] | 1-(1H-indazol-4-yl)-7-chloro-1,3-dihydroquinazoline-2,4-dione | m/z [M + H]+ 313.0 |
| 255 | 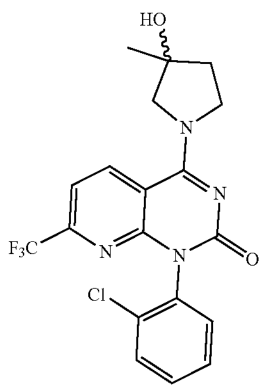 [SMILES: CC1(O)CCN(c2nc(=O)n(-c3ccccc3Cl)c3nc(C(F)(F)F)ccc23)C1] | 1-(2-chlorophenyl)-4-(3-hydroxy-3-methylpyrrolidin-1-yl)-7-(trifluoromethyphydropyridino-[2,3-d]pyrimidin-2-one | m/z [M + H]+ 425.37 |
| 256 | 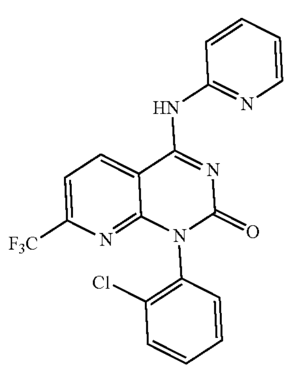 [SMILES: O=c1nc(Nc2ccccn2)c2ccc(C(F)(F)F)nc2n1-c1ccccc1Cl] | 1-(2-chlorophenyl)-4-(2-pyridylamino)-7-(trifluoromethyl)pyrido[2,3-d]pyrimidin-2(1H)-one | m/z [M + H]+ 418.35 |

TABLE 1-continued

| Cpd. No. | Structure | Name | Mass Spec. |
|---|---|---|---|
| 257 | 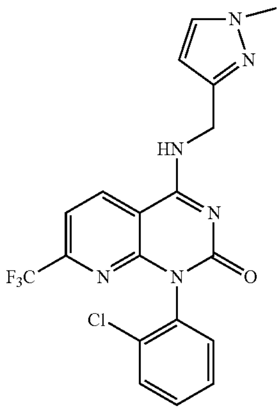 [SMILES: Cn1ccc(CNc2nc(=O)n(-c3ccccc3Cl)c3nc(C(F)(F)F)ccc23)n1] | 1-(2-chlorophenyl)-4-{[(1-methyl-pyrazol-3-yl)methyl]amino }-7-(trifluoro-methyl)-pyrido[2,3-d]pyrimidin-2(1H)-one | m/z [M + H]+ 435.35 |
| 258 | 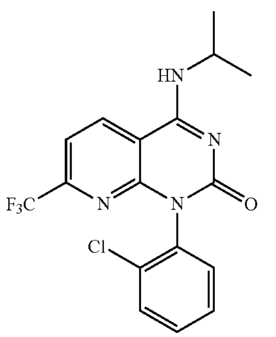 [SMILES: CC(C)Nc1nc(=O)n(-c2ccccc2Cl)c2nc(C(F)(F)F)ccc12] | 1-(2-chlorophenyl)-4-Rmethylethyl)-amino]-7-(trifluoromethyl)pyrido[2,3-d]-pyrimidin-2(1H)-one | m/z [M + H]+ 383.34 |
| 259 | 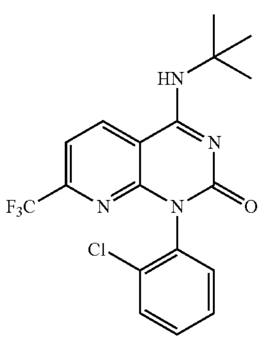 [SMILES: CC(C)(C)Nc1nc(=O)n(-c2ccccc2Cl)c2nc(C(F)(F)F)ccc12] | 4-[(tert-butyl)amino]-1-(2-chloro-phenyl)-7-(trifluoromethyl)pyrido-[2,3-d]pyrimidin-2(1H)-one | m/z [M + H]+ 397.39 |
| 260 | 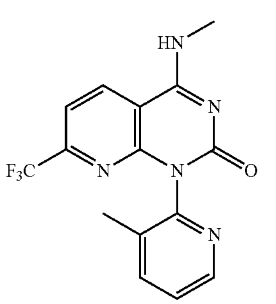 [SMILES: CNc1nc(=O)n(-c2ncccc2C)c2nc(C(F)(F)F)ccc12] | 1-(3-methyl(2-pyridyl))-4-(methyl-amino)-7-(trifluoromethyl)pyrido[2,3-d]-pyrimidin-2(1H)-one | m/z [M + H]+ 336.37 |

TABLE 1-continued

| Cpd. No. | Structure | Name | Mass Spec. |
|---|---|---|---|
| 261 | 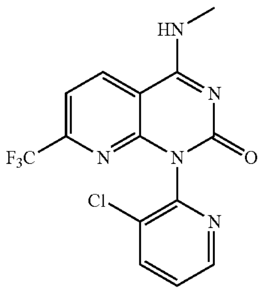 [SMILES: CNc1nc(=O)n(-c2ncccc2Cl)c2nc(C(F)(F)F)ccc12] | 1-(3-chloro(2-pyridyl))-4-(methylamino)-7-(trifluoromethyl)pyrido[2,3-d]-pyrimidin-2(1H)-one | m/z [M + H]+ 356.36 |
| 262 | 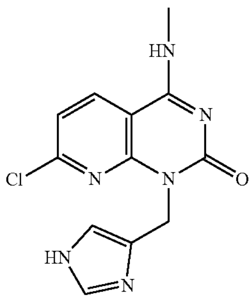 [SMILES: CNc1nc(=O)n(Cc2c[nH]cn2)c2nc(Cl)ccc12] | 7-chloro-1-(imidazol-4-ylmethyl)-4-(methylamino)hydroquinazolin-2-one | m/z [M + H]+ 290.36 |
| 263 | 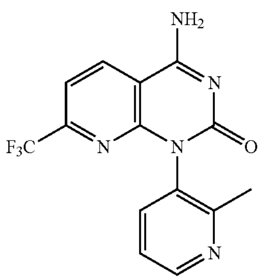 [SMILES: Cc1ncccc1-n1c(=O)nc(N)c2ccc(C(F)(F)F)nc21] | 4-amino-1-(2-methyl(3-pyridyl))-7-(trifluoromethyl pyrido[2,3-d]pyrimidin-2(1H)-one | m/z [M + H]+ 322.10 |
| 264 | 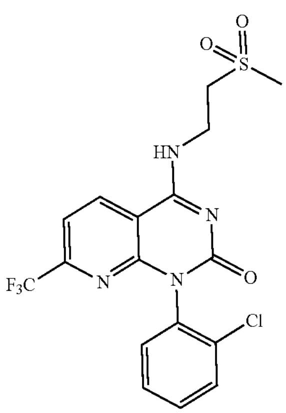 [SMILES: CS(=O)(=O)CCNc1nc(=O)n(-c2ccccc2Cl)c2nc(C(F)(F)F)ccc12] | 1-(2-chlorophenyl)-4-1[2-(methylsulfonyl)ethyl]amino}-7-(trifluoromethyl)pyrido[2,3-d]pyrimidin-2 (1H)-one | m/z [M + H]+ 447.00 |
| 265 | 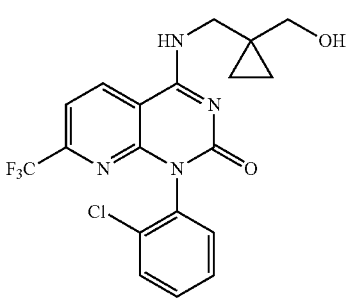 [SMILES: O=c1nc(NCC2(CO)CC2)c2ccc(C(F)(F)F)nc2n1-c1ccccc1Cl] | 1-(2-chlorophenyl)-4(((1-(hydroxymethyl)cyclopropyl)methypamino)-7-(trifluoromethyl)-pyrido [2,3-d]-pyrimidin-2(1H)-one | m/z [M + H]+ 425.00 |

TABLE 1-continued

| Cpd. No. | Structure | Name | Mass Spec. |
|---|---|---|---|
| 266 | 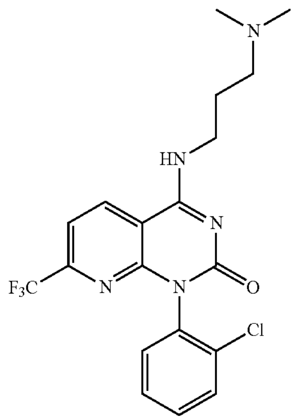 [SMILES: CN(C)CCCNc1nc(=O)n(-c2ccccc2Cl)c2nc(C(F)(F)F)ccc12] | 4-{[3-(dimethylamino)propyl]amino}-1-(2-chlorophenyl)-7-(trifluoromethyl)-pyrido[2,3-d]pyrimidin-2(1H)-one | m/z [M + H]+ 426.00 |
| 267 | 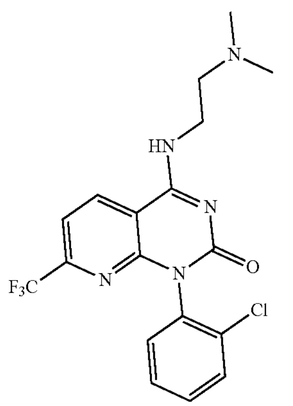 [SMILES: CN(C)CCNc1nc(=O)n(-c2ccccc2Cl)c2nc(C(F)(F)F)ccc12] | 4-{[2-(dimethylamino)ethyl]amino}-1-(2-chlorophenyl)-7-(trifluoromethyl)-pyrido[2,3-d]pyrimidin-2(1H)-one | m/z [M + H]+ 412.00 |
| 268 | 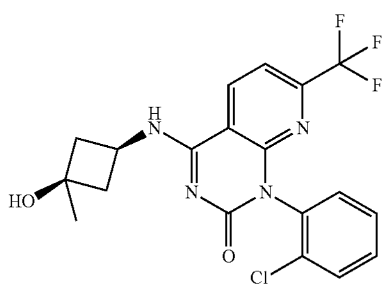 [SMILES: C[C@]1(O)C[C@@H](Nc2nc(=O)n(-c3ccccc3Cl)c3nc(C(F)(F)F)ccc23)C1] | 1-(2-chlorophenyl)-4-(((1s,3s)-3-hydroxy-3-methylcyclobutyl)amino)-7-(trifluoromethyl)pyrido[2,3-d]pyrimidin-2(1H)-one | m/z [M + H]+ 425.00 |
| 269 | 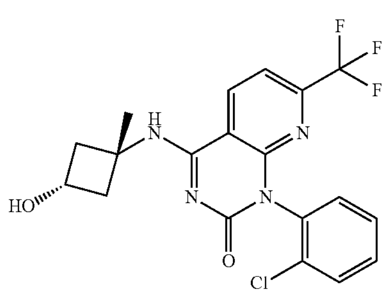 [SMILES: C[C@]1(Nc2nc(=O)n(-c3ccccc3Cl)c3nc(C(F)(F)F)ccc23)C[C@@H](O)C1] | 1-(2-chlorophenyl)-4-(((1s,3s)-3-hydroxy-1-methylcyclobutyl)amino)-7-(trifluoromethyl)pyrido[2,3-d]pyrimidin-2(1H)-one | m/z [M + H]+ 425.00 |

TABLE 1-continued

| Cpd. No. | Structure | Name | Mass Spec. |
|---|---|---|---|
| 270 | 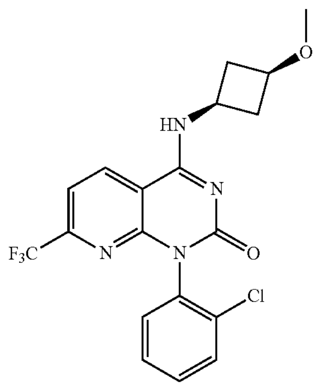 [SMILES: CO[C@H]1C[C@@H](Nc2nc(=O)n(-c3ccccc3Cl)c3nc(C(F)(F)F)ccc23)C1] | 1-(2-chlorophenyl)-4-(((1s,3s)-3-methoxycyclobutyl)amino)-7-(trifluoromethyl)pyrido[2,3-d]pyrimidin-2(1H)-one | m/z [M + H]+ 425.00 |
| 271 | 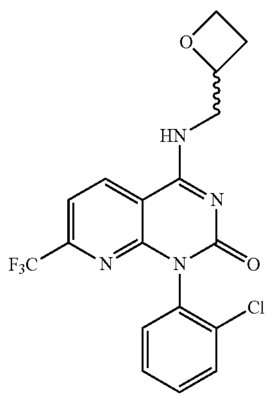 [SMILES: O=c1nc(NCC2CCO2)c2ccc(C(F)(F)F)nc2n1-c1ccccc1Cl] | 1-(2-chlorophenyl)-4-[(oxetan-2-ylmethyl)amino]-7-(trifluoromethyl)-pyrido[2,3-d]pyrimidin-2(1H)-one | m/z [M + H]+ 411.00 |
| 272 | 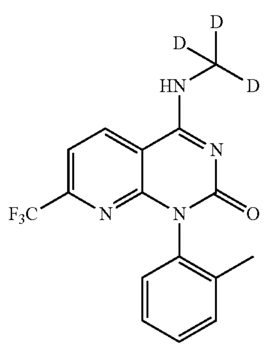 [SMILES: [2H]C([2H])([2H])Nc1nc(=O)n(-c2ccccc2C)c2nc(C(F)(F)F)ccc12] | 4-((methyl-d3)amino)-1-(2-methylphenyl)-7-(trifluoromethyl)pyrido[2,3-d]pyrimidin-2(1H)-one | m/z [M + H]+ 338.20 |
| 273 | 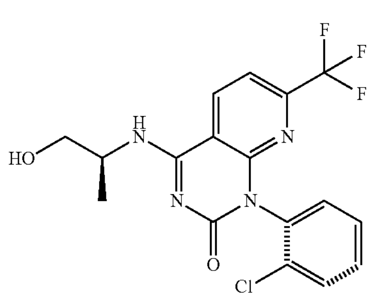 | 4-[((1S)-2-hydroxy-isopropyl)amino]-(1Ra)-(2-chlorophenyl)-7-(trifluoromethyl)-pyrido[2,3-d]pyrimidin-2(1M-one | m/z [M + H]+ 399.00 |

TABLE 1-continued

| Cpd. No. | Structure | Name | Mass Spec. |
|---|---|---|---|
| 274 | 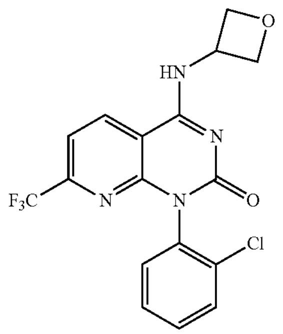 [SMILES: O=c1nc(NC2COC2)c2ccc(C(F)(F)F)nc2n1-c1ccccc1Cl] | 1-(2-chlorophenyl)-4-(oxetan-3-yl-amino)-7-(trifluoromethyl)pyrido[2,3-d]pyrimidin-2(1H)-one | m/z [M + H]+ 397.0 |
| 275 | 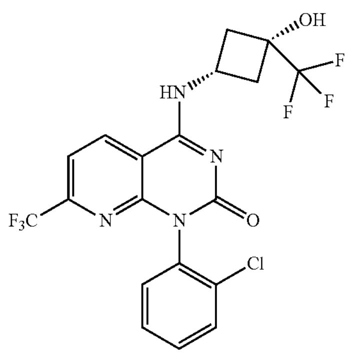 [SMILES: O=c1nc(N[C@H]2C[C@](O)(C(F)(F)F)C2)c2ccc(C(F)(F)F)nc2n1-c1ccccc1Cl] | 4-{[(cis)-3-hydroxy-3-(trifluoromethyl)-cyclobutyl]amino}-1-(2-chlorophenyl)-7-(trifluoromethyl)pyrido[2,3-d]-pyrimidin-2(1H)-one | m/z [M + H]+ 479.00 |
| 276 | 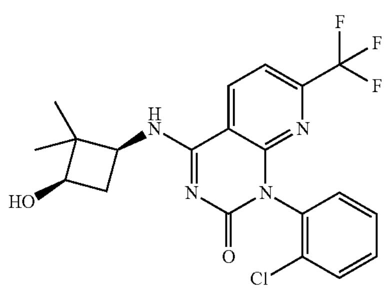 [SMILES: CC1(C)[C@H](O)C[C@@H]1Nc1nc(=O)n(-c2ccccc2Cl)c2nc(C(F)(F)F)ccc12] | 4-[((cis)-3-hydroxy-2,2-dimethylcyclo-butyl)amino]-1-(2-chlorophenyl)-7-(trifluoromethyl)-pyrido[2,3-d]-pyrimidin-2(1H)-one | m/z [M + H]+ 439.00 |
| 277 | 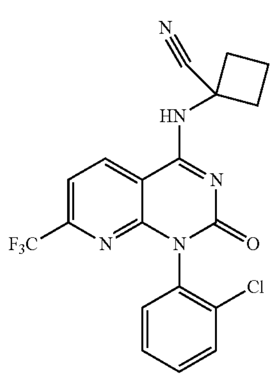 [SMILES: N#CC1(Nc2nc(=O)n(-c3ccccc3Cl)c3nc(C(F)(F)F)ccc23)CCC1] | 1-((1-(2-chlorophenyl)-2-oxo-7-(trifluoromethyl)-1,2-dihydropyrido[2,3-d]pyrimidin-4-yl)amino)cyclobutane-1-carbonitrile | m/z [M + H]+ 420.00 |

TABLE 1-continued

| Cpd. No. | Structure | Name | Mass Spec. |
|---|---|---|---|
| 278 | 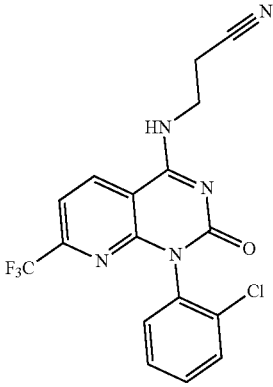 [SMILES: N#CCCNc1nc(=O)n(-c2ccccc2Cl)c2nc(C(F)(F)F)ccc12] | 3-((1-(2-chlorophenyl)-2-oxo-7-(trifluoro-methyl)-1,2-dihydropyrido-[2,3-d]pyrimidin-4-yl)amino)-propanenitrile | m/z [M + H]$^+$ 394.00 |
| 279 | 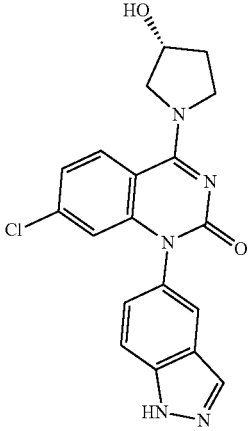 [SMILES: O=c1nc(N2CC[C@@H](O)C2)c2ccc(Cl)cc2n1-c1ccc2[nH]ncc2c1] | (R)-7-chloro-4-(3-hydroxypyrrolidin-1-yl)-1-(1H-indazol-5-yl)quinazolin-2(1H)-one | m/z [M + H]$^+$ 382.0 |
| 280 | 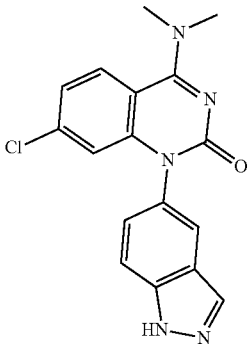 [SMILES: CN(C)c1nc(=O)n(-c2ccc3[nH]ncc3c2)c2cc(Cl)ccc12] | 7-chloro-4-(dimethylamino)-1-(1H-indazol-5-yl)quinazolin-2(1H)-one | m/z [M + H]$^+$ 340.0 |
| 281 | 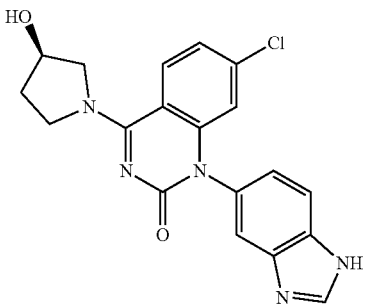 [SMILES: O=c1nc(N2CC[C@@H](O)C2)c2ccc(Cl)cc2n1-c1ccc2[nH]cnc2c1] | (R)-7-chloro-4-(3-hydroxypyrrolidin-1-yl)-1-(1H-benzimidazol-5-yl)quinazolin-2(1H)-one | m/z [M + H]$^+$ 382.0 |

TABLE 1-continued

| Cpd. No. | Structure | Name | Mass Spec. |
|---|---|---|---|
| 282 | 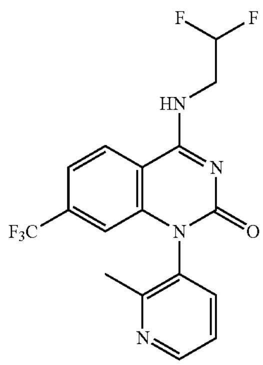 [SMILES: Cc1ncccc1-n1c(=O)nc(NCC(F)F)c2ccc(C(F)(F)F)cc21] | 4-((2,2-difluoroethyl)amino)-1-(2-methylpyridin-3-yl)-7-(trifluoromethyl)-quinazolin-2(1H)-one | m/z [M + H]+ 385.0 |
| 283 | 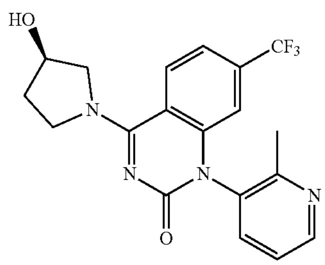 [SMILES: Cc1ncccc1-n1c(=O)nc(N2CC[C@@H](O)C2)c2ccc(C(F)(F)F)cc21] | 4-((3R)-3-hydroxypyrrolidinyl)-1-(2-methylpyridin-3-yl))-7-(trifluoromethyl)-hydroquinazolin-2-one | m/z [M + H]+ 391.0 |
| 284 | 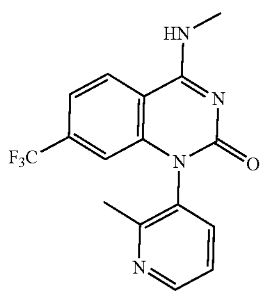 [SMILES: CNc1nc(=O)n(-c2cccnc2C)c2cc(C(F)(F)F)ccc12] | 1-(2-methylpyridin-3-yl))-4-(methyl-amino)-7-(trifluoromethyl)hydro-quinazolin-2-one | m/z [M + H]+ 335.0 |
| 285 | 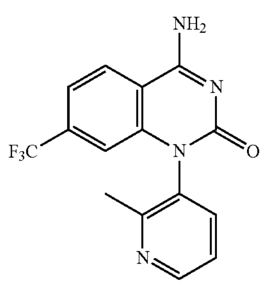 [SMILES: Cc1ncccc1-n1c(=O)nc(N)c2ccc(C(F)(F)F)cc21] | 4-amino-1-(2-methylpyridin-3-yl))-7-(trifluoromethyl)hydroquinazolin-2-one | m/z [M + H]+ 321.0 |
| 286 | 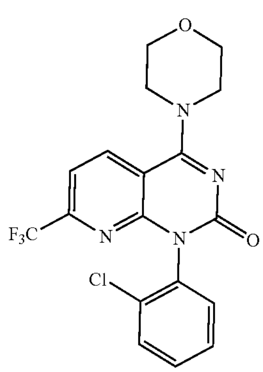 [SMILES: O=c1nc(N2CCOCC2)c2ccc(C(F)(F)F)nc2n1-c1ccccc1Cl] | 1-(2-chlorophenyl)-4-morpholin-4-yl-7-(trifluoromethyl)pyrido[2,3-d]pyrimidin-2(1H)-one | m/z [M + H]+ 411.40 |

TABLE 1-continued

| Cpd. No. | Structure | Name | Mass Spec. |
|---|---|---|---|
| 287 | 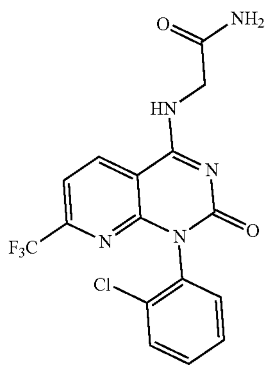 [SMILES: NC(=O)CNc1nc(=O)n(-c2ccccc2Cl)c2nc(C(F)(F)F)ccc12] | 2-((1-(2-chlorophenyl)-2-oxo-7-(trifluoromethyl)-1,2-dihydropyrido[2,3-d]pyrimidin-4-yl)amino)acetamide | m/z [M + H]+ 398.36 |
| 288 | 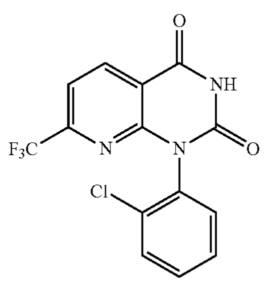 [SMILES: O=c1[nH]c(=O)n(-c2ccccc2Cl)c2nc(C(F)(F)F)ccc12] | 1-(2-chlorophenyl)-4-hydroxy-7-(trifluoromethyl)hydropyridino[2,3-d]-pyrimidin-2-one | m/z [M + H]+ 342.31 |
| 289 | 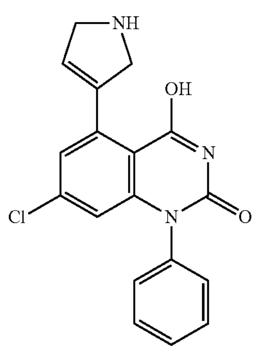 [SMILES: O=c1nc(O)c2c(C3=CCNC3)cc(Cl)cc2n1-c1ccccc1] | 7-chloro-5-(2,5-dihydro-1H-pyrrol-3-yl)-4-hydroxy-1-phenylquinazolin-2(1H)-one | m/z [M + H]+ 340.37 |
| 290 | 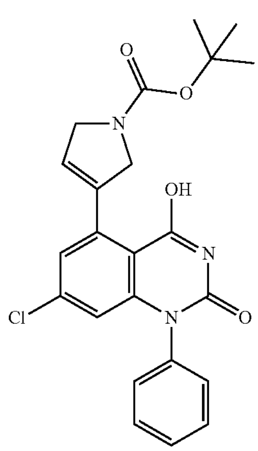 [SMILES: CC(C)(C)OC(=O)N1CC=C(c2cc(Cl)cc3c2c(O)nc(=O)n3-c2ccccc2)C1] | tert-butyl 3-(7-chloro-4-hydroxy-2-oxo-1-phenyl-1,2-dihydroquinazolin-5-yl)-2,5-dihydro-1H-pyrrole-1-carboxylate | m/z [M + H]+ 440.12 |

TABLE 1-continued

| Cpd. No. | Structure | Name | Mass Spec. |
|---|---|---|---|
| 291 | 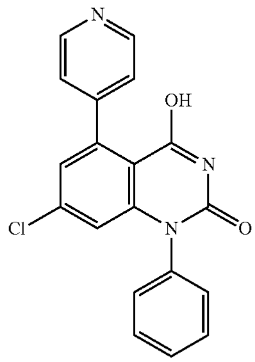 [SMILES: O=c1nc(O)c2c(-c3ccncc3)cc(Cl)cc2n1-c1ccccc1] | 7-chloro-4-hydroxy-1-phenyl-5-(pyridin-4-yl)quinazolin-2(1H)-one | m/z [M + H]+ 350.09 |
| 292 | 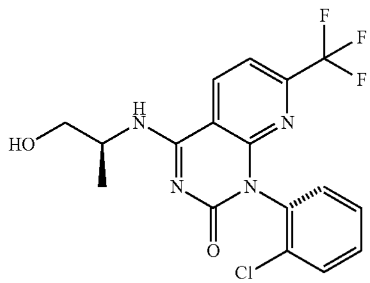 | 4-[((1S)-2-hydroxy-isopropyl)amino]-F(1Sa)-(2-chlorophenyl)-7-(trifluoro-1methyl)-pyrido[2,3-d]pyrimidin-2(1H)-one | m/z [M + H]+ 399.10 |
| 293 | 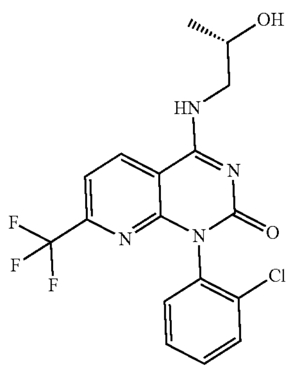 [SMILES: C[C@H](O)CNc1nc(=O)n(-c2ccccc2Cl)c2nc(C(F)(F)F)ccc12] | 4-[((2S)-2-hydroxypropyl)amino]-1-(2-chlorophenyl)-7-(trifluoromethyl)-pyrido[2,3-d]pyrimidin-2(1H)-one | m/z [M + H]+ 399.10 |
| 294 | 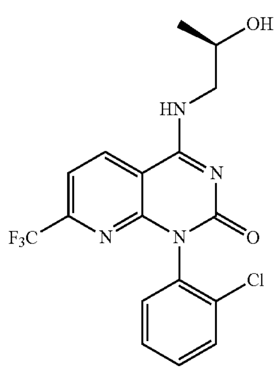 [SMILES: C[C@@H](O)CNc1nc(=O)n(-c2ccccc2Cl)c2nc(C(F)(F)F)ccc12] | 4-[((2R)-2-hydroxypropyl)amino]-1-(2-chlorophenyl)-7-(trifluoromethyl)-pyrido[2,3-d]pyrimidin-2(1H)-one | m/z [M + H]+ 399.10 |

TABLE 1-continued

| Cpd. No. | Structure | Name | Mass Spec. |
|---|---|---|---|
| 295 | 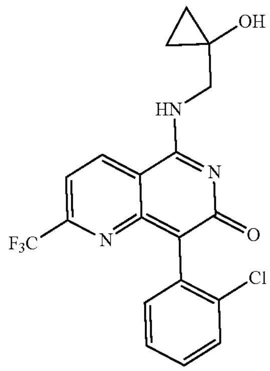 | 1-(2-chlorophenyl)-4-{[(hydroxycyclopropyl)methyl]amino}-7-(trifluoromethyl)-pyrido[2,3-d]pyrimidin-2(1H)-one | m/z [M + H]+ 411.10 |
| 296 | 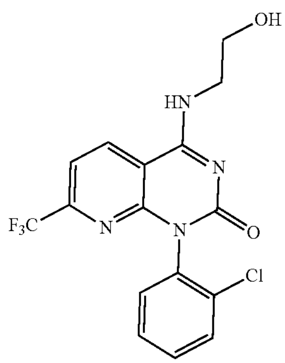 [SMILES: O=c1nc(NCCO)c2ccc(C(F)(F)F)nc2n1-c1ccccc1Cl] | 1-(2-chlorophenyl)-4-[(2-hydroxylethyl)amino]-7-(trifluoromethyl)pyrido[2,3-d]pyrimidin-2(1H)-one | m/z [M + H]+ 385.10 |
| 297 | 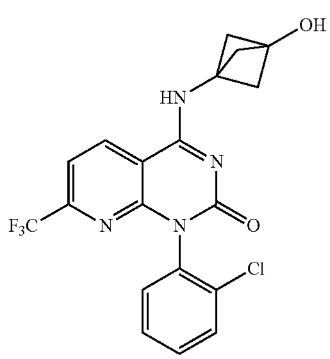 [SMILES: O=c1nc(NC23CC(O)(C2)C3)c2ccc(C(F)(F)F)nc2n1-c1ccccc1Cl] | 1-(2-chlorophenyl)-4-[(3-hydroxybicyclo[1.1.1]pentyl)amino]-7-(trifluoro-methyl)-pyrido [2,3-d]pyrimidin-2(1H)-one | m/z [M + H]+ 423.10 |
| 298 | 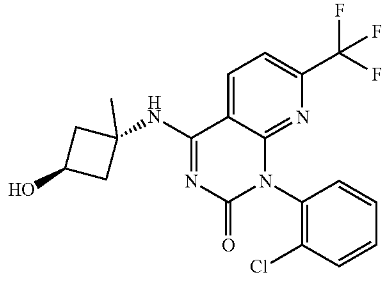 [SMILES: C[C@]1(Nc2nc(=O)n(-c3ccccc3Cl)c3nc(C(F)(F)F)ccc23)C[C@H](O)C1] | 4-[((trans)-3-hydroxy-1-methylcyclobutyl)amino]-1-(2-chlorophenyl)-7-(trifluoromethyl)-pyrido [2,3-d]pyrimidin-2(1H)-one | m/z [M + H]+ 425.10 |

TABLE 1-continued

| Cpd. No. | Structure | Name | Mass Spec. |
|---|---|---|---|
| 299 | 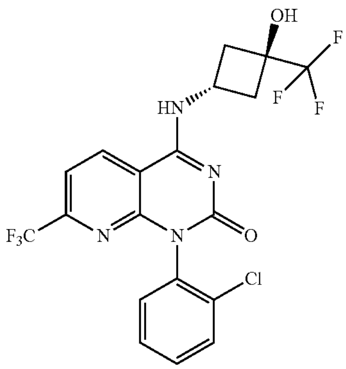 [SMILES: O=c1nc(N[C@H]2C[C@@](O)(C(F)(F)F)C2)c2ccc(C(F)(F)F)nc2n1-c1ccccc1Cl] | 4-{[(trans)-3-hydroxy-3-(trifluoromethyl)cyclobutyl]amino}-1-(2-chlorophenyl)-7-(trifluoromethyl)pyrido-[2,3-d]pyrimidin-2(1H)-one | m/z [M + H]⁺ 479.10 |
| 300 | 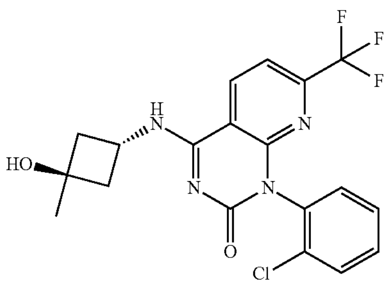 [SMILES: C[C@]1(O)C[C@H](Nc2nc(=O)n(-c3ccccc3Cl)c3nc(C(F)(F)F)ccc23)C1] | 4-[((trans)-3-hydroxy-3-methylcyclobutyl)amino]-1-(2-chlorophenyl)-7-(trifluoromethyl)pyrido[2,3-d]pyrimidin-2(1H)-one | m/z [M + H]⁺ 425.10 |
| 301 | 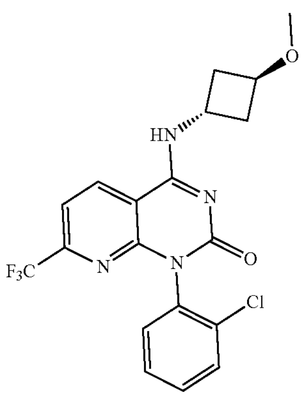 [SMILES: CO[C@H]1C[C@H](Nc2nc(=O)n(-c3ccccc3Cl)c3nc(C(F)(F)F)ccc23)C1] | 4-[(trans)-3-methoxycyclobutyl)amino]-1-(2-chlorophenyl)-7-(trifluoromethyl)-pyrido[2,3-d]pyrimidin-2(1H)-one | m/z [M + H]⁺ 425.10 |
| 302 | 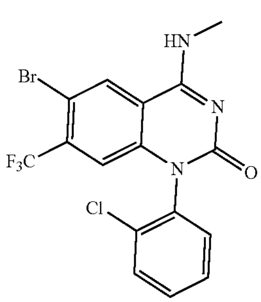 [SMILES: CNc1nc(=O)n(-c2ccccc2Cl)c2cc(C(F)(F)F)c(Br)cc12] | 6-bromo-1-(2-chlorophenyl)-4-(methylamino)-7-(trifluoromethyl)-quinazolin-2(1H)-one | m/z [M + H]⁺ 432.0 |

TABLE 1-continued

| Cpd. No. | Structure | Name | Mass Spec. |
|---|---|---|---|
| 303 | 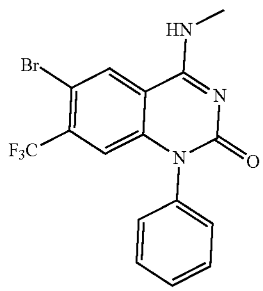 [SMILES: CNc1nc(=O)n(-c2ccccc2)c2cc(C(F)(F)F)c(Br)cc12] | 6-bromo-4-(methylamino)-1-phenyl-7-(trifluoromethyl)quinazolin-2(1H)-one | m/z [M + H]+ 398.0 |
| 304 | 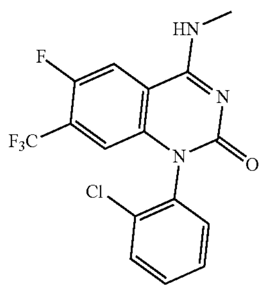 [SMILES: CNc1nc(=O)n(-c2ccccc2Cl)c2cc(C(F)(F)F)c(F)cc12] | 1-(2-chlorophenyl)-6-fluoro-4-(methyl-amino)-7-(trifluoromethyl)hydro-quinazolin-2-one | m/z [M + H]+ 372.0 |
| 305 | 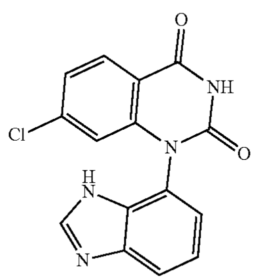 [SMILES: O=c1[nH]c(=O)n(-c2cccc3nc[nH]c23)c2cc(Cl)ccc12] | 1-benzimidazol-7-yl-7-chloro-1,3-dihydroquinazoline-2,4-dione | m/z [M + H]+ 313.0 |
| 306 | 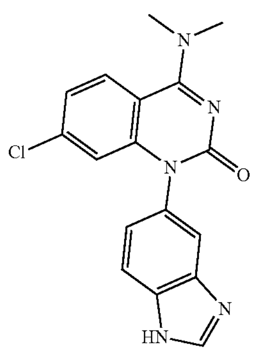 [SMILES: CN(C)c1nc(=O)n(-c2ccc3[nH]cnc3c2)c2cc(Cl)ccc12] | 1-benzimidazol-5-yl-4-(dimethylamino)-7-chlorohydroquinazolin-2-one | m/z [M + H]+ 340.0 |
| 307 | 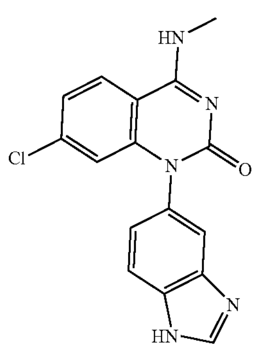 [SMILES: CNc1nc(=O)n(-c2ccc3[nH]cnc3c2)c2cc(Cl)ccc12] | 1-benzimidazol-5-yl-7-chloro-4-(methyl-amino)hydroquinazolin-2-one | m/z [M + H]+ 326.0 |

TABLE 1-continued

| Cpd. No. | Structure | Name | Mass Spec. |
|---|---|---|---|
| 308 | 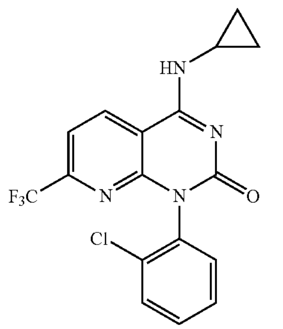 [SMILES: O=c1nc(NC2CC2)c2ccc(C(F)(F)F)nc2n1-c1ccccc1Cl] | 1-(2-chlorophenyl)-4-(cyclopropyl-amino)-7-(trifluoromethyl)pyrido[2,3-d]pyrimidin-2(1H)-one | m/z [M + H]+ 381.28 |
| 309 | 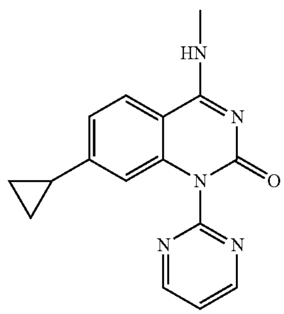 [SMILES: CNc1nc(=O)n(-c2ncccn2)c2cc(C3CC3)ccc12] | 7-cyclopropyl-4-(methylamino)-1-pyrimidin-2-ylhydroquinazolin-2-one | m/z [M + H]+ 294.30 |
| 310 | 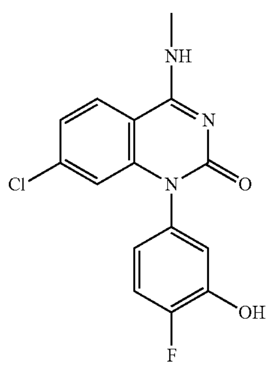 [SMILES: CNc1nc(=O)n(-c2ccc(F)c(O)c2)c2cc(Cl)ccc12] | 7-chloro-1-(4-fluoro-3-hydroxyphenyl)-4-(methylamino)hydroquinazolin-2-one | m/z [M + H]+ 320.34 |
| 311 | 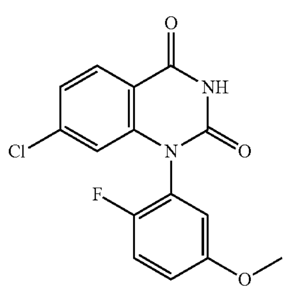 [SMILES: COc1ccc(F)c(-n2c(=O)[nH]c(=O)c3ccc(Cl)cc32)c1] | 7-chloro-1-(2-fluoro-5-methoxyphenyl)-quinazoline-2,4(1H,3H)-dione | m/z [M + H]+ 321.31 |
| 312 | 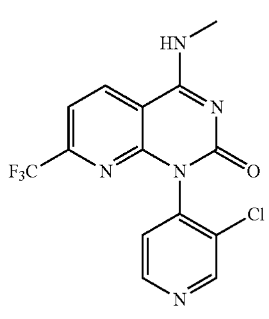 [SMILES: CNc1nc(=O)n(-c2ccncc2Cl)c2nc(C(F)(F)F)ccc12] | 1-(3-chloro-pyridin-4-yl))-4-(methyl-amino)-7-(trifluoromethyl)pyrido[2,3-d]-pyrimidin-2(1H)-one | m/z [M + H]+ 356.00 |

TABLE 1-continued

| Cpd. No. | Structure | Name | Mass Spec. |
|---|---|---|---|
| 313 | 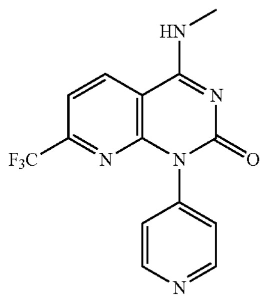 [SMILES: CNc1nc(=O)n(-c2ccncc2)c2nc(C(F)(F)F)ccc12] | 4-(methylamino)-1-(pyridin-4-yl))-7-(trifluoromethyl)pyrido[2,3-d]pyrimidin-2(1H)-one | m/z [M + H]+ 322.00 |
| 314 | 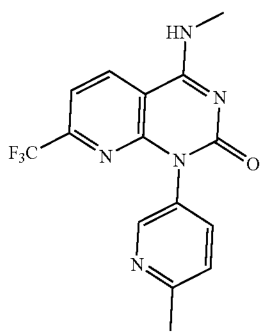 [SMILES: CNc1nc(=O)n(-c2ccc(C)nc2)c2nc(C(F)(F)F)ccc12] | 1-(6-methyl--pyridin-3-yl))-4-(methyl-amino)-7-(trifluoromethyl)pyrido[2,3-d]-pyrimidin-2(1H)-one | m/z [M + H]+ 336.0 |
| 315 | 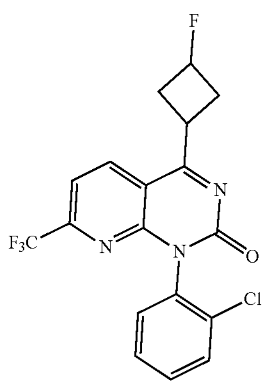 [SMILES: O=c1nc(C2CC(F)C2)c2ccc(C(F)(F)F)nc2n1-c1ccccc1Cl] | 1-(2-chlorophenyl)-4-(3-fluoroazetidin-1-yl)-7-(trifluoromethyl)pyrido[2,3-d]pyrimidin-2(1H)-one | m/z [M + H]+ 399.10 |
| 316 | 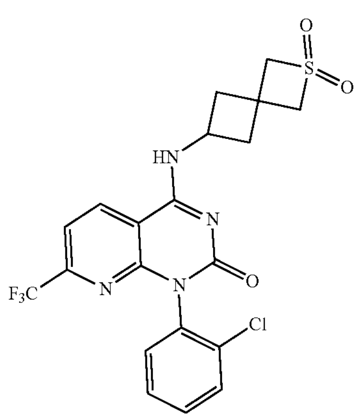 [SMILES: O=c1nc(NC2CC3(C2)CS(=O)(=O)C3)c2ccc(C(F)(F)F)nc2n1-c1ccccc1Cl] | 1-(2-chlorophenyl)-4-((2,2-dioxido-2-thiaspiro[3.3]heptan-6-yl)amino)-7-(trifluoromethyl)pyrido[2,3-d]pyrimidin-2(1H)-one | m/z [M + H]+ 485.10 |

TABLE 1-continued

| Cpd. No. | Structure | Name | Mass Spec. |
|---|---|---|---|
| 317 | 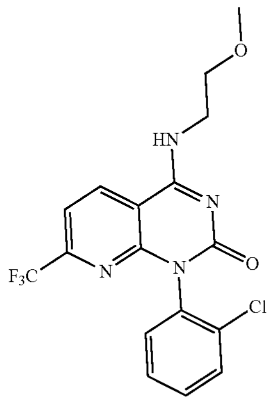 [SMILES: COCCNc1nc(=O)n(-c2ccccc2Cl)c2nc(C(F)(F)F)ccc12] | 1-(2-chlorophenyl)-4-[(2-methoxyethyl)-amino]-7-(trifluoromethyl)pyrido[2,3-d]-pyrimidin-2(1H)-one | m/z [M + H]+ 399.10 |
| 318 | 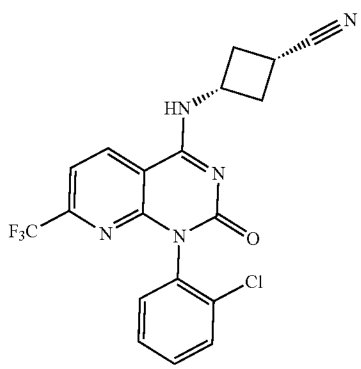 [SMILES: N#C[C@H]1C[C@@H](Nc2nc(=O)n(-c3ccccc3Cl)c3nc(C(F)(F)F)ccc23)C1] | (1s,3s)-3-((1-(2-chlorophenyl)-2-oxo-7-(trifluoromethyl)-1,2-dihydropyrido[2,3-d]pyrimidin-4-yl)amino)cyclobutane-1-carbonitrile | m/z [M + H]+ 420.10 |
| 319 | 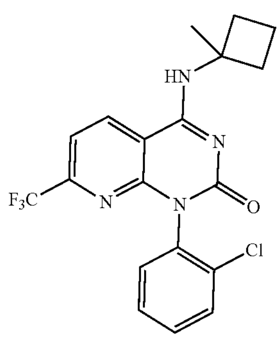 [SMILES: CC1(Nc2nc(=O)n(-c3ccccc3Cl)c3nc(C(F)(F)F)ccc23)CCC1] | 1-(2-chlorophenyl)-4-[(methylcyclo-butypamino]-7-(trifluoromethyl)pyrido-[2,3-d]pyrimidin-2(1H)-one | m/z [M + H]+ 409.20 |
| 320 | 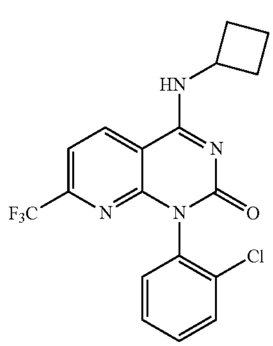 [SMILES: O=c1nc(NC2CCC2)c2ccc(C(F)(F)F)nc2n1-c1ccccc1Cl] | 1-(2-chlorophenyl)-4-(cyclobutylamino)-7-(trifluoromethyl)pyrido [2,3-d]-pyrimidin-2(1H)-one | m/z [M + H]+ 395.10 |

TABLE 1-continued

| Cpd. No. | Structure | Name | Mass Spec. |
|---|---|---|---|
| 321 | 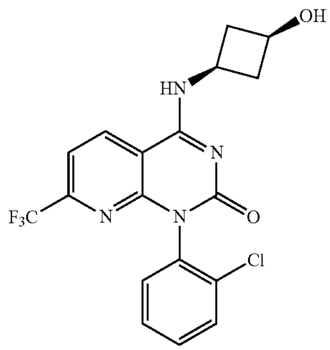 [SMILES: O=c1nc(N[C@H]2C[C@@H](O)C2)c2ccc(C(F)(F)F)nc2n1-c1ccccc1Cl] | (1s,3s)-3-((1-(2-chlorophenyl)-2-oxo-7-(trifluoromethyl)-1,2-dihydropyrido[2,3-d]pyrimidin-4-yl)amino)cyclobutane-1-carbonitrile | m/z [M + H]+ 411.10 |
| 322 | 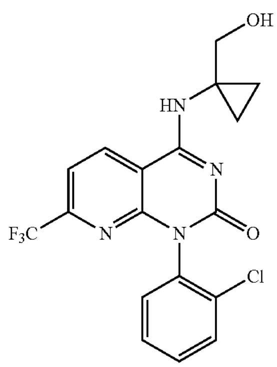 [SMILES: O=c1nc(NC2(CO)CC2)c2ccc(C(F)(F)F)nc2n1-c1ccccc1Cl] | 1-(2-chlorophenyl)-4-{[(hydroxy-methyl)cyclopropyl]amino 1-7-(trifluoro-methyl)-pyrido[2,3-d]pyrimidin-2(1H)-one | m/z [M + H]+ 411.10 |
| 323 | 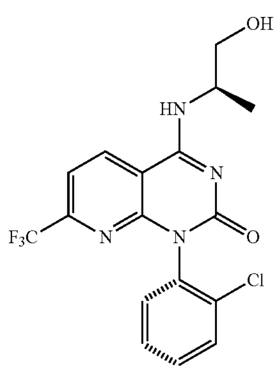 | (R)-(1S$_a$)-(2-chlorophenyl)-4-((1-hydroxypropan-2-yl)amino)-7-(trifluoro-methyl)pyrido-[2,3-d]pyrimidin-2(1H)-one | m/z [M + H]+ 399.10 |
| 324 | 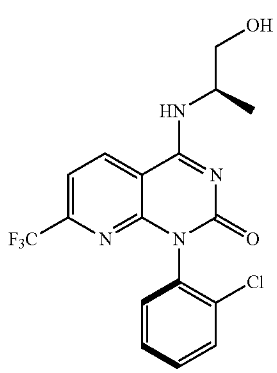 | (R)-(1R$_a$)-(2-chlorophenyl)-4-((1-hydroxypropan-2-yl)amino)-7-(trifluoro-methyl)pyrido-[2,3-d]pyrimidin-2(1H)-one | m/z [M + H]+ 399.10 |

TABLE 1-continued

| Cpd. No. | Structure | Name | Mass Spec. |
|---|---|---|---|
| 325 | 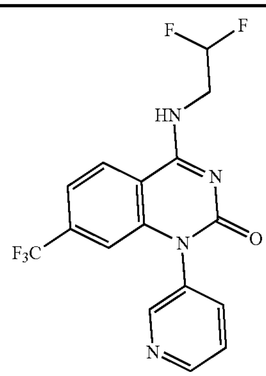 | 4-[(2,2-difluoroethyl)amino]-1-(pyridin-3-yl)-7-(trifluoromethyl)hydroquinazolin-2-one | m/z [M + H]+ 371.0 |
| 326 | 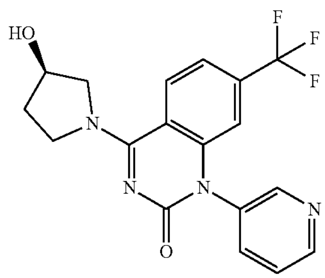 [SMILES: O=c1nc(N2CC[C@@H](O)C2)c2ccc(C(F)(F)F)cc2n1-c1cccnc1] | 4-((3R)-3-hydroxypyrrolidinyl)-1-(pyridin-3-yl)-7-(trifluoromethyl)-hydroquinazolin-2-one | m/z [M + H]+ 372.0 |
| 327 | 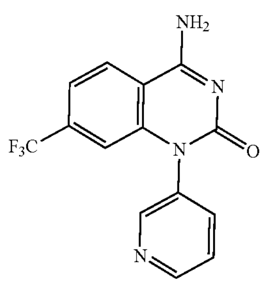 [SMILES: Nc1nc(=O)n(-c2cccnc2)c2cc(C(F)(F)F)ccc12] | 4-amino-1-(pyridin-3-yl)-7-(trifluoromethyl)hydroquinazolin-2-one | m/z [M + H]+ 307.0 |
| 328 | 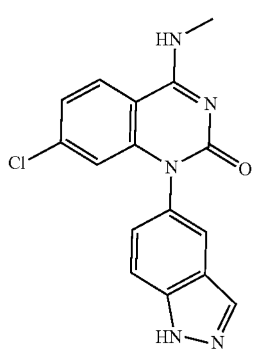 [SMILES: CNc1nc(=O)n(-c2ccc3[nH]ncc3c2)c2cc(Cl)ccc12] | 1-(1H-indazol-5-yl)-7-chloro-4-(methyl-amino)hydroquinazolin-2-one | m/z [M + H]+ 326.0 |
| 329 | 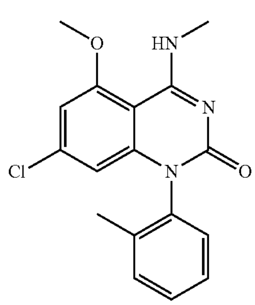 [SMILES: CNc1nc(=O)n(-c2ccccc2C)c2cc(Cl)cc(OC)c12] | 7-chloro-5-methoxy-4-(methylamino)-1-(2-methylphenyl)hydroquinazolin-2-one | m/z [M + H]+ 330.1 |

TABLE 1-continued

| Cpd. No. | Structure | Name | Mass Spec. |
|---|---|---|---|
| 330 | 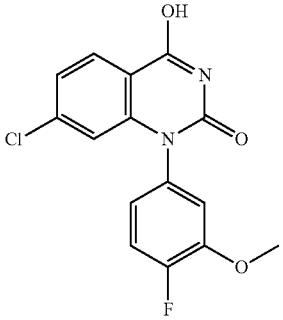 [SMILES: COc1cc(-n2c(=O)nc(O)c3ccc(Cl)cc32)ccc1F] | 7-chloro-1-(4-fluoro-3-methoxyphenyl)-4-hydroxyhydroquinazolin-2-one | m/z [M + H]+ 319.05 |
| 331 | 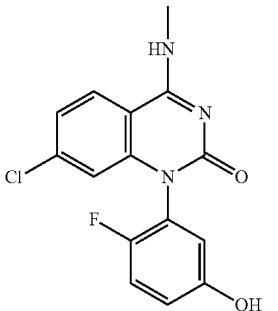 [SMILES: CNc1nc(=O)n(-c2cc(O)ccc2F)c2cc(Cl)ccc12] | 7-chloro-1-(6-fluoro-3-hydroxyphenyl)-4-(methylamino)hydroquinazolin-2-one | m/z [M + H]+ 319.06 |
| 332 | 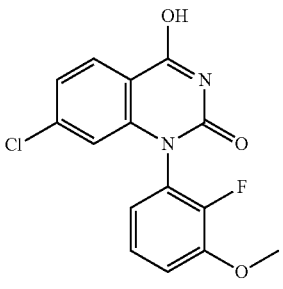 [SMILES: COc1cccc(-n2c(=O)nc(O)c3ccc(Cl)cc32)c1F] | 7-chloro-1-(2-fluoro-3-methoxyphenyl)-4-hydroxyhydroquinazolin-2-one | m/z [M + H]+ 320.06 |
| 333 | 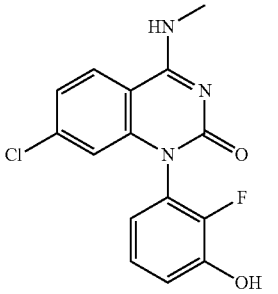 [SMILES: CNc1nc(=O)n(-c2cccc(O)c2F)c2cc(Cl)ccc12] | 7-chloro-1-(2-fluoro-3-hydroxyphenyl)-4-(methylamino)quinazolin-2(1H)-one | m/z [M + H]+ 320.27 |
| 334 | 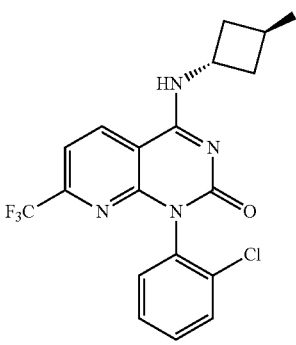 | 1-(2-chlorophenyl)-4-(((1r,3r)-3-hydroxycyclobutyl)amino)-7-(trifluoromethyl)pyrido[2,3-d]pyrimidin-2(1H)-one | m/z [M + H]+ 411.00 |

TABLE 1-continued

| Cpd. No. | Structure | Name | Mass Spec. |
|---|---|---|---|
| 335 | 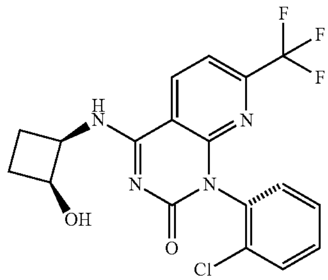 | 4-[((2 S,1R)-2-hydroxycyclobutyl)-amino]-(1S$_a$)-(2-chlorophenyl)-7-(trifluoromethyl)hydro-pyrido[2,3-d]-pyrimidin-2(1H)-one | m/z [M + H]$^+$ 411.00 |
| 336 | 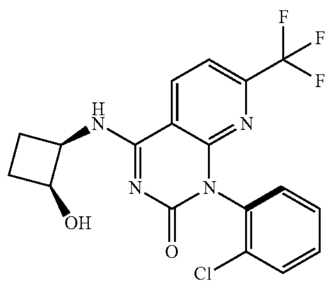 | 4-[((2S,1R)-2-hydroxycyclo-butyl)amino]-(1R$_a$)-(2-chlorophenyl)-7-(trifluoromethyl)hydro-pyridino [2,3-d]-pyrimidin-2-one | m/z [M + H]$^+$ 411.00 |
| 337 | 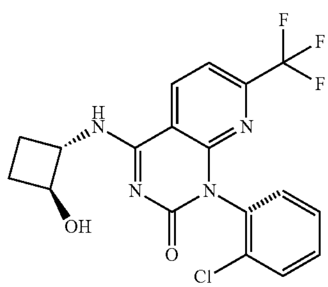 | 4-[((1S,2S)-2-hydroxycyclobutyl)-amino]-(1Sa)-(2-chlorophenyl)-7-(trifluoromethyl)hydro-pyridino[2,3-d]-pyrimidin-2-one | m/z [M + H]$^+$ 411.00 |
| 338 | 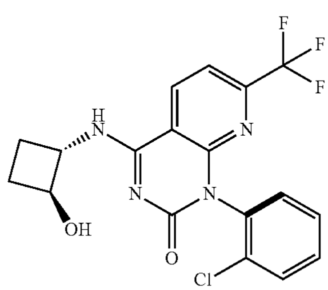 | 4-[((1S,2S)-2-hydroxycyclobutyl)-amino]-(1Ra)-(2-chlorophenyl)-7-(trifluoromethyl)hydro-pyridino[2,3-d]-pyrimidin-2-one | m/z [M + H]$^+$ 411.00 |
| 339 | 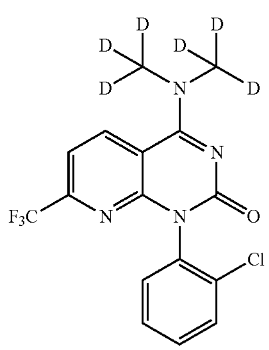 [SMILES: [2H]C([2H])([2H])N(c1nc(=O)n(-c2ccccc2Cl)c2nc(C(F)(F)F)ccc12)C([2H])([2H])[2H]] | 4-(bis(methyl-d3)amino)-1-(2-chloro-phenyl)-7-(trifluoromethyl)-pyrido[2,3-d]pyrimidin-2(1H)-one | m/z [M + H]$^+$ 375.00 |

TABLE 1-continued

| Cpd. No. | Structure | Name | Mass Spec. |
|---|---|---|---|
| 340 | 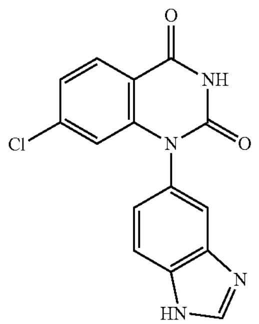 [SMILES: O=c1[nH]c(=O)n(-c2ccc3[nH]cnc3c2)c2cc(Cl)ccc12] | 1-(1H-benzo[d]imidazol-5-yl)-7-chloro-quinazoline-2,4(1H,3H)-dione | m/z [M + H]+ 313.0 |
| 341 | 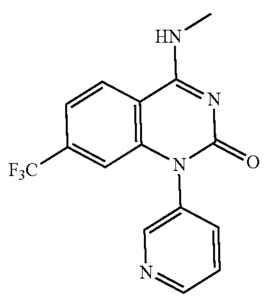 [SMILES: CNc1nc(=O)n(-c2cccnc2)c2cc(C(F)(F)F)ccc12] | 4-(methylamino)-1-(pyridin-3-yl)-7-(trifluoromethyl)hydroquinazolin-2-one | m/z [M + H]+ 321.0 |
| 342 | 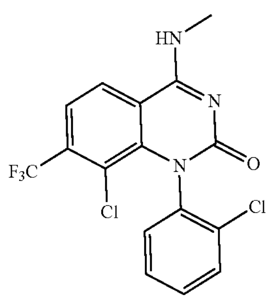 [SMILES: CNc1nc(=O)n(-c2ccccc2Cl)c2c(Cl)c(C(F)(F)F)ccc12] | 8-chloro-1-(2-chlorophenyl)-4-(methylamino)-7-(trifluoromethyl)-hydroquinazolin-2-one | m/z [M + H]+ 388.0 |
| 343 | 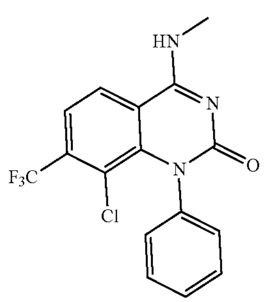 [SMILES: CNc1nc(=O)n(-c2ccccc2)c2c(Cl)c(C(F)(F)F)ccc12] | 8-chloro-4-(methylamino)-1-phenyl-7-(trifluoromethyl)hydroquinazolin-2-one | m/z [M + H]+ 354.04 |
| 344 | 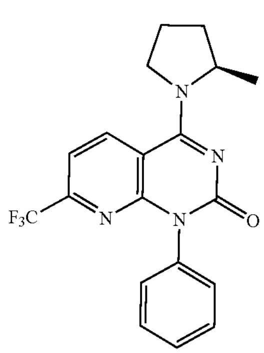 [SMILES: C[C@@H]1CCCN1c1nc(=O)n(-c2ccccc2)c2nc(C(F)(F)F)ccc12] | 4-((2R)-2-methylpyrrolidin-1-yl)-1-phenyl-7-(trifluoromethyl)pyrido[2,3-d]-pyrimidin-2(1H)-one | m/z [M + H]+ 375.1 |

TABLE 1-continued

| Cpd. No. | Structure | Name | Mass Spec. |
|---|---|---|---|
| 345 | 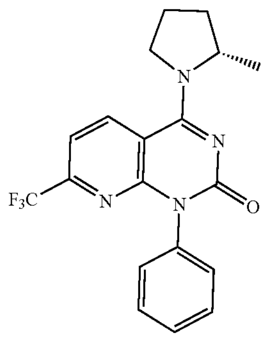 [SMILES: C[C@H]1CCCN1c1nc(=O)n(-c2ccccc2)c2nc(C(F)(F)F)ccc12] | 4-((2S)-2-methylpyrrolidin-1-yl)-1-phenyl-7-(trifluoromethyl)pyrido[2,3-d]-pyrimidin-2(1H)-one | m/z [M + H]+ 375.1 |
| 346 | 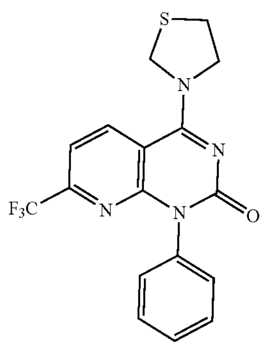 [SMILES: O=c1nc(N2CCSC2)c2ccc(C(F)(F)F)nc2n1-c1ccccc1] | 1-phenyl-4-(1,3-thiazolidin-3-yl)-7-(trifluoromethyl) pyrido[2,3-d]-pyrimidin-2(1H)-one | m/z [M + H]+ 379.1 |
| 347 | 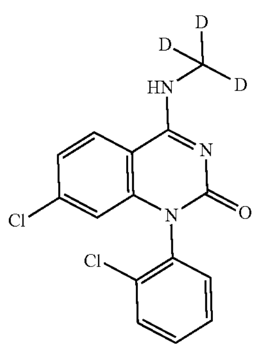 [SMILES: [2H]C([2H])([2H])Nc1nc(=O)n(-c2ccccc2Cl)c2cc(Cl)ccc12] | 7-chloro-1-(2-chlorophenyl)-4-((methyl-d3)amino)quinazolin-2(1H)-one | m/z [M + H]+ 324.1 |
| 348 | 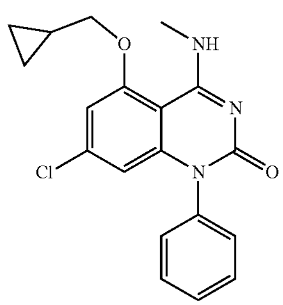 [SMILES: CNc1nc(=O)n(-c2ccccc2)c2cc(Cl)cc(OCC3CC3)c12] | 7-chloro-5-(cyclopropylmethoxy)-4-(methylamino)-1-phenylhydro-quinazolin-2-one | m/z [M + H]+ 356.32 |

TABLE 1-continued

| Cpd. No. | Structure | Name | Mass Spec. |
|---|---|---|---|
| 349 | 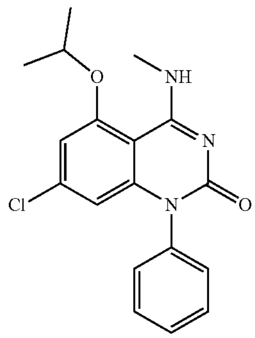 [SMILES: CNc1nc(=O)n(-c2ccccc2)c2cc(Cl)cc(OC(C)C)c12] | 7-chloro-4-(methylamino)-5-(methylethoxy)-1-phenylhydroquinazolin-2-one | m/z [M + H]+ 344.33 |
| 350 | 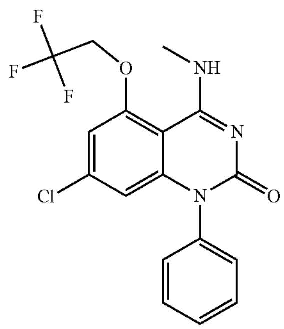 [SMILES: CNc1nc(=O)n(-c2ccccc2)c2cc(Cl)cc(OCC(F)(F)F)c12] | 7-chloro-4-(methylamino)-1-phenyl-5-(2,2,2-trifluoroethoxy)hydroquinazolin-2-one | m/z [M + H]+ 384.31 |
| 351 | 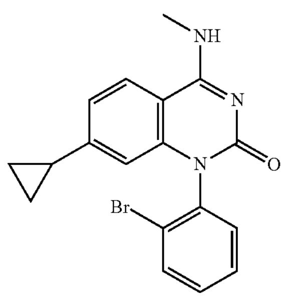 [SMILES: CNc1nc(=O)n(-c2ccccc2Br)c2cc(C3CC3)ccc12] | 1-(2-bromophenyl)-7-cyclopropyl-4-(methylamino)hydroquinazolin-2-one | m/z [M + H]+ 370.26 |
| 352 | 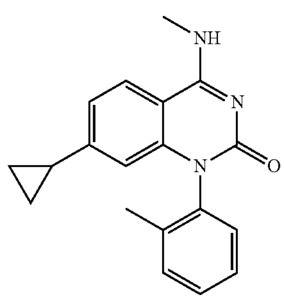 [SMILES: CNc1nc(=O)n(-c2ccccc2C)c2cc(C3CC3)ccc12] | 7-cyclopropyl-4-(methylamino)-1-(2-methylphenyl)hydroquinazolin-2-one | m/z [M + H]+ 306.33 |
| 353 | 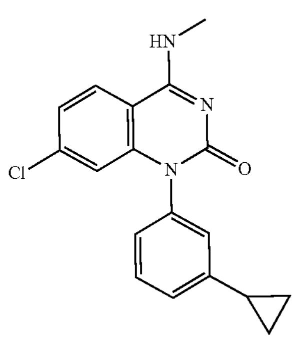 [SMILES: CNc1nc(=O)n(-c2cccc(C3CC3)c2)c2cc(Cl)ccc12] | 7-chloro-1-(3-cyclopropylphenyl)-4-(methylamino)hydroquinazolin-2-one | m/z [M + H]+ 326.32 |

TABLE 1-continued

| Cpd. No. | Structure | Name | Mass Spec. |
|---|---|---|---|
| 354 | 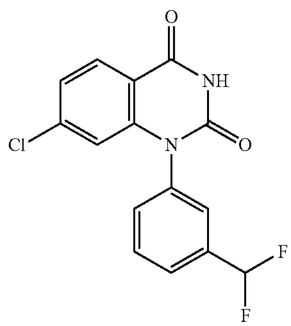 [SMILES: O=c1[nH]c(=O)n(-c2cccc(C(F)F)c2)c2cc(Cl)ccc12] | 7-chloro-1-(3-difluoromethylphenyl)-quinazoline-2,4(1H,3H)-dione | m/z [M + H]+ 323.26 |
| 355 | 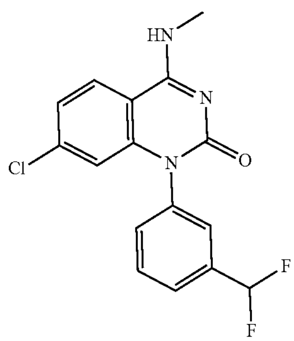 [SMILES: CNc1nc(=O)n(-c2cccc(C(F)F)c2)c2cc(Cl)ccc12] | 7-chloro-1-(3-(difluoromethyl)phenyl)-4-(methylamino)-3,4-dihydroquinazolin-2(1H)-one | m/z [M + H]+ 336.30 |
| 356 | 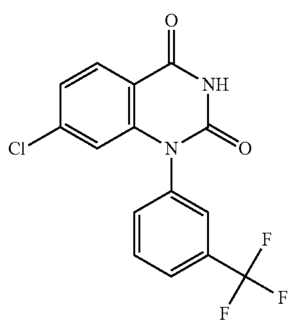 [SMILES: O=c1[nH]c(=O)n(-c2cccc(C(F)(F)F)c2)c2cc(Cl)ccc12] | 7-chloro-1-(3-trifluoromethylphenyl)-quinazoline-2,4(1H,3H)-dione | m/z [M + H]+ 339.29 |
| 357 | 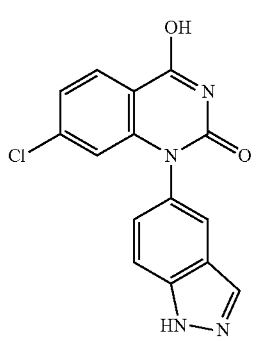 [SMILES: O=c1nc(O)c2ccc(Cl)cc2n1-c1ccc2[nH]ncc2c1] | 1-(1H-indazol-5-yl)-7-chloro-4-hydroxy-hydroquinazolin-2-one | m/z [M + H]+ 313.0 |

TABLE 1-continued

| Cpd. No. | Structure | Name | Mass Spec. |
|---|---|---|---|
| 358 | 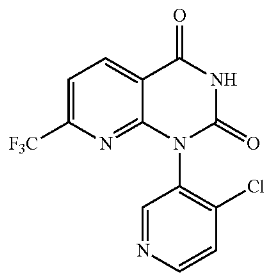 [SMILES: O=c1[nH]c(=O)n(-c2cnccc2Cl)c2nc(C(F)(F)F)ccc12] | 1-(4-chloropyridin-3-yl)-7-(trifluoro-methyl)pyrido[2,3-d]pyrimidine-2,4(1H,3H)-dione | m/z [M + H]+ 343.0 |
| 359 | 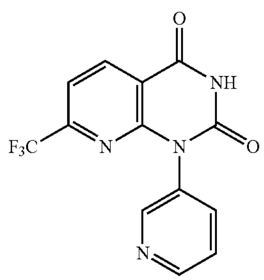 [SMILES: O=c1[nH]c(=O)n(-c2cccnc2)c2nc(C(F)(F)F)ccc12] | 1-(pyridin-3-yl)-7-(trifluoromethyl)-pyrido[2,3-d]pyrimidine-2,4(1H,3H)-dione | m/z [M + H]+ 309.00 |
| 360 | 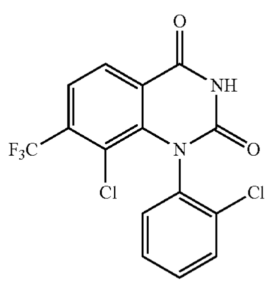 [SMILES: O=c1[nH]c(=O)n(-c2ccccc2Cl)c2c(Cl)c(C(F)(F)F)ccc12] | 8-chloro-1-(2-chlorophenyl)-7-(trifluoro-methyl)pyrido[2,3-d]pyrimidine-2,4(1H,3H)-dione-1 | m/z [M-H]- 373.0 |
| 361 | 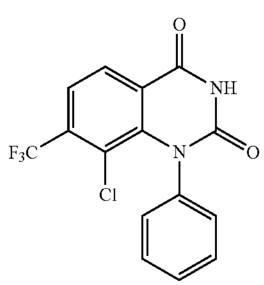 [SMILES: O=c1[nH]c(=O)n(-c2ccccc2)c2c(Cl)c(C(F)(F)F)ccc12] | 8-chloro-1-phenyl-7-(trifluoromethyl)-pyrido[2,3-d]pyrimidine-2,4(1H,3H)-dione | m/z [M-H]- 339.0 |
| 362 | 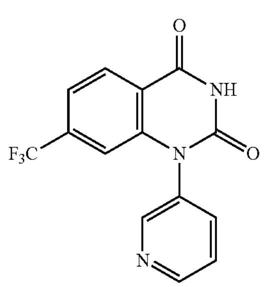 [SMILES: O=c1[nH]c(=O)n(-c2cccnc2)c2cc(C(F)(F)F)ccc12] | 1-(pyridin-3-yl)-7-(trifluoromethyl)-1,3-dihydroquinazoline-2,4-dione | m/z [M + H]+ 308.0 |

TABLE 1-continued

| Cpd. No. | Structure | Name | Mass Spec. |
|---|---|---|---|
| 363 | 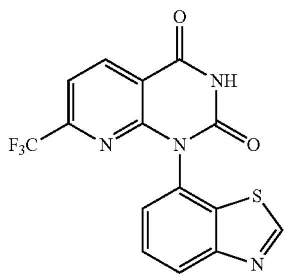 [SMILES: O=c1[nH]c(=O)n(-c2cccc3ncsc23)c2nc(C(F)(F)F)ccc12] | 1-benzothiazol-7-yl-7-(trifluoromethyl)-pyrido[2,3-d]pyrimidine-2,4(1H,3H)-dione | m/z [M + H]+ 365.0 |
| 364 | 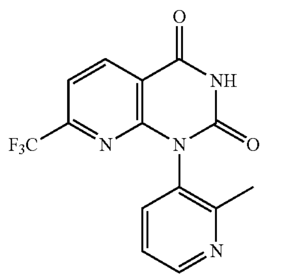 [SMILES: Cc1ncccc1-n1c(=O)[nH]c(=O)c2ccc(C(F)(F)F)nc21] | 1-(2-methylpyridin-3-yl)-7-(trifluoromethyl)pyrido[2,3-d]pyrimidine-2,4(1H,3H)-dione | m/z [M + H]+ 323.1 |
| 365 | 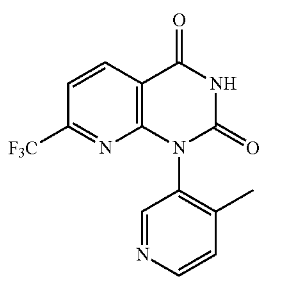 [SMILES: Cc1ccncc1-n1c(=O)[nH]c(=O)c2ccc(C(F)(F)F)nc21] | 1-(4-methylpyridin-3-yl)-7-(trifluoromethyl)pyrido[2,3-d]pyrimidine-2,4(1H,3H)-dione | m/z [M + H]+ 323.1 |
| 366 | 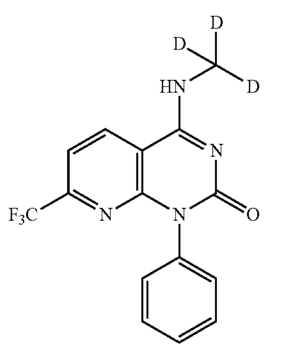 [SMILES: [2H]C([2H])([2H])Nc1nc(=O)n(-c2ccccc2)c2nc(C(F)(F)F)ccc12] | 4-((methyl-d3)amino)-1-phenyl-7-(trifluoromethyl)pyrido[2,3-d]pyrimidin-2(1H)-one | m/z [M + H]+ 324.1 |
| 367 | 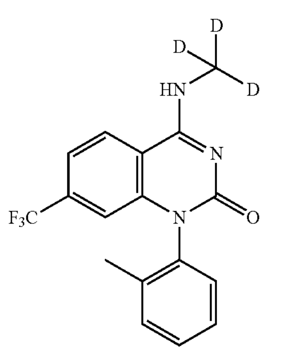 [SMILES: [2H]C([2H])([2H])Nc1nc(=O)n(-c2ccccc2C)c2cc(C(F)(F)F)ccc12] | 4-((methyl-d3)amino)-1-(o-tolyl)-7-(trifluoromethyl)quinazolin-2(1H)-one | m/z [M + H]+ 337.2 |

TABLE 1-continued

| Cpd. No. | Structure | Name | Mass Spec. |
|---|---|---|---|
| 368 | 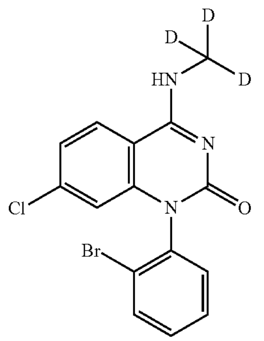 [SMILES: [2H]C([2H])([2H])Nc1nc(=O)n(-c2ccccc2Br)c2cc(Cl)ccc12] | 1-(2-bromophenyl)-7-chloro-4-((methyl-d3)amino)quinazolin-2(1H)-one | m/z [M + H]+ 367.0 |
| 369 | 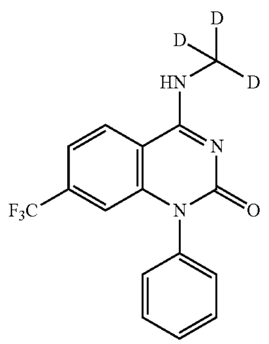 [SMILES: [2H]C([2H])([2H])Nc1nc(=O)n(-c2ccccc2)c2cc(C(F)(F)F)ccc12] | 4-((methyl-d3)amino)-1-phenyl-7-(trifluoromethyl)quinazolin-2(1H)-one | m/z [M + H]+ 323.2 |
| 370 | 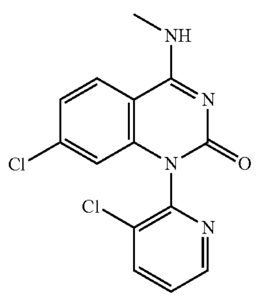 [SMILES: CNc1nc(=O)n(-c2ncccc2Cl)c2cc(Cl)ccc12] | 7-chloro-1-(3-chloro(2-pyridyl))-4-(methylamino)hydroquinazolin-2-one | m/z [M + H]+ 321.26 |
| 371 | 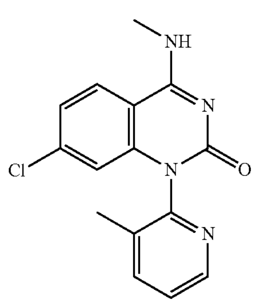 [SMILES: CNc1nc(=O)n(-c2ncccc2C)c2cc(Cl)ccc12] | 7-chloro-1-(3-methylpyridin-2-yl))-4-(methylamino)hydroquinazolin-2-one | m/z [M + H]+ 301.3 |

TABLE 1-continued

| Cpd. No. | Structure | Name | Mass Spec. |
|---|---|---|---|
| 372 | 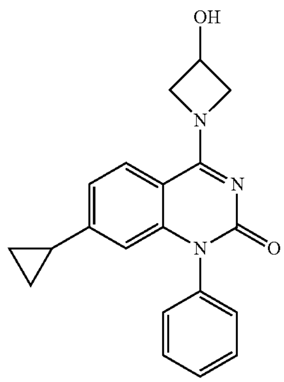 [SMILES: O=c1nc(N2CC(O)C2)c2ccc(C3CC3)cc2n1-c1ccccc1] | 7-cyclopropyl-4-(3-hydroxyazetidin-1-yl)-1-phenylhydroquinazolin-2-one | m/z [M + H]+ 334.36 |
| 373 | 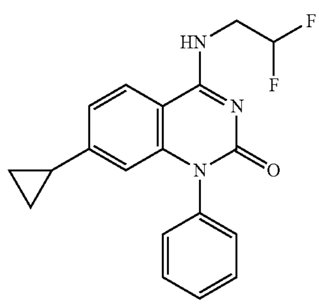 [SMILES: O=c1nc(NCC(F)F)c2ccc(C3CC3)cc2n1-c1ccccc1] | 7-cyclopropyl-4-((2-fluoropropyl)-amino)-1-phenylquinazolin-2(1H)-one | m/z [M + H]+ 342.35 |
| 374 | 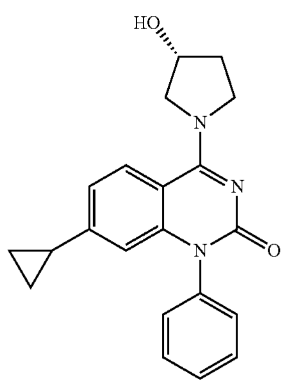 [SMILES: O=c1nc(N2CC[C@@H](O)C2)c2ccc(C3CC3)cc2n1-c1ccccc1] | 4-((3R)-3-hydroxypyrrolidinyl)-7-cyclopropyl-1-phenylhydroquazolin-2-one | m/z [M + H]+ 348.37 |
| 375 | 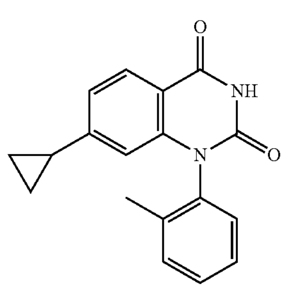 [SMILES: Cc1ccccc1-n1c(=O)[nH]c(=O)c2ccc(C3CC3)cc21] | 7-cyclopropyl-1-(o-tolyl)quinazoline-2,4(1H,3H)-dione | m/z [M + H]+ 293.25 |

TABLE 1-continued

| Cpd. No. | Structure | Name | Mass Spec. |
|---|---|---|---|
| 376 | 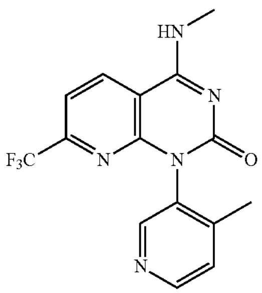 [SMILES: CNc1nc(=O)n(-c2cnccc2C)c2nc(C(F)(F)F)ccc12] | 4-(methylamino)-1-(4-methylpyridin-3-yl)-7-(trifluoromethyl)pyrido[2,3-d]-pyrimidin-2(1H)-one | m/z [M + H]+ 336.1 |
| 377 | 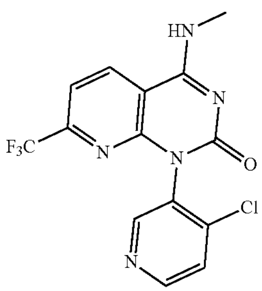 [SMILES: CNc1nc(=O)n(-c2cnccc2Cl)c2nc(C(F)(F)F)ccc12] | 1-(4-chloropyridin-3-yl)-4-(methyl-amino)-7-(trifluoromethyl)pyrido[2,3-d]pyrimidin-2(1H)-one | m/z [M + H]+ 356.00 |
| 378 | 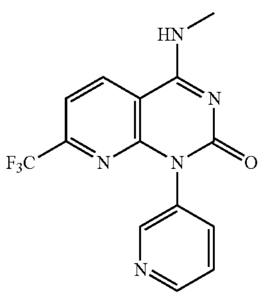 [SMILES: CNc1nc(=O)n(-c2cccnc2)c2nc(C(F)(F)F)ccc12] | 4-(methylamino)-1-(pyridin-3-yl)-7-(trifluoromethyl)pyrido[2,3-d]pyrimidin-2(1H)-one | m/z [M + H]+ 322.10 |
| 379 | 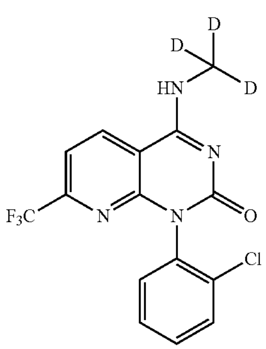 [SMILES: [2H]C([2H])([2H])Nc1nc(=O)n(-c2ccccc2Cl)c2nc(C(F)(F)F)ccc12] | 1-(2-chlorophenyl)-4-((methyl-d3)-amino)-7-(trifluoromethyl)pyrido[2,3-d]pyrimidin-2(1H)-one | m/z [M + H]+ 358.00 |
| 380 | 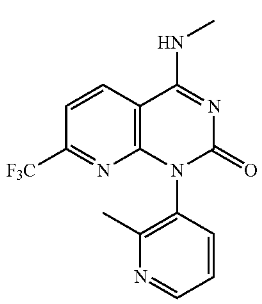 [SMILES: CNc1nc(=O)n(-c2cccnc2C)c2nc(C(F)(F)F)ccc12] | 4-(methylamino)-1-(2-methylpyridin-3-yl)-7-(trifluoromethyl)pyrido[2,3-d]-pyrimidin-2(1H)-one | m/z [M + H]+ 336.1 |

TABLE 1-continued

| Cpd. No. | Structure | Name | Mass Spec. |
|---|---|---|---|
| 381 | 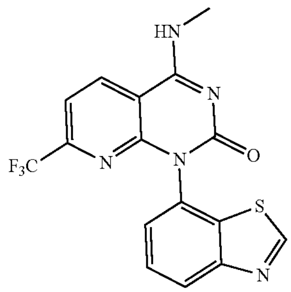 [SMILES: CNc1nc(=O)n(-c2cccc3ncsc23)c2nc(C(F)(F)F)ccc12] | 1-benzothiazol-7-yl-4-(methylamino)-7-(trifluoromethyl)pyrido[2,3-d]pyrimidin-2(1H)-one | m/z [M + H]+ 378.0 |
| 382 | 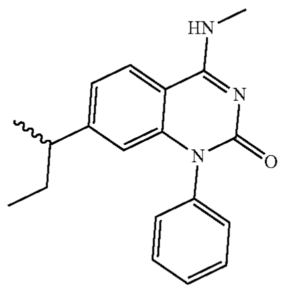 [SMILES: CCC(C)c1ccc2c(NC)nc(=O)n(-c3ccccc3)c2c1] | 4-(methylamino)-7-(methylpropyl)-1-phenylhydroquinazolin-2-one | m/z [M + H]+ 308.2 |
| 383 | 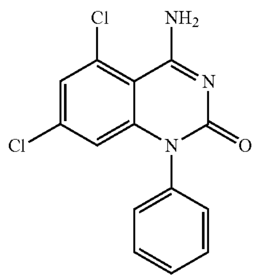 [SMILES: Nc1nc(=O)n(-c2ccccc2)c2cc(Cl)cc(Cl)c12] | 4-amino-5,7-dichloro-1-phenyl-hydroquinazolin-2-one | m/z [M + H]+ 306.23 |
| 384 | 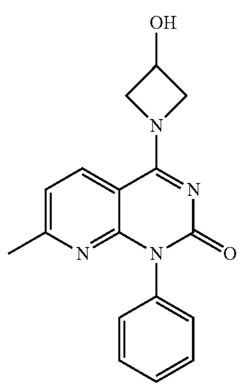 [SMILES: Cc1ccc2c(N3CC(O)C3)nc(=O)n(-c3ccccc3)c2n1] | 4-(3-hydroxyazetidin-1-yl)-7-methyl-1-phenylpyrido[2,3-d]pyrimidin-2(1H)-one | m/z [M + H]+ 309.32 |
| 385 | 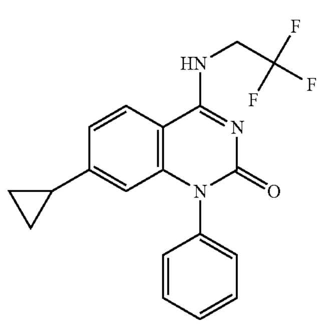 [SMILES: O=c1nc(NCC(F)(F)F)c2ccc(C3CC3)cc2n1-c1ccccc1] | 7-cyclopropyl-1-phenyl-4-[(2,2,2-trifluoroethyl)amino]hydroquinazolin-2-one | m/z [M + H]+ 360.36 |

TABLE 1-continued

| Cpd. No. | Structure | Name | Mass Spec. |
|---|---|---|---|
| 386 | 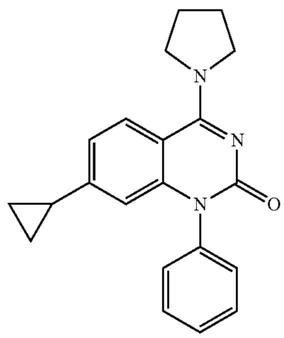 [SMILES: O=c1nc(N2CCCC2)c2ccc(C3CC3)cc2n1-c1ccccc1] | 7-cyclopropyl-1-phenyl-4-pyrrolidin-1-ylhydroquinazolin-2-one | m/z [M + H]⁺ 332.38 |
| 387 | 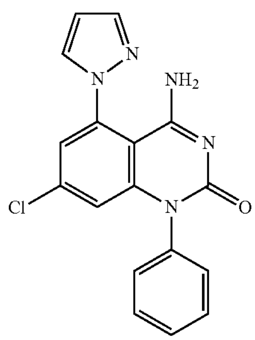 [SMILES: Nc1nc(=O)n(-c2ccccc2)c2cc(Cl)cc(-n3cccn3)c12] | 4-amino-7-chloro-1-phenyl-5-pyrazol-1-ylhydroquinazolin-2-one | m/z [M + H]⁺ 338.31 |
| 388 | 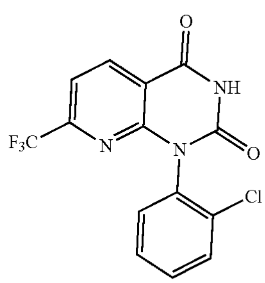 [SMILES: O=c1[nH]c(=O)n(-c2ccccc2Cl)c2nc(C(F)(F)F)ccc12] | 1-(2-chlorophenyl)-7-(trifluoromethyl)-1,3-dihydropyridino[2,3-d]pyrimidine-2,4-dione | m/z [M + H]⁺ 342.0 |
| 389 | 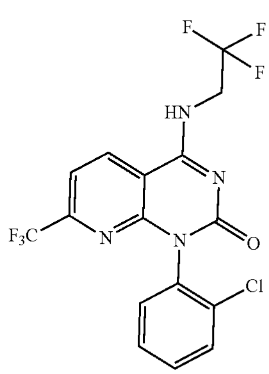 [SMILES: O=c1nc(NCC(F)(F)F)c2ccc(C(F)(F)F)nc2n1-c1ccccc1Cl] | 1-(2-chlorophenyl)-4-[(2,2,2-trifluoroin ethyl)amo]-7-(trifluoro-methyl)-pyrido[2,3-d]pyrimidin-2(1H)-one | m/z [M + H]⁺ 423.10 |

TABLE 1-continued

| Cpd. No. | Structure | Name | Mass Spec. |
|---|---|---|---|
| 390 | 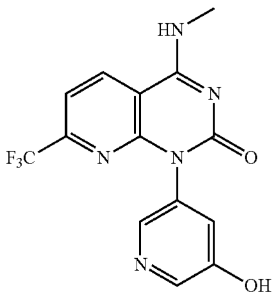 [SMILES: CNc1nc(=O)n(-c2cncc(O)c2)c2nc(C(F)(F)F)ccc12] | 1-(5-hydroxypyridin-3-yl)-4-(methylamino)-7-(trifluoromethyl)pyrido[2,3-d]-pyrimidin-2(1H)-one | m/z [M + H]+ 338.10 |
| 391 | 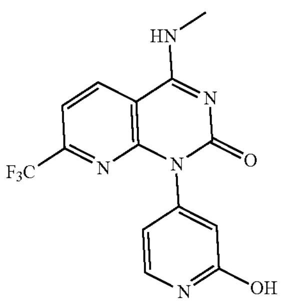 [SMILES: CNc1nc(=O)n(-c2ccnc(O)c2)c2nc(C(F)(F)F)ccc12] | 1-(2-hydroxypyridin-4-yl)-4-(methylamino)-7-(trifluoromethyl)-pyrido[2,3-d]pyrimidin-2(1H)-one | m/z [M + H]+ 338.10 |
| 392 | 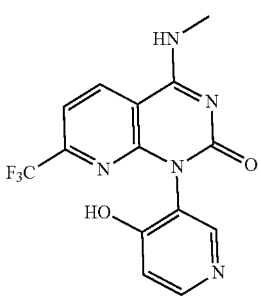 [SMILES: CNc1nc(=O)n(-c2cnccc2O)c2nc(C(F)(F)F)ccc12] | 1-(4-hydroxypyridin-3-yl)-4-(methylamino)-7-(trifluoromethyl)pyrido[2,3-d]-pyrimidin-2(1H)-one | m/z [M + H]+ 338.10 |
| 393 | 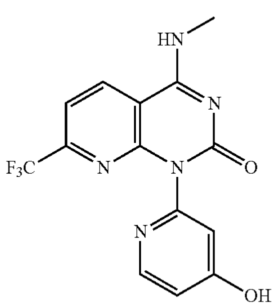 [SMILES: CNc1nc(=O)n(-c2cc(O)ccn2)c2nc(C(F)(F)F)ccc12] | 1-(5-hydroxypyridin-2-yl)-4-(methylamino)-7-(trifluoromethyl)pyrido[2,3-d]-pyrimidin-2(1H)-one | m/z [M + H]+ 338.10 |
| 394 | 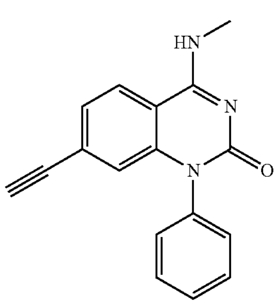 [SMILES: C#Cc1ccc2c(NC)nc(=O)n(-c3ccccc3)c2c1] | 7-ethynyl-4-(methylamino)-1-phenyl-hydroquinazolin-2-one | m/z [M + H]+ 276.0 |

TABLE 1-continued

| Cpd. No. | Structure | Name | Mass Spec. |
|---|---|---|---|
| 395 | 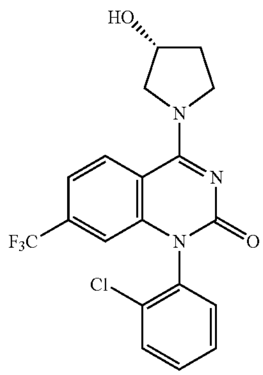 [SMILES: O=c1nc(N2CC[C@@H](O)C2)c2ccc(C(F)(F)F)cc2n1-c1ccccc1Cl] | 4-((3R)-3-hydroxypyrrolidin-1-yl)-1-(2-chlorophenyl)-7-(trifluoromethyl)hydro-quinazolin-2-one | m/z [M + H]⁺ 410.0 |
| 396 | 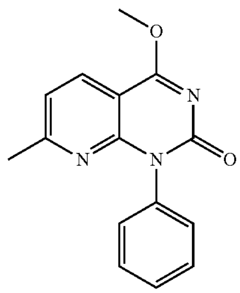 [SMILES: COc1nc(=O)n(-c2ccccc2)c2nc(C)ccc12] | 4-methoxy-7-methyl-1-phenylpyrido-[2,3-d]pyrimidin-2(1H)-one | m/z [M + H]⁺ 268.12 |
| 397 | 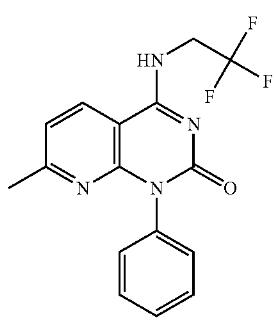 [SMILES: Cc1ccc2c(NCC(F)(F)F)nc(=O)n(-c3ccccc3)c2n1] | 7-methyl-1-phenyl-4-[(2,2,2-trifluoro-ethyl)amino]pyrido[2,3-d]pyrimidin-2(1H)-one | m/z [M + H]⁺ 335.16 |
| 398 | 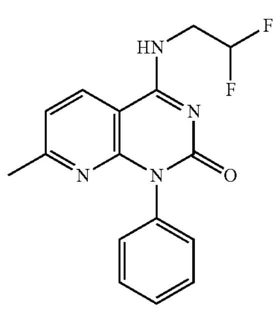 [SMILES: Cc1ccc2c(NCC(F)F)nc(=O)n(-c3ccccc3)c2n1] | 4-[(2,2-difluoroethyl)amino]-7-methyl-1-phenylpyrido[2,3-d]pyrimidin-2(1H)-one | m/z [M + H]⁺ 317.17 |
| 399 | 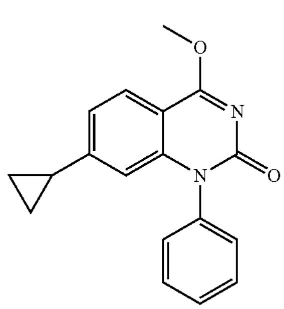 [SMILES: COc1nc(=O)n(-c2ccccc2)c2cc(C3CC3)ccc12] | 7-cyclopropyl-4-methoxy-1-phenyl-hydroquinazolin-2-one | m/z [M + H]⁺ 293.1 |

TABLE 1-continued

| Cpd. No. | Structure | Name | Mass Spec. |
|---|---|---|---|
| 400 | 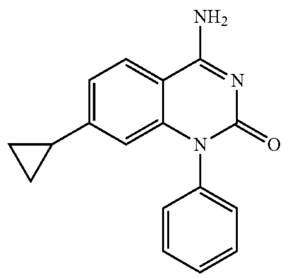 [SMILES: Nc1nc(=O)n(-c2ccccc2)c2cc(C3CC3)ccc12] | 4-amino-7-cyclopropyl-1-phenylhydroquinazolin-2-one | m/z [M + H]+ 278.21 |
| 401 | 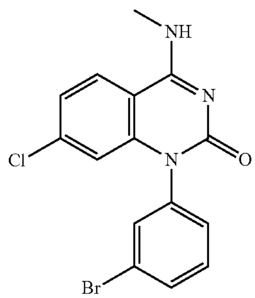 [SMILES: CNc1nc(=O)n(-c2cccc(Br)c2)c2cc(Cl)ccc12] | 1-(3-bromophenyl)-7-chloro-4-(methylamino)hydroquinazolin-2-one | m/z [M + H]+ 363.97 |
| 402 | 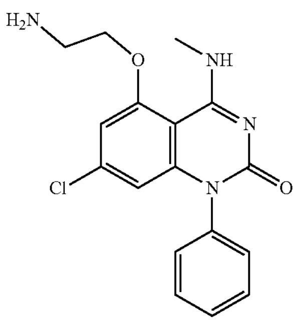 [SMILES: CNc1nc(=O)n(-c2ccccc2)c2cc(Cl)cc(OCCN)c12] | 5-(2-aminoethoxy)-7-chloro-4-(methylamino)-1-phenylhydroquinazolin-2-one | m/z [M + H]+ 345.1 |
| 403 | 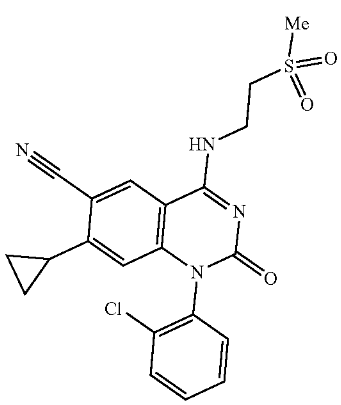 [SMILES: CS(=O)(=O)CCNc1nc(=O)n(-c2ccccc2Cl)c2cc(C3CC3)c(C#N)cc12] | 1-(2-chlorophenyl)-7-cyclopropyl-4-((2-(methylsulfonyl)ethyl)amino)-2-oxo-1,2-dihydroquinazoline-6-carbonitrile | m/z [M + H]+ 443.1 |

TABLE 1-continued

| Cpd. No. | Structure | Name | Mass Spec. |
|---|---|---|---|
| 404 | 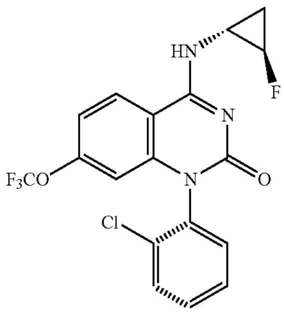 | 4-[((1R,2R)-2-fluorocyclopropyl)-amino]-1-(2-chlorophenyl)-7-(trifluoromethoxy)hydroquinazolin-2-one | m/z [M + H]+ 414.0. |
| 405 | 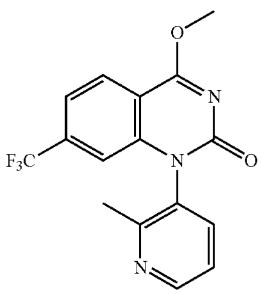 [SMILES: COc1nc(=O)n(-c2cccnc2C)c2cc(C(F)(F)F)ccc12] | 4-methoxy-7-methyl-1-(2-methyl-pyridin-3-yl)quinazolin-2(1H)-one | m/z [M + H]+ 336.40 |
| 406 | 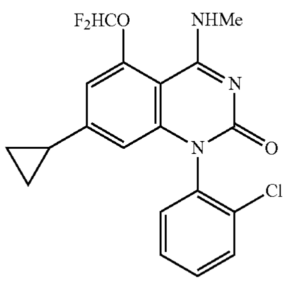 [SMILES: CNc1nc(=O)n(-c2ccccc2Cl)c2cc(C3CC3)cc(OC(F)F)c12] | 5-(difluoromethoxy)-1-(2-chlorophenyl)-7-cyclopropyl-4-(methylamino)hydro-quinazolin-2-one | m/z [M + H]+ 392.3. |
| 407 | 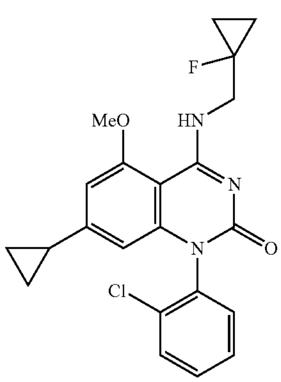 [SMILES: COc1cc(C2CC2)cc2c1c(NCC1(F)CC1)nc(=O)n2-c1ccccc1Cl] | 1-(2-chlorophenyl)-7-cyclopropyl-4-{[(fluorocyclopropyl)methyl]amino}-5-methoxyhydroquinazolin-2-one | m/z [M + H]+ 414.39 |

TABLE 1-continued

| Cpd. No. | Structure | Name | Mass Spec. |
|---|---|---|---|
| 408 | 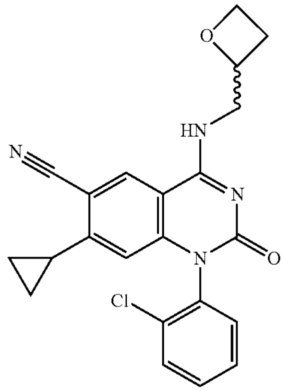 [SMILES: N#Cc1cc2c(NCC3CCO3)nc(=O)n(-c3ccccc3Cl)c2cc1C1CC1] | 1-(2-chlorophenyl)-7-cyclopropyl-4-((oxetan-2-ylmethyl)amino)-2-oxo-1,2-dihydroquinazoline-6-carbonitrile | m/z [M + H]+ 407.0 |
| 409 | 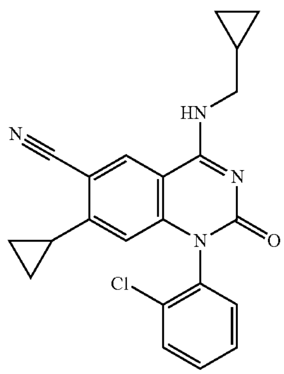 [SMILES: N#Cc1cc2c(NCC3CC3)nc(=O)n(-c3ccccc3Cl)c2cc1C1CC1] | 1-(2-chlorophenyl)-7-cyclopropyl-4-((cyclopropylmethyl)amino)-2-oxo-1,2-dihydroquinazoline-6-carbonitrile | m/z [M + H]+ 391.0 |
| 410 | 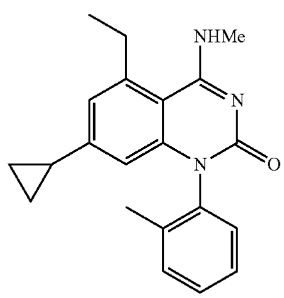 [SMILES: CCc1cc(C2CC2)cc2c1c(NC)nc(=O)n2-c1ccccc1C] | 7-cyclopropyl-5-ethyl-4-(methylamino)-1-(2-methylphenyl)hydroquinazolin-2-one | m/z [M + H]+ 334.37. |
| 411 | 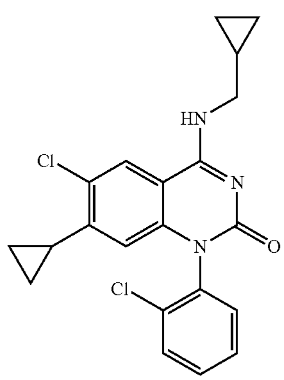 [SMILES: O=c1nc(NCC2CC2)c2cc(Cl)c(C3CC3)cc2n1-c1ccccc1Cl] | 6-chloro-1-(2-chlorophenyl)-7-cyclopropyl-4-[(cyclopropylmethyl)amino]-hydroquinazolin-2-one | m/z [M + H]+ 400.1. |

TABLE 1-continued

| Cpd. No. | Structure | Name | Mass Spec. |
|---|---|---|---|
| 412 | 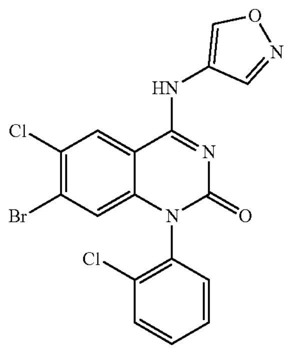 [SMILES: O=c1nc(Nc2cnoc2)c2cc(Cl)c(Br)cc2n1-c1ccccc1Cl] | 7-bromo-6-chloro-1-(2-chlorophenyl)-4-(isoxazol-4-ylamino)hydroquinazolin-2-one | m/z [M + H]+ 452.9 (major) |
| 413 | 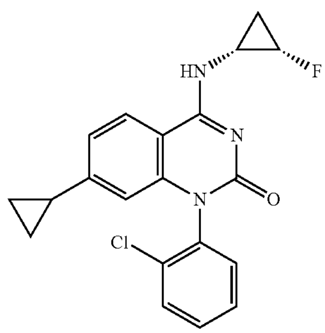 [SMILES: O=c1nc(N[C@@H]2C[C@@H]2F)c2ccc(C3CC3)cc2n1-c1ccccc1Cl] | 4-[((2S,1R)-2-fluorocyclopropyl)amino]-1-(2-chlorophenyl)-7-cyclopropyl-hydroquinazolin-2-one | m/z [M + H]+ 370.0 |
| 414 | 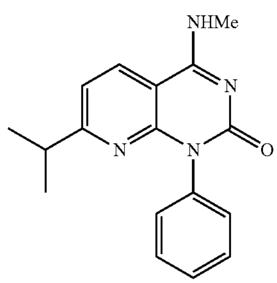 [SMILES: CNc1nc(=O)n(-c2ccccc2)c2nc(C(C)C)ccc12] | 4-(methylamino)-7-(methylethyl)-1-phenylpyrido[2,3-d]pyrimidin-2(1H)-2-one | m/z [M + H]+ 295.1 |
| 415 | 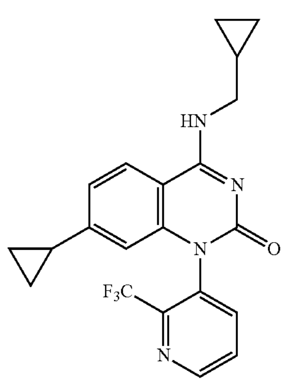 | 7-cyclopropyl-4[(cyclopropylmethyl)-amino]-1-[2-(trifluoromethyl)(3-pyridyl)]hydroquinazolin-2-one | m/z [M + H]+ 399.1 |

TABLE 1-continued

| Cpd. No. | Structure | Name | Mass Spec. |
|---|---|---|---|
| 416 | 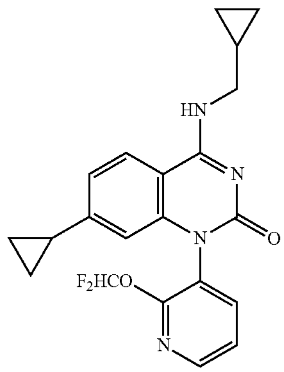 [SMILES: O=c1nc(NCC2CC2)c2ccc(C3CC3)cc2n1-c1cccnc1OC(F)F] | 1-[2-(difluoromethoxy)(3-pyridyl)]-7-cyclopropyl-4-[(cyclopropylmethyl)-amino]hydroquinazolin-2-one | m/z [M + H]+ 401.1. |
| 417 | 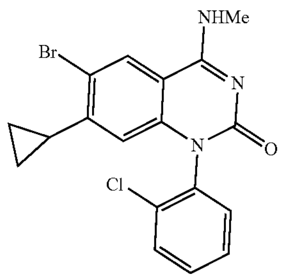 [SMILES: CNc1nc(=O)n(-c2ccccc2Cl)c2cc(C3CC3)c(Br)cc12] | 6-bromo-1-(2-chlorophenyl)-7-cyclopropyl-4-(methylamino)hydroquinazolin-2-one | m/z [M + H]+ 404.0 |
| 418 | 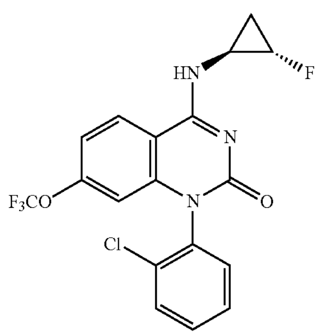 [SMILES: O=c1nc(N[C@H]2C[C@@H]2F)c2ccc(OC(F)(F)F)cc2n1-c1ccccc1Cl] | 1-(2-chlorophenyl)-4-(((1S,2S)-2-fluorocyclopropyl)amino)-7-(trifluoromethoxy)quinazolin-2(1H)-one | m/z [M + H]+ 414.0. |
| 419 | 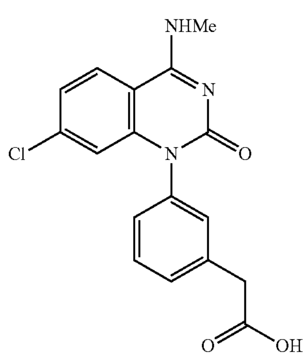 [SMILES: CNc1nc(=O)n(-c2cccc(CC(=O)O)c2)c2cc(Cl)ccc12] | 2-(3-(7-chloro-4-(methylamino)-2-oxoquinazolin-1(2H)-yl)phenyl)acetic acid | m/z [M + H]+ 344.30. |

TABLE 1-continued

| Cpd. No. | Structure | Name | Mass Spec. |
|---|---|---|---|
| 420 | 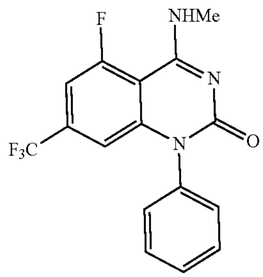 [SMILES: CNc1nc(=O)n(-c2ccccc2)c2cc(C(F)(F)F)cc(F)c12] | 5-fluoro-4-(methylamino)-1-phenyl-7-(trifluoromethyl)hydroquinazolin-2-one | m/z [M + H]+ 338.1. |
| 421 | 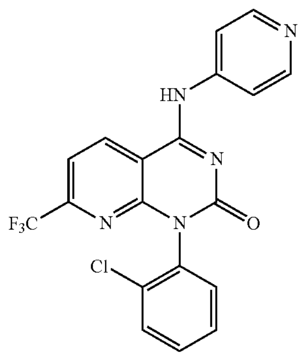 [SMILES: O=c1nc(Nc2ccncc2)c2ccc(C(F)(F)F)nc2n1-c1ccccc1Cl] | 1-(2-chlorophenyl)-4-(pyridin-4-yl-amino)-7-(trifluoromethyl)pyrido[2,3-d]-pyrimidin-2(1H)-one | m/z [M + H]+ 418.00. |
| 422 | 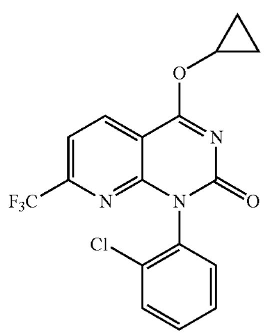 [SMILES: O=c1nc(OC2CC2)c2ccc(C(F)(F)F)nc2n1-c1ccccc1Cl] | 1-(2-chlorophenyl)-4-cyclopropoxy-7-(trifluoromethyl)pyrido[2,3-d]pyrimidin-2(1H)-one | m/z [M + H]+ 382.33 |
| 423 | 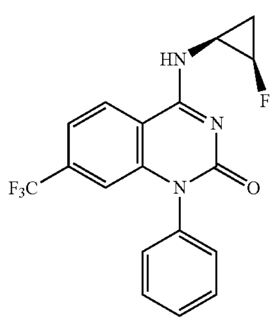 [SMILES: O=c1nc(N[C@H]2C[C@H]2F)c2ccc(C(F)(F)F)cc2n1-c1ccccc1] | 1-(2-chlorophenyl)-7-cyclopropyl-4-methoxyhydroquinazolin-2-one | m/z [M + H]+ 327.16. |
| 424 | 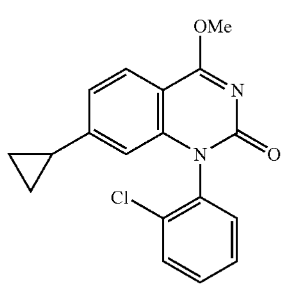 [SMILES: COc1nc(=O)n(-c2ccccc2Cl)c2cc(C3CC3)ccc12] | 4(((1S,2R)-2-fluorocyclopropyl)amino)-1-phenyl-7-(trifluoromethyl)quinazolin-2(1H)-one | m/z [M + H]+ 364.1 |

TABLE 1-continued

| Cpd. No. | Structure | Name | Mass Spec. |
|---|---|---|---|
| 425 | 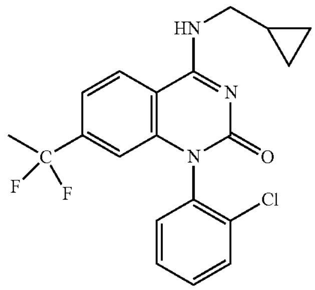 [SMILES: CC(F)(F)c1ccc2c(NCC3CC3)nc(=O)n(-c3ccccc3Cl)c2c1] | 1-(2-chlorophenyl)-4-((cyclopropyl-methyl)amino)-7-(1,1-difluoroethyl)-quinazolin-2(1H)-one | m/z [M + H]+ 390.1 |
| 426 | 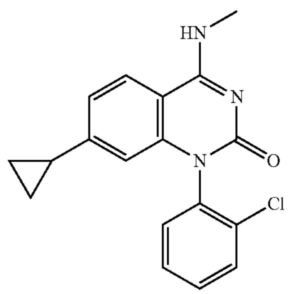 [SMILES: CNc1nc(=O)n(-c2ccccc2Cl)c2cc(C3CC3)ccc12] | 1-(2-chlorophenyl)-7-cyclopropyl-4-(methylamino)quinazolin-2(1H)-one | m/z [M + H]+ 326.0 |
| 427 | 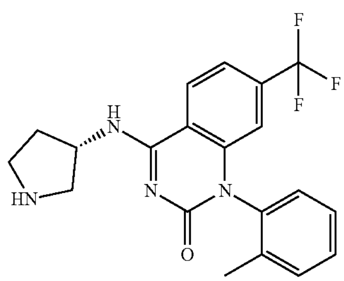 [SMILES: Cc1ccccc1-n1c(=O)nc(N[C@H]2CCNC2)c2ccc(C(F)(F)F)cc21] | (S)-4-(pyrrolidin-3-ylamino)-1-(o-tolyl)-7-(trifluoromethyl)quinazolin-2(1H)-one | m/z [M + H] 389.15 |
| 428 | 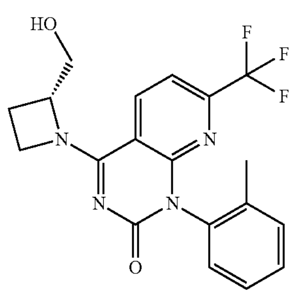 [SMILES: Cc1ccccc1-n1c(=O)nc(N2CC[C@@H]2CO)c2ccc(C(F)(F)F)nc21] | (R)-4-(2-(hydroxymethyl)azetidin-1-yl)-1-(o-tolyl)-7-(trifluoromethyl)pyrido-[2,3-d]pyrimidin-2(1H)-one | m/z [M + H] 391.1 |
| 429 | 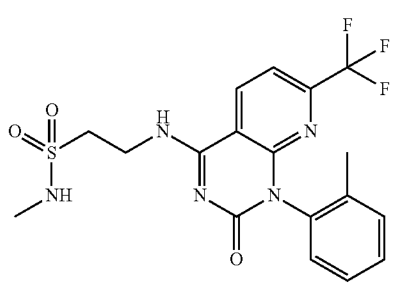 [SMILES: CNS(=O)(=O)CCNc1nc(=O)n(-c2ccccc2C)c2nc(C(F)(F)F)ccc12] | N-methyl-2-((2-oxo-1-(o-tolyl)-7-(trifluoromethyl)-1,2-dihydropyrido[2,3-d]pyrimidin-4-yl)amino)ethane-1-sulfonamide | m/z [M + H] 442.1 |

TABLE 1-continued

| Cpd. No. | Structure | Name | Mass Spec. |
|---|---|---|---|
| 430 | 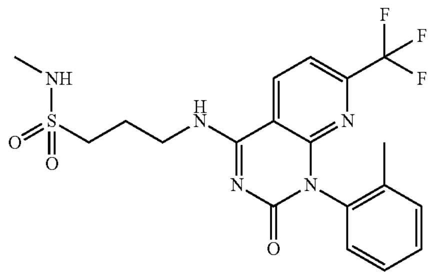 [SMILES: CNS(=O)(=O)CCCNc1nc(=O)n(-c2ccccc2C)c2nc(C(F)(F)F)ccc12] | N-methyl-3-((2-oxo-1-(o-tolyl)-7-(trifluoromethyl)-1,2-dihydropyrido[2,3-d]pyrimidin-4-yl)amino)propane-1-sulfonamide | m/z [M + H] 456.1 |
| 431 | 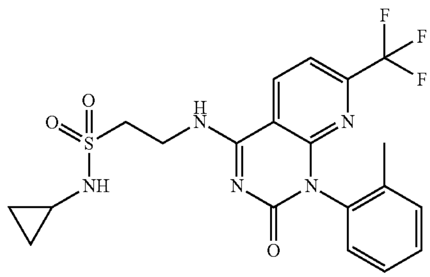 [SMILES: Cc1ccccc1-n1c(=O)nc(NCCS(=O)(=O)NC2CC2)c2ccc(C(F)(F)F)nc21] | N-cyclopropyl-2-((2-oxo-1-(o-tolyl)-7-(trifluoromethyl)-1,2-dihydropyrido[2,3-d]pyrimidin-4-yl)amino)ethane-1-sulfonamide | m/z [M + H] 468.1 |
| 432 | 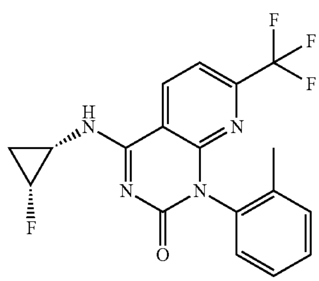 [SMILES: Cc1ccccc1-n1c(=O)nc(N[C@H]2C[C@H]2F)c2ccc(C(F)(F)F)nc21] | 4-(((1S,2R)-2-fluorocyclopropyl)amino)-1-(o-tolyl)-7-(trifluoromethyl)pyrido-[2,3-d]pyrimidin-2(1H)-one | m/z [M + H] 379.1 |
| 433 | 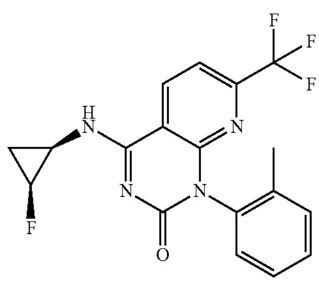 [SMILES: Cc1ccccc1-n1c(=O)nc(N[C@@H]2C[C@@H]2F)c2ccc(C(F)(F)F)nc21] | 4-(((1R,2S)-2-fluorocyclopropyl)amino)-1-(o-tolyl)-7-(trifluoromethyl)pyrido-[2,3-d]pyrimidin-2(1H)-one | m/z [M + H] 379.1 |
| 434 | 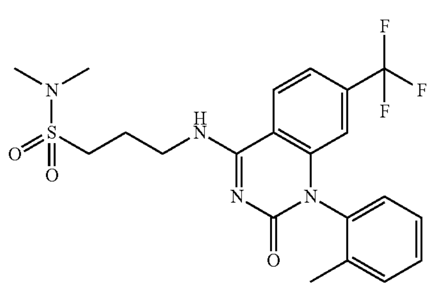 [SMILES: Cc1ccccc1-n1c(=O)nc(NCCCS(=O)(=O)N(C)C)c2ccc(C(F)(F)F)cc21] | N,N-dimethyl-3-((2-oxo-1-(o-tolyl)-7-(trifluoromethyl)-1,2-dihydroquinazolin-4-yl)amino)propane-1-sulfonamide | m/z [M + H] 469.1 |

TABLE 1-continued

| Cpd. No. | Structure | Name | Mass Spec. |
|---|---|---|---|
| 435 | 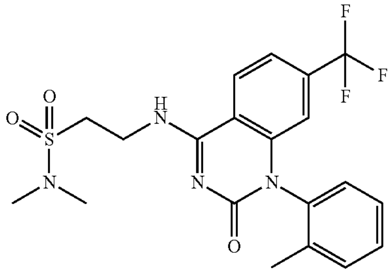 [SMILES: Cc1ccccc1-n1c(=O)nc(NCCS(=O)(=O)N(C)C)c2ccc(C(F)(F)F)cc21] | N,N-dimethyl-2-((2-oxo-1-(o-tolyl)-7-(trifluoromethyl)-1,2-dihydroquinazolin-4-yl)amino)ethane-1-sulfonamide | m/z [M + H]$^+$ 455.1 |
| 436 | 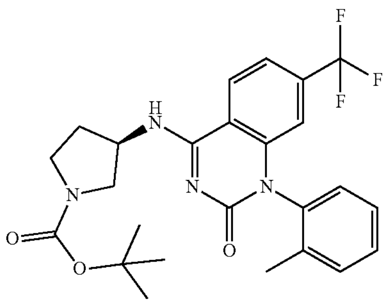 [SMILES: Cc1ccccc1-n1c(=O)nc(N[C@@H]2CCN(C(=O)OC(C)(C)C)C2)c2ccc(C(F)(F)F)cc21] | tert-butyl (R)-3-((2-oxo-1-(o-tolyl)-7-(trifluoromethyl)-1,2-dihydroquinazolin-4-yl)amino)pyrrolidine-1-carboxylate | m/z [M + H]$^+$ 489.2 |
| 437 | 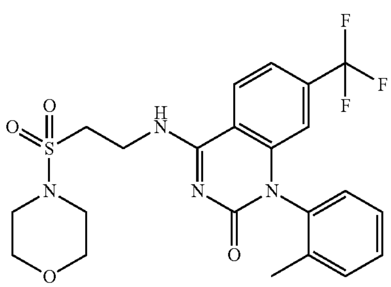 [SMILES: Cc1ccccc1-n1c(=O)nc(NCCS(=O)(=O)N2CCOCC2)c2ccc(C(F)(F)F)cc21] | 4-((2-(morpholinosulfonyl)ethyl)amino)-1-(o-tolyl)-7-(trifluoromethyl)-quinazolin-2(1H)-one | m/z [M + H] 497.1 |
| 438 | 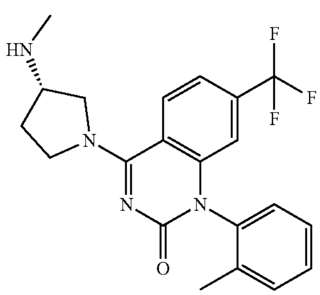 [SMILES: CN[C@H]1CCN(c2nc(=O)n(-c3ccccc3C)c3cc(C(F)(F)F)ccc23)C1] | (S)-4-(3-(methylamino)pyrrolidin-1-yl)-1-(o-tolyl)-7-(trifluoromethyl)-quinazolin-2(1H)-one | m/z [M + H] 403.1 |
| 439 | 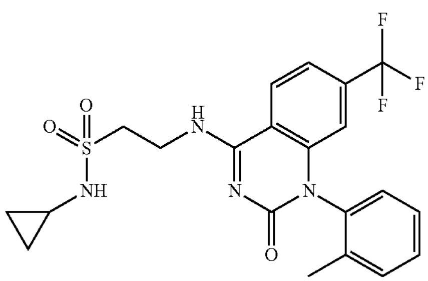 [SMILES: Cc1ccccc1-n1c(=O)nc(NCCS(=O)(=O)NC2CC2)c2ccc(C(F)(F)F)cc21] | N-cyclopropyl-2-((2-oxo-1-(o-tolyl)-7-(trifluoromethyl)-1,2-dihydroquinazolin-4-yl)amino)ethane-1-sulfonamide | m/z [M + H] 467.1 |

TABLE 1-continued

| Cpd. No. | Structure | Name | Mass Spec. |
|---|---|---|---|
| 440 | 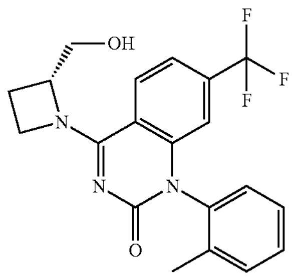 [SMILES: Cc1ccccc1-n1c(=O)nc(N2CC[C@@H]2CO)c2ccc(C(F)(F)F)cc21] | (R)-4-(2-(hydroxymethyl)azetidin-1-yl)-1-(o-tolyl)-7-(trifluoromethyl)-quinazolin-2(1H)-one | m/z [M + H] 390.1 |
| 441 | 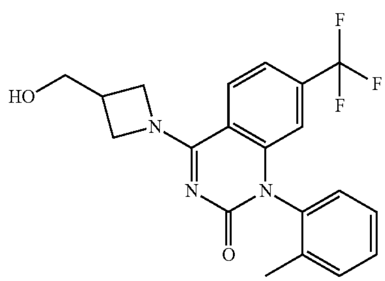 [SMILES: Cc1ccccc1-n1c(=O)nc(N2CC(CO)C2)c2ccc(C(F)(F)F)cc21] | 4-(3-(hydroxymethyl)azetidin-1-yl)-1-(o-tolyl)-7-(trifluoromethyl)quinazolin-2(1H)-one | m/z [M + H] 390.1 |
| 442 | 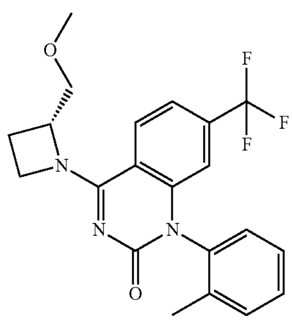 [SMILES: COC[C@H]1CCN1c1nc(=O)n(-c2ccccc2C)c2cc(C(F)(F)F)ccc12] | (R)-4-(2-(methoxymethyl)azetidin-1-yl)-1-(o-tolyl)-7-(trifluoromethyl)-quinazolin-2(1H)-one | m/z [M + H] 404 |
| 443 | 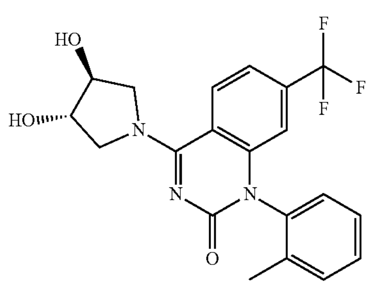 [SMILES: Cc1ccccc1-n1c(=O)nc(N2C[C@H](O)[C@@H](O)C2)c2ccc(C(F)(F)F)cc21] | 4-((3S,4S)-3,4-dihydroxypyrrolidin-1-yl)-1-(o-tolyl)-7-(trifluoromethyl)-quinazolin-2(1H)-one | m/z [M + H] 406.1 |
| 444 | 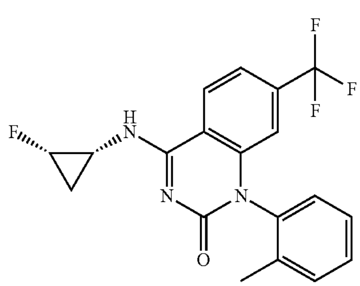 [SMILES: Cc1ccccc1-n1c(=O)nc(N[C@@H]2C[C@@H]2F)c2ccc(C(F)(F)F)cc21] | 4-(((1R,2S)-2-fluorocyclopropyl)amino)-1-(o-tolyl)-7-(trifluoromethyl)-quinazolin-2(1H)-one | m/z [M + H] 378.1 |

TABLE 1-continued

| Cpd. No. | Structure | Name | Mass Spec. |
|---|---|---|---|
| 445 | 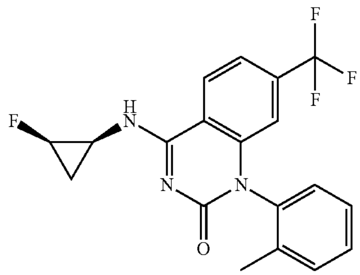 [SMILES: Cc1ccccc1-n1c(=O)nc(N[C@H]2C[C@H]2F)c2ccc(C(F)(F)F)cc21] | 4-(((1S,2R)-2-fluorocyclopropyl)amino)-1-(o-tolyl)-7-(trifluoromethyl)-quinazolin-2(1H)-one | m/z [M + H] 378.1 |
| 446 | 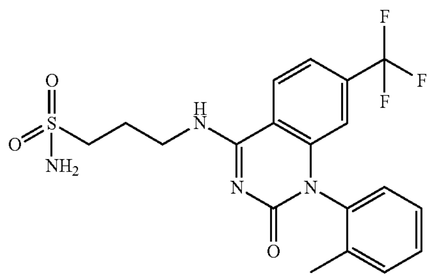 [SMILES: Cc1ccccc1-n1c(=O)nc(NCCCS(N)(=O)=O)c2ccc(C(F)(F)F)cc21] | 3-((2-oxo-1-(o-tolyl)-7-(trifluoromethyl)-1,2-dihydroquinazolin-4-yl)amino)propane-1-sulfonamide | m/z [M + H] 441.1 |
| 447 | 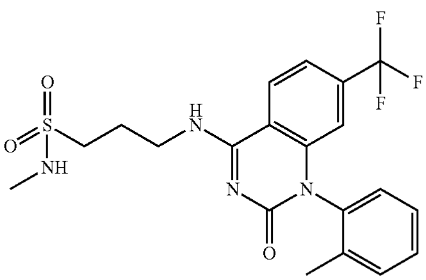 [SMILES: CNS(=O)(=O)CCCNc1nc(=O)n(-c2ccccc2C)c2cc(C(F)(F)F)ccc12] | N-methyl-3-((2-oxo-1-(o-tolyl)-7-(trifluoromethyl)-1,2-dihydroquinazolin-4-yl)amino)propane-1-sulfonamide | m/z [M + H] 455.1 |
| 448 | 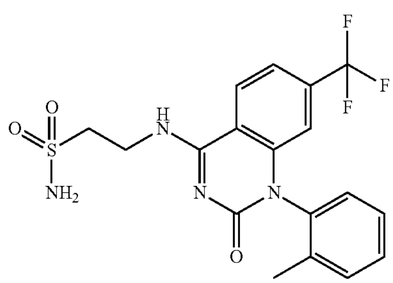 [SMILES: Cc1ccccc1-n1c(=O)nc(NCCS(N)(=O)=O)c2ccc(C(F)(F)F)cc21] | 2-((2-oxo-1-(o-tolyl)-7-(trifluoromethyl)-1,2-dihydroquinazolin-4-yl)amino)ethane-1-sulfonamide | m/z [M + H] 427.05 |
| 449 | 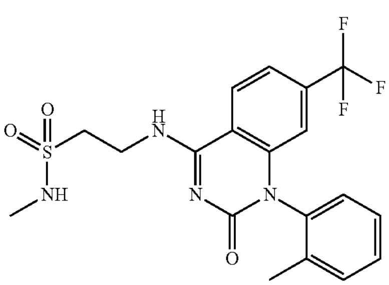 [SMILES: CNS(=O)(=O)CCNc1nc(=O)n(-c2ccccc2C)c2cc(C(F)(F)F)ccc12] | N-methyl-2-((2-oxo-1-(o-tolyl)-7-(trifluoromethyl)-1,2-dihydroquinazolin-4-yl)amino)ethane-1-sulfonamide | m/z [M + H] 441.1 |

TABLE 1-continued

| Cpd. No. | Structure | Name | Mass Spec. |
|---|---|---|---|
| 450 | 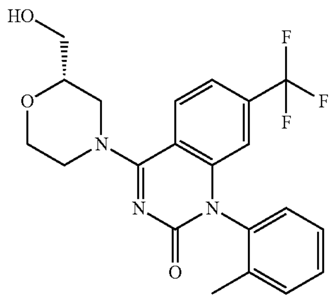 [SMILES: Cc1ccccc1-n1c(=O)nc(N2CCO[C@H](CO)C2)c2ccc(C(F)(F)F)cc21] | (S)-4-(2-(hydroxymethyl)morpholino)-1-(o-tolyl)-7-(trifluoromethyl)quinazolin-2(1H)-one | m/z [M + H] 420.1 |
| 451 | 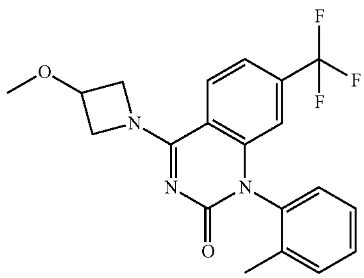 [SMILES: COC1CN(c2nc(=O)n(-c3ccccc3C)c3cc(C(F)(F)F)ccc23)C1] | 4-(3-methoxyazetidin-1-yl)-1-(o-tolyl)-7-(trifluoromethyl)quinazolin-2(1H)-one | m/z [M + H] 390.1 |
| 452 | 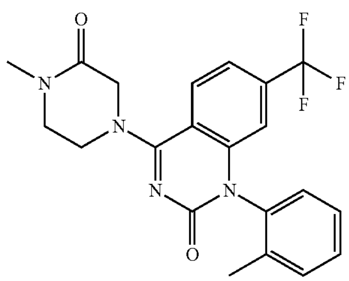 [SMILES: Cc1ccccc1-n1c(=O)nc(N2CCN(C)C(=O)C2)c2ccc(C(F)(F)F)cc21] | (4-(4-methyl-3-oxopiperazin-1-yl)-1-(o-tolyl)-7-(trifluoromethyl)quinazolin-2(1H)-one | m/z [M + H] 417.1 |
| 453 | 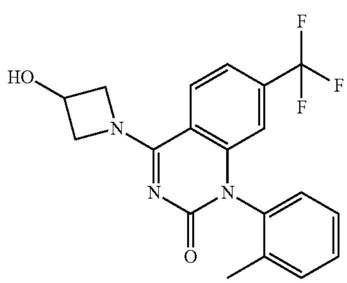 [SMILES: Cc1ccccc1-n1c(=O)nc(N2CC(O)C2)c2ccc(C(F)(F)F)cc21] | 4-(3-hydroxyazetidin-1-yl)-1-(o-tolyl)-7-(trifluoromethyl)quinazolin-2(1H)-one | m/z [M + H] 376.1 |
| 454 | 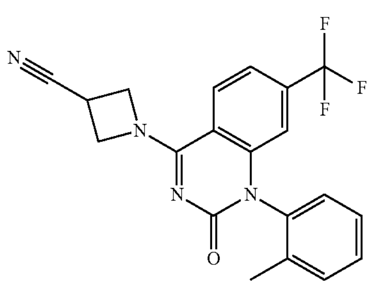 [SMILES: Cc1ccccc1-n1c(=O)nc(N2CC(C#N)C2)c2ccc(C(F)(F)F)cc21] | 1-(2-oxo-1-(o-tolyl)-7-(trifluoromethyl)-1,2-dihydroquinazolin-4-yl)azetidine-3-carbonitrile | m/z [M + H] 385.1 |

TABLE 1-continued

| Cpd. No. | Structure | Name | Mass Spec. |
|---|---|---|---|
| 455 | 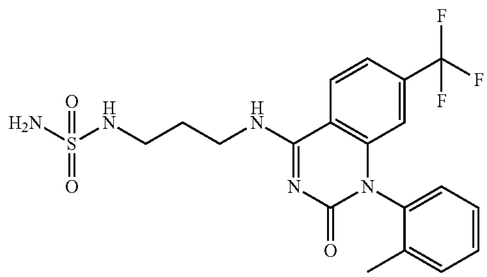 [SMILES: Cc1ccccc1-n1c(=O)nc(NCCCNS(N)(=O)=O)c2ccc(C(F)(F)F)cc21] | amino(3-{[1-(2-methylphenyl)-2-oxo-7-(trifluoromethyl)hydroquinazolin-4-yl]-amino}propyl)sulfonamide | m/z [M + H] 456.1 |
| 456 | 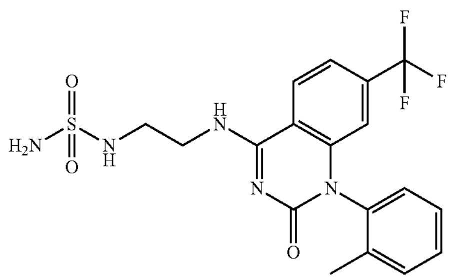 [SMILES: Cc1ccccc1-n1c(=O)nc(NCCNS(N)(=O)=O)c2ccc(C(F)(F)F)cc21] | amino(2-{[1-(2-methylphenyl)-2-oxo-7-(trifluoromethyl)hydroquinazolin-4-yl]-amino}ethyl)sulfonamide | m/z [M + H] 442.1 |
| 457 | 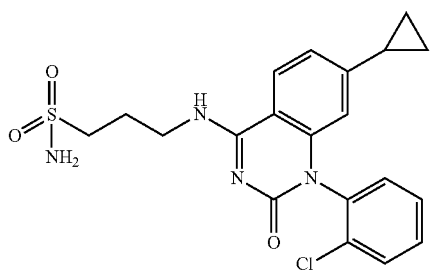 | (3-((1-(2-chlorophenyl)-7-cyclopropyl-2-oxo-1,2-dihydroquinazolin-4-yl)-amino)propane-1-sulfonamide | m/z [M + H] 433.1 |
| 458 | 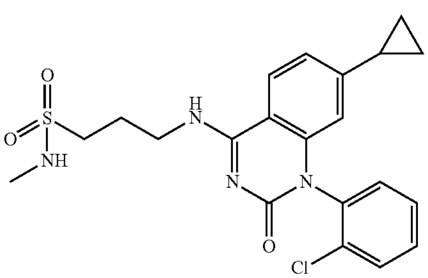 | 3-((1-(2-chlorophenyl)-7-cyclopropyl-2-oxo-1,2-dihydroquinazolin-4-yl)amino)-N-methylpropane-1-sulfonamide | m/z [M + H] 447.0 |
| 459 | 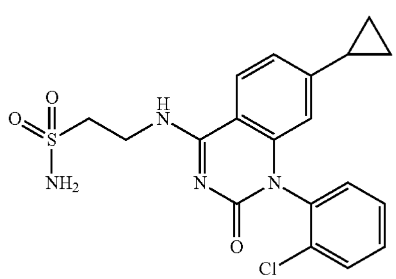 [SMILES: NS(=O)(=O)CCNc1nc(=O)n(-c2ccccc2Cl)c2cc(C3CC3)ccc12] | 2-((1-(2-chlorophenyl)-7-cyclopropyl-2-oxo-1,2-dihydroquinazolin-4-yl)-amino)ethane-1-sulfonamide | m/z [M + H] 419.0 |

TABLE 1-continued

| Cpd. No. | Structure | Name | Mass Spec. |
|---|---|---|---|
| 460 | 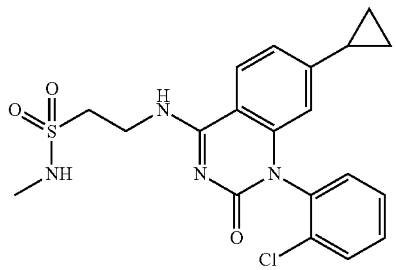 [SMILES: CNS(=O)(=O)CCNc1nc(=O)n(-c2ccccc2Cl)c2cc(C3CC3)ccc12] | 2-((1-(2-chlorophenyl)-7-cyclopropyl-2-oxo-1,2-dihydroquinazolin-4-yl)amino)-N-methylethane-1-sulfonamide | m/z [M + H] 433.1 |
| 461 | 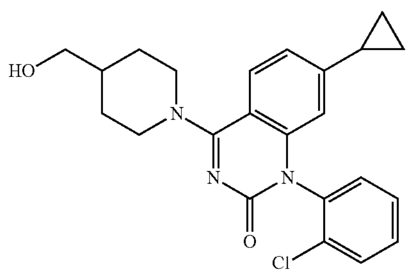 [SMILES: O=c1nc(N2CCC(CO)CC2)c2ccc(C3CC3)cc2n1-c1ccccc1Cl] | 1-(2-chlorophenyl)-7-cyclopropyl-4-(4-(hydroxymethyl)piperidin-1-yl)-quinazolin-2(1H)-one | m/z [M + H] 410.11 |
| 462 | 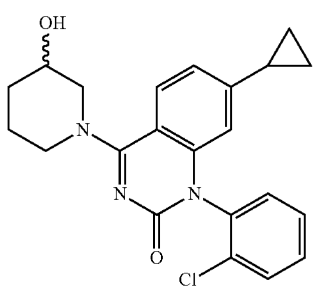 [SMILES: O=c1nc(N2CCCC(O)C2)c2ccc(C3CC3)cc2n1-c1ccccc1Cl] | 1-(2-chlorophenyl)-7-cyclopropyl-4-(3-hydroxypiperidin-1-yl)quinazolin-2(1H)-one | m/z [M + H] 396.1 |
| 463 | 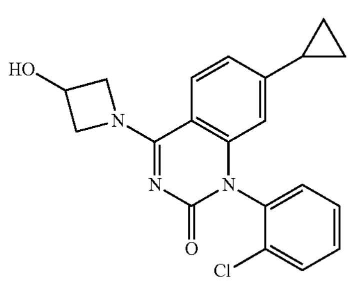 [SMILES: O=c1nc(N2CC(O)C2)c2ccc(C3CC3)cc2n1-c1ccccc1Cl] | 1-(2-chlorophenyl)-7-cyclopropyl-4-(3-hydroxyazetidin-1-yl)quinazolin-2(1H)-one | m/z [M + H] 368.1 |
| 464 | 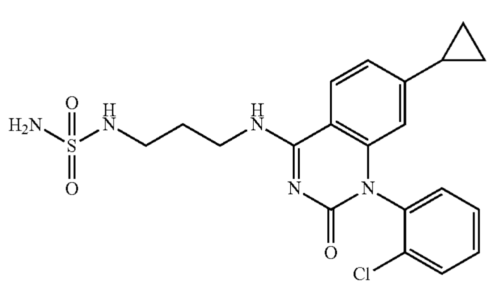 [SMILES: NS(=O)(=O)NCCCNc1nc(=O)n(-c2ccccc2Cl)c2cc(C3CC3)ccc12] | (3-{[1-(2-chlorophenyl)-7-cyclopropyl-2-oxohydroquinazolin-4-yl]amino}-propyl)sulfonamide | m/z [M + H] 448.1 |

TABLE 1-continued

| Cpd. No. | Structure | Name | Mass Spec. |
|---|---|---|---|
| 465 | 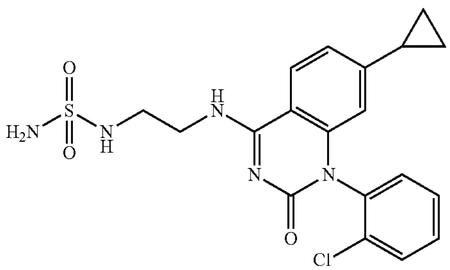 [SMILES: NS(=O)(=O)NCCNc1nc(=O)n(-c2ccccc2Cl)c2cc(C3CC3)ccc12] | (2-{[1-(2-chlorophenyl)-7-cyclopropyl-2-oxohydroquinazolin-4-yl]amino}-ethyl)sulfonamide | m/z [M + H] 434.0 |
| 466 | 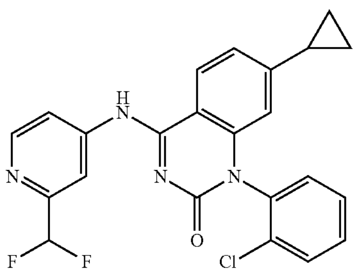 [SMILES: O=c1nc(Nc2ccnc(C(F)F)c2)c2ccc(C3CC3)cc2n1-c1ccccc1Cl] | 1-(2-chlorophenyl)-7-cyclopropyl-4-((2-(difluoromethyl)pyridin-4-yl)amino)-quinazolin-2(1H)-one | m/z [M + H] 439.1 |
| 467 | 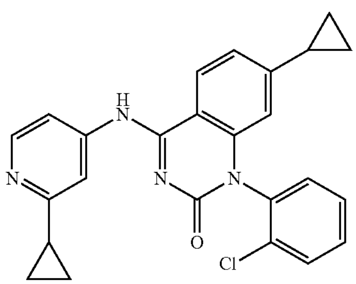 [SMILES: O=c1nc(Nc2ccnc(C3CC3)c2)c2ccc(C3CC3)cc2n1-c1ccccc1Cl] | 1-(2-chlorophenyl)-7-cyclopropyl-4-((2-cyclopropylpyridin-4-yl)amino)-quinazolin-2(1H)-one | m/z [M + H] 429.1 |
| 468 | 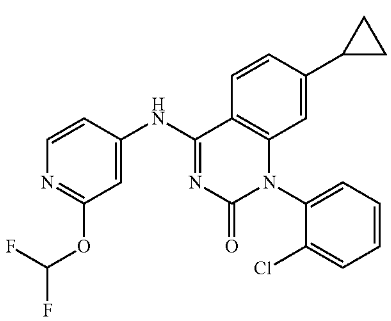 [SMILES: O=c1nc(Nc2ccnc(OC(F)F)c2)c2ccc(C3CC3)cc2n1-c1ccccc1Cl] | 1-(2-chlorophenyl)-7-cyclopropyl-4-((2-(difluoromethoxy)pyridin-4-yl)amino)-quinazolin-2(1H)-one | m/z [M + H] 455.1 |
| 469 | 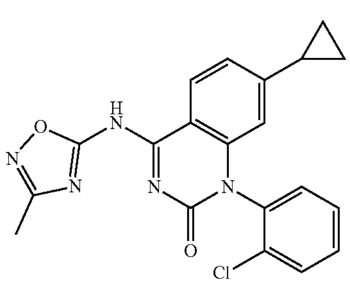 [SMILES: Cc1noc(Nc2nc(=O)n(-c3ccccc3Cl)c3cc(C4CC4)ccc23)n1] | 1-(2-chlorophenyl)-7-cyclopropyl-4-((3-methyl-1,2,4-oxadiazol-5-yl)amino)-quinazolin-2(1H)-one | m/z [M + H] 394.1 |

TABLE 1-continued

| Cpd. No. | Structure | Name | Mass Spec. |
|---|---|---|---|
| 470 | 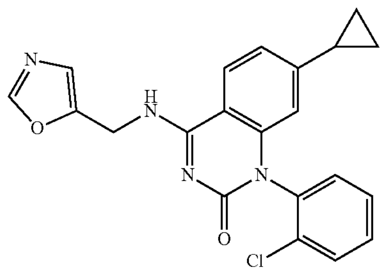 [SMILES: O=c1nc(NCc2cnco2)c2ccc(C3CC3)cc2n1-c1ccccc1Cl] | 1-(2-chlorophenyl)-7-cyclopropyl-4-((oxazol-5-ylmethyl)amino)quinazolin-2(1H)-one | m/z [M + H] 393.1 |
| 471 | 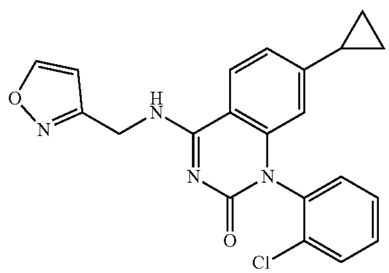 [SMILES: O=c1nc(NCc2ccon2)c2ccc(C3CC3)cc2n1-c1ccccc1Cl] | 1-(2-chlorophenyl)-7-cyclopropyl-4-((isoxazol-3-ylmethyl)amino)quinazolin-2(1H)-one | m/z [M + H] 393.1 |
| 472 | 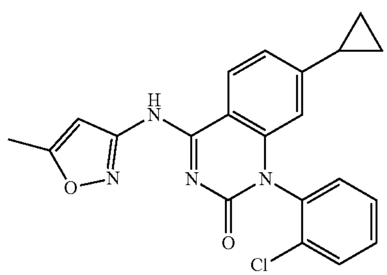 [SMILES: Cc1cc(Nc2nc(=O)n(-c3ccccc3Cl)c3cc(C4CC4)ccc23)no1] | 1-(2-chlorophenyl)-7-cyclopropyl-4-((5-methylisoxazol-3-yl)amino)quinazolin-2(1H)-one | m/z [M + H] 393.1 |
| 473 | 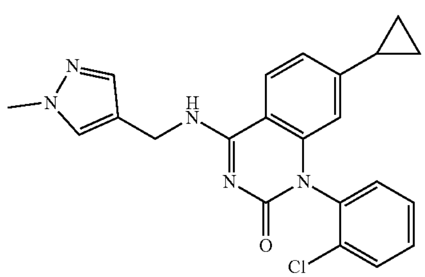 [SMILES: Cn1cc(CNc2nc(=O)n(-c3ccccc3Cl)c3cc(C4CC4)ccc23)cn1] | 1-(2-chlorophenyl)-7-cyclopropyl-4-(((1-methyl-1H-pyrazol-4-yl)methyl)amino)-quinazolin-2(1H)-one | m/z [M + H] 406.1 |
| 474 | 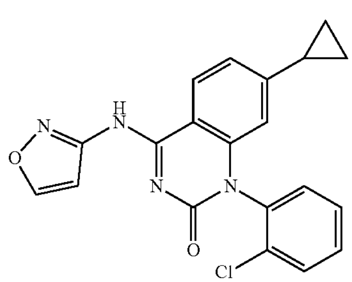 [SMILES: O=c1nc(Nc2ccon2)c2ccc(C3CC3)cc2n1-c1ccccc1Cl] | 1-(2-chlorophenyl)-7-cyclopropyl-4-(isoxazol-3-ylamino)quinazolin-2(1H)-one | m/z [M + H] 379.05 |

TABLE 1-continued

| Cpd. No. | Structure | Name | Mass Spec. |
|---|---|---|---|
| 475 | 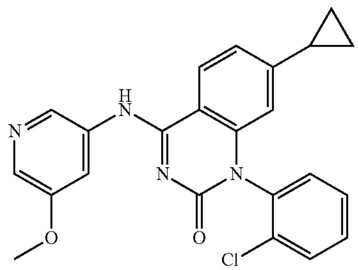 [SMILES: COc1cncc(Nc2nc(=O)n(-c3ccccc3Cl)c3cc(C4CC4)ccc23)c1] | 1-(2-chlorophenyl)-7-cyclopropyl-4-((5-methoxypyridin-3-yl)amino)quinazolin-2(1H)-one | m/z [M + H] 419.1 |
| 476 | 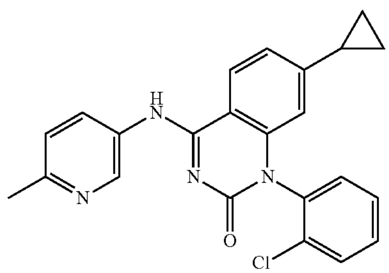 [SMILES: Cc1ccc(Nc2nc(=O)n(-c3ccccc3Cl)c3cc(C4CC4)ccc23)cn1] | 1-(2-chlorophenyl)-7-cyclopropyl-4-((6-methylpyridin-3-yl)amino)quinazolin-2(1H)-one | m/z [M + H] 403.1 |
| 477 | 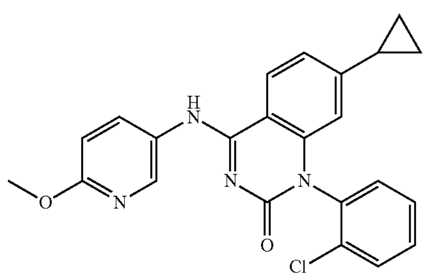 [SMILES: COc1ccc(Nc2nc(=O)n(-c3ccccc3Cl)c3cc(C4CC4)ccc23)cn1] | 1-(2-chlorophenyl)-7-cyclopropyl-4-((6-methoxypyridin-3-yl)amino)quinazolin-2(1H)-one | m/z [M + H] 419.1 |
| 478 | 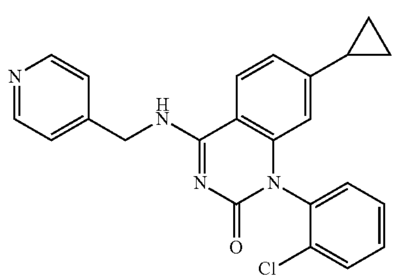 [SMILES: O=c1nc(NCc2ccncc2)c2ccc(C3CC3)cc2n1-c1ccccc1Cl] | 1-(2-chlorophenyl)-7-cyclopropyl-4-((pyridin-4-ylmethyl)amino)quinazolin-2(1H)-one | m/z [M + H] 403.1 |
| 479 | 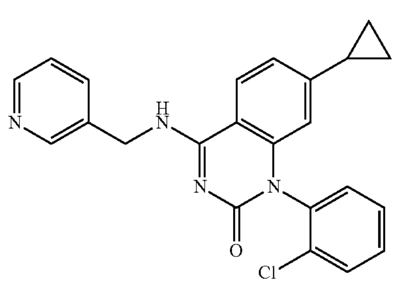 [SMILES: O=c1nc(NCc2cccnc2)c2ccc(C3CC3)cc2n1-c1ccccc1Cl] | 1-(2-chlorophenyl)-7-cyclopropyl-4-((pyridin-3-ylmethyl)amino)quinazolin-2(1H)-one | m/z [M + H] 403.1 |

TABLE 1-continued

| Cpd. No. | Structure | Name | Mass Spec. |
|---|---|---|---|
| 480 | 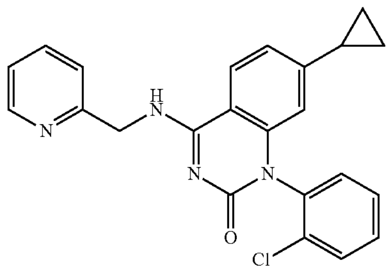 [SMILES: O=c1nc(NCc2ccccn2)c2ccc(C3CC3)cc2n1-c1ccccc1Cl] | 1-(2-chlorophenyl)-7-cyclopropyl-4-((pyridin-2-ylmethyl)amino)quinazolin-2(1H)-one | m/z [M + H] 403.1 |
| 481 | 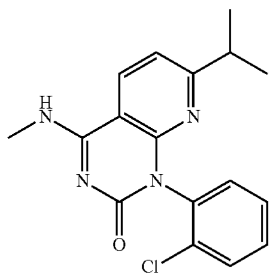 [SMILES: CNc1nc(=O)n(-c2ccccc2Cl)c2nc(C(C)C)ccc12] | 1-(2-chlorophenyl)-7-isopropyl-4-(methylamino)pyrido[2,3-d]pyrimidin-2(1H)-one | m/z [M + H] 329.1 |
| 482 | 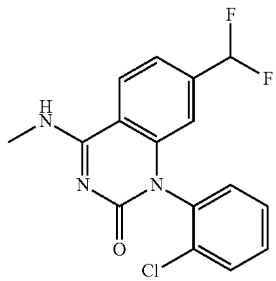 [SMILES: CNc1nc(=O)n(-c2ccccc2Cl)c2cc(C(F)F)ccc12] | 1-(2-chlorophenyl)-7-(difluoromethyl)-4-(methylamino)quinazolin-2(1H)-one | m/z [M + H] 336.0 |
| 483 | 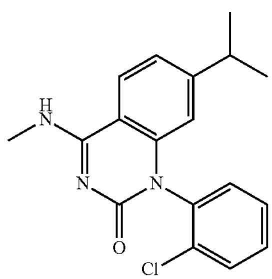 [SMILES: CNc1nc(=O)n(-c2ccccc2Cl)c2cc(C(C)C)ccc12] | 1-(2-chlorophenyl)-7-isopropyl-4-(methylamino)quinazolin-2(1H)-one | m/z [M + H] 328.1 |
| 484 | 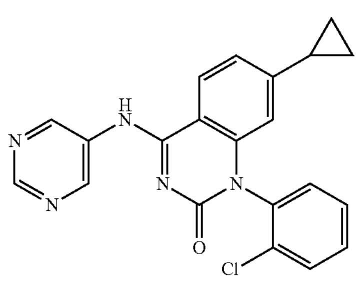 [SMILES: O=c1nc(Nc2cncnc2)c2ccc(C3CC3)cc2n1-c1ccccc1Cl] | 1-(2-chlorophenyl)-7-cyclopropyl-4-(pyrimidin-5-ylamino)quinazolin-2(1H)-one | m/z [M + H] 390.05 |

TABLE 1-continued

| Cpd. No. | Structure | Name | Mass Spec. |
|---|---|---|---|
| 485 | 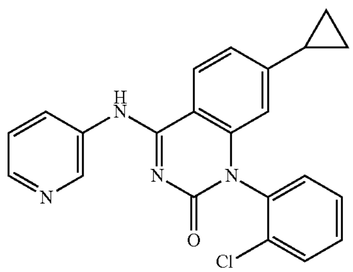 [SMILES: O=c1nc(Nc2cccnc2)c2ccc(C3CC3)cc2n1-c1ccccc1Cl] | 1-(2-chlorophenyl)-7-cyclopropyl-4-(pyridin-3-ylamino)quinazolin-2(1H)-one | m/z [M + H] 389.05 |
| 486 | 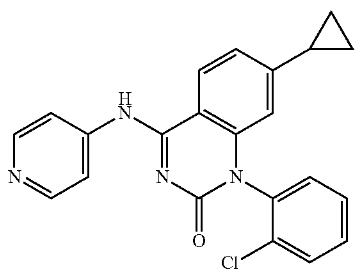 [SMILES: O=c1nc(Nc2ccncc2)c2ccc(C3CC3)cc2n1-c1ccccc1Cl] | 1-(2-chlorophenyl)-7-cyclopropyl-4-(pyridin-4-ylamino)quinazolin-2(1H)-one | m/z [M + H] 389.05 |
| 487 | 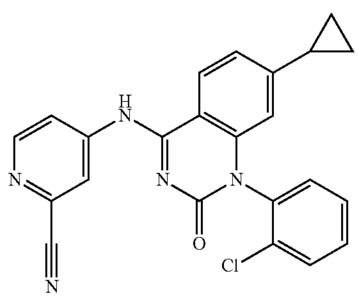 [SMILES: N#Cc1cc(Nc2nc(=O)n(-c3ccccc3Cl)c3cc(C4CC4)ccc23)ccn1] | 4-((1-(2-chlorophenyl)-7-cyclopropyl-2-oxo-1,2-dihydroquinazolin-4-yl)amino)picolinonitrile | m/z [M + H] 414.1 |
| 488 | 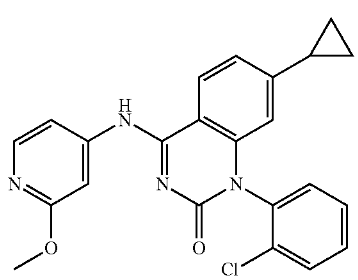 [SMILES: COc1cc(Nc2nc(=O)n(-c3ccccc3Cl)c3cc(C4CC4)ccc23)ccn1] | 1-(2-chlorophenyl)-7-cyclopropyl-4-((2-methoxypyridin-4-yl)amino)quinazolin-2(1H)-one | m/z [M + H] 419.1 |
| 489 | 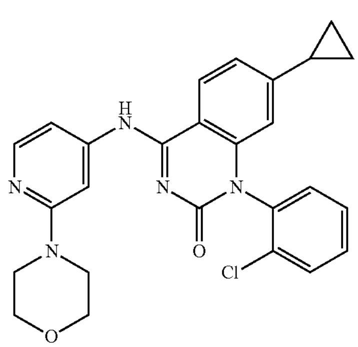 [SMILES: O=c1nc(Nc2ccnc(N3CCOCC3)c2)c2ccc(C3CC3)cc2n1-c1ccccc1Cl] | 1-(2-chlorophenyl)-7-cyclopropyl-4-((2-morpholinopyridin-4-yl)amino)-quinazolin-2(1H)-one | m/z [M + H] 474.1 |

TABLE 1-continued

| Cpd. No. | Structure | Name | Mass Spec. |
|---|---|---|---|
| 490 | 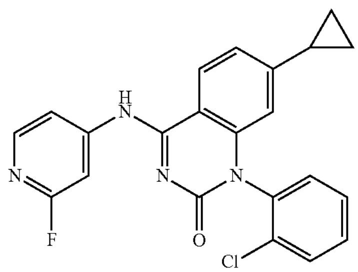 | 1-(2-chlorophenyl)-7-cyclopropyl-4-((2-fluoropyridin-4-yl)amino)quinazolin-2(1H)-one | m/z [M + H] 407.0 |
| 491 | 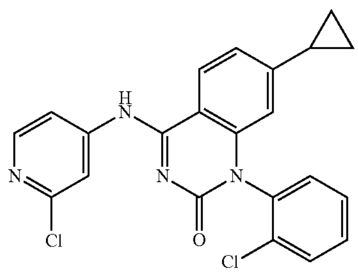 [SMILES: O=c1nc(Nc2ccnc(Cl)c2)c2ccc(C3CC3)cc2n1-c1ccccc1Cl] | 1-(2-chlorophenyl)-4-((2-chloropyridin-4-yl)amino)-7-cyclopropylquinazolin-2(1H)-one | m/z [M + H] 423.0 |
| 492 | 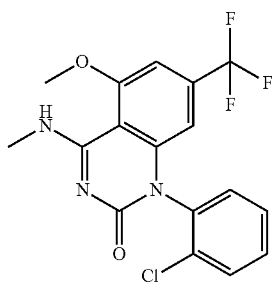 [SMILES: CNc1nc(=O)n(-c2ccccc2Cl)c2cc(C(F)(F)F)cc(OC)c12] | 1-(2-chlorophenyl)-5-methoxy-4-(methylamino)-7-(trifluoromethyl)-quinazolin-2(1H)-one | m/z [M + H] 384.1 |
| 493 | 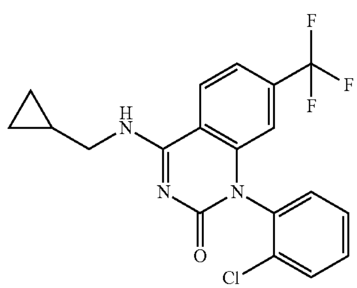 [SMILES: O=c1nc(NCC2CC2)c2ccc(C(F)(F)F)cc2n1-c1ccccc1Cl] | 1-(2-chlorophenyl)-4-((cyclopropylmethyl)amino)-7-(trifluoromethyl)-quinazolin-2(1H)-one | m/z [M + H] 394.1 |
| 494 | 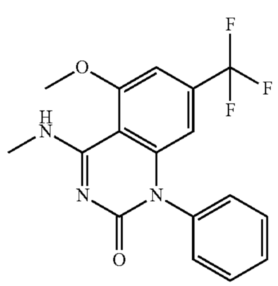 [SMILES: CNc1nc(=O)n(-c2ccccc2)c2cc(C(F)(F)F)cc(OC)c12] | 5-methoxy-4-(methylamino)-1-phenyl-7-(trifluoromethyl)quinazolin-2(1H)-one | m/z [M + H] 350.1 |

TABLE 1-continued

| Cpd. No. | Structure | Name | Mass Spec. |
|---|---|---|---|
| 495 | 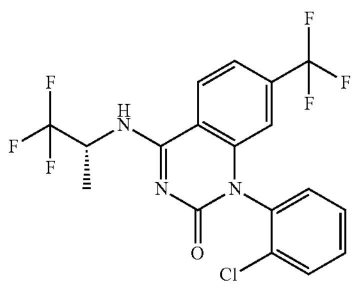 [SMILES: C[C@@H](Nc1nc(=O)n(-c2ccccc2Cl)c2cc(C(F)(F)F)ccc12)C(F)(F)F] | (R)-1-(2-chlorophenyl)-7-(trifluoromethyl)-4-((1,1,1-trifluoropropan-2-yl)amino)quinazolin-2(1H)-one | m/z [M + H] 436.0 |
| 496 | 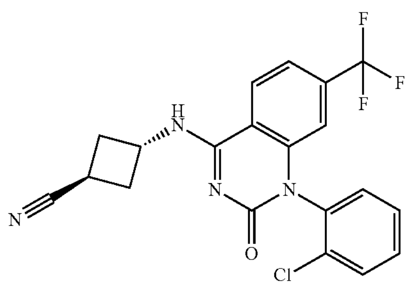 [SMILES: N#C[C@H]1C[C@H](Nc2nc(=O)n(-c3ccccc3Cl)c3cc(C(F)(F)F)ccc23)C1] | (1,3-trans)-3-((1-(2-chlorophenyl)-2-oxo-7-(trifluoromethyl)-1,2-dihydroquinazolin-4-yl)amino)-cyclobutane-1-carbonitrile | m/z [M + H] 419.05 |
| 497 | 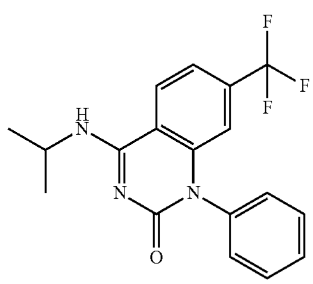 [SMILES: CC(C)Nc1nc(=O)n(-c2ccccc2)c2cc(C(F)(F)F)ccc12] | 4-(isopropylamino)-1-phenyl-7-(trifluoromethyl)quinazolin-2(1H)-one | m/z [M + H] 348.1 |
| 498 | 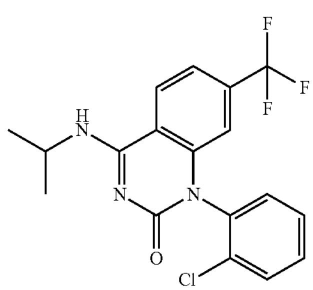 [SMILES: CC(C)Nc1nc(=O)n(-c2ccccc2Cl)c2cc(C(F)(F)F)ccc12] | 1-(2-chlorophenyl)-4-(isopropylamino)-7-(trifluoromethyl)quinazolin-2(1H)-one | m/z [M + H] 382.0 |
| 499 | 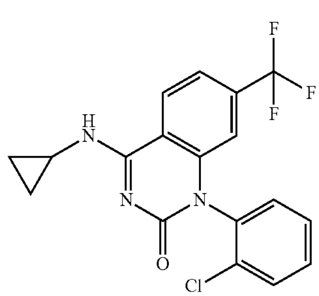 [SMILES: O=c1nc(NC2CC2)c2ccc(C(F)(F)F)cc2n1-c1ccccc1Cl] | 1-(2-chlorophenyl)-4-(cyclopropylamino)-7-(trifluoromethyl)quinazolin-2(1H)-one | m/z [M + H] 380.0 |

TABLE 1-continued

| Cpd. No. | Structure | Name | Mass Spec. |
|---|---|---|---|
| 500 | 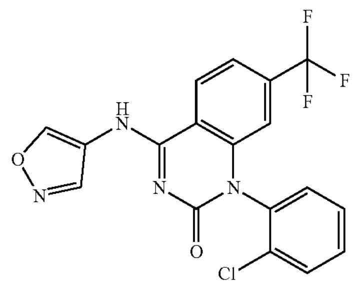 [SMILES: O=c1nc(Nc2cnoc2)c2ccc(C(F)(F)F)cc2n1-c1ccccc1Cl] | 1-(2-chlorophenyl)-4-(isoxazol-4-yl-amino)-7-(trifluoromethyl)quinazolin-2(1H)-one | m/z [M + H] 406.75 |
| 501 | 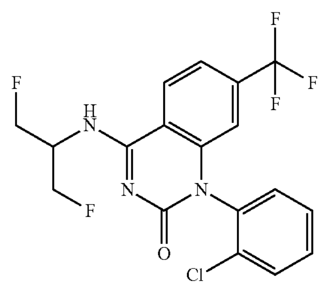 [SMILES: O=c1nc(NC(CF)CF)c2ccc(C(F)(F)F)cc2n1-c1ccccc1Cl] | 1-(2-chlorophenyl)-4((1,3-difluoro-propan-2-yl)amino)-7-(trifluoromethyl)-quinazolin-2(1H)-one | m/z [M + H] 418.1 |
| 502 | 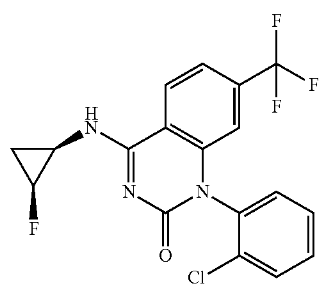 [SMILES: O=c1nc(N[C@@H]2C[C@@H]2F)c2ccc(C(F)(F)F)cc2n1-c1ccccc1Cl] | 1-(2-chlorophenyl)-4-(((1R,2S)-2-fluorocyclopropyl)amino)-7-(trifluoro-methyl)quinazolin-2(1H)-one | m/z [M + H] 398.05 |
| 503 | 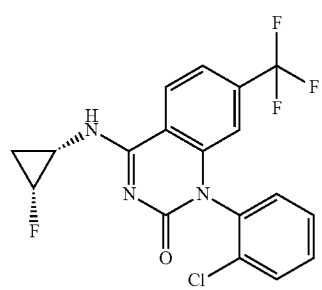 [SMILES: O=c1nc(N[C@H]2C[C@H]2F)c2ccc(C(F)(F)F)cc2n1-c1ccccc1Cl] | 1-(2-chlorophenyl)-4-(((1S,2R)-2-fluorocyclopropyl)amino)-7-(trifluoro-methyl)quinazolin-2(1H)-one | m/z [M + H] 398.1 |
| 504 | 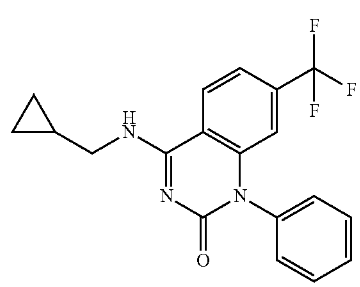 [SMILES: O=c1nc(NCC2CC2)c2ccc(C(F)(F)F)cc2n1-c1ccccc1] | 4-((cyclopropylmethyl)amino)-1-phenyl-7-(trifluoromethyl)quinazolin-2(1H)-one | m/z [M + H] 360.1 |

TABLE 1-continued

| Cpd. No. | Structure | Name | Mass Spec. |
|---|---|---|---|
| 505 | 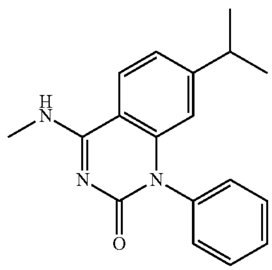 [SMILES: CNc1nc(=O)n(-c2ccccc2)c2cc(C(C)C)ccc12] | 7-isopropyl-4-(methylamino)-1-phenyl-quinazolin-2(1H)-one | m/z [M + H] 294.2 |
| 506 | 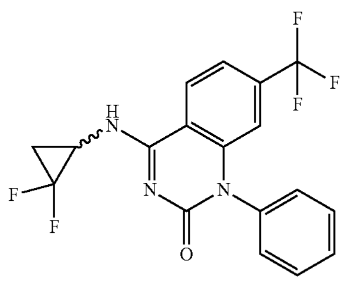 [SMILES: O=c1nc(NC2CC2(F)F)c2ccc(C(F)(F)F)cc2n1-c1ccccc1] | 4-((2,2-difluorocyclopropyl)amino)-1-phenyl-7-(trifluoromethyl)quinazolin-2(1H)-one | m/z [M + H] 382.05 |
| 507 | 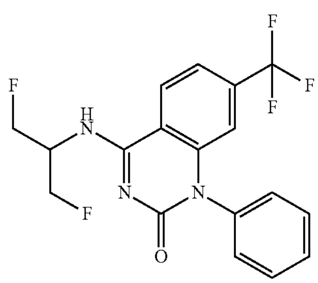 [SMILES: O=c1nc(NC(CF)CF)c2ccc(C(F)(F)F)cc2n1-c1ccccc1] | 4-((1,3-difluoropropan-2-yl)amino)-1-phenyl-7-(trifluoromethyl)quinazolin-2(1H)-one | m/z [M + H] 384.1 |
| 508 | 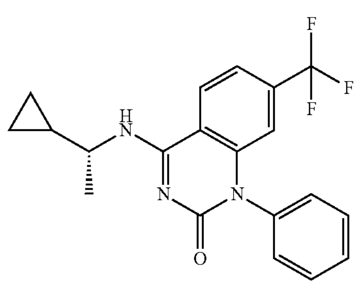 [SMILES: C[C@@H](Nc1nc(=O)n(-c2ccccc2)c2cc(C(F)(F)F)ccc12)C1CC1] | (R)-4-((1-cyclopropylethyl)amino)-1-phenyl-7-(trifluoromethyl)quinazolin-2(1H)-one | m/z [M + H] 374.1 |
| 509 | 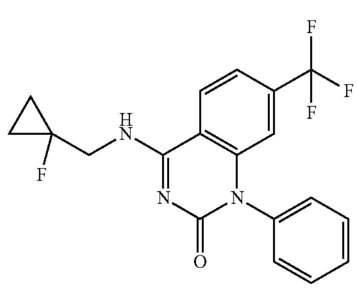 | 4-(((1-fluorocyclopropyl)methyl)amino)-1-phenyl-7-(trifluoromethyl)quinazolin-2(1H)-one | m/z [M + H] 378.1 |

TABLE 1-continued

| Cpd. No. | Structure | Name | Mass Spec. |
|---|---|---|---|
| 510 | 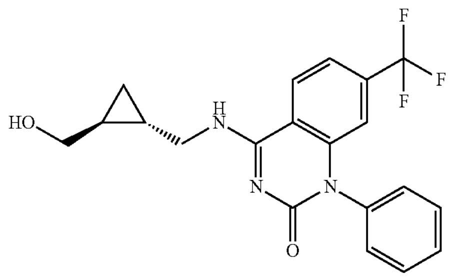 [SMILES: O=c1nc(NC[C@H]2C[C@@H]2CO)c2ccc(C(F)(F)F)cc2n1-c1ccccc1] | 4-((((trans)-2-(hydroxymethyl)cyclopropyl)methyl)amino)-1-phenyl-7-(trifluoromethyl)quinazolin-2(1H)-one | m/z [M + H] 390.1 |
| 511 | 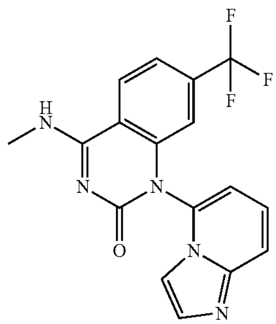 [SMILES: CNc1nc(=O)n(-c2cccc3nccn23)c2cc(C(F)(F)F)ccc12] | 1-(imidazo[1,2-a]pyridin-5-yl)-4-(methylamino)-7-(trifluoromethyl)-quinazolin-2(1H)-one | m/z [M + H] 360.1 |
| 512 | 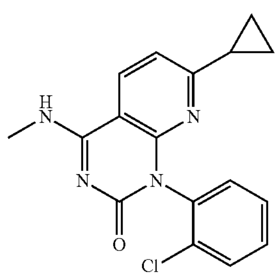 [SMILES: CNc1nc(=O)n(-c2ccccc2Cl)c2nc(C3CC3)ccc12] | 1-(2-chlorophenyl)-7-cyclopropyl-4-(methylamino)pyrido[2,3-d]pyrimidin-2(1H)-one | m/z [M + H] 327.1 |
| 513 | 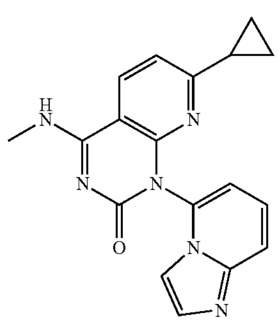 [SMILES: CNc1nc(=O)n(-c2cccc3nccn23)c2nc(C3CC3)ccc12] | 7-cyclopropyl-1-(imidazo[1,2-a]pyridin-5-yl)-4-(methylamino)pyrido[2,3-d]-pyrimidin-2(1H)-one | m/z [M + H] 333.1 |
| 514 | 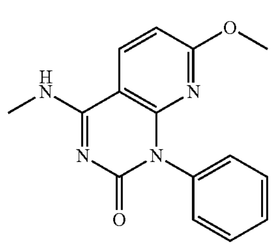 | 7-methoxy-4-(methylamino)-1-phenyl-pyrido[2,3-d]pyrimidin-2(1H)-one | m/z [M + H] 283.1 |

TABLE 1-continued

| Cpd. No. | Structure | Name | Mass Spec. |
|---|---|---|---|
| 515 | 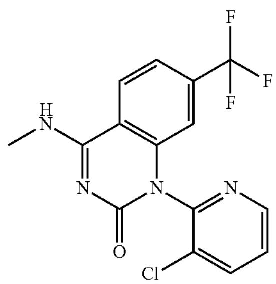 [SMILES: CNc1nc(=O)n(-c2ncccc2Cl)c2cc(C(F)(F)F)ccc12] | 1-(3-chloropyridin-2-yl)-4-(methyl-amino)-7-(trifluoromethyl)quinazolin-2(1H)-one | m/z [M + H] 355.0 |
| 516 | 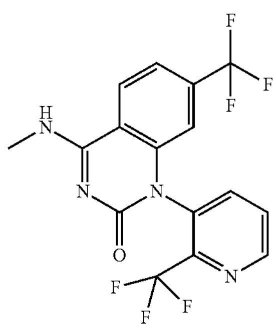 [SMILES: CNc1nc(=O)n(-c2cccnc2C(F)(F)F)c2cc(C(F)(F)F)ccc12] | 4-(methylamino)-7-(trifluoromethyl)-1-(2-(trifluoromethyl)pyridin-3-yl)-quinazolin-2(1H)-one | m/z [M + H] 389.1 |
| 517 | 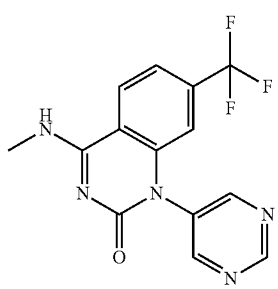 [SMILES: CNc1nc(=O)n(-c2cncnc2)c2cc(C(F)(F)F)ccc12] | 4-(methylamino)-1-(pyrimidin-5-yl)-7-(trifluoromethyl)quinazolin-2(1H)-one | m/z [M + H] 322.1 |
| 518 | 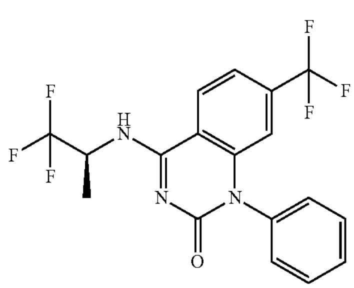 [SMILES: C[C@H](Nc1nc(=O)n(-c2ccccc2)c2cc(C(F)(F)F)ccc12)C(F)(F)F] | (S)-1-phenyl-7-(trifluoromethyl)-4-((1,1,1-trifluoropropan-2-yl)amino)-quinazolin-2(1H)-one | m/z [M + H] 402.1 |
| 519 | 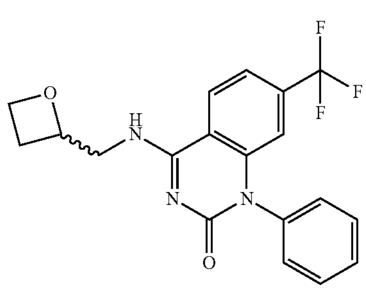 [SMILES: O=c1nc(NCC2CCO2)c2ccc(C(F)(F)F)cc2n1-c1ccccc1] | 4-((oxetan-2-ylmethyl)amino)-1-phenyl-7-(trifluoromethyl)quinazolin-2(1H)-one | m/z [M + H] 376.1 |

TABLE 1-continued

| Cpd. No. | Structure | Name | Mass Spec. |
|---|---|---|---|
| 520 | 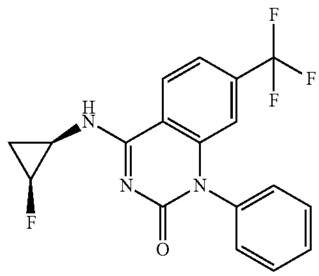 [SMILES: O=c1nc(N[C@@H]2C[C@@H]2F)c2ccc(C(F)(F)F)cc2n1-c1ccccc1] | 4-(((1R,2S)-2-fluorocyclopropyl)amino)-1-phenyl-7-(trifluoromethyl)quinazolin-2(1H)-one | m/z [M + H] 364.1 |
| 521 | 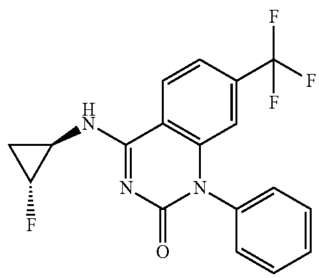 [SMILES: O=c1nc(N[C@@H]2C[C@H]2F)c2ccc(C(F)(F)F)cc2n1-c1ccccc1] | 4-(((1,2-trans)-2-fluorocyclopropyl)-amino)-1-phenyl-7-(trifluoromethyl)quinazolin-2(1H)-one | m/z [M + H] 364.1 |
| 522 | 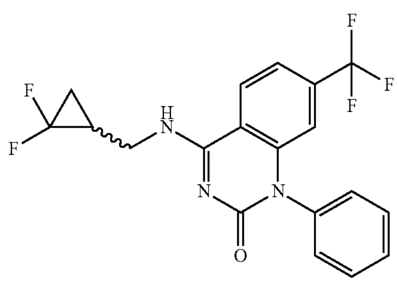 [SMILES: O=c1nc(NCC2CC2(F)F)c2ccc(C(F)(F)F)cc2n1-c1ccccc1] | 4-(((2,2-difluorocyclopropyl)methyl)-amino)-1-phenyl-7-(trifluoromethyl)-quinazolin-2(1H)-one | m/z [M + H] 396.1 |
| 523 | 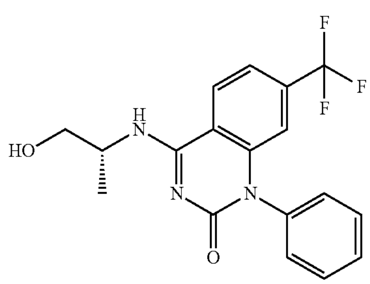 [SMILES: C[C@H](CO)Nc1nc(=O)n(-c2ccccc2)c2cc(C(F)(F)F)ccc12] | (R)-4-((1-hydroxypropan-2-yl)amino)-1-phenyl-7-(trifluoromethyl)quinazolin-2(1H)-one | m/z [M + H] 364.1 |
| 524 | 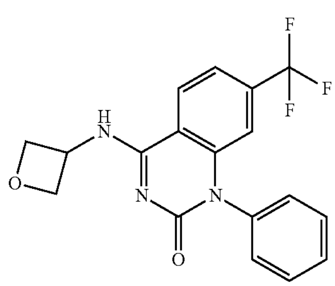 [SMILES: O=c1nc(NC2COC2)c2ccc(C(F)(F)F)cc2n1-c1ccccc1] | 4-(oxetan-3-ylamino)-1-phenyl-7-(trifluoromethyl)quinazolin-2(1H)-one | m/z [M + H] 362.1 |

TABLE 1-continued

| Cpd. No. | Structure | Name | Mass Spec. |
|---|---|---|---|
| 525 | 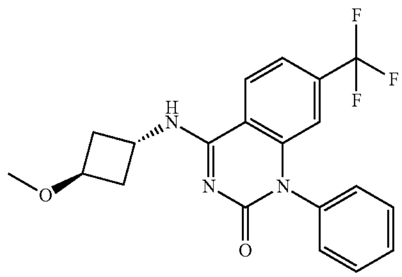 [SMILES: CO[C@H]1C[C@H](Nc2nc(=O)n(-c3ccccc3)c3cc(C(F)(F)F)ccc23)C1] | 4-(((1,3-trans)-3-methoxycyclobutyl)-amino)-1-phenyl-7-(trifluoromethyl)-quinazolin-2(1H)-one | m/z [M + H] 390.1 |
| 526 | 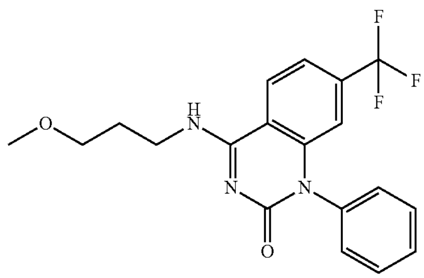 [SMILES: COCCCNc1nc(=O)n(-c2ccccc2)c2cc(C(F)(F)F)ccc12] | 4-((3-methoxypropyl)amino)-1-phenyl-7-(trifluoromethyl)quinazolin-2(1H)-one | m/z [M + H] 378.1 |
| 527 | 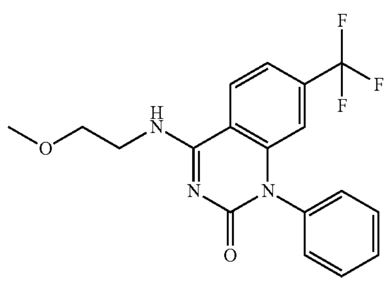 [SMILES: COCCNc1nc(=O)n(-c2ccccc2)c2cc(C(F)(F)F)ccc12] | 4-((2-methoxyethyl)amino)-1-phenyl-7-(trifluoromethyl)quinazolin-2(1H)-one | m/z [M + H] 364.1 |
| 528 | 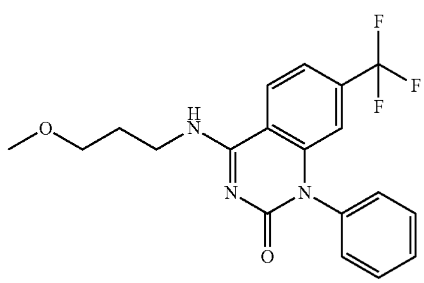 [SMILES: COCCCNc1nc(=O)n(-c2ccccc2)c2cc(C(F)(F)F)ccc12] | 4-((3-methoxypropyl)amino)-1-phenyl-7-(trifluoromethyl)quinazolin-2(1H)-one | m/z [M + H] 378.1 |
| 530 | 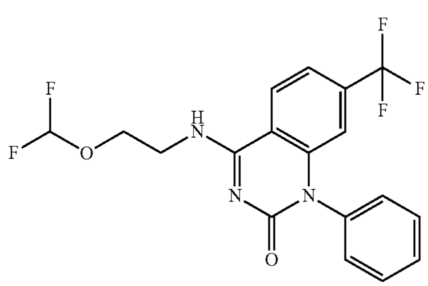 [SMILES: O=c1nc(NCCOC(F)F)c2ccc(C(F)(F)F)cc2n1-c1ccccc1] | 4-((2-(difluoromethoxy)ethyl)amino)-1-phenyl-7-(trifluoromethyl)quinazolin-2(1H)-one | m/z [M + H] 400.1 |

TABLE 1-continued

| Cpd. No. | Structure | Name | Mass Spec. |
|---|---|---|---|
| 531 | 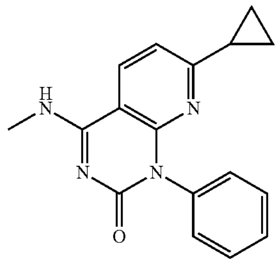 [SMILES: CNc1nc(=O)n(-c2ccccc2)c2nc(C3CC3)ccc12] | 7-cyclopropyl-4-(methylamino)-1-phenylpyrido[2,3-d]pyrimidin-2(1H)-one | m/z [M + H] 293.1 |
| 532 | 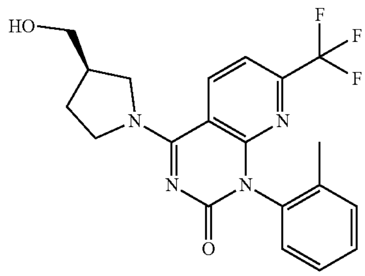 | (R)-4-(3-(hydroxymethyl)pyrrolidin-1-yl)-1-(o-tolyl)-7-(trifluoromethyl)-pyrido[2,3-d]pyrimidin-2(1H)-one | m/z [M + H] 405.00 |
| 533 | 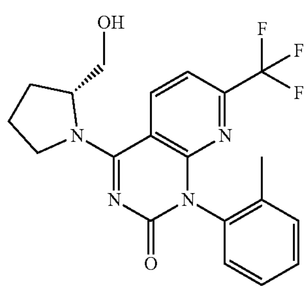 | (R)-4-(2-(hydroxymethyl)pyrrolidin-1-yl)-1-(o-tolyl)-7-(trifluoromethyl)pyrido-[2,3-d]pyrimidin-2(1H)-one | m/z [M + H] 405.00 |
| 534 | 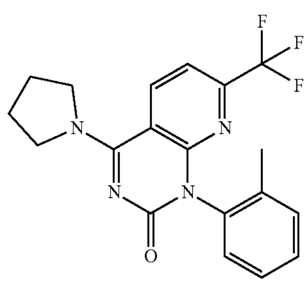 [SMILES: Cc1ccccc1-n1c(=O)nc(N2CCCC2)c2ccc(C(F)(F)F)nc21] | 4-(pyrrolidin-1-yl)-1-(o-tolyl)-7-(trifluoromethyl)pyrido[2,3-d]pyrimidin-2(1H)-one | m/z [M + H] 375.2 |
| 535 | 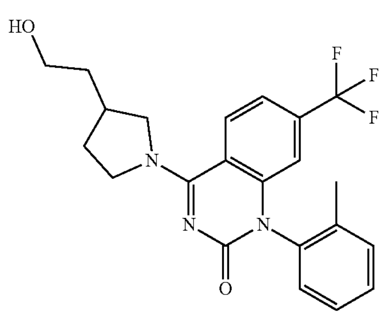 [SMILES: Cc1ccccc1-n1c(=O)nc(N2CCC(CCO)C2)c2ccc(C(F)(F)F)cc21] | 4-(3-(2-hydroxyethyl)pyrrolidin-1-yl)-1-(o-tolyl)-7-(trifluoromethyl)quinazolin-2(1H)-one | m/z [M + H] 418.1 |

TABLE 1-continued

| Cpd. No. | Structure | Name | Mass Spec. |
|---|---|---|---|
| 536 | 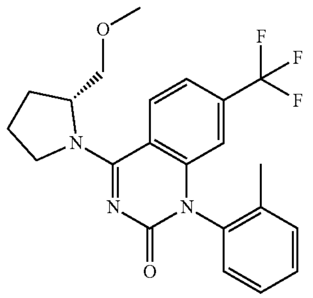 [SMILES: COC[C@H]1CCCN1c1nc(=O)n(-c2ccccc2C)c2cc(C(F)(F)F)ccc12] | (R)-4-(2-(methoxymethyl)pyrrolidin-1-yl)-1-(o-tolyl)-7-(trifluoromethyl)-quinazolin-2(1H)-one | m/z [M + H] 418.1 |
| 537 | 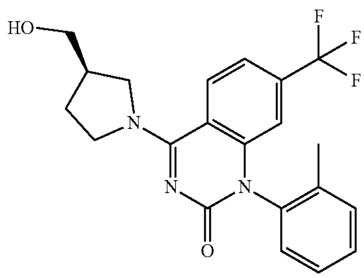 | (R)-4-(3-(hydroxymethyl)pyrrolidin-1-yl)-1-(o-tolyl)-7-(trifluoromethyl)-quinazolin-2(1H)-one | m/z [M + H] 404.1 |
| 538 | 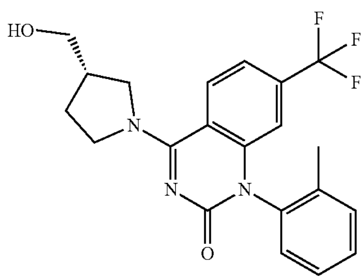 [SMILES: Cc1ccccc1-n1c(=O)nc(N2CC[C@H](CO)C2)c2ccc(C(F)(F)F)cc21] | (S)-4-(3-(hydroxymethyl)pyrrolidin-1-yl)-1-(o-tolyl)-7-(trifluoromethyl)-quinazolin-2(1H)-one | m/z [M + H] 404.1 |
| 539 | 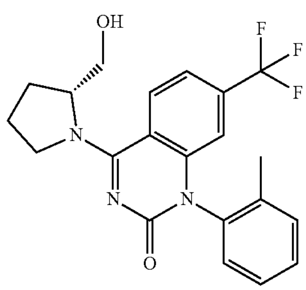 [SMILES: Cc1ccccc1-n1c(=O)nc(N2CCC[C@@H]2CO)c2ccc(C(F)(F)F)cc21] | (R)-4-(2-(hydroxymethyl)pyrrolidin-1-yl)-1-(o-tolyl)-7-(trifluoromethyl)-quinazolin-2(1H)-one | m/z [M + H] 404.1 |
| 540 | 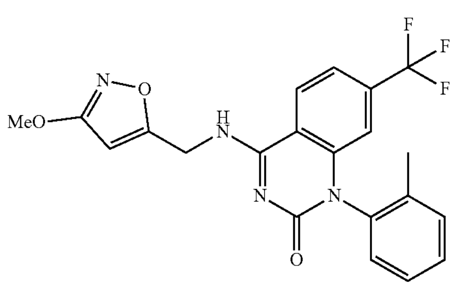 [SMILES: COc1cc(CNc2nc(=O)n(-c3ccccc3C)c3cc(C(F)(F)F)ccc23)on1] | 4(((3-methoxyisoxazol-5-yl)methyl)-amino)-1-(o-tolyl)-7-(trifluoromethyl)-quinazolin-2(1H)-one | m/z [M + H] 431.1 |

TABLE 1-continued

| Cpd. No. | Structure | Name | Mass Spec. |
|---|---|---|---|
| 541 | 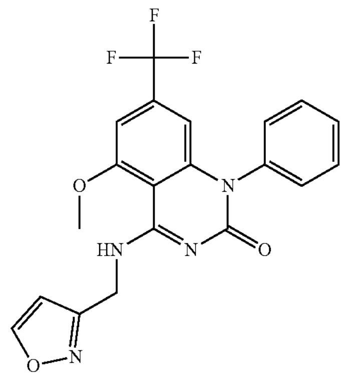 [SMILES: COc1cc(C(F)(F)F)cc2c1c(NCc1ccon1)nc(=O)n2-c1ccccc1] | 4-((isoxazol-3-ylmethyl)amino)-5-methoxy-1-phenyl-7-(trifluoromethyl)-quinazolin-2(1H)-one | m/z [M + H] 417.1 |
| 542 | 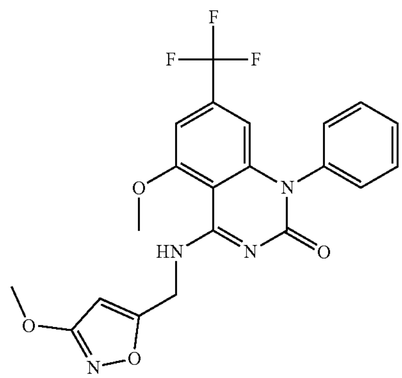 [SMILES: COc1cc(CNc2nc(=O)n(-c3ccccc3)c3cc(C(F)(F)F)cc(OC)c23)on1] | 5-methoxy-4(((3-methoxyisoxazol-5-yl)methyl)amino)-1-phenyl-7-(trifluoromethyl)quinazolin-2(1H)-one | m/z [M + H] 447.1 |
| 543 | 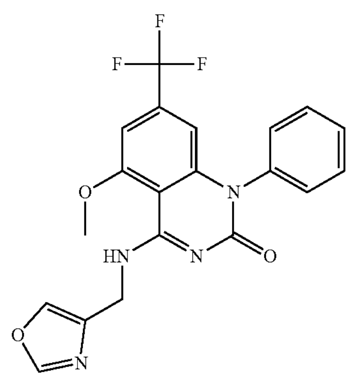 [SMILES: COc1cc(C(F)(F)F)cc2c1c(NCc1cocn1)nc(=O)n2-c1ccccc1] | 5-methoxy-4-((oxazol-4-ylmethyl)-amino)-1-phenyl-7-(trifluoromethyl)-quinazolin-2(1H)-one | m/z [M + H] 417.1 |
| 544 | 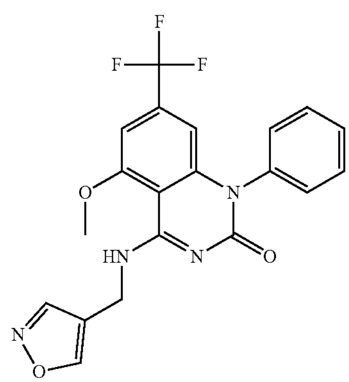 [SMILES: COc1cc(C(F)(F)F)cc2c1c(NCc1cnoc1)nc(=O)n2-c1ccccc1] | 4-((isoxazol-4-ylmethyl)amino)-5-methoxy-1-phenyl-7-(trifluoromethyl)-quinazolin-2(1H)-one | m/z [M + H] 417.1 |

TABLE 1-continued

| Cpd. No. | Structure | Name | Mass Spec. |
|---|---|---|---|
| 545 | 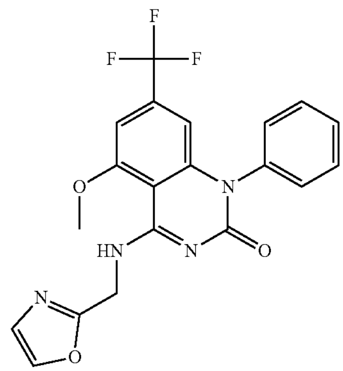 [SMILES: COc1cc(C(F)(F)F)cc2c1c(NCc1ncco1)nc(=O)n2-c1ccccc1] | 5-methoxy-4-((oxazol-2-ylmethyl)-amino)-1-phenyl-7-(trifluoromethyl)quinazolin-2(1H)-one | m/z [M + H] 417.1 |
| 546 | 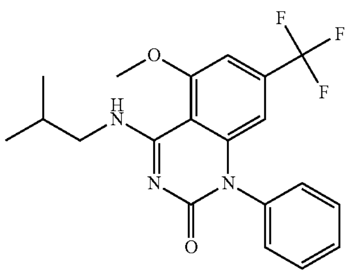 [SMILES: COc1cc(C(F)(F)F)cc2c1c(NCC(C)C)nc(=O)n2-c1ccccc1] | 4-(isobutylamino)-5-methoxy-1-phenyl-7-(trifluoromethyl)quinazolin-2(1H)-one | m/z [M + H] 392.15 |
| 547 | 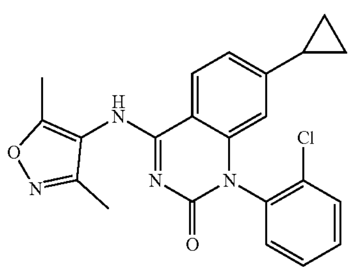 [SMILES: Cc1noc(C)c1Nc1nc(=O)n(-c2ccccc2Cl)c2cc(C3CC3)ccc12] | 1-(2-chlorophenyl)-7-cyclopropyl-4-((3,5-dimethylisoxazol-4-yl)amino)-quinazolin-2(1H)-one | m/z [M + H] 407.1 |
| 548 | 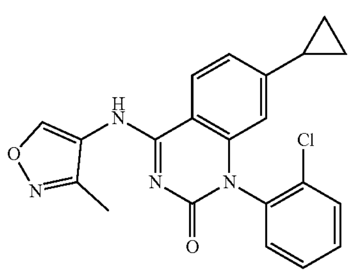 [SMILES: Cc1nocc1Nc1nc(=O)n(-c2ccccc2Cl)c2cc(C3CC3)ccc12] | 1-(2-chlorophenyl)-7-cyclopropyl-4-((3-methylisoxazol-4-yl)amino)quinazolin-2(1H)-one | m/z [M + H] 393.1 |
| 549 | 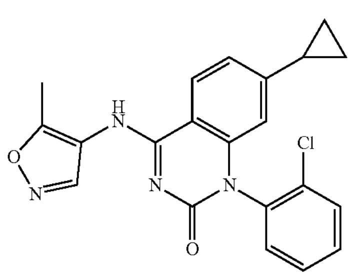 [SMILES: Cc1oncc1Nc1nc(=O)n(-c2ccccc2Cl)c2cc(C3CC3)ccc12] | 1-(2-chlorophenyl)-7-cyclopropyl-4-((5-methylisoxazol-4-yl)amino)quinazolin-2(1H)-one | m/z [M + H] 393.1 |

TABLE 1-continued

| Cpd. No. | Structure | Name | Mass Spec. |
|---|---|---|---|
| 550 | 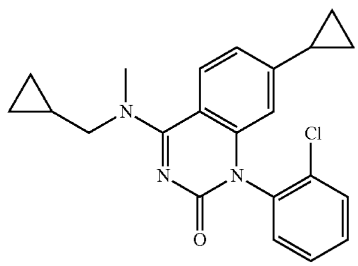 [SMILES: CN(CC1CC1)c1nc(=O)n(-c2ccccc2Cl)c2cc(C3CC3)ccc12] | 1-(2-chlorophenyl)-7-cyclopropyl-4-((cyclopropylmethyl)(methyl)amino)quinazolin-2(1H)-one | m/z [M + H] 380.15 |
| 551 | 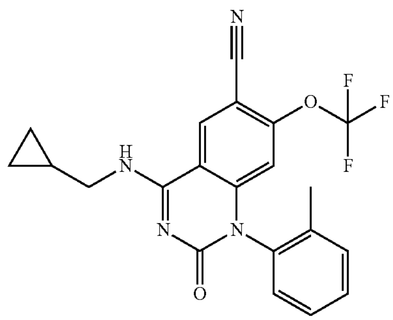 [SMILES: Cc1ccccc1-n1c(=O)nc(NCC2CC2)c2cc(C#N)c(OC(F)(F)F)cc21] | 4-((cyclopropylmethyl)amino)-2-oxo-1-(o-tolyl)-7-(trifluoromethoxy)-1,2-dihydroquinazoline-6-carbonitrile | m/z [M + H] 415.1 |
| 552 | 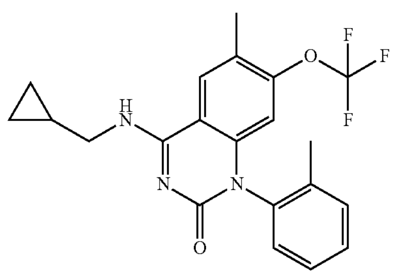 [SMILES: Cc1cc2c(NCC3CC3)nc(=O)n(-c3ccccc3C)c2cc1OC(F)(F)F] | 4-((cyclopropylmethyl)amino)-6-methyl-1-(o-tolyl)-7-(trifluoromethoxy)-quinazolin-2(1H)-one | m/z [M + H] 404.1 |
| 553 | 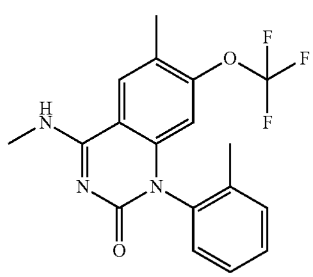 [SMILES: CNc1nc(=O)n(-c2ccccc2C)c2cc(OC(F)(F)F)c(C)cc12] | 6-methyl-4-(methylamino)-1-(o-tolyl)-7-(trifluoromethoxy)quinazolin-2(1H)-one | m/z [M + H] 364.1 |
| 554 | 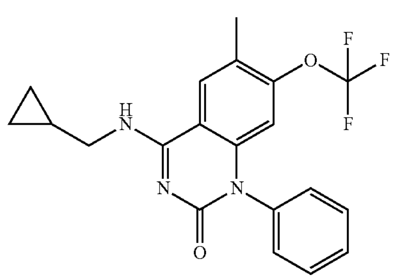 [SMILES: Cc1cc2c(NCC3CC3)nc(=O)n(-c3ccccc3)c2cc1OC(F)(F)F] | 4-((cyclopropylmethyl)amino)-6-methyl-1-phenyl-7-(trifluoromethoxy)-quinazolin-2(1H)-one | m/z [M + H] 390.1 |

TABLE 1-continued

| Cpd. No. | Structure | Name | Mass Spec. |
|---|---|---|---|
| 555 | 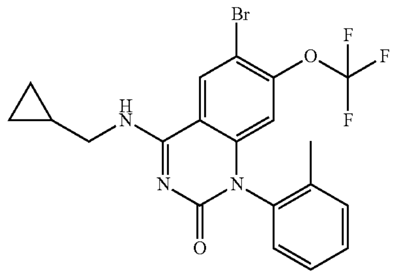 [SMILES: Cc1ccccc1-n1c(=O)nc(NCC2CC2)c2cc(Br)c(OC(F)(F)F)cc21] | 6-bromo-4-((cyclopropylmethyl)amino)-1-(o-tolyl)-7-(trifluoromethoxy)-quinazolin-2(1H)-one | m/z [M + H] 468.0, 470.0 |
| 556 | 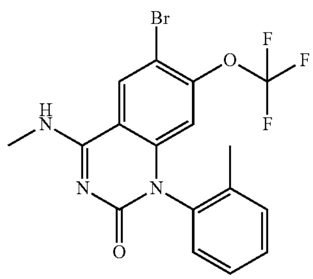 [SMILES: CNc1nc(=O)n(-c2ccccc2C)c2cc(OC(F)(F)F)c(Br)cc12] | 6-bromo-4-(methylamino)-1-(o-tolyl)-7-(trifluoromethoxy)quinazolin-2(1H)-one | m/z [M + H] 430.0, 428.0 |
| 557 | 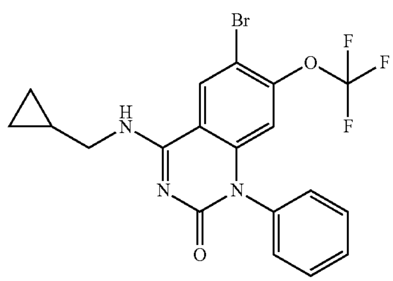 [SMILES: O=c1nc(NCC2CC2)c2cc(Br)c(OC(F)(F)F)cc2n1-c1ccccc1] | 6-bromo-4-((cyclopropylmethyl)amino)-1-phenyl-7-(trifluoromethoxy)-quinazolin-2(1H)-one | m/z [M + H] 456.1, 454.1 |
| 558 | 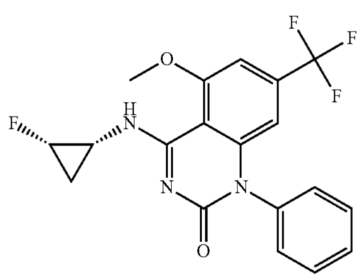 [SMILES: COc1cc(C(F)(F)F)cc2c1c(N[C@@H]1C[C@@H]1F)nc(=O)n2-c1ccccc1] | 4-(((1R,2S)-2-fluorocyclopropyl)amino)-5-methoxy-1-phenyl-7-(trifluoromethyl)-quinazolin-2(1H)-one | m/z [M + H] 394.05 |
| 559 | 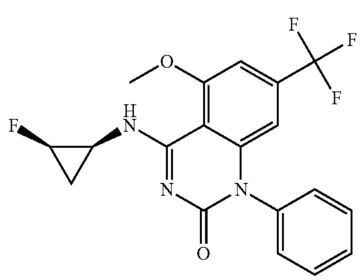 [SMILES: COc1cc(C(F)(F)F)cc2c1c(N[C@H]1C[C@H]1F)nc(=O)n2-c1ccccc1] | 4-(((1S,2R)-2-fluorocyclopropyl)amino)-5-methoxy-1-phenyl-7-(trifluoromethyl)-quinazolin-2(1H)-one | m/z [M + H] 394.05 |

TABLE 1-continued

| Cpd. No. | Structure | Name | Mass Spec. |
|---|---|---|---|
| 560 | 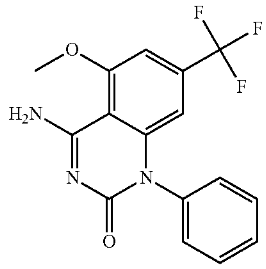 [SMILES: COc1cc(C(F)(F)F)cc2c1c(N)nc(=O)n2-c1ccccc1] | 4-amino-5-methoxy-1-phenyl-7-(trifluoromethyl)quinazolin-2(1H)-one | m/z [M + H] 336.0 |
| 561 | 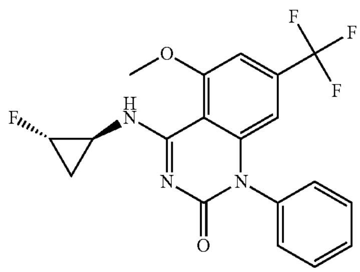 | 4-(((trans)-2-fluorocyclopropyl)amino)-5-methoxy-1-phenyl-7-(trifluoromethyl)-quinazolin-2(1H)-one | m/z [M + H] 394.05 |
| 562 | 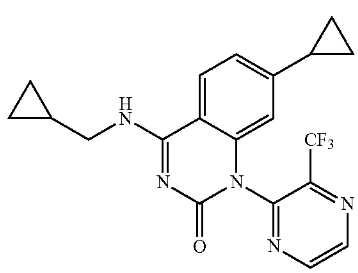 [SMILES: O=c1nc(NCC2CC2)c2ccc(C3CC3)cc2n1-c1nccnc1C(F)(F)F] | 7-cyclopropyl-4-(cyclopropylmethylamino)-1-(3-(trifluoromethyl)pyrazin-2-yl)-quinazolin-2(1H)-one | m/z [M + H] 402.1 |
| 563 | 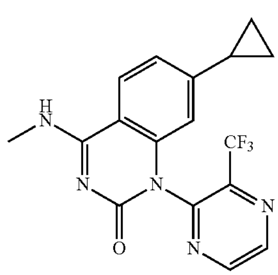 [SMILES: CNc1nc(=O)n(-c2nccnc2C(F)(F)F)c2cc(C3CC3)ccc12] | 7-cyclopropyl-4-(methylamino)-1-(3-(trifluoromethyl)pyrazin-2-yl)quinazolin-2(1H)-one | m/z [M + H] 362.1 |
| 564 | 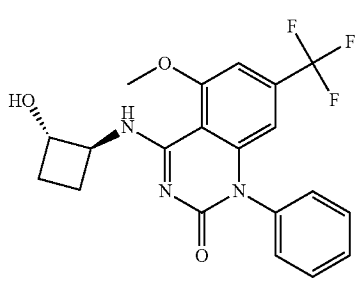 [SMILES: COc1cc(C(F)(F)F)cc2c1c(N[C@H]1CC[C@@H]1O)nc(=O)n2-c1ccccc1] | 4-(((trans)-2-hydroxycyclobutyl)amino)-5-methoxy-1-phenyl-7-(trifluoromethyl)-quinazolin-2(1H)-one | m/z [M + H] 406.1 |

TABLE 1-continued

| Cpd. No. | Structure | Name | Mass Spec. |
|---|---|---|---|
| 565 | 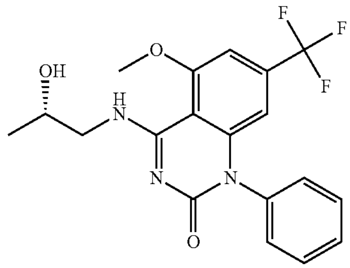 [SMILES: COc1cc(C(F)(F)F)cc2c1c(NC[C@H](C)O)nc(=O)n2-c1ccccc1] | (S)-4-((2-hydroxypropyl)amino)-5-methoxy-1-phenyl-7-(trifluoromethyl)-quinazolin-2(1H)-one | m/z [M + H] 394.1 |
| 566 | 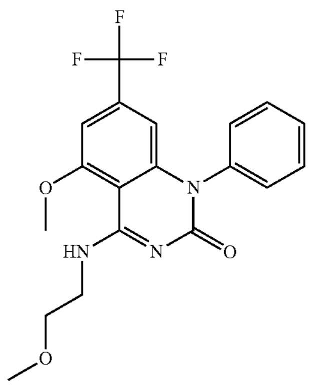 [SMILES: COCCNc1nc(=O)n(-c2ccccc2)c2cc(C(F)(F)F)cc(OC)c12] | 5-methoxy-4-((2-methoxyethyl)amino)-1-phenyl-7-(trifluoromethyl)quinazolin-2(1H)-one | m/z [M + H] 394.1 |
| 567 | 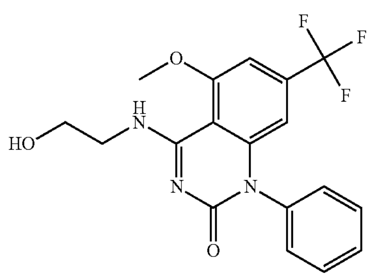 [SMILES: COc1cc(C(F)(F)F)cc2c1c(NCCO)nc(=O)n2-c1ccccc1] | 4-((2-hydroxyethyl)amino)-5-methoxy-1-phenyl-7-(trifluoromethyl)quinazolin-2(1H)-one | m/z [M + H] 380.1 |
| 568 | 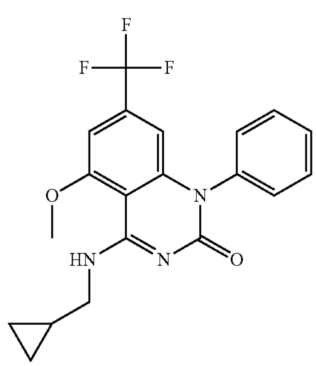 [SMILES: COc1cc(C(F)(F)F)cc2c1c(NCC1CC1)nc(=O)n2-c1ccccc1] | 4-((cyclopropylmethyl)amino)-5-methoxy-1-phenyl-7-(trifluoromethyl)-quinazolin-2(1H)-one | m/z [M + H] 390.1 |
| 569 | 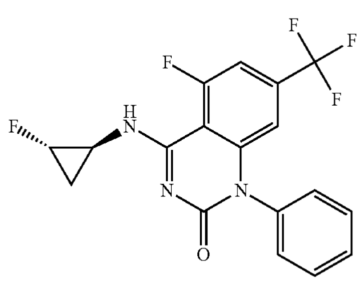 [SMILES: O=c1nc(N[C@H]2C[C@@H]2F)c2c(F)cc(C(F)(F)F)cc2n1-c1ccccc1] | 5-fluoro-4-((trans-2-fluorocyclopropyl)amino)-1-phenyl-7-(trifluoromethyl)-quinazolin-2(1H)-one | m/z [M + H] 382.1 |

TABLE 1-continued

| Cpd. No. | Structure | Name | Mass Spec. |
|---|---|---|---|
| 570 | 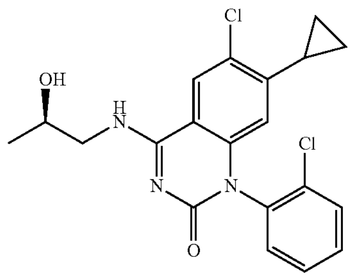 [SMILES: C[C@@H](O)CNc1nc(=O)n(-c2ccccc2Cl)c2cc(C3CC3)c(Cl)cc12] | (R)-6-chloro-1-(2-chlorophenyl)-7-cyclopropyl-4((2-hydroxypropyl)-amino)-quinazolin-2(1H)-one | m/z [M + H] 405.05 |
| 571 | 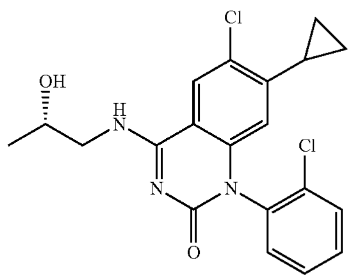 [SMILES: C[C@H](O)CNc1nc(=O)n(-c2ccccc2Cl)c2cc(C3CC3)c(Cl)cc12] | (S)-6-chloro-1-(2-chlorophenyl)-7-cyclopropyl-4((2-hydroxypropyl)-amino)-quinazolin-2(1H)-one | m/z [M + H] 405.1 |
| 572 | 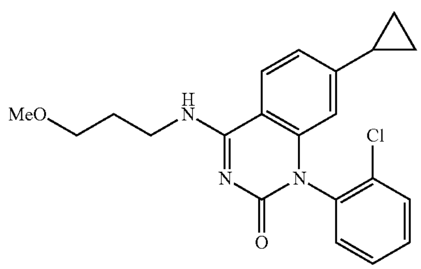 [SMILES: COCCCNc1nc(=O)n(-c2ccccc2Cl)c2cc(C3CC3)ccc12] | 1-(2-chlorophenyl)-7-cyclopropyl-4-((3-methoxypropyl)amino)quinazolin-2(1H)-one | m/z [M + H] 384.1 |
| 573 | 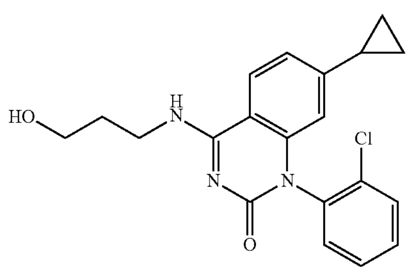 [SMILES: O=c1nc(NCCCO)c2ccc(C3CC3)cc2n1-c1ccccc1Cl] | 1-(2-chlorophenyl)-7-cyclopropyl-4-((3-hydroxypropyl)amino)quinazolin-2(1H)-one | m/z [M + H] 370.1 |
| 574 | 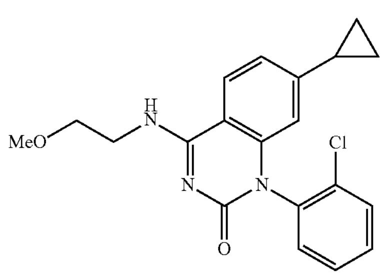 [SMILES: COCCNc1nc(=O)n(-c2ccccc2Cl)c2cc(C3CC3)ccc12] | 1-(2-chlorophenyl)-7-cyclopropyl-4-((2-methoxyethyl)amino)quinazolin-2(1H)-one | m/z [M + H] 370.1 |

TABLE 1-continued

| Cpd. No. | Structure | Name | Mass Spec. |
|---|---|---|---|
| 575 | 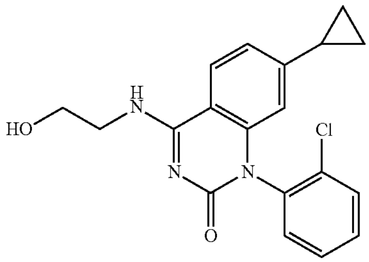 [SMILES: O=c1nc(NCCO)c2ccc(C3CC3)cc2n1-c1ccccc1Cl] | 1-(2-chlorophenyl)-7-cyclopropyl-4-((2-hydroxyethyl)amino)quinazolin-2(1H)-one | m/z [M + H] 356.1 |
| 576 | 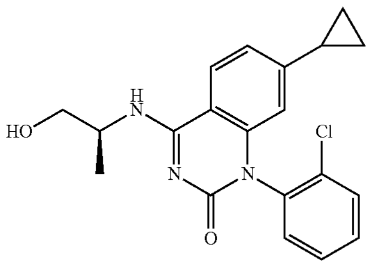 [SMILES: C[C@@H](CO)Nc1nc(=O)n(-c2ccccc2Cl)c2cc(C3CC3)ccc12] | 1-(2-chlorophenyl)-7-cyclopropyl-4-(((S)-1-hydroxypropan-2-yl)amino)-quinazolin-2(1H)-one | m/z [M + H] 370.1 |
| 577 | 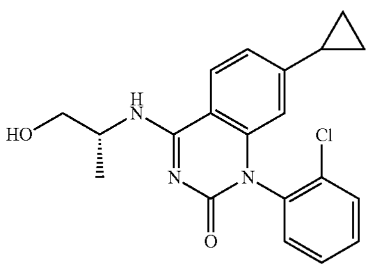 [SMILES: C[C@H](CO)Nc1nc(=O)n(-c2ccccc2Cl)c2cc(C3CC3)ccc12] | 1-(2-chlorophenyl)-7-cyclopropyl-4-(((R)-1-hydroxypropan-2-yl)amino)-quinazolin-2(1H)-one | m/z [M + H] 370.1 |
| 578 | 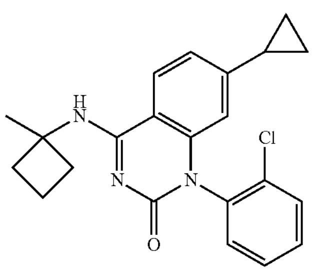 [SMILES: CC1(Nc2nc(=O)n(-c3ccccc3Cl)c3cc(C4CC4)ccc23)CCC1] | 1-(2-chlorophenyl)-7-cyclopropyl-4-((1-methylcyclobutyl)amino)quinazolin-2(1H)-one | m/z [M + H] 380.15 |
| 579 | 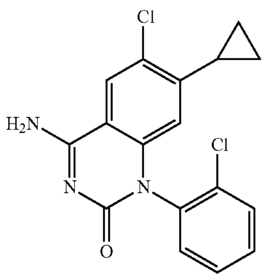 [SMILES: Nc1nc(=O)n(-c2ccccc2Cl)c2cc(C3CC3)c(Cl)cc12] | 4-amino-6-chloro-1-(2-chlorophenyl)-7-cyclopropylquinazolin-2(1H)-one | m/z [M + H] 347.0 |

TABLE 1-continued

| Cpd. No. | Structure | Name | Mass Spec. |
|---|---|---|---|
| 580 | 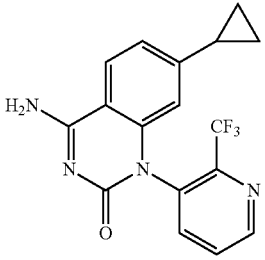 [SMILES: Nc1nc(=O)n(-c2cccnc2C(F)(F)F)c2cc(C3CC3)ccc12] | 4-amino-7-cyclopropyl-1-(2-(trifluoromethyl)pyridin-3-yl)quinazolin-2(1H)-one | m/z [M + H] 347.0 |
| 581 | 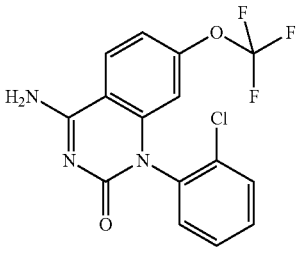 [SMILES: Nc1nc(=O)n(-c2ccccc2Cl)c2cc(OC(F)(F)F)ccc12] | 4-amino-1-(2-chlorophenyl)-7-(trifluoromethoxy)quinazolin-2(1H)-one | m/z [M + H] 356.0 |
| 582 | 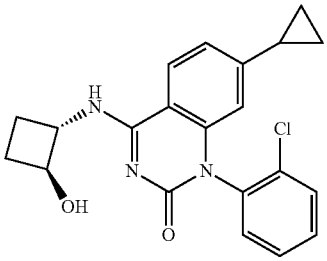 [SMILES: O=c1nc(N[C@H]2CC[C@@H]2O)c2ccc(C3CC3)cc2n1-c1ccccc1Cl] | 1-(2-chlorophenyl)-7-cyclopropyl-4-(((trans)-2-hydroxycyclobutyl)amino)-quinazolin-2(1H)-one | m/z [M + H] 382.1 |
| 583 | 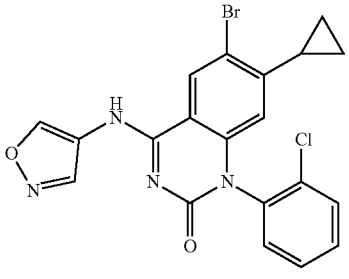 [SMILES: O=c1nc(Nc2cnoc2)c2cc(Br)c(C3CC3)cc2n1-c1ccccc1Cl] | 6-bromo-1-(2-chlorophenyl)-7-cyclopropyl-4-(isoxazol-4-ylamino)-quinazolin-2(1H)-one | m/z [M + H] 458.0 |
| 584 | 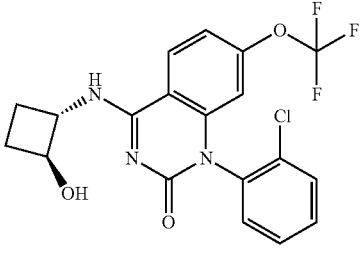 [SMILES: O=c1nc(N[C@H]2CC[C@@H]2O)c2ccc(OC(F)(F)F)cc2n1-c1ccccc1Cl] | 1-(2-chlorophenyl)-4-(((trans)-2-hydroxycyclobutyl)amino)-7-(trifluoromethoxy)-quinazolin-2(1H)-one | m/z [M + H] 426.1 |

TABLE 1-continued

| Cpd. No. | Structure | Name | Mass Spec. |
|---|---|---|---|
| 585 | 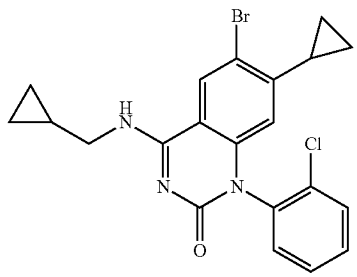 [SMILES: O=c1nc(NCC2CC2)c2cc(Br)c(C3CC3)cc2n1-c1ccccc1Cl] | 6-bromo-1-(2-chlorophenyl)-7-cyclopropyl-4-((cyclopropylmethyl)-amino)-quinazolin-2(1H)-one | m/z [M + H] 445.0 |
| 586 | 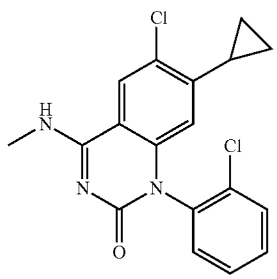 [SMILES: CNc1nc(=O)n(-c2ccccc2Cl)c2cc(C3CC3)c(Cl)cc12] | 6-chloro-1-(2-chlorophenyl)-7-cyclopropyl-4-(methylamino)quinazolin-2(1H)-one | m/z [M + H] 360.0 |
| 587 | 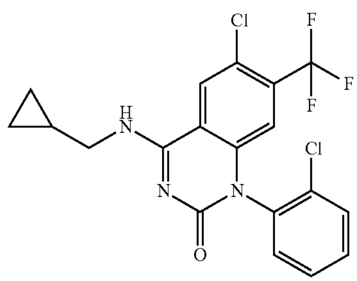 [SMILES: O=c1nc(NCC2CC2)c2cc(Cl)c(C(F)(F)F)cc2n1-c1ccccc1Cl] | 6-chloro-1-(2-chlorophenyl)-4-((cyclopropylmethyl)amino)-7-(trifluoromethyl)-quinazolin-2(1H)-one | m/z [M + H] 428.0 |
| 588 | 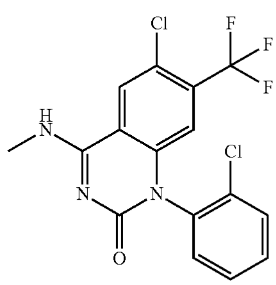 [SMILES: CNc1nc(=O)n(-c2ccccc2Cl)c2cc(C(F)(F)F)c(Cl)cc12] | 6-chloro-1-(2-chlorophenyl)-4-(methylamino)-7-(trifluoromethyl)-quinazolin-2(1H)-one | m/z [M + H] 388.0 |
| 589 | 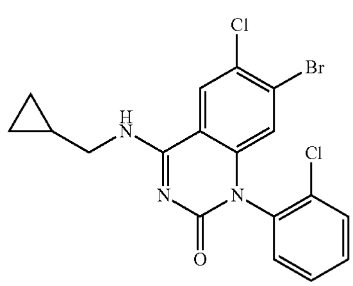 [SMILES: O=c1nc(NCC2CC2)c2cc(Cl)c(Br)cc2n1-c1ccccc1Cl] | 7-bromo-6-chloro-1-(2-chlorophenyl)-4-((cyclopropylmethyl)amino)quinazolin-2(1H)-one | m/z [M + H] 439.9 |

TABLE 1-continued

| Cpd. No. | Structure | Name | Mass Spec. |
|---|---|---|---|
| 590 | 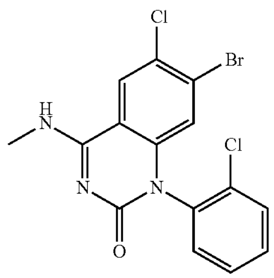 [SMILES: CNc1nc(=O)n(-c2ccccc2Cl)c2cc(Br)c(Cl)cc12] | 7-bromo-6-chloro-1-(2-chlorophenyl)-4-(methylamino)quinazolin-2(1H)-one | m/z [M + H] 399.9 |
| 591 | 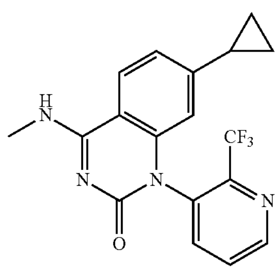 | 7-cyclopropyl-4-(methylamino)-1-(2-(trifluoromethyl)pyridin-3-yl)quinazolin-2(1H)-one | m/z [M + H] 361.1 |
| 592 | 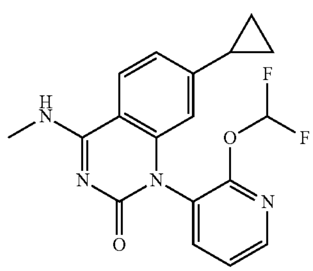 [SMILES: CNc1nc(=O)n(-c2cccnc2OC(F)F)c2cc(C3CC3)ccc12] | 7-cyclopropyl-1-(2-(difluoromethoxy)pyridin-3-yl)-4-(methylamino)-quinazolin-2(1H)-one | m/z [M + H] 359.1 |
| 593 | 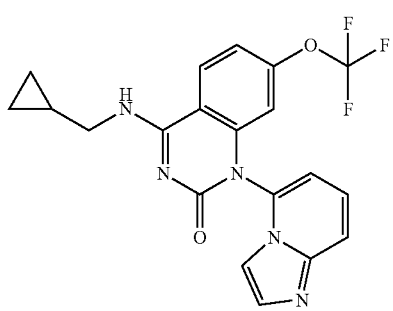 [SMILES: O=c1nc(NCC2CC2)c2ccc(OC(F)(F)F)cc2n1-c1cccc2nccn12] | 4-((cyclopropylmethyl)amino)-1-(imadazo[1,2-a]pyridin-5-yl)-7-(trifluoromethoxy)-quinazolin-2(1H)-one | m/z [M + H] 416.1 |
| 594 | 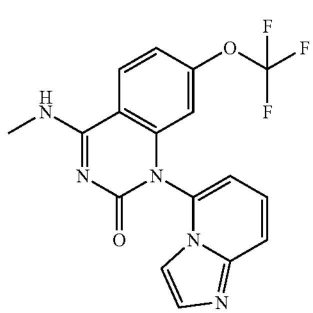 [SMILES: CNc1nc(=O)n(-c2cccc3nccn23)c2cc(OC(F)(F)F)ccc12] | 1-(imidazo[1,2-a]pyridin-5-yl)-4-(methylamino)-7-(trifluoromethoxy)-quinazolin-2(1H)-one | m/z [M + H] 376.1 |

TABLE 1-continued

| Cpd. No. | Structure | Name | Mass Spec. |
|---|---|---|---|
| 595 | 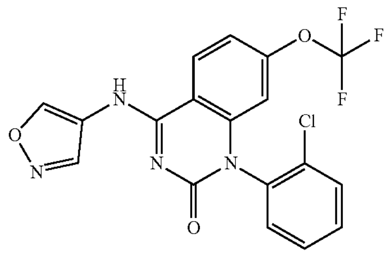 [SMILES: O=c1nc(Nc2cnoc2)c2ccc(OC(F)(F)F)cc2n1-c1ccccc1Cl] | 1-(2-chlorophenyl)-4-(isoxazol-4-ylamino)-7-(trifluoromethoxy)-quinazolin-2(1H)-one | m/z [M + H] 423.0 |
| 596 | 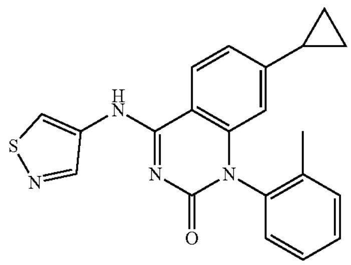 [SMILES: Cc1ccccc1-n1c(=O)nc(Nc2cnsc2)c2ccc(C3CC3)cc21] | 7-cyclopropyl-4-(isothiazol-4-ylamino)-1-(o-tolyl)quinazolin-2(1H)-one | m/z [M + H] 375.1 |
| 597 | 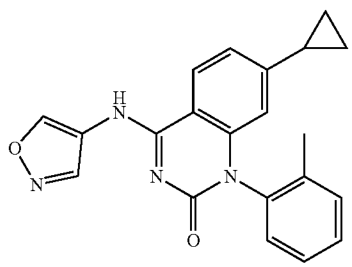 [SMILES: Cc1ccccc1-n1c(=O)nc(Nc2cnoc2)c2ccc(C3CC3)cc21] | 7-cyclopropyl-4-(isoxazol-4-ylamino)-1-(o-tolyl)quinazolin-2(1H)-one | m/z [M + H] 359.1 |
| 598 | 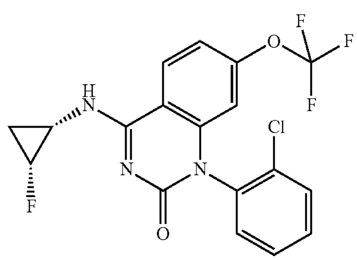 [SMILES: O=c1nc(N[C@H]2C[C@H]2F)c2ccc(OC(F)(F)F)cc2n1-c1ccccc1Cl] | 1-(2-chlorophenyl)-4-(((1S,2R)-2-fluorocyclopropyl)amino)-7-(trifluoromethoxy)-quinazolin-2(1H)-one | m/z [M + H] 414.05 |
| 599 | 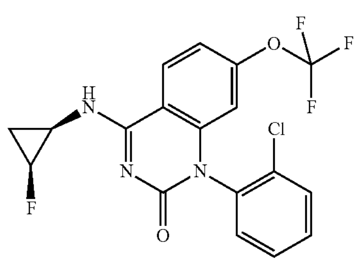 [SMILES: O=c1nc(N[C@@H]2C[C@@H]2F)c2ccc(OC(F)(F)F)cc2n1-c1ccccc1Cl] | 1-(2-chlorophenyl)-4-(((1R,2S)-2-fluorocyclopropyl)amino)-7-(trifluoromethoxy)-quinazolin-2(1H)-one | m/z [M + H] 414.05 |
| 600 | 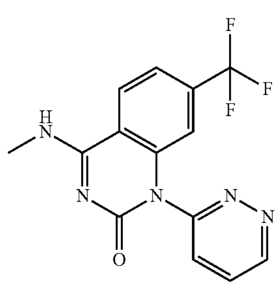 | 1-(2-chlorophenyl)-4-(isothiazol-4-ylamino)-7-(trifluoromethyl)pyrido[2,3-d]pyrimidin-2(1H)-one | m/z [M + H] 424.0 |

TABLE 1-continued

| Cpd. No. | Structure | Name | Mass Spec. |
|---|---|---|---|
| 601 | 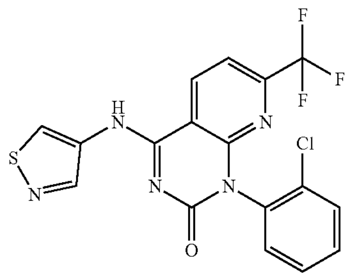 [SMILES: O=c1nc(Nc2cnsc2)c2ccc(C(F)(F)F)nc2n1-c1ccccc1Cl] | 4-(methylamino)-1-(pyridazin-3-yl)-7-(trifluoromethyl)quinazolin-2(1H)-one | m/z [M + H] 322.1 |
| 602 | 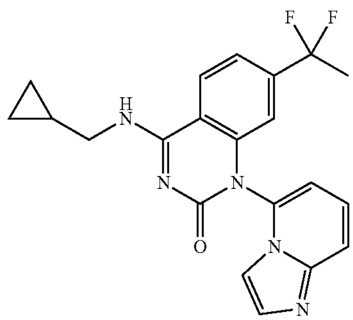 [SMILES: CC(F)(F)c1ccc2c(NCC3CC3)nc(=O)n(-c3cccc4nccn34)c2c1] | 4-((cyclopropylmethyl)amino)-7-(1,1-difluoroethyl)-1-(imidazo[1,2-a]pyridin-5-yl)quinazolin-2(1H)-one | m/z [M + H] 396.2 |
| 603 | 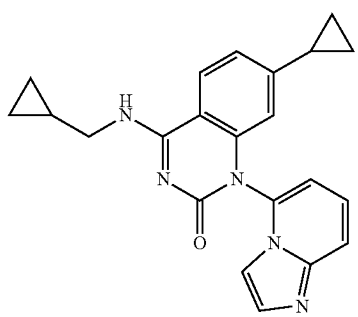 [SMILES: O=c1nc(NCC2CC2)c2ccc(C3CC3)cc2n1-c1cccc2nccn12] | 7-cyclopropyl-4-((cyclopropylmethyl)amino)-1-(imidazo[1,2-a]pyridin-5-yl)-quinazolin-2(1H)-one | m/z [M + H] 372.15 |
| 604 | 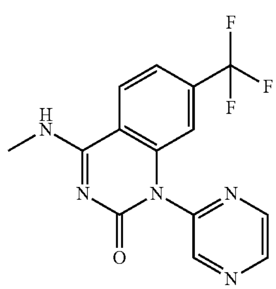 [SMILES: CNc1nc(=O)n(-c2cnccn2)c2cc(C(F)(F)F)ccc12] | 4-(methylamino)-1-(pyrazin-2-yl)-7-(trifluoromethyl)quinazolin-2(1H)-one | m/z [M + H] 322.1 |
| 605 | 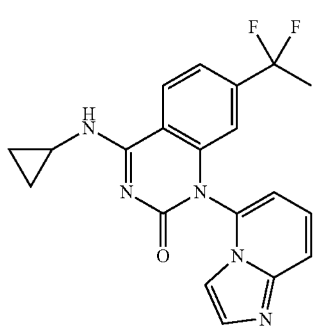 [SMILES: CC(F)(F)c1ccc2c(NC3CC3)nc(=O)n(-c3cccc4nccn34)c2c1] | 4-(cyclopropylamino)-7-(1,1-difluoroethyl)-1-(imidazo[1,2-a]pyridin-5-yl)quinazolin-2(1H)-one | m/z [M + H] 382.2 |

TABLE 1-continued

| Cpd. No. | Structure | Name | Mass Spec. |
|---|---|---|---|
| 606 | 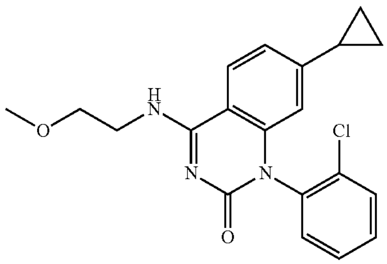 [SMILES: COCCNc1nc(=O)n(-c2ccccc2Cl)c2cc(C3CC3)ccc12] | 1-(2-chlorophenyl)-7-cyclopropyl-4-((2-methoxyethyl)amino)quinazolin-2(1H)-one | m/z [M + H] 370.1 |
| 607 | 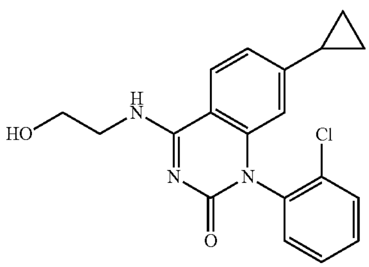 | 1-(2-chlorophenyl)-7-cyclopropyl-4-((2-hydroxyethyl)amino)quinazolin-2(1H)-one | m/z [M + H] 356.1 |
| 608 | 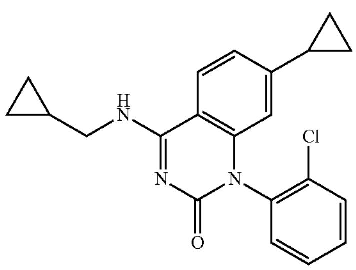 [SMILES: O=c1nc(NCC2CC2)c2ccc(C3CC3)cc2n1-c1ccccc1Cl] | 1-(2-chlorophenyl)-7-cyclopropyl-4-((cyclopropylmethyl)amino)quinazolin-2(1H)-one | m/z [M + H] 366.1 |
| 609 | 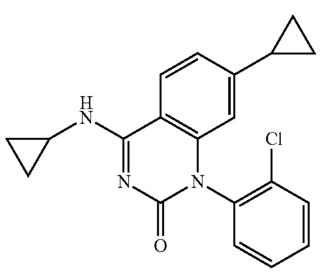 [SMILES: O=c1nc(NC2CC2)c2ccc(C3CC3)cc2n1-c1ccccc1Cl] | 1-(2-chlorophenyl)-7-cyclopropyl-4-(cyclopropylamino)quinazolin-2(1H)-one | m/z [M + H] 352.1 |
| 610 | 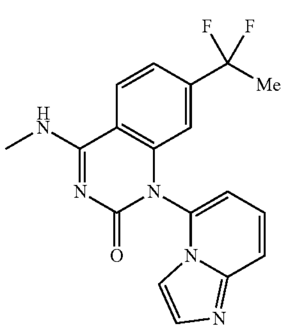 [SMILES: CNc1nc(=O)n(-c2cccc3nccn23)c2cc(C(C)(F)F)ccc12] | 7-(1,1-difluoroethyl)-1-(imidazo[1,2-a]pyridin-5-yl)-4-(methylamino)-quinazolin-2(1H)-one | m/z [M + H] 356.1 |

TABLE 1-continued

| Cpd. No. | Structure | Name | Mass Spec. |
|---|---|---|---|
| 611 | 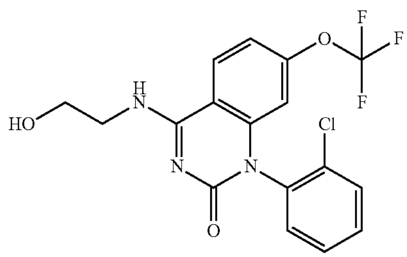 [SMILES: O=c1nc(NCCO)c2ccc(OC(F)(F)F)cc2n1-c1ccccc1Cl] | 1-(2-chlorophenyl)-4-((2-hydroxyethyl)-amino)-7-(trifluoromethoxy)quinazolin-2(1H)-one | m/z [M + H] 400.1 |
| 612 | 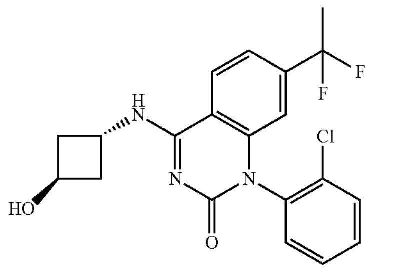 [SMILES: CC(F)(F)c1ccc2c(N[C@H]3C[C@H](O)C3)nc(=O)n(-c3ccccc3Cl)c2c1] | 1-(2-chlorophenyl)-7-(1,1-difluoroethyl)-4-(((trans)-3-hydroxycyclobutyl)amino)-quinazolin-2(1H)-one | m/z [M + H] 406.1 |
| 613 | 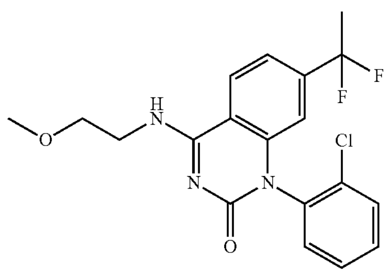 [SMILES: COCCNc1nc(=O)n(-c2ccccc2Cl)c2cc(C(C)(F)F)ccc12] | 1-(2-chlorophenyl)-7-(1,1-difluoroethyl)-4-((2-methoxyethyl)amino)quinazolin-2(1H)-one | m/z [M + H] 394.05 |
| 614 | 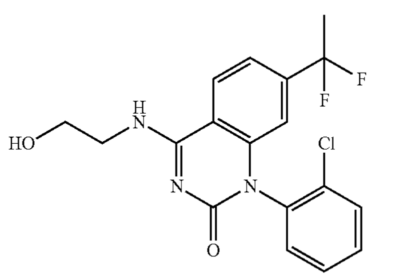 [SMILES: CC(F)(F)c1ccc2c(NCCO)nc(=O)n(-c3ccccc3Cl)c2c1] | 1-(2-chlorophenyl)-7-(1,1-difluoroethyl)-4-((2-hydroxyethyl)amino)quinazolin-2(1H)-one | m/z [M + H] 380.05 |
| 615 | 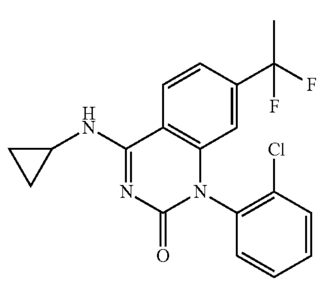 [SMILES: CC(F)(F)c1ccc2c(NC3CC3)nc(=O)n(-c3ccccc3Cl)c2c1] | 1-(2-chlorophenyl)-4-(cyclopropyl-amino)-7-(1,1-difluoroethyl)quinazolin-2(1H)-one | m/z [M + H] 376.1 |

TABLE 1-continued

| Cpd. No. | Structure | Name | Mass Spec. |
|---|---|---|---|
| 616 | 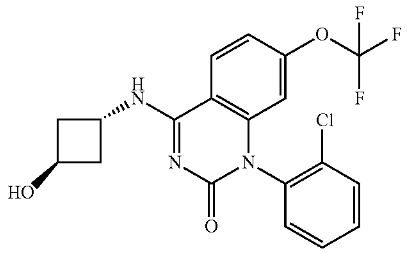 [SMILES: O=c1nc(N[C@H]2C[C@H](O)C2)c2ccc(OC(F)(F)F)cc2n1-c1ccccc1Cl] | 1-(2-chlorophenyl)-4-(((trans)-3-hydroxycyclobutyl)amino)-7-(trifluoromethoxy)-quinazolin-2(1H)-one | m/z [M + H] 426.1 |
| 617 | 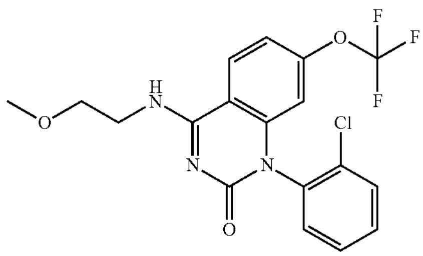 [SMILES: COCCNc1nc(=O)n(-c2ccccc2Cl)c2cc(OC(F)(F)F)ccc12] | 1-(2-chlorophenyl)-4((2-methoxyethyl)-amino)-7-(trifluoromethoxy)quinazolin-2(1H)-one | m/z [M + H] 414.0 |
| 618 | 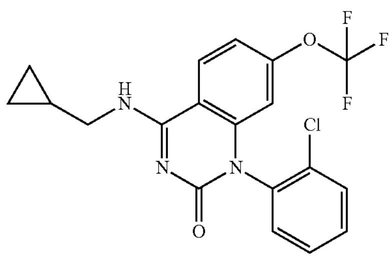 [SMILES: O=c1nc(NCC2CC2)c2ccc(OC(F)(F)F)cc2n1-c1ccccc1Cl] | 1-(2-chlorophenyl)-4-((cyclopropyl-methyl)amino)-7-(trifluoromethoxy)-quinazolin-2(1H)-one | m/z [M + H] 410.0 |
| 619 | 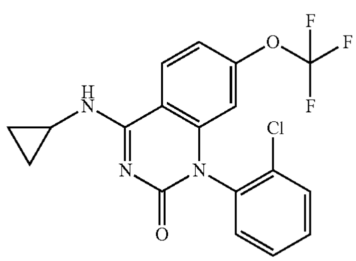 [SMILES: O=c1nc(NC2CC2)c2ccc(OC(F)(F)F)cc2n1-c1ccccc1Cl] | 1-(2-chlorophenyl)-4-(cyclopropyl-amino)-7-(trifluoromethoxy)quinazolin-2(1H)-one | m/z [M + H] 396.0 |
| 620 | 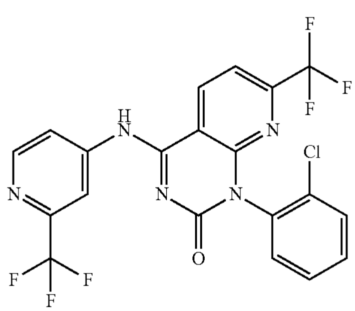 [SMILES: O=c1nc(Nc2ccnc(C(F)(F)F)c2)c2ccc(C(F)(F)F)nc2n1-c1ccccc1Cl] | 1-(2-chlorophenyl)-7-(trifluoromethyl)-4((2-(trifluoromethyl)pyridin-4-yl)-amino)-pyrido[2,3-d]pyrimidin-2(1H)-one | m/z [M + H] 486.05 |
| 621 | 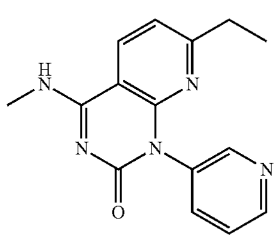 [SMILES: CCc1ccc2c(NC)nc(=O)n(-c3cccnc3)c2n1] | 7-ethyl-4-(methylamino)-1-(pyridin-3-yl)pyrido[2,3-d]pyrimidin-2(1H)-one | m/z [M + H] 282.15 |

TABLE 1-continued

| Cpd. No. | Structure | Name | Mass Spec. |
|---|---|---|---|
| 622 | 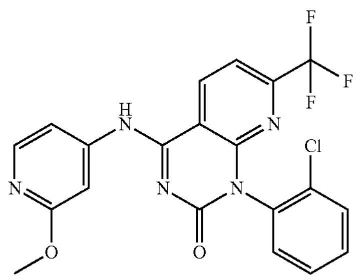 [SMILES: COc1cc(Nc2nc(=O)n(-c3ccccc3Cl)c3nc(C(F)(F)F)ccc23)ccn1] | 1-(2-chlorophenyl)-4-((2-methoxy-pyridin-4-yl)amino)-7-(trifluoromethyl)-pyrido-[2,3-d]pyrimidin-2(1H)-one | m/z [M + H] 448.1 |
| 623 | 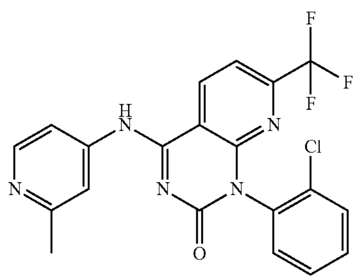 [SMILES: Cc1cc(Nc2nc(=O)n(-c3ccccc3Cl)c3nc(C(F)(F)F)ccc23)ccn1] | 1-(2-chlorophenyl)-4-((2-methylpyridin-4-yl)amino)-7-(trifluoromethyl)-pyrido[2,3-d]pyrimidin-2(1H)-one | |
| 624 | 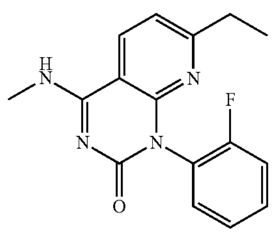 [SMILES: CCc1ccc2c(NC)nc(=O)n(-c3ccccc3F)c2n1] | 7-ethyl-1-(2-fluorophenyl)-4-(methyl-amino)pyrido[2,3-d]pyrimidin-2(1H)-one | m/z [M + H] 299.1 |
| 625 | 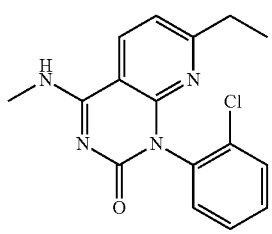 [SMILES: CCc1ccc2c(NC)nc(=O)n(-c3ccccc3Cl)c2n1] | 1-(2-chlorophenyl)-7-ethyl-4-(methyl-amino)pyrido[2,3-d]pyrimidin-2(1H)-one | m/z [M + H] 315.1 |
| 626 | 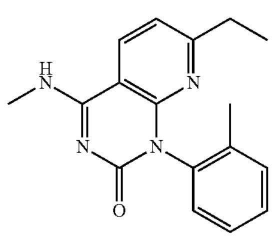 [SMILES: CCc1ccc2c(NC)nc(=O)n(-c3ccccc3C)c2n1] | 7-ethyl-4-(methylamino)-1-(o-tolyl)-pyrido[2,3-d]pyrimidin-2(1H)-one | m/z [M + H] 295.15 |
| 627 | 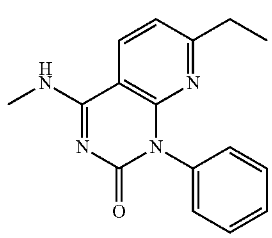 [SMILES: CCc1ccc2c(NC)nc(=O)n(-c3ccccc3)c2n1] | 7-ethyl-4-(methylamino)-1-phenyl-pyrido[2,3-d]pyrimidin-2(1H)-one | m/z [M + H] 281.2 |

TABLE 1-continued

| Cpd. No. | Structure | Name | Mass Spec. |
|---|---|---|---|
| 628 | 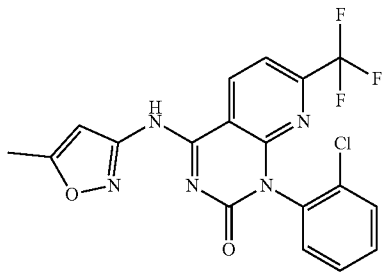 [SMILES: Cc1cc(Nc2nc(=O)n(-c3ccccc3Cl)c3nc(C(F)(F)F)ccc23)no1] | 1-(2-chlorophenyl)-4-((5-methyl-isoxazol-3-yl)amino)-7-(trifluoro-methyl)pyrido[2,3-d]pyrimidin-2(1H)-one | m/z [M + H] 422.05 |
| 629 | 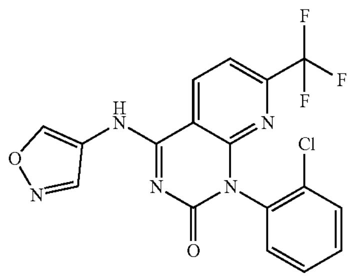 | 1-(2-chlorophenyl)-4-(isoxazol-4-yl-amino)-7-(trifluoromethyl)pyrido[2,3-d]-pyrimidin-2(1H)-one | m/z [M + H] 408.0 |
| 630 | 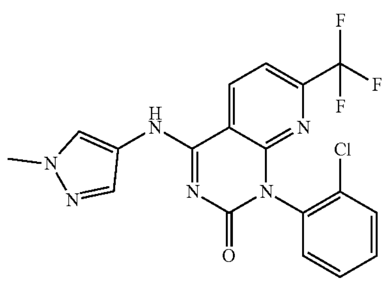 [SMILES: Cn1cc(Nc2nc(=O)n(-c3ccccc3Cl)c3nc(C(F)(F)F)ccc23)cn1] | 1-(2-chlorophenyl)-4-((1-methyl-1H-pyrazol-4-yl)amino)-7-(trifluoromethyl)-pyrido[2,3-d]pyrimidin-2(1H)-one | m/z [M + H] 421.0 |
| 631 | 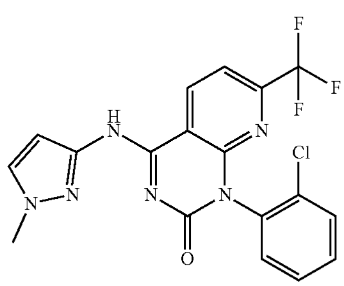 [SMILES: Cn1ccc(Nc2nc(=O)n(-c3ccccc3Cl)c3nc(C(F)(F)F)ccc23)n1] | 1-(2-chlorophenyl)-4-((1-methyl-1H-pyrazol-3-yl)amino)-7-(trifluoro-methyl)pyrido-[2,3-d]pyrimidin-2(1H)-one | m/z [M + H] 421.0 |
| 632 | 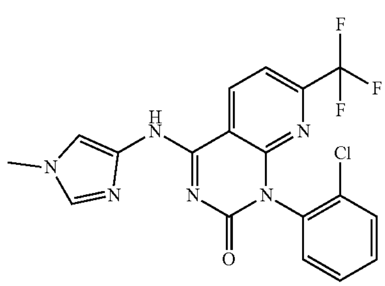 [SMILES: Cn1cnc(Nc2nc(=O)n(-c3ccccc3Cl)c3nc(C(F)(F)F)ccc23)c1] | 1-(2-chlorophenyl)-4-((1-methyl-1H-imidazol-4-yl)amino)-7-(trifluoro-methyl)-pyrido[2,3-d]pyrimidin-2(1H)-one | m/z [M + H] 421.0 |

TABLE 1-continued

| Cpd. No. | Structure | Name | Mass Spec. |
|---|---|---|---|
| 633 | 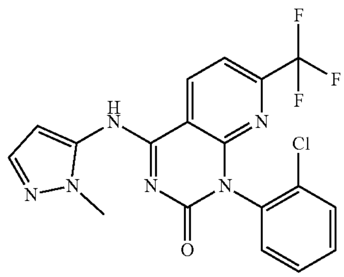 [SMILES: Cn1nccc1Nc1nc(=O)n(-c2ccccc2Cl)c2nc(C(F)(F)F)ccc12] | 1-(2-chlorophenyl)-4-((1-methyl-1H-pyrazol-5-yl)amino)-7-(trifluoromethyl)-pyrido[2,3-d]pyrimidin-2(1H)-one | m/z [M + H] 421.0 |
| 634 | 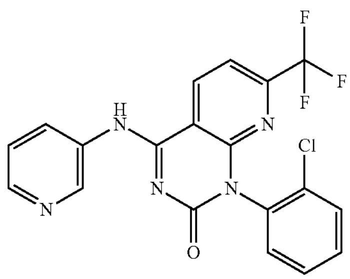 [SMILES: O=c1nc(Nc2cccnc2)c2ccc(C(F)(F)F)nc2n1-c1ccccc1Cl] | 1-(2-chlorophenyl)-4-(pyridin-3-yl-amino)-7-(trifluoromethyl)pyrido[2,3-d]-pyrimidin-2(1H)-one | m/z [M + H] 418.0 |
| 635 | 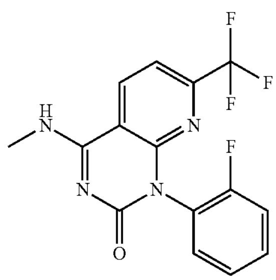 [SMILES: CNc1nc(=O)n(-c2ccccc2F)c2nc(C(F)(F)F)ccc12] | 1-(2-fluorophenyl)-4-(methylamino)-7-(trifluoromethyl)pyrido[2,3-d]pyrimidin-2(1H)-one | m/z [M + H] 339.1 |
| 636 | 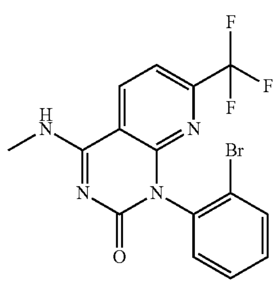 | 1-(2-bromophenyl)-4-(methylamino)-7-(trifluoromethyl)pyrido[2,3-d]pyrimidin-2(1H)-one | m/z [M + H] 401.0, 399.0 |
| 637 | 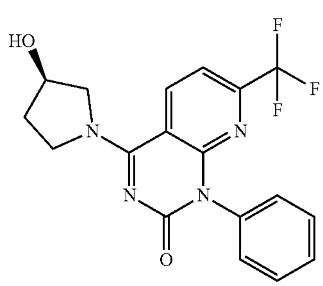 [SMILES: O=c1nc(N2CC[C@@H](O)C2)c2ccc(C(F)(F)F)nc2n1-c1ccccc1] | (R)-4-(3-hydroxypyrrolidin-1-yl)-1-phenyl-7-(trifluoromethyl)pyrido[2,3-d]-pyrimidin-2(1H)-one | m/z [M + H] 377.1 |

TABLE 1-continued

| Cpd. No. | Structure | Name | Mass Spec. |
|---|---|---|---|
| 638 | 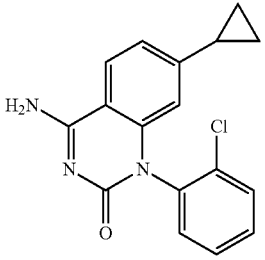 [SMILES: Nc1nc(=O)n(-c2ccccc2Cl)c2cc(C3CC3)ccc12] | 4-amino-1-(2-chlorophenyl)-7-cyclopropylquinazolin-2(1H)-one | m/z [M + H] 312.00 |
| 639 | 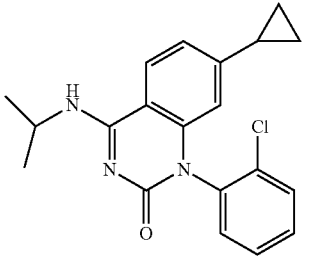 [SMILES: CC(C)Nc1nc(=O)n(-c2ccccc2Cl)c2cc(C3CC3)ccc12] | 1-(2-chlorophenyl)-7-cyclopropyl-4-(isopropylamino)quinazolin-2(1H)-one | m/z [M + H] 354.20 |
| 640 | 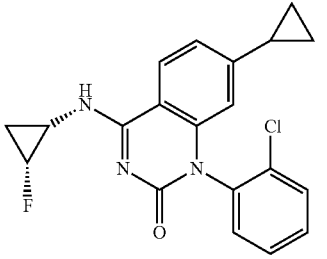 | 1-(2-chlorophenyl)-7-cyclopropyl-4-(((1S,2R)-2-fluorocyclopropyl)amino)-quinazolin-2(1H)-one | m/z [M + H] 370.00 |
| 641 | 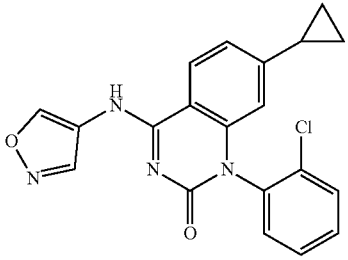 [SMILES: O=c1nc(Nc2cnoc2)c2ccc(C3CC3)cc2n1-c1ccccc1Cl] | 1-(2-chlorophenyl)-7-cyclopropyl-4-(isoxazol-4-ylamino)quinazolin-2(1H)-one | m/z [M + H] 379.00 |
| 642 | 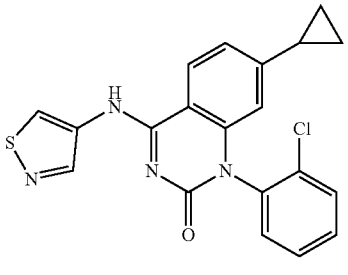 [SMILES: O=c1nc(Nc2cnsc2)c2ccc(C3CC3)cc2n1-c1ccccc1Cl] | 1-(2-chlorophenyl)-7-cyclopropyl-4-(isothiazol-4-ylamino)quinazolin-2(1H)-one | m/z [M + H] 395.00 |

TABLE 1-continued

| Cpd. No. | Structure | Name | Mass Spec. |
|---|---|---|---|
| 643 | 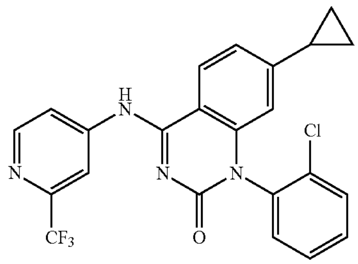 [SMILES: O=c1nc(Nc2ccnc(C(F)(F)F)c2)c2ccc(C3CC3)cc2n1-c1ccccc1Cl] | 1-(2-chlorophenyl)-7-cyclopropyl-4-((2-(trifluoromethyl)pyridin-4-yl)amino)-quinazolin-2(1H)-one | m/z [M + H] 457.00 |
| 644 | 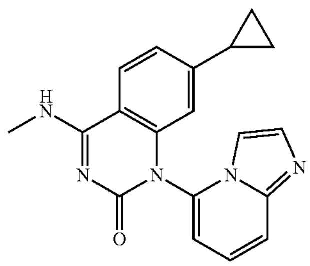 [SMILES: CNc1nc(=O)n(-c2cccc3nccn23)c2cc(C3CC3)ccc12] | 7-cyclopropyl-1-(imidazo[1,2-a]pyridin-5-yl)-4-(methylamino)quinazolin-2(1H)-one | m/z [M + H] 332.00 |
| 645 | 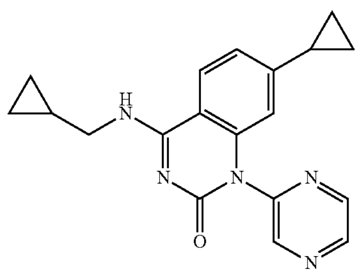 [SMILES: O=c1nc(NCC2CC2)c2ccc(C3CC3)cc2n1-c1cnccn1] | 7-cyclopropyl-4-((cyclopropylmethyl)amino)-1-(pyrazin-2-yl)quinazolin-2(1H)-one | m/z [M + H] 334.20 |
| 646 | 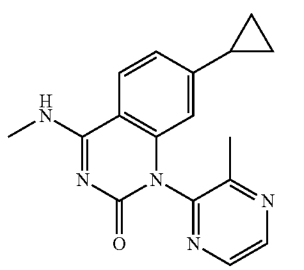 [SMILES: CNc1nc(=O)n(-c2nccnc2C)c2cc(C3CC3)ccc12] | 7-cyclopropyl-4-(methylamino)-1-(3-methylpyrazin-2-yl)quinazolin-2(1H)-one | m/z [M + H] 308.20 |
| 647 | 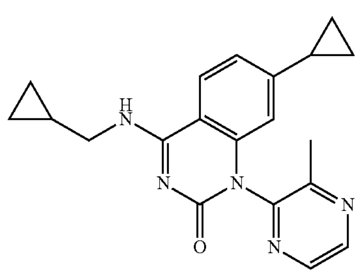 [SMILES: Cc1nccnc1-n1c(=O)nc(NCC2CC2)c2ccc(C3CC3)cc21] | 7-cyclopropyl-4-((cyclopropylmethyl)amino)-1-(3-methylpyrazin-2-yl)-quinazolin-2(1H)-one | m/z [M + H] 348.20 |

TABLE 1-continued

| Cpd. No. | Structure | Name | Mass Spec. |
|---|---|---|---|
| 648 | 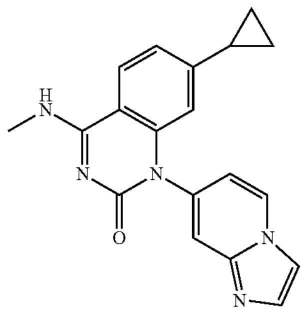 [SMILES: CNc1nc(=O)n(-c2ccn3ccnc3c2)c2cc(C3CC3)ccc12] | 7-cyclopropyl-1-(imidazo[1,2-a]pyridin-7-yl)-4-(methylamino)quinazolin-2(1H)-one | m/z [M + H] 332.00 |
| 649 | 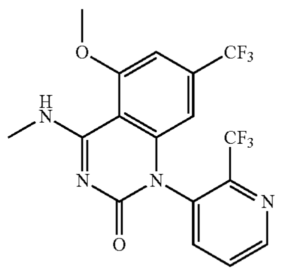 [SMILES: CNc1nc(=O)n(-c2cccnc2C(F)(F)F)c2cc(C(F)(F)F)cc(OC)c12] | 5-methoxy-4-(methylamino)-7-(trifluoromethyl)-1-(2-(trifluoromethyl)-pyridin-3-yl)quinazolin-2(1H)-one | m/z [M + H] 419.00 |
| 650 | 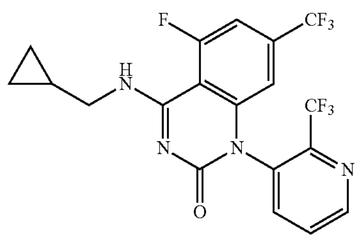 [SMILES: O=c1nc(NCC2CC2)c2c(F)cc(C(F)(F)F)cc2n1-c1cccnc1C(F)(F)F] | 4-((cyclopropylmethyl)amino)-5-fluoro-7-(trifluoromethyl)-1-(2-(trifluoromethyl)-pyridin-3-yl)quinazolin-2(1H)-one | m/z [M + H] 447.00 |
| 651 | 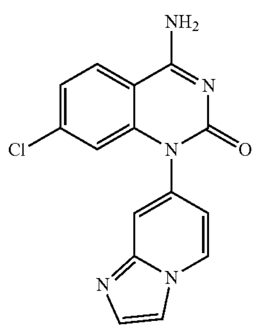 [SMILES: Nc1nc(=O)n(-c2ccn3ccnc3c2)c2cc(Cl)ccc12] | 4-amino-7-chloro-1-(imidazo[1,2-a]pyridin-7-yl)quinazolin-2(1H)-one | m/z [M + H] 312.0 |
| 652 | 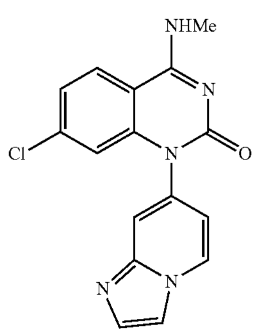 [SMILES: CNc1nc(=O)n(-c2ccn3ccnc3c2)c2cc(Cl)ccc12] | 7-chloro-1-(imidazo[1,2-a]pyridin-7-yl)-4-(methylamino)quinazolin-2(1H)-one | m/z [M + H] 326.0 |

TABLE 1-continued

| Cpd. No. | Structure | Name | Mass Spec. |
|---|---|---|---|
| 653 | 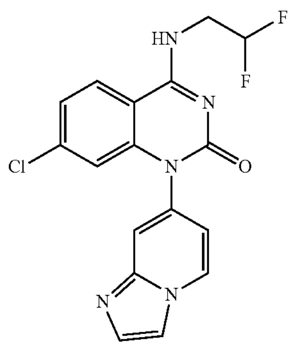 [SMILES: O=c1nc(NCC(F)F)c2ccc(Cl)cc2n1-c1ccn2ccnc2c1] | 7-chloro-4-((2,2-difluoroethyl)amino)-1-(imidazo[1,2-a]pyridin-7-yl)quinazolin-2(1H)-one | m/z [M + H] 376.0 |
| 654 | 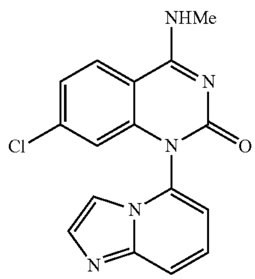 [SMILES: CNc1nc(=O)n(-c2cccc3nccn23)c2cc(Cl)ccc12] | 7-chloro-1-(imidazo[1,2-a]pyridin-5-yl)-4-(methylamino)quinazolin-2(1H)-one | m/z [M + H] 326.0 |
| 655 | 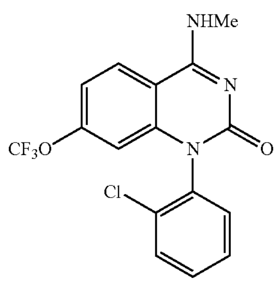 | 1-(2-chlorophenyl)-4-(methylamino)-7-(trifluoromethoxy)quinazolin-2(1H)-one | m/z [M + H] 370.1 |
| 656 | 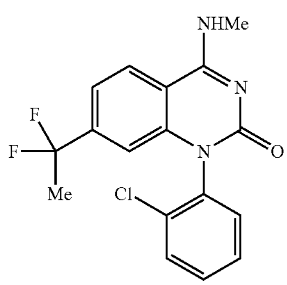 [SMILES: CNc1nc(=O)n(-c2ccccc2Cl)c2cc(C(C)(F)F)ccc12] | 4-amino-1-(2-chlorophenyl)-7-(1,1-difluoroethyl)quinazolin-2(1H)-one | m/z [M + H] 336.1 |
| 657 | 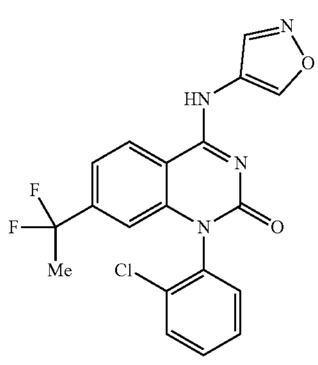 [SMILES: CC(F)(F)c1ccc2c(Nc3cnoc3)nc(=O)n(-c3ccccc3Cl)c2c1] | 1-(2-chlorophenyl)-7-(1,1-difluoroethyl)-4-(isoxazol-4-ylamino)quinazolin-2(1H)-one | m/z [M + H] 403.0 |

TABLE 1-continued

| Cpd. No. | Structure | Name | Mass Spec. |
|---|---|---|---|
| 658 | 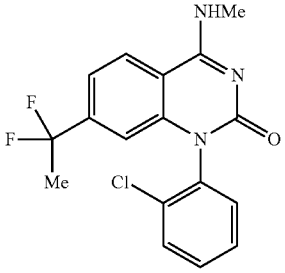 [SMILES: CNc1nc(=O)n(-c2ccccc2Cl)c2cc(C(C)(F)F)ccc12] | 1-(2-chlorophenyl)-7-(1,1-difluoroethyl)-4-(methylamino)quinazolin-2(1H)-one | m/z [M + H] 350.1 |
| 659 | 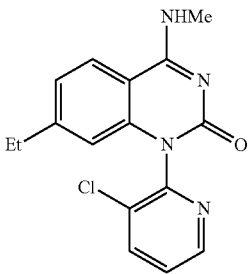 [SMILES: CCc1ccc2c(NC)nc(=O)n(-c3ncccc3Cl)c2c1] | 1-(3-chloropyridin-2-yl)-7-ethyl-4-(methylamino)quinazolin-2(1H)-one | m/z [M + H] 315.0 |
| 660 | 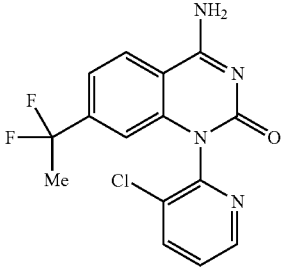 [SMILES: CC(F)(F)c1ccc2c(N)nc(=O)n(-c3ncccc3Cl)c2c1] | 4-amino-1-(3-chloropyridin-2-yl)-7-(1,1-difluoroethyl)quinazolin-2(1H)-one | m/z [M + H] 337.0. |
| 661 | 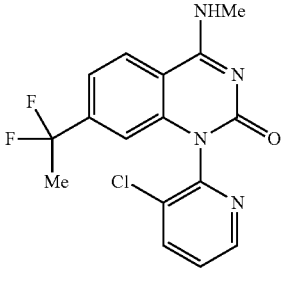 [SMILES: CNc1nc(=O)n(-c2ncccc2Cl)c2cc(C(C)(F)F)ccc12] | 1-(3-chloropyridin-2-yl)-7-(1,1-difluoroethyl)-4-(methylamino)-quinazolin-2(1H)-one | m/z [M + H] 351.0 |
| 662 | 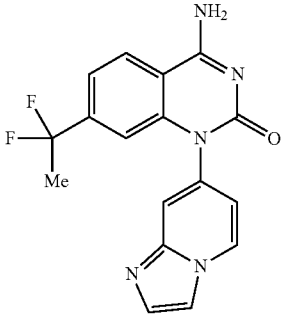 [SMILES: CC(F)(F)c1ccc2c(N)nc(=O)n(-c3ccn4ccnc4c3)c2c1] | 4-amino-7-(1,1-difluoroethyl)-1-(imidazo[1,2-a]pyridin-7-yl)quinazolin-2(1H)-one | m/z [M + H] 342.1 |

TABLE 1-continued

| Cpd. No. | Structure | Name | Mass Spec. |
|---|---|---|---|
| 663 | 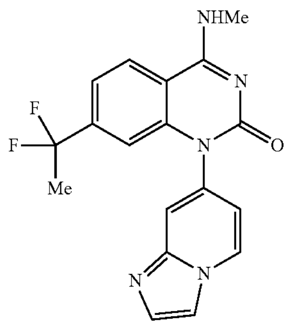 [SMILES: CNc1nc(=O)n(-c2ccn3ccnc3c2)c2cc(C(C)(F)F)ccc12] | 7-(1,1-difluoroethyl)-1-(imidazo[1,2-a]pyridin-7-yl)-4-(methylamino)-quinazolin-2(1H)-one | m/z [M + H] 356.0 |
| 664 | 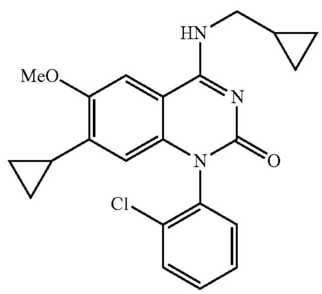 | 1-(2-chlorophenyl)-7-cyclopropyl-4-((cyclopropylmethyl)amino)-6-methoxyquinazolin-2(1H)-one | m/z [M + H] 396.2 |
| 665 | 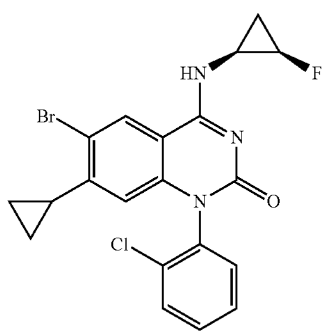 | 6-bromo-1-(2-chlorophenyl)-7-cyclopropyl-4-(((1S,2R)-2-fluorocyclopropyl)amino)quinazolin-2(1H)-one | m/z [M + H] 448.0/450.0 |
| 666 | 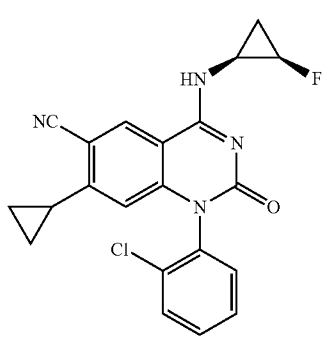 | 1-(2-chlorophenyl)-7-cyclopropyl-4-(((1S,2R)-2-fluorocyclopropyl)amino)-2-oxo-1,2-dihydroquinazoline-6-carbonitrile | m/z [M + H] 395.0 |

TABLE 1-continued

| Cpd. No. | Structure | Name | Mass Spec. |
|---|---|---|---|
| 667 | 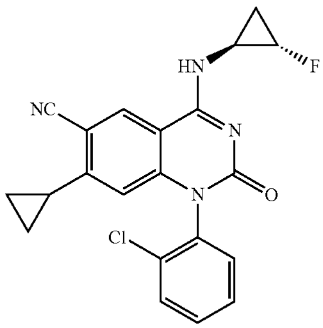 [SMILES: N#Cc1cc2c(N[C@H]3C[C@@H]3F)nc(=O)n(-c3ccccc3Cl)c2cc1C1CC1] | 1-(2-chlorophenyl)-7-cyclopropyl-4-(((trans)-2-fluorocyclopropyl)amino)-2-oxo-1,2-dihydroquinazoline-6-carbonitrile | m/z [M + H] 395.0 |
| 668 | 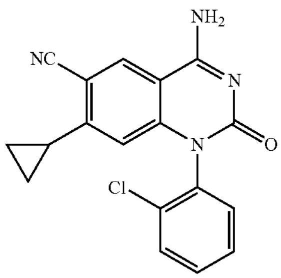 [SMILES: N#Cc1cc2c(N)nc(=O)n(-c3ccccc3Cl)c2cc1C1CC1] | 4-amino-1-(2-chlorophenyl)-7-cyclopropyl-2-oxo-1,2-dihydroquinazoline-6-carbonitrile | m/z [M + H] 337.0 |
| 669 | 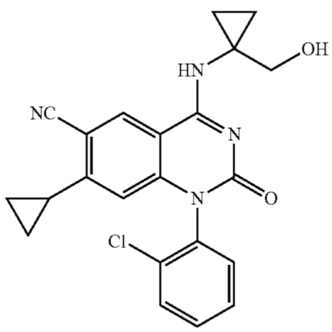 [SMILES: N#Cc1cc2c(NC3(CO)CC3)nc(=O)n(-c3ccccc3Cl)c2cc1C1CC1] | 1-(2-chlorophenyl)-7-cyclopropyl-4-(hydroxymethyl)cyclopropyl)amino)-2-oxo-1,2-dihydroquinazoline-6-carbonitrile | m/z [M + H] 421.0 |
| 670 | 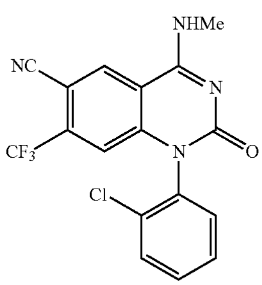 [SMILES: CNc1nc(=O)n(-c2ccccc2Cl)c2cc(C(F)(F)F)c(C#N)cc12] | 1-(2-chlorophenyl)-4-(methylamino)-2-oxo-7-(trifluoromethyl)-1,2-dihydroquinazoline-6-carbonitrile | m/z [M + H] 379.0 |
| 671 | 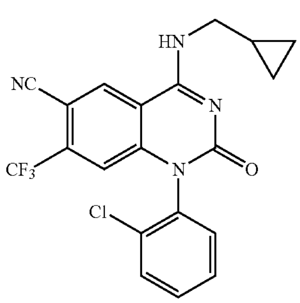 [SMILES: N#Cc1cc2c(NCC3CC3)nc(=O)n(-c3ccccc3Cl)c2cc1C(F)(F)F] | 1-(2-chlorophenyl)-4-((cyclopropylmethyl)amino)-2-oxo-7-(trifluoromethyl)-1,2-dihydroquinazoline-6-carbonitrile | m/z [M + H] 419.0 |

TABLE 1-continued

| Cpd. No. | Structure | Name | Mass Spec. |
|---|---|---|---|
| 672 | 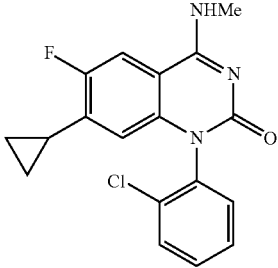 [SMILES: CNc1nc(=O)n(-c2ccccc2Cl)c2cc(C3CC3)c(F)cc12] | 1-(2-chlorophenyl)-7-cyclopropyl-6-fluoro-4-(methylamino)quinazolin-2(1H)-one | m/z [M + H] 344.0 |
| 673 | 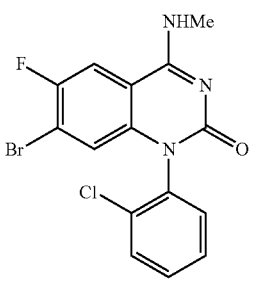 | 7-bromo-1-(2-chlorophenyl)-6-fluoro-4-(methylamino)quinazolin-2(1H)-one | m/z [M + H] 381.9/384.0. |
| 674 | 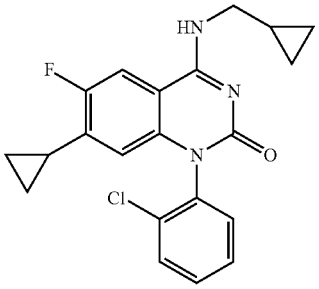 [SMILES: O=c1nc(NCC2CC2)c2cc(F)c(C3CC3)cc2n1-c1ccccc1Cl] | 1-(2-chlorophenyl)-7-cyclopropyl-4-((cyclopropylmethyl)amino)-6-fluoro-quinazolin-2(1H)-one | m/z [M + H] 384.0 |
| 675 | 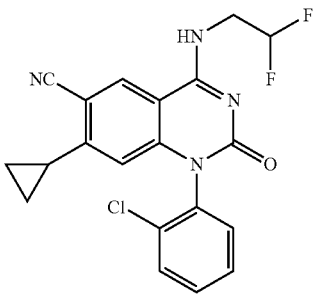 [SMILES: N#Cc1cc2c(NCC(F)F)nc(=O)n(-c3ccccc3Cl)c2cc1C1CC1] | 1-(2-chlorophenyl)-7-cyclopropyl-4-((2,2-difluoroethyl)amino)-2-oxo-1,2-dihydro-quinazoline-6-carbonitrile | m/z [M + H] 410.1 |
| 676 | 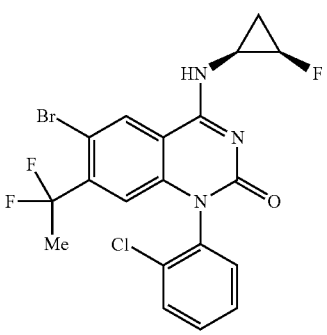 [SMILES: CC(F)(F)c1cc2c(cc1Br)c(N[C@H]1C[C@H]1F)nc(=O)n2-c1ccccc1Cl] | 6-bromo-1-(2-chlorophenyl)-7-(1,1-difluoroethyl)-4-(methylamino)-quinazolin-2(1H)-one | m/z [M + H] 428.0/430.0 |

TABLE 1-continued

| Cpd. No. | Structure | Name | Mass Spec. |
|---|---|---|---|
| 677 | 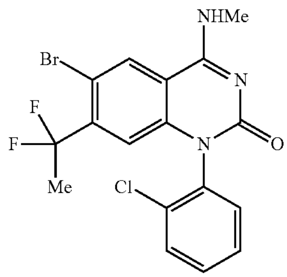 | 6-bromo-1-(2-chlorophenyl)-7-(1,1-difluoroethyl)-4(((1S,2R)-2-fluorocyclopropyl)amino)quinazolin-2(1H)-one | m/z [M + H] 472.0/474.0 |
| 678 | 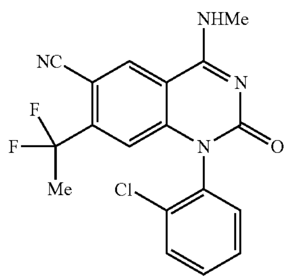 | 1-(2-chlorophenyl)-7-(1,1-difluoroethyl)-4-(methylamino)-2-oxo-1,2-dihydro-quinazoline-6-carbonitrile | m/z [M + H] 375.0 |
| 679 | 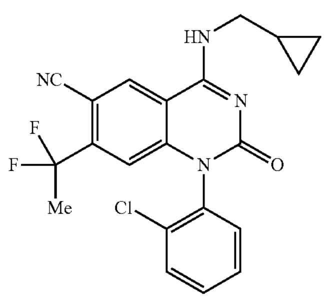 [SMILES: CC(F)(F)c1cc2c(cc1C#N)c(NCC1CC1)nc(=O)n2-c1ccccc1Cl] | 1-(2-chlorophenyl)-4-((cyclopropyl-methyl)amino)-7-(1,1-difluoroethyl)-2-oxo-1,2-dihydroquinazoline-6-carbonitrile | m/z [M + H] 415.0 |
| 680 | 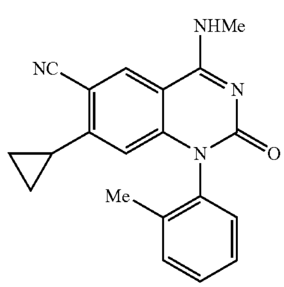 | 7-cyclopropyl-4-(methylamino)-2-oxo-1-(o-tolyl)-1,2-dihydroquinazoline-6-carbonitrile | m/z [M + H] 331.2 |
| 681 | 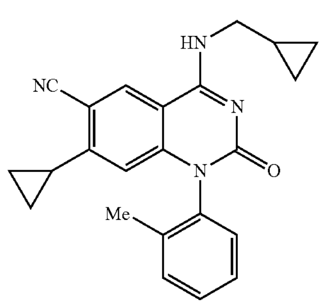 [SMILES: Cc1ccccc1-n1c(=O)nc(NCC2CC2)c2cc(C#N)c(C3CC3)cc21] | 7-cyclopropyl-4-((cyclopropylmethyl)amino)-2-oxo-1-(o-tolyl)-1,2-dihydro-quinazoline-6-carbonitrile | m/z [M + H] 371.2 |

TABLE 1-continued

| Cpd. No. | Structure | Name | Mass Spec. |
|---|---|---|---|
| 682 | 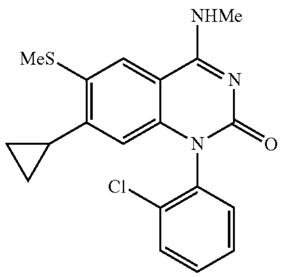 [SMILES: CNc1nc(=O)n(-c2ccccc2Cl)c2cc(C3CC3)c(SC)cc12] | 1-(2-chlorophenyl)-7-cyclopropyl-4-(methylamino)-6-(methylthio)-quinazolin-2(1H)-one | m/z [M + H] 372.0 |
| 683 | 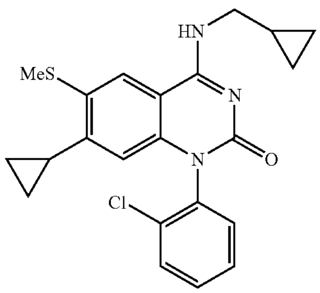 | 1-(2-chlorophenyl)-7-cyclopropyl-4-((cyclopropylmethyl)amino)-6-(methylthio)quinazolin-2(1H)-one | m/z [M + H] 412.0 |
| 684 | 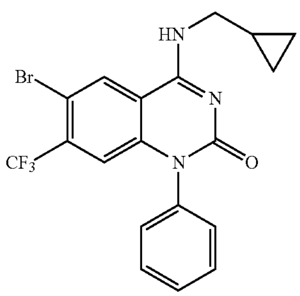 [SMILES: O=c1nc(NCC2CC2)c2cc(Br)c(C(F)(F)F)cc2n1-c1ccccc1] | 6-bromo-4-((cyclopropylmethyl)amino)-1-phenyl-7-(trifluoromethyl)quinazolin-2(1H)-one | m/z [M + H] 438.0/440.0 |
| 685 | 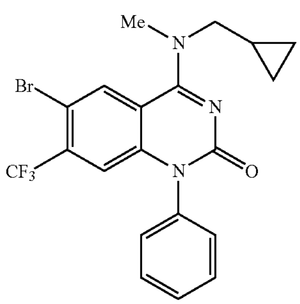 [SMILES: CN(CC1CC1)c1nc(=O)n(-c2ccccc2)c2cc(C(F)(F)F)c(Br)cc12] | 6-bromo-4-((cyclopropylmethyl)(methyl)amino)-1-phenyl-7-(trifluoromethyl)-quinazolin-2(1H)-one | m/z [M + H] 452.0/454.0 |
| 686 | 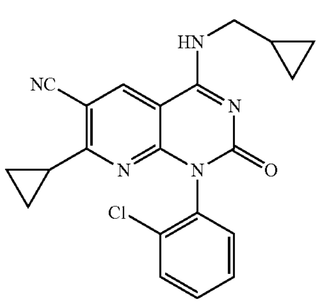 [SMILES: N#Cc1cc2c(NCC3CC3)nc(=O)n(-c3ccccc3Cl)c2nc1C1CC1] | 1-(2-chlorophenyl)-7-cyclopropyl-4-((cyclopropylmethyl)amino)-2-oxo-1,2-dihydropyrido[2,3-d]pyrimidine-6-carbonitrile | m/z [M + H] 392.1 |

TABLE 1-continued

| Cpd. No. | Structure | Name | Mass Spec. |
|---|---|---|---|
| 687 | 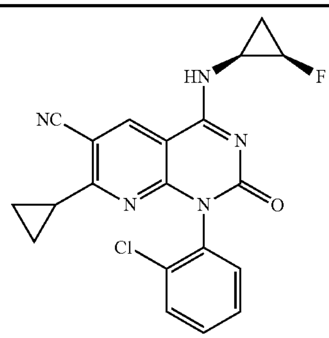 | 1-(2-chlorophenyl)-7-cyclopropyl-4-(((1S,2R)-2-fluorocyclopropyl)amino)-2-oxo-1,2-dihydropyrido[2,3-d]-pyrimidine-6-carbonitrile | m/z [M + H] 396.0 |
| 688 | 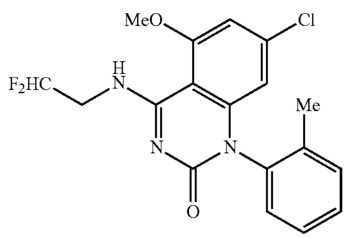 [SMILES: COc1cc(Cl)cc2c1c(NCC(F)F)nc(=O)n2-c1ccccc1C] | 7-chloro-4-((2,2-difluoroethyl)amino)-5-methoxy-1-(o-tolyl)quinazolin-2(1H)-one | m/z [M + H] 380.35 |
| 689 | 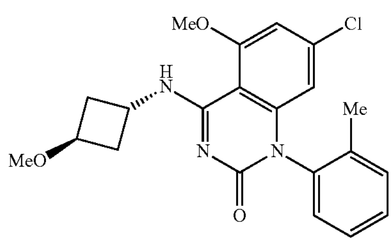 | 7-chloro-5-fluoro-4-(((1r,3r)-3-methoxy-cyclobutyl)amino)-1-(o-tolyl)quinazolin-2(1H)-one | m/z [M + H] 400.33 |
| 690 | 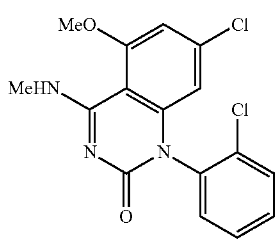 [SMILES: CNc1nc(=O)n(-c2ccccc2Cl)c2cc(Cl)cc(OC)c12] | 7-chloro-1-(2-chlorophenyl)-5-methoxy-4-(methylamino)quinazolin-2(1H)-one | m/z [M + H] 350.2 |
| 691 | 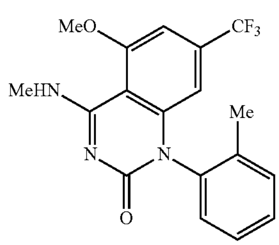 | 5-methoxy-4-(methylamino)-1-(o-tolyl)-7-(trifluoromethyl)quinazolin-2(1H)-one | m/z [M + H] 364.19 |
| 692 | 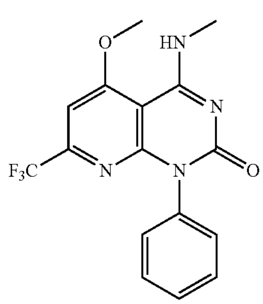 [SMILES: CNc1nc(=O)n(-c2ccccc2)c2nc(C(F)(F)F)cc(OC)c12] | 5-methoxy-4-(methylamino)-1-phenyl-7-(trifluoromethyl)pyrido[2,3-d]pyrimidin-2(1H)-one | m/z [M + H] 351.3 |

TABLE 1-continued

| Cpd. No. | Structure | Name | Mass Spec. |
|---|---|---|---|
| 693 | 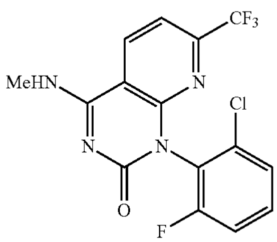 [SMILES: CNc1nc(=O)n(-c2c(F)cccc2Cl)c2nc(C(F)(F)F)ccc12] | 1-(2-chloro-6-fluorophenyl)-4-(methylamino)-7-(trifluoromethyl)pyrido[2,3-d]-pyrimidin-2(1H)-one | m/z [M + H] 373.2 |
| 694 | 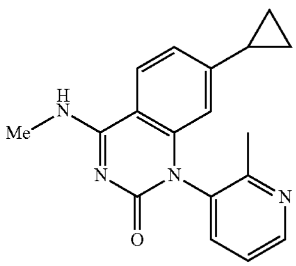 [SMILES: CNc1nc(=O)n(-c2cccnc2C)c2cc(C3CC3)ccc12] | 7-cyclopropyl-4-(methylamino)-1-(2-methylpyridin-3-yl)quinazolin-2(1H) one | m/z [M + H] 307.22 |
| 695 | 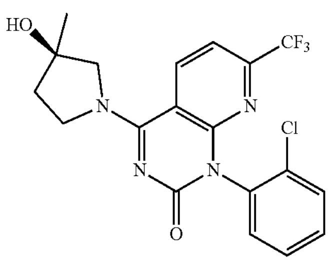 [SMILES: C[C@@]1(O)CCN(c2nc(=O)n(-c3ccccc3Cl)c3nc(C(F)(F)F)ccc23)C1] | 1-(2-chlorophenyl)-4-(3-hydroxy-3-methylpyrrolidin-1-yl)-7-(trifluoromethyl) pyrido[2,3-d]pyrimidin-2(1H)-one, single unknown enantiomer | m/z [M + H] 425.1 |
| 696 | 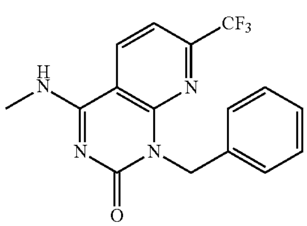 [SMILES: CNc1nc(=O)n(Cc2ccccc2)c2nc(C(F)(F)F)ccc12] | 1-benzyl-4-(methylamino)-7-(trifluoromethyl)pyrido[2,3-d]pyrimidin-2(1H)-one | m/z [M + H] 335.3 |
| 697 | 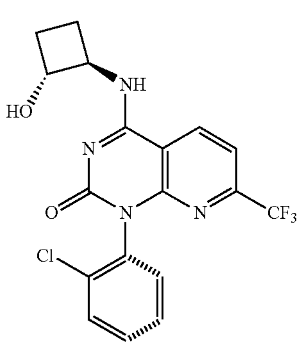 | 1-(2-chlorophenyl)-4-(((trans)-2-hydroxycyclobutyl)amino)-7-(trifluoromethyl)-pyrido[2,3-d]pyrimidin-2(1H)-one, single unknown enantiomer/atropisomer | m/z [M + H] 411.3 |

TABLE 1-continued

| Cpd. No. | Structure | Name | Mass Spec. |
|---|---|---|---|
| 698 | 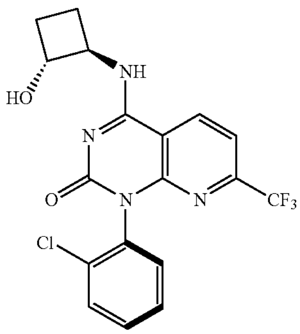 | 1-(2-chlorophenyl)-4-(((trans)-2-hydroxycyclobutyl)amino)-7-(trifluoromethyl)-pyrido[2,3-d]pyrimidin-2(1H)-one, single unknown enantiomer/atropisomer | m/z [M + H] 411.3 |
| 699 | 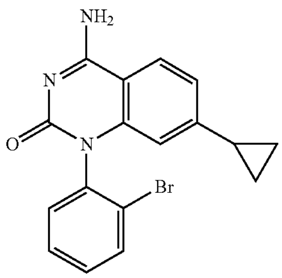 [SMILES: Nc1nc(=O)n(-c2ccccc2Br)c2cc(C3CC3)ccc12] | 4-amino-1-(2-bromophenyl)-7-cyclopropylquinazolin-2(1H)-one | m/z [M + H] 356.1 |
| 700 | 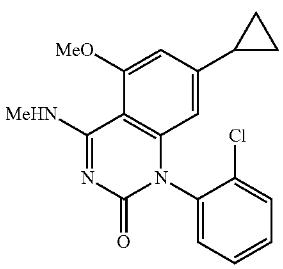 | 1-(2-chlorophenyl)-7-cyclopropyl-5-methoxy-(methylamino)quinazolin-2(1H)-one | m/z [M + H] 356.35 |
| 701 | 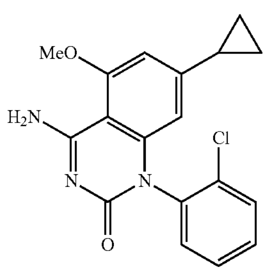 [SMILES: COc1cc(C2CC2)cc2c1c(N)nc(=O)n2-c1ccccc1Cl] | 4-amino-1-(2-chlorophenyl)-7-cyclopropyl-5-methoxyquinazolin-2(1H)-one | m/z [M + H] 342.31 |
| 702 | 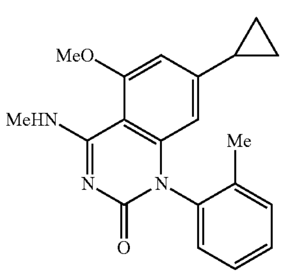 | 7-cyclopropyl-5-methoxy-4-(methylamino)-1-(o-tolyl)quinazolin-2(1H)-one | m/z [M + H] 366.44 |

TABLE 1-continued

| Cpd. No. | Structure | Name | Mass Spec. |
|---|---|---|---|
| 703 | 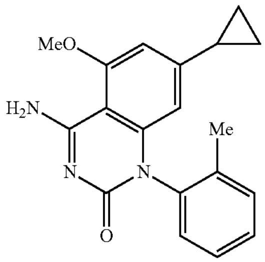 [SMILES: COc1cc(C2CC2)cc2c1c(N)nc(=O)n2-c1ccccc1C] | 4-amino-7-cyclopropyl-5-methoxy-1-(o-tolyl)quinazolin-2(1H)-one | m/z [M + H] 322.36 |
| 704 | 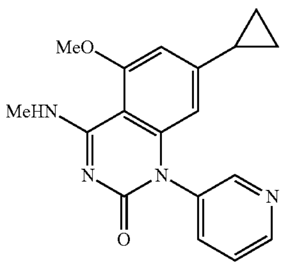 [SMILES: CNc1nc(=O)n(-c2cccnc2)c2cc(C3CC3)cc(OC)c12] | 7-cyclopropyl-5-methoxy-4-(methyl-amino)-1-(pyridin-3-yl)quinazolin-2(1H)-one | m/z [M + H] 323.36 |
| 705 | 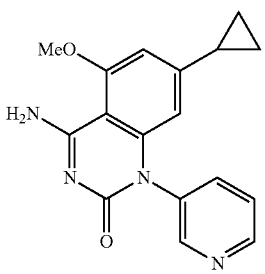 [SMILES: COc1cc(C2CC2)cc2c1c(N)nc(=O)n2-c1cccnc1] | 4-amino-7-cyclopropyl-5-methoxy-1-(pyridin-3-yl)quinazolin-2(1H)-one | m/z [M + H] 309.36 |
| 706 | 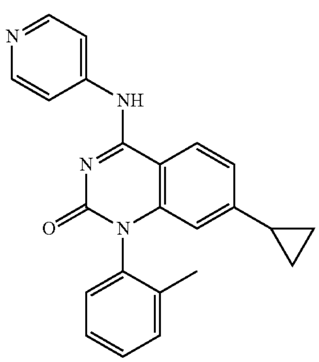 [SMILES: Cc1ccccc1-n1c(=O)nc(Nc2ccncc2)c2ccc(C3CC3)cc21] | 7-cyclopropyl-4-(pyridin-4-ylamino)-1-(o-tolyl)quinazolin-2(1H)-one | m/z [M + H] 369.39 |
| 707 | 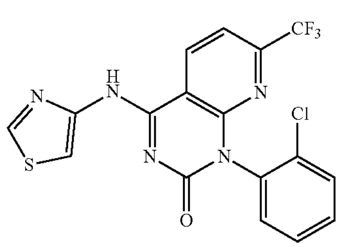 [SMILES: O=c1nc(Nc2cscn2)c2ccc(C(F)(F)F)nc2n1-c1ccccc1Cl] | 1-(2-chlorophenyl)-4-(thiazol-4-ylamino)-7-(trifluoromethyl)pyrido[2,3-d]pyrimidin-2(1H)-one | m/z [M + H] 424.2 |

TABLE 1-continued

| Cpd. No. | Structure | Name | Mass Spec. |
|---|---|---|---|
| 708 | 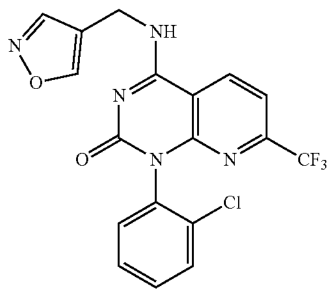 [SMILES: O=c1nc(NCc2cnoc2)c2ccc(C(F)(F)F)nc2n1-c1ccccc1Cl] | 1-(2-chlorophenyl)-4-((isoxazol-4-yl-methyl)amino)-7-(trifluoromethyl)pyrido[2,3-d]pyrimidin-2(1H)-one | m/z [M + H] 422.3 |
| 709 | 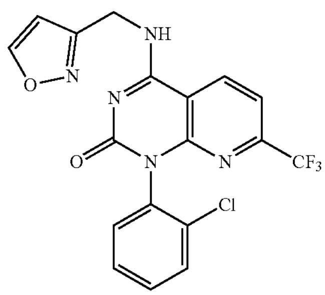 [SMILES: O=c1nc(NCc2ccon2)c2ccc(C(F)(F)F)nc2n1-c1ccccc1Cl] | 1-(2-chlorophenyl)-4-((isoxazol-3-yl-methyl)amino)-7-(trifluoromethyl)pyrido[2,3-d]pyrimidin-2(1H)-one | m/z [M + H] 422.3 |
| 710 | 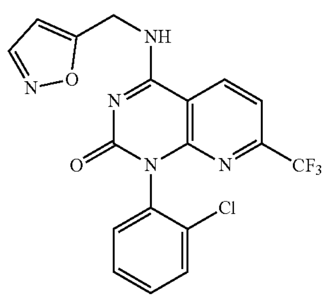 [SMILES: O=c1nc(NCc2ccno2)c2ccc(C(F)(F)F)nc2n1-c1ccccc1Cl] | 1-(2-chlorophenyl)-4-((isoxazol-5-yl-methyl)amino)-7-(trifluoromethyl)pyrido[2,3-d]pyrimidin-2(1H)-one | m/z [M + H] 422.2 |
| 711 | 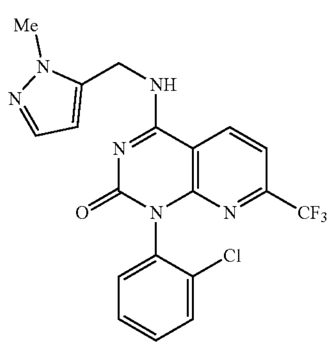 [SMILES: Cn1nccc1CNc1nc(=O)n(-c2ccccc2Cl)c2nc(C(F)(F)F)ccc12] | 1-(2-chlorophenyl)-4-(((1-methyl-1H-pyrazol-5-yl)methyl)amino)-7-(trifluoro-methyl)pyrido[2,3-d]pyrimidin-2(1H)-one | m/z [M + H] 435.27 |
| 712 | 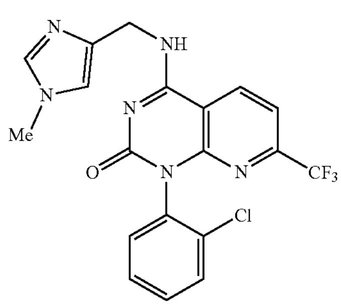 [SMILES: Cn1cnc(CNc2nc(=O)n(-c3ccccc3Cl)c3nc(C(F)(F)F)ccc23)c1] | 2-chlorophenyl)-4-(((1-methyl-1H-imidazol-4-yl)methyl)amino)-7-(trifluoro-methyl)-pyrido[2,3-d]-pyrimidin-2(1H)-one | m/z [M + H] 435.27 |

TABLE 1-continued

| Cpd. No. | Structure | Name | Mass Spec. |
|---|---|---|---|
| 713 | 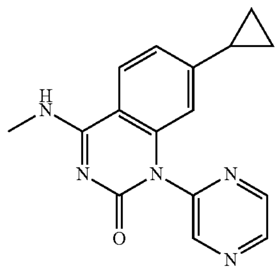 [SMILES: CNc1nc(=O)n(-c2cnccn2)c2cc(C3CC3)ccc12] | cyclopropyl-4-(methylamino)-1-(pyrazin-2-yl)quinazolin-2(1H)-one | m/z [M + H] 294.4 |
| 714 | 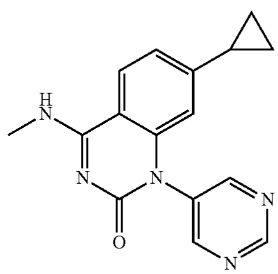 [SMILES: CNc1nc(=O)n(-c2cncnc2)c2cc(C3CC3)ccc12] | 7-cyclopropyl-4-(methylamino)-1-(pyrimidin-5-yl)quinazolin-2(1H)-one | m/z [M + H] 294.33 |
| 715 | 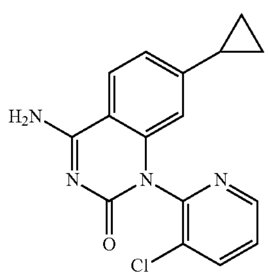 [SMILES: Nc1nc(=O)n(-c2ncccc2Cl)c2cc(C3CC3)ccc12] | 4-amino-1-(3-chloropyridin-2-yl)-7-cyclopropylquinazolin-2(1H)-one | m/z [M + H] 313.3 |
| 716 | 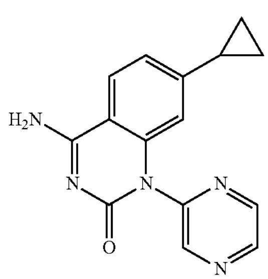 [SMILES: Nc1nc(=O)n(-c2cnccn2)c2cc(C3CC3)ccc12] | 4-amino-7-cyclopropyl-1-(pyrazin-2-yl)-quinazolin-2(1H)-one | m/z [M + H] 280.4 |
| 717 | 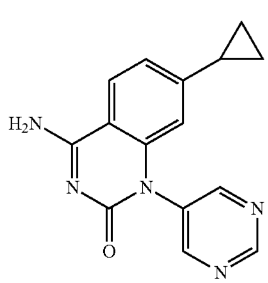 [SMILES: Nc1nc(=O)n(-c2cncnc2)c2cc(C3CC3)ccc12] | 4-amino-7-cyclopropyl-1-(pyrimidin-5-yl)quinazolin-2(1H)-one | m/z [M + H] 280.26 |

TABLE 1-continued

| Cpd. No. | Structure | Name | Mass Spec. |
|---|---|---|---|
| 718 | 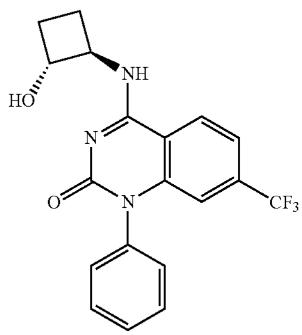 [SMILES: O=c1nc(N[C@@H]2CC[C@H]2O)c2ccc(C(F)(F)F)cc2n1-c1ccccc1] | 4-((trans-2-hydroxycyclobutyl) amino)-1-phenyl-7-(trifluoromethyl) quinazolin-2(1H)-one | m/z [M + H] 376.36 |
| 719 | 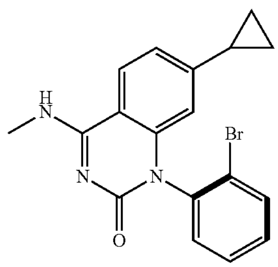 | 1-(2-bromophenyl)-7-cyclopropyl-4-(methylamino)quinazolin-2(1H)-one, a single atropisomer | m/z [M + H] 370.3 |
| 720 | 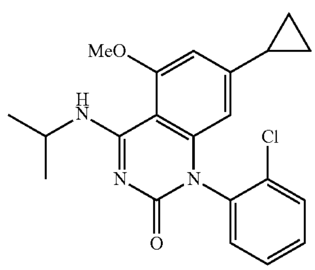 [SMILES: COc1cc(C2CC2)cc2c1c(NC(C)C)nc(=O)n2-c1ccccc1Cl] | 1-(2-chlorophenyl)-7-cyclopropyl-4-(isopropylamino)-5-methoxy quinazolin-2(1H)-one | m/z [M + H] 384.4 |
| 721 | 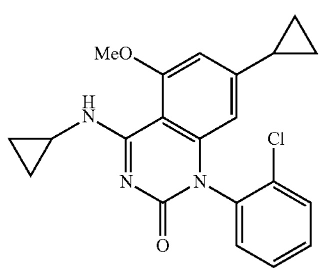 [SMILES: COc1cc(C2CC2)cc2c1c(NC1CC1)nc(=O)n2-c1ccccc1Cl] | 1-(2-chlorophenyl)-7-cyclopropyl-4-(cyclopropylamino)-5-methoxy-quinazolin-2(1H)-one | m/z [M + H] 382.35 |
| 722 | 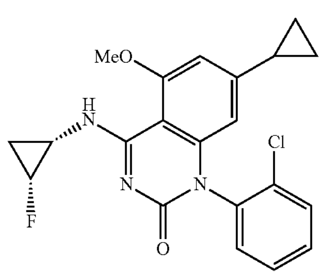 | 1-(2-chlorophenyl)-7-cyclopropyl-4-(((1S,2R)-2-fluorocyclopropyl) amino)-5-methoxyquinazolin-2(1H)-one | m/z [M + H] 400.33 |

TABLE 1-continued

| Cpd. No. | Structure | Name | Mass Spec. |
|---|---|---|---|
| 723 | 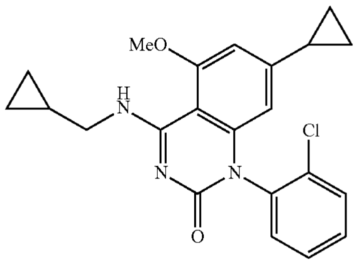 [SMILES: COc1cc(C2CC2)cc2c1c(NCC1CC1)nc(=O)n2-c1ccccc1Cl] | 1-(2-chlorophenyl)-7-cyclopropyl-4-((cyclopropylmethyl)amino)-5-methoxy-quinazolin-2(1H)-one | m/z [M + H] 396.4 |
| 724 | 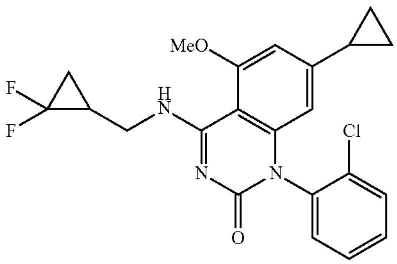 [SMILES: COc1cc(C2CC2)cc2c1c(NCC1CC1(F)F)nc(=O)n2-c1ccccc1Cl] | 1-(2-chlorophenyl)-7-cyclopropyl-4-(((2,2-difluorocyclopropyl)methyl)-amino)-5-methoxyquinazolin-2(1H)-one | m/z [M + H] 432.4 |
| 725 | 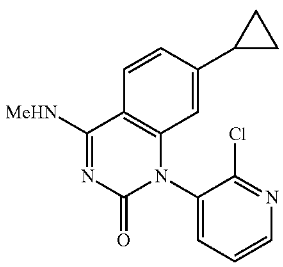 [SMILES: CNc1nc(=O)n(-c2cccnc2Cl)c2cc(C3CC3)ccc12] | 1-(2-chloropyridin-3-yl)-7-cyclopropyl-4-(methylamino)quinazolin-2(1H)-one | m/z [M + H] 327.3 |
| 726 | 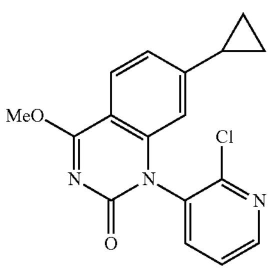 [SMILES: COc1nc(=O)n(-c2cccnc2Cl)c2cc(C3CC3)ccc12] | 1-(2-chloropyridin-3-yl)-7-cyclopropyl-4-methoxyquinazolin-2(1H)-one | m/z [M + H] 328.3 |
| 727 | 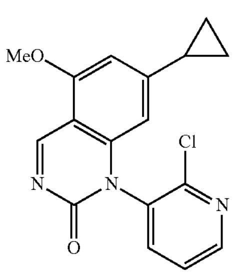 [SMILES: COc1cc(C2CC2)cc2c1cnc(=O)n2-c1cccnc1Cl] | 1-(2-chloropyridin-3-yl)-7-cyclopropyl-5-methoxy-4-(methylamino)quinazolin-2(1H)-one | m/z [M + H] 357.37 |

TABLE 1-continued

| Cpd. No. | Structure | Name | Mass Spec. |
|---|---|---|---|
| 728 | 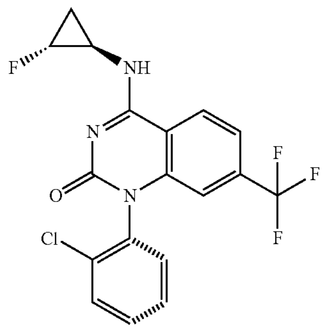 | 1-(2-chlorophenyl)-4-(((1S,2S)-2-fluorocyclopropyl)amino)-7-(trifluoromethyl)-quinazolin-2(1H)-one, single unknown enantiomer/atropisomer | m/z [M + H] 398.3 |
| 729 | 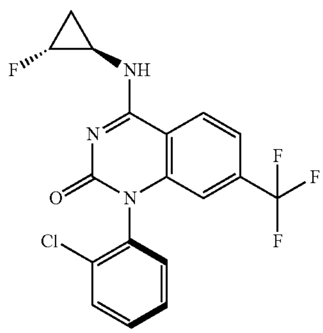 | 1-(2-chlorophenyl)-4-(((1S,2S)-2-fluorocyclopropyl)amino)-7-(trifluoromethyl)-quinazolin-2(1H)-one, single unknown enantiomer/atropisomer | m/z [M + H] 398.3 |
| 730 | 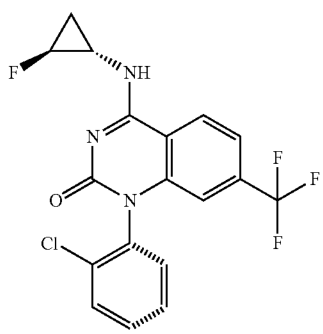 | 1-(2-chlorophenyl)-4-(((1R,2R)-2-fluorocyclopropyl)amino)-7-(trifluoromethyl)-quinazolin-2(1H)-one, single unknown enantiomer/atropisomer | m/z [M + H] 398.3 |
| 731 | 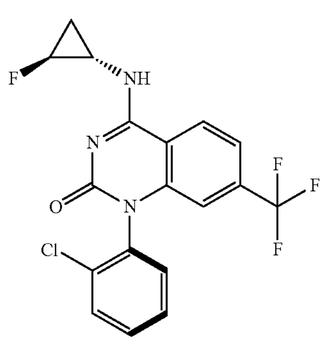 | 1-(2-chlorophenyl)-4-(((1R,2R)-2-fluorocyclopropyl)amino)-7-(trifluoromethyl)-quinazolin-2(1H)-one, single unknown enantiomer/atropisomer | m/z [M + H] 398.3 |

TABLE 1-continued

| Cpd. No. | Structure | Name | Mass Spec. |
|---|---|---|---|
| 732 | 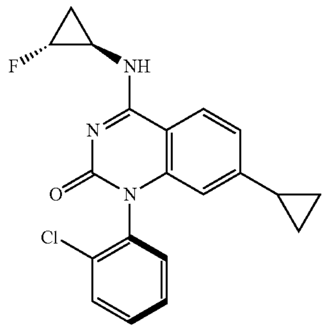 | 1-(2-chlorophenyl)-7-cyclopropyl-4-(((1S,2S)-2-fluorocyclopropyl)amino)-quinazolin-2(1H)-one, single unknown enantiomer/atropisomer | m/z [M + H] 370.34 |
| 733 | 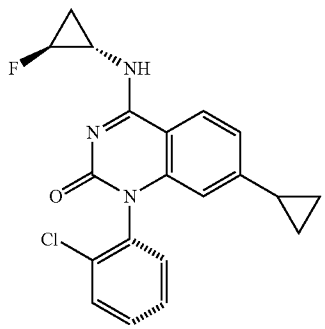 | 1-(2-chlorophenyl)-7-cyclopropyl-4-(((1S,2S)-2-fluorocyclopropyl)amino)-quinazolin-2(1H)-one, single unknown enantiomer/atropisomer | m/z [M + H] 370.34 |
| 734 | 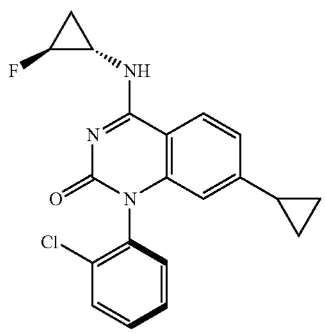 | 1-(2-chlorophenyl)-7-cyclopropyl-4-(((1S,2S)-2-fluorocyclopropyl)amino)-quinazolin-2(1H)-one, single unknown enantiomer/atropisomer | m/z [M + H] 370.34 |
| 735 | 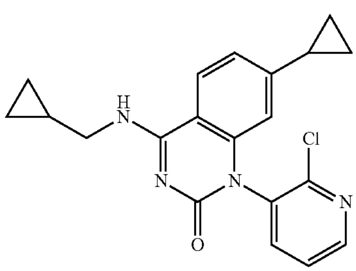 [SMILES: O=c1nc(NCC2CC2)c2ccc(C3CC3)cc2n1-c1cccnc1Cl] | 1-(2-chloropyridin-3-yl)-7-cyclopropyl-4-((cyclopropylmethyl)amino)-quinazolin-2(1H)-one | m/z [M + H] 367.4 |
| 736 | 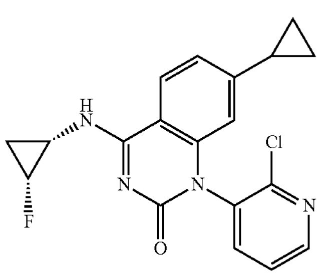 [SMILES: O=c1nc(N[C@H]2C[C@H]2F)c2ccc(C3CC3)cc2n1-c1cccnc1Cl] | 1-(2-chloropyridin-3-yl)-7-cyclopropyl-4-(((1S,2R)-2-fluorocyclopropyl)amino)-quinazolin-2(1H)-one | m/z [M + H] 371.3 |

TABLE 1-continued

| Cpd. No. | Structure | Name | Mass Spec. |
|---|---|---|---|
| 737 | 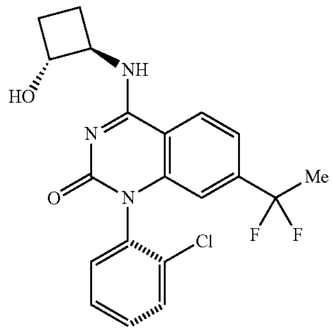 | 1-(2-chlorophenyl)-7-(1,1-difluoroethyl)-4-(((1R,2R)-2-hydroxycyclobutyl)-aminolquinazolin-2(1H)-one, single unknown enantiomer/atropisomer | m/z [M + H] 406.37 |
| 738 | 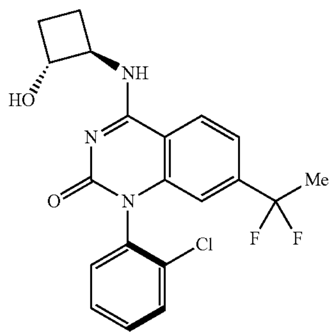 | 1-(2-chlorophenyl)-7-(1,1-difluoroethyl)-4-(((1R,2R)-2-hydroxycyclobutyl)-aminolquinazolin-2(1H)-one, single unknown enantiomer/atropisomer | m/z [M + H] 406.37 |
| 739 | 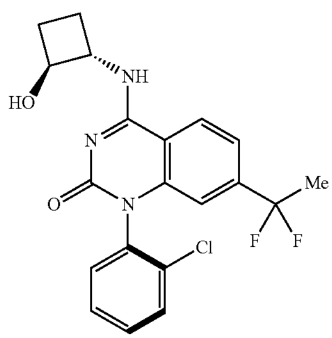 | 1-(2-chlorophenyl)-7-(1,1-difluoroethyl)-4-(((1S,2S)-2-hydroxycyclobutyl)-aminolquinazolin-2(1H)-one, single unknown enantiomer/atropisomer | m/z [M + H] 406.37 |
| 740 | 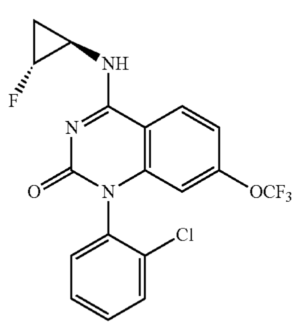 [SMILES: O=c1nc(N[C@@H]2C[C@H]2F)c2ccc(OC(F)(F)F)cc2n1-c1ccccc1Cl] | 1-(2-chlorophenyl)-4-(((1R,2R)-2-fluorocyclopropyl)amino)-7-(trifluoromethoxy)quinazolin-2(1H)-one, single unknown enantiomer | m/z [M + H] 414.3 |

TABLE 1-continued

| Cpd. No. | Structure | Name | Mass Spec. |
|---|---|---|---|
| 741 | 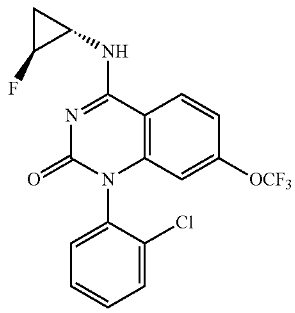 [SMILES: O=c1nc(N[C@H]2C[C@@H]2F)c2ccc(OC(F)(F)F)cc2n1-c1ccccc1Cl] | 1-(2-chlorophenyl)-4-(((1S,2S)-2-fluorocyclopropyl)amino)-7-(trifluoromethoxy)quinazolin-2(1H)-one, single unknown enantiomer | m/z [M + H] 414.3 |
| 742 | 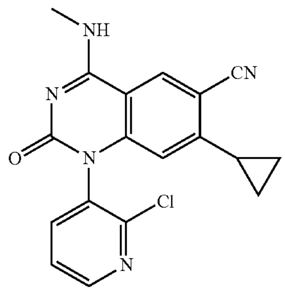 [SMILES: CNc1nc(=O)n(-c2cccnc2Cl)c2cc(C3CC3)c(C#N)cc12] | 1-(2-chloropyridin-3-yl)-7-cyclopropyl-4-(methylamino)-2-oxo-1,2-dihydro-quinazoline-6-carbonitrile | m/z [M + H] 352.4 |
| 743 | 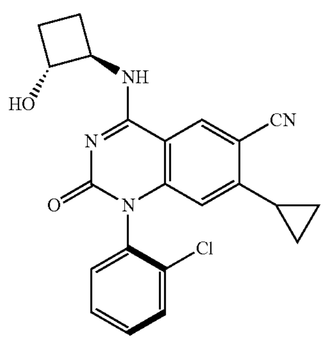 | 1-(2-chlorophenyl)-7-cyclopropyl-4-(((1S,2S)-2-hydroxycyclobutyl)amino)-2-oxo-1,2-dihydroquinazoline-6-carbonitrile, single unknown enantiomer/atropisomer | m/z [M + H] 407.47 |
| 744 | 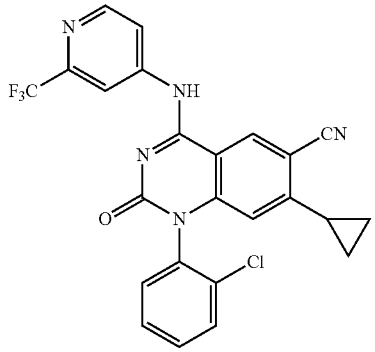 [SMILES: N#Cc1cc2c(Nc3ccnc(C(F)(F)F)c3)nc(=O)n(-c3ccccc3Cl)c2cc1C1CC1] | 1-(2-chlorophenyl)-7-cyclopropyl-2-oxo-4-((2-(trifluoromethyl)pyridin-4-yl)-amino)-1,2-dihydroquinazoline-6-carbonitrile | m/z [M + H] 482.5 |

TABLE 1-continued

| Cpd. No. | Structure | Name | Mass Spec. |
|---|---|---|---|
| 745 | 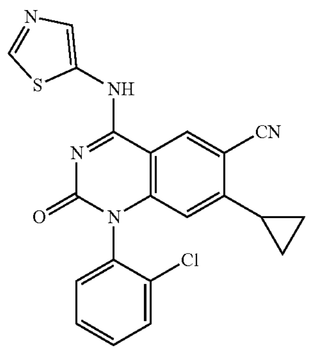 [SMILES: N#Cc1cc2c(Nc3cncs3)nc(=O)n(-c3ccccc3Cl)c2cc1C1CC1] | 1-(2-chlorophenyl)-7-cyclopropyl-2-oxo-4-(thiazol-5-ylamino)-1,2-dihydroquinazoline-6-carbonitrile | m/z [M + H] 420.1 |
| 746 | 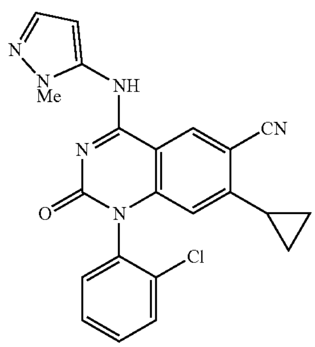 [SMILES: Cn1nccc1Nc1nc(=O)n(-c2ccccc2Cl)c2cc(C3CC3)c(C#N)cc12] | 1-(2-chlorophenyl)-7-cyclopropyl-4-((1-methyl-1H-pyrazol-5-yl)amino)-2-oxo-1,2-dihydroquinazoline-6-carbonitrile | m/z [M + H] 417.36 |
| 747 | 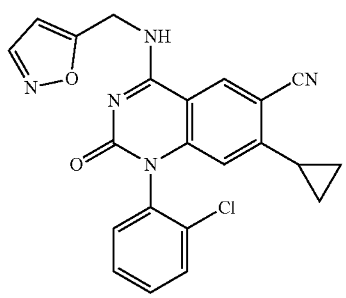 [SMILES: N#Cc1cc2c(NCc3ccno3)nc(=O)n(-c3ccccc3Cl)c2cc1C1CC1] | 1-(2-chlorophenyl)-7-cyclopropyl-4-((isoxazol-5-ylmethyl)amino)-2-oxo-1,2-dihydroquinazoline-6-carbonitrile | m/z [M + H] 418.35 |
| 748 | 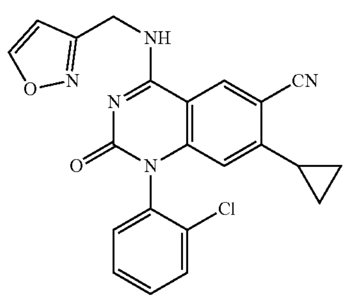 [SMILES: N#Cc1cc2c(NCc3ccon3)nc(=O)n(-c3ccccc3Cl)c2cc1C1CC1] | 1-(2-chlorophenyl)-7-cyclopropyl-4-((isoxazol-3-ylmethyl)amino)-2-oxo-1,2-dihydroquinazoline-6-carbonitrile | m/z [M + H] 418.3 |
| 749 | 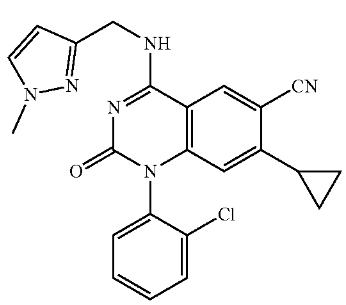 [SMILES: Cn1ccc(CNc2nc(=O)n(-c3ccccc3Cl)c3cc(C4CC4)c(C#N)cc23)n1] | 1-(2-chlorophenyl)-7-cyclopropyl-4-(((1-methyl-1H-pyrazol-3-yl)methyl)amino)-2-oxo-1,2-dihydroquinazoline-6-carbonitrile | m/z [M + H] 431.38 |

TABLE 1-continued

| Cpd. No. | Structure | Name | Mass Spec. |
|---|---|---|---|
| 750 | 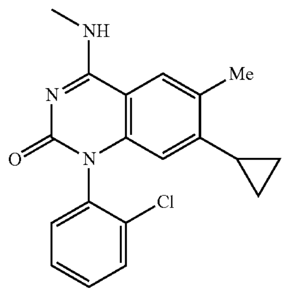 [SMILES: CNc1nc(=O)n(-c2ccccc2Cl)c2cc(C3CC3)c(C)cc12] | 1-(2-chlorophenyl)-7-cyclopropyl-6-methyl-4-(methylamino) quinazolin-2(1H)-one | m/z [M + H] 340.34 |
| 751 | 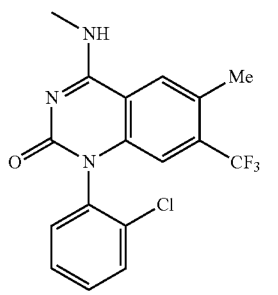 [SMILES: CNc1nc(=O)n(-c2ccccc2Cl)c2cc(C(F)(F)F)c(C)cc12] | 1-(2-chlorophenyl)-6-methyl-4-(methylamino)-7-(trifluoromethyl)-quinazolin-2(1H)-one | m/z [M + H] 368.4 |
| 752 | 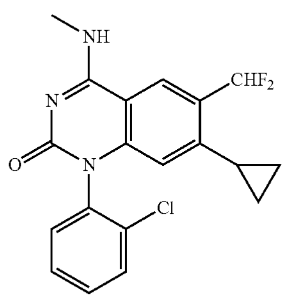 [SMILES: CNc1nc(=O)n(-c2ccccc2Cl)c2cc(C3CC3)c(C(F)F)cc12] | 1-(2-chlorophenyl)-7-cyclopropyl-6-(difluoromethyl)-4-(methylamino)-quinazolin-2(1H)-one | m/z [M + H] 376.4 |
| 753 | 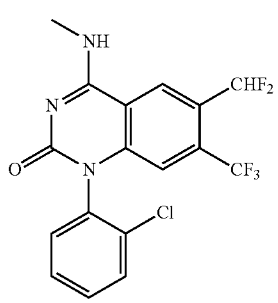 [SMILES: CNc1nc(=O)n(-c2ccccc2Cl)c2cc(C(F)(F)F)c(C(F)F)cc12] | 1-(2-chlorophenyl)-6-(difluoromethyl)-4-(methylamino)-7-(trifluoromethyl)-quinazolin-2(1H)-one | m/z [M + H] 404.4 |
| 754 | 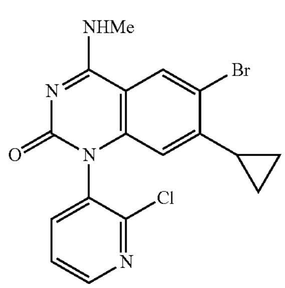 [SMILES: CNc1nc(=O)n(-c2cccnc2Cl)c2cc(C3CC3)c(Br)cc12] | 6-bromo-1-(2-chloropyridin-3-yl)-7-cyclopropyl-4-(methylamino)quinazolin-2(1H)-one | m/z [M + H] 405.2 |

TABLE 1-continued

| Cpd. No. | Structure | Name | Mass Spec. |
|---|---|---|---|
| 755 | 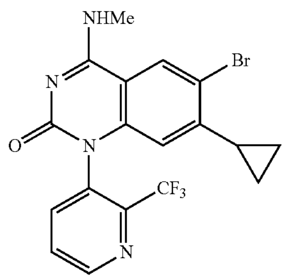 | 6-bromo-7-cyclopropyl-4-(methyl-amino)-1-(2-(trifluoromethyl)pyridin-3-yl)-quinazolin-2(1H)-one | m/z [M + H] 439.4 |
| 756 | 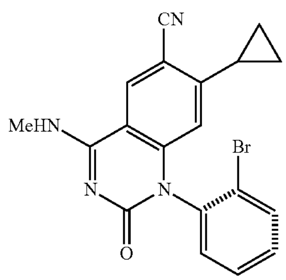 | 1-(2-bromophenyl)-7-cyclopropyl-4-(methylamino)-2-oxo-1,2-dihydro-quinazoline-6-carbonitrile, single unknown atropisomer | m/z [M + H] 395.41 |
| 757 | 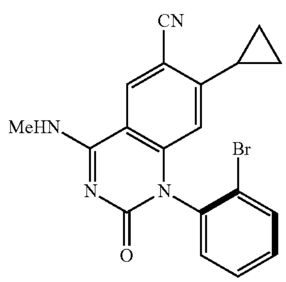 | 1-(2-bromophenyl)-7-cyclopropyl-4-(methylamino)-2-oxo-1,2-dihydro-quinazoline-6-carbonitrile, single unknown atropisomer | m/z [M + H] 395.41 |
| 758 | 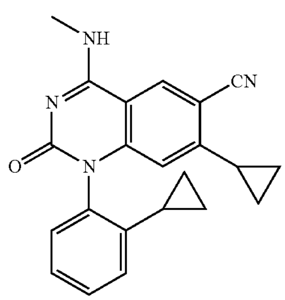 [SMILES: CNc1nc(=O)n(-c2ccccc2C2CC2)c2cc(C3CC3)c(C#N)cc12] | 7-cyclopropyl-1-(2-cyclopropylphenyl)-4-(methylamino)-2-oxo-1,2-dihydro-quinazoline-6-carbonitrile | m/z [M + H] 357.40 |
| 759 | 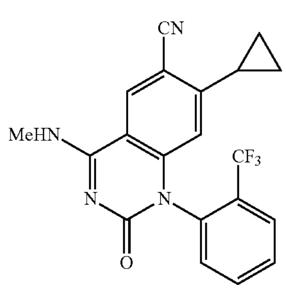 [SMILES: CNc1nc(=O)n(-c2ccccc2C(F)(F)F)c2cc(C3CC3)c(C#N)cc12] | 7-cyclopropyl-4-(methylamino)-2-oxo-1-(2-(trifluoromethyl)phenyl)-1,2-dihydro-quinazoline-6-carbonitrile | m/z [M + H] 385.44 |

TABLE 1-continued

| Cpd. No. | Structure | Name | Mass Spec. |
|---|---|---|---|
| 760 | 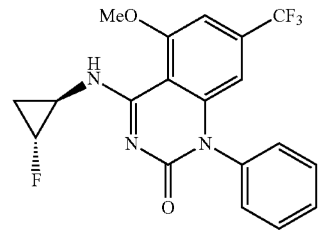 [SMILES: COc1cc(C(F)(F)F)cc2c1c(N[C@@H]1C[C@H]1F)nc(=O)n2-c1ccccc1] | 4-(((1R,2R)-2-fluorocyclopropyl)-amino)-5-methoxy-1-phenyl-7-(trifluoromethyl)quinazolin-2(1H)-one, single unknown enantiomer | m/z [M + H] 394.4 |
| 761 | 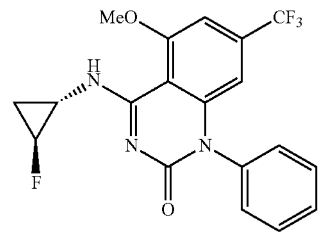 [SMILES: COc1cc(C(F)(F)F)cc2c1c(N[C@H]1C[C@@H]1F)nc(=O)n2-c1ccccc1] | 4-(((1S,2S)-2-fluorocyclopropyl)amino)-5-methoxy-1-phenyl-7-(trifluoromethyl)quinazolin-2(1H)-one, single unknown enantiomer | m/z [M + H] 394.4 |
| 762 | 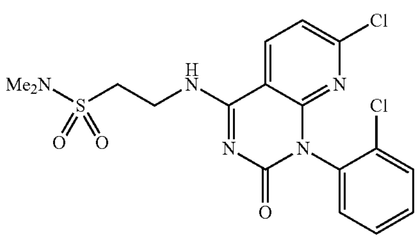 | 2-((1-(2-chlorophenyl)-2-oxo-7-(trifluoromethyl)-1,2-dihydropyrido[2,3-4pyrimidin-4-yl)amino)-N,N-dimethylethanesulfonamide | m/z [M + H] 454.19 |
| 763 | 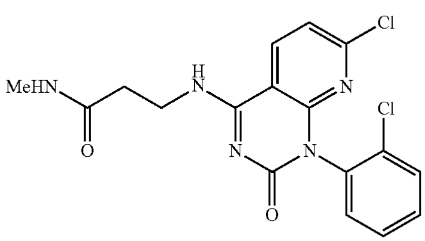 [SMILES: CNC(=O)CCNc1nc(=O)n(-c2ccccc2Cl)c2nc(Cl)ccc12] | 3-((1-(2-chlorophenyl)-2-oxo-7-(trifluoromethyl)-1,2-dihydropyrido[2,3-d]-pyrimidin-4-yl)amino)-N-methylpropanamide | m/z [M + H] 426.4. |
| 764 | 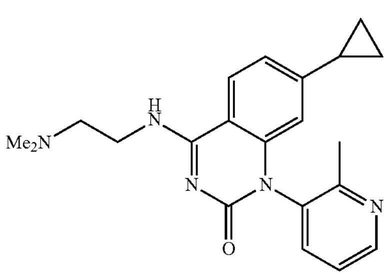 [SMILES: Cc1ncccc1-n1c(=O)nc(NCCN(C)C)c2ccc(C3CC3)cc21] | 7-cyclopropyl-4((2-(dimethylamino)-ethyl)amino)-1-(2-methylpyridin-3-yl)-quinazolin-2(1H)-one | m/z [M-H] 362.52 |
| 765 | 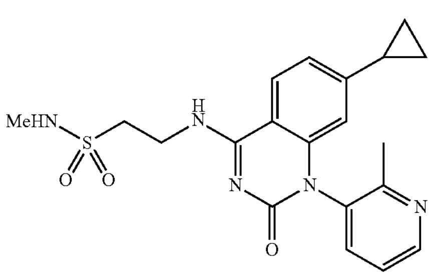 | 2-((7-cyclopropyl-1-(2-methylpyridin-3-yl)-2-oxo-1,2-dihydroquinazolin-4-yl)-amino)-N,N-dimethylethane-1-sulfonamide | m/z [M + H] 428.49 |

TABLE 1-continued

| Cpd. No. | Structure | Name | Mass Spec. |
|---|---|---|---|
| 766 | 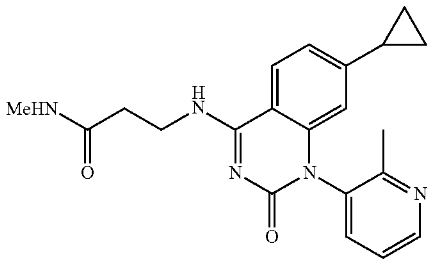 [SMILES: CNC(=O)CCNc1nc(=O)n(-c2cccnc2C)c2cc(C3CC3)ccc12] | 3-((7-cyclopropyl-1-(2-methylpyridin-3-yl)-2-oxo-1,2-dihydroquinazolin-4-yl)-amino)-N-methylpropanamide | m/z [M + H] 378.47 |
| 767 | 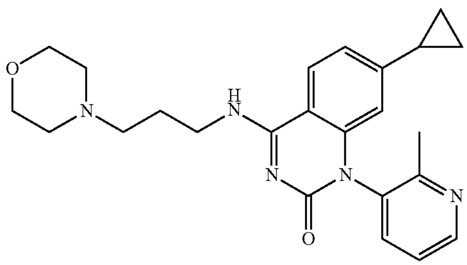 [SMILES: Cc1ncccc1-n1c(=O)nc(NCCCN2CCOCC2)c2ccc(C3CC3)cc21] | 7-cyclopropyl-1-(2-methylpyridin-3-yl)-4-((3-morpholinopropyl)amino)-quinazolin-2(1H)-one | m/z [M + H] 420.31 |
| 768 | 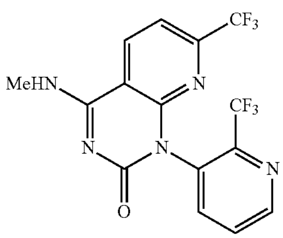 | 4-(methylamino)-7-(trifluoromethyl)-1-(2-(trifluoromethyl)pyridin-3-yl)pyrido[2,3-d]-pyrimidin-2(1H)-one | m/z [M + H] 390.4 |
| 769 | 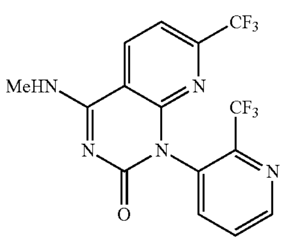 | 1-(2-chloropyridin-3-yl)-4-(methylamino)-7-(trifluoromethyl)-pyrido[2,3-d]-pyrimidin-2(1H)-one | m/z [M + H] 356.3 |
| 770 | 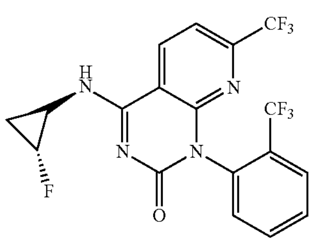 | 1-(2-chlorophenyl)-4-(((1S,2R)-2-fluorocyclopropyl)amino)-7-(trifluoromethyl)pyrido[2,3-d]pyrimidin-2(1H)-one, single unknown enantiomer | m/z [M + H] 399.4 |
| 771 | 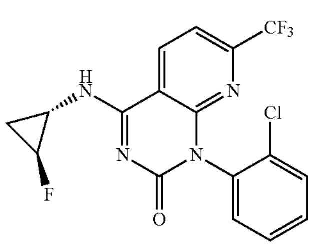 [SMILES: O=c1nc(N[C@H]2C[C@@H]2F)c2ccc(C(F)(F)F)nc2n1-c1ccccc1Cl] | 1-(2-chlorophenyl)-4-(((1R,2S)-2-fluorocyclopropyl)amino)-7-(trifluoromethyl)pyrido[2,3-d]pyrimidin-2(1H)-one, single unknown enantiomer | m/z [M + H] 399.4 |

TABLE 1-continued

| Cpd. No. | Structure | Name | Mass Spec. |
|---|---|---|---|
| 772 | 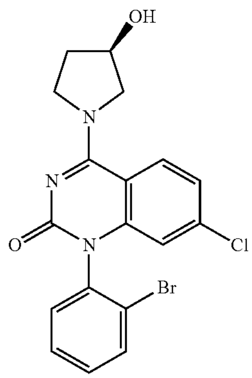 [SMILES: O=c1nc(N2CC[C@@H](O)C2)c2ccc(Cl)cc2n1-c1ccccc1Br] | (R)-1-(2-bromophenyl)-7-chloro-4-(3-hydroxypyrrolidin-1-yl)quinazolin-2(1H)-one | m/z [M + H] 420.0, 422.0 |
| 773 | 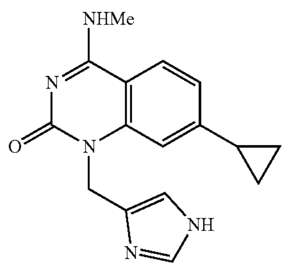 [SMILES: CNc1nc(=O)n(Cc2c[nH]cn2)c2cc(C3CC3)ccc12] | 1-((1H-imidazol-4-yl)methyl)-7-cyclopropyl-4-(methylamino)quinazolin-2(1H)-one | m/z [M + H] 294.4 |
| 774 | 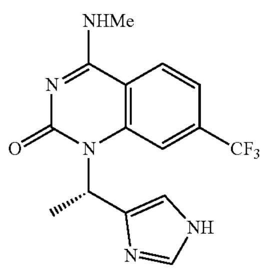 [SMILES: CNc1nc(=O)n([C@@H](C)c2c[nH]cn2)c2cc(C(F)(F)F)ccc12] | (S)-1-(1-(1H-imidazol-4-yl)ethyl)-4-(methylamino)-7-(trifluoromethyl)-quinazolin-2(1H)-one, Single unknown enantiomer | m/z [M + H] 338.3. |
| 775 | 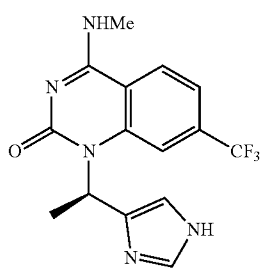 [SMILES: CNc1nc(=O)n([C@H](C)c2c[nH]cn2)c2cc(C(F)(F)F)ccc12] | (R)-1-(1-(1H-imidazol-4-yl)ethyl)-4-(methylamino)-7-(trifluoromethyl)quinazolin-2(1H)-one, single unknown enantiomer | m/z [M + H] 338.3 |
| 776 | 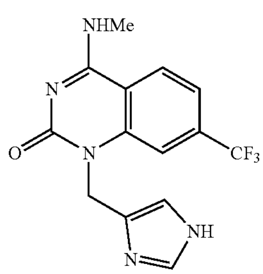 [SMILES: CNc1nc(=O)n(Cc2c[nH]cn2)c2cc(C(F)(F)F)ccc12] | 1-(2-chlorophenyl)-7-cyclopropyl-4-(methylamino)-6-(methylthio)-quinazolin-2(1H)-one | m/z [M + H] 324.35 |

Additional compounds of Formula (I) that are contemplated are disclosed in Table 2 below:

TABLE 2

| Structure | Name |
|---|---|
| 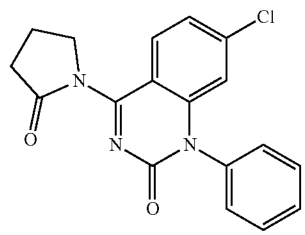 [SMILES: O=C1CCCN1c1nc(=O)n(-c2ccccc2)c2cc(Cl)ccc12] | 7-chloro-4-(2-oxopyrrolidin-1-yl)-1-phenylquinazolin-2(1H)-one |
| 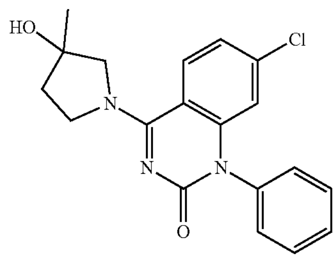 [SMILES: CC1(O)CCN(c2nc(=O)n(-c3ccccc3)c3cc(Cl)ccc23)C1] | 7-chloro-4-(3-hydroxy-3-methylpyrrolidin-1-yl)-1-phenylquinazolin-2(1H)-one |
| 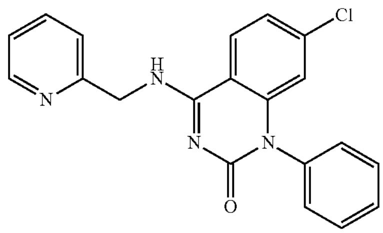 [SMILES: O=c1nc(NCc2ccccn2)c2ccc(Cl)cc2n1-c1ccccc1] | 7-chloro-1-phenyl-4-((pyridin-2-ylmethyl)amino)-quinazolin-2(1H)-one |
| 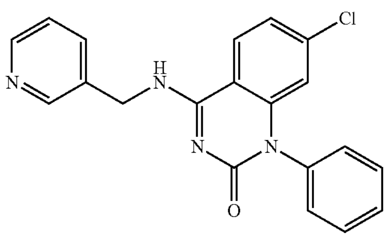 [SMILES: O=c1nc(NCc2cccnc2)c2ccc(Cl)cc2n1-c1ccccc1] | 7-chloro-1-phenyl-4-((pyridin-3-ylmethyl)amino-)quinazolin-2(1H)-one |
| 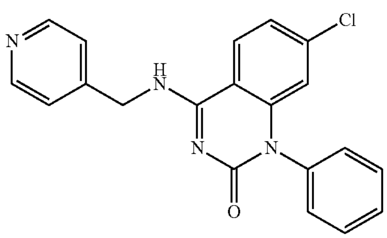 [SMILES: O=c1nc(NCc2ccncc2)c2ccc(Cl)cc2n1-c1ccccc1] | 7-chloro-1-phenyl-4-((pyridin-4-ylmethyl)amino)-quinazolin-2(1H)-one |
| 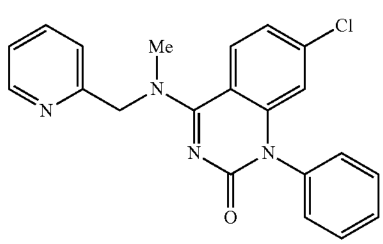 [SMILES: CN(Cc1ccccn1)c1nc(=O)n(-c2ccccc2)c2cc(Cl)ccc12] | 7-chloro-4-(methyl(pyridin-2-ylmethyl)amino)-1-phenylquinazolin-2(1H)-one |

TABLE 2-continued

| Structure | Name |
|---|---|
| | 7-chloro-4-(methyl(pyridin-3-ylmethyl)amino)-1-phenylquinazolin-2(1H)-one |
| 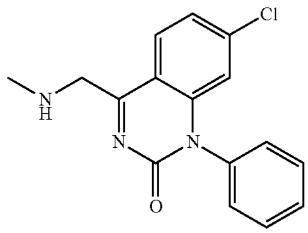 [SMILES: CNCc1nc(=O)n(-c2ccccc2)c2cc(Cl)ccc12] | 7-chloro-4-((methylamino)methyl)-1-phenylquinazolin-2(1H)-one |
| 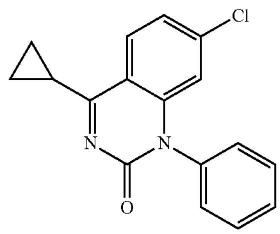 [SMILES: O=c1nc(C2CC2)c2ccc(Cl)cc2n1-c1ccccc1] | 7-chloro-4-cyclopropyl-1-phenylquinazolin-2(1H)-one |
| 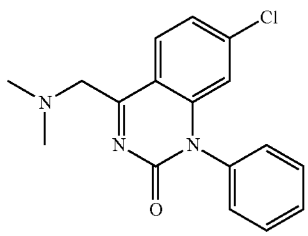 [SMILES: CN(C)Cc1nc(=O)n(-c2ccccc2)c2cc(Cl)ccc12] | 7-chloro-4-((dimethylamino)methyl)-1-phenylquinazolin-2(1H)-one |
| 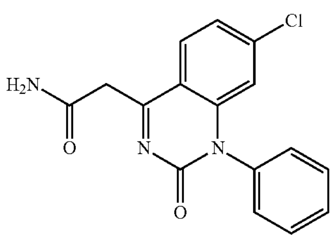 [SMILES: NC(=O)Cc1nc(=O)n(-c2ccccc2)c2cc(Cl)ccc12] | 2-(7-chloro-2-oxo-1-phenyl-1,2-dihydroquinazolin-4-yl)acetamide |
| 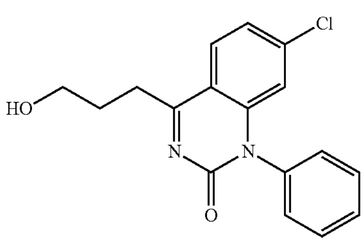 [SMILES: O=c1nc(CCCO)c2ccc(Cl)cc2n1-c1ccccc1] | 7-chloro-4-(3-hydroxypropyl)-1-phenylquinazolin-2(1H)-one |

TABLE 2-continued

| Structure | Name |
|---|---|
| 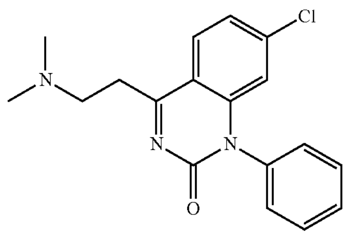 [SMILES: CN(C)CCc1nc(=O)n(-c2ccccc2)c2cc(Cl)ccc12] | 7-chloro-4-(2-(dimethylamino)ethyl)-1-phenylquinazolin-2(1H)-one |
| 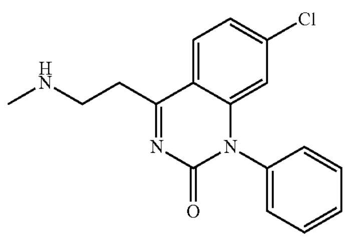 [SMILES: CNCCc1nc(=O)n(-c2ccccc2)c2cc(Cl)ccc12] | 7-chloro-4-(2-(methylamino)ethyl)-1-phenylquinazolin-2(1H)-one |
| 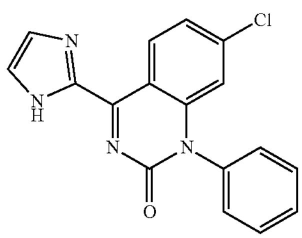 [SMILES: O=c1nc(-c2ncc[nH]2)c2ccc(Cl)cc2n1-c1ccccc1] | 7-chloro-4-(1H-imidazol-2-yl)-1-phenylquinazolin-2(1H)-one |
| 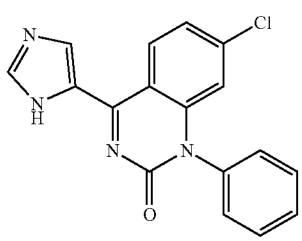 [SMILES: O=c1nc(-c2cnc[nH]2)c2ccc(Cl)cc2n1-c1ccccc1] | 7-chloro-4-(1H-imidazol-5-yl)-1-phenylquinazolin-2(1H)-one |
| 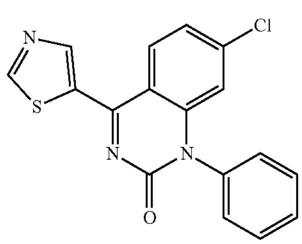 [SMILES: O=c1nc(-c2cncs2)c2ccc(Cl)cc2n1-c1ccccc1] | 7-chloro-1-phenyl-4-(thiazol-5-yl)quinazolin-2(1H)-one |
| 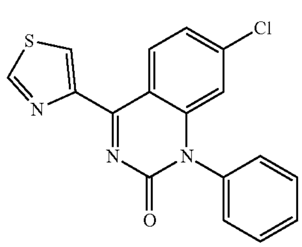 [SMILES: O=c1nc(-c2cscn2)c2ccc(Cl)cc2n1-c1ccccc1] | 7-chloro-1-phenyl-4-(thiazol-4-yl)quinazolin-2(1H)-one |

TABLE 2-continued

| Structure | Name |
|---|---|
| 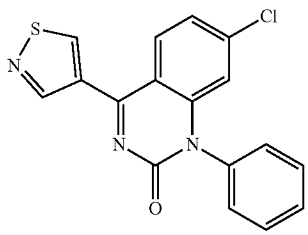 [SMILES: O=c1nc(-c2cnsc2)c2ccc(Cl)cc2n1-c1ccccc1] | 7-chloro-4-(isothiazol-4-yl)-1-phenylquinazolin-2(1H)-one |
| 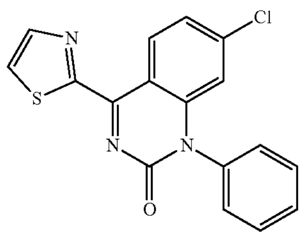 [SMILES: O=c1nc(-c2nccs2)c2ccc(Cl)cc2n1-c1ccccc1] | 7-chloro-1-phenyl-4-(thiazol-2-yl)quinazolin-2(1H)-one |
| 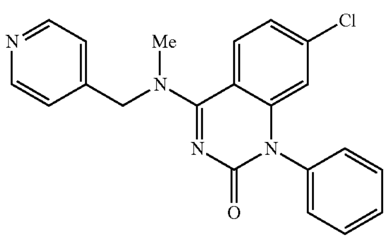 [SMILES: CN(Cc1ccncc1)c1nc(=O)n(-c2ccccc2)c2cc(Cl)ccc12] | 7-chloro-4-(methyl(pyridin-4-ylmethyl)amino)-1-phenylquinazolin-2(1H)-one |
| 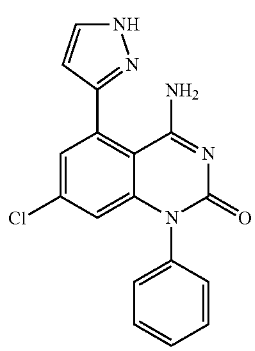 [SMILES: Nc1nc(=O)n(-c2ccccc2)c2cc(Cl)cc(-c3cc[nH]n3)c12] | 4-amino-7-chloro-1-phenyl-5-(1H-pyrazol-3-yl)quinazolin-2(1H)-one |
| 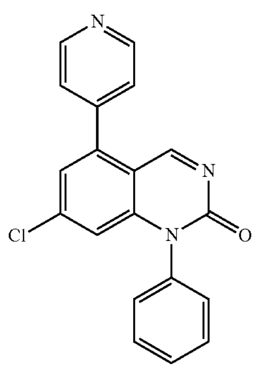 [SMILES: O=c1ncc2c(-c3ccncc3)cc(Cl)cc2n1-c1ccccc1] | 7-chloro-1-phenyl-5-(pyridin-4-yl)quinazolin-2(1H)-one |

TABLE 2-continued
| Structure | Name |
|---|---|
| 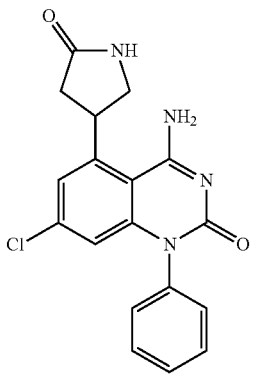 [SMILES: Nc1nc(=O)n(-c2ccccc2)c2cc(Cl)cc(C3CNC(=O)C3)c12] | 4-amino-7-chloro-5-(5-oxopyrrolidin-3-yl)-1-phenylquinazolin-2(1H)-one |
| 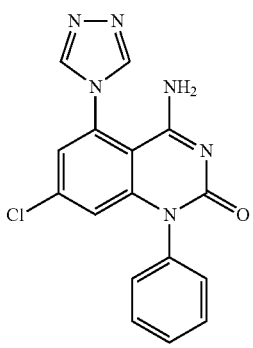 [SMILES: Nc1nc(=O)n(-c2ccccc2)c2cc(Cl)cc(-n3cnnc3)c12] | 4-amino-7-chloro-1-phenyl-5-(4H-1,2,4-triazol-4-yl)quinazolin-2(1H)-one |
| 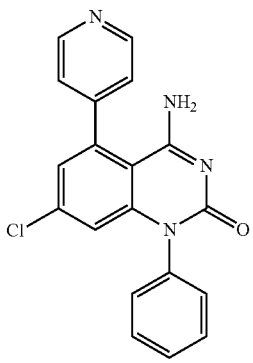 [SMILES: Nc1nc(=O)n(-c2ccccc2)c2cc(Cl)cc(-c3ccncc3)c12] | 4-amino-7-chloro-1-phenyl-5-(pyridin-4-yl)quinazolin-2(1H)-one |
| 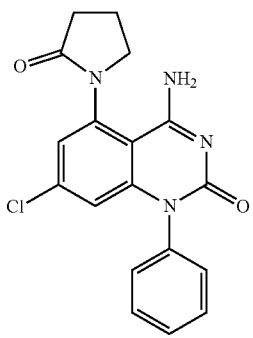 [SMILES: Nc1nc(=O)n(-c2ccccc2)c2cc(Cl)cc(N3CCCC3=O)c12] | 4-amino-7-chloro-5-(2-oxopyrrolidin-1-yl)-1-phenylquinazolin-2(1H)-one |

TABLE 2-continued

| Structure | Name |
|---|---|
| 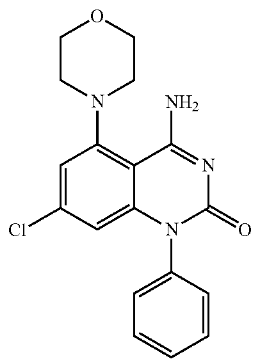 [SMILES: Nc1nc(=O)n(-c2ccccc2)c2cc(Cl)cc(N3CCOCC3)c12] | 4-amino-7-chloro-5-morpholino-1-phenylquinazolin-2(1H)-one |
| 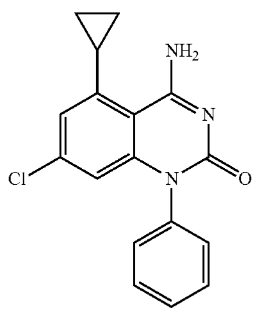 [SMILES: Nc1nc(=O)n(-c2ccccc2)c2cc(Cl)cc(C3CC3)c12] | 4-amino-7-chloro-5-cyclopropyl-1-phenylquinazolin-2(1H)-one |
| 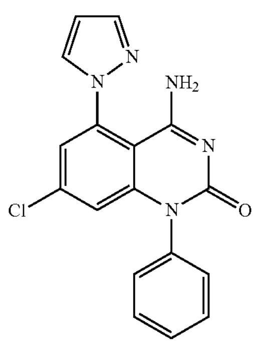 [SMILES: Nc1nc(=O)n(-c2ccccc2)c2cc(Cl)cc(-n3cccn3)c12] | 4-amino-7-chloro-1-phenyl-5-(1H-pyrazol-1-yl)quinazolin-2(1H)-one |
| | 5-(4-amino-7-chloro-2-oxo-1-phenyl-1,2-dihydroquinazolin-5-yl)oxazolidin-2-one |

TABLE 2-continued

| Structure | Name |
|---|---|
| 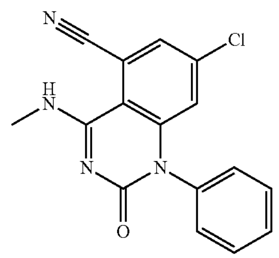 [SMILES: CNc1nc(=O)n(-c2ccccc2)c2cc(Cl)cc(C#N)c12] | 7-chloro-4-(methylamino)-2-oxo-1-phenyl-1,2-dihydroquinazoline-5-carbonitrile |
| 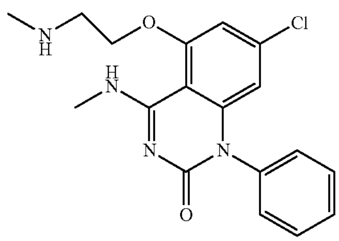 [SMILES: CNCCOc1cc(Cl)cc2c1c(NC)nc(=O)n2-c1ccccc1] | 7-chloro-4-(methylamino)-5-(2-(methylamino)ethoxy)-1-phenylquinazolin-2(1H)-one |
| 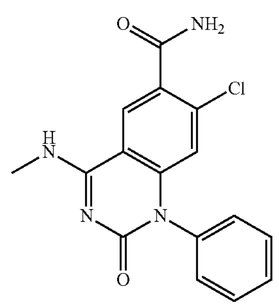 [SMILES: CNc1nc(=O)n(-c2ccccc2)c2cc(Cl)c(C(N)=O)cc12] | 7-chloro-4-(methylamino)-2-oxo-1-phenyl-1,2-dihydroquinazoline-6-carboxamide |
| 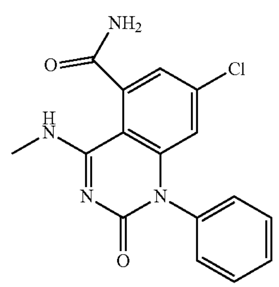 [SMILES: CNc1nc(=O)n(-c2ccccc2)c2cc(Cl)cc(C(N)=O)c12] | 7-chloro-4-(methylamino)-2-oxo-1-phenyl-1,2-dihydroquinazoline-5-carboxamide |
| 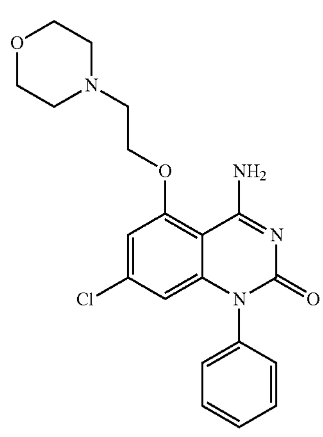 [SMILES: Nc1nc(=O)n(-c2ccccc2)c2cc(Cl)cc(OCCN3CCOCC3)c12] | 4-amino-7-chloro-5-(2-morpholinoethoxy)-1-phenylquinazolin-2(1H)-one |

TABLE 2-continued

| Structure | Name |
|---|---|
| 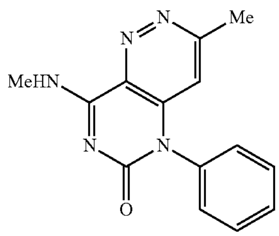 [SMILES: CNc1nc(=O)n(-c2ccccc2)c2cc(C)nnc12] | 3-methyl-8-(methylamino)-5-phenylpyrimido[5,4-c]pyridazin-6(5H)-one |
| 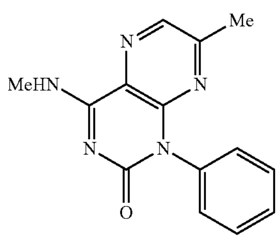 [SMILES: CNc1nc(=O)n(-c2ccccc2)c2nc(C)cnc12] | 7-methyl-4-(methylamino)-1-phenylpteridin-2(1H)-one |
| 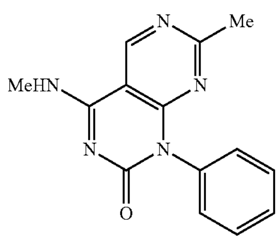 [SMILES: CNc1nc(=O)n(-c2ccccc2)c2nc(C)ncc12] | 7-methyl-4-(methylamino)-1-phenylpyrimido2(1H)-one |
| 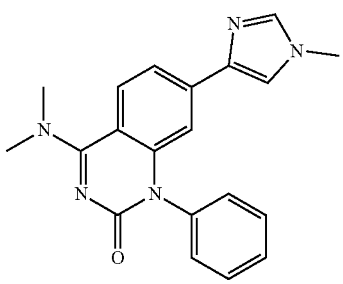 | 4-(dimethylamino)-7-(1-methyl-1H-imidazol-4-yl)-1-phenyl-quinazolin-2(1H)-one |
| 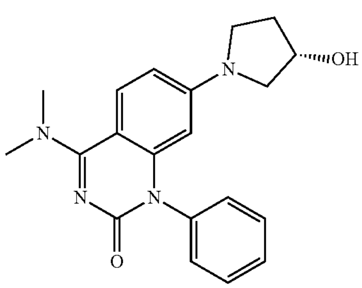 [SMILES: CN(C)c1nc(=O)n(-c2ccccc2)c2cc(N3CC[C@H](O)C3)ccc12] | (S)-4-(dimethylamino)-7-(3-hydroxypyrrolidin-1-yl)-1-phenyl-quinazolin-2(1H)-one |
| 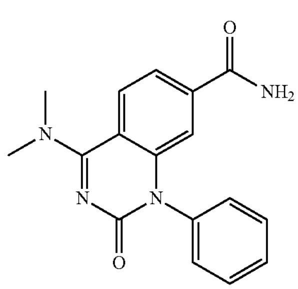 [SMILES: CN(C)c1nc(=O)n(-c2ccccc2)c2cc(C(N)=O)ccc12] | 4-(dimethylamino)-2-oxo-1-phenyl-1,2-dihydroquinazoline-7-carboxamide |

TABLE 2-continued

| Structure | Name |
|---|---|
| 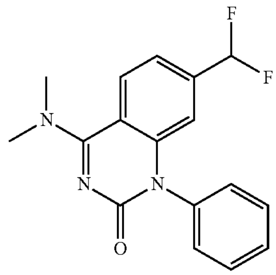 [SMILES: CN(C)c1nc(=O)n(-c2ccccc2)c2cc(C(F)F)ccc12] | 7-(difluoromethyl)-4-(dimethylamino)-1-phenylquinazolin-2(1H)-one |
| 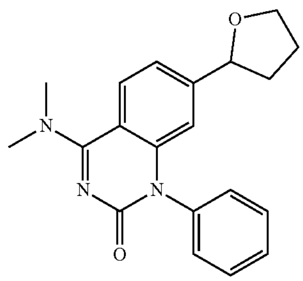 [SMILES: CN(C)c1nc(=O)n(-c2ccccc2)c2cc(C3CCCO3)ccc12] | 4-(dimethylamino)-1-phenyl-7-(tetrahydrofuran-2-yl)quinazolin-2(1H)-one |
| 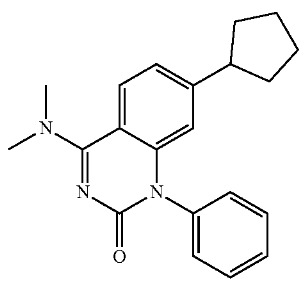 [SMILES: CN(C)c1nc(=O)n(-c2ccccc2)c2cc(C3CCCC3)ccc12] | 7-cyclopentyl-4-(dimethylamino)-1-phenylquinazolin-2(1H)-one |
| 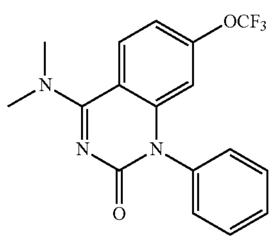 [SMILES: CN(C)c1nc(=O)n(-c2ccccc2)c2cc(OC(F)(F)F)ccc12] | 4-(dimethylamino)-1-phenyl-7-(trifluoromethoxy)quinazolin-2(1H)-one |
| 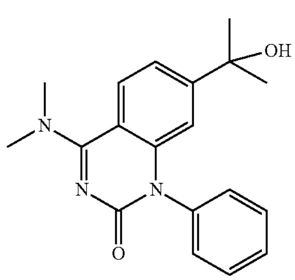 [SMILES: CN(C)c1nc(=O)n(-c2ccccc2)c2cc(C(C)(C)O)ccc12] | 4-(dimethylamino)-7-(2-hydroxypropan-2-yl)-1-phenylquinazolin-2(1H)-one |

TABLE 2-continued

| Structure | Name |
|---|---|
| 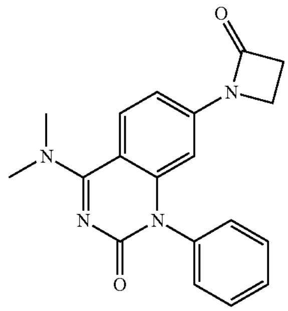 [SMILES: CN(C)c1nc(=O)n(-c2ccccc2)c2cc(N3CCC3=O)ccc12] | 4-(dimethylamino)-7-(2-oxoazetidin-1-yl)-1-phenylquinazolin-2(1H)-one |
| 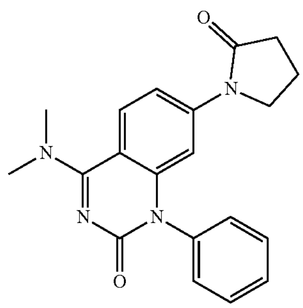 [SMILES: CN(C)c1nc(=O)n(-c2ccccc2)c2cc(N3CCCC3=O)ccc12] | 4-(dimethylamino)-7-(2-oxopyrrolidin-1-yl)-1-phenylquinazolin-2(1H)-one |
| 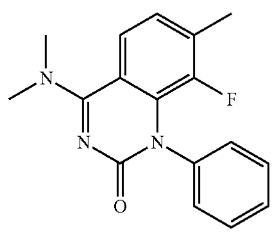 [SMILES: Cc1ccc2c(N(C)C)nc(=O)n(-c3ccccc3)c2c1F] | 4-(dimethylamino)-8-fluoro-7-methyl-1-phenylquinazolin-2(1H)-one |
| 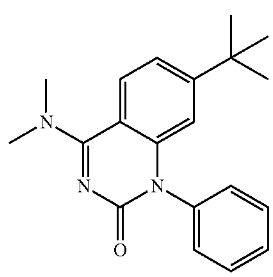 [SMILES: CN(C)c1nc(=O)n(-c2ccccc2)c2cc(C(C)(C)C)ccc12] | 7-(tert-butyl)-4-(dimethylamino)-1-phenylquinazolin-2(1H)-one |
| 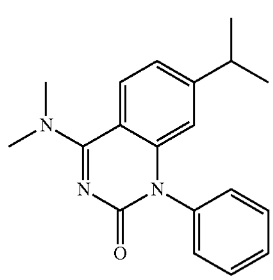 [SMILES: CC(C)c1ccc2c(N(C)C)nc(=O)n(-c3ccccc3)c2c1] | 4-(dimethylamino)-7-isopropyl-1-phenylquinazolin-2(1H)-one |

TABLE 2-continued

| Structure | Name |
|---|---|
| 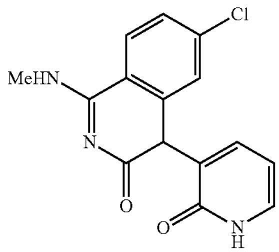 [SMILES: CNC1=NC(=O)C(c2ccc[nH]c2=O)c2cc(Cl)ccc21] | 7-chloro-4-(methylamino)-1-(4-oxo-1,4-dihydropyridin-3-yl)quinazolin-2(1H)-one |
| 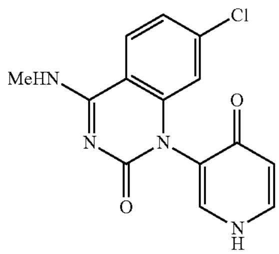 [SMILES: CNc1nc(=O)n(-c2c[nH]ccc2=O)c2cc(Cl)ccc12] | 6-chloro-1-(methylamino)-4-(2-oxo-1,2-dihydropyridin-3-yl)isoquinolin-3(4H)-one |
| 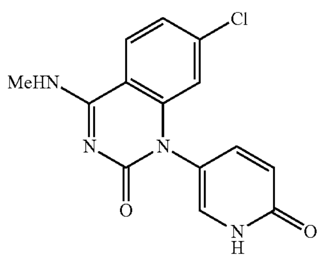 [SMILES: CNc1nc(=O)n(-c2ccc(=O)[nH]c2)c2cc(Cl)ccc12] | 7-chloro-4-(methylamino)-1-(6-oxo-1,6-dihydropyridin-3-yl)quinazolin-2(1H)-one |
| 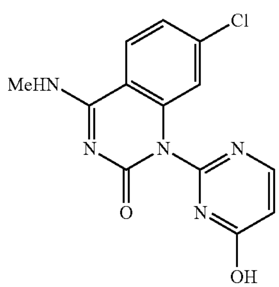 [SMILES: CNc1nc(=O)n(-c2nccc(O)n2)c2cc(Cl)ccc12] | 7-chloro-1-(4-hydroxypyrimidin-2-yl)-4-(methylamino)quinazolin-2(1H)-one |
| 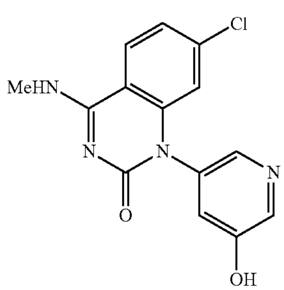 [SMILES: CNc1nc(=O)n(-c2cncc(O)c2)c2cc(Cl)ccc12] | 7-chloro-1-(5-hydroxypyridin-3-yl)-4-(methylamino)quinazolin-2(1H)-one |

TABLE 2-continued

| Structure | Name |
|---|---|
| 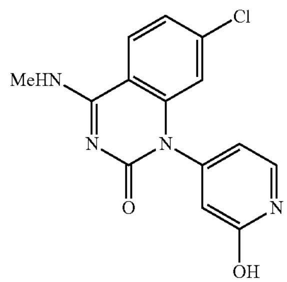 [SMILES: CNc1nc(=O)n(-c2ccnc(O)c2)c2cc(Cl)ccc12] | 7-chloro-1-(2-hydroxypyridin-4-yl)-4-(methylamino)quinazolin-2(1H)-one |
| 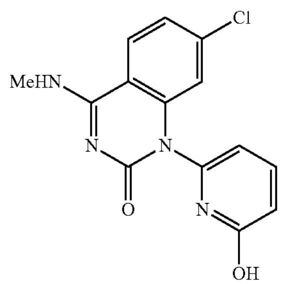 [SMILES: CNc1nc(=O)n(-c2cccc(O)n2)c2cc(Cl)ccc12] | 7-chloro-1-(6-hydroxypyridin-2-yl)-4-(methylamino)quinazolin-2(1H)-one |
| 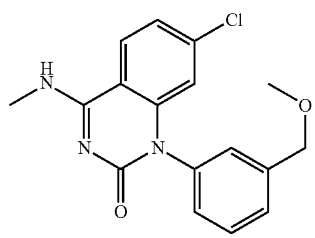 [SMILES: CNc1nc(=O)n(-c2cccc(COC)c2)c2cc(Cl)ccc12] | 7-chloro-1-(3-(methoxymethyl)phenyl)-4-(methylamino)quinazolin-2(1H)-one |
| 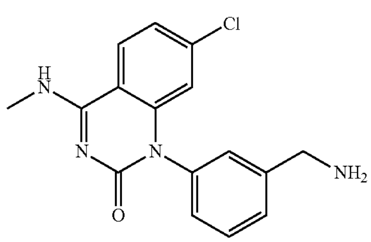 [SMILES: CNc1nc(=O)n(-c2cccc(CN)c2)c2cc(Cl)ccc12] | 1-(3-(aminomethyl)phenyl)-7-chloro-4-(methylamino)quinazolin-2(1H)-one |
| 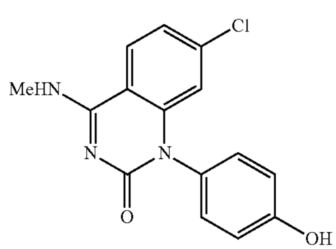 [SMILES: CNc1nc(=O)n(-c2ccc(O)cc2)c2cc(Cl)ccc12] | 7-chloro-1-(4-hydroxyphenyl)-4-(methylamino)quinazolin-2(1H)-one |
| 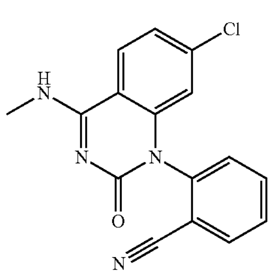 [SMILES: CNc1nc(=O)n(-c2ccccc2C#N)c2cc(Cl)ccc12] | 2-(7-chloro-4-(methylamino)-2-oxoquinazolin-1(2H)-yl)benzonitrile |

TABLE 2-continued

| Structure | Name |
|---|---|
| 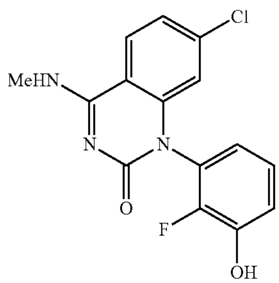 [SMILES: CNc1nc(=O)n(-c2cccc(O)c2F)c2cc(Cl)ccc12] | 7-chloro-1-(2-fluoro-3-hydroxyphenyl)-4-(methylamino)quinazolin-2(1H)-one |
| 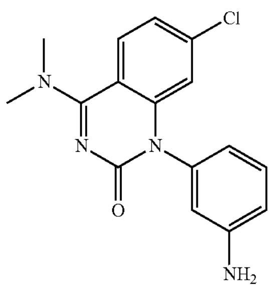 [SMILES: CN(C)c1nc(=O)n(-c2cccc(N)c2)c2cc(Cl)ccc12] | 1-(3-aminophenyl)-7-chloro-4-(dimethylamino)quinazolin-2(1H)- |
| 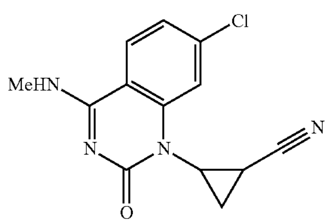 [SMILES: CNc1nc(=O)n(C2CC2C#N)c2cc(Cl)ccc12] | 2-(7-chloro-4-(methylamino)-2-oxoquinazolin-1(2H)-yl)-cyclopropane-1-carbonitrile |
| 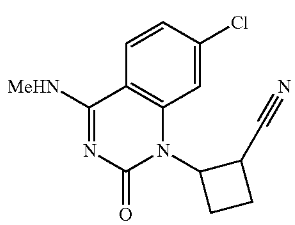 [SMILES: CNc1nc(=O)n(C2CCC2C#N)c2cc(Cl)ccc12] | 2-(7-chloro-4-(methylamino)-2-oxoquinazolin-1(2H)-yl)-cyclobutane-1-carbonitrile |
| 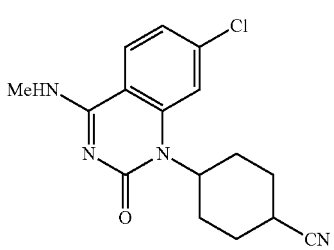 [SMILES: CNc1nc(=O)n(C2CCC(C#N)CC2)c2cc(Cl)ccc12] | 4-(7-chloro-4-(methylamino)-2-oxoquinazolin-1(2H)-yl)-cyclohexane-1-carbonitrile |
| 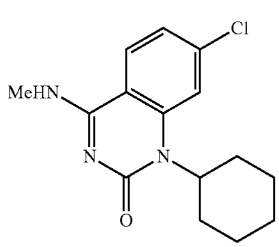 [SMILES: CNc1nc(=O)n(C2CCCCC2)c2cc(Cl)ccc12] | 7-chloro-1-cyclohexyl-4-(methylamino)quinazolin-2(1H)-one |

TABLE 2-continued

| Structure | Name |
|---|---|
| 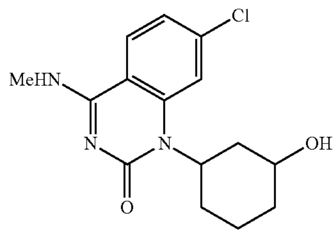 [SMILES: CNc1nc(=O)n(C2CCCC(O)C2)c2cc(Cl)ccc12] | 7-chloro-1-(3-hydroxycyclohexyl)-4-(methylamino)quinazolin-2(1H)-one |
| 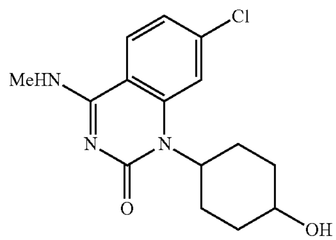 | 7-chloro-1-(4-hydroxycyclohexyl)-4-(methylamino)quinazolin-2(1H)-one |
| 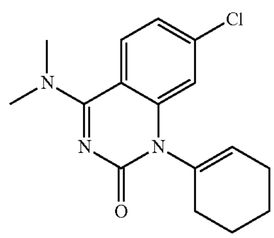 [SMILES: CN(C)c1nc(=O)n(C2=CCCCC2)c2cc(Cl)ccc12] | 7-chloro-1-(cyclohex-1-en-1-yl)-4-(dimethylamino)quinazolin-2(1H)-one |
| 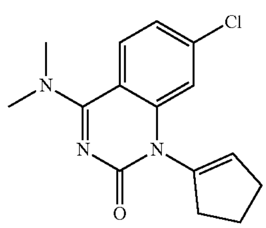 [SMILES: CN(C)c1nc(=O)n(C2=CCCC2)c2cc(Cl)ccc12] | 7-chloro-1-(cyclopent-1-en-1-yl)-4-(dimethylamino)quinazolin-2(1H)-one |
| 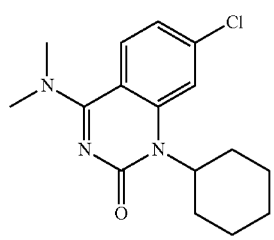 [SMILES: CN(C)c1nc(=O)n(C2CCCCC2)c2cc(Cl)ccc12] | 7-chloro-1-cyclohexyl-4-(dimethylamino)quinazolin-2(1H)-one |
| 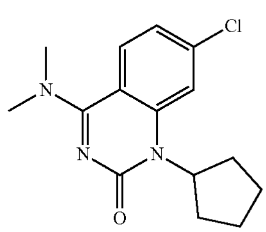 [SMILES: CN(C)c1nc(=O)n(C2CCCC2)c2cc(Cl)ccc12] | 7-chloro-1-cyclopentyl-4-(dimethylamino)quinazolin-2(1H)-one |

TABLE 2-continued

| Structure | Name |
|---|---|
| 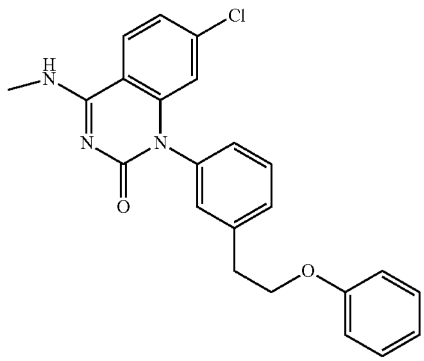 [SMILES: CNc1nc(=O)n(-c2cccc(CCOc3ccccc3)c2)c2cc(Cl)ccc12] | 7-chloro-4-(methylamino)-1-(3-(2-phenoxyethyl)phenyl)quinazolin-2(1H)-one |
| 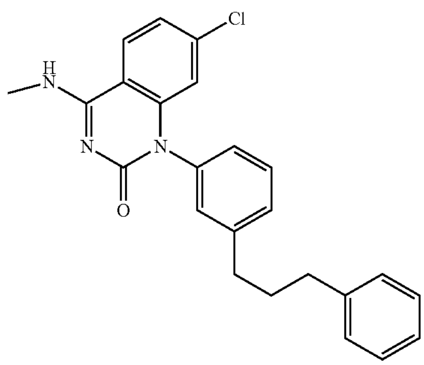 [SMILES: CNc1nc(=O)n(-c2cccc(CCCc3ccccc3)c2)c2cc(Cl)ccc12] | 7-chloro-4-(methylamino)-1-(3-(3-phenylpropyl)phenyl)quinazolin-2(1H)-one |
| 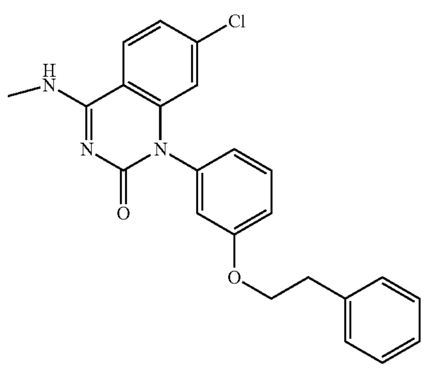 [SMILES: CNc1nc(=O)n(-c2cccc(OCCc3ccccc3)c2)c2cc(Cl)ccc12] | 7-chloro-4-(methylamino)-1-(3-phenethoxyphenyl)quinazolin-2(1H)-one |
| 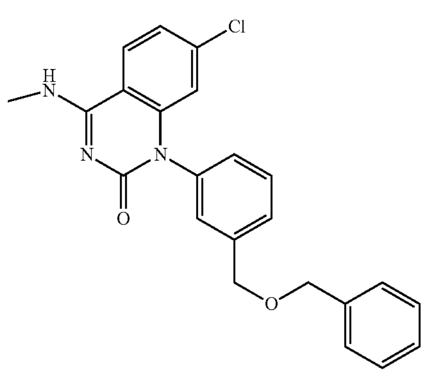 [SMILES: CNc1nc(=O)n(-c2cccc(COCc3ccccc3)c2)c2cc(Cl)ccc12] | 1-(3-((benzyloxy)methyl)phenyl)-7-chloro-4-(methylamino)quinazolin-2(1H)-one |

TABLE 2-continued

| Structure | Name |
| --- | --- |
| 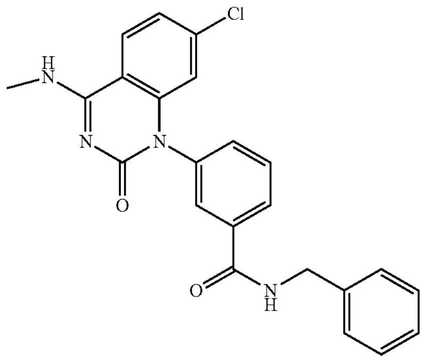 [SMILES: CNc1nc(=O)n(-c2cccc(C(=O)NCc3ccccc3)c2)c2cc(Cl)ccc12] | N-benzyl-3-(7-chloro-4-(methylamino)-2-oxoquinazolin-1(2H)-yl)benzamide |
| 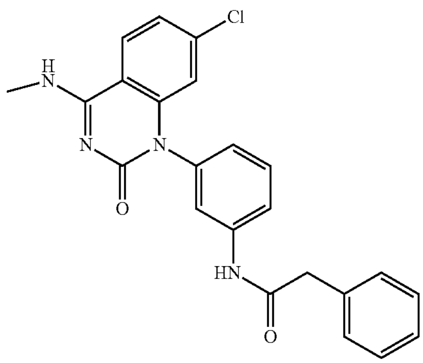 [SMILES: CNc1nc(=O)n(-c2cccc(NC(=O)Cc3ccccc3)c2)c2cc(Cl)ccc12] | N-(3-(7-chloro-4-(methylamino)-2-oxoquinazolin-1(2H)-yl)phenyl)-2-phenylacetamide |
| 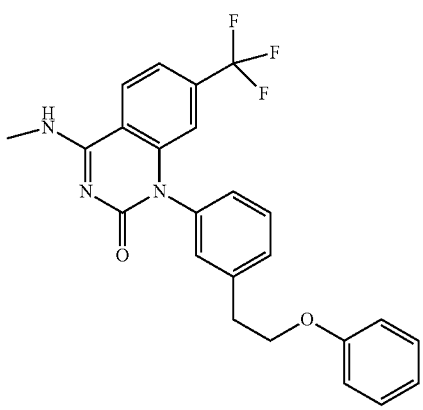 [SMILES: CNc1nc(=O)n(-c2cccc(CCOc3ccccc3)c2)c2cc(C(F)(F)F)ccc12] | 4-(methylamino)-1-(3-(2-phenoxyethyl)phenyl)-7-(trifluoromethyl)quinazolin-2(1H)-one |
|  | 7-chloro-1-(3-(2-(3-(hydroxymethyl)phenoxy)ethyl)phenyl)-4-(methylamino)quinazolin-2(1H)-one |

TABLE 2-continued

| Structure | Name |
|---|---|
| 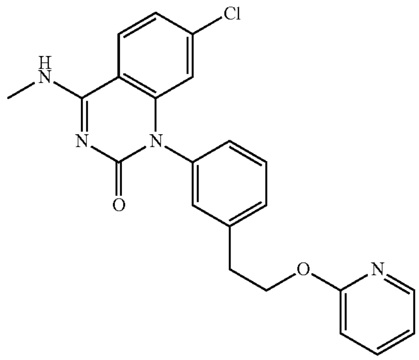 [SMILES: CNc1nc(=O)n(-c2cccc(CCOc3ccccn3)c2)c2cc(Cl)ccc12] | 7-chloro-4-(methylamino)-1-(3-(2-(pyridin-2-yloxy)ethyl)phenyl)quinazolin-2(1H)-one |
| 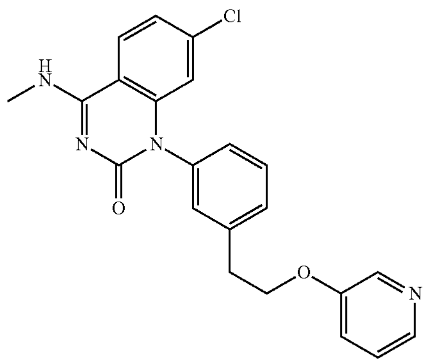 [SMILES: CNc1nc(=O)n(-c2cccc(CCOc3cccnc3)c2)c2cc(Cl)ccc12] | 7-chloro-4-(methylamino)-1-(3-(2-(pyridin-3-yloxy)ethyl)phenyl)quinazolin-2(1H)-one |
| 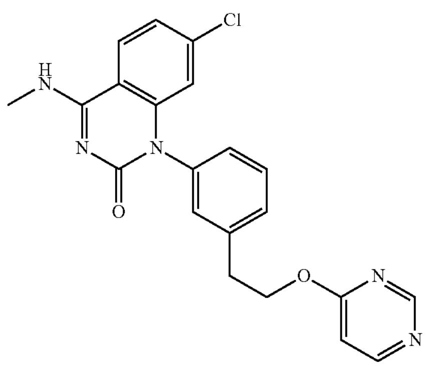 [SMILES: CNc1nc(=O)n(-c2cccc(CCOc3ccncn3)c2)c2cc(Cl)ccc12] | 7-chloro-4-(methylamino)-1-(3-(2-(pyrimidin-4-yloxy)ethyl)phenyl)quinazolin-2(1H)-one |
| 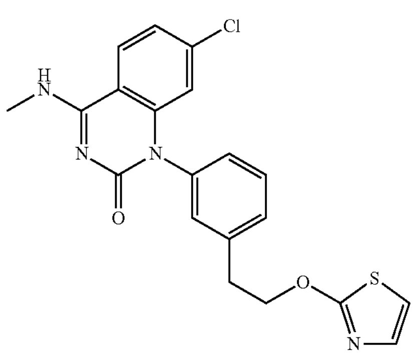 [SMILES: CNc1nc(=O)n(-c2cccc(CCOc3nccs3)c2)c2cc(Cl)ccc12] | 7-chloro-4-(methylamino)-1-(3-(2-(thiazol-2-yloxy)ethyl)phenyl)quinazolin-2(1H)-one |

TABLE 2-continued

| Structure | Name |
|---|---|
| 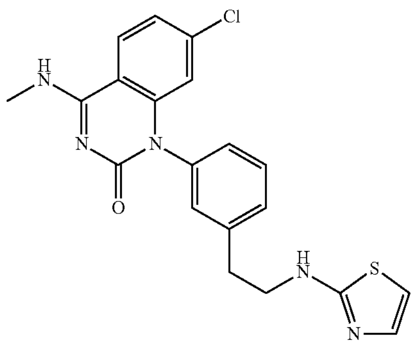 [SMILES: CNc1nc(=O)n(-c2cccc(CCNc3nccs3)c2)c2cc(Cl)ccc12] | 7-chloro-4-(methylamino)-1-(3-(2-(thiazol-2-ylamino)ethyl)phenyl)quinazolin-2(1H)-one |
| 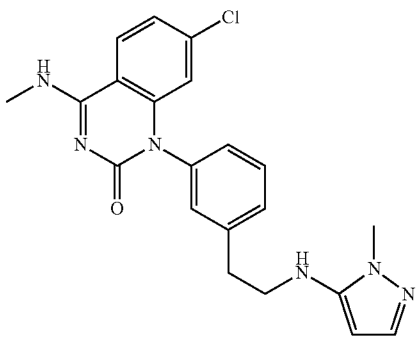 [SMILES: CNc1nc(=O)n(-c2cccc(CCNc3ccnn3C)c2)c2cc(Cl)ccc12] | 7-chloro-1-(3-(2-((1-methyl-1H-pyrazol-5-yl)amino)ethyl)phenyl)-4-(methylamino)-quinazolin-2(1H)-one |
| 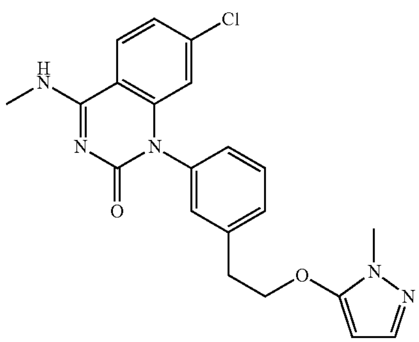 [SMILES: CNc1nc(=O)n(-c2cccc(CCOc3ccnn3C)c2)c2cc(Cl)ccc12] | 7-chloro-1-(3-(2-((1-methyl-1H-pyrazol-5-yl)oxy)ethyl)phenyl)-4-(methylamino)-quinazolin-2(1H)-one |
| 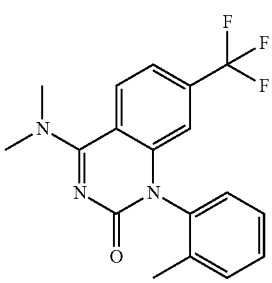 [SMILES: Cc1ccccc1-n1c(=O)nc(N(C)C)c2ccc(C(F)(F)F)cc21] | 4-(dimethylamino)-1-(o-tolyl)-7-(trifluoromethyl)quinazolin-2(1H)-one |
| 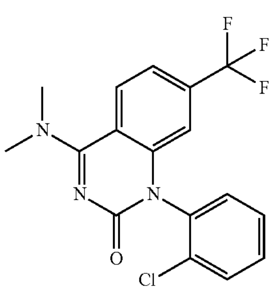 [SMILES: CN(C)c1nc(=O)n(-c2ccccc2Cl)c2cc(C(F)(F)F)ccc12] | 1-(2-chlorophenyl)-4-(dimethylamino)-7-(trifluoromethyl)-quinazolin-2(1H)-one |

TABLE 2-continued

| Structure | Name |
|---|---|
| 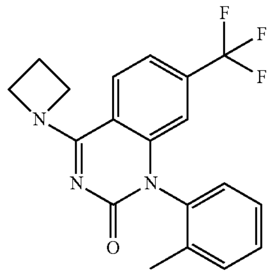 [SMILES: Cc1ccccc1-n1c(=O)nc(N2CCC2)c2ccc(C(F)(F)F)cc21] | 4-(azetidin-1-yl)-1-(o-tolyl)-7-(trifluoromethyl)quinazolin-2(1H)-one |
| 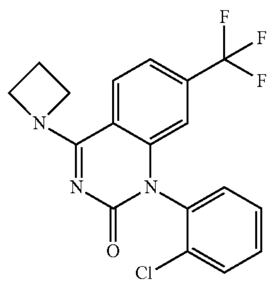 [SMILES: O=c1nc(N2CCC2)c2ccc(C(F)(F)F)cc2n1-c1ccccc1Cl] | 4-(azetidin-1-yl)-1-(2-chlorophenyl)-7-(trifluoromethyl)quinazolin-2(1H)-one |
| 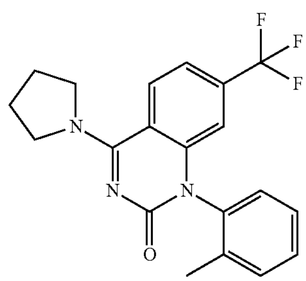 [SMILES: Cc1ccccc1-n1c(=O)nc(N2CCCC2)c2ccc(C(F)(F)F)cc21] | 4-(pyrrolidin-1-yl)-1-(o-tolyl)-7-(trifluoromethyl)quinazolin-2(1H)-one |
| 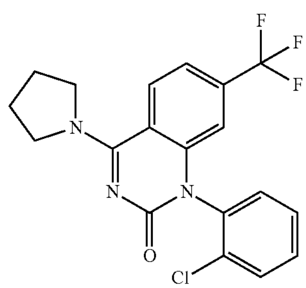 [SMILES: O=c1nc(N2CCCC2)c2ccc(C(F)(F)F)cc2n1-c1ccccc1Cl] | 1-(2-chlorophenyl)-4-(pyrrolidin-1-yl)-7-(trifluoromethyl)-quinazolin-2(1H)-one |
| 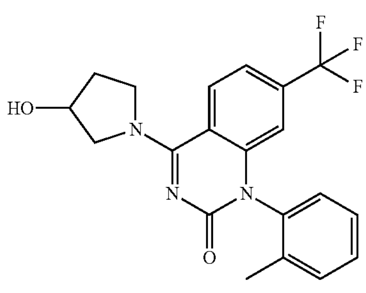 [SMILES: Cc1ccccc1-n1c(=O)nc(N2CCC(O)C2)c2ccc(C(F)(F)F)cc21] | 4-(3-hydroxypyrrolidin-1-yl)-1-(o-tolyl)-7-(trifluoromethyl)-quinazolin-2(1H)-one |

TABLE 2-continued

| Structure | Name |
|---|---|
| 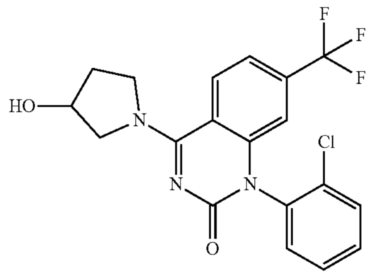 [SMILES: O=c1nc(N2CCC(O)C2)c2ccc(C(F)(F)F)cc2n1-c1ccccc1Cl] | 1-(2-chlorophenyl)-4-(3-hydroxypyrrolidin-1-yl)-7-(trifluoromethyl)-quinazolin-2(1H)-one |
| 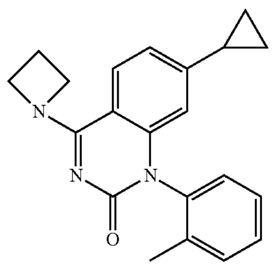 [SMILES: Cc1ccccc1-n1c(=O)nc(N2CCC2)c2ccc(C3CC3)cc21] | 4-(azetidin-1-yl)-7-cyclopropyl-1-(o-tolyl)quinazolin-2(1H)-one |
| 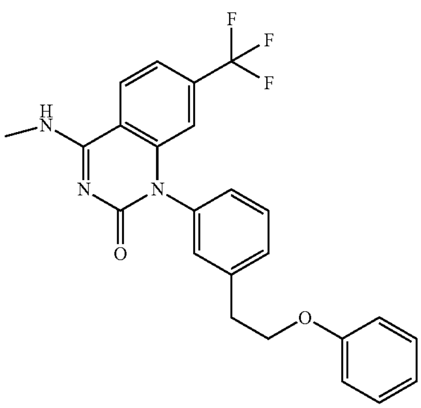 [SMILES: CNc1nc(=O)n(-c2cccc(CCOc3ccccc3)c2)c2cc(C(F)(F)F)ccc12] | 4-(methylamino)-1-(3-(2-phenoxyethyl)phenyl)-7-(trifluoromethyl)-quinazolin-2(1H)-one |
| 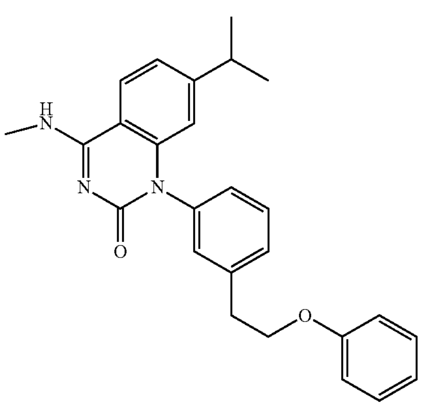 [SMILES: CNc1nc(=O)n(-c2cccc(CCOc3ccccc3)c2)c2cc(C(C)C)ccc12] | 7-isopropyl-4-(methylamino)-1-(3-(2-phenoxyethyl)phenyl)-quinazolin-2(1H)-one |

TABLE 2-continued

| Structure | Name |
|---|---|
| 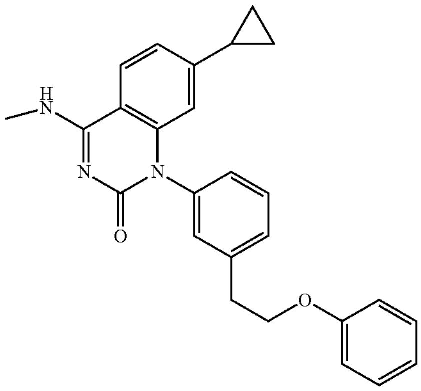 [SMILES: CNc1nc(=O)n(-c2cccc(CCOc3ccccc3)c2)c2cc(C3CC3)ccc12] | 7-cyclopropyl-4-(methylamino)-1-(3-(2-phenoxyethyl)phenyl)-quinazolin-2(1H)-one |
| 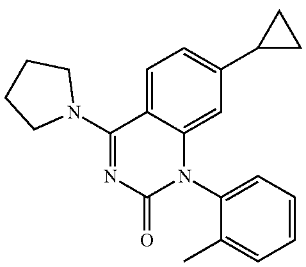 [SMILES: Cc1ccccc1-n1c(=O)nc(N2CCCC2)c2ccc(C3CC3)cc21] | 7-cyclopropyl-4-(pyrrolidin-1-yl)-1-(o-tolyl)quinazolin-2(1H)-one |
| 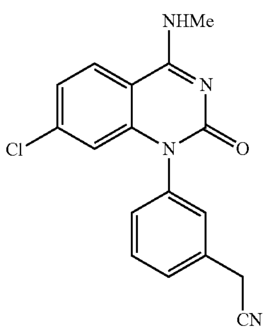 [SMILES: CNc1nc(=O)n(-c2cccc(CC#N)c2)c2cc(Cl)ccc12] | 2-(3-(7-chloro-4-(methylamino)-2-oxoquinazolin-1(2H)-yl)phenyl)acetonitrile |
| 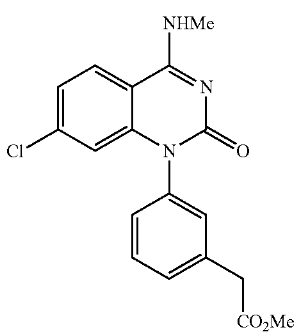 [SMILES: CNc1nc(=O)n(-c2cccc(CC(=O)OC)c2)c2cc(Cl)ccc12] | methyl 2-(3-(7-chloro-4-(methylamino)-2-oxoquinazolin-1(2H)-yl)phenyl)acetate |
| 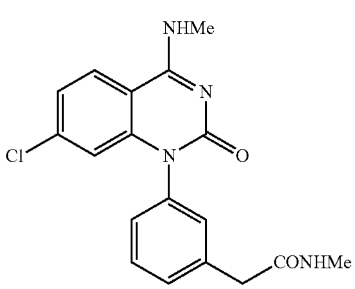 | 2-(3-(7-chloro-4-(methylamino)-2-oxoquinazolin-1(2H)-yl)phenyl)-N-methylacetamide |

TABLE 2-continued

| Structure | Name |
|---|---|
| 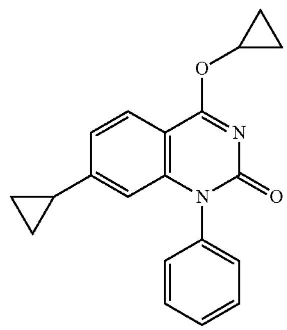 [SMILES: O=c1nc(OC2CC2)c2ccc(C3CC3)cc2n1-c1ccccc1] | 4-cyclopropoxy-7-cyclopropyl-1-phenylquinazolin-2(1H)-one |
| 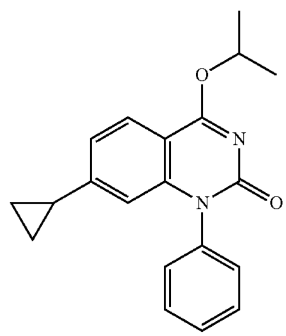 [SMILES: CC(C)Oc1nc(=O)n(-c2ccccc2)c2cc(C3CC3)ccc12] | 7-cyclopropyl-4-isopropoxy-1-phenylquinazolin-2(1H)-one |
| 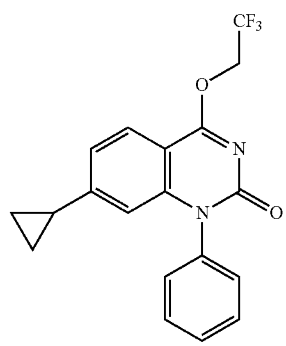 [SMILES: O=c1nc(OCC(F)(F)F)c2ccc(C3CC3)cc2n1-c1ccccc1] | 7-cyclopropyl-1-phenyl-4-(2,2,2-trifluoroethoxy)quinazolin-2(1H)-one |
| 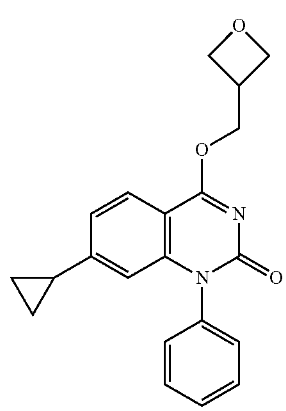 [SMILES: O=c1nc(OCC2COC2)c2ccc(C3CC3)cc2n1-c1ccccc1] | 7-cyclopropyl-4-(oxetan-3-ylmethoxy)-1-phenylquinazolin-2(1H)-one |

TABLE 2-continued

| Structure | Name |
|---|---|
| 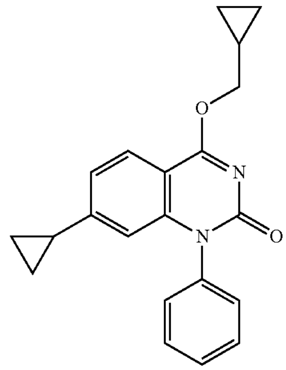 [SMILES: O=c1nc(OCC2CC2)c2ccc(C3CC3)cc2n1-c1ccccc1] | 7-cyclopropyl-4-(cyclopropylmethoxy)-1-phenylquinazolin-2(1H)-one |
| 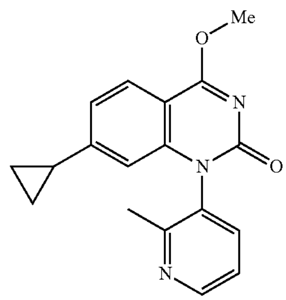 [SMILES: COc1nc(=O)n(-c2cccnc2C)c2cc(C3CC3)ccc12] | 7-cyclopropyl-4-methoxy-1-(2-methylpyridin-3-yl)quinazolin-2(1H)-one |
| 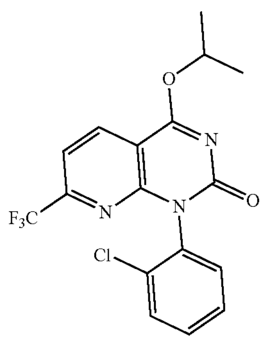 [SMILES: CC(C)Oc1nc(=O)n(-c2ccccc2Cl)c2nc(C(F)(F)F)ccc12] | 1-(2-chlorophenyl)-4-isopropoxy-7-(trifluoromethyl)pyrido[2,3-d]pyrimidin-2(1H)-one |
| 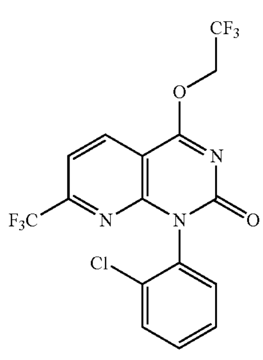 [SMILES: O=c1nc(OCC(F)(F)F)c2ccc(C(F)(F)F)nc2n1-c1ccccc1Cl] | 1-(2-chlorophenyl)-4-(2,2,2-trifluoroethoxy)-7-(trifluoromethyl)pyrido[2,3-d]pyrimidin-2(1H)-one |

TABLE 2-continued

| Structure | Name |
|---|---|
| 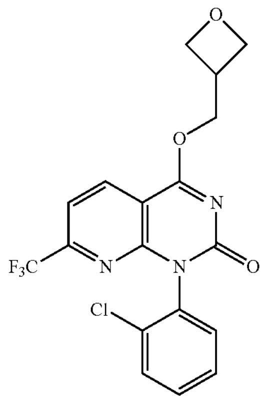 [SMILES: O=c1nc(OCC2COC2)c2ccc(C(F)(F)F)nc2n1-c1ccccc1Cl] | 1-(2-chlorophenyl)-4-(oxetan-3-ylmethoxy)-7-(trifluoromethyppyrido |
| 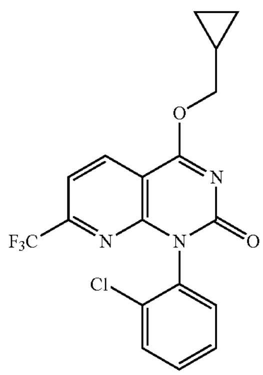 [SMILES: O=c1nc(OCC2CC2)c2ccc(C(F)(F)F)nc2n1-c1ccccc1Cl] | 1-(2-chlorophenyl)-4-(cyclopropylmethoxy)-7-(trifluoromethyppyrido |
| 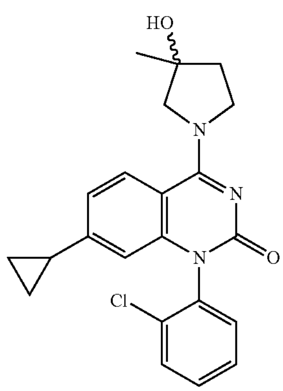 [SMILES: CC1(O)CCN(c2nc(=O)n(-c3ccccc3Cl)c3cc(C4CC4)ccc23)C1] | 1-(2-chlorophenyl)-7-cyclopropyl-4-(3-hydroxy-3-methylpyrrolidin-1-yl)quinazolin-2(1H)-one |
| 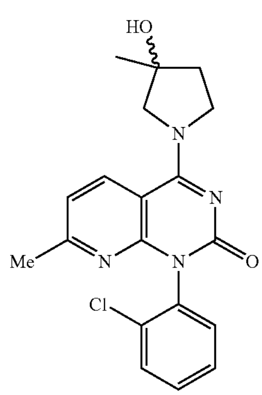 [SMILES: Cc1ccc2c(N3CCC(C)(O)C3)nc(=O)n(-c3ccccc3Cl)c2n1] | 1-(2-chlorophenyl)-4-(3-hydroxy-3-methylpyrrolidin-1-yl)-7-methylpyrido |

TABLE 2-continued

| Structure | Name |
|---|---|
| 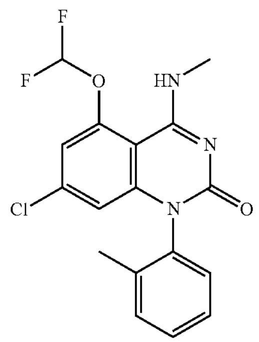 [SMILES: CNc1nc(=O)n(-c2ccccc2C)c2cc(Cl)cc(OC(F)F)c12] | 7-chloro-5-(difluoromethoxy)-4-(methylamino)-1-(o-tolyl)quinazolin-2(1H)-one |
| 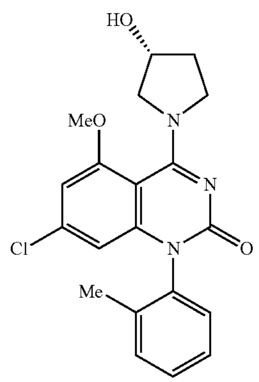 [SMILES: COc1cc(Cl)cc2c1c(N1CC[C@@H](O)C1)nc(=O)n2-c1ccccc1C] | (R)-7-chloro-4-(3-hydroxypyrrolidin-1-yl)-5-methoxy-1-(o-tolyl)quinazolin-2(1H)-one |
| 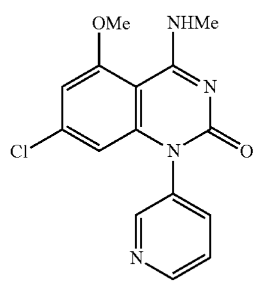 [SMILES: CNc1nc(=O)n(-c2cccnc2)c2cc(Cl)cc(OC)c12] | 7-chloro-5-methoxy-4-(methylamino)-1-(pyridin-3-yl)quinazolin-2(1H)-one |
| 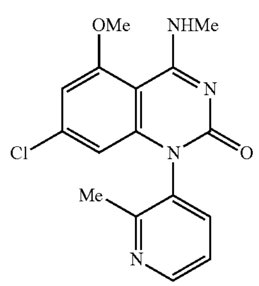 [SMILES: CNc1nc(=O)n(-c2cccnc2C)c2cc(Cl)cc(OC)c12] | 7-chloro-5-methoxy-4-(methylamino)-1-(2-methylpyridin-3-yl)quinazolin-2(1H)-one |
| 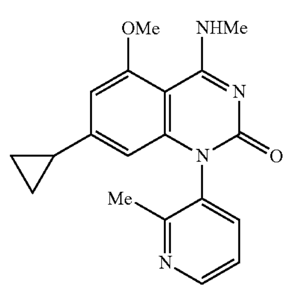 [SMILES: CNc1nc(=O)n(-c2cccnc2C)c2cc(C3CC3)cc(OC)c12] | 7-cyclopropyl-5-methoxy-4-(methylamino)-1-(2-methylpyridin-3-yl)quinazolin-2(1H)-one |

TABLE 2-continued

| Structure | Name |
|---|---|
| 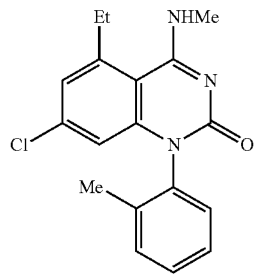 [SMILES: CCc1cc(Cl)cc2c1c(NC)nc(=O)n2-c1ccccc1C] | 7-chloro-5-ethyl-4-(methylamino)-1-(o-tolyl)quinazolin-2(1H)-one |
| 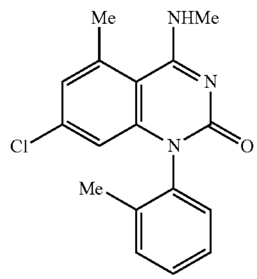 [SMILES: CNc1nc(=O)n(-c2ccccc2C)c2cc(Cl)cc(C)c12] | 7-chloro-5-methyl-4-(methylamino)-1-(o-tolyl)quinazolin-2(1H)-one |
| 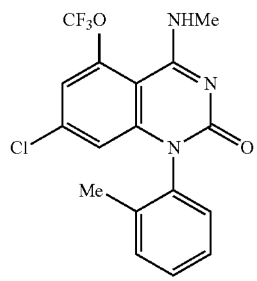 | 7-chloro-4-(methylamino)-1-(o-tolyl)-5-(trifluoromethoxy)quinazolin-2(1H)-one |
| 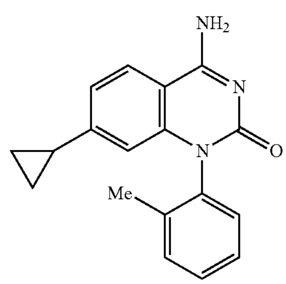 [SMILES: Cc1ccccc1-n1c(=O)nc(N)c2ccc(C3CC3)cc21] | 4-amino-7-cyclopropyl-1-(o-tolyl)quinazolin-2(1H)-one |
| | 1-(2-chlorophenyl)-4-((((1R,2R)-2-methoxycyclobutyl)amino)-7-(trifluoromethyl)pyrido |

TABLE 2-continued

| Structure | Name |
|---|---|
| 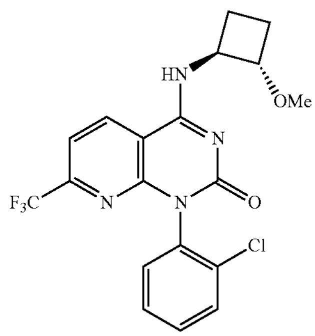 [SMILES: CO[C@H]1CC[C@@H]1Nc1nc(=O)n(-c2ccccc2Cl)c2nc(C(F)(F)F)ccc12] | 1-(2-chlorophenyl)-4-(((1S,2S)-2-methoxycyclobutyl)amino)-7-(trifluoromethyl)pyrido |
| 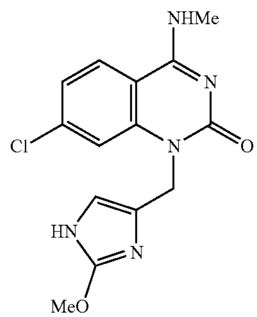 [SMILES: CNc1nc(=O)n(Cc2c[nH]c(OC)n2)c2cc(Cl)ccc12] | 7-chloro-1-((2-methoxy-1H-imidazol-4-yl)methyl)-4-(methylamino)quinazolin-2(1H)-one |
| 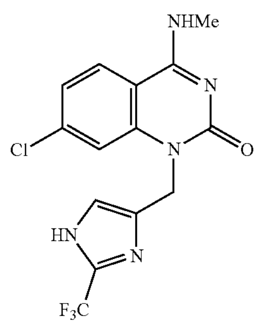 [SMILES: CNc1nc(=O)n(Cc2c[nH]c(C(F)(F)F)n2)c2cc(Cl)ccc12] | 7-chloro-4-(methylamino)-1-((2-(trifluoromethyl)-1H-imidazol-4-yl)methyl)quinazolin-2(1H)-one |
| 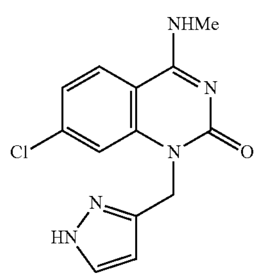 [SMILES: CNc1nc(=O)n(Cc2cc[nH]n2)c2cc(Cl)ccc12] | 1-((1H-pyrazol-3-yl)methyl)-7-chloro-4-(methylamino)quinazolin-2(1H)-one |
| 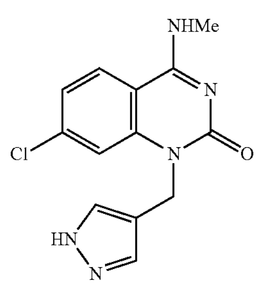 [SMILES: CNc1nc(=O)n(Cc2cn[nH]c2)c2cc(Cl)ccc12] | 1-((1H-pyrazol-4-yl)methyl)-7-chloro-4-(methylamino)quinazolin-2(1H)-one |

TABLE 2-continued

| Structure | Name |
|---|---|
| 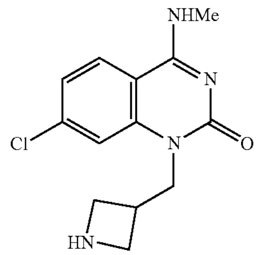 [SMILES: CNc1nc(=O)n(CC2CNC2)c2cc(Cl)ccc12] | 1-(azetidin-3-ylmethyl)-7-chloro-4-(methylamino)quinazolin-2(1H)-one |
| 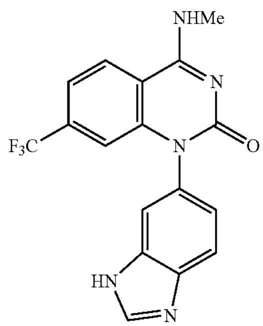 [SMILES: CNc1nc(=O)n(-c2ccc3nc[nH]c3c2)c2cc(C(F)(F)F)ccc12] | 1-(1H-benzo[d]imidazol-6-yl)-4-(methylamino)-7-(trifluoromethyl)quinazolin-2(1H)-one |
| 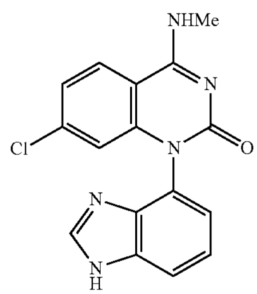 [SMILES: CNc1nc(=O)n(-c2cccc3[nH]cnc23)c2cc(Cl)ccc12] | 1-(1H-benzo[d]imidazol-4-yl)-7-chloro-4-(methylamino)quinazolin-2(1H)-one |
| 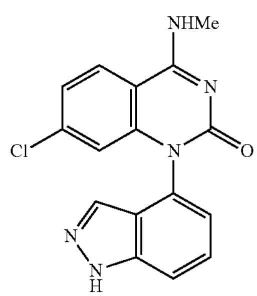 [SMILES: CNc1nc(=O)n(-c2cccc3[nH]ncc23)c2cc(Cl)ccc12] | 7-chloro-1-(1H-indazol-4-yl)-4-(methylamino)quinazolin-2(1H)-one |
| 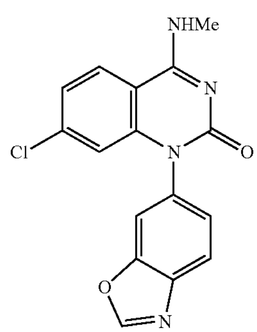 [SMILES: CNc1nc(=O)n(-c2ccc3ncoc3c2)c2cc(Cl)ccc12] | 1-(benzo[d]oxazol-6-yl)-7-chloro-4-(methylamino)quinazolin-2(1H)-one |

TABLE 2-continued

| Structure | Name |
|---|---|
| 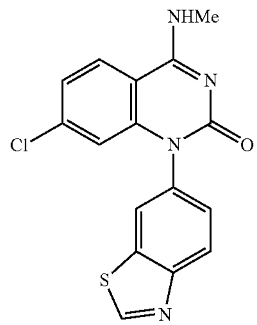 [SMILES: CNc1nc(=O)n(-c2ccc3ncsc3c2)c2cc(Cl)ccc12] | 1-(benzo[d]thiazol-6-yl)-7-chloro-4-(methylamino)quinazolin-2(1H)-one |
| 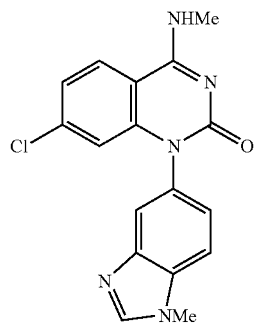 [SMILES: CNc1nc(=O)n(-c2ccc3c(c2)ncn3C)c2cc(Cl)ccc12] | 7-chloro-1-(1-methyl-1H-benzo[d]imidazol-5-yl)-4-(methylamino)quinazolin-2(1H)-one |
| 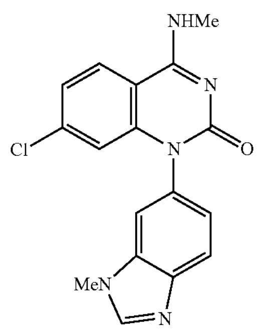 [SMILES: CNc1nc(=O)n(-c2ccc3ncn(C)c3c2)c2cc(Cl)ccc12] | 7-chloro-1-(1-methyl-1H-benzo[d]imidazol-6-yl)-4-(methylamino)quinazolin-2(1H)-one |
| 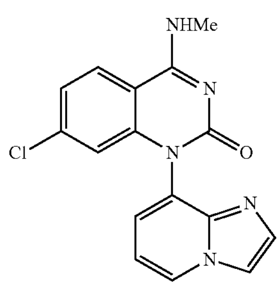 [SMILES: CNc1nc(=O)n(-c2cccn3ccnc23)c2cc(Cl)ccc12] | 7-chloro-1-(imidazo[1,2-a]pyridin-8-yl)-4-(methylamino)quinazolin-2(1H)-one |
| 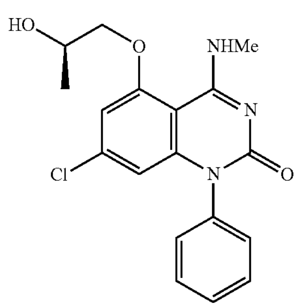 [SMILES: CNc1nc(=O)n(-c2ccccc2)c2cc(Cl)cc(OC[C@@H](C)O)c12] | (R)-7-chloro-5-(2-hydroxypropoxy)-4-(methylamino)-1-phenylquinazolin-2(1H)-one |

TABLE 2-continued

| Structure | Name |
|---|---|
| 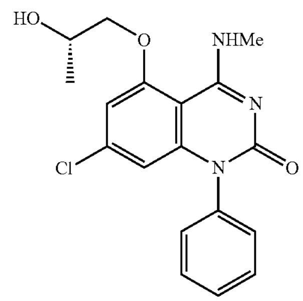 [SMILES: CNc1nc(=O)n(-c2ccccc2)c2cc(Cl)cc(OC[C@H](C)O)c12] | (S)-7-chloro-5-(2-hydroxypropoxy)-4-(methylamino)-1-phenylquinazolin-2(1H)-one |
| 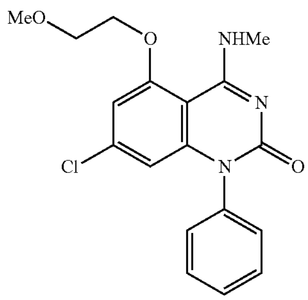 [SMILES: CNc1nc(=O)n(-c2ccccc2)c2cc(Cl)cc(OCCOC)c12] | 7-chloro-5-(2-methoxyethoxy)-4-(methylamino)-1-phenylquinazolin-2(1H)-one |
| 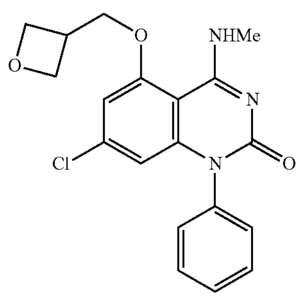 [SMILES: CNc1nc(=O)n(-c2ccccc2)c2cc(Cl)cc(OCC3COC3)c12] | 7-chloro-4-(methylamino)-5-(oxetan-3-ylmethoxy)-1-phenylquinazolin-2(1H)-one |
| 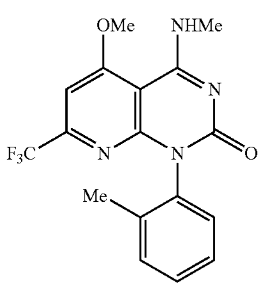 [SMILES: CNc1nc(=O)n(-c2ccccc2C)c2nc(C(F)(F)F)cc(OC)c12] | 5-methoxy-4-(methylamino)-1-(o-tolyl)-7-(trifluoromethyl)pyrido[2,3-d]pyrimidin-2(1H)-one |
| 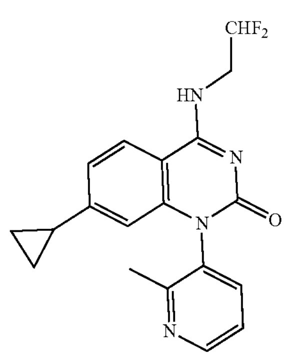 [SMILES: Cc1ncccc1-n1c(=O)nc(NCC(F)F)c2ccc(C3CC3)cc21] | 7-cyclopropyl-4-((2,2-difluoroethyl)amino)-1-(2-methylpyridin-3-yl)quinazolin-2(1H)-one |

TABLE 2-continued

| Structure | Name |
|---|---|
| 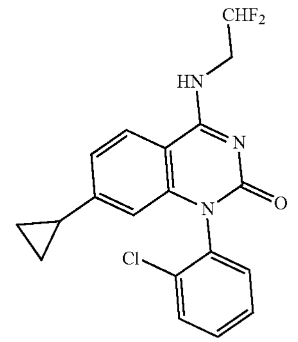 [SMILES: O=c1nc(NCC(F)F)c2ccc(C3CC3)cc2n1-c1ccccc1Cl] | 1-(2-chlorophenyl)-7-cyclopropyl-4-((2,2-difluoroethyl)amino)quinazolin-2(1H)-one |
| 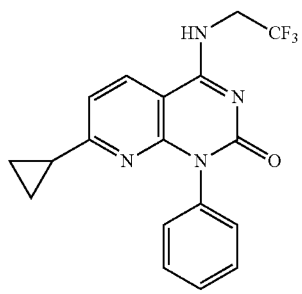 [SMILES: O=c1nc(NCC(F)(F)F)c2ccc(C3CC3)nc2n1-c1ccccc1] | 7-cyclopropyl-1-phenyl-4-((2,2,2-trifluoroethyl)amino)pyrido[2,3-d]pyrimidin-2(1H)-one |
| 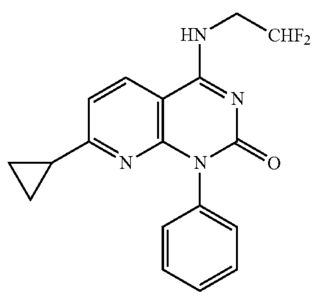 [SMILES: O=c1nc(NCC(F)F)c2ccc(C3CC3)nc2n1-c1ccccc1] | 7-cyclopropyl-4-((2,2-difluoroethyl)amino)-1-phenylpyrido[2,3-d]pyrimidin-2(1H)-one |
| 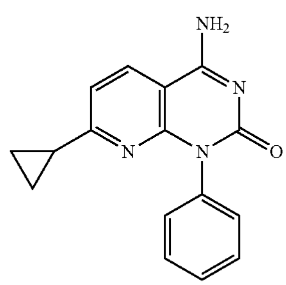 [SMILES: Nc1nc(=O)n(-c2ccccc2)c2nc(C3CC3)ccc12] | 4-amino-7-cyclopropyl-1-phenylpyrido[2,3-d]pyrimidin-2(1H)-one |
| 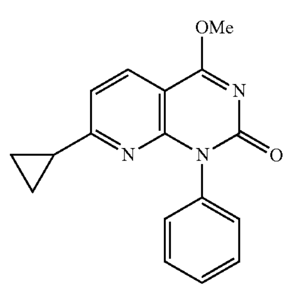 [SMILES: COc1nc(=O)n(-c2ccccc2)c2nc(C3CC3)ccc12] | 7-cyclopropyl-4-methoxy-1-phenylpyrido[2,3-d]pyrimidin-2(1H)-one |

TABLE 2-continued

| Structure | Name |
|---|---|
| 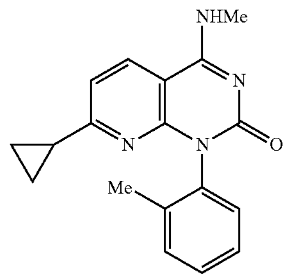 [SMILES: CNc1nc(=O)n(-c2ccccc2C)c2nc(C3CC3)ccc12] | 7-cyclopropyl-4-(methylamino)-1-(o-tolyl)pyrido[2,3-d]pyrimidin-2(1H)-one |
| 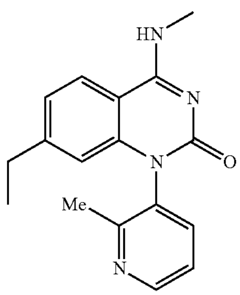 [SMILES: CCc1ccc2c(NC)nc(=O)n(-c3cccnc3C)c2c1] | 7-ethyl-4-(methylamino)-1-(2-methylpyridin-3-yl)quinazolin-2(1H)-one |
| 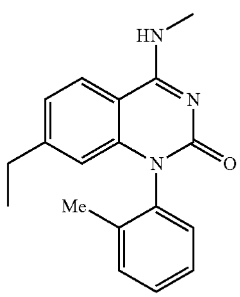 [SMILES: CCc1ccc2c(NC)nc(=O)n(-c3ccccc3C)c2c1] | 7-ethyl-4-(methylamino)-1-(o-tolyl)quinazolin-2(1H)-one |
| 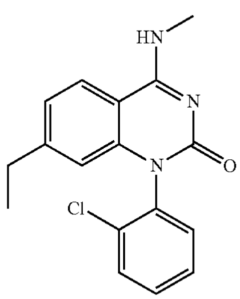 [SMILES: CCc1ccc2c(NC)nc(=O)n(-c3ccccc3Cl)c2c1] | 1-(2-chlorophenyl)-7-ethyl-4-(methylamino)quinazolin-2(1H)-one |

EMBODIMENTS

In further embodiments 1 to 34 below, the present disclosure includes:

1A. In embodiment 1A, provided is a compound of Formula (IA'), (IA), (IIA') or (IIA) or a pharmaceutically acceptable salt thereof, where w, x, y, z, $R^1$ and $R^2$ are as described in the Summary above. In a first subembodiment of first embodiment, the compound or a pharmaceutically acceptable salt thereof has structure (IA). In a second subembodiment of first embodiment, the compound or a pharmaceutically acceptable salt thereof has structure (IIA). In a third subembodiment of first embodiment, the compound or a pharmaceutically acceptable salt thereof has structure (IA'). In a fourth subembodiment of first embodiment, the compound or a pharmaceutically acceptable salt thereof has structure (IIA').

1. In embodiment 1, provided is a compound of Formula (I), (IA), (IA'), (II), (IIA), (IIA') or a subembodiment describe herein; or a pharmaceutically acceptable salt thereof, where w, x, y, z, $R^1$ and $R^2$ are as described in the Summary above. In a first subembodiment of first embodiment, the compound or a pharmaceutically acceptable salt thereof has structure (I). In a second subembodiment of first embodiment, the compound or a pharmaceutically acceptable salt thereof has structure (II).

2. In embodiment 2, the compound of any one of embodiments 1A or 1 and subembodiments contained therein, or a pharmaceutically acceptable salt thereof is wherein
$R^1$ is $R^7$ wherein $R^7$ is cycloalkyl, bridged cycloalkyl, fused cycloalkyl, spirocycloalkyl, phenyl, heteroaryl, heterocyclyl, bridged heterocyclyl, fused heterocyclyl, or spiroheterocyclyl, wherein aryl, heteroaryl, and heterocyclyl are unsubstituted or substituted with $R^d$, $R^e$, and/or $R^f$; and $R^2$ is alkyl, halo, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$. In a first subembodiment of embodiment 2, $R^2$ is alkyl, haloalkyl, hydroxyalkyl, alkoxyalkyl, aminoalkyl, aminocarbonylalkyl, aminosulfonylalkyl, —O—$R^8$, —$NR^9R^{10}$, or $R^{11}$.

3. In embodiment 3, the compound of any one of embodiments 1A or 1 and subembodiments contained therein, or a pharmaceutically acceptable salt thereof is wherein
$R^1$ is alkyl, alkenyl, haloalkyl, hydroxyalkyl, alkoxyalkyl, aminoalkyl, aminocarbonylalkyl, or aminosulfonylalkyl; and
$R^2$ is alkyl, halo, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$. In a first subembodiment of embodiment 3, $R^2$ is alkyl, haloalkyl, hydroxyalkyl, alkoxyalkyl, aminoalkyl, aminocarbonylalkyl, aminosulfonylalkyl, —O—R', —$NR^9R^{10}$, or $R^{11}$.

4. In embodiment 4, the compound of any one of embodiments 1A or 1 and subembodiments contained therein, or a pharmaceutically acceptable salt thereof is wherein $R^1$ is $R^7$ wherein $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$.

5. In embodiment 5, the compound of any one of embodiments 1A and 1 to 4 and subembodiments contained therein, or a pharmaceutically acceptable salt thereof has a structure of formula (IIIa), (IIIb), (IIIc), (IIId), (IIIe), (IIIf), or (IIIg) below:

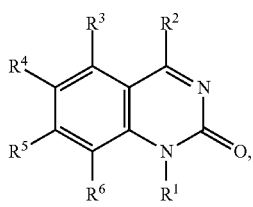
(IIIa)

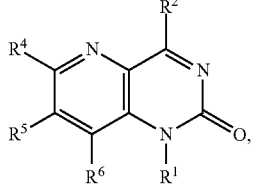
(IIIb)

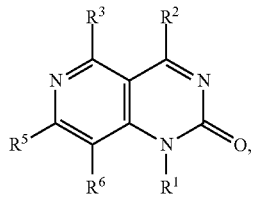
(IIIc)

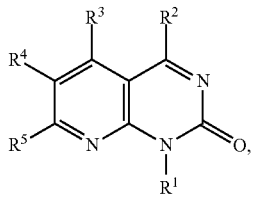
(IIId)

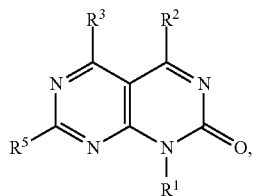
(IIIe)

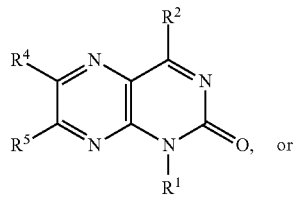
(IIIf)

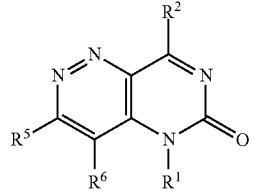
(IIIg)

In a first sub-embodiment of embodiment 5, the compound or a pharmaceutically acceptable salt thereof has a structure of formula (IIIa). In second sub-embodiment of embodiment 5, the compound or a pharmaceutically acceptable salt thereof has a structure of formula (IIIb). In third sub-embodiment of embodiment 5, the compound or a pharmaceutically acceptable salt thereof has a structure of formula (IIIc). In fourth sub-embodiment of embodiment 5, the compound or a pharmaceutically acceptable salt thereof has a structure of formula (IIId). In fifth sub-embodiment of embodiment 5, the compound or a pharmaceutically acceptable salt thereof has a structure of formula (IIIe). In sixth sub-embodiment of embodiment 5, the compound or a pharmaceutically acceptable salt thereof has a structure of formula (IIIf). In seventh sub-embodiment of embodiment 5, the compound or a pharmaceutically acceptable salt thereof has a structure of formula (IIIg).

6. In embodiment 6, the compound of any one of embodiments 1A and 1 to 5 and subembodiments contained therein (e.g., compounds of formulae (IIIa), (IIIb), (IIIc), (IIId), (IIIe), (IIIf) and (IIIg)), or a pharmaceutically acceptable salt thereof is wherein $R^2$ is —$NR^9R^{10}$.

7. In embodiment 7, the compound of any one of embodiments 1A and 1 to 5 and subembodiments contained therein, or a pharmaceutically acceptable salt thereof is wherein $R^2$ is —OR'.

8. In embodiment 8, the compound of any one of embodiments 1A and 1 to 5 and subembodiments contained therein or a pharmaceutically acceptable salt thereof is wherein $R^2$ is $R^{11}$.

9. In embodiment 9, the compound of any one of embodiments 1A and 1 to 5 and subembodiments contained therein, or a pharmaceutically acceptable salt thereof is wherein $R^2$ is -(alkylene)-$R^{11}$. In a first subembodiment of embodiment 9, alkylene is methylene or ethylene. In a second embodiment of embodiment 9 alkylene is methylene.

10. In embodiment 10, the compound of any one of embodiments 1A and 1 to 6 and subembodiments contained therein, or a pharmaceutically acceptable salt thereof is wherein $R^9$ is hydrogen, methyl, ethyl, cyclopropyl, or trideuteromethyl. In a first subembodiment of embodiment 10, $R^9$ is hydrogen, methyl, ethyl, or cyclopropyl. In a second subembodiment of embodiment 10, $R^9$ is hydrogen, methyl, or cyclopropyl. In a third subembodiment of embodiment 4, $R^9$ is hydrogen. In a fourth subembodiment of embodiment 10, $R^9$ is methyl. In a fifth subembodiment of embodiment 10, $R^9$ is cyclopropyl. In a sixth subembodiment of embodiment 10, $R^9$ is hydrogen or methyl. In a seventh subembodiment of embodiment 10, $R^9$ is tri-deuteromethyl.

11. In embodiment 11, the compound of any one of embodiments 1A and 1 to 6 and 10 and subembodiments contained therein, or a pharmaceutically acceptable salt thereof is wherein $R^{10}$ is hydrogen, alkyl, deuteroalkyl, haloalkyl, hydroxyalkyl, alkoxyalkyl, aminoalkyl, alkylcarbonyl, alkoxycarbonyl, alkylaminocarbonyl, dialkylaminocarbonyl, alkylaminocarbonylalkyl, or dialkylaminocarbonylalkyl, preferably $R^{10}$ is hydrogen, alkyl, haloalkyl, hydroxyalkyl, alkoxyalkyl, aminoalkyl, alkylcarbonyl, alkoxycarbonyl, alkylaminocarbonyl, dialkylaminocarbonyl, alkylaminocarbonylalkyl, or dialkylaminocarbonylalkyl. In a first subembodiment of embodiment 11, $R^{10}$ is hydrogen. In a second subembodiment of embodiment 11, $R^{10}$ is alkyl, preferably methyl, ethyl, isopropyl, isobutyl, or tert-butyl, preferably methyl. In a third subembodiment of embodiment 11, $R^{10}$ is haloalkyl, preferably 2,2-difluoroethyl or 2,2,2-trifluoroethyl. In a fourth subembodiment of embodiment 11, $R^{10}$ is hydroxyalkyl, preferably 2-hydroxyethyl, 3-hydroxypropyl, or dihydroxypropyl. In a fifth subembodiment of embodiment 5, $R^{10}$ is aminoalkyl, preferably aminoethyl, methylaminoethyl, dimethylaminoethyl, or diethylaminoethyl. In a sixth subembodiment of embodiment 11, $R^{10}$ is alkoxyalkyl, preferably methoxyethyl, ethoxyethyl, methoxypropyl, or ethoxypropyl. In a seventh subembodiment of embodiment 11, $R^{10}$ is alkylcarbonyl, alkylaminocarbonyl, or dialkylaminocarbonyl, preferably acetyl, methylaminocarbonyl, ethylaminocarbonyl, dimethylaminocarbonyl, or diethylaminocarbonyl. In an eight subembodiment of embodiment 11, $R^{10}$ is alkylaminocarbonylalkyl or dialkylaminocarbonylalkyl, preferably methyaminocarbonylmethyl or dimethylaminocarbonylmethyl. In a ninth subembodiment of embodiment 11, $R^{10}$ is trideuteromethyl.

12. In embodiment 12, the compound of any one of embodiments 1A, 1 to 5 and 7 and subembodiments contained therein, or a pharmaceutically acceptable salt thereof is wherein $R^8$ is alkyl, haloalkyl, hydroxyalkyl, alkoxyalkyl, or aminoalkyl. In a first subembodiment of embodiment 12, $R^8$ is alkyl, preferably methyl, ethyl, isopropyl, isobutyl, or tert-butyl. In a second subembodiment of embodiment 12, R is haloalkyl, preferably trifluoromethyl or 2,2,2-trifluoroethyl. In a third subembodiment of embodiment 12, R is hydroxyalkyl, preferably 2-hydroxyethyl, hydroxypropyl, or dihydroxypropyl. In a fourth subembodiment of embodiment 12, $R^8$ is aminoalkyl, preferably aminoethyl, methylaminoethyl, dimethylaminoethyl, or diethylaminoethyl. In a fifth subembodiment of embodiment 12, $R^8$ is alkoxyalkyl, preferably methoxyethyl, ethoxyethyl, methoxypropyl, or ethoxypropyl.

13. In embodiment 13, the compound of any one of embodiments 1A, 1 to 7, and 10, and subembodiments contained therein, or a pharmaceutically acceptable salt thereof is wherein $R^8$ and $R^{10}$ are independently cycloalkyl, cycloalkylalkyl, cycloalkoxyalkyl, bridged cycloalkyl, bridged cycloalkylalkyl, fused cycloalkyl, spirocycloalkyl, or spirocycloalkylalkyl. In a first subembodiment of embodiment 13, $R^8$ and $R^{10}$ are independently cycloalkyl, preferably cyclopropyl, cyclobutyl, cyclopentyl, or cyclohexyl, preferably cyclopropyl, each ring may independently be unsubstituted or substituted with one or two substituents independently selected from alkyl, halo, alkoxy, hydroxy, or cyano. In a second subembodiment of embodiment 13, $R^8$ and $R^{10}$ are independently cycloalkyl, preferably cyclopropyl, cyclobutyl, cyclopentyl, or cyclohexyl, preferably cyclopropyl, each ring may independently be unsubstituted or substituted with one or two substituents independently selected from methyl, fluoro, or cyano. In a third subembodiment of embodiment 13, $R^8$ and $R^{10}$ are independently cycloalkylalkyl, preferably cyclopropylmethyl, cyclopropylethyl, cyclobutylmethyl, cyclobutylmethyl, cyclobutylethyl, cyclopentylmethyl, cyclopentylethyl, cyclohexylmethyl, or cyclohexylethyl, the ring in each group may independently be unsubstituted or substituted with one or two substituents independently selected from alkyl, halo, alkoxy, hydroxy, or cyano. In a fourth subembodiment of embodiment 13, $R^8$ and $R^{10}$ are independently cycloalkyloxyalkyl, preferably cyclopropyloxyethyl, cyclobutyloxyethyl, cyclopentyloxyethyl, or cyclohexyloxyethyl, preferably cyclopropyloxyethyl, the ring in each group may independently be unsubstituted or substituted with one or two substituents independently selected from alkyl, halo, alkoxy, hydroxy, or cyano. In a fifth subembodiment of embodiment 13, $R^8$ and $R^{10}$ are independently bridged cycloalkyl or bridged cycloalkylalkyl. In a sixth subembodiment of embodiment 13, $R^8$ and $R^{10}$ are independently spirocycloalkyl, or spirocycloalkylalkyl. In a seventh subembodiment of embodiment 13, $R^8$ and $R^{10}$ are independently cycloalkyl or cycloalkylalkyl, preferably cyclopropyl or cyclopropylmethyl, each ring may independently be unsubstituted or substituted with one or two substituents independently selected from alkyl, halo, or cyano. In an eighth subembodiment of embodiment 13, $R^8$ and $R^{10}$ are independently cyclopropyl or cyclopropylmethyl, each ring may independently be unsubstituted or substituted with one or two substituents independently selected from methyl, fluoro, or cyano. In a ninth subembodiment of embodiment 13, $R^8$ and $R^{10}$ are independently $R^8$ and $R^{10}$ are independently cyclopropyl, cyclobutyl, 1-methylcyclopropyl, (cis)-3-hydroxy-3-methylcyclobutyl, (cis)-3-hydroxy-2,2-dimethylcyclobutyl, 1-cyanocyclobutyl, cyclopropylmethyl, 1-hydroxycyclopropmethyl, 1-fluorocyclopropmethyl, (trans)-3-hydroxy-1-methylcyclobutyl, (cis)-3-cyanocyclobutyl, 1-methylcyclobutyl, (cis)-3-hydroxycyclobutyl, (trans)-3-hydroxycyclobutyl, (trans)-3-cyanocyclobutyl, (2S,1R)-2-hydroxycyclobutyl, (1S,2S)-2-hydroxycyclobutyl, (1S,2R)-2-hydroxycyclobutyl, (1R,2R)-2-hydroxycyclobutyl, (1R,2R)-2-fluorocyclopropyl, 1-fluorocyclopropylmethyl, (1S,2R)-2-fluorocyclopropyl, (1R,2S)-2-fluorocyclopropyl, (1S,2S)-2-fluorocyclopropyl, 2,2-difluorocyclopropyl, (R)-1-cyclopropylethyl, or 2,2-difluorocyclopropylmethyl. In a tenth subembodiment of embodiment 13, $R^8$ and $R^{10}$ are independently cyclopropyl, cyclobutyl, 1-methylcyclopropyl, (cis)-3-hydroxy-3-methylcyclobutyl, (cis)-3-hydroxy-2,2-dimethylcyclobutyl, 1-cyanocyclobutyl, (trans)-3-hydroxy-1-methylcyclobutyl (cis-3-cyanocyclobutyl, 1-methylcyclobutyl, (cis)-3-hydroxycyclobutyl, (trans)-3-hydroxycyclobutyl, (trans)-3-cyanocyclobutyl, (2S,1R)-2-hydroxycyclobutyl, (1S,2S)-2-hydroxycyclobutyl, (1S,2R)-2-hydroxycyclobutyl, (1R,2R)-2-hydroxycyclobutyl, (1R,2R)-2-fluorocyclopropyl, (1S,2R)-2-fluorocyclopropyl, (1R,2S)-2-fluorocyclopropyl, (1S,2S)-2-fluorocyclopropyl, or 2,2-difluorocyclopropyl. In a eleventh subembodiment of embodiment 13, $R^8$ and $R^{10}$ are independently cyclopropylmethyl, 1-hydroxycyclopropmethyl, 1-fluorocyclopropmethyl, 1-fluorocyclopropylmethyl, (R)-1-cyclopropylethyl, or 2,2-difluorocyclopropylmethyl.

14. In embodiment 14, the compound of any one of embodiments 1A, 1 to 7 and 10, and subembodiments contained therein, or a pharmaceutically acceptable salt thereof is wherein $R^8$ and $R^{10}$ are independently phenyl or phenylalkyl (preferably benzyl or phenethyl) wherein phenyl, by itself or as part of aralkyl, is unsubstituted or substituted with $R^j$, $R^k$, and/or $R^l$.

15. In embodiment 15, the compound of any one of embodiments 1 to 7 and 10 and subembodiments contained therein, or a pharmaceutically acceptable salt thereof is wherein $R^8$ and $R^{10}$ are independently heteroaryl or heteroaralkyl wherein heteroaryl, by itself or as part heteroaralkyl, is unsubstituted or substituted with $R^j$, $R^k$, and/or $R^l$. In a first subemebodiment of embodiment 15, $R^8$ and $R^{10}$ are heteroaryl independently selected from pyrazolyl, oxazolyl, isoxazolyl, imidazolyl, thienyl, pyrrolyl, pyridinyl, pyrimidinyl, pyrazinyl, pyridazinyl, quinolinyl, isoquinolinyl, indolyl, and indazolyl, preferably pyrazolyl, imidazolyl, thienyl, pyrrolyl, pyridinyl, pyrimidinly, pyrazinyl, pyridazinyl, quinolinyl, isoquinolinyl, indolyl, and indazolyl, each ring unsubstituted or substituted with $R^j$, $R^k$, and/or $R^l$. In a second subemebodiment of embodiment 15, $R^8$ and $R^{10}$ are heteroaralkyl independently selected from pyrazolylmethyl, pyrazolylethyl, oxazolylmethyl, isoxazolylmethyl, imidazolylmethyl, imidazolylethyl, thienylmethyl, thienylethyl, pyrrolylmethyl, pyrrolylethyl, pyridinylmethyl, pyridinylethyl, pyrimidinylmethyl, pyrimidinylethyl, pyrazinylmethyl, pyrazinylethyl, pyridazinylmethyl, pyridazinylethyl, quinolinylmethyl, quinolinylethyl, isoquinolinylmethyl, isoquinolinylethyl, indolylmethyl, indolylethyl, indazolylmethyl and indazolylethyl, preferably pyrazolylmethyl, pyrazolylethyl, imidazolylmethyl, imidazolylethyl, thienylmethyl, thienylethyl, pyrrolylmethyl, pyrrolylethyl, pyridinylmethyl, pyridinylethyl, pyrimidinylmethyl, pyrimidinylethyl, pyrazinylmethyl, pyrazinylethyl, pyridazinylmethyl, pyridazinylethyl, quinolinylmethyl, quinolinylethyl, isoquinolinylmethyl, isoquinolinylethyl, indolylmethyl, indolylethyl, indazolylmethyl and indazolylethyl, preferably pyrazolylmethyl or pyridinylmethyl, each ring unsubstituted or substituted with $R^j$, $R^k$, and/or $R^l$. In a third subembodiment of embodiment 15, $R^8$ and $R^{10}$ 1-methyl-1H-pyrazol-5-yl, isoxazol-4-yl, 3-methyl-1,2,4-oxadiazol-5-yl, 5-methylisoxazol-3-yl, 5-methylisoxazol-4-yl, 3-methoxyisoxazol-5-yl, 3,5-dimethylisoxazol-4-yl, 3-methylisoxazol-4-yl, thiazol-4-yl, thiazol-5-yl, isothiazol-4-yl, pyridin-2-yl, pyridin-3-yl, pyridin-4-yl, 2-(difluoromethyl)pyridin-4-yl, 2-(difluoromethoxy)pyridin-4-yl, 5-methoxypyridin-3-yl, 6-methylpyridin-3-yl, 6-methoxypyridin-3-yl, 3-cyanopyridin-4-yl, 3-methoxypyridin-4-yl, 3-fluoropyridin-4-yl, 3-chloropyridin-4-yl, 2-(trifluoromethyl)pyridin-4-yl, 2-methylpyridin-4-yl, pyrimidin-5-yl, 1-methyl-H-imidazol-4-yl, 1-methylpyrazol-3-ylmethyl, 3-methoxyisoxazol-5-ylmethyl, oxazol-2-ylmethyl, oxazol-4-ylmethyl, oxazol-5-ylmethyl, isoxazol-3-ylmethyl, isoxazol-4-ylmethyl, isoxazol-5-ylmethyl, 1-methyl-1H-pyrazol-3-ylmethyl, 1-methyl-1H-pyrazol-4-ylmethyl, 1-methyl-1H-pyrazol-5-ylmethyl, pyridin-4-ylmethyl, pyridin-3-ylmethyl, or pyridin-2-ylmethyl.

16. In embodiment 16, the compound of any one of embodiments 1A, 1 to 7 and 10 and subembodiments contained therein, or a pharmaceutically acceptable salt thereof is wherein $R^8$ and $R^{10}$ are independently heterocylyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl wherein heterocyclyl, by itself or as part of another group, is unsubstituted or substituted with $R^j$, $R^k$, and/or $R^l$. In a first subembodiment of embodiment 16, $R^8$ and $R^{10}$ are independently heterocyclyl, preferably oxetanyl, azetidinyl, tetrahydrofuranyl, pyrrolidinyl, piperidinyl, piperazinyl, or morpholinyl, each ring is unsubstituted or substituted with $R^j$, $R^k$, and/or $R^l$. In a second subembodiment of embodiment 16, $R^8$ and $R^{10}$ are independently heterocyclylalkyl, preferably oxetanylmethyl, oxetanylethyl, azetidinylmethyl, azetidinylethyl, pyrrolidinylmethyl, pyrrolidinylethyl, piperidinylmethyl, piperidinylethyl, morpholinylmethyl, or morpholinylethyl, each ring is unsubstituted or substituted with $R^j$, $R^k$, and/or $R^l$. In a third subembodiment of embodiment 16, $R^8$ and $R^{10}$ are independently heterocyclyloxyalkyl which is unsubstituted or substituted with $R^j$, $R^k$, and/or $R^l$. In a fourth subembodiment of embodiment 16, $R^8$ and $R^{10}$ are independently bridged heterocyclyl, bridged heterocyclylalkyl. In a fifth subembodiment of embodiment 16, $R^8$ and $R^{10}$ are independently spiroheterocyclyl, or spiroheterocyclylalkyl.

17. In embodiment 17, the compound of any one of embodiments 1A, 1 to 5, 8, and 9 and subembodiments contained therein, or a pharmaceutically acceptable salt thereof is wherein $R^{11}$ is heterocyclyl which is unsubstituted or substituted with $R^m$, $R^n$, and/or $R^o$. In a first subembodiment of embodiment 17, $R^{11}$ is oxetanyl, azetidinyl, 2-oxoazetidinyl, pyrrolidinyl, 2-oxopyrrolidinyl, piperidinyl, piperazinyl, or morpholinyl, preferably azetidin-1-yl, 2-oxoazetidin-1-yl, pyrrolidin-1-yl, 2-oxopyrrolidin-1-yl, piperidin-1-yl, piperazin-1-yl, or morpholin-4-yl, each ring is unsubstituted or substituted with $R^a$, $R^b$, and/or $R^c$. In a second subembodiment of embodiment 17, $R^{11}$ is azetidin-1-yl, 4-hydroxyazetidin-1-yl, 4-methylaminocarbonylazetidin-1-yl, 4-dimethylaminocarbonylazetidin-1-yl, 2-hydromethylazetidin-1-yl, 2-methylazetidin-1-yl, 2-oxoazetidin-1-yl, pyrrolidin-1-yl, 2-oxopyrrolidin-1-yl, 3-hydroxypyrrolidin-1-yl, 3,3-dimethylpyrrolidin-1-yl, 3-methoxypyrrolidin-1-yl, 3-hydroxy-3-methylpyrrolidin-1-yl, piperidin-1-yl, 2-carboxypiperidin-1-yl, 2-aminocarbonylpiperidin-1-yl, piperazin-1-yl, 4-methylpiperazin-1-yl, or morpholin-4-yl. In a third subembodiment of embodiment 17, $R^{11}$ is 3-hydroxypyrrolidin-1-yl.

18. In embodiment 18, the compound of any one of embodiments 1A, 1 to 5, 8, and 9, and subembodiments contained therein, or a pharmaceutically acceptable salt thereof is wherein $R^{11}$ is cycloalkyl. In a first subembodiment of embodiment 18, $R^{11}$ is cycloalkyl, preferably cyclopropyl, cyclobutyl, cyclopentyl, or cyclohexyl, preferably cyclopropyl, each ring may independently be unsubstituted or substituted with one or two substituents independently selected from alkyl, halo, alkoxy, hydroxy, or cyano.

19. In embodiment 19, the compound of any one of embodiments 1A, 1 to 5, 8 and 9 and subembodiments contained therein, or a pharmaceutically acceptable salt thereof is wherein $R^{11}$ is heteroaryl which is unsubstituted or substituted with $R^j$, $R^k$, and/or $R^l$. In a first subembodiment of embodiment 19, $R^{11}$ is pyrazolyl, imidazolyl, thiazolyl, isothiazolyl, oxazolyl, isoxazolyl, triazolyl, thienyl, pyrrolyl, pyridinyl, pyrimidinyl, pyrazinyl, pyridazinyl, quinolinyl, isoquinolinyl, indolyl, and indazolyl, each ring unsubstituted or substituted with $R^j$, $R^k$, and/or $R^l$. In a second subembodiment of embodiment 19, $R^{11}$ is pyrazolyl, imidazolyl-2-yl, imidazolyl-4-yl, thiazol-2-yl, thiazol-4-yl, thiazol-5-yl, or isothiazol-4-yl.

20. In embodiment 20, the compound of any one of embodiments 1A, 1 to 5 and subembodiments contained therein, or a pharmaceutically acceptable salt thereof is wherein $R^2$ is hydroxyalkyl, aminoalkyl, aminocarbonylalkyl.

21. In embodiment 21, the compound of any one of embodiments 1A, 1 to 20 and subembodiments contained therein, or a pharmaceutically acceptable salt thereof is wherein $R^4$ and $R^6$ are independently selected from hydrogen, methyl, chloro, fluoro, bromo, methoxy, methylsulfonyl, trifluoromethyl, trifluoromethoxy, cyano, amino, methylamino, dimethylamino, methylaminocarbonyl, or dimethylaminocarbonyl. In a first subembodiment of embodiment 21, $R^4$ is hydrogen, fluoro, methoxy, cyano and $R^6$ is hydrogen. In a second subembodiment of embodiment 21, $R^4$ and $R^6$ are hydrogen. In a second subembodiment of embodiment 21, $R^4$ and $R^6$ are hydrogen. In a third subembodiment of embodiment 21, $R^4$ and $R^6$ are independently selected from hydrogen, methyl, chloro, fluoro, methoxy, methylsulfonyl, trifluoromethyl, trifluoromethoxy, cyano, amino, methylamino, dimethylamino, methylaminocarbonyl, or dimethylaminocarbonyl. In a fifth subembodiment of embodiment 21, $R^4$ is hydrogen, fluoro, bromo, methyl, methoxy, or cyano and $R^6$ is hydrogen.

22. In embodiment 22, the compound of any one of embodiments 1A, 1 to 21 and subembodiments contained therein, or a pharmaceutically acceptable salt thereof is wherein $R^5$ is alkyl, alkoxy, alkylsulfonyl, halo, haloalkyl, haloalkoxy, cycloalkyl, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, heterocyclyloxyalkylamino, preferably $R^5$ is alkyl, alkoxy, halo, haloalkyl, haloalkoxy, cycloalkyl, cyano, aminocarbonyl, heteroaryl, heterocyclyl, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl. In a first subembodiment of embodiment 22, $R^5$ is methyl, ethyl, isopropyl, tert-butyl, methoxy, ethoxy, fluoro, chloro, bromo, trifluoromethyl, difluoromethyl, trifluoromethoxy, difluoromethoxy, cyclopropyl, cyclopentyl, cyano, methylsulfonyl, methylamino, or dimethylamino. In a second subembodiment of embodiment 22, $R^5$ is hydroxymethyloxy, hydroxyethyloxy, hydroxymethylamino, hydroxyethylamino, aminoethyloxy, methylaminoethyloxy, dimethylaminoethyloxy, diethylaminoethyloxy, aminoethylamino, methylaminoethylamino, dimethylaminoethylamino, or diethylaminoethylamino. In a third subembodiment of embodiment 22, $R^5$ is 5- or 6-membered heteroaryl such as pyrazolyl, imidazolyl, thienyl, thiazolyl, oxazolyl, isoxazolyl, pyridinyl, or pyrimidinyl each of which is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl. In a fourth subembodiment of embodiment 22, $R^5$ is 4- or 6-membered heterocyclyl, preferably oxetan-3-yl, pyrrolidin-1-yl, tetrahydrofuranyl, 2-oxoazetidin-1-yl, 2-oxopyrrolidin-1-yl each ring is unsubstituted or substituted with $R^a$ and/or $R^b$. In a fifth subembodiment of embodiment 22, $R^5$ is halo, alkyl, haloalkyl, or cycloalkyl. In a sixth subembodiment of embodiment 22, $R^5$ is chloro, methyl, ethyl, trifluoromethyl, or cyclopropyl. In a seventh subembodiment of embodiment 22, $R^5$ is trifluoromethyl, 1,1-difluoroethyl, or cyclopropyl. In an eighth subembodiment of embodiment 22, $R^5$ is chloro, methyl, ethyl, trifluoromethyl, 1,1-difluoroethyl, or cyclopropyl.

23. In embodiment 23, the compound of any one of embodiments 1A, 1 to 23 and subembodiments contained therein, or a pharmaceutically acceptable salt thereof is wherein $R^3$ is hydrogen, alkyl, alkoxy, alkylsulfonyl, halo, haloalkyl, haloalkoxy, cycloalkyl, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl. In a first subembodiment of embodiment 23, $R^3$ is hydrogen. In a second subembodiment of embodiment 23, $R^3$ is methyl, ethyl, methoxy, ethoxy, fluoro, chloro, bromo, trifluoromethyl, difluoromethyl, trifluoromethoxy, difluoromethoxy, cyclopropyl, cyano, methylsulfonyl, aminocarbonyl, methylamino, or dimethylamino. In a third subembodiment of embodiment 23, $R^3$ is hydroxymethyloxy, hydroxyethyloxy, hydroxymethylamino, hydroxyethylamino, aminoethyloxy, methylaminoethyloxy, dimethylaminoethyloxy, diethylaminoethyloxy, aminoethylamino, methylaminoethylamino, dimethylaminoethylamino, or diethylaminoethylamino. In a fourth subembodiment of embodiment 23, $R^3$ is heteroaryl, preferably 5- or 6-membered heteroaryl such as pyrazolyl, imidazolyl, triazolyl, thienyl, thiazolyl, oxazolyl, isoxazolyl, pyridinyl, or pyrimidinyl each ring either unsubstituted or substituted with $R^a$, $R^b$, and/or $R^c$. In a fifth subembodiment of embodiment 23, $R^3$ is heteroaryloxy, heteroarylamino, heterocyclyl, heterocyclyloxy, heterocyclylamino, heterocyclyloxyalkoxy, heterocyclyloxyalkylamino, wherein heterocyclyl or heteroaryl, by itself or as part of another group, is unsubstituted or substituted with $R^a$, $R^b$, and/or $R^c$. In a sixth subembodiment of embodiment 3, $R^3$ is oxopyrrolidinyl, morpholin-4-yl, or 2-morpholin-4-ylethyloxy. In a fifth subembodiment of embodiment 23, $R^3$ is hydrogen or methoxy. In an eighth subembodiment of embodiment 23, when $R^3$ is a group of second, third, fourth, fifth or sixth subembodiment, then $R^2$ is amino or methylamino, $R^4$ and $R^6$ are hydrogen and $R^5$ is other than hydrogen.

24. In embodiment 24, the compound of any one of embodiments 1A, 1, 3, 5 to 23 and subembodiments contained therein, or a pharmaceutically acceptable salt thereof is wherein $R^1$ is alkyl, preferably methyl, ethyl, or isopropyl.

25. In embodiment 25, the compound of any one of embodiments 1A, 1, 3, 5 to 23 and subembodiments contained therein, or a pharmaceutically acceptable salt thereof is wherein $R^1$ is haloalkyl, preferably trifluoromethyl.

26. In embodiment 26, the compound of any one of embodiments 1A, 1, 3, 5 to 23 and subembodiments contained therein, or a pharmaceutically acceptable salt thereof is wherein $R^1$ is hydroxyalkyl, alkoxyalkyl, aminoalkyl, aminocarbonylalkyl, or aminosulfonylalkyl.

27. In embodiment 27, the compound of any one of embodiments 1A, 1, 2, 4 to 23 and subembodiments contained therein, or a pharmaceutically acceptable salt thereof is wherein $R^1$ is $R^7$ wherein $R^7$ is cycloalkyl, bridged cycloalkyl, fused cycloalkyl, or spirocycloalkyl. In a first subembodiment of embodiment 27, $R^7$ is cycloalkyl, preferably cyclopropyl, cyclobutyl, cyclopentyl, or cyclohexyl which is unsubstituted or substituted with one or two substituents independently selected from alkyl, hydroxy, alkoxy, cyano or halo. In a first subembodiment of embodiment 27, $R^7$ is cycloalkenyl, cyclopentenyl, or cyclohexenyl which is unsubstituted or substituted with one or two substituents independently selected from alkyl, hydroxy, alkoxy, cyano or halo.

28. In embodiment 28, the compound of any one of embodiments 1A, 1, 2, 4 to 23 and subembodiments contained therein, or a pharmaceutically acceptable salt thereof is wherein $R^1$ is $R^7$ wherein $R^7$ is aryl which is unsubstituted or substituted with $R^d$, $R^e$, and/or $R^f$ wherein $R^f$ is selected from alkyl, haloalkyl, haloalkoxy, alkoxy, hydroxy, halo, cyano, optionally substituted aryl, optionally substituted heteroaryl, or optionally substituted heterocyclyl. In a first subembodiment of embodiment 28, $R^7$ is phenyl which is unsubstituted or substituted with $R^d$, $R^e$, and/or $R^f$. In a second subembodiment of embodiment 28, $R^7$ is phenyl which is unsubstituted or substituted with $R^d$, $R^e$, and/or $R^f$ where $R^d$ and $R^e$ are independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is selected from hydroxy, fluoro, chloro, cyano or methyl. In a third subembodiment of embodiment 28, $R^7$ is phenyl which is substituted with $R^d$, $R^e$, and/or $R^f$ where $R^d$ and $R^e$ are independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is selected from hydroxy, fluoro, chloro, cyano or methyl and wherein $R^d$, $R^e$, and/or $R^f$ are attached to carbon atoms on the phenyl ring that are ortho or meta to the carbon atom of the phenyl ring attached to quinazolone nitrogen. In a fourth subembodiment of embodiment 28, $R^7$ is phenyl which is unsubstituted or substituted with $R^e$ and/or $R^f$ where $R^e$ is methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is fluoro, chloro, cyano or methyl and wherein $R^f$ is attached to carbon atoms on the phenyl ring that is ortho to the carbon atom of the phenyl ring attached to quinazolone nitrogen. In a fifth subembodiment of embodiment 28, $R^7$ is phenyl which is unsubstituted or substituted with $R^f$ wherein $R^f$ is fluoro, chloro, bromo, or methyl and wherein $R^f$ is attached to carbon atoms on the phenyl ring that is ortho to the carbon atom of the phenyl ring attached to quinazolone nitrogen.

29. In embodiment 28, the compound of any one of embodiments 1A, 1, 2, and 4 to 23 and subembodiments contained therein, or a pharmaceutically acceptable salt thereof is wherein $R^1$ is $R^7$ wherein $R^7$ is heteroaryl which is unsubstituted or substituted with $R^d$, $R^e$, and/or $R^f$ wherein $R^f$ is selected from alkyl, haloalkyl, haloalkoxy, alkoxy, hydroxy, halo, cyano, optionally substituted aryl, optionally substituted heteroaryl, or optionally substituted heterocyclyl. In a first subembodiment of embodiment 29, $R^7$ is 5 or 6-membered heteroaryl ring such as pyrrolyl, pyrazolyl, thiazolyl, imidazolyl, pyridinyl, pyrimidinyl, pyridazinyl, or pyrazinyl, which is unsubstituted or substituted with $R^d$, $R^e$, and/or $R^f$ In a second subembodiment of embodiment 29, $R^d$ and $R^e$ are independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is selected from hydroxy, fluoro, chloro, cyano or methyl. In a third subembodiment of embodiment 29, $R^d$, $R^e$, and/or $R^f$ where $R^d$ and $R^e$ independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is selected from hydroxy, fluoro, chloro, cyano or methyl and wherein $R^d$, $R^e$, and/or $R^f$ are attached to carbon atoms on the heteroaryl ring that are ortho or meta to the carbon atom of the heteroaryl ring attached to quinazolone nitrogen. In a fourth subembodiment of embodiment 29, $R^7$ is pyridinyl or pyrimidinyl, preferably pyridin-3-yl or pyrimidin-4-yl, which is unsubstituted or substituted with $R^e$ and/or $R^f$ where $R^e$ is methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is fluoro, chloro, cyano or methyl and wherein $R^f$ is attached to carbon atoms on the pyridinyl or pyrimidinyl ring that is ortho to the carbon atom of the phenyl ring attached to quinazolone nitrogen. In a fifth subembodiment of embodiment 29, $R^7$ is pyridinyl, preferably pyridin-2-yl or pyridin-3-yl, which is unsubstituted or substituted with $R^f$ where $R^f$ is fluoro, chloro, or methyl and wherein $R^f$ is attached to carbon atoms on the pyridinyl ring that is ortho to the carbon atom of the phenyl ring attached to quinazolone nitrogen.

30. In embodiment 30, the compound of any one of embodiments 1A, 1, 2, and 4 to 23 and subembodiments contained therein, or a pharmaceutically acceptable salt thereof is wherein $R^1$ is $R^7$ wherein $R^7$ is heterocyclyl, bridged heterocyclyl, fused heterocyclyl, or spiroheterocyclyl, wherein heterocyclyl is unsubstituted or substituted with $R^d$, $R^e$, and/or $R^f$ wherein $R^f$ is selected from alkyl, haloalkyl, haloalkoxy, alkoxy, hydroxy, halo, cyano, optionally substituted aryl, optionally substituted heteroaryl, or optionally substituted heterocyclyl. In a first subembodiment of embodiment 30, $R^7$ is pyrrolidinyl, piperidinyl, piperazinyl, oxetanyl, tetrahydrofuranyl, or morpholinyl, each ring independently unsubstituted or substituted with $R^d$, $R^e$, and/or $R^f$. In a second subembodiment of embodiment 30, $R^7$ is pyrrolidinyl, piperidinyl, piperazinyl, oxetanyl, tetrahydrofuranyl, or morpholinyl, each ring independently unsubstituted or substituted with $R^d$, $R^e$, and/or wherein $R^d$, $R^e$, and/or $R^f$ independently selected from methyl, ethyl, fluoro, chloro, bromo, methoxy, ethoxy, hydroxy, methylsulfonyl, aminomethyl, 2-hydroxyethyl, or 3-hydroxypropyl.

31. In embodiment 31, the compound of any one of embodiments 1A, 1, 2, and 4 to 23 and subembodiments contained therein, or a pharmaceutically acceptable salt thereof is wherein $R^1$ is $R^7$ wherein $R^7$ is aryl which is substituted with $R^d$, $R^e$, and/or $R^f$ wherein $R^f$ is —$X^c$—$R^{12}$ where $X^c$ is alkylene or heteroalkylene and $R^{12}$ is optionally substituted aryl, optionally substituted heteroaryl, or optionally substituted heterocyclyl. In a first subembodiment of embodiment 28, $R^7$ is phenyl substituted with $R^d$, $R^e$, and/or $R^f$. In a second subembodiment of embodiment 28, $R^7$ is phenyl which is unsubstituted or substituted with $R^d$, $R^e$, and/or $R^f$ where $R^d$ and $R^e$ are independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is selected from 2-phenyloxyethyl, 2-phenylaminoethyl, 2-phenylethyloxy, or 2-phenylaminoethyl wherein phenyl is optionally substituted with one or two substituents independently selected from methyl, fluoro, chloro, methoxy, hydroxy, trifluoromethyl, or trifluoromethoxy. In a third subembodiment of embodiment 31, $R^f$ is attached to a carbon atom on the phenyl ring that are ortho or meta to the carbon atom of the phenyl ring attached to quinazolone nitrogen.

32. In embodiment 32, the compound of any one of embodiments 1A, 1, 2, and 4 to 23 and subembodiments contained therein, or a pharmaceutically acceptable salt thereof is wherein $R^1$ is $R^7$ wherein $R^7$ is heteroaryl which is substituted with $R^d$, $R^e$, and/or $R^f$ wherein $R^f$ is —$X^c$—$R^{12}$ where $X^c$ is alkylene or heteroalkylene and $R^{12}$ is optionally substituted aryl, optionally substituted heteroaryl, or optionally substituted heterocyclyl. In a first subembodiment of embodiment 32, $R^7$ is 5 or 6-membered heteroaryl ring such as pyrrolyl, pyrazolyl, thiazolyl, imidazolyl, pyridinyl, pyrimidinyl, pyridazinyl, or pyrazinyl, which is unsubstituted or substituted with $R^d$, $R^e$, and/or $R^f$. In a second subembodiment of embodiment 32, $R^d$ and $R^e$ are independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is selected from 2-phenyloxyethyl, 2-phenylaminoethyl, 2-phenylethyloxy, or 2-phenylaminoethyl wherein phenyl is optionally substituted with one or two substituents independently selected from methyl, fluoro, chloro, methoxy, hydroxy, trifluoromethyl, or trifluoromethoxy. In a third subembodiment of embodiment 32, $R^f$ is attached to an atom of the heteroaryl ring that are ortho or meta to the carbon atom of the heteroaryl ring attached to quinazolone nitrogen.

33. In embodiment 33, the compound of any one of embodiments 1A, 1, 2, 4 to 23 and subembodiments contained therein, or a pharmaceutically acceptable salt thereof is wherein $R^1$ is —$X^a$—$R^7$ wherein $X^a$ is alkylene and $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$.

It is understood that the embodiments set forth above include all combination of embodiments and subembodiments listed therein. For example, the $R^1$ group listed in embodiment 30 and/or first and/or second subembodiments therein, can independently combine with one or more of the embodiments 1-28 and 31 to 33 and/or subembodiments contained therein.

The present disclosure includes additional embodiment 35 to 90 below.

35. A compound of Formula (IA):

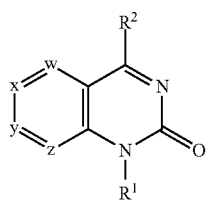

(IA)

where:

w is $CR^3$ or N; x is $CR^4$ or N; y is CR or N; and z is $CR^6$ or N, wherein:

$R^3$ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;

$R^5$ is hydrogen, alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^1$ is $R^7$ wherein $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is alkyl, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl, deuteroalkyl, or cycloalkyl; and $R^{10}$ is hydrogen, alkyl, deuteroalkyl, haloalkyl, hydroxyalkyl, alkoxyalkyl, aminoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, cycloalkylsulfonylamino, cyano, cyanoalkyl, alkoxycarbonylalkyl, carboxyalkyl, aminocarbonylalkyl, or —$X^c$—$R^{12}$ where $X^c$ is bond, alkylene, or heteroalkylene and $R^{12}$ is optionally substituted aryl, optionally substituted heteroaryl, and optionally substituted heterocyclyl; or a pharmaceutically acceptable salt thereof; provided that:

(1) when

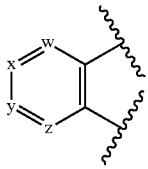

is

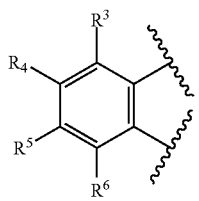

where: (a) when $R^2$ is piperazin-1-yl, 2-methylpiperazin-1-yl, or 1H-benzo[d][1,2,3]triazol-1-yl, $R^3$ and $R^6$ are hydrogen, $R^4$ is chloro and $R^5$ is bromo or 5-methylindazol-4-yl, then $R^1$ is not 2-isopropylphenyl; (b) when $R^2$ and $R^6$ are methyl and $R^3$, $R^4$, and $R^5$ are hydrogen; or $R^2$ and $R^3$ are methyl and $R^4$, $R^5$, and $R^6$ are hydrogen, then $R^1$ is not 2,5-, 2,6- or 2,8-dimethylquinolin-4-yl or 2-methyl-5-methoxy-, 2-methyl-6-methoxy- or 2-methyl-8-methoxyquinolin-4-yl; (c) when $R^2$ is amino or acetylamino, $R^4$ is dimethylamino, and $R^3$, $R^5$, and $R^6$ are hydrogen, then $R^1$ is not 4-hydroxy-5-hydroxymethyl-tetrahydrofuran-2-yl; (d) when $R^5$ is fluoro, $R^3$, $R^4$ and $R^6$ are hydrogen, and $R^2$ is 4-aminocarbonylmethyl-2-methylphenylamino, then $R^1$ is not 4-fluoro-2-(2-thiazol-2-ylmethoxy)phenyl, 4-fluoro-2-(2-pyridin-2-ylmethoxy)phenyl, or 4-chloro-2-methoxyphenyl; (e) when $R^6$ is fluoro, $R^3$, $R^4$ and $R^5$ are hydrogen, and $R^2$ is 4-aminocarbonylmethyl-2-methylphenylamino, then $R^1$ is not 4-fluoro-2-methoxyphenyl; (f) when $R^1$ is 4-chloro-2-ethoxyphenyl, $R^5$ is fluoro, and $R^3$, $R^4$ and $R^6$ are hydrogen, then $R^2$ is not 3-(2-oxoimidazolidin-1-yl)-2-methylphenylamino;

(2) when

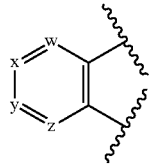

is

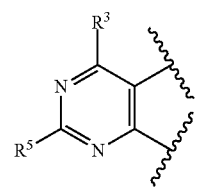

then when $R^1$ is 4-hydroxy-5-hydroxymethylfuran-1-yl, $R^5$ is amino, and $R^3$ is methoxy; then $R^2$ is not amino; and (3) when

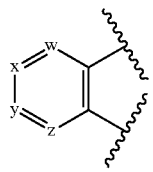

is

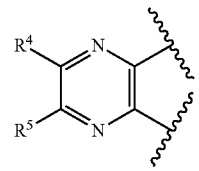

then when $R^1$ is 4-hydroxy-5-hydroxymethylfuran-1-yl, one of $R^4$ and $R^5$ is hydrogen, and the other of $R^4$ and $R^5$ is methyl or both of $R^4$ and $R^5$ are methyl, then $R^2$ is not amino.

36. The compound of embodiment 35 wherein the compound has a structure of Formula (I):

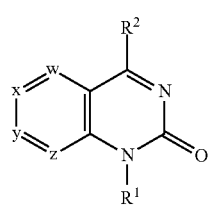

where:
where:
w is $CR^3$ or N; x is $CR^4$ or N; y is CR or N; and z is $CR^6$ or N; wherein: $R^3$ and $R^5$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^1$ is $R^7$ wherein $R^7$ is cycloalkyl, bridged cycloalkyl, fused cycloalkyl, spirocycloalkyl, phenyl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is alkyl, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl or cycloalkyl; and $R^{10}$ is hydrogen, alkyl, haloalkyl, hydroxyalkyl, alkoxyalkyl, aminoalkyl, alkylcarbonyl, alkoxycarbonyl, alkylaminocarbonyl, dialkylaminocarbonyl, aminocarbonylalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, haloalkyl, haloalkoxy, alkoxy, hydroxy, halo, cyano, or —$X^c$—$R^{12}$ where $X^c$ is bond, alkylene or heteroalkylene and $R^{12}$ is optionally substituted aryl, optionally substituted heteroaryl, or optionally substituted heterocyclyl; or a pharmaceutically acceptable salt thereof.

37. The compound of embodiment 35 or 36, or a pharmaceutically acceptable salt thereof having a structure of formula (IIIa), (IIIb), (IIIc), (IIId), (IIIe), or (IIIg) below:

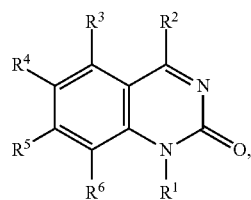

(IIIa)

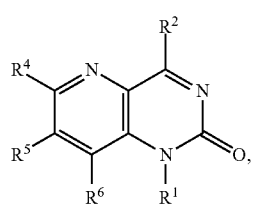

(IIIb)

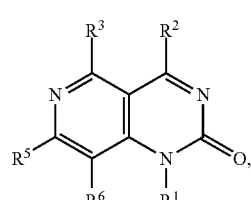

(IIIc)

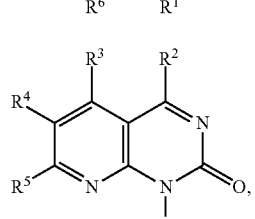

(IIId)

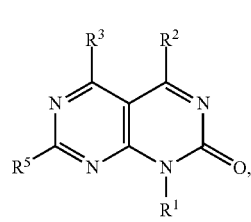

(IIIe)

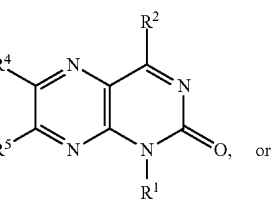

(IIIf)

or

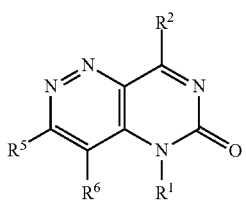

(IIIg)

38. The compound of embodiment 35 or 36, or a pharmaceutically acceptable salt thereof having structure of formula (IIIa).

39. The compound of embodiment 35 or 36, or a pharmaceutically acceptable salt thereof having structure of formula (IIIb).

40. The compound of embodiment 35 or 36, or a pharmaceutically acceptable salt thereof having structure of formula (IIIc).

41. The compound of embodiment 35 or 36, or a pharmaceutically acceptable salt thereof having structure of formula (IIId).

42. The compound of embodiment 35 or 36, or a pharmaceutically acceptable salt thereof having structure of formula (IIIe).

43. The compound of embodiment 35 or 36, or a pharmaceutically acceptable salt thereof having structure of formula (IIIf).

44. The compound of embodiment 35 or 36, or a pharmaceutically acceptable salt thereof having structure of formula (IIIg).

45. The compound of any one of embodiments 35 to 44 wherein $R^2$ is —$NR^9R^{10}$.

46. The compound of any one of embodiments 35 to 44 wherein $R^2$ is —$OR^8$.

47. The compound of any one of embodiments 35 to 44 wherein $R^2$ is $R^{11}$.

48. The compound of any one of embodiments 35 to 45 wherein $R^9$ is deuteroalkyl, preferably trideuteromethyl.

49. The compound of any one of embodiments 35 to 45 wherein $R^9$ is hydrogen.

50. The compound of any one of embodiments 35 to 45 wherein $R^9$ is alkyl, preferably methyl or ethyl.

51. The compound of any one of embodiments 35 to 45 wherein $R^9$ is cycloalkyl, preferably cyclopropyl.

52. The compound of any one of embodiments 35 to 45 and 49 to 51 wherein $R^1$ is hydrogen, alkyl, haloalkyl, hydroxyalkyl, alkoxyalkyl, aminoalkyl, alkylcarbonyl, alkoxycarbonyl, alkylaminocarbonyl, dialkylaminocarbonyl, alkylaminocarbonylalkyl, or dialkylaminocarbonylalkyl.

53. The compound of embodiment 52 or a pharmaceutically acceptable salt thereof wherein $R^{10}$ is hydrogen.

54. The compound of embodiment 46 or 52 or a pharmaceutically acceptable salt thereof wherein $R^8$ and $R^{10}$ are alkyl, preferably methyl.

55. The compound of embodiment 52 or a pharmaceutically acceptable salt thereof wherein $R^{10}$ is alkylaminocarbonylalkyl, or dialkylaminocarbonylalkyl, preferably methyaminocarbonyl-methyl or dimethylaminocarbonylmethyl.

56. The compound of any one of embodiments 35 to 46 and 49 to 51 or a pharmaceutically acceptable salt thereof wherein $R^8$ and $R^{10}$ are independently phenyl or phenylalkyl, preferably benzyl or phenethyl, wherein phenyl, by itself or as part of benzyl and phenethyl, is unsubstituted or substituted with $R^j$, $R^k$, and/or $R^l$.

57. The compound of any one of embodiments 35 to 46 and 49 to 51 or a pharmaceutically acceptable salt thereof wherein $R^8$ and $R^{10}$ are independently cycloalkyl or cycloalkylalkyl, each ring may independently be unsubstituted or substituted with one or two substituents independently selected from alkyl, halo, or cyano.

58. The compound of any one of embodiments 35 to 46 and 49 to 51 or a pharmaceutically acceptable salt thereof wherein $R^8$ and $R^{10}$ are independently heteroaryl or heteroaralkyl wherein heteroaryl, by itself or as part heteroaralkyl, is unsubstituted or substituted with $R^j$, $R^k$, and/or $R^l$.

59. The compound of embodiment 58 or a pharmaceutically acceptable salt thereof wherein $R^8$ and $R^{10}$ are heteroaryl independently selected from pyrazolyl, imidazolyl, thienyl, pyrrolyl, pyridinyl, pyrimidinly, pyrazinyl, pyridazinyl, quinolinyl, isoquinolinyl, indolyl, and indazolyl, each ring unsubstituted or substituted with $R^j$, $R^k$, and/or $R^l$.

60. The compound of embodiment 58 or a pharmaceutically acceptable salt thereof wherein $R^8$ and $R^{10}$ are heteroaralkyl independently selected from pyrazolylmethyl, pyrazolylethyl, imidazolylmethyl, imidazolylethyl, thienylmethyl, thienylethyl, pyrrolylmethyl, pyrrolylethyl, pyridinylmethyl, pyridinylethyl, pyrimidinylmethyl, pyrimidinylethyl, pyrazinylmethyl, pyrazinylethyl, pyridazinylmethyl, pyridazinylethyl, quinolinylmethyl, quinolinylethyl, isoquinolinylmethyl, isoquinolinylethyl, indolylmethyl, indolylethyl, indazolylmethyl and indazolylethyl, each ring unsubstituted or substituted with $R^j$, $R^k$, and/or $R^l$.

61. The compound of any one of embodiments 35 to 46 and 49 to 51 or a pharmaceutically acceptable salt thereof wherein $R^8$ and $R^{10}$ are independently heterocyclyl, preferably oxetanyl, azetidinyl, tetrahydrofuranyl, pyrrolidinyl, piperidinyl, piperazinyl, or morpholinyl, each ring is unsubstituted or substituted with $R^j$, $R^k$, and/or $R^l$.

62. The compound of any one of embodiments 35 to 46 and 49 to 51 or a pharmaceutically acceptable salt thereof wherein $R^8$ and $R^{10}$ are independently heterocyclylalkyl, preferably oxetanylmethyl, oxetanylethyl, azetidinylmethyl, azetidinylethyl, pyrrolidinylmethyl, pyrrolidinylethyl, piperidinylmethyl, piperidinylethyl, morpholinylmethyl, or morpholinylethyl, each ring is unsubstituted or substituted with $R^j$, $R^k$, and/or $R^l$.

63. The compound of any one of embodiments 35 to 44 and 47 or a pharmaceutically acceptable salt thereof wherein $R^2$ is $R^{11}$ wherein $R^{11}$ is heterocyclyl which is unsubstituted or substituted with $R^m$, $R^n$, and/or $R^o$.

64. The compound of embodiment 63 or a pharmaceutically acceptable salt thereof wherein $R^{11}$ is oxetanyl, azetidinyl, 2-oxoazetidinyl, pyrrolidinyl, 2-oxopyrrolidinyl, piperidinyl, piperazinyl, or morpholinyl, preferably azetidin-1-yl, 2-oxoazetidin-1-yl, pyrrolidin-1-yl, 2-oxopyrrolidin-1-yl, piperidin-1-yl, piperazin-1-yl, or morpholin-4-yl, each ring is unsubstituted or substituted with $R^m$, $R^n$, and/or $R^o$, preferably $R^{11}$ is azetidin-1-yl, 4-hydroxyazetidin-1-yl, 4-methylaminocarbonylazetidin-1-yl, 4-dimethylaminocarbonylazetidin-1-yl, 2-hydromethyl-azetidin-1-yl, 2-methylazetidin-1-yl, 2-oxoazetidin-1-yl, pyrrolidin-1-yl, 2-oxopyrrolidin-1-yl, 3-hydroxypyrrolidin-1-yl, 3,3-dimethylpyrrolidin-1-yl, 3-methoxypyrrolidin-1-yl, 3-hydroxy-3-methylpyrrolidin-1-yl, piperidin-1-yl, 2-carboxypiperidin-1-yl, 2-aminocarbonylpiperidin-1-yl, piperazin-1-yl, 4-methylpiperazin-1-yl, or morpholin-4-yl.

65. The compound of any one of embodiments 35 to 44 and 47, or a pharmaceutically acceptable salt thereof wherein $R^2$ is $R^{11}$ wherein $R^{11}$ is heteroaryl which is unsubstituted or substituted with $R^m$, $R^n$, and/or $R^o$, preferably $R^{11}$ is pyrazolyl, imidazolyl, thiazolyl, isothiazolyl, oxazolyl, isoxazolyl, triazolyl, thienyl, pyrrolyl, pyridinyl, pyrimidinyl, pyrazinyl, pyridazinyl, quinolinyl, isoquinolinyl, indolyl, and indazolyl, each ring unsubstituted or substituted with $R^m$, $R^n$, and/or $R^o$.

66. The compound of any one of embodiments 35 to 44, or a pharmaceutically acceptable salt thereof wherein $R^2$ is hydroxyalkyl, aminoalkyl, or aminocarbonylalkyl.

67. The compound of any one of embodiments 35 to 66, or a pharmaceutically acceptable salt thereof wherein $R^5$ is alkyl, alkoxy, halo, haloalkyl, haloalkoxy, cycloalkyl, cyano, aminocarbonyl, heteroaryl, heterocyclyl, wherein heterocyclyl or heteroaryl is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl.

68. The compound of embodiment 67, or a pharmaceutically acceptable salt thereof wherein $R^5$ is methyl, ethyl, isopropyl, tert-butyl, methoxy, ethoxy, fluoro, chloro, bromo, trifluoromethyl, difluoromethyl, trifluoromethoxy, difluoromethoxy, cyclopropyl, cyclopentyl, cyano, pyrazolyl, imidazolyl, thienyl, thiazolyl, oxazolyl, isoxazolyl, pyridinyl, pyrimidinyl, oxetan-3-yl, pyrrolidin-1-yl, tetrahydrofuranyl, 2-oxoazetidin-1-yl, or 2-oxopyrrolidin-1-yl, wherein heterocyclyl or heteroaryl rings are unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl.

69. The compound of embodiment 67, or a pharmaceutically acceptable salt thereof wherein $R^5$ is chloro, methyl, ethyl, trifluoromethyl, 1,1-difluoroethyl, or cyclopropyl.

70. The compound of embodiment 68 wherein $R^5$ is chloro, trifluoromethyl, or ethyl.

71. The compound of any one of embodiments 35 to 70, or a pharmaceutically acceptable salt thereof wherein $R^4$ and $R^6$ are independently selected from hydrogen, methyl, chloro, fluoro, methoxy, methylsulfonyl, trifluoromethyl, trifluoromethoxy, cyano, amino, methylamino, dimethylamino, methylaminocarbonyl, or dimethylaminocarbonyl.

72. The compound of any one of embodiments 35 to 70, or a pharmaceutically acceptable salt thereof wherein $R^4$ is hydrogen, fluoro, methoxy, cyano and $R^6$ is hydrogen.

73. The compound of any one of embodiments 35 to 70, or a pharmaceutically acceptable salt thereof wherein $R^4$ is hydrogen or bromo and $R^6$ is hydrogen.

74. The compound of any one of embodiments 35 to 70, or a pharmaceutically acceptable salt thereof wherein $R^4$ and $R^6$ are hydrogen.

75. The compound of any one of embodiments 35 to 74, or a pharmaceutically acceptable salt thereof wherein $R^3$ is hydrogen, alkyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl.

76. The compound of embodiment 75 or a pharmaceutically acceptable salt thereof wherein
$R^3$ is hydrogen.

77. The compound of embodiment 75 or a pharmaceutically acceptable salt thereof wherein $R^3$ is methyl, ethyl, methoxy, ethoxy, fluoro, chloro, bromo, trifluoromethyl, difluoromethyl, trifluoromethoxy, difluoromethoxy, cyclopropyl, cyano, methylsulfonyl, aminocarbonyl, methylamino, or dimethylamino.

78. The compound of any one of embodiments 35 to 74, or a pharmaceutically acceptable salt thereof wherein $R^3$ is heteroaryl, preferably 5- or 6-membered heteroaryl such as pyrazolyl, imidazolyl, triazolyl, thienyl, thiazolyl, oxazolyl, isoxazolyl, pyridinyl, or pyrimidinyl, each ring either unsubstituted or substituted with $R^a$, $R^b$, and/or $R^c$.

79. The compound of any one of embodiments 35 to 74, or a pharmaceutically acceptable salt thereof wherein $R^3$ is heterocyclyl, preferably, oxopyrrolidinyl, morpholin-4-yl, or 2-morpholin-4-ylethyloxy.

80. The compound of any one of embodiments 35 to 79, or a pharmaceutically acceptable salt thereof wherein $R^1$ is $R^7$ wherein $R^7$ is cycloalkyl, preferably cyclopropyl, cyclobutyl, cyclopentyl, or cyclohexyl, each ring is either unsubstituted or substituted with one or two substituents independently selected from alkyl, hydroxy, alkoxy, cyano or halo.

81. The compound of any one of embodiments 35 to 79, or a pharmaceutically acceptable salt thereof wherein $R^1$ is $R^7$ wherein $R^7$ is phenyl which is unsubstituted or substituted with $R^d$, $R^e$, and/or $R^f$ where $R^d$ and $R^e$ are independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is selected from hydroxy, fluoro, chloro, cyano. and methyl.

82. The compound of any one of embodiments 35 to 79, or a pharmaceutically acceptable salt thereof wherein $R^1$ is $R^7$ wherein $R^7$ is phenyl which is unsubstituted or substituted with $R^f$ wherein $R^f$ is fluoro, chloro, bromo, or methyl and wherein $R^f$ is attached to carbon atoms on the phenyl ring that is ortho to the carbon atom of the phenyl ring attached to quinazolone nitrogen.

83. The compound of any one of embodiments 35 to 79, or a pharmaceutically acceptable salt thereof wherein $R^1$ is $R^7$ wherein $R^7$ is 5 or 6-membered heteroaryl ring such as pyrrolyl, pyrazolyl, thiazolyl, imidazolyl, pyridinyl, pyrimidinyl, pyridazinyl, or pyrazinyl, which is unsubstituted or substituted with $R^d$ and/or $R^e$ independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and/or $R^f$ selected from hydroxy, fluoro, chloro, cyano, and methyl.

84. The compound of any one of embodiments 35 to 79, or a pharmaceutically acceptable salt thereof wherein $R^1$ is $R^7$ wherein $R^7$ is phenyl which is substituted with $R^d$, $R^e$, and/or $R^f$ where $R^d$ and $R^e$ are independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is selected —$X^cR^{12}$ where $X^c$ is alkylene or heteroalkylene, preferably heteroalkylene.

85. The compound of any one of embodiments 35 to 79, or a pharmaceutically acceptable salt thereof wherein $R^1$ is $R^7$ wherein $R^7$ is 5 or 6-membered heteroaryl ring such as pyrrolyl, pyrazolyl, thiazolyl, imidazolyl, pyridinyl, pyrimidinyl, pyridazinyl, or pyrazinyl, which is substituted with $R^d$, $R^e$, and/or $R^f$ where $R^d$ and $R^e$ are independently selected from methyl, ethyl, fluoro, chloro, bromo, methoxy, ethoxy, cyclopropyl, cyano, methylsulfonyl, methoxymethyl, aminomethyl, 2-hydroxyethyl, or 3-hydroxypropyl and $R^f$ is selected —$X^cR^{12}$ where $X^c$ is alkylene or heteroalkylene, preferably heteroalkylene.

86 A pharmaceutical composition comprising a compound of any one of embodiments 35 to 85, or a pharmaceutically acceptable salt thereof at least one pharmaceutically acceptable excipient.

87. A method for treating a disease mediated by MAT2A in a patient comprising administering to the patient a therapeutically effective amount of:

(a) a compound of Formula (IIA):

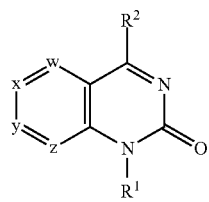

(IIA)

where:

w is $CR^3$ or N; x is $CR^4$ or N; y is CR or N; and z is $CR^6$ or N, wherein:

$R^3$ is hydrogen, alkyl, alkenyl, alkynyl, alkoxy, alkylsulfonyl, halo, haloalkyl, haloalkoxy, cycloalkyl, cycloalkylalkyloxy, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroaralkyloxy, heteroarylamino, heterocyclyl, heterocyclyloxy, heterocyclylamino, heterocyclylalkyloxy, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, alkoxycarbonyl, hydroxyalkyl, alkoxyalkyl, or aminoalkyl;

$R^5$ is hydrogen, alkyl, alkenyl, alkynyl, alkoxy, alkylsulfonyl, halo, haloalkyl, haloalkoxy, cycloalkyl, cyano, amino, alkylamino, dialkylamino, alkoxycarbonyl, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl;

provided that: (i) no more than two of w, x, y, and z can be N and (ii) at least one of $R^3$, $R^4$, $R^5$, and $R^6$ is other than hydrogen;

$R^1$ is $R^7$ wherein $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is alkyl, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl, deuteroalkyl, or cycloalkyl; and $R^{10}$ is hydrogen, alkyl, deuteroalkyl, haloalkyl, hydroxyalkyl, alkoxyalkyl, aminoalkyl, alkylsulfonyl, alkylsulfonylalkyl, cyanoalkyl, alkylcarbonyl, alkoxycarbonyl, alkylaminocarbonyl, dialkylaminocarbonyl, aminocarbonylalkyl, cycloalkyl, cycloalkylalkyl, substituted cycloalkyl, substituted cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, hydroxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, cycloalkyl, haloalkyl, haloalkoxy, alkoxy, hydroxy, halo, amino, cycloalkylsulfonylamino, cyano, cyanoalkyl, alkoxycarbonylalkyl, carboxyalkyl, aminocarbonylalkyl, or —$X^c$—$R^{12}$ where $X^c$ is bond, alkylene, or heteroalkylene and $R^{12}$ is optionally substituted aryl, optionally substituted heteroaryl, and optionally substituted heterocyclyl;

(b) a compound of Formula (II):

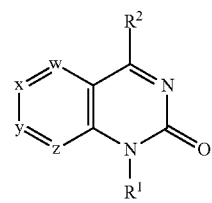

(II)

where:

w is $CR^3$ or N; x is $CR^4$ or N; y is CR or N; and z is $CR^6$ or N; wherein:

$R^3$ and $R^5$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, dialkylaminocarbonyl, hydroxyalkyl, hydroxyalkoxy, hydroxyalkylamino, alkoxyalkyl, alkoxyalkoxy, alkoxyalkylamino, aminoalkyl, aminoalkoxy, aminoalkylamino, heteroaryl, heteroaryloxy, heteroarylamino, heterocyclyl, heterocyclyloxy, heterocyclylamino, heterocyclyloxyalkoxy, or heterocyclyloxyalkylamino, wherein heterocyclyl or heteroaryl, by itself or as part of another group, is unsubstituted or substituted with $R^a$, $R^b$, and/or $R^c$ independently selected from alkyl, cycloalkyl, haloalkyl, haloalkoxy, alkoxy, hydroxy, halo, cyano, hydroxyalkyl, alkoxyalkyl, or aminoalkyl;

$R^4$ and $R^6$ are independently hydrogen, alkyl, alkenyl, alkynyl, alkoxy, alkylsulfonyl, halo, haloalkyl, haloalkoxy, cycloalkyl, cyano, amino, alkylamino, dialkylamino, aminocarbonyl, alkylaminocarbonyl, or dialkylaminocarbonyl; provided that: (i) no more than two of w, x, y, and z can be N and (ii) at least one of $R^3$, $R^4$, $R^5$, and $R^6$ is other than hydrogen;

$R^1$ is alkyl, alkenyl, haloalkyl, hydroxyalkyl, alkoxyalkyl, aminoalkyl, aminocarbonylalkyl, aminosulfonylalkyl, or —$X^a$—$R^7$ wherein $X^a$ is a bond or alkylene and $R^7$ is cycloalkyl, bridged cycloalkyl, fused cycloalkyl, spirocycloalkyl, aryl, heteroaryl, heterocyclyl, bridged heterocyclyl, fused heterocyclyl, or spiroheterocyclyl, wherein aryl, heteroaryl, or heterocyclyl is unsubstituted or substituted with $R^d$, $R^e$, and/or $R^f$;

$R^2$ is hydrogen, alkyl, halo, haloalkyl, hydroxyalkyl, alkoxyalkyl, aminoalkyl, aminocarbonylalkyl, aminosulfonylalkyl, —O—$R^8$, —$NR^9R^{10}$, or —$X^b$—$R^{11}$ wherein:

$R^8$ is alkyl, haloalkyl, hydroxyalkyl, alkoxyalkyl, aminoalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heterocyclyl, heterocyclylalkyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^g$, $R^h$, and/or $R^i$;

$R^9$ is hydrogen, alkyl or cycloalkyl; and $R^{10}$ is hydrogen, alkyl, haloalkyl, hydroxyalkyl, alkoxyalkyl, aminoalkyl, alkylcarbonyl, alkoxycarbonyl, alkylaminocarbonyl, dialkylaminocarbonyl, aminocarbonylalkyl, cycloalkyl, cycloalkylalkyl, cycloalkoxyalkyl, bridged cycloalkyl, bridged cycloalkylalkyl, fused cycloalkyl, spirocycloalkyl, spirocycloalkylalkyl, aryl, aralkyl, heteroaryl, heteroaralkyl, heteroarylcarbonyl, heterocyclyl, heterocyclylalkyl, heterocyclylcarbonyl, heterocyclyloxyalkyl, fused heterocyclyl, fused heterocyclylalkyl, bridged heterocyclyl, bridged heterocyclylalkyl, spiroheterocyclyl, or spiroheterocyclylalkyl, wherein aryl, heteroaryl, or heterocyclyl, by itself or as part of another group, is unsubstituted or substituted with $R^j$, $R^k$, and/or $R^l$;

$X^b$ is a bond or alkylene; and $R^{11}$ is cycloalkyl, bridged cycloalkyl, fused cycloalkyl, spirocycloalkyl, heteroaryl, heterocyclyl, bridged heterocyclyl, fused heterocyclyl, or spiroheterocyclyl, wherein heteroaryl or heterocyclyl is unsubstituted or substituted with $R^m$, $R^n$, and/or $R^o$; and $R^d$, $R^e$, $R^g$, $R^h$, $R^j$, $R^k$, $R^m$, and $R^n$ are independently selected from alkyl, haloalkyl, haloalkoxy, alkoxy, alkylsulfonyl, halo, cyano, carboxy, alkoxycarbonyl, hydroxyalkyl, alkoxyalkyl, aminoalkyl, aminosulfonyl, alkylaminosulfonyl, dialkylaminosulfonyl, sulfonylamino, aminocarbonyl, alkylaminocarbonyl, dialkylaminocarbonyl, heterocyclylcarbonyl, and ureido; and $R^f$, $R^i$, $R^l$, and $R^o$ are independently selected from alkyl, haloalkyl, haloalkoxy, alkoxy, hydroxy, halo, cyano, or —$X^c$—$R^{12}$ where $X^c$ is bond, alkylene or heteroalkylene and $R^{12}$ is optionally substituted aryl, optionally substituted heteroaryl, or optionally substituted heterocyclyl; or a pharmaceutically acceptable salt thereof; or (c). a compound of any one of embodiments 35 to 85, or a pharmaceutically acceptable salt thereof.

88. The method of embodiment 87, wherein the disease is cancer.

89. A method of treating a MTAP null cancer in a patient comprising administering to the patient a therapeutically effective amount of a compound of Formula (IIA) or (II) as defined in embodiment 87, a pharmaceutically acceptable salt thereof; or a compound of any one of embodiments 35 to 85 or a pharmaceutically acceptable salt thereof optionally in a pharmaceutical composition.

90. A method for treating a cancer in a patient, wherein the cancer is characterized by a reduction or absence of MTAP gene expression, the absence of the MTAP gene, or reduced function of MTAP protein, comprising administering to the subject a therapeutically effective amount of a compound of Formula (IIA) or (II) as defined in embodiment 87, a pharmaceutically acceptable salt thereof; or a compound of any one of embodiments 35 to 85 or a pharmaceutically acceptable salt thereof optionally in a pharmaceutical composition. General Synthetic General Synthesis Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of Formula (I) and (II) and the subembodiments described herein where w, x, y, and z are not nitrogen, $R^2$ is other than hydrogen, and other groups are as defined in the Summary can be prepared the method illustrated and described in Scheme 1 below.

Scheme 1

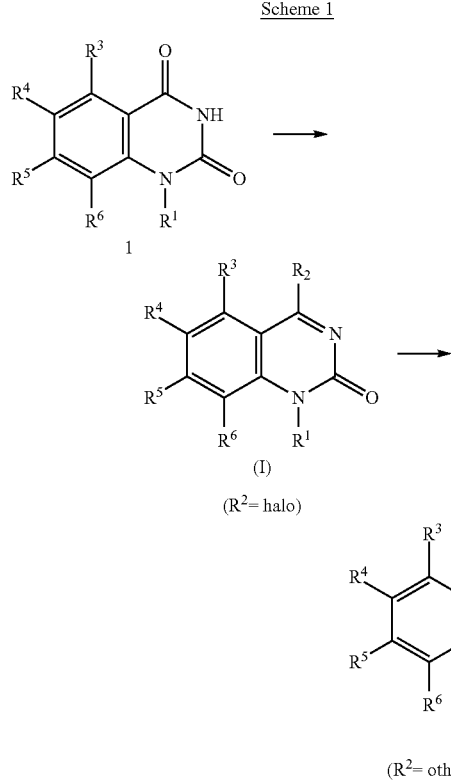

(I)
(R² = halo)

(I)
(R² = other than halo)

2,4-Dioxoquinazoline compound for formula 1, where $R^1$, $R^3$, $R^4$, $R^5$ and $R^6$ are as described in Summary or a precursor group thereof, can be readily converted to a compound of Formula (I) where $R^2$ is halo by methods well known in the art. For example, treatment of compound 1 with $POCl_3$ in the presence of an organic base such as triethylamine in an inert organic solvent provides a compound of Formula (I) where $R^2$ is chloro, which can then be converted to compounds of Formula (I) where $R^2$ is other than halo by methods well known in the art. For example, compounds of Formula (I) where $R^2$ is —$NR^9R^{10}$, heterocycle containing at least a nitrogen atom, or heteroaryl with a basic nitrogen can be prepared by treating corresponding compound of Formula (I) where $R^2$ is chloro with an amine of formula —$NR^9R^{10}$, heterocycle containing at least a nitrogen atom, and heteroaryl with a basic nitrogen, in the presence of a based in the presence of a base such as triethylamine, pyridine, diisopropylamine in an organic solvent such as DMF, and the like. Amine of formula —$NR^9R^{10}$ or heterocycle containing at least a nitrogen atom are commercially available. For example, methylamine, dimethylamine, ethylamine, dimethylamine, cyclopropylamine, 2-aminooxetane, tetrahydrofuran-2-amine, benzylamine, azetidine, pyrrolidine, piperidine, piperazine, morpholine, pyrazole, 2-pyridineamine, 3-pyridineamine, 3-pyridineamine, and cyclopropylmethylamine are commercially available.

Alternatively, compounds containing —NR9R10 can be from compounds of Formula (I) where $R^2$ is —$NH_2$ under alkylation or arylation conditions by methods well known in the art.

Compound of Formula (I) where $R^2$ is $R^{11}$ where $R^{11}$ is heteroaryl can be prepared from compounds of Formula (I) where $R^2$ is halo, under Suzuki reaction conditions.

Compounds of formula 1 can be prepared by methods known in the art. Some such methods are illustrated and described below.

Synthesis from 2-Halobenzamides:

Method (a)

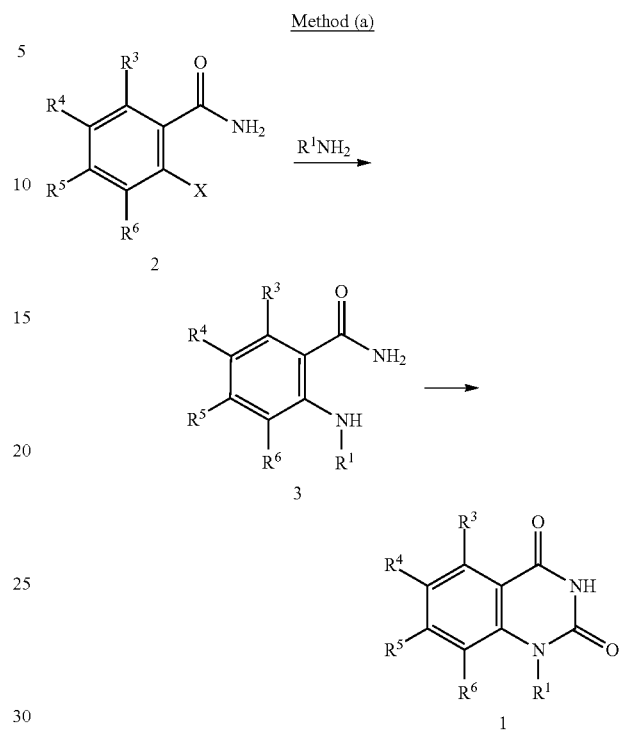

Treatment of a compound of formula 2 where X is halo such as chloro and other groups are as defined in Summary or a precursor group thereof, with an amine of formula $R^1NH_2$ where $R^1$ is as defined in Summary or a precursor group thereof in the presence of an inorganic based such as potassium carbonate, cesium carbonate and the like, and copper provides a compound of formula 3. Compounds of formula 2 are either commercially available or can be made by methods well known in the art. Compounds of formula 2 are converted to compounds of formula 1 by treatment with a base such as sodium hydride in the presence of N,N-carbonyldiimidazole under conditions well known in the art.

Alternatively, compounds of formula 1 from compound 2 can be prepared as shown in Method b below.

Method (b)

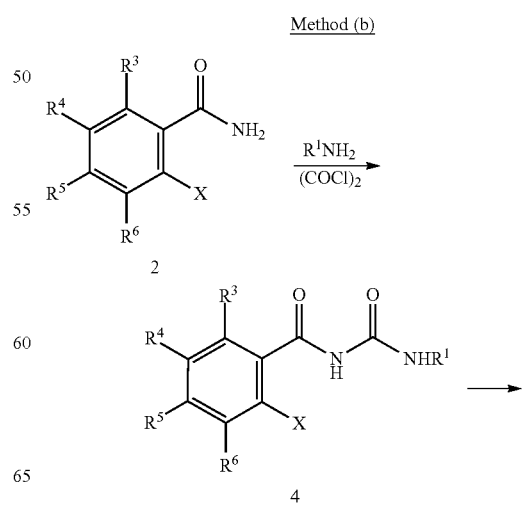

-continued

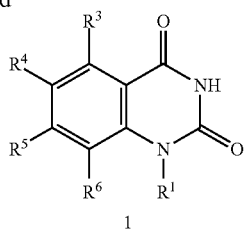

1

Treatment of a compound of formula 2 where X is halo, preferably chloro and other groups are as defined in Summary or a precursor group thereof, with an amine of formula $R^1NH_2$ in the presence of oxalyl chloride in an chlorinated organic solvent or an isocyanate of formula $R^1NCO$ where $R^1$ is as defined in Summary or a precursor group thereof provides an acylurea compound of formula 4 which is then cyclized to provide a compound of formula 1 in the presence of a base such as sodium hydride or KHMDS, and the like under conditions well known in the art.

Synthesis from 2-Halobenzoic Acids:

Treatment of a benzoic acid compound of formula 5 where X is halo, preferably chloro and other groups are as defined in Summary or a precursor group thereof, with an amine of formula $R^1NH_2$ where $R^1$ is as defined in Summary or a precursor group thereof in the presence of an inorganic based such as potassium carbonate, cesium carbonate and the like, and copper provides a compound of formula 6. Alternatively, the amination reaction can be carried out in the presence of LDA in THF at −78° C. Compounds of formula 5 are either commercially available or can be made by methods well known in the art. Compounds of formula 6 are converted to compounds of formula 1 by treatment with urea under conditions well known in the art.

Alternatively, compounds of formula 6 can be converted to amido compounds of formula 3 by treating 6 with HATU or EDCI/HOBt and ammonium chloride in the presence of an organic base such as diisopropylethylamine in an organic solvent such as THF and the like. Compound 6 is then converted to a compound 1 can be prepared as shown in Method a or method b above.

Method (c)

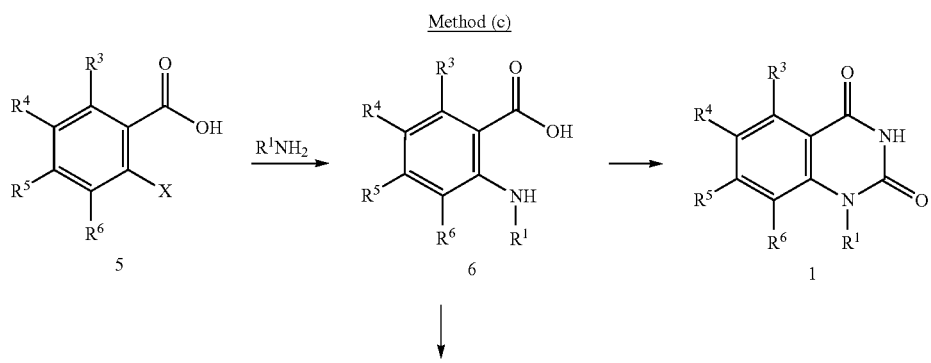

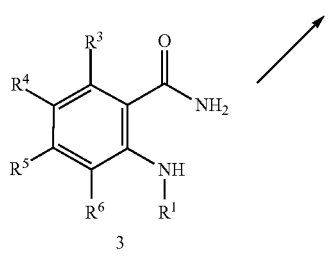

3

Synthesis from 2-Aminobenzoic Acids:

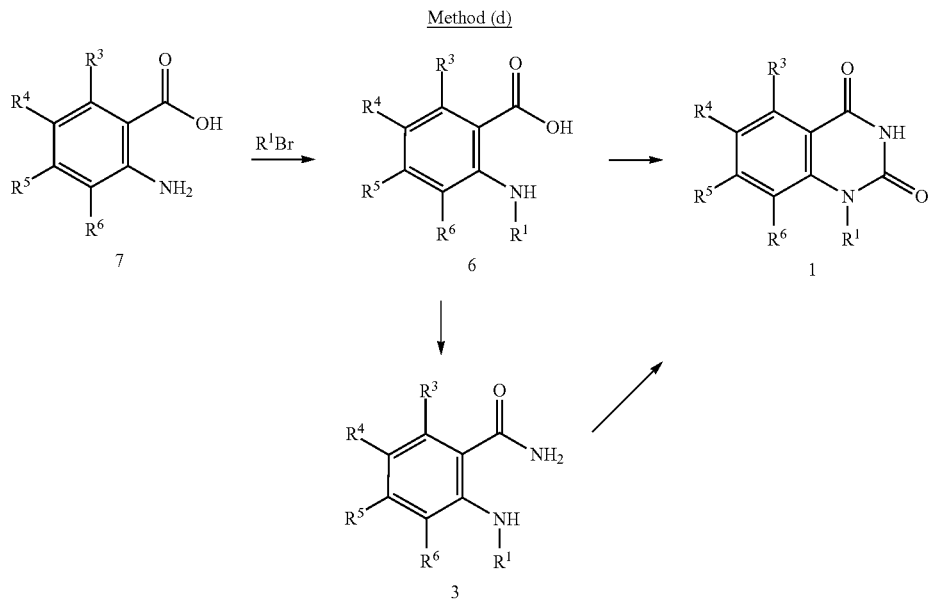

Method (d)

Treatment of a 2-aminobenzoic acid compound of formula 7 where $R^3$ to $R^6$ groups are as defined in Summary or a precursor group thereof, with a halide of $R^1Br$ where $R^1$ is as defined in Summary or a precursor group thereof in the presence of in the presence of copper acetate in and a base such as triethylamine, pyridine, and the like provides compound 6 which can then be converted to a compound of formula 1 as described above.

Synthesis from 2-Aminobenzamide:

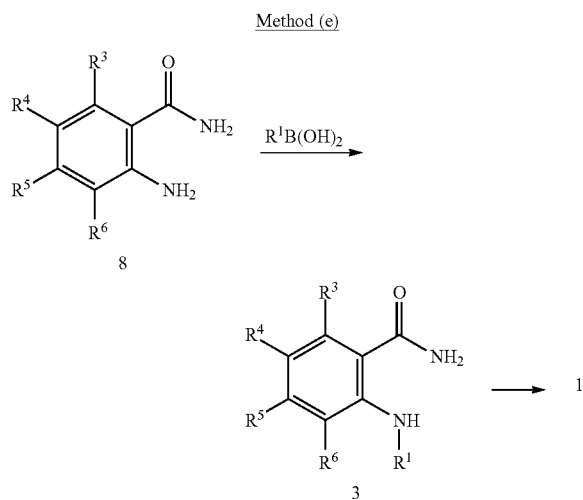

Method (e)

Treatment of a 2-aminobenamide compound of formula 8 where $R^3$ to $R^6$ groups are as defined in Summary or a precursor group thereof, with a boronic acid of formula $R^1B(OH)_2$ where $R^1$ is as defined in Summary or a precursor group thereof in the presence of in the presence of copper(I) chloride in the presence of a base such as triethylamine, pyridine, and the like, provides a compound of formula 3 which can then be converted to a compound of formula 1 as described above.

Compounds of Formula (I) and (II) and the subembodiments described herein can be converted to other compounds of Formula (I) and (II) respectively, by methods well known in the art. For example, a compound of Formula (I) or (II) where $R^5$ is halo (a precursor group) can be converted to a corresponding compound of Formula (I) or (II) respectively where $R^5$ is methoxy by treating it with sodium methoxide in presence of CuI in DMF. A compound of Formula (I) or (II) where $R^5$ is halo (a precursor group) can be converted to a corresponding compound of Formula (I) or (II) respectively where $R^5$ is cyano by treating it with zinc cyanide in presence of Pd catalyst such as $Pd(PH_3)_4$ in DMF. A compound of Formula (I) where $R^5$ is halo (a precursor group) can be converted to a corresponding compound of Formula (I) where $R^5$ is trifluoromethyl by treating it with methyl 2,2-difluoro-2-(fluorosulfonyl)acetate in presence of CuI in DMF.

Utility

Overexpression of the enzyme MAT2A has been demonstrated to mediate certain cancers. In an embodiment, the cancer is neuroblastoma, intestine carcinoma (such as rectum carcinoma, colon carcinoma, familiary adenomatous polyposis carcinoma and hereditary non-polyposis colorectal cancer), esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors (such as glioblastoma, astrocytoma, meningioma, medulloblastoma and peripheral neuroectodermal tumors), Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

In another embodiment, the cancer is lung cancer, non-small cell lung (NSLC) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endonetrium, carcinoma of the vagina, carcinoma of the vulva, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers.

Methylthioadenosine phosphorylase (MTAP) is an enzyme found in all normal tissues that catalyzes the conversion of methylthioadenosine (MTA) into adenine and 5-methylthio-ribose-1-phosphate. The adenine is salvaged to generate adenosine monophosphate, and the 5-methylthioribose-1-phosphate is converted to methionine and formate. Because of this salvage pathway, MTA can serve as an alternative purine source when de novo purine synthesis is blocked, e.g., with antimetabolites, such as L-alanosine.

Many human and murine malignant cells lack MTAP activity. MTAP deficiency is not only found in tissue culture cells but the deficiency is also present in primary leukemias, gliomas, melanomas, pancreatic cancers, non-small cell lung cancers (NSLC), bladder cancers, astrocytomas, osteosarcomas, head and neck cancers, myxoid chondrosarcomas, ovarian cancers, endometrial cancers, breast cancers, soft tissue sarcomas, non-Hodgkin lymphomas, and mesotheliomas. It has been reported by K. Marjon et al., Cell Reports 15 (2016) 574-587, incorporated herein by reference, that proliferation of cancer cells that are MTAP null is inhibited by knocking down MAT2A expression with shRNA. An MTAP null cancer is a cancer in which the MTAP gene has been deleted or lost or otherwise deactivated or a cancer in which the MTAP protein has a reduced or impaired function.

Accordingly, in an embodiment of the present disclosure there is provided a method for treating an MTAP null cancer in a patient wherein said cancer is characterized by a reduction or absence of MTAP expression or absence of the MTAP gene or reduced function of MTAP protein as compared to cancers where the MTAP gene is present and fully functioning, said method comprising administering to the patient in need thereof a therapeutically effective amount of a compound of Formula (I), (IA), (IA'), (II), (IIA), (IA'), or a subembodiment described herein or a pharmaceutically acceptable salt thereof. In another embodiment, provided is a method of treating an MTAP null cancer in a patient comprising administering to the patient in need thereof an effective amount of a compound of Formula (I) (IA), (IA'), (II), (IIA), (IIA'), or a subembodiment described herein or a pharmaceutically acceptable salt thereof. In an embodiment, the MTAP null cancer is leukemia, glioma, melanoma, pancreatic, non-small cell lung cancer (NSLC), bladder cancer, astrocytoma, osteosarcoma, head and neck cancer, myxoid chondrosarcoma, ovarian cancer, endometrial cancer, breast cancer, soft tissue sarcoma, non-Hodgkin lymphoma or mesothelioma. In another embodiment, the MTAP null cancer is pancreatic cancer. In yet another embodiment, the MTAP null cancer is bladder cancer, melanoma, brain cancer, lung cancer, pancreatic cancer, breast cancer, esophageal cancer, head and neck cancer, kidney cancer, colon cancer, diffuse large B cell lymphoma (DLBCL), acute lymphoblastic leukemia (ALL) or mantle cell lymphoma (MCL). In yet another embodiment, the MTAP null cancer is gastric cancer. In yet another embodiment, the cancer is colon cancer. In yet another embodiment, the MTAP null cancer is liver cancer. In yet another embodiment, the MTAP null cancer is glioblastoma multiforme (GBM). In yet another embodiment, the MTAP null cancer is bladder cancer. In yet another embodiment, the MTAP null cancer is esophageal cancer. In yet another embodiment, the MTAP null cancer is breast cancer. In yet another embodiment, the MTAP null cancer is NSLCC. In yet another embodiment, the MT AP null cancer is MCL. In yet another embodiment, the MTAP null cancer is DLBCL. In yet another embodiment, the MTAP null cancer is ALL.

Genomic analysis of MTAP null cell lines has shown that cell lines that also incorporate a KRAS mutation or a p53 mutation were sensitive to MAT2A inhibition. Accordingly, also provided is a method for treating a cancer in a patient wherein said cancer is characterized by reduction or absence of MTAP expression or absence of the MTAP gene or reduced function of MTAP protein (i.e., MTAP null) and further characterized by the presence of mutant KRAS and/or mutant p53, said method comprising administering to the patient a therapeutically effective amount of a compound of Formula (I), (IA), (IA'), (II), (IIA), (IIA'), or a subembodiment described herein. In one embodiment, the cancer is MTAP null and KRAS mutant. In another embodiment, the cancer is MTAP null and p53 mutant. In yet another embodiment, the cancer is MTAP null, KRAS mutant and p53 mutant.

The term "mutant KRAS" or "KRAS mutation" refers to KRAS protein (or gene encoding said protein) incorporating an activating mutation that alters its normal function. For example, a mutant KRAS protein may incorporate a single amino acid substitution at position 12 or 13. In a particular embodiment, the KRAS mutant incorporates a G12X or G13X substitution, wherein X represents any amino acid change at the indicated position. In a particular embodiment, the substitution is G12V, G12R, G12C or G13D. In another embodiment, the substitution is G13D. By "mutant p53" or "p53 mutation" is meant p53 protein (or gene encoding said protein) incorporating a mutation that inhibits or eliminates its tumor suppressor function. In an embodiment, said p53 mutation is, Y126_splice, K132Q, M133K, R174fs, R175H, R196*, C238S, C242Y, G245S, R248W, R248Q, I255T, D259V, S261_splice, R267P, R273C, R282W, A159V or R280K. In an embodiment, the foregoing cancer is non-small cell lung cancer (NSLCC), pancreatic cancer, head and neck cancer, gastric cancer, breast cancer, colon cancer or ovarian cancer.

Assay

The ability of compounds of the disclosure to inhibit MAT2A can be measured as described in Biological Example 1 below.

Pharmaceutical Composition

The compounds of Formula (I), (IA), (IA'), (II), (IIA), (IIA'), or a subembodiment described herein, or a pharmaceutically acceptable salt thereof, may be in the form of compositions suitable for administration to a subject. In general, such compositions are pharmaceutical compositions comprising a compound of Formula (I), (IA), (IA'), (II), (IIA), (IIA'), or a subembodiment described herein or a pharmaceutically acceptable salt thereof and one or more pharmaceutically acceptable or physiologically acceptable excipients. In certain embodiments, the compound of Formula (I), (IA), (IA'), (II), (IIA), (IIA'), or a subembodiment described herein, or a pharmaceutically acceptable salt thereof is present in a therapeutically effective amount. The pharmaceutical compositions may be used in the methods disclosed herein; thus, for example, the pharmaceutical compositions can be administered ex vivo or in vivo to a subject in order to practice the therapeutic methods and uses described herein.

The pharmaceutical compositions can be formulated to be compatible with the intended method or route of administration; exemplary routes of administration are set forth herein. Furthermore, the pharmaceutical compositions may be used in combination with other therapeutically active agents or compounds as described herein in order to treat the diseases, disorders and conditions contemplated by the present disclosure.

The pharmaceutical compositions containing the active ingredient (e.g., a compound of Formula (I), (IA), (IA'), (II), (IA), (IIA'), or a subembodiment described herein, a pharmaceutically acceptable salt thereof) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets, capsules, and the like. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl di-stearate may be employed. The tablets may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinyl acetate, methylcellulose, carboxymethylcellulose, protamine sulfate, or lactide and glycolide copolymers, polylactide and glycolide copolymers, or ethylene vinyl acetate copolymers in order to control delivery of an administered composition. For example, the oral agent can be entrapped in microcapsules prepared by coacervation techniques or by interfacial polymerization, by the use of hydroxymethyl cellulose or gelatin-microcapsules or poly (methyl methacrylate) microcapsules, respectively, or in a colloid drug delivery system. Colloidal dispersion systems include macromolecule complexes, nanocapsules, microspheres, microbeads, and lipid-based systems, including oil-in-water emulsions, micelles, mixed micelles, and liposomes. Methods for the preparation of the above-mentioned formulations are known in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, (hydroxypropyl)methyl cellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., poly-oxyethylene stearate), or condensation products of ethylene oxide with long chain aliphatic alcohols (e.g., for heptdecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a compound of Formula (I), (IA), (IA'), (II), (IIA), (IIA'), or a subembodiment described herein, or a salt thereof, and one or more pharmaceutically acceptable excipient. Suitable pharmaceutically acceptable excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver a compound of Formula (I), (IA), (IA'), (II), (IIA), (IIA'), or a subembodiment described herein, or a salt thereof, including implants (e.g., implantable pumps) and catheter systems, slow injection pumps and devices, all of which are well known to the skilled artisan.

Depot injections, which are generally administered subcutaneously or intramuscularly, may also be utilized to release the compound of Formula (I), (IA), (IA'), (II), (IIA), (IIA'), or a subembodiment described herein, or a salt thereof over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. The suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose, any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

A compound of Formula (I), (IA), (IA'), (II), (IIA), (IIA'), or a subembodiment described herein, or a salt thereof may also be administered in the form of suppositories for rectal administration or sprays for nasal or inhalation use. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

Routes of Administration

Compounds of Formula (I), (IA), (IA'), (II), (IIA), (IIA'), or a subembodiment described herein, or a salt thereof and compositions containing the same may be administered in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to administer the compounds of Formula (I), (IA), (IA'), (II), (IIA), (IIA'), or a subembodiment described herein, or a salt thereof over a defined period of time. Particular embodiments of the present invention contemplate oral administration.

Combination Therapy

The present invention contemplates the use of compounds of Formula (I), (IA), (IA'), (II), (IIA), (IIA'), or a subembodiment described herein, or a salt thereof in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the compounds of Formula (I), (IA), (IA'), (II), (IIA), (IIA'), or a subembodiment described herein, or a salt thereof are administered or applied sequentially, e.g., where one agent is administered prior to one or more other agents. In other embodiments, the compounds of Formula (I), (IA), (IA'), (II), (IIA), (IIA'), or a subembodiment described herein, or a salt thereof are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The compounds of (I), (IA), (IA'), (II), (IIA), (IIA'), or a subembodiment described herein, or a salt thereof may be used in combination with at least one other (active) agent in any manner appropriate under the circumstances. In one embodiment, treatment with the at least one active agent and at least one compound of Formula (I), (IA), (IA'), (II), (IIA), (IIA'), or a subembodiment described herein, or a salt thereof is maintained over a period of time. In another embodiment, treatment with the at least one active agent is reduced or discontinued (e.g., when the subject is stable), while treatment with the compound of Formula (I), (IA), (IA'), (II), (IIA), (IIA'), or a subembodiment described herein, or a salt thereof is maintained at a constant dosing regimen. In a further embodiment, treatment with the at least one active agent is reduced or discontinued (e.g., when the subject is stable), while treatment with a compound of Formula (I), (IA), (IA'), (II), (IIA), (IIA'), or a subembodiment described herein, or a salt thereof is reduced (e.g., lower dose, less frequent dosing or shorter treatment regimen). In yet another embodiment, treatment with the at least one active agent is reduced or discontinued (e.g., when the subject is stable), and treatment with the compound of Formula (I), (IA), (IA'), (II), (IIA), (IIA'), or a subembodiment described herein, or a salt thereof is increased (e.g., higher dose, more frequent dosing or longer treatment regimen). In yet another embodiment, treatment with the at least one active agent is maintained and treatment with the compound of Formula (I), (IA), (IA'), (II), (IIA), (IIA'), or a subembodiment described herein, or a salt thereof is reduced or discontinued (e.g., lower dose, less frequent dosing or shorter treatment regimen). In yet another embodiment, treatment with the at least one active agent and treatment with the compound of Formula (I), (IA), (IA'), (II), (IIA), (IIA'), or a subembodiment described herein, or a salt thereof are reduced or discontinued (e.g., lower dose, less frequent dosing or shorter treatment regimen).

The present disclosure provides methods for treating cancer with a compound of Formula (I), (IA), (IA'), (II), (IIA), (IIA'), or a subembodiment described herein, or a salt thereof and at least one additional therapeutic or diagnostic agent.

In some embodiments, the compound of Formula (I), (IA), (IA'), (II), (IIA), (IIA'), or a subembodiment described herein, or a salt thereof is administered in combination with at least one additional therapeutic agent, selected from Temozolomide, Pemetrexed, Pegylated liposomal doxorubicin (Doxil), Eribulin (Halaven), Ixabepilone (Ixempra), Protein-bound paclitaxel (Abraxane), Oxaliplatin, Irinotecan, Venatoclax (bcl2 inhibitor), 5-azacytadine, Anti-CD20 therapeutics, such as Rituxan and obinutuzumab, Hormonal agents (anastrozole, exemestand, letrozole, zoladex, lupon eligard), CDK4/6 inhibitors, Palbociclib, Abemaciclib, CPI (Avelumab, Cemiplimab-rwlc, and Bevacizumab.

In certain embodiments, the present disclosure provides methods for treating cancer comprising administration of a compound of Formula (I), (IA), (IA'), (II), (IIA), (IIA'), or a subembodiment described herein, or a salt thereof in combination with a signal transduction inhibitor (STI) to achieve additive or synergistic suppression of tumor growth. As used herein, the term "signal transduction inhibitor" refers to an agent that selectively inhibits one or more steps in a signaling pathway. Examples of signal transduction inhibitors (STIs) useful in methods described herein include, but are not limited to: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with one or more compounds of Formula (I), (IA), (IA'), (II), (IIA), (IIA'), or a subembodiment described herein, or a salt thereof for the suppression of tumor growth in cancer patients.

In certain embodiments, the present disclosure provides methods for treating cancer comprising administration of a compound of Formula (I), (IA), (IA'), (II), (IIA), (IIA'), or a subembodiment described herein, or a salt thereof in combination with a chemotherapeutic agents. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above. In a particular embodiment, compounds of the present disclosure are coadministered with a cytostatic compound selected from the group consisting of cisplatin, doxorubicin, taxol, taxotere and mitomycin C. In a particular embodiment, the cytostatic compound is doxorubicin.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, enzalutamide, apalutamide, abiraterone acetate, leuprolide, and goserelin; and pharmaceutically acceptable salts, acids or derivatives of any of the above. In certain embodiments, combination therapy comprises administration of a hormone or related hormonal agent.

The present disclosure also contemplates the use of the compounds of Formula (I), (IA), (IA'), (II), (IIA), (IIA'), or a subembodiment described herein, or a salt thereof in combination with immune checkpoint inhibitors. The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism. Examples of immune checkpoint inhibitors include but are not limited to CTLA-4, PD-1, PD-L1, BTLA, TIM3, LAG3, OX40, 41BB, VISTA, CD96, TGFβ, CD73, CD39, A2AR, A2BR, IDO1, TDO2, Arginase, B7-H3, B7-H4. Cell-based modulators of anti-cancer immunity are also contemplated. Examples of such modulators include but are not limited to chimeric antigen receptor T-cells, tumor infiltrating T-cells and dendritic-cells.

The present disclosure contemplates the use of compounds of Formula (I), (IA), (IA'), (II), (IIA), (IIA'), or a subembodiment described herein, or a salt thereof in combination with inhibitors of the aforementioned immune-checkpoint receptors and ligands, for example ipilimumab, abatacept, nivolumab, pembrolizumab, atezolizumab, nivolumab, and durvalumab.

Additional treatment modalities that may be used in combination with a compound of Formula (I), (IA), (IA'), (II), (IIA), (IIA'), or a subembodiment described herein, or a salt thereof include radiotherapy, a monoclonal antibody against a tumor antigen, a complex of a monoclonal antibody and toxin, a T-cell adjuvant, bone marrow transplant, or antigen presenting cells (e.g., dendritic cell therapy).

The present disclosure contemplates the use of compounds of Formula (I), (IA), (IA'), (II), (IIA), (IIA'), or a subembodiment described herein, or a salt thereof for the treatment of glioblastoma either alone or in combination with radiation and/or temozolomide (TMZ), avastin or lomustine.

The present disclosure encompasses pharmaceutically acceptable salts, acids or derivatives of any of the above.

Dosing

The compounds of Formula (I), (IA), (IA'), (II), (IIA), (IIA'), or a subembodiment described herein, or a salt thereof may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of a compound of Formula (I), (IA), (IA'), (II), (IIA), (IIA'), or a subembodiment described herein, or a salt thereof may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, more than 90%, where 100% is defined as the diagnostic parameter, measure, marker and the like exhibited by a normal subject.

In certain embodiments, the compounds of (I), (IA), (IA'), (II), (IIA), (IIA'), or a subembodiment described herein, or a salt thereof may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the compound of Formula (I), (IA), (IA'), (II), (IIA), (IIA'), or a subembodiment described herein, or a salt thereof is contained in a "unit dosage form". The phrase "unit dosage form" refers to physically discrete units, each unit containing a predetermined amount of the compound of Formula (I), (IA), (IA'), (II), (IIA), (IIA'), or a subembodiment described herein, or a salt thereof, either alone or in combination with one or more additional agents, sufficient to produce the desired effect. It will be appreciated that the parameters of a unit dosage form will depend on the particular agent and the effect to be achieved.

Kits

The present invention also contemplates kits comprising a compound of Formula (I), (IA), (IA'), (II), (IIA), (IIA'), or a subembodiment described herein, or a salt thereof, and pharmaceutical compositions thereof. The kits are generally in the form of a physical structure housing various components, as described below, and may be utilized, for example, in practicing the methods described above.

A kit can include one or more of the compound of Formula (I), (IA), (IA'), (II), (IIA), (IIA'), or a subembodiment described herein, or a salt thereof (provided in, e.g., a sterile container), which may be in the form of a pharmaceutical composition suitable for administration to a subject. The compound of Formula (I), (IA), (IA'), (II), (IIA), (IIA'), or a subembodiment described herein, or a salt thereof can be provided in a form that is ready for use (e.g., a tablet or capsule) or in a form requiring, for example, reconstitution or dilution (e.g., a powder) prior to administration. When the compounds of Formula (I), (IA), (IA'), (II), (IIA), (IIA'), or a subembodiment described herein, or a salt thereof are in a form that needs to be reconstituted or diluted by a user, the kit may also include diluents (e.g., sterile water), buffers, pharmaceutically acceptable excipients, and the like, packaged with or separately from the compounds of Formula (I), (IA), (IA'), (II), (IIA), (IIA'), or a subembodiment described herein, for a salt thereof. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXAMPLES

The following examples and references (intermediates) are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: μg=microgram; μl or μL=microliter; mM=millimolar; μM=micromolar; aa=amino acid(s); Ac$_2$O=acetic anhydride; AcCl=acetylchloride; ACN= acetonitrile; AIBN=2,2'-Azobis(2-methylpropionitrile); BID=twice daily; BINAP=2,2'-bis(diphenylphosphino)-1,1'-binaphthyl; Boc$_2$O or (Boc)$_2$O=di-tert-butyl dicarbonate; bp=base pair(s); BSA=bovine serum albumin; BW=body weight; d=doublet; dd=doublet of doublets; DEAD=diethyl azodicarboxylate; DIBAL=diisobutylaluminium hydride DIEA=N,N-diisopropylethylamine; DIPEA=N,N-diisopropylethylamine; dl or dL=deciliter; DMA=dimethyl- acetamide; DMAP=dimethylaminopyridine; DME=1,2-dimethoxyethane; DMEM=Dulbeco's Modification of Eagle's Medium; DMF=N,N-dimethylformamide; DMSO=dimethylsulfoxide; dppf=1,1'-Bis(diphenylphosphino)ferrocene; DTT=dithiothreitol; EDTA=ethylenediaminetetraacetic acid; ES=electrospray; EtOAc=ethyl acetate; EtOH= ethanol; g=gram; h or hr=hour(s); HATU=2-(1H-7-azabenzotriazol-1-yl)-1,1,3,3-tetramethyluronium hexafluorophosphate; HEPES=4-(2-hydroxyethyl)-1-piperazineethanesulfonic acid; HOAc=acetic acid; HPLC=high performance liquid chromatography; HPLC=high pressure liquid chromatography; i.m.=intramuscular(ly); i.p.=intraperitoneal(ly); IHC=immunohistochemistry; IPA=isopropyl alcohol; kb=kilobase(s); kDa=kilodalton; kg=kilogram; 1 or L=liter; LC=liquid chromatography; LCMS=liquid chromatography and mass spectrometry; m/z=mass to charge ratio; M=molar; m=multiplet; MeCN=acetonitrile; MeOH= methanol; MeSO$_2$Cl=methanesulfonylchloride; mg= milligram; min=minute(s); min=minutes; ml or mL=milliliter; mM=millimolar; MS=mass spectrometry; MsCl=meth- anesulfonylchloride; N=normal; NADPH=nicotinamide adenine dinucleotide phosphate; NBS=N-bromosuccinamide; ng=nanogram; nm=nanometer; nM=nanomolar; NMP=N-methylpyrrolidone; NMR=nuclear magnetic resonance; ns=not statistically significant; nt=nucleotides(s); PBS=phosphate-buffered saline; Pd/C=palladium on carbon; Pd$_2$(dba)$_3$=Tris(debenzylideneactone) dipalladium; Pd(dppf)Cl$_2$=1,1'-bis(diphenylphosphino)ferrocene-palladium(ll)dichloride; PE=petroleum ether; QD=daily; QM=monthly; QW=weekly; rac=racemic; Rt=retention time; s=singlet; s or see=second(s); sat.=saturated; SC or SQ=subcutaneous(ly); t=triplet; TBAB=tetra-n-butylammonium bromide; TEA=triethylamine; TFA=trifluoroacetic acid; THF=tetrahydrofuran; TLC=thin layer chromatography; TMSCl=trimethylsilylchloride; TsOH=p-toluenesulfonic acid; U=unit; wt=wildtype.

Synthetic Examples

Reference 1

Synthesis of
7-chloro-4-hydroxy-1-phenylquinazolin-2(1H)-one

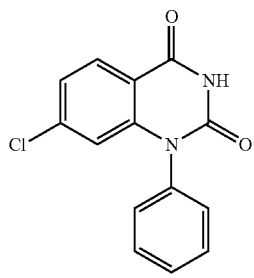

Step 1: Synthesis of
4-chloro-2-(phenylamino)benzoic acid

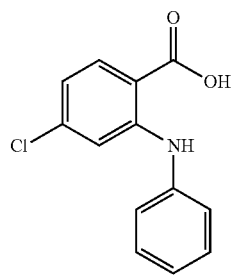 [SMILES: O=C(O)c1ccc(Cl)cc1Nc1ccccc1]

To a stirred solution of 2,4-dichlorobenzoic acid (1 equiv) in DMF (0.5 M) were added aniline (1.5 equiv), copper(0) powder (0.5 equiv) and potassium carbonate (2 equiv) and the reaction mixture was stirred at 150° C. for 5 h. After completion of reaction, the reaction mixture was brought to room temperature and filtered through a Celite pad. The obtained filtrate was acidified with 2 N HCl. The solid formed was filtered and dried under vacuum to provide 4-chloro-2-(phenylamino)benzoic acid as brown solid.

Step 2: Synthesis of
7-chloro-4-hydroxy-1-phenylquinazolin-2(1H)-one

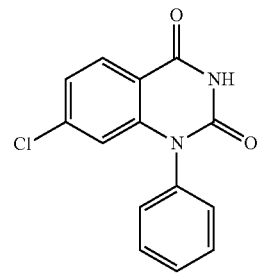 [SMILES: O=c1[nH]c(=O)n(-c2ccccc2)c2cc(Cl)ccc12]

A mixture of 4-chloro-2-(phenylamino)benzoic acid (1 equiv) and urea (5 equiv) was charged in a round bottom flask equipped with a stir bar and heated at 200° C. for 2 h. The crude was poured into water and extracted with EtOAc. The combined organic layers were separated, dried over anhydrous sodium sulfate, filtered and concentrated under reduced pressure to afford crude product. The crude was purified by column chromatography (20-30% EtOAc/Hexane) to provide the title compound as a yellow solid. $^1$H NMR (400 MHz, DMSO-d$_6$): δ=11.82 (s, 1H), 8.04 (d, J=8.3 Hz, 1H), 7.66-7.56 (m, 3H), 7.48-7.44 (m, 2H), 7.31 (dd, J=8.3, 1.9 Hz, 1H), 6.31 (d, J=1.8 Hz, 1H). m/z [M+H]$^+$ 273.18

Reference 2

Synthesis of 7-chloro-1-(pyridin-3-yl)quinazoline-2,4(1H,3H)-dione

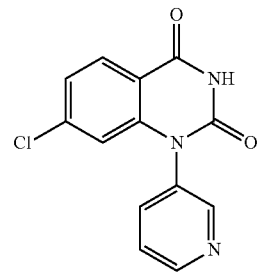 [SMILES: O=c1[nH]c(=O)n(-c2cccnc2)c2cc(Cl)ccc12]

Step 1: Synthesis of
4-chloro-2-(pyridin-3-ylamino)benzamide

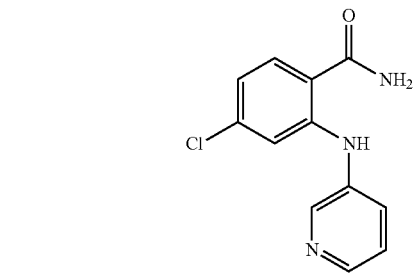 [SMILES: NC(=O)c1ccc(Cl)cc1Nc1cccnc1]

To a stirred solution of 2,4-dichlorobenzamide (1 equiv) in DMF (0.5 M) were added 3-aminopyridine (1.5 equiv), copper(0) powder (0.5 equiv) and potassium carbonate (2 equiv) and the reaction mixture was stirred at 150° C. for 5 h. After completion of reaction, the reaction mixture was brought to room temperature and filtered through a Celite pad. The obtained filtrate was acidified with 2 N HCl. The solid formed was filtered and dried under vacuum to provide the title compound as a brown solid. m/z [M+H]⁺ 249.1

Step 2: Synthesis of 7-chloro-1-(pyridin-3-yl)quinazoline-2,4(1H,3H)-dione

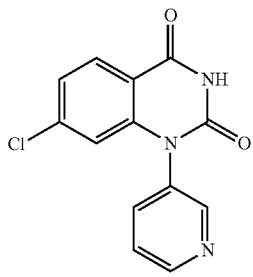

A vial was charged with 4-chloro-2-(pyridin-3-ylamino) benzamide (1.0 equiv) and DMF (0.2 M). To the reaction vessel at 0° C. was added NaH (60% in mineral oil, 3.0 equiv) and the reaction mixture was stirred at room temperature for 10 min. To the vessel was added CDI (1.5 equiv) and the reaction mixture was stirred at room temperature for 20 min. The reaction was quenched by the addition of MeOH (0.5 mL) and AcOH (0.2 mL). The crude reaction mixture was directly purified by reverse phase column chromatography (20-75% MeCN/water, 0.1% formic acid). ¹H NMR (400 MHz, DMSO-d₆) δ 11.82 (s, 1H), 8.69 (d, J=4.9 Hz, 1H), 8.61 (s, 1H), 7.99 (d, J=8.4 Hz, 1H), 7.91 (d, J=7.9 Hz, 1H), 7.68-7.50 (m, 1H), 7.27 (d, J=8.6 Hz, 1H), 6.32 (s, 1H). m/z [M+H]⁺ 274.0

Proceeding as described in Reference 2, Step 1, 2-((2-chlorophenyl)amino)-6-cyclopropyl-nicotinamide was prepared by using 2-chloro aniline and 2-chloro-6-cyclopropylnicotinamide instead of 3-aminopyridine and 2,4-dichlorobenzamide respectively.

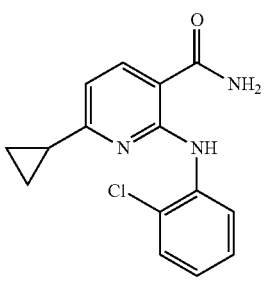

m/z [M + H]⁺ 288.0.

Proceeding as described in Step 2 above, the following compounds were prepared:

7-Chloro-1-(pyridin-4-yl)quinazoline-2,4(1H,3H)-dione was prepared using 4-chloro-2-(pyridin-4-ylamino)benzamide

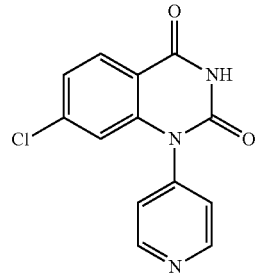

m/z [M + H]⁺ 274.0.

1-(2-Chlorophenyl)-7-cyclopropylpyrido[2,3-d]pyrimidine-2,4(1H,3H)-dione was prepared using 2-((2-chlorophenyl)amino)-6-cyclopropylnicotinamide.

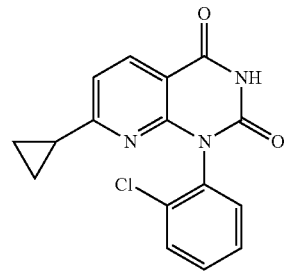

m/z [M + H]⁺ 314.0.

1-(2-Bromophenyl)-7-(trifluoromethyl)pyrido[2,3-d]pyrimidine-2,4(1H,3H)-dione was prepared using 2-((2-bromophenyl)amino)-6-(trifluoromethyl)nicotinamide.

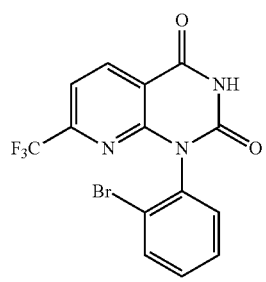

m/z [M + H]⁺ 387.0, 385.9.

1-(2-Fluorophenyl)-7-(trifluoromethyl)pyrido[2,3-d]pyrimidine-2,4(1H,3H)-dione was prepared using 2-((2-fluorophenyl)amino)-6-(trifluoromethyl)nicotinamide.

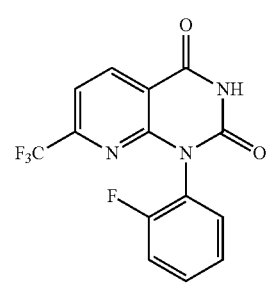

m/z [M + H]⁺ 326.0.

3-(7-Chloro-2,4-dioxo-3,4-dihydroquinazolin-1(2H)-yl)benzonitrile was prepared using 4-chloro-2-((3-cyanophenyl)amino)benzamide. $^1$H NMR (400 MHz, DMSO-$d_6$) δ 11.92 (s, 1H), 8.13-8.00 (m, 3H), 7.85 (dd, J=8.3, 1.7 Hz, 2H), 7.34 (dt, J=8.5, 1.7 Hz, 1H), 6.43 (d, J=1.7 Hz, 1H).

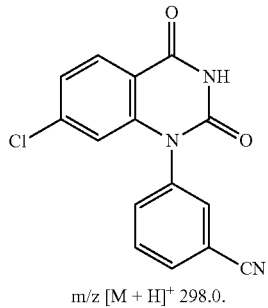 [SMILES: N#Cc1cccc(-n2c(=O)[nH]c(=O)c3ccc(Cl)cc32)c1]

m/z [M + H]$^+$ 298.0.

Reference 3

Synthesis of 7-chloro-5-fluoro-1-phenylquinazoline-2,4(1H,3H)-dione

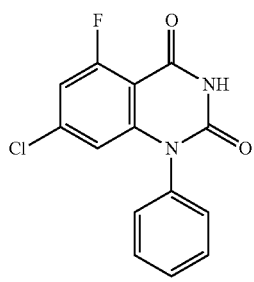 [SMILES: O=c1[nH]c(=O)n(-c2ccccc2)c2cc(Cl)cc(F)c12]

Step 1: Synthesis of 4-chloro-2-fluoro-6-(phenylamino)benzoic acid

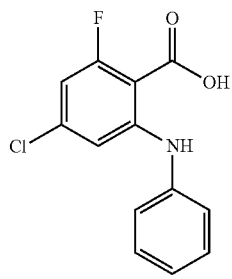 [SMILES: O=C(O)c1c(F)cc(Cl)cc1Nc1ccccc1]

To a stirred solution of aniline (2 equiv) in THF (1 M) was added LDA (3 equiv) at −78° C. and the reaction mixture was stirred for 10 min. 4-chloro-2,6-difluorobenzoic acid (1 equiv) in THF (1 M) was added at −78° C. and the reaction mixture was stirred for 48 h at room temperature. After completion of the reaction, the crude was poured into 1 N HCl solution and extracted with EtOAc. The combined organic layers were separated, dried over anhydrous sodium sulfate, and concentrated under reduced pressure to afford desired 4-chloro-2-fluoro-6-(phenylamino)benzoic acid as a pale yellow solid.

Step 2: Synthesis of 4-chloro-2-fluoro-6-(phenylamino)benzamide

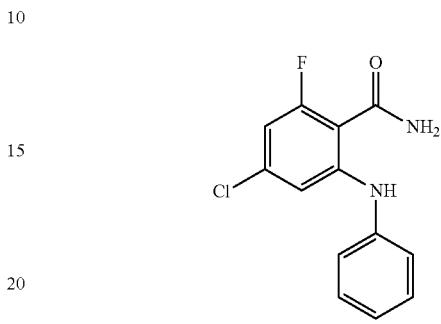

To a stirred solution of 4-chloro-2-fluoro-6-(phenylamino)benzoic acid (1 equiv) in DMF (0.4 M) were added HATU (1.5 equiv), DIPEA (5 equiv) at room temperature and stirred for 30 min. Ammonium chloride (5 equiv) was added to the reaction mixture and stirring was continued for 16 h at room temperature. After completion, the crude was poured into ice cold water and stirred for 30 min, the solid filtered and dried under vacuum to afford 4-chloro-2-fluoro-6-(phenylamino)benzamide as an off-white solid.

Step 3: Synthesis of 7-chloro-5-fluoro-1-phenylquinazoline-2,4(1H,3H)-dione

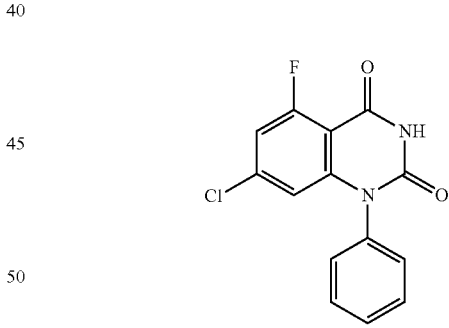

To a stirred solution of 4-chloro-2-fluoro-6-(phenylamino)benzamide (1 equiv) in DMF (0.33 M) was added NaH (2.2 equiv) at 0° C. and the reaction was stirred for 30 min. CDI (1.1 equiv) was added to the reaction mixture at 0° C. and stirring was continued for 30 min at 0° C. The crude was poured into ice cold water and the mixture was stirred for 30 min, the solid filtered and dried under vacuum to afford the title compound (1.1 g, 57%) as an off white solid. $^1$H NMR (400 MHz, DMSO-$d_6$) δ 11.77 (br s, 1H), 7.61 (m, 3H), 7.44 (m, 2H), 7.29 (dd, J=10.8, 1.8 Hz, 1H), 6.10 (s, 1H). m/z [M+H]$^+$ 291.3

Proceeding as described in Reference 3, Step 2 above, the following compounds were prepared:

2-Chloro-4-methoxy-6-(trifluoromethyl)nicotinamide was prepared using 2-chloro-4-methoxy-6-(trifluoromethyl) nicotinic acid.

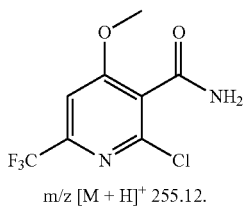 [SMILES: COc1cc(C(F)(F)F)nc(Cl)c1C(N)=O]

m/z [M + H]⁺ 255.12.

2,6-Dichloro-4-(trifluoromethyl)benzamide was prepared using 2,6-dichloro-4-(trifluoromethyl) benzoic acid.

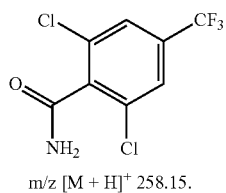 [SMILES: NC(=O)c1c(Cl)cc(C(F)(F)F)cc1Cl]

m/z [M + H]⁺ 258.15.

5-Bromo-2-fluoro-4-(trifluoromethyl)benzamide was prepared using 5-bromo-2-fluoro-4-(trifluoromethyl)benzoic acid.

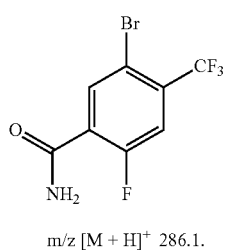 [SMILES: NC(=O)c1cc(Br)c(C(F)(F)F)cc1F]

m/z [M + H]⁺ 286.1.

Reference 4

Synthesis of 7-chloro-1-[3-(methoxymethyl)phenyl]-1,3-dihydroquinazoline-2,4-dione

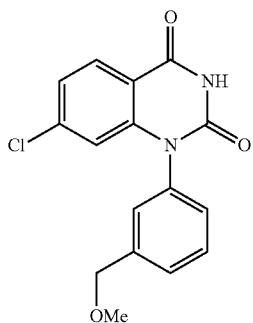 [SMILES: COCc1cccc(-n2c(=O)[nH]c(=O)c3ccc(Cl)cc32)c1]

Step 1: Synthesis of 4-chloro-2-((3-(methoxymethyl)phenyl)amino)benzamide

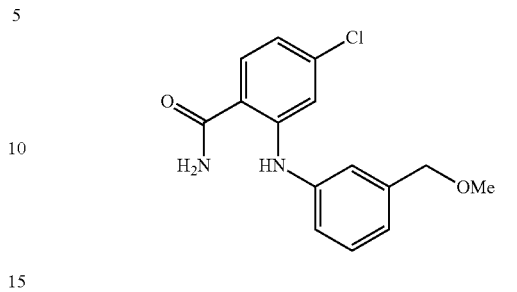

A vial was charged under air with 2-amino-4-chlorobenzamide (1.0 equiv), copper chloride (0.15 equiv), 3-(methoxymethyl)phenylboronic acid (1.5 equiv) and triethylamine (0.5 equiv). To the reaction vessel was added MeOH (0.4 M) and the reaction mixture was stirred at room temperature for 3-12 h. The crude reaction mixture was directly purified by reverse phase chromatography (20-65% MeCN/water) to give the title compound. m/z [M+H]⁺ 291.1

Step 2: Synthesis of 7-chloro-1-[3-(methoxymethyl)phenyl]-1,3-dihydroquinazoline-2,4-dione

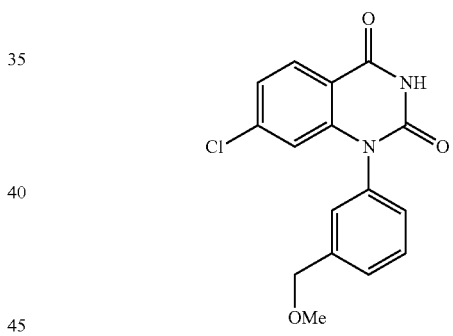

A vial was charged under nitrogen with 4-chloro-2-((3-(methoxymethyl)phenyl)-amino)benzamide (1.0 equiv) and DMF (0.2 M). To the reaction mixture at 0° C. was added NaH (60% in mineral oil, 3.0 equiv) and the reaction mixture was stirred at room temperature for 10 min. CDI (1.5 equiv) was added and the reaction mixture was stirred at room temperature for 20 min. The reaction mixture was quenched by the addition of MeOH and AcOH. The crude reaction mixture was directly purified by reverse phase column chromatography (20-75% MeCN/water, 0.1% formic acid) to give the title compound. ¹H NMR (400 MHz, DMSO-$d_6$) δ 11.80 (s, 1H), 8.03 (dd, J=8.4, 1.3 Hz, 1H), 7.60 (t, J=7.6 Hz, 1H), 7.50 (d, J=7.8 Hz, 1H), 7.41-7.34 (m, 2H), 7.30 (dt, J=8.4, 1.7 Hz, 1H), 6.30 (t, J=1.6 Hz, 1H), 4.50 (s, 2H) m/z [M+H]⁺ 317.1

Proceeding analogously as described above, the following compounds were prepared:

7-Chloro-1-(3-hydroxyphenyl)-1,3-dihydroquinazoline-2,4-dione was prepared by substituting 3-hydroxyphenylboronic acid for 3-(methoxymethyl)phenylboronic acid

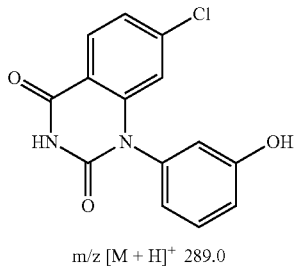 [SMILES: O=c1[nH]c(=O)n(-c2cccc(O)c2)c2cc(Cl)ccc12]

m/z [M + H]⁺ 289.0

7-Chloro-1-[3-(2-hydroxyethyl)phenyl]-1,3-dihydroquinazoline-2,4-dione was prepared by substituting (3-(2-hydroxyethyl)phenyl)boronic acid for 3-(methoxymethyl)phenylboronic acid

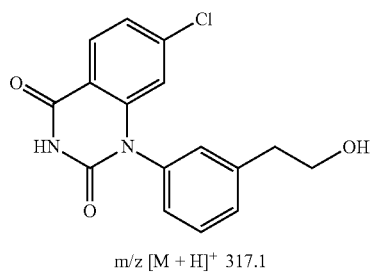 [SMILES: O=c1[nH]c(=O)n(-c2cccc(CCO)c2)c2cc(Cl)ccc12]

m/z [M + H]⁺ 317.1

7-Chloro-1-(3-fluorophenyl)-1,3-dihydroquinazoline-2,4-dione was prepared by substituting (3-fluorophenyl)boronic acid for 3-(methoxymethyl)phenylboronic acid

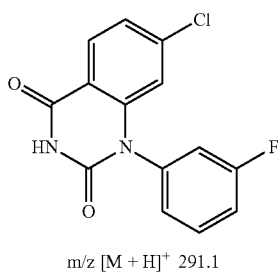 [SMILES: O=c1[nH]c(=O)n(-c2cccc(F)c2)c2cc(Cl)ccc12]

m/z [M + H]⁺ 291.1

7-Chloro-1-(3-methylphenyl)-1,3-dihydroquinazoline-2,4-dione was prepared by substituting m-tolylboronic acid for 3-(methoxymethyl)phenylboronic acid

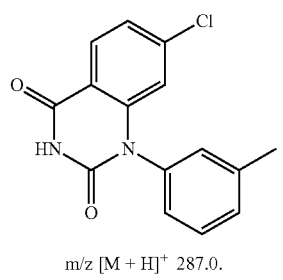 [SMILES: Cc1cccc(-n2c(=O)[nH]c(=O)c3ccc(Cl)cc32)c1]

m/z [M + H]⁺ 287.0.

7-Chloro-1-[3-(3-hydroxypropyl)phenyl]-1,3-dihydroquinazoline-2,4-dione was prepared by substituting 3-(3-hydroxypropyl)phenylboronic acid for 3-(methoxymethyl)phenylboronic acid

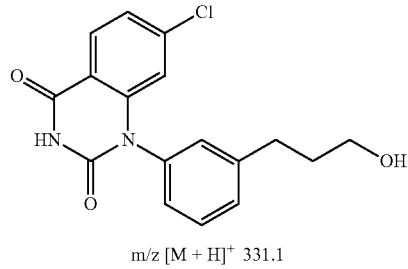 [SMILES: O=c1[nH]c(=O)n(-c2cccc(CCCO)c2)c2cc(Cl)ccc12]

m/z [M + H]⁺ 331.1

7-Chloro-1-(3-chlorophenyl)-1,3-dihydroquinazoline-2,4-dione was prepared by substituting (3-chlorophenyl)boronic acid for 3-(methoxymethyl)phenylboronic acid

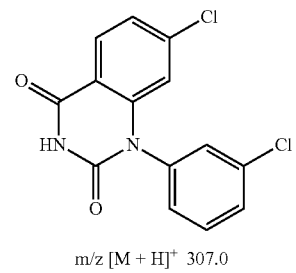 [SMILES: O=c1[nH]c(=O)n(-c2cccc(Cl)c2)c2cc(Cl)ccc12]

m/z [M + H]⁺ 307.0

7-Chloro-1-[3-(hydroxymethyl)phenyl]-1,3-dihydroquinazoline-2,4-dione was prepared by substituting (3-(hydroxymethyl)phenyl)boronic acid for 3-(methoxymethyl)phenylboronic acid

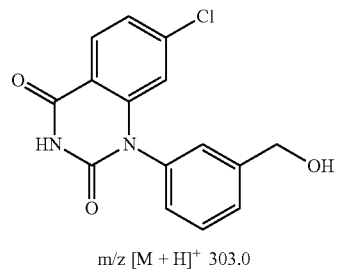 [SMILES: O=c1[nH]c(=O)n(-c2cccc(CO)c2)c2cc(Cl)ccc12]

m/z [M + H]⁺ 303.0

3-(7-Chloro-2,4-dioxo-3,4-dihydroquinazolin-1(2H)-yl)benzonitrile was prepared by substituting (3-cyanophenyl)boronic acid for 3-(methoxymethyl)phenylboronic acid

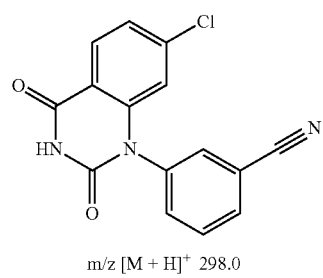 [SMILES: N#Cc1cccc(-n2c(=O)[nH]c(=O)c3ccc(Cl)cc32)c1]

m/z [M + H]⁺ 298.0 tert-butyl (3-(7-chloro-2,4-dioxo-3,4-dihydroquinazolin-1(2H)-yl)benzyl)carbamate was prepared by substituting 3-((tert-butoxycarbonylamino)methyl)phenylboronic acid for 3-(methoxymethyl)phenylboronic acid

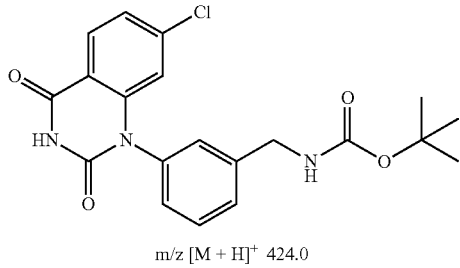 [SMILES: CC(C)(C)OC(=O)NCc1cccc(-n2c(=O)[nH]c(=O)c3ccc(Cl)cc32)c1]

m/z [M + H]⁺ 424.0

7-Chloro-1-(3-methoxyphenyl)-1,3-dihydroquinazoline-2,4-dione was prepared by substituting (3-methoxyphenyl)boronic acid for 3-(methoxymethyl)phenylboronic acid

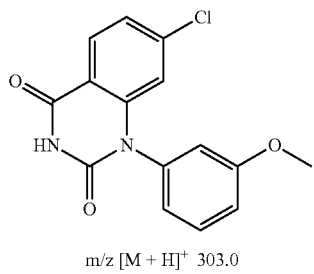 [SMILES: COc1cccc(-n2c(=O)[nH]c(=O)c3ccc(Cl)cc32)c1]

m/z [M + H]⁺ 303.0

7-Chloro-1-(5-fluoro-3-hydroxyphenyl)-1,3-dihydroquinazoline-2,4-dione was prepared by substituting 3-fluoro-5-hydroxyphenylboronic acid for 3-(methoxymethyl)phenylboronic acid

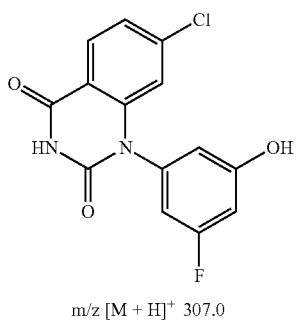 [SMILES: O=c1[nH]c(=O)n(-c2cc(O)cc(F)c2)c2cc(Cl)ccc12]

m/z [M + H]⁺ 307.0

7-Chloro-1-(4-fluorophenyl)-1,3-dihydroquinazoline-2,4-dione was prepared by substituting (4-fluorophenyl)boronic acid for 3-(methoxymethyl)phenylboronic acid

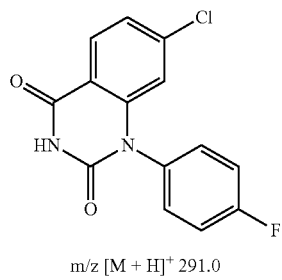 [SMILES: O=c1[nH]c(=O)n(-c2ccc(F)cc2)c2cc(Cl)ccc12]

m/z [M + H]⁺ 291.0

7-Chloro-1-(2-fluoro-3-hydroxyphenyl)-1,3-dihydroquinazoline-2,4-dione was prepared by substituting 2-fluoro-3-hydroxyphenylboronic acid for 3-(methoxymethyl)phenylboronic acid

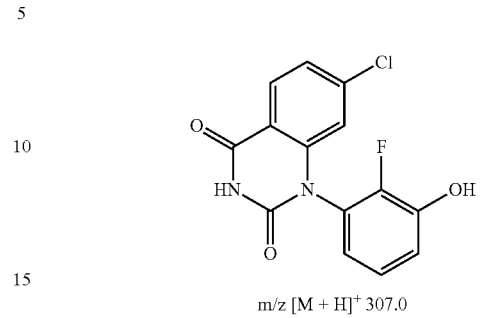

m/z [M + H]⁺ 307.0

7-Chloro-1-(4-fluoro-3-hydroxyphenyl)-1,3-dihydroquinazoline-2,4-dione was prepared by substituting 4-fluoro-3-hydroxyphenylboronic acid for 3-(methoxymethyl)phenylboronic acid

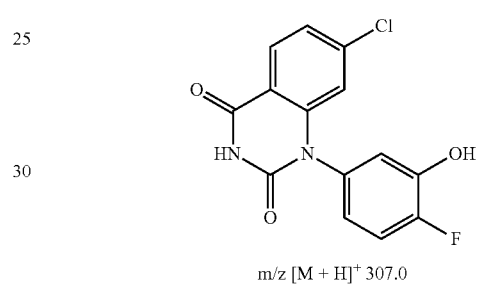

m/z [M + H]⁺ 307.0

Reference 5

Synthesis of 1-[3-(aminomethyl)phenyl]-7-chloro-1,3-dihydroquinazoline-2,4-dione

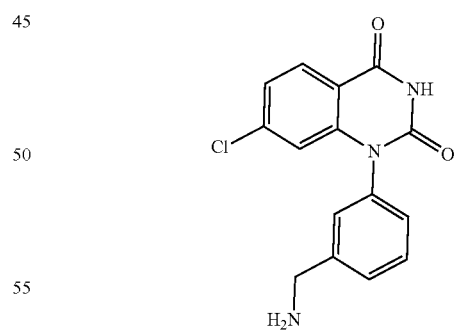

A vial was charged under nitrogen with tert-butyl (3-(7-chloro-2,4-dioxo-3,4-dihydroquinazolin-1(2H)-yl)benzyl) carbamate (1.0 equiv) and MeCN (0.2 M), 4N HCl/dioxane (10 equiv) was added and the reaction mixture was stirred at room temperature for 30 min. The solvent was evaporated and the crude reaction mixture was directly purified by reverse phase purification (10-45% MeCN/water, 0.1% formic acid) to give the title compound. ¹H NMR (400 MHz, DMSO-d₆) δ 8.30 (s, 1H), 8.05 (d, J=8.4 Hz, 1H), 7.60 (d, J=7.3 Hz, 2H), 7.44 (s, 1H), 7.39-7.23 (m, 2H), 6.35 (s, 1H), 3.93 (s, 3H). m/z [M+H]$^+$ 302.0

Reference 6

Synthesis of 7-chloro-1-(o-tolyl)quinazoline-2,4(1H,3H)-dione

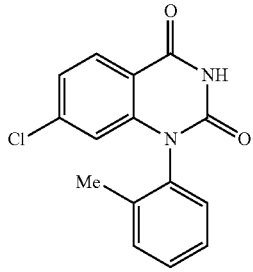 [SMILES: Cc1ccccc1-n1c(=O)[nH]c(=O)c2ccc(Cl)cc21]

Step 1: Synthesis of 2,4-dichloro-N-(o-tolylcarbamoyl)benzamide

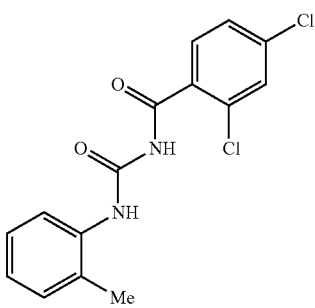 [SMILES: Cc1ccccc1NC(=O)NC(=O)c1ccc(Cl)cc1Cl]

A slurry of 2,4-dichlorobenzamide (1 equiv.) in DCE (0.5 M) was treated dropwise with oxalyl chloride (1.35 equiv.) at room temperature. The reaction mixture was then warmed to 55° C. for 1 h and was then further warmed to reflux for 20 h. The reaction mixture was concentrated in vacuo to afford the crude as a yellow oil. A solution of this crude isocyanate in DCE (1.2 M) at 0° C. was added dropwise to a cooled solution of o-toluidine in DCE (0.4 M). The ice bath was removed and the reaction mixture stirred at room temperature for 45 min. The solids were filtered, washed with DCM, and dried to obtain the title compound as a white solid. m/z [M+H]$^+$ 324.0

Step 2: Synthesis of 7-chloro-1-(o-tolyl)quinazoline-2,4(1H,3H)-dione

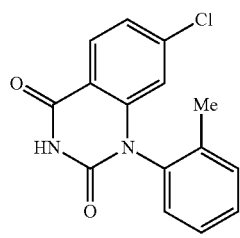 [SMILES: Cc1ccccc1-n1c(=O)[nH]c(=O)c2ccc(Cl)cc21]

A slurry of 2,4-dichloro-N-(o-tolylcarbamoyl)benzamide in DME:toluene (0.06 M, 1:1 v/v) was cooled to 0° C. and treated portion-wise with NaH (60% dispersion in oil, 3.1 equiv). After addition, the ice-bath was removed and the reaction mixture was warmed to reflux for 18 h. The reaction mixture was cooled to RT and poured into 20% aq. HCl. The resulting mixture was stirred vigorously and the off-white solid was filtered, washed with Et$_2$O and dried to obtain crude product which was used in the next step without purification. m/z [M+H]$^+$ 287.0

Proceeding analogously as described in Step 1 above, the following compounds were prepared:

4-(1,1-difluoroethyl)-2-fluoro-N-(imidazo[1,2-a]pyridin-5-ylcarbamoyl)benzamide was prepared by substituting imidazo[1,2-a]pyridin-5-amine for o-toluidine and 4-(1,1-difluoroethyl)-2-fluorobenzamide for 2,4-dichlorobenzamide.

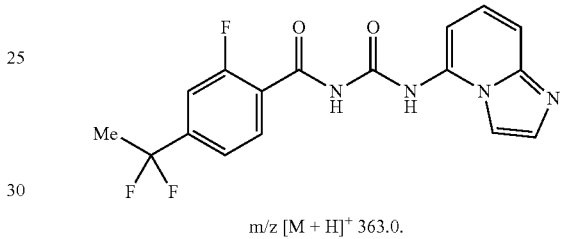

m/z [M + H]$^+$ 363.0.

5-Cyano-4-cyclopropyl-2-fluoro-N-(o-tolylcarbamoyl)benzamide was prepared using 5-cyano-4-cyclopropyl-2-fluorobenzamide for 2,4-dichlorobenzamide.

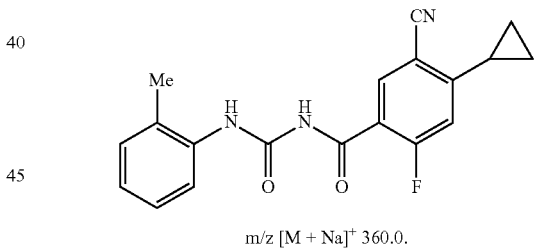

m/z [M + Na]$^+$ 360.0.

N-((2-Chlorophenyl)carbamoyl)-4-(1,1-difluoroethyl)-2-fluorobenzamide was prepared by substituting 2-chloroaniline for o-toluidine and using 4-(1,1-difluoroethyl)-2-fluorobenzamide for 2,4-dichlorobenzamide (Pharmablock, PBU1050).

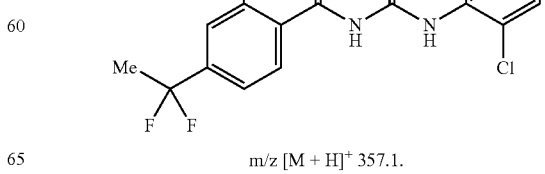

m/z [M + H]$^+$ 357.1.

4-Chloro-2-fluoro-N-(imidazo[1,2-a]pyridin-5-ylcarbamoyl)benzamide was prepared by substituting imidazo[1,2-a]pyridin-5-amine for o-toluidine and 4-chloro-2-fluorobenzamide for 2,4-dichlorobenzamide.

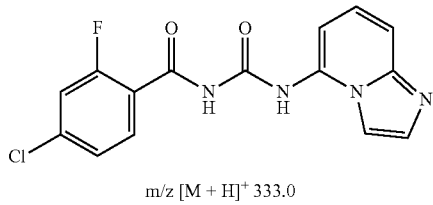 [SMILES: O=C(NC(=O)c1ccc(Cl)cc1F)Nc1cccc2nccn12]

m/z [M + H]+ 333.0

4-Chloro-2-fluoro-N-(imidazo[1,2-a]pyridin-7-ylcarbamoyl)benzamide was prepared by substituting imidazo[1,2-a]pyridin-7-amine for o-toluidine and 4-chloro-2-fluorobenzamide for 2,4-dichlorobenzamide.

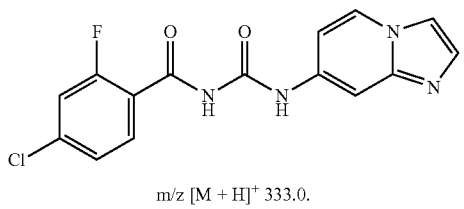 [SMILES: O=C(NC(=O)c1ccc(Cl)cc1F)Nc1ccn2ccnc2c1]

m/z [M + H]+ 333.0.

N-((2-Chlorophenyl)carbamoyl)-4-cyclopropyl-2-fluorobenzamide was synthesized using 4-cyclopropyl-2-fluorobenzamide for 2,4-dichlorobenzamide and 2-chloroaniline for o-toluidine.

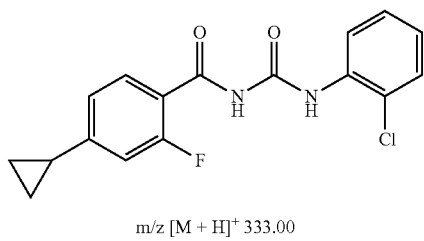 [SMILES: O=C(NC(=O)c1ccc(C2CC2)cc1F)Nc1ccccc1Cl]

m/z [M + H]+ 333.00

2,4-Dichloro-N-(pyrimidin-2-ylcarbamoyl)benzamide was prepared using 2,4-dichlorobenzamide for 2,4-dichlorobenzamide and pyrimidin-2-amine.

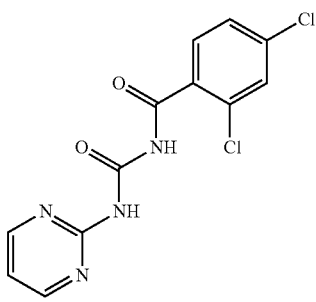

m/z [M + H]+ 311.0.

4-Cyclopropyl-2-fluoro-N-((3-methylpyrazin-2-yl)carbamoyl)benzamide was synthesized using 4-cyclopropyl-2-fluorobenzamide for 2,4-dichlorobenzamide and 3-methylpyrazin-2-amine for o-toluidine.

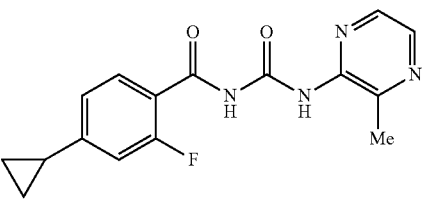

m/z [M + H]+ 315.20

4-Cyclopropyl-2-fluoro-N-(pyrazin-2-ylcarbamoyl)benzamide was synthesized using 4-cyclopropyl-2-fluorobenzamide for 2,4-dichlorobenzamide and pyrazin-2-amine for o-toluidine.

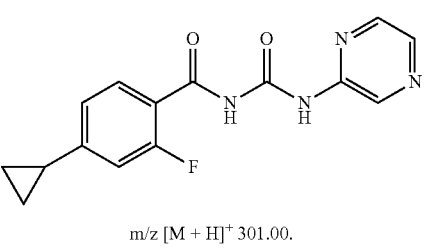 [SMILES: O=C(NC(=O)c1ccc(C2CC2)cc1F)Nc1cnccn1]

m/z [M + H]+ 301.00.

4-Cyclopropyl-2-fluoro-N-(imidazo[1,2-a]pyridin-5-ylcarbamoyl)benzamide was synthesized using 4-cyclopropyl-2-fluorobenzamide for 2,4-dichlorobenzamide and imidazo[1,2-a]pyridin-5-amine for o-toluidine

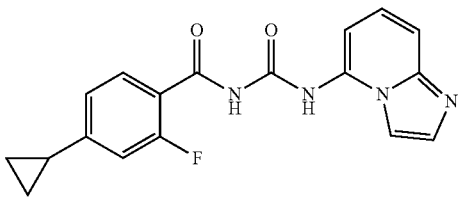

m/z [M + H]+ 339.00

N-((3-chloropyridin-2-yl)carbamoyl)-4-ethyl-2-fluorobenzamide was prepared by substituting 3-chloropyridin-2-amine for o-toluidine and 4-ethyl-2-fluorobenzamide for 2,4-dichlorobenzamide.

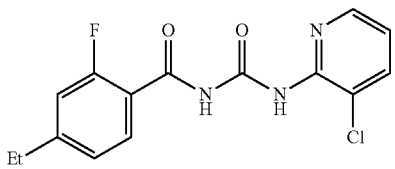

m/z [M + H]+ 322.0.

483

N-((3-chloropyridin-2-yl)carbamoyl)-4-(1,1-difluoroethyl)-2-fluorobenzamide was prepared by substituting 3-chloropyridin-2-amine for o-toluidine and 4-(1,1-difluoroethyl)-2-fluorobenzamide for 2,4-dichlorobenzamide.

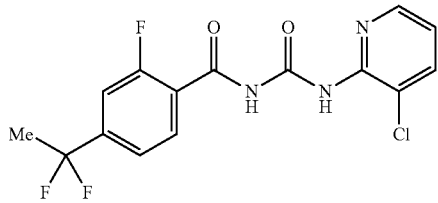

m/z [M + H]+ 358.0.

4-(1,1-difluoroethyl)-2-fluoro-N-(imidazo[1,2-a]pyridin-7-ylcarbamoyl)benzamide was prepared by substituting imidazo[1,2-a]pyridin-7-amine for o-toluidine and 4-(1,1-difluoroethyl)-2-fluorobenzamide for 2,4-dichlorobenzamide.

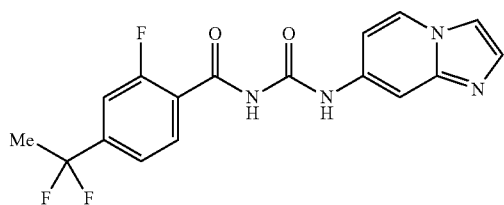

m/z [M + H]+ 363.0.

2-Fluoro-N-(pyrazin-2-ylcarbamoyl)-4-(trifluoromethyl)benzamide was prepared by substituting 2-fluoro-4-(trifluoromethyl)benzamide for 2,4-dichlorobenzamide and pyrazin-2-amine for o-toluidine

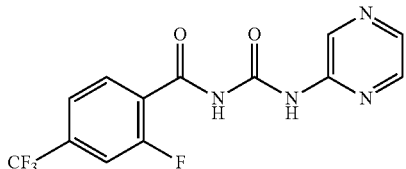

m/z [M + H]+ 329.05

2-Fluoro-N-(pyridazin-3-ylcarbamoyl)-4-(trifluoromethyl)benzamide was prepared by substituting 2-fluoro-4-(trifluoromethyl)benzamide for 2,4-dichlorobenzamide and pyridazin-3-amine for o-toluidine

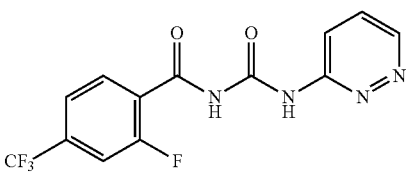

m/z [M + H]+ 329.05

484

2-Fluoro-N-(imidazo[1,2-a]pyridin-5-ylcarbamoyl)-4-(trifluoromethoxy)benzamide was prepared by substituting 2-fluoro-4-(trifluoromethoxy)benzamide for 2,4-dichlorobenzamide and imidazo[1,2-a]pyridin-5-amine for o-toluidine.

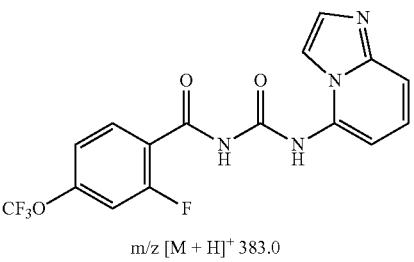

m/z [M + H]+ 383.0

2-Chloro-4-cyclopropyl-N-((3-(trifluoromethyl)pyrazin-2-yl)carbamoyl)benzamide was prepared by substituting 2-chloro-4-cyclopropylbenzamide for 2,4-dichlorobenzamide and 3-(trifluoromethyl)pyrazin-2-amine for o-toluidine

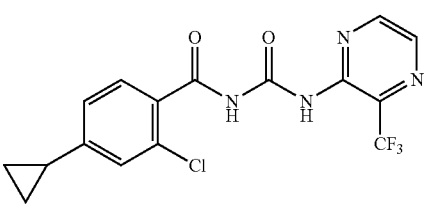 [SMILES: O=C(NC(=O)c1ccc(C2CC2)cc1Cl)Nc1nccnc1C(F)(F)F]

5-Bromo-2-fluoro-N-(o-tolylcarbamoyl)-4-(trifluoromethoxy)benzamide was prepared by substituting 5-bromo-2-fluoro-4-(trifluoromethoxy)benzamide for 2,4-dichlorobenzamide.

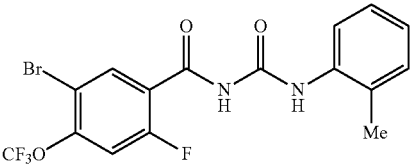

m/z [M + Na]+ 456.0, 454.0

5-Bromo-2-fluoro-N-(phenylcarbamoyl)-4-(trifluoromethoxy)benzamide was prepared by substituting 5-bromo-2-fluoro-4-(trifluoromethoxy)benzamide for 2,4-dichlorobenzamide and aniline for o-toluidine

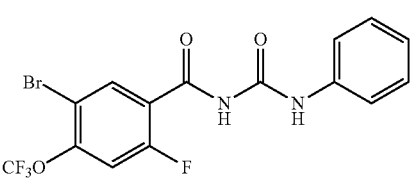

485

4-Bromo-N-((2-chlorophenyl)carbamoyl)-2,5-difluorobenzamide was prepared by substituting 4-bromo-2,5-difluorobenzamide for 2,4-dichlorobenzamide and 2-chloroaniline for o-toluidine

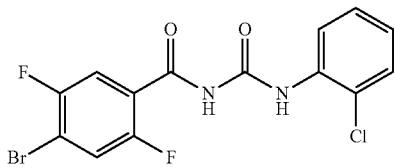 [SMILES: O=C(NC(=O)c1cc(F)c(Br)cc1F)Nc1ccccc1Cl]

2,6-difluoro-4-(trifluoromethyl)-N-((2-(trifluoromethyl)pyridin-3-yl)carbamoyl)benzamide was prepared by substituting 2,6-difluoro-4-(trifluoromethyl)benzamide for 2,4-dichlorobenzamide and 2-(trifluoromethyl)pyridin-3-amine for o-toluidine.

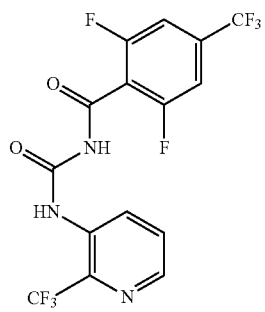 [SMILES: O=C(NC(=O)c1c(F)cc(C(F)(F)F)cc1F)Nc1cccnc1C(F)(F)F]

4-cyclopropyl-2-fluoro-N-(imidazo[1,2-a]pyridin-7-yl-carbamoyl)benzamide was prepared by substituting 4-cyclopropyl-2-fluorobenzamide for 2,4-dichlorobenzamide and imidazo[1,2-a]pyridin-7-amine for o-toluidine

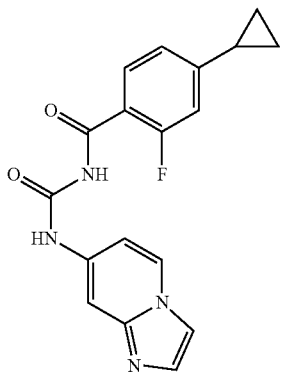 [SMILES: O=C(NC(=O)c1ccc(C2CC2)cc1F)Nc1ccn2ccnc2c1]

2-Chloro-N-((2-chloropyridin-3-yl)carbamoyl)-6-(trifluoromethyl)nicotinamide was prepared by substituting 2-chloro-6-(trifluoromethyl)nicotinamide for 2,4-dichlorobenzamide and 2-chloropyridin-3-amine for o-toluidine

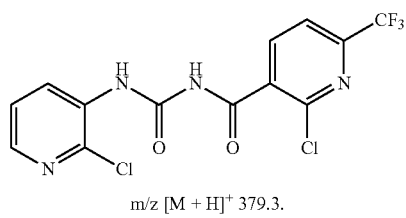 [SMILES: O=C(NC(=O)c1ccc(C(F)(F)F)nc1Cl)Nc1cccnc1Cl]

m/z [M + H]+ 379.3.

486

2-Chloro-6-(trifluoromethyl)-N-((2-(trifluoromethyl)pyridin-3-yl)carbamoyl)nicotinamide was prepared by substituting 2-chloro-6-(trifluoromethyl)nicotinamide for 2,4-dichlorobenzamide and 2-(trifluoromethyl)pyridin-3-amine for o-toluidine.

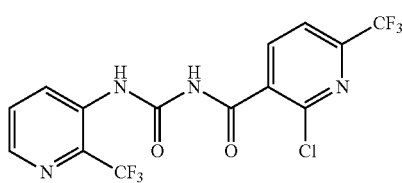

m/z [M + H]+ 413.11.

5-Bromo-4-cyclopropyl-2-fluoro-N-((2-(trifluoromethyl)phenyl)carbamoyl) benzamide was prepared by substituting 5-bromo-4-cyclopropyl-2-fluorobenzamide for 2,4-dichlorobenzamide and 2-(trifluoromethyl)aniline for o-toluidine.

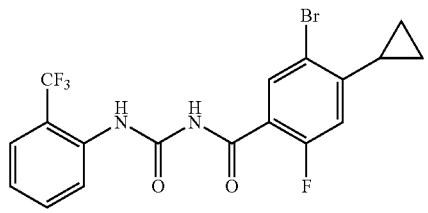

m/z [M + H]+ 447.2.

5-Bromo-4-cyclopropyl-N-((2-cyclopropylphenyl)carbamoyl)-2-fluorobenzamide was prepared by substituting 5-bromo-4-cyclopropyl-2-fluorobenzamide for 2,4-dichlorobenzamide and 2-cyclopropylaniline for o-toluidine.

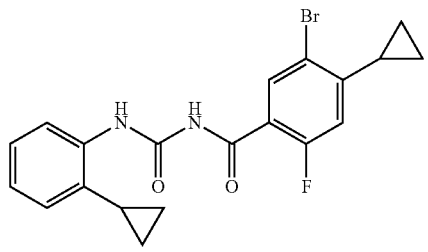

m/z [M + H]+ 417.36.

5-Bromo-N-((2-bromophenyl)carbamoyl)-4-cyclopropyl-2-fluorobenzamide was prepared by substituting 5-bromo-4-cyclopropyl-2-fluorobenzamide for 2,4-dichlorobenzamide and 2-bromoaniline for o-toluidine

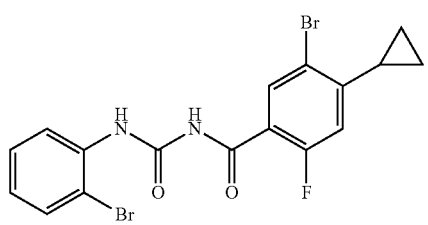 [SMILES: O=C(NC(=O)c1cc(Br)c(C2CC2)cc1F)Nc1ccccc1Br]

5-Bromo-4-cyclopropyl-2-fluoro-N-((2-(trifluoromethyl)pyridin-3-yl)carbamoyl)benzamide was prepared by substituting 5-bromo-4-cyclopropyl-2-fluorobenzamide for 2,4-dichlorobenzamide and 2-(trifluoromethyl)pyridin-3-amine for o-toluidine.

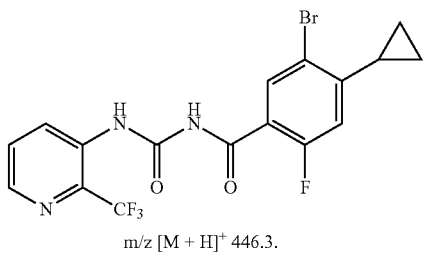 [SMILES: O=C(NC(=O)c1cc(Br)c(C2CC2)cc1F)Nc1cccnc1C(F)(F)F]

m/z [M + H]$^+$ 446.3.

5-Bromo-N-((2-chlorophenyl)carbamoyl)-4-cyclopropyl-2-fluorobenzamide was prepared by substituting 5-bromo-2-fluoro-4-(trifluoromethyl)benzamide for 2,4-dichlorobenzamide and 2-chloroaniline for o-toluidine

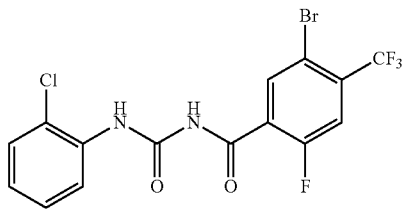 [SMILES: O=C(NC(=O)c1cc(Br)c(C(F)(F)F)cc1F)Nc1ccccc1Cl]

5-Bromo-N-((2-chloropyridin-3-yl)carbamoyl)-4-cyclopropyl-2-fluorobenzamide was prepared by substituting 5-bromo-4-cyclopropyl-2-fluorobenzamide for 2,4-dichlorobenzamide and 2-chloropyridin-3-amine for o-toluidine.

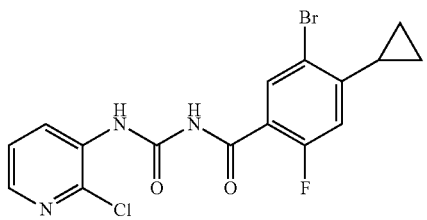

m/z [M + H]$^+$ 412.3.

N-((2-Chloropyridin-3-yl)carbamoyl)-4-cyclopropyl-2-fluoro-6-methoxybenzamide was prepared by substituting 4-cyclopropyl-2-fluoro-6-methoxybenzamide for 2,4-dichlorobenzamide and 2-chloropyridin-3-amine for o-toluidine.

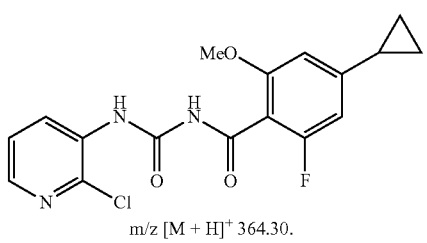 [SMILES: COc1cc(C2CC2)cc(F)c1C(=O)NC(=O)Nc1cccnc1Cl]

m/z [M + H]$^+$ 364.30.

N-((2-Chloropyridin-3-yl)carbamoyl)-4-cyclopropyl-2-fluorobenzamide was prepared by substituting 4-cyclopropyl-2-fluorobenzamide for 2,4-dichlorobenzamide and 2-chloropyridin-3-amine for o-toluidine.

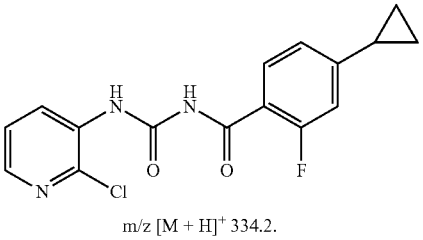 [SMILES: O=C(NC(=O)c1ccc(C2CC2)cc1F)Nc1cccnc1Cl]

m/z [M + H]$^+$ 334.2.

2-Fluoro-4-(trifluoromethyl)-N-((1-(1-((2-(trimethylsilyl)ethoxy)methyl)-1H-imidazol-4-yl)ethyl)carbamoyl)benzamide was prepared by substituting 2-fluoro-4-(trifluoromethyl)benzamide for 2,4-dichlorobenzamide and 1-(1-((2-(trimethylsilyl)ethoxy)methyl)-1H-imidazol-4-yl)ethan-1-amine for o-toluidine.

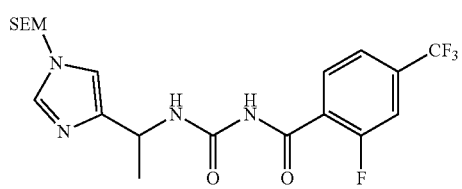

m/z [M + H]$^+$ 475.54.

2-Fluoro-N-(phenylcarbamoyl)-4-(trifluoromethyl)benzamide was prepared by substituting 2-fluoro-4-(trifluoromethyl)benzamide for 2,4-dichlorobenzamide and aniline for o-toluidine.

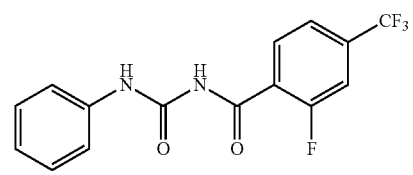

m/z [M + H]$^+$ 327.24.

N-((3-Chloropyridin-2-yl)carbamoyl)-4-cyclopropyl-2-fluorobenzamide was prepared by substituting 4-cyclopropyl-2-fluorobenzamide for 2,4-dichlorobenzamide and 3-chloropyridin-2-amine for o-toluidine.

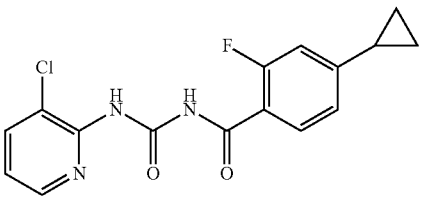

m/z [M + H]$^+$ 334.2.

4-Cyclopropyl-2-fluoro-N-(pyrimidin-5-ylcarbamoyl) benzamide was prepared by substituting 4-cyclopropyl-2-fluorobenzamide for 2,4-dichlorobenzamide and pyrimidin-5-amine for o-toluidine.

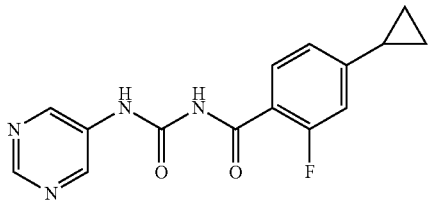 [SMILES: O=C(NC(=O)c1ccc(C2CC2)cc1F)Nc1cncnc1]

4-Cyclopropyl-2-fluoro-N-(o-tolylcarbamoyl)benzamide was prepared by substituting 4-cyclopropyl-2-fluorobenzamide for 2,4-dichlorobenzamide.

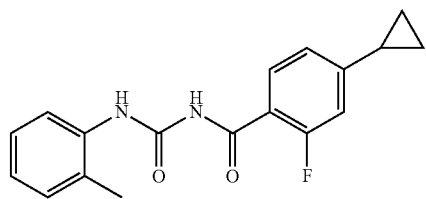

m/z [M + H]$^+$ 313.29.

2-Fluoro-4-(trifluoromethyl)-N-(((1-((2-(trimethylsilyl) ethoxy)methyl)-1H-imidazol-5-yl)methyl)carbamoyl)benzamide was prepared by substituting 2-fluoro-4-(trifluoromethyl)benzamide for 2,4-dichlorobenzamide and (1-((2-(trimethylsilyl) ethoxy) methyl)-1H-imidazol-4-yl)methanamine for o-toluidine.

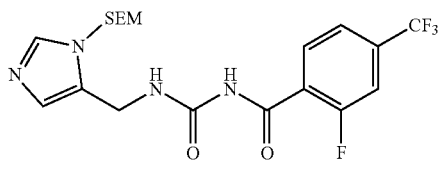

m/z [M + H]$^+$ 461.4.

4-Cyclopropyl-2-fluoro-N-(((1-((2-(trimethylsilyl) ethoxy) methyl)-1H-imidazol-5-yl) methyl) carbamoyl) benzamide was prepared by substituting 4-cyclopropyl-2-fluorobenzamide for 2,4-dichlorobenzamide and (1-((2-(trimethylsilyl) ethoxy) methyl)-1H-imidazol-4-yl)methanamine for o-toluidine.

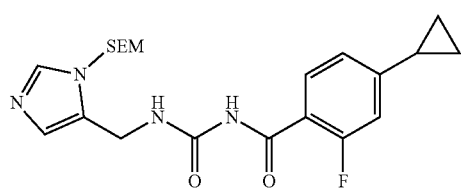

m/z [M + H]$^+$ 433.4.

N-((2-Bromophenyl)carbamoyl)-4-cyclopropyl-2-fluorobenzamide was prepared by substituting 4-cyclopropyl-2-fluorobenzamide for 2,4-dichlorobenzamide and 2-bromoaniline for o-toluidine.

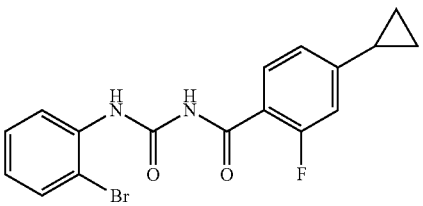

m/z [M + H]$^+$ 377.23.

4-Cyclopropyl-2-fluoro-6-methoxy-N-(pyridin-3-ylcarbamoyl)benzamide was prepared by substituting 4-cyclopropyl-2-fluoro-6-methoxybenzamide for 2,4-dichlorobenzamide and pyridin-3-amine for o-toluidine.

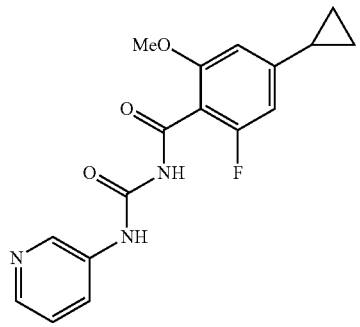

m/z [M + H]$^+$ 330.36.

4-Cyclopropyl-2-fluoro-6-methoxy-N-(o-tolylcarbamoyl)benzamide was prepared by substituting 4-cyclopropyl-2-fluoro-6-methoxybenzamide for 2,4-dichlorobenzamide.

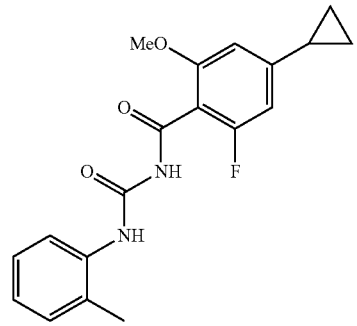

m/z [M + H]$^+$ 343.34.

4-chloro-N-((2-chlorophenyl)carbamoyl)-2,6-difluorobenzamide was prepared by substituting 4-chloro-2,6-difluorobenzamide for 2,4-dichlorobenzamide and 2-chloroaniline for o-toluidine.

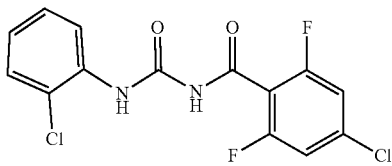

m/z [M + H]⁺ 345.2.

4-Chloro-2,6-difluoro-N-(o-tolylcarbamoyl)benzamide was prepared by substituting 4-chloro-2,6-difluorobenzamide for 2,4-dichlorobenzamide.

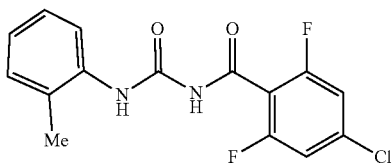

m/z [M + H]⁺ 325.22.

N-(Benzylcarbamoyl)-2-chloro-6-(trifluoromethyl)nicotinamide was prepared by substituting 2-chloro-6-(trifluoromethyl)nicotinamide for 2,4-dichlorobenzamide and benzylamine for o-toluidine.

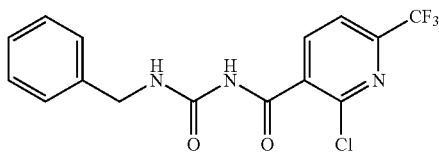

m/z [M + H]⁺ 358.0.

4-Cyclopropyl-2-fluoro-N-((2-methylpyridin-3-yl)carbamoyl)benzamide was prepared by substituting 4-cyclopropyl-2-fluorobenzamide for 2,4-dichlorobenzamide and 2-methylpyridin-3-amine for o-toluidine.

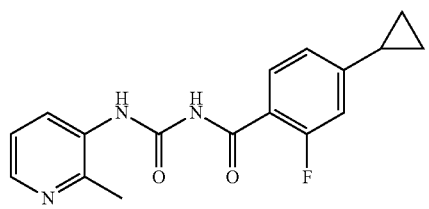

m/z [M + H]⁺ 314.2.

2-Chloro-N-((2-chloro-6-fluorophenyl)carbamoyl)-6-(trifluoromethyl) nicotinamide was prepared by substituting 2-chloro-6-(trifluoromethyl)nicotinamide for 2,4-dichlorobenzamide and 2-chloro-6-fluoroaniline for o-toluidine.

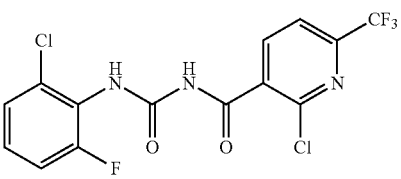 [SMILES: O=C(NC(=O)c1ccc(C(F)(F)F)nc1Cl)Nc1c(F)cccc1Cl]

Proceeding analogously as described in Step 2 above the following compounds were prepared:

7-Chloro-1-(2-fluorophenyl)quinazoline-2,4(1H,3H)-dione was prepared by substituting 2-fluoroaniline for o-toluidine.

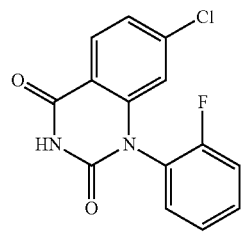

m/z [M + H]⁺ 291.0

1-(3-Bromophenyl)-7-chloroquinazoline-2,4(1H,3H)-dione was prepared by substituting 3-bromoaniline for o-toluidine.

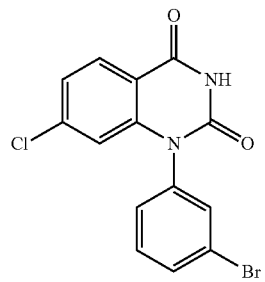

m/z [M + H]⁺ 351.0

7-(1,1-Difluoroethyl)-1-(imidazo[1,2-a]pyridin-8-yl)quinazoline-2,4(1H,3H)-dione was prepared using 4-(1,1-difluoroethyl)-2-fluoro-N-(imidazo[1,2-a]pyridin-5-ylcarbamoyl)benzamide.

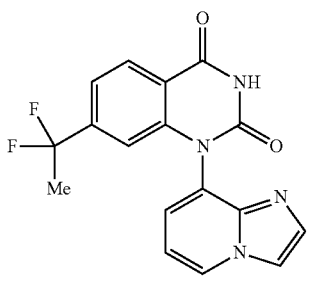

m/z [M + H]⁺ 343.0.

7-cyclopropyl-2,4-dioxo-1-(o-tolyl)-1,2,3,4-tetrahydroquinazoline-6-carbonitrile was prepared using 5-cyano-4-cyclopropyl-2-fluoro-N-(o-tolylcarbamoyl)benzamide.

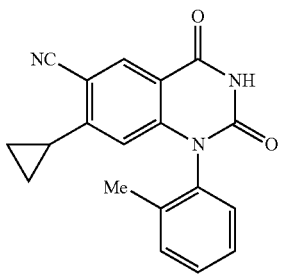

m/z [M + H]⁺ 318.0.

7-Chloro-1-(imidazo[1,2-a]pyridin-5-yl)quinazoline-2,4(1H,3H)-dione was prepared using 4-chloro-2-fluoro-N-(imidazo[1,2-a]pyridin-5-ylcarbamoyl)benzamide.

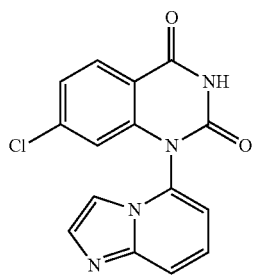

m/z [M + H]⁺ 313.0.

7-Chloro-1-(imidazo[1,2-a]pyridin-7-yl)quinazoline-2,4(1H,3H)-dione was prepared using 4-chloro-2-fluoro-N-(imidazo[1,2-a]pyridin-7-ylcarbamoyl)benzamide.

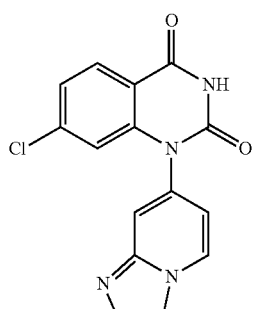

m/z [M + H]⁺ 313.0.

1-(2-Chlorophenyl)-7-cyclopropylquinazoline-2,4(1H,3H)-dione was prepared using N-((2-chlorophenyl)carbamoyl)-4-cyclopropyl-2-fluorobenzamide.

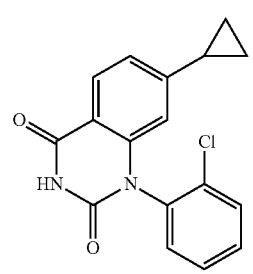

m/z [M+H]⁺ 313.00.

Reference 7

Synthesis of 6-bromo-1-(2-chlorophenyl)-7-cyclopropylquinazoline-2,4(1H,3H)-dione

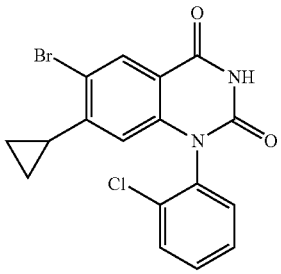 [SMILES: O=c1[nH]c(=O)n(-c2ccccc2Cl)c2cc(C3CC3)c(Br)cc12]

Step 1: Synthesis of 4-cyclopropyl-2-fluorobenzamide

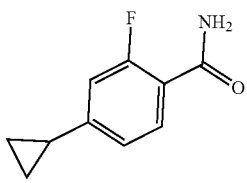 [SMILES: NC(=O)c1ccc(C2CC2)cc1F]

A vial was charged with 4-bromo-2-fluorobenzamide (1 equiv), cyclopropylboronic acid (3 equiv) and 1,1'-bis(diphenylphosphino)ferrocene dichloropalladium (II) (0.1 equiv). A 1:1 mixture of toluene:t-butanol (0.1 M) was added followed by aqueous potassium carbonate (2 M, 4 equiv). The reaction mixture was heated to 100° C. for 2 h and then cooled. The crude reaction mixture was diluted with ethyl acetate, filtered and concentrated under reduced pressure. The residue was purified by flash column chromatography (0-100% ethyl acetate/hexane) to give the title compound.

Step 2: Synthesis of 5-bromo-4-cyclopropyl-2-fluorobenzamide

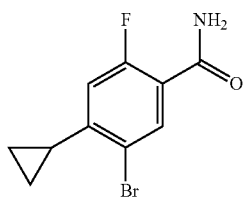 [SMILES: NC(=O)c1cc(Br)c(C2CC2)cc1F]

A vial was charged with 4-cyclopropyl-2-fluorobenzamide (1 equiv) and N-bromo-succinimide (1.2 equiv). Trifluoroacetic acid (0.5 M) as added followed by a catalytic amount of sulfuric acid. The reaction mixture was heated to 40° C. for 2 h and then cooled. The crude reaction mixture was poured into water and the title compound was collected by filtration.

Step 3: Synthesis of 5-bromo-N-((2-chlorophenyl)carbamoyl)-4-cyclopropyl-2-fluorobenzamide

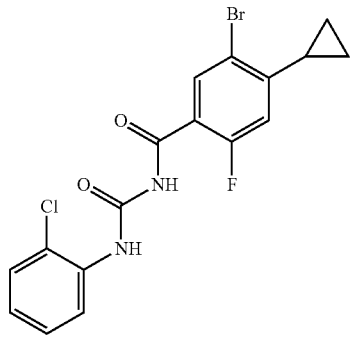 [SMILES: O=C(NC(=O)c1cc(Br)c(C2CC2)cc1F)Nc1ccccc1Cl]

A slurry of 5-bromo-4-cyclopropyl-2-fluorobenzamide (1 equiv.) in DCE (0.5 M) was treated dropwise with oxalyl chloride (1.35 equiv.) at room temperature. The reaction mixture was then warmed to 55° C. for 1 h and was then further warmed to reflux for 20 h. The reaction mixture was concentrated in vacuo to afford the crude as a yellow oil. A solution of this crude isocyanate in DCE (1.2 M) at 0° C. was added dropwise to a cooled solution of 2-chloroaniline in DCE (0.4 M). The ice bath was removed and the reaction mixture stirred at room temperature for 45 min. The solids were filtered, washed with DCM, and dried to obtain the title compound as a white solid.

Step 4: Synthesis of 6-bromo-1-(2-chlorophenyl)-7-cyclopropylquinazoline-2,4(1H,3H)-dione

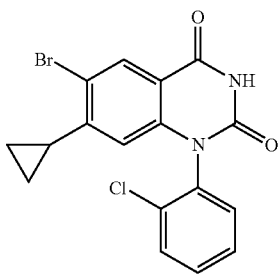 [SMILES: O=c1[nH]c(=O)n(-c2ccccc2Cl)c2cc(C3CC3)c(Br)cc12]

A slurry of 5-bromo-N-((2-chlorophenyl)carbamoyl)-4-cyclopropyl-2-fluorobenzamide in DME:toluene (0.06 M, 1:1 v/v) was cooled to 0° C. and treated portion-wise with NaH (60% dispersion in oil, 3.1 equiv). After addition, the ice-bath was removed and the reaction mixture was warmed to reflux for 18 h. The reaction mixture was cooled to RT and poured into 20% aq. HCl. The resulting mixture was stirred vigorously and the off-white solid was filtered, washed with Et$_2$O, dried to obtain crude product which was used in the next step without purification. m/z [M+H]$^+$ 392.0.

Reference 8

Synthesis of 2,4-dichloro-N-(pyrazin-2-ylcarbamoyl)benzamide

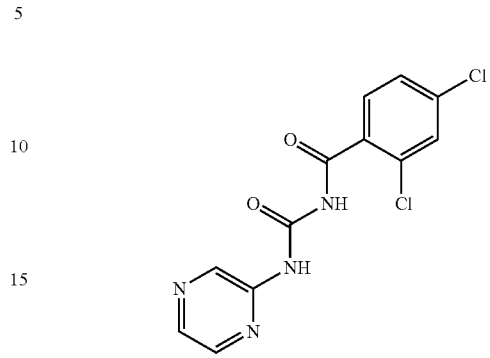

A slurry of 2,4-dichlorobenzamide (1 equiv.) in DCE (0.5 M) was treated dropwise with oxalyl chloride (1.35 equiv.) at room temperature. The reaction mixture was then warmed to 55° C. for 1 h and was then further warmed to reflux for 20 h. The reaction mixture was concentrated in vacuo to afford the crude 2,4-dichlorobenzoylisocyanate as a yellow oil. A solution of this crude product in DCE (1.2 M) at 0° C. was added dropwise to a cooled solution of pyrazin-2-amine in DCE (0.4 M). The ice bath was removed and the reaction mixture stirred at room temperature for 45 min. The solids were then filtered, washed with DCM, and dried to obtain the title compound as a white solid. m/z [M+H]$^+$ 311.0.

Proceeding analogously as described above, the following compounds were prepared.

2,4-Dichloro-N-(pyridin-2-ylcarbamoyl)benzamide

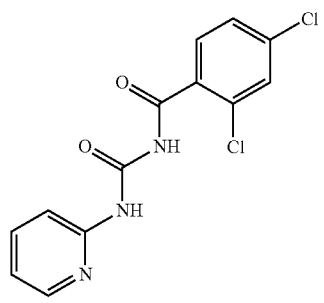

m/z [M+H]$^+$ 312.0

2,4-Dichloro-N-(pyrimidin-2-ylcarbamoyl)benzamide was prepared using 2,4-dichlorobenzamide and pyridin-2-amine.

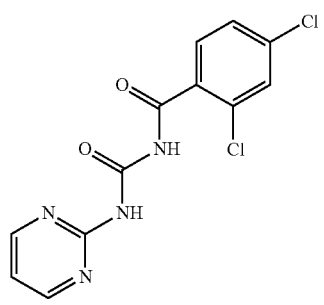

m/z [M+H]$^+$ 312.0.

497

2,4-Dichloro-N-(pyridazin-3-ylcarbamoyl)benzamide was prepared using 2,4-dichlorobenzamide and pyridazin-3-amine.

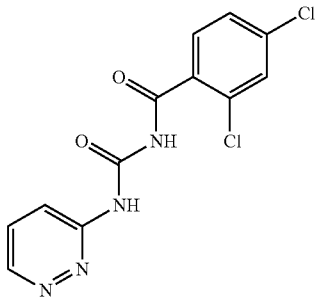

m/z [M+H]⁺ 311.0

2,4-Dichloro-N-(pyrimidin-5-ylcarbamoyl)benzamide was prepared using 2,4-dichlorobenzamide and pyrimidin-5-amine.

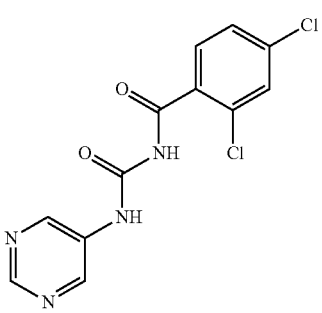

m/z [M+H]⁺ 311.0

N-((1H-pyrazol-4-yl)carbamoyl)-2,4-dichlorobenzamide was prepared using 2,4-dichlorobenzamide and 1H-pyrazol-4-amine.

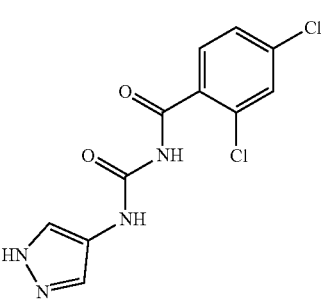

m/z [M+H]⁺ 299.0

498

N-((1H-imidazol-2-yl)carbamoyl)-2,4-dichlorobenzamide was prepared using 2,4-dichlorobenzamide and 1H-imidazol-2-amine.

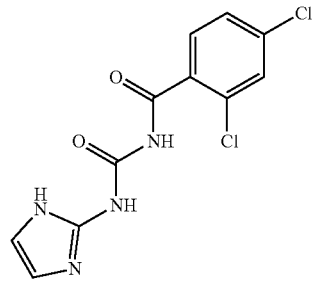

m/z [M+H]⁺ 299.0

2,4-Dichloro-N-(thiazol-2-ylcarbamoyl)benzamide was prepared using 2,4-dichlorobenzamide and thiazol-2-amine.

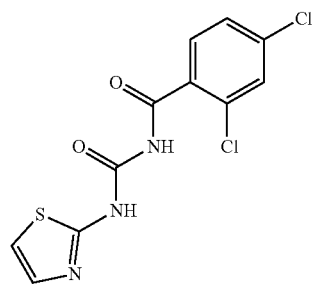

m/z [M+H]⁺ 316.0

2,4-Dichloro-N-(thiazol-5-ylcarbamoyl)benzamide was prepared using 2,4-dichlorobenzamide and thiazol-5-amine.

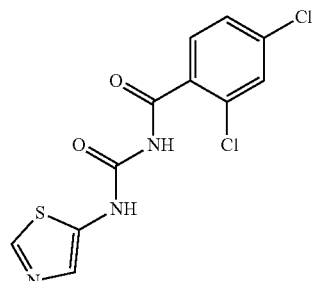

m/z [M+H]⁺ 316.0

N-((1H-Pyrazol-5-yl)carbamoyl)-2,4-dichlorobenzamide was prepared using 2,4-dichlorobenzamide and 1H-pyrazol-5-amine.

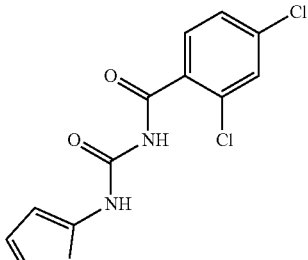

m/z [M + H]⁺ 299.0

2-Chloro-N-((2-chlorophenyl)carbamoyl)-6-(trifluoromethyl)nicotinamide was prepared using 2-chloro-6-(trifluoromethyl)nicotinamide and 2-chloroaniline.

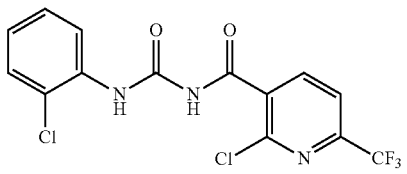

m/z [M + H]⁺ 377.98.

2-Chloro-N-((3-methylpyridin-2-yl)carbamoyl)-6-(trifluoromethyl)nicotinamide was prepared using 2-chloro-6-(trifluoromethyl)nicotinamide and 3-methylpyridin-2-amine.

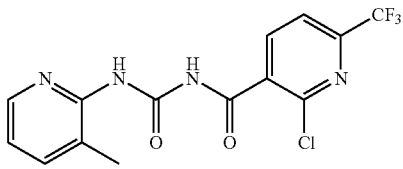

m/z [M + H]⁺ 359.24

2-Chloro-N-((3-chloropyridin-2-yl)carbamoyl)-6-(trifluoromethyl)nicotinamide was prepared using 2-chloro-6-(trifluoromethyl)nicotinamide and 3-chloropyridin-2-amine.

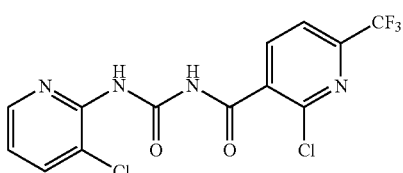

m/z [M + H]⁺ 379.22

2-Chloro-6-isopropyl-N-(phenylcarbamoyl)nicotinamide was prepared using 2-chloro-6-isopropylnicotinamidenicotinamide and aniline.

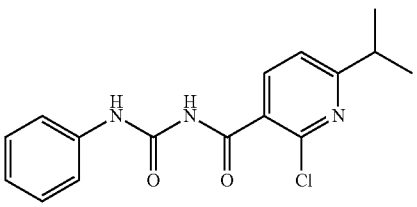

m/z [M + H]⁺ 318.1

2,6-Difluoro-N-(phenylcarbamoyl)-4-(trifluoromethyl)benzamide was prepared using 2,6-difluoro-4-(trifluoromethyl)benzamide and aniline.

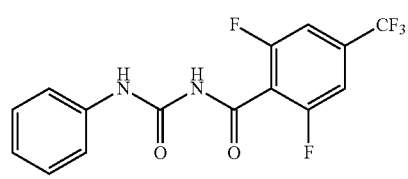 [SMILES: O=C(NC(=O)c1c(F)cc(C(F)(F)F)cc1F)Nc1ccccc1]

2-Fluoro-N-((2-methylpyridin-3-yl)carbamoyl)-4-(trifluoromethyl)benzamide was prepared using 2-fluoro-4-(trifluoromethyl)benzamide and 2-methylpyridin-3-amine.

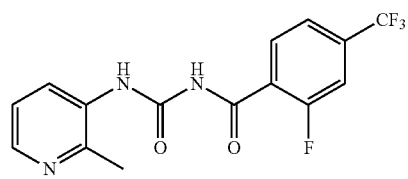 [SMILES: Cc1ncccc1NC(=O)NC(=O)c1ccc(C(F)(F)F)cc1F]

N-((2-Chlorophenyl)carbamoyl)-2-fluoro-4-(trifluoromethoxy)benzamide was prepared using 2-fluoro-4-(trifluoromethoxy)benzamide and 2-methylpyridin-3-amine.

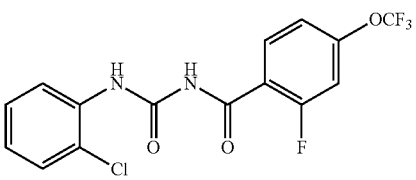

m/z [M + H]⁺ 377.27.

4-Bromo-5-chloro-N-((2-chlorophenyl)carbamoyl)-2-fluorobenzamide was prepared using 4-bromo-5-chloro-2-fluorobenzamide and 2-chloroaniline.

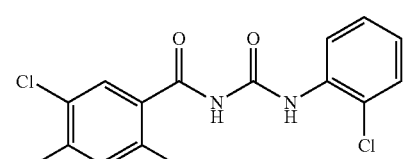

m/z [M + H]⁺ 406.9 (major).

4-Cyclopropyl-2-fluoro-N-((2-(trifluoromethyl)pyridin-3-yl)carbamoyl)benzamide was prepared using 4-cyclopropyl-2-fluorobenzamide and 2-(trifluoromethyl)pyridin-3-amine.

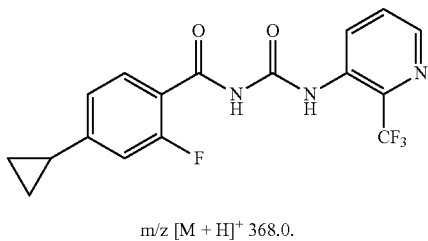 [SMILES: O=C(NC(=O)c1ccc(C2CC2)cc1F)Nc1cccnc1C(F)(F)F]

m/z [M + H]⁺ 368.0.

4-Cyclopropyl-N-((2-(difluoromethoxy)pyridin-3-yl)carbamoyl)-2-fluorobenzamide was prepared using 4-cyclopropyl-2-fluorobenzamide and 2-(trifluoromethoxy)pyridin-3-amine.

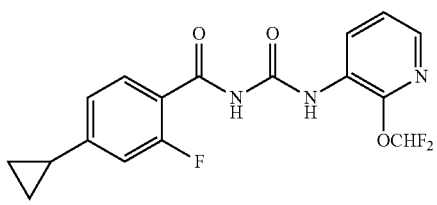

m/z [M + H]⁺ 366.1.

Reference 9

Synthesis of 7-chloro-1-(pyrazin-2-yl)quinazoline-2,4(1H,3H)-dione

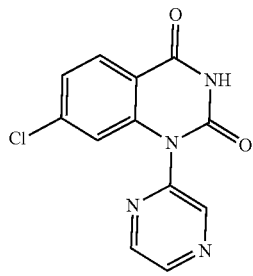 [SMILES: O=c1[nH]c(=O)n(-c2cnccn2)c2cc(Cl)ccc12]

A slurry of 2,4-dichloro-N-(pyrazin-2-ylcarbamoyl)benzamide in DMF (0.06 M) at rt was treated dropwise with KHMDS (3 equiv). The reaction mixture was heated to 95° C. for 18 h. Water was added to the reaction mixture upon completion to fully solubilize the product, which was immediately purified via reverse phase column chromatography (20-60% MeCN/water, 0.1% formic acid) to give the title compound. m/z [M+H]⁺ 276.0

Proceeding analogously as described above, the following compounds were prepared by substituting 2,4-dichloro-N-(pyrazin-2-ylcarbamoyl)benzamide:

7-Chloro-1-(pyridin-2-yl)quinazoline-2,4(1H,3H)-dione was prepared by using 2,4-dichloro-N-(pyridin-2-ylcarbamoyl)benzamide

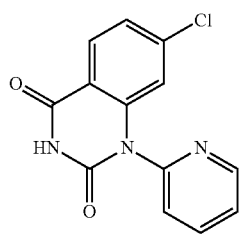

m/z [M + H]⁺ 274.0.

7-Chloro-1-(pyrimidin-2-yl)quinazoline-2,4(1H,3H)-dione was prepared by using 2,4-dichloro-N-(pyrimidin-2-ylcarbamoyl)benzamide

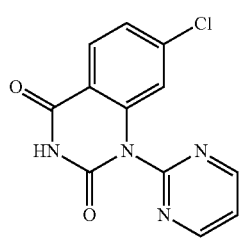

m/z [M + H]+ 276.0

7-Chloro-1-(pyridazin-3-yl)quinazoline-2,4(1H,3H)-dione was prepared by using 2,4-dichloro-N-(pyridazin-3-ylcarbamoyl)benzamide

m/z [M + H] ⁺ 276.0

7-Chloro-1-(pyrimidin-5-yl)quinazoline-2,4(1H,3H)-dione was prepared by using 2,4-dichloro-N-(pyrimidin-5-ylcarbamoyl)benzamide

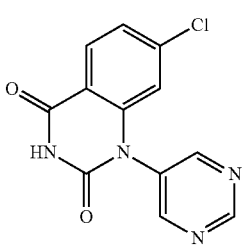 [SMILES: O=c1[nH]c(=O)n(-c2cncnc2)c2cc(Cl)ccc12]

503

7-Chloro-1-(1H-pyrazol-4-yl)quinazoline-2,4(1H,3H)-dione was prepared by using N-((1H-pyrazol-4-yl)carbamoyl)-2,4-dichlorobenzamide

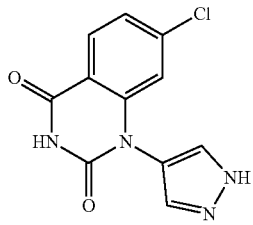 [SMILES: O=c1[nH]c(=O)n(-c2cn[nH]c2)c2cc(Cl)ccc12]

7-Chloro-1-(1H-imidazol-2-yl)quinazoline-2,4(1H,3H)-dione was prepared by using N-((1H-imidazol-2-yl)carbamoyl)-2,4-dichlorobenzamide

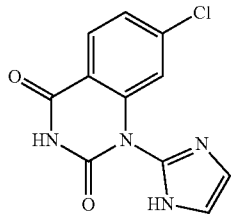 [SMILES: O=c1[nH]c(=O)n(-c2ncc[nH]2)c2cc(Cl)ccc12]

7-Chloro-1-(thiazol-2-yl)quinazoline-2,4(1H,3H)-dione was prepared by using 2,4-dichloro-N-(thiazol-2-ylcarbamoyl)benzamide

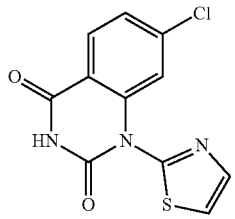

7-Chloro-1-(thiazol-5-yl)quinazoline-2,4(1H,3H)-dione was prepared by using 2,4-dichloro-N-(thiazol-5-ylcarbamoyl)benzamide

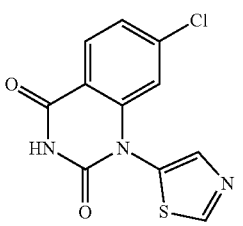 [SMILES: O=c1[nH]c(=O)n(-c2cncs2)c2cc(Cl)ccc12]

504

7-Chloro-1-(1-pyrazol-5-yl)quinazoline-2,4(1H,3H)-dione as prepared by using N-((1H-pyrazol-5-yl)carbamoyl)-2,4-dichlorobenzamide

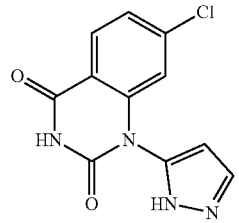 [SMILES: O=c1[nH]c(=O)n(-c2ccn[nH]2)c2cc(Cl)ccc12]

1-(2-Chlorophenyl)-7-(trifluoromethyl)pyrido[2,3-d]pyrimidine-2,4(1H,3H)-dione was prepared by using N-((2-chlorophenyl)carbamoyl)-2-fluoro-6-(trifluoromethyl)nicotinamide

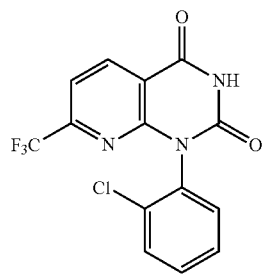 [SMILES: O=c1[nH]c(=O)n(-c2ccccc2Cl)c2nc(C(F)(F)F)ccc12]

1-(3-Chloropyridin-2-yl)-7-(trifluoromethyl)pyrido[2,3-d]pyrimidine-2,4(1H,3H)-dione was prepared by using N-((2-chlorophenyl)carbamoyl)-2-fluoro-6-(trifluoromethyl)nicotinamide

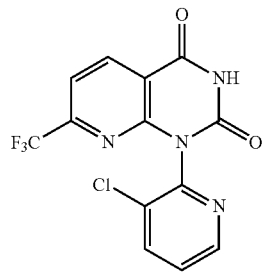 [SMILES: O=c1[nH]c(=O)n(-c2ncccc2Cl)c2nc(C(F)(F)F)ccc12]

1-(3-Methylpyridin-2-yl)-7-(trifluoromethyl)pyrido[2,3-d]pyrimidine-2,4(1H,3H)-dione by using 2-fluoro-N-((3-methylpyridin-2-yl)carbamoyl)-6-(trifluoromethyl)nicotinamide

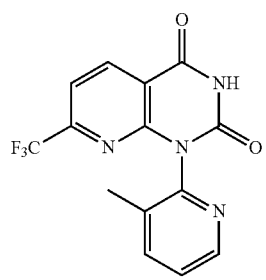 [SMILES: Cc1cccnc1-n1c(=O)[nH]c(=O)c2ccc(C(F)(F)F)nc21]

505

7-Isopropyl-1-phenylpyrido[2,3-d]pyrimidine-2,4(1H,3H)-dione by using 2-fluoro-6-isopropyl-N-(phenylcarbamoyl)nicotinamide

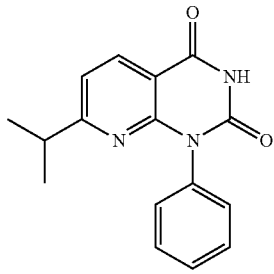 [SMILES: CC(C)c1ccc2c(=O)[nH]c(=O)n(-c3ccccc3)c2n1]

5-Fluoro-1-phenyl-7-(trifluoromethyl)quinazoline-2,4(1H,3H)-dione was prepared by using 2,6-difluoro-N-(phenylcarbamoyl)-4-(trifluoromethyl)benzamide

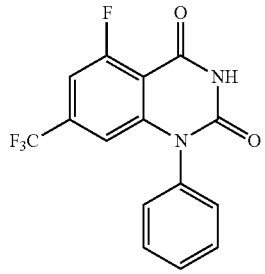 [SMILES: O=c1[nH]c(=O)n(-c2ccccc2)c2cc(C(F)(F)F)cc(F)c12]

1-(2-Methylpyridin-3-yl)-7-(trifluoromethyl)quinazoline-2,4(1H,3H)-dione was prepared by using 2-fluoro-N-((2-methylpyridin-3-yl)carbamoyl)-4-(trifluoromethyl)benzamide

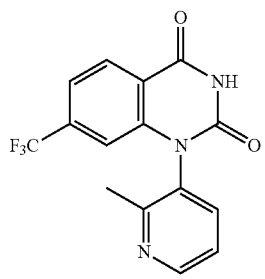 [SMILES: Cc1ncccc1-n1c(=O)[nH]c(=O)c2ccc(C(F)(F)F)cc21]

1-(2-Chlorophenyl)-7-(trifluoromethoxy)quinazoline-2,4(1H,3H)-dione was prepared by using N-((2-chlorophenyl)carbamoyl)-2-fluoro-4-(trifluoromethoxy)benzamide

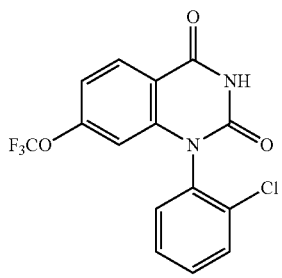 [SMILES: O=c1[nH]c(=O)n(-c2ccccc2Cl)c2cc(OC(F)(F)F)ccc12]

506

7-Bromo-6-chloro-1-(2-chlorophenyl)quinazoline-2,4(1H,3H)-dione was prepared by using 4-bromo-5-chloro-N-((2-chlorophenyl)carbamoyl)-2-fluorobenzamide

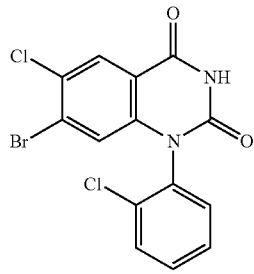 [SMILES: O=c1[nH]c(=O)n(-c2ccccc2Cl)c2cc(Br)c(Cl)cc12]

7-Cyclopropyl-1-(2-(trifluoromethyl)pyridin-3-yl)quinazoline-2,4(1H,3H)-dione was prepared by using 4-cyclopropyl-2-fluoro-N-((2-(trifluoromethyl)pyridin-3-yl)carbamoyl)benzamide

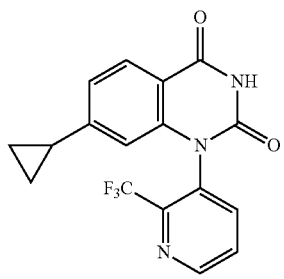 [SMILES: O=c1[nH]c(=O)n(-c2cccnc2C(F)(F)F)c2cc(C3CC3)ccc12]

7-Cyclopropyl-1-(2-(difluoromethoxy)pyridin-3-yl)quinazoline-2,4(1H,3H)-dione was prepared by using 4-cyclopropyl-N-((2-(difluoromethoxy)pyridin-3-yl)carbamoyl)-2-fluorobenzamide

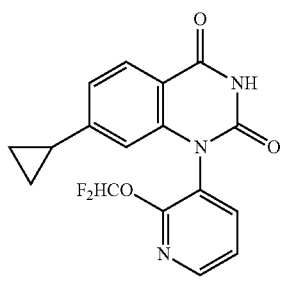

m/z [H + M]$^+$ 346.1

1-(2-Chlorophenyl)-7-(1,1-difluoroethyl)quinazoline-2,4(1H,3H)-dione was prepared by using N-((2-chlorophenyl)carbamoyl)-4-(1,1-difluoroethyl)-2-fluorobenzamide

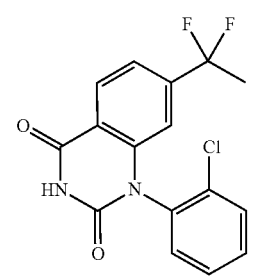 [SMILES: CC(F)(F)c1ccc2c(=O)[nH]c(=O)n(-c3ccccc3Cl)c2c1]

7-Chloro-1-(2-fluorophenyl)pyrido[2,3-d]pyrimidine-2,4 (1H,3H)-dione was prepared by using 2,6-dichloro-N-((2-fluorophenyl)carbamoyl)nicotinamide.

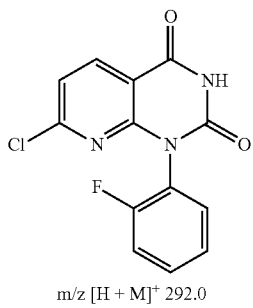 [SMILES: O=c1[nH]c(=O)n(-c2ccccc2F)c2nc(Cl)ccc12]

m/z [H + M]+ 292.0

7-Chloro-1-(2-chlorophenyl)pyrido[2,3-d]pyrimidine-2,4 (1H,3H)-dione was prepared by using 2,6-dichloro-N-((2-chlorophenyl)carbamoyl)nicotinamide.

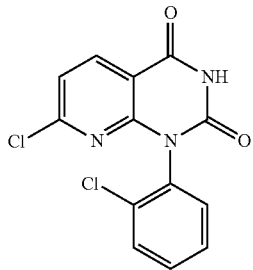

m/z [H + M]+ 308.0

7-Chloro-1-(o-tolyl)pyrido[2,3-d]pyrimidine-2,4(1H,3H)-dione was prepared by using 2,6-dichloro-N-(o-tolylcarbamoyl)nicotinamide

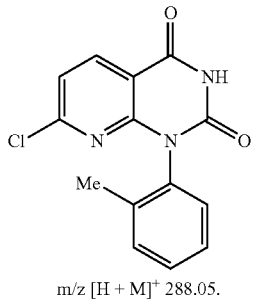 [SMILES: Cc1ccccc1-n1c(=O)[nH]c(=O)c2ccc(Cl)nc21]

m/z [H + M]+ 288.05.

7-Chloro-1-phenylpyrido[2,3-d]pyrimidine-2,4(1H,3H)-dione was prepared by using 2,6-dichloro-N-(phenylcarbamoyl)nicotinamide.

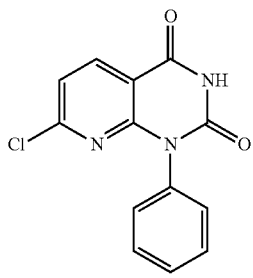

m/z [H + M]+ 374.05

7-Chloro-1-(pyridin-3-yl)pyrido[2,3-d]pyrimidine-2,4 (1H,3H)-dione was prepared by using 2,6-dichloro-N-(pyridin-3-ylcarbamoyl)nicotinamide.

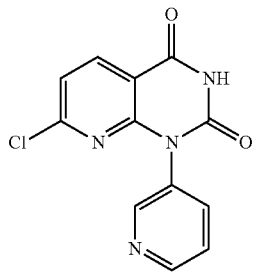

m/z [H + M]+ 275.0

6-Bromo-1-phenyl-7-(trifluoromethoxy)quinazoline-2,4 (1H,3H)-dione was prepared by using 5-bromo-2-fluoro-N-(phenylcarbamoyl)-4-(trifluoromethoxy)benzamide.

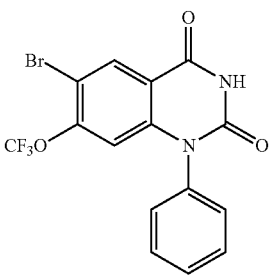

m/z [H + M]+ 402.9, 400.9

6-Bromo-1-(o-tolyl)-7-(trifluoromethoxy)quinazoline-2,4(1H,3H)-dione was prepared by using 5-bromo-2-fluoro-N-(o-tolylcarbamoyl)-4-(trifluoromethoxy)benzamide.

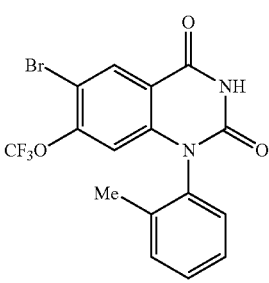

m/z [H + M]+ 416.9, 414.9

7-Cyclopropyl-1-(3-(trifluoromethyl)pyrazin-2-yl)quinazoline-2,4(1H,3H)-dione was prepared by using 2-chloro-4-cyclopropyl-N-((3-(trifluoromethyl)pyrazin-2-yl)carbamoyl)benzamide.

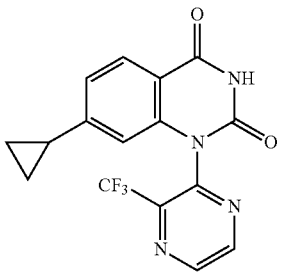

m/z [H + M]+ 349.0.

509

1-(Imidazo[1,2-a]pyridin-5-yl)-7-(trifluoromethoxy)quinazoline-2,4(1H,3H)-dione was prepared by using 2-fluoro-N-(imidazo[1,2-a]pyridin-5-ylcarbamoyl)-4-(trifluoromethoxy)benzamide.

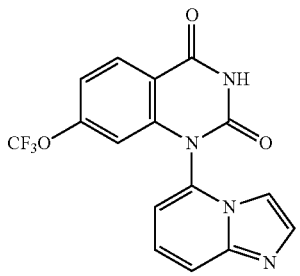

m/z [H + M]⁺ 363.0.

1-(Pyridazin-3-yl)-7-(trifluoromethyl)quinazoline-2,4(1H,3H)-dione was prepared by using 2-fluoro-N-(pyridazin-3-ylcarbamoyl)-4-(trifluoromethyl)benzamide.

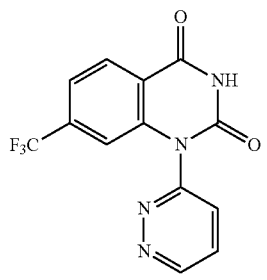

m/z [H + M]⁺ 309.05.

1-(Pyrazin-2-yl)-7-(trifluoromethyl)quinazoline-2,4(1H,3H)-dione was prepared by using 2-fluoro-N-(pyrazin-2-ylcarbamoyl)-4-(trifluoromethyl)benzamide.

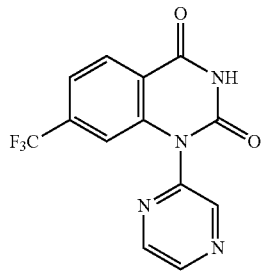

m/z [H + M]⁺ 309.05.

510

7-Cyclopropyl-1-(imidazo[1,2-a]pyridin-7-yl)quinazoline-2,4(1H,3H)-dione was prepared by using 4-cyclopropyl-2-fluoro-N-(imidazo[1,2-a]pyridin-7-ylcarbamoyl)benzamide.

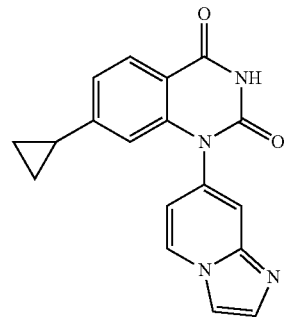

m/z [H + M]⁺ 319.00

5-Fluoro-7-(trifluoromethyl)-1-(2-(trifluoromethyl)pyridin-3-yl)quinazoline-2,4(1H,3H)-dione was prepared by using 2,6-difluoro-4-(trifluoromethyl)-N-((2-(trifluoromethyl)pyridin-3-yl)carbamoyl)benzamide.

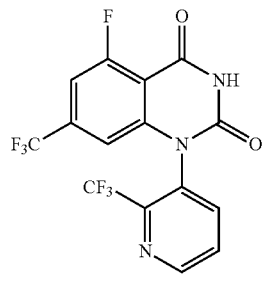

m/z [H + M]⁺ 394.00.

7-Cyclopropyl-1-(imidazo[1,2-a]pyridin-5-yl)quinazoline-2,4(1H,3H)-dione was prepared by using 4-cyclopropyl-2-fluoro-N-(imidazo[1,2-a]pyridin-5-ylcarbamoyl)benzamide.

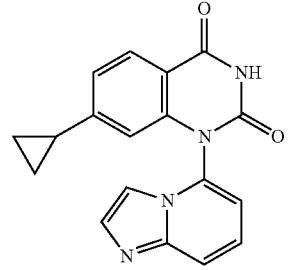 [SMILES: O=c1[nH]c(=O)n(-c2cccc3nccn23)c2cc(C3CC3)ccc12]

7-Cyclopropyl-1-(pyrazin-2-yl)quinazoline-2,4(1H,3H)-dione was prepared by using 4-cyclopropyl-2-fluoro-N-(pyrazin-2-ylcarbamoyl)benzamide.

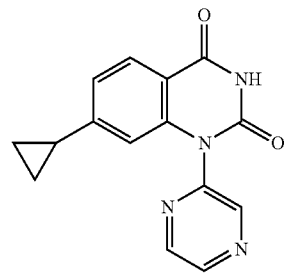

m/z [M + H]⁺ 281.00.

7-Cyclopropyl-1-(3-methylpyrazin-2-yl)quinazoline-2,4 (1H,3H)-dione was prepared by using 4-cyclopropyl-2-fluoro-N-((3-methylpyrazin-2-yl)carbamoyl)benzamide.

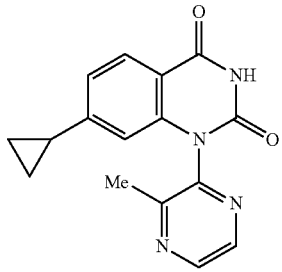

m/z [M + H]+ 295.00.

1-(3-Chloropyridin-2-yl)-7-ethylquinazoline-2,4(1H,3H)-dione was prepared by using N-((3-chloropyridin-2-yl)carbamoyl)-4-ethyl-2-fluorobenzamide

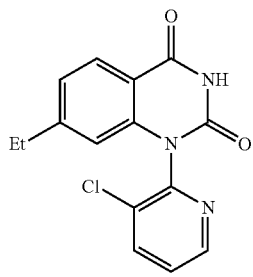

m/z [M + H]+ 302.0.

1-(3-Chloropyridin-2-yl)-7-(1,1-difluoroethyl)quinazoline-2,4(1H,3H)-dione was prepared by using N-((3-chloropyridin-2-yl)carbamoyl)-4-(1,1-difluoroethyl)-2-fluorobenzamide.

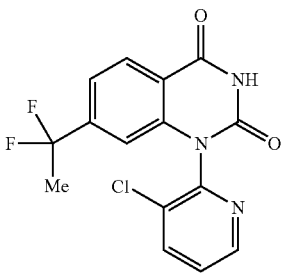

m/z [M + H]+ 338.0.

7-(1,1-Difluoroethyl)-1-(imidazo[1,2-a]pyridin-7-yl)quinazoline-2,4(1H,3H)-dione was prepared by using 4-(1,1-difluoroethyl)-2-fluoro-N-(imidazo[1,2-a]pyridin-7-ylcarbamoyl)benzamide.

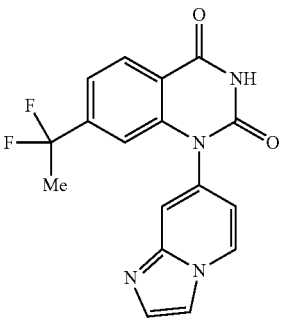

m/z [M + H]+ 343.0.

1-(2-Chlorophenyl)-2,4-dioxo-7-(trifluoromethyl)-1,2,3,4-tetrahydroquinazoline-6-carbonitrile was prepared using N-((2-chlorophenyl)carbamoyl)-5-cyano-2-fluoro-4-(trifluoromethyl)benzamide.

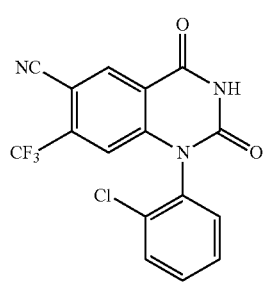

m/z [M + H]+ 366.0.

7-Bromo-1-(2-chlorophenyl)-6-fluoroquinazoline-2,4(1H,3H)-dione was prepared by using 4-bromo-N-((2-chlorophenyl)carbamoyl)-2,5-difluorobenzamide.

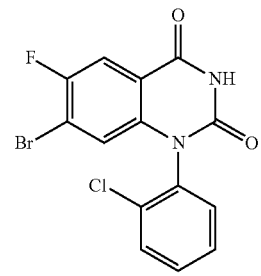 [SMILES: O=c1[nH]c(=O)n(-c2ccccc2Cl)c2cc(Br)c(F)cc12]

513

1-(2-Chloropyridin-3-yl)-7-(trifluoromethyl)pyrido[2,3-d]pyrimidine-2,4(1H,3H)-dione was prepared by using 2-chloro-N-((2-chloropyridin-3-yl)carbamoyl)-6-(trifluoromethyl)nicotinamide.

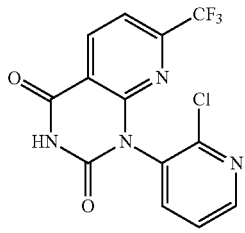 [SMILES: O=c1[nH]c(=O)n(-c2cccnc2C(F)(F)F)c2nc(C(F)(F)F)ccc12]

m/z [M + H]+ 343.1

7-(Trifluoromethyl)-1-(2-(trifluoromethyl)pyridin-3-yl)pyrido[2,3-d]pyrimidine-2,4(1H,3H)-dione was prepared by using 2-Chloro-6-(trifluoromethyl)-N-((2-(trifluoromethyl)pyridin-3-yl)carbamoyl)nicotinamide.

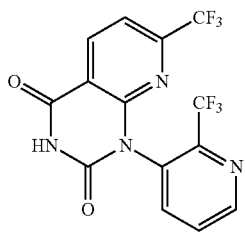

6-Bromo-7-cyclopropyl-1-(2-(trifluoromethyl)phenyl)quinazoline-2,4(1H,3H)-dione was prepared by using 5-bromo-4-cyclopropyl-2-fluoro-N-((2-(trifluoromethyl)phenyl)-carbamoyl)benzamide.

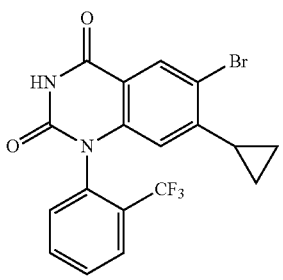

m/z [M + H]+ 425.27.

6-Bromo-7-cyclopropyl-1-(2-cyclopropylphenyl)quinazoline-2,4(1H,3H)-dione was prepared by using 5-bromo-4-cyclopropyl-N-((2-cyclopropylphenyl)carbamoyl)-2-fluorobenzamide.

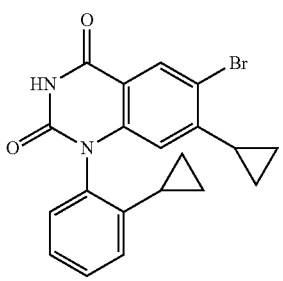

m/z [M + H]+ 397.36.

514

6-Bromo-1-(2-bromophenyl)-7-cyclopropylquinazoline-2,4(1H,3H)-dione was prepared by using 5-bromo-N-((2-bromophenyl)carbamoyl)-4-cyclopropyl-2-fluorobenzamide.

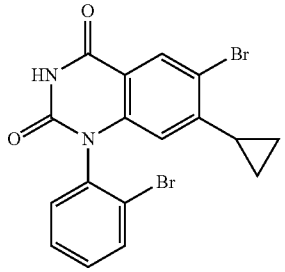

m/z [M + H]+ 435.24.

6-Bromo-7-cyclopropyl-1-(2-(trifluoromethyl)pyridin-3-yl)quinazoline-2,4(1H,3H)-dione was prepared by using 5-bromo-4-cyclopropyl-2-fluoro-N-((2-(trifluoromethyl)pyridin-3-yl)carbamoyl)benzamide.

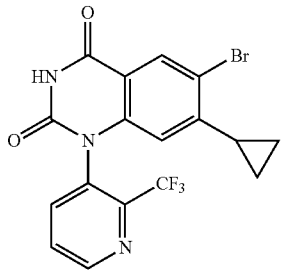 [SMILES: O=c1[nH]c(=O)n(-c2cccnc2C(F)(F)F)c2cc(C3CC3)c(Br)cc12]

5-Chloro-1-(o-tolyl)-7-(trifluoromethyl)quinazoline-2,4(1H,3H)-dione was prepared by using 2,6-dichloro-N-(o-tolylcarbamoyl)-4-(trifluoromethyl)benzamide.

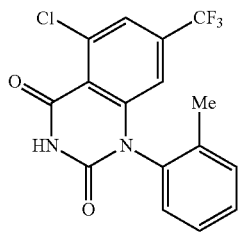

m/z [M + H]+ 355.29.

1-(2-Chloropyridin-3-yl)-7-cyclopropyl-5-methoxyquinazoline-2,4(1H,3H)-dione was prepared by using N-((2-chloropyridin-3-yl)carbamoyl)-4-cyclopropyl-2-fluoro-6-methoxybenzamide.

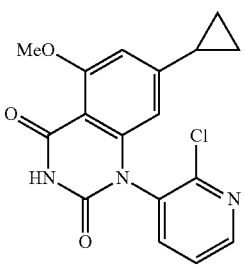

m/z [M + H]+ 344.33.

1-(2-Chloropyridin-3-yl)-7-cyclopropylquinazoline-2,4 (1H,3H)-dione was prepared by using N-((2-chloropyridin-3-yl)carbamoyl)-4-cyclopropyl-2-fluorobenzamide

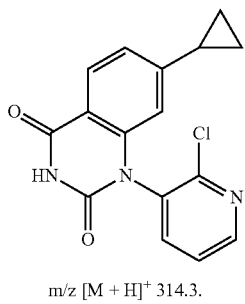 [SMILES: O=c1[nH]c(=O)n(-c2cccnc2Cl)c2cc(C3CC3)ccc12]

m/z [M + H]+ 314.3.

7-(Trifluoromethyl)-1-(1-(1-((2-(trimethylsilyl)ethoxy) methyl)-1H-imidazol-4-yl)ethyl)quinazoline-2,4(1H,3H)-dione was prepared by using 2-fluoro-4-(trifluoromethyl)-N-((1-(1-((2-(trimethylsilyl)ethoxy)methyl)-1H-imidazol-4-yl)ethyl)carbamoyl)benzamide.

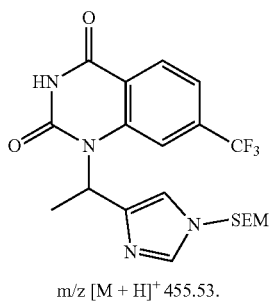 [SMILES: CC(c1cn(COCC[Si](C)(C)C)cn1)n1c(=O)[nH]c(=O)c2ccc(C(F)(F)F)cc21]

m/z [M + H]+ 455.53.

1-Phenyl-7-(trifluoromethyl)quinazoline-2,4(1H,3H)-dione was prepared by using 2-fluoro-N-(phenylcarbamoyl)-4-(trifluoromethyl)benzamide.

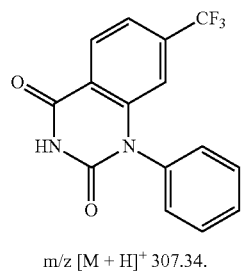 [SMILES: O=c1[nH]c(=O)n(-c2ccccc2)c2cc(C(F)(F)F)ccc12]

m/z [M + H]+ 307.34.

1-(3-Chloropyridin-2-yl)-7-cyclopropylquinazoline-2,4 (1H,3H)-dione was prepared by using N-((3-chloropyridin-2-yl)carbamoyl)-4-cyclopropyl-2-fluorobenzamide.

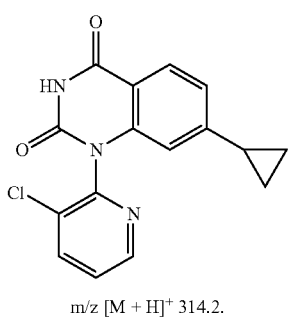 [SMILES: O=c1[nH]c(=O)n(-c2ncccc2Cl)c2cc(C3CC3)ccc12]

m/z [M + H]+ 314.2.

7-Cyclopropyl-1-(pyrimidin-5-yl)quinazoline-2,4(1H, 3H)-dione was prepared by with 4-cyclopropyl-2-fluoro-N-(pyrimidin-5-ylcarbamoyl)benzamide.

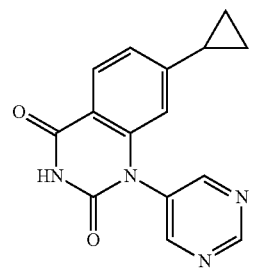 [SMILES: O=c1[nH]c(=O)n(-c2cncnc2)c2cc(C3CC3)ccc12]

7-(Trifluoromethyl)-1-((1-((2-(trimethylsilyl)ethoxy) methyl)-1H-imidazol-4-yl)methyl)quinazoline-2,4(1H,3H)-dione was prepared by using 2-fluoro-4-(trifluoromethyl)-N-(((1-((2-(trimethylsilyl)ethoxy)methyl)-1H-imidazol-5-yl)methyl)carbamoyl)benzamide.

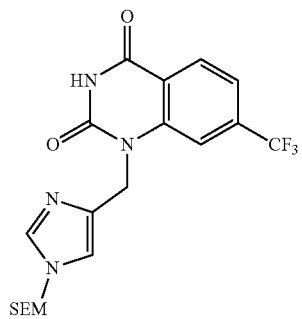

m/z [M + H]+ 441.34.

7-Cyclopropyl-1-((1-((2-(trimethylsilyl)ethoxy)methyl)-1H-imidazol-4-yl)methyl)quinazoline-2,4(1H,3H)-dione was prepared by using 2-chloro-4-cyclopropyl-N-(((1-((2-(trimethylsilyl)ethoxy)methyl)-1H-imidazol-5-yl) methyl) carbamoyl) benzamide.

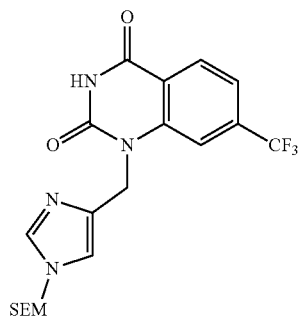

m/z [M + H]+ 413.47.

517

1-(2-Bromophenyl)-7-cyclopropylquinazoline-2,4(1H,3H)-dione was prepared by using N-((2-Bromophenyl)carbamoyl)-4-cyclopropyl-2-fluorobenzamide.

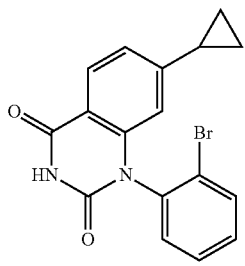

m/z [M + H]⁺ 357.24.

7-Cyclopropyl-5-methoxy-1-(pyridin-3-yl)quinazoline-2,4(1H,3H)-dione was prepared by using 4-cyclopropyl-2-fluoro-6-methoxy-N-(pyridin-3-ylcarbamoyl)benzamide.

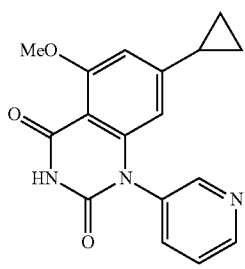

m/z [M + H]⁺ 310.28.

7-cyclopropyl-5-methoxy-1-(o-tolyl)quinazoline-2,4(1H,3H)-dione was prepared by using 4-cyclopropyl-2-fluoro-6-methoxy-N-(o-tolylcarbamoyl)benzamide.

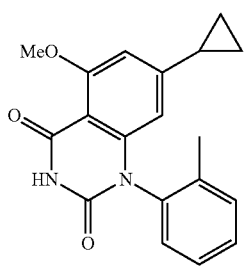

m/z [M +]⁺ 323.38.

7-Chloro-5-fluoro-1-(o-tolyl)quinazoline-2,4(1H,3H)-dione was prepared by using 4-chloro-2,6-difluoro-N-(o-tolylcarbamoyl)benzamide.

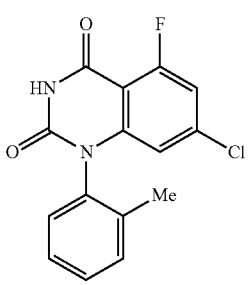

m/z [M + H]⁺ 305.20.

518

1-Benzyl-7-(trifluoromethyl)pyrido[2,3-d]pyrimidine-2,4(1H,3H)-dione was prepared by using N-(benzylcarbamoyl)-2-chloro-6-(trifluoromethyl)nicotinamide.

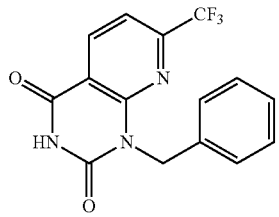

m/z [M + H]⁺ 322.2.

7-Cyclopropyl-1-(2-methylpyridin-3-yl)quinazoline-2,4(1H,3H)-dione was prepared by using 4-cyclopropyl-2-fluoro-N-((2-methylpyridin-3-yl)carbamoyl)benzamide.

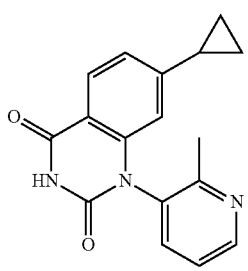

m/z [M + H]⁺ 294.2.

1-(2-Chloro-6-fluorophenyl)-7-(trifluoromethyl)pyrido[2,3-d]pyrimidine-2,4(1H,3H)-dione was prepared by using 2-chloro-N-((2-chloro-6-fluorophenyl)carbamoyl)-6-(trifluoromethyl)nicotinamide.

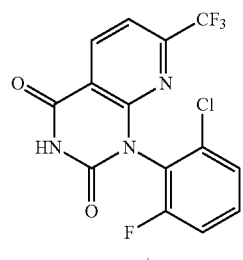

m/z [M + H]⁺ 360.2.

5-methoxy-1-phenyl-7-(trifluoromethyl)pyrido[2,3-d]pyrimidine-2,4(1H,3H)-dione was prepared by using 2-chloro-4-methoxy-N-(phenylcarbamoyl)-6-(trifluoromethyl)nicotinamide.

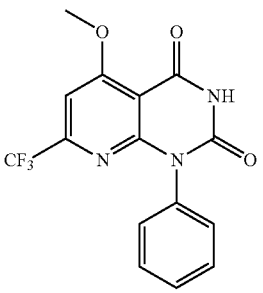

m/z [M + H]⁺ 338.26.

Reference 10

Synthesis of 7-chloro-6-fluoro-1-phenylquinazoline-2,4(1H,3H)-dione

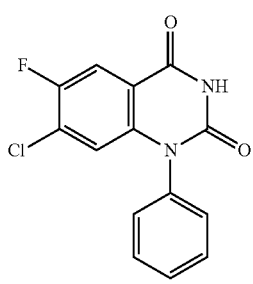 [SMILES: O=c1[nH]c(=O)n(-c2ccccc2)c2cc(Cl)c(F)cc12]

Step 1: Synthesis of 4-chloro-2,5-difluorobenzamide

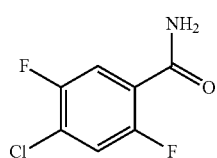

To a stirred solution of 4-chloro-2,5-difluorobenzoic acid (1 equiv) in THF (0.9 M) were added DIPEA (5 equiv), HATU (1.2 equiv) and NH$_3$ (0.4 M in THF, 3 equiv) in a sealed flask at 0° C. The resulting reaction mixture was stirred at room temperature for 16 h, and the reaction progress was monitored by TLC. The reaction mixture was stirred with crushed ice for 2 h, then filtered and dried under high vacuum to afford 4-chloro-2,5-difluorobenzamide as a white solid.

Step 2: Synthesis of 4-chloro-2,5-difluoro-N-(phenylcarbamoyl)benzamide

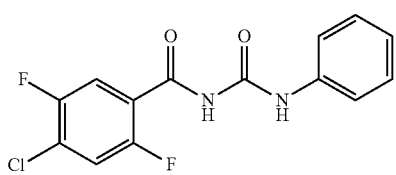 [SMILES: O=C(NC(=O)c1cc(F)c(Cl)cc1F)Nc1ccccc1]

To a stirred solution of 4-chloro-2,5-difluorobenzamide (1 equiv) in toluene (0.5 M) was added phenyl isocynate (1 equiv) and the resulting reaction mixture was refluxed for 16 h. The reaction mixture was diluted with EtOAc then washed with water. The combined organic layers were separated, dried over anhydrous sodium sulfate, and then concentrated. The crude was purified by column chromatography (10% EtOAc/Hexanes) to afford the title compound as an off white solid.

Step 3: Synthesis of 7-chloro-6-fluoro-1-phenylquinazoline-2,4(1H,3H)-dione

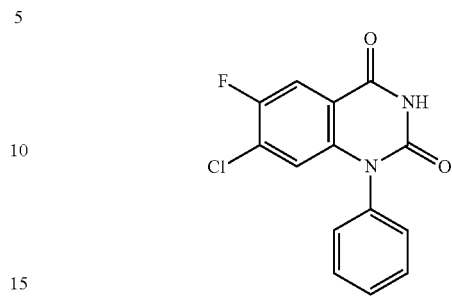

To a stirred solution of 4-chloro-2,5-difluoro-N-(phenylcarbamoyl)benzamide (1 equiv) in THF (0.25 M) was added KHMDS (1 M in THF, 1 equiv) at 0° C. The resulting reaction mixture was warmed to RT and 18-crown-6 (0.01, g, cat.) was added. After heating at 75° C. for 4 h, the reaction mixture was diluted with EtOAc and then washed with water. The organic layers were dried over sodium sulfate and concentrated. The crude solid was washed with diethyl ether and n-pentane, then filtered and dried under high vacuum to afford the title compound as an off white solid. $^1$H NMR (400 MHz, DMSO-d$_6$) δ ppm 12.13-11.95 (m, 1H), 7.96 (d, J=8.61 Hz, 1H), 7.77-7.55 (m, 3H), 7.46 (m, 2H), 6.43 (d, J=5.89 Hz, 1H). m/z [M+H]$^+$ 291.13.

Proceeding analogously as described in Reference 1, Step 2 above, the following compounds were prepared:

2,6-Dichloro-N-((2-fluorophenyl)carbamoyl)nicotinamide was prepared using 1-fluoro-2-isocyanatobenzene and 2,6-dichloronicotinamide

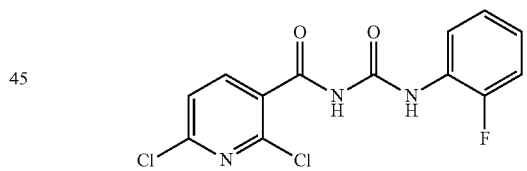

m/z [M + H]$^+$ 329.0.

2,6-dichloro-n-((2-chlorophenyl)carbamoyl)nicotinamide was prepared using 1-chloro-2-isocyanatobenzene and 2,6-dichloronicotinamide

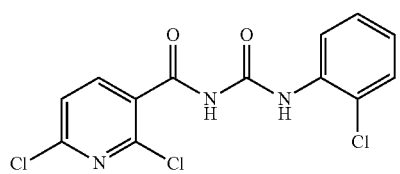

m/z [M + H]$^+$ 343.95.

2,6-dichloro-N-(o-tolylcarbamoyl)nicotinamide was prepared using 1-isocyanato-2-methylbenzene and 2,6-dichloronicotinamide

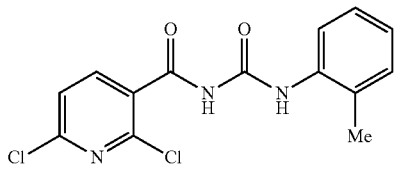

m/z [H + M]⁺ 324.0

2,6-Dichloro-N-(phenylcarbamoyl)nicotinamide was prepared using 2,6-dichloronicotinamide

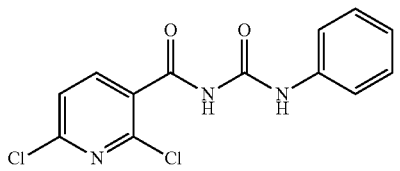

m/z [H + M]⁺ 310.0

2,6-Dichloro-N-(pyridin-3-ylcarbamoyl)nicotinamide was prepared using 3-isocyanatopyridine and 2,6-dichloronicotinamide

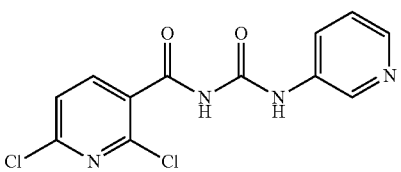

m/z [H + M]⁺ 312.2

2,6-Dichloro-N-(o-tolylcarbamoyl)-4-(trifluoromethyl) benzamide was prepared using 2,6-dichloro-4-(trifluoromethyl)benzamide and 1-isocyanato-2-methylbenzene.

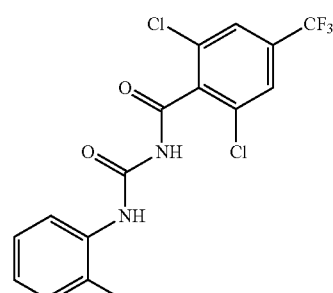

m/z [H + M]⁺ 391.35.

2-chloro-4-methoxy-N-(phenylcarbamoyl)-6-(trifluoromethyl)nicotinamide was prepared using 2-chloro-4-methoxy-6-(trifluoromethyl)nicotinamide and phenyl isocyanate.

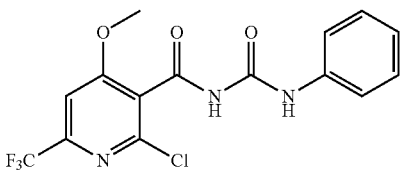

m/z [H + M]⁺ 374.23.

Proceeding analogously as described in Reference 10, Step 3 above, the following compounds were prepared:

7-Cyclopropyl-1-(o-tolyl)quinazoline-2,4(1H,3H)-dione

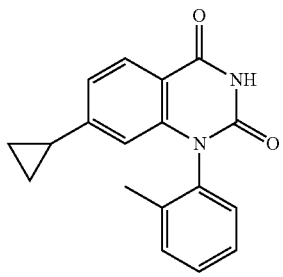

m/z [H + M]⁺ 293.25

6-Bromo-1-phenyl-7-(trifluoromethyl)quinazoline-2,4 (1H,3H)-dione

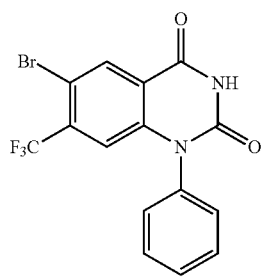

m/z [H + M]⁺ 384.9.

6-Bromo-1-(2-chlorophenyl)-7-(trifluoromethyl)quinazoline-2,4(1H,3H)-dione

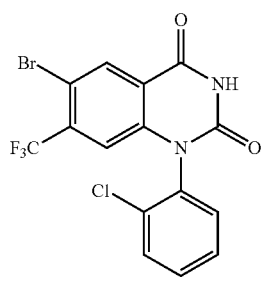

m/z [H + M]⁺ 418.8.

Reference 11

Synthesis of
7,8-dichloro-1-phenylquinazoline-2,4(1H,3H)-dione

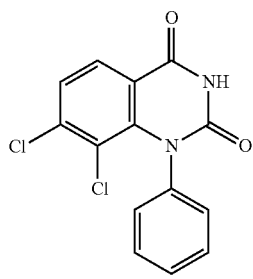

Step 1: Synthesis of
3,4-dichloro-2-(phenylamino)benzoic acid

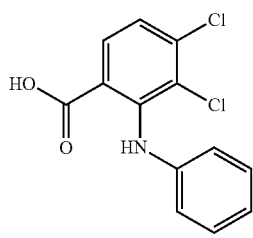 [SMILES: O=C(O)c1ccc(Cl)c(Cl)c1Nc1ccccc1]

A flask was charged with 2-amino-3,4-dichlorobenzoic acid (1 equiv), triethylamine (4 equiv) and bromobenzene (1 equiv). Dioxane (1 M) and copper (II) acetate (1 equiv) were added and the reaction mixture was heated to 110° C. for 18 h. The reaction mixture was cooled, additional bromobenzene was added (1 equiv) and then heated to 110° C. for 24 h. The crude reaction mixture was diluted with saturated ammonium chloride solution and extracted with dichloromethane. The organic layer was washed with 1 N HCl and brine, dried over sodium sulfate, filtered and concentrated under reduced pressure. The residue was purified by flash column chromatography (0-50% ethyl acetate/hexane) to give the title compound.

Step 2: Synthesis of
3,4-dichloro-2-(phenylamino)benzamide

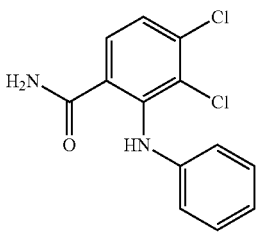 [SMILES: NC(=O)c1ccc(Cl)c(Cl)c1Nc1ccccc1]

To a stirred solution of 3,4-dichloro-2-(phenylamino)benzoic acid (1 equiv) in THF (0.9 M) were added DIPEA (5 equiv), HATU (1.2 equiv) and then added NH$_3$ (0.4 M in THF, 3 equiv) in a sealed flask at 0° C. The resulting reaction mixture was stirred at room temperature for 16 h. The reaction mixture was stirred with crushed ice for 2 h, then filtered and dried under high vacuum to afford the title compound as a white solid.

Step 3: Synthesis of
7,8-dichloro-1-phenylquinazoline-2,4(1H,3H)-dione

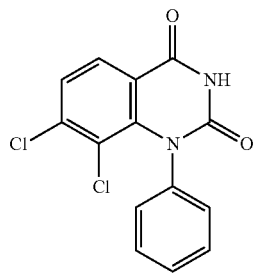 [SMILES: O=c1[nH]c(=O)n(-c2ccccc2)c2c(Cl)c(Cl)ccc12]

A vial was charged under nitrogen with 3,4-dichloro-2-(phenylamino)benzamide (1.0 equiv) and DMF (0.2 M). To the reaction vessel at 0° C. was added NaH (60% in mineral oil, 3.0 equiv) and the reaction mixture was stirred at room temperature for 10 min. CDI (1.5 equiv) was added and the reaction mixture was stirred at room temperature for 20 min. The reaction was quenched by the addition of MeOH (0.5 mL) and AcOH (0.2 mL). The crude reaction mixture was directly purified by reverse phase column chromatography (20-75% MeCN/water, 0.1% formic acid). $^1$H NMR (400 MHz, Chloroform-d) δ 8.29 (s, 1H), 8.13 (d, J=8.5 Hz, 1H), 7.48-7.43 (m, 3H), 7.29 (d, J=7.8 Hz, 2H). m/z [M+H]$^+$ 307.0 Reference 12

Synthesis of 7-chloro-8-methyl-1-phenylquinazoline-2,4(1H,3H)-dione

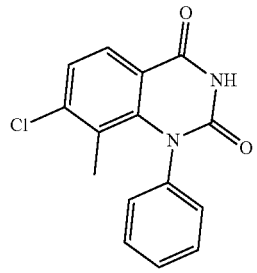 [SMILES: Cc1c(Cl)ccc2c(=O)[nH]c(=O)n(-c3ccccc3)c12]

Step 1: Synthesis of
4-chloro-2-fluoro-3-methylbenzamide

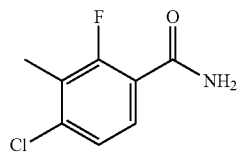

A flask was charged with 4-chloro-2-fluoro-3-methylbenzoic acid, (1 equiv), hydroxybenzotriazole (0.2 equiv) and N-(3-dimethylaminopropyl)-N'-ethylcarbodiimide hydrochloride (1.5 equiv). DMF (0.5 M) was added followed by diisopropylethyl amine (2 equiv). The reaction mixture was stirred for 15 min, followed by addition of ammonium chloride (5 equiv). The reaction mixture was stirred at room temperature for 2 h. The crude reaction mixture was diluted with saturated sodium bicarbonate solution and extracted with dichloromethane. The organic layer was washed with 1 N HCl and brine, dried over sodium sulfate, filtered and concentrated under reduced pressure to give the title compound.

Step 2: Synthesis of 4-chloro-2-fluoro-3-methyl-N-(phenylcarbamoyl)benzamide

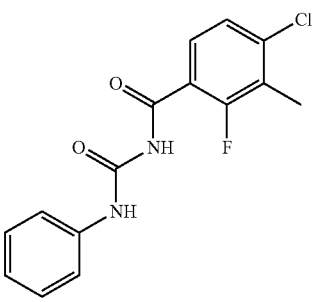 [SMILES: Cc1c(Cl)ccc(C(=O)NC(=O)Nc2ccccc2)c1F]

A slurry of 4-chloro-2-fluoro-3-methylbenzamide (1 equiv.) in DCE (0.5 M) was treated dropwise with oxalyl chloride (1.35 equiv.) at room temperature. The reaction mixture was then warmed to 55° C. for 1 h and was then further warmed to reflux for 20 h. The reaction mixture was concentrated in vacuo to afford the crude as a yellow oil. A solution of this crude 4-chloro-2-fluoro-3-methylbenzoyl isocyanate in DCE (1.2 M) at 0° C. was added dropwise to a cooled solution of aniline in DCE (0.4 M). The ice bath was removed and the reaction mixture stirred at room temperature for 45 min. The solids were then filtered, washed with DCM, and dried to obtain the title compound as a white solid.

Step 3: Synthesis of 7-chloro-8-methyl-1-phenylquinazoline-2,4(1H,3H)-dione

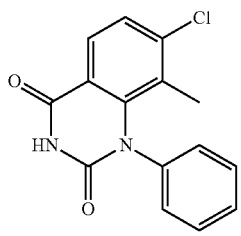 [SMILES: Cc1c(Cl)ccc2c(=O)[nH]c(=O)n(-c3ccccc3)c12]

A slurry of 4-chloro-2-fluoro-3-methyl-N-(phenylcarbamoyl)benzamide in DMF (0.06 M) was cooled to 0° C. and treated portion-wise with NaH (60% dispersion in oil, 3.1 equiv). After addition was complete the ice-bath was removed and the reaction mixture was refluxed for 18 h. The reaction mixture was cooled to rt and poured into 20% aq. HCl. The resulting mixture was stirred vigorously, and the off-white solid was filtered, washed with $Et_2O$, dried to obtain the title compound and used as such in the next step without purification. $^1$H NMR (400 MHz, Chloroform-d) δ 8.21 (s, 1H), 8.05 (d, J=8.2 Hz, 1H), 7.47 (t, J=7.2 Hz, 2H), 7.42 (d, J=6.9 Hz, 1H), 7.37 (d, J=8.6 Hz, 1H), 7.30 (d, J=7.6 Hz, 2H), 1.71 (s, 3H). m/z [M+H]$^+$ 287.0.

Proceeding analogously as described above, following compounds were prepared by substituting for 4-chloro-2-fluoro-3-methylbenzamide:

2-Fluoro-N-(o-tolylcarbamoyl)-4-(trifluoromethyl)benzamide was prepared by using o-toluidine and 2-fluoro-4-(trifluoromethyl)benzamide

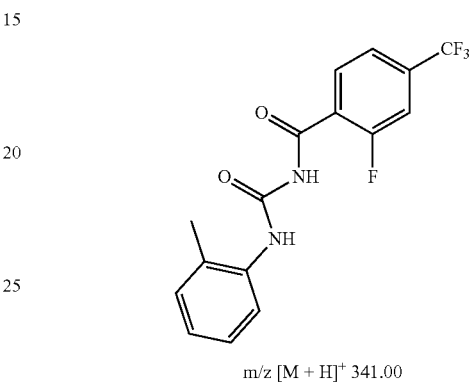

m/z [M + H]$^+$ 341.00

1-(o-Tolyl)-7-trifluoromethylquinazoline-2,4(1H,3H)-dione was prepared by using 2-fluoro-N-(o-tolylcarbamoyl)-4-(trifluoromethyl)benzamide.

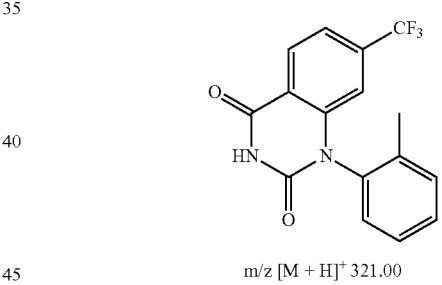

m/z [M + H]$^+$ 321.00

Reference 13

Synthesis of 1-phenyl-7-(trifluoromethyl)pyrido[2,3-d]pyrimidine-2,4(1H,3H)-dione

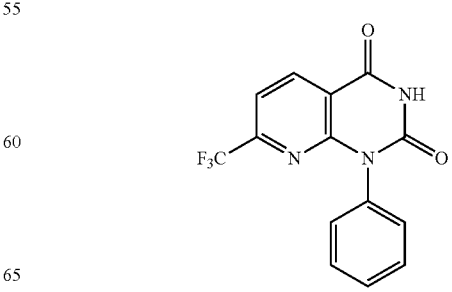

Step 1: Synthesis of 2-(phenylamino)-6-(trifluoromethyl)nicotinamide

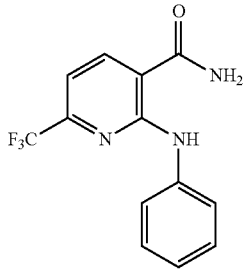 [SMILES: NC(=O)c1ccc(C(F)(F)F)nc1Nc1ccccc1]

A round bottom flask was purged with nitrogen and a solution of KHMDS (2.5 equiv, 1 M THF) was added to the flask containing a vigorously stirred suspension of 2-chloro-6-(trifluoromethyl)nicotinamide (1 equiv) and aniline (1.1 equiv) in toluene or THF (0.4 M) at room temperature. After 2 h, the reaction mixture was evaporated to half volume to remove THF. The solid portion was filtered, washed with additional toluene, and dried under vacuum to provide the title compound. m/z [M+H]$^+$ 282.1

Step 2: Synthesis of 1-phenyl-7-(trifluoromethyl)pyrido[2,3-d]pyrimidine-2,4(1H,3H)-dione

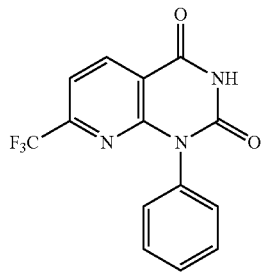 [SMILES: O=c1[nH]c(=O)n(-c2ccccc2)c2nc(C(F)(F)F)ccc12]

Proceeding analogously as described in Reference 2 above but substituting 4-chloro-2-(pyridin-3-ylamino)benzamide with 2-(phenylamino)-6-(trifluoromethyl)nicotinamide, gave the title compound.

Proceeding analogously as described in Reference 13, Step 1 above, the following compounds were prepared:

2-((2-Fluorophenyl)amino)-6-(trifluoromethyl)nicotinamide was prepared by substituting aniline with 2-fluoroaniline.

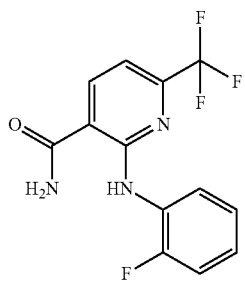

m/z [M + H]$^+$ 300.0.

2-((2-Bromophenyl)amino)-6-(trifluoromethyl)nicotinamide was prepared by substituting aniline with 2-bromoaniline.

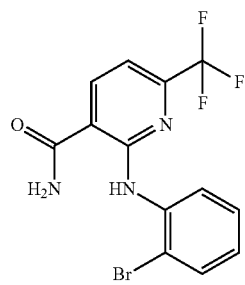

m/z [M + H]$^+$ 360.0, 362.0

Reference 14

Synthesis of 1-(2-chlorophenyl)-7-cyclopropyl-2,4-dioxo-1,2,3,4-tetrahydroquinazoline-6-carbonitrile

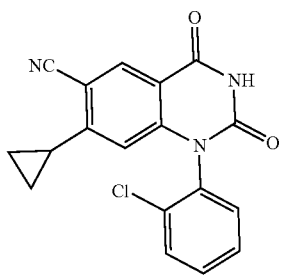 [SMILES: N#Cc1cc2c(=O)[nH]c(=O)n(-c3ccccc3Cl)c2cc1C1CC1]

A vial was charged with 6-bromo-1-(2-chlorophenyl)-7-cyclopropylquinazoline-2,4(1H,3H)-dione (1 equiv) and copper cyanide (2 equiv). Dimethylformamide was added (0.5 M) and the reaction mixture was heated to 120° C. for 18 h and then cooled. The crude reaction mixture was filtered and purified by reverse phase purification (30-60% MeCN/water, 0.1% formic acid) to give the title compound. m/z [M+H]$^+$ 338.0.

Proceeding analogously as described in Reference 14 above, the following compounds were prepared:

1-(2-Chlorophenyl)-7-cyclopropyl-2,4-dioxo-1,2,3,4-tetrahydropyrido[2,3-d]pyrimidine-6-carbonitrile was prepared using 6-bromo-1-(2-chlorophenyl)-7-cyclopropylpyrido[2,3-d]pyrimidine-2,4(1H,3H)-dione.

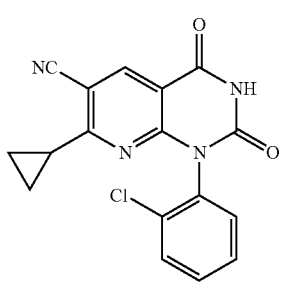

m/z [M + H]$^+$ 339.0.

1-(2-Chlorophenyl)-7-(1,1-difluoroethyl)-2,4-dioxo-1,2,3,4-tetrahydroquinazoline-6-carbonitrile was prepared using 6-bromo-1-(2-chlorophenyl)-7-(1,1-difluoroethyl)quinazoline-2,4(1H,3H)-dione.

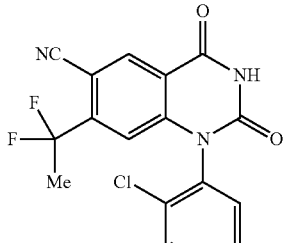

m/z [M + H]⁺ 362.0.

7-Cyclopropyl-2,4-dioxo-1-(2-(trifluoromethyl)phenyl)-1,2,3,4-tetrahydroquinazoline-6-carbonitrile was prepared using 6-bromo-7-cyclopropyl-1-(2-(trifluoromethyl)phenyl)quinazoline-2,4(1H,3H)-dione.

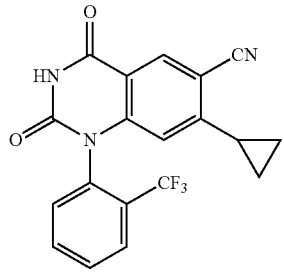

m/z [M + H]⁺ 372.3.

7-Cyclopropyl-1-(2-cyclopropylphenyl)-2,4-dioxo-1,2,3,4-tetrahydroquinazoline-6-carbonitrile was prepared using 6-bromo-7-cyclopropyl-1-(2-cyclopropylphenyl)quinazoline-2,4(1H,3H)-dione.

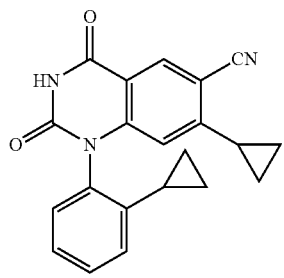

m/z [M + H]⁺ 344.46.

1-(2-Bromophenyl)-7-cyclopropyl-2,4-dioxo-1,2,3,4-tetrahydroquinazoline-6-carbonitrile was prepared using 6-bromo-1-(2-bromophenyl)-7-cyclopropylquinazoline-2,4(1H,3H)-dione.

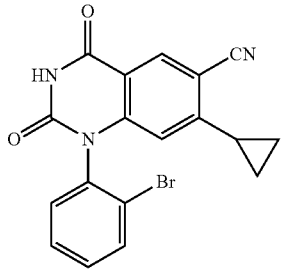

m/z [M + H]⁺ 382.28.

1-(2-Chloropyridin-3-yl)-7-cyclopropyl-4-hydroxy-2-oxo-1,2-dihydroquinazoline-6-carbonitrile was prepared 6-bromo-1-(2-chloropyridin-3-yl)-7-cyclopropyl-4-hydroxyquinazolin-2(1H)-one.

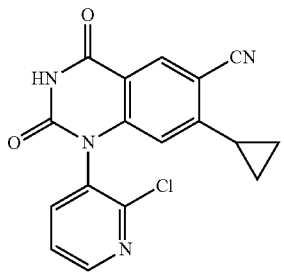

m/z [M + H]⁺ 339.4.

Reference 15

Synthesis of 7-chloro-1-(3-vinylphenyl)quinazoline-2,4(1H,3H)-dione

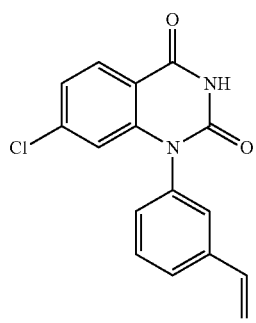 [SMILES: C=Cc1cccc(-n2c(=O)[nH]c(=O)c3ccc(Cl)cc32)c1]

To a stirred solution of 1-(3-bromophenyl)-7-chloro-4-hydroxyquinazolin-2(1H)-one (8 g, 22.8 mmol) in 1,4-dioxane (0.11 M) in a sealed tube was added potassium fluoride (3 equiv) and tributyl(vinyl)stannane (1.5 equiv) at room temperature. The reaction mixture was degassed with argon gas for 20 min. Pd (OAc)₂ (10 mol %) was added and the reaction mixture was again degassed for 5 min. The resulting reaction mixture was stirred at 100° C. for 16 h. Upon completion, the reaction mixture was filtered through a celite bed. The filtrate was diluted with water and extracted with EtOAc. The combined organic layer was washed with water, brine solution, dried over Na₂SO₄. The organics were then filtered and concentrated under reduced pressure to get crude compound. The crude was purified by column chromatography (1:6 EtOAc/hex) to afford the title compound as a yellow solid. m/z [M−H]⁺ 298.73.

Reference 16

Synthesis of 7-cyclopropyl-5-ethyl-4-hydroxy-1-(o-tolyl)quinazolin-2(1H)-one

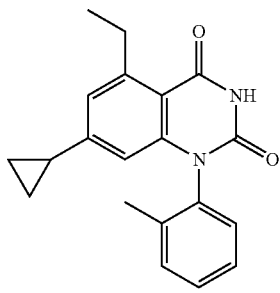 [SMILES: CCc1cc(C2CC2)cc2c1c(=O)[nH]c(=O)n2-c1ccccc1C]

Step 1: Synthesis of 2-bromo-4,6-dichlorobenzoic acid

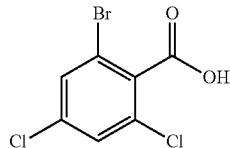 [SMILES: O=C(O)c1c(Cl)cc(Cl)cc1Br]

Butyl nitrite (2 equiv) was added dropwise at 0° C. to a suspension of CuBr₂ (1.2 equiv) in acetonitrile (0.25 M). The reaction was stirred for 10 min and 2-amino-4,6-dichlorobenzoic acid (1 equiv) was added portion wise. The reaction mixture was stirred at 0° C. for 2 h, then allowed to warm to room temperature and stirred for 16 h. The reaction mixture was cooled to 0° C., and the reaction mixture was quenched with 1N HCl. The solution was then extracted with diethyl ether. The pH of the organic phase was adjusted to pH 12 with 2 N NaOH. The water phase was adjusted to pH 2 with 2 N HCl and then extracted with diethyl ether. The combined organic layers were dried over anhydrous sodium sulfate, filtered and concentrated under reduced pressure to afford 2-bromo-4,6-dichlorobenzoic acid as an off white solid.

Step 2: Synthesis of 2,4-dichloro-6-vinylbenzoic acid

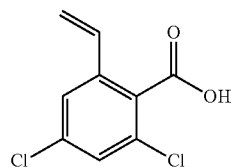

To a stirred solution of 2-bromo-4,6-dichlorobenzoic acid (1 equiv) in DMSO:H₂O (3:1, 0.2 M) was added vinyl boronic acid pinacol ester (1.2 equiv), K₂CO₃ (3 equiv) and Pd(dppf)Cl₂ (5 mol %) at room temperature. The reaction mixture was purged under argon for 10 min., and then heated to 120° C. and stirred for 16 h. The reaction mixture was diluted with 1 N HCl and EtOAc and then washed with brine solution. The combined organic layers were separated, dried over anhydrous sodium sulfate, and then concentrated under reduced pressure. The crude was purified using column chromatography (20% EtOAc/Hexane) then concentrated under reduced pressure to afford 2,4-dichloro-6-vinylbenzoic acid as an off white semi-solid.

Step 3: Synthesis of 2,4-dichloro-6-ethylbenzoic acid

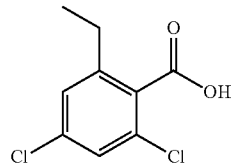

To stirred solution of 2,4-dichloro-6-vinylbenzoic acid (1 equiv) in EtOAc (0.3 M) was added 10% Pd/Ca (10 mol %) at room temperature. The reaction mixture was stirred under hydrogen atmosphere (1 atm) for 16 h and then filtered through a celite bed and washed several times with ethyl acetate. The filtrate was concentrated under reduced pressure to afford 2,4-dichloro-6-ethylbenzoic acid as viscous liquid which was further used in the next step without any purification.

Step 4: Synthesis of 2,4-dichloro-6-ethylbenzamide

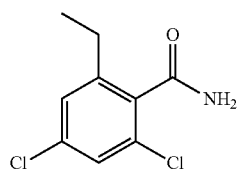

To a stirred solution of 2,4-dichloro-6-ethylbenzoic acid (1 equiv) in DMF (0.4 M) was added HATU (1.5 equiv), DIPEA (5 equiv) followed by addition of NH₄Cl (5 equiv) at room temperature. Then the reaction mixture was stirred at RT for 16 h and then diluted with EtOAc and washed with water. The combined organic layers were separated, dried over anhydrous sodium sulfate, and then concentrated under reduced pressure to give a crude product. The crude product was purified using column chromatography (30% EtOAc/Hexane) and concentrated under reduced pressure to afford the title compound as an off white solid.

Step 5: Synthesis of 2,4-dichloro-6-ethyl-N-(o-tolylcarbamoyl)benzamide

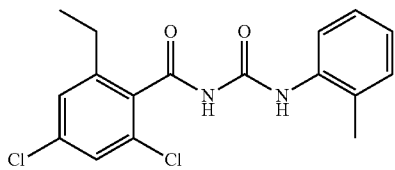 [SMILES: CCc1cc(Cl)cc(Cl)c1C(=O)NC(=O)Nc1ccccc1C]

To a stirred solution of 2,4-dichloro-6-ethylbenzamide (1 equiv) in DCE (0.3 M) were added oxalyl chloride (1.9 equiv) at room temperature. The reaction was stirred at 100° C. for 16 h and then concentrated to give crude 2,4-dichloro-6-ethylbenzoylisocyanate as gummy liquid. To a stirred solution of o-toluidine (1.2 equiv) in DCE (1.4 M) at 0° C. was slowly added the crude isocyanate in suspension of DCE (1.5 M) at 0° C. The reaction mixture was stirred at room temperature for 2 h and then concentrated under vacuum. The solid residue was washed with pentane and dried under vacuum to afford the title compound as an off white solid.

Step 6: Synthesis of 7-chloro-5-ethyl-4-hydroxy-1-(o-tolyl)quinazolin-2(1H)-one

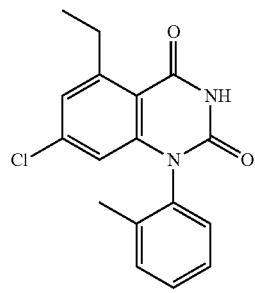 [SMILES: CCc1cc(Cl)cc2c1c(=O)[nH]c(=O)n2-c1ccccc1C]

To a stirred solution of 2,4-dichloro-6-ethyl-N-(o-tolylcarbamoyl)benzamide (1 g, 2.9 mmol) in DMF (0.7 M) was slowly added KHMDS (2 equiv, 1.0 M in THF) dropwise at 0° C. The reaction was stirred at 100° C. for 1 h and then diluted with water and slowly added 1 N HCl. The precipated solids were filtered and washed with water, dried under vacuum to afford the title compound as a pale yellow solid.

Step 7: Synthesis of 7-cyclopropyl-5-ethyl-4-hydroxy-1-(o-tolyl)quinazolin-2(1H)-one

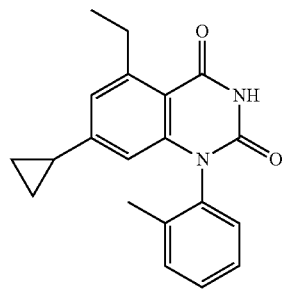 [SMILES: CCc1cc(C2CC2)cc2c1c(=O)[nH]c(=O)n2-c1ccccc1C]

To a stirred solution of 7-chloro-5-ethyl-4-hydroxy-1-(o-tolyl)quinazolin-2(1H)-one (1 equiv) in toluene:$H_2O$ (8:2, 0.6 M) was added cyclopropyl boronic acid (10 equiv), $K_3PO_4$ (3 equiv) at room temperature. The reaction mixture was purged with argon for 5 min, and $Pd(PPh_3)_4$ (10 mol %) was added. After stirring the reaction mixture at 150° C. in the microwave for 1 h, it was diluted with water and extracted with EtOAc. The combined organic layers were separated, washed with brine solution, dried over anhydrous sodium sulphate, filtered and concentrated. The crude was purified by column chromatography (10-20% EtOAc/Hexane) and concentrated under reduced pressure to afford the title compound as an off white solid. m/z [M+H]$^+$ 321.41.

Reference 17

Synthesis of 1-(2-chlorophenyl)-7-cyclopropyl-5-(difluoromethoxy)quinazoline-2,4(1H,3H)-dione

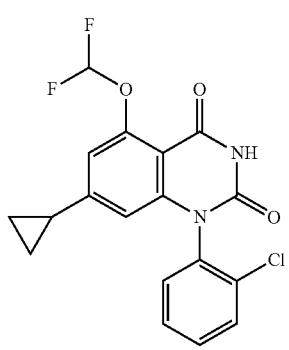 [SMILES: O=c1[nH]c(=O)n(-c2ccccc2Cl)c2cc(C3CC3)cc(OC(F)F)c12]

Step 1: Synthesis of 4-bromo-2-fluoro-6-hydroxybenzoic acid

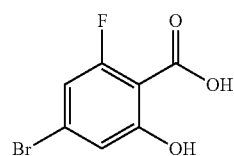

To a stirred solution of 4-bromo-2,6-difluorobenzoic acid (1 equiv) in N-methyl-2-pyrrolidone (0.85 M) was added sodium hydroxide (4 equiv) at RT. The reaction mixture was stirred for 45 min. at 120° C. and then cooled to RT and ice water was added. This mixture was acidified with 2 N HCl (100 mL) until approximately pH 1 and the precipitates were filtered and washed with water to afford the title compound as an off white solid.

Step 2: Synthesis of methyl 4-bromo-2-fluoro-6-hydroxybenzoate

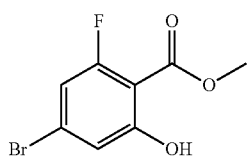

To a stirred solution of 4-bromo-2-fluoro-6-hydroxybenzoic acid (1 equiv) in methanol (0.4 M) was added thionyl chloride (0.36 equiv) at 0° C. The reaction mixture was stirred at 90° C. for 72 h and then concentrated under reduced pressure. The residue was quenched with saturated aqueous sodium bicarbonate solution and extracted with DCM. The combined organic layer was washed with brine solution, dried over anhydrous $Na_2SO_4$, filtered, concentrated under reduced pressure to afford the title compound as an off white solid.

Step 3: Synthesis of methyl 4-bromo-2-(difluoromethoxy)-6-fluorobenzoate

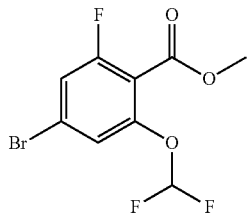 [SMILES: COC(=O)c1c(F)cc(Br)cc1OC(F)F]

To a stirred solution of methyl 4-bromo-2-fluoro-6-hydroxybenzoate (1 equiv) in acetonitrile/water (1:1, 0.2 M) was added potassium hydroxide (20 equiv) at room temperature. The solution was cooled to −78° C. and diethyl (bromodifluoromethyl)phosphonate (2 equiv) was added. The reaction mixture was stirred for 20 min. at RT and then diluted with water and extracted with ether. The combined organic layers were washed with brine, dried over anhydrous $Na_2SO_4$, filtered and concentrated under reduced pressure to afford crude product. Purification by column chromatography (5% EtOAC/Hexane) gave the title compound as a colorless liquid.

Step 4: Synthesis of methyl 4-cyclopropyl-2-(difluoromethoxy)-6-fluorobenzoate

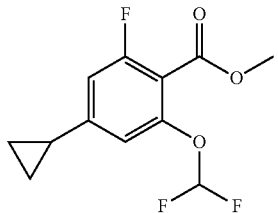 [SMILES: COC(=O)c1c(F)cc(C2CC2)cc1OC(F)F]

To a stirred solution of methyl 4-bromo-2-(difluoromethoxy)-6-fluorobenzoate (1 equiv) in toluene/water (1:1, 0.2 M) were added cyclopropylboronic acid (1.5 equiv) and $Na_2CO_3$ (3 equiv). The resulting reaction mixture was degassed for 20 min under argon atmosphere and $PdCl_2$(dppf)-DCM (10 mol %) was added. After stirring at 120° C. for 16 h, the reaction mixture was filtered through celite and the filtrate was extracted with EtOAc. The combined organic layers were washed with brine solution, dried over anhydrous $Na_2SO_4$, filtered and concentrated under reduced pressure to afford the crude product. Purification by column chromatography using silica (5% EtOAc/Hexanes) and concentrated under reduced pressure gave the title compound as a colorless liquid.

Step 5: Synthesis of 4-cyclopropyl-2-(difluoromethoxy)-6-fluorobenzoic acid

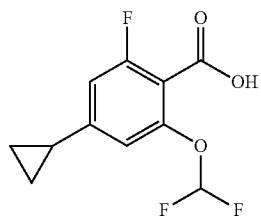 [SMILES: O=C(O)c1c(F)cc(C2CC2)cc1OC(F)F]

To a stirred solution of methyl 4-cyclopropyl-2-(difluoromethoxy)-6-fluorobenzoate (1 equiv) in MeOH/THF/$H_2O$ (2:2:1, 0.17 M) was added LiOH.$H_2O$ (2 equiv) at room temperature. The reaction mixture was stirred for 16 h at RT. Methanol was removed under reduced pressure and water was added to the remaining residue and the solution was acidified with 2 N HCl to about pH 1. The precipitates were filtered and dried to afford the title compound as an off white solid.

Step 6: Synthesis of 4-cyclopropyl-2-(difluoromethoxy)-6-fluorobenzamide

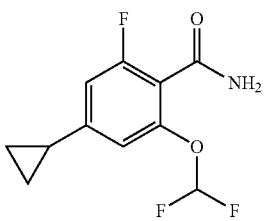 [SMILES: NC(=O)c1c(F)cc(C2CC2)cc1OC(F)F]

To a stirred solution of 4-cyclopropyl-2-(difluoromethoxy)-6-fluorobenzoic acid (1 equiv) in DMF (0.4 M) were added NH₄Cl (5 equiv), DIPEA (3 equiv) and HATU (1.5 equiv) at RT. The reaction mixture was stirred at RT for 16 h and then diluted with water and extracted with EtOAc. The combined organic layers were washed with cold water and brine. The organic layer was dried over anhydrous Na₂SO₄, filtered and concentrated under reduced pressure to afford the title compound as a light yellow solid.

Step 7: Synthesis of N-((2-chlorophenyl)carbamoyl)-4-cyclopropyl-2-(difluoromethoxy)-6-fluorobenzamide

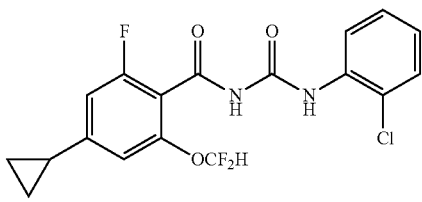

To a stirred solution of 4-cyclopropyl-2-(difluoromethoxy)-6-fluorobenzamide (1 equiv) in DCE (0.4 M) was added oxalyl chloride (1.4 equiv) and the reaction mixture was stirred at 100° C. for 20 h. The reaction mixture was concentrated under reduced pressure to afford crude 4-cyclopropyl-2-(difluoromethoxy)-6-fluorobenzoyl isocyanate. A stirred solution of 2-chloroaniline (1 equiv) in DCE (0.7 M) was added to a mixture of the crude isocyanate in THF (1 M) at 0° C. and the reaction mixture was stirred at RT for 2 h. The reaction mixture was diluted with water and extracted with EtOAc and the combined organic layers were washed with brine, dried over anhydrous Na₂SO₄, filtered and concentrated. The crude product was purified by column chromatography (10% EtOAc/Hexane) and concentrated under reduced pressure to afford the title compound as a light brown solid.

Step 8: Synthesis of 1-(2-chlorophenyl)-7-cyclopropyl-5-(difluoromethoxy)quinazoline-2,4(1H,3H)-dione

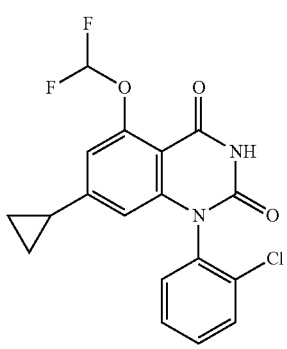 [SMILES: O=c1[nH]c(=O)n(-c2ccccc2Cl)c2cc(C3CC3)cc(OC(F)F)c12]

To a stirred solution of N-((2-chlorophenyl)carbamoyl)-4-cyclopropyl-2-(difluoro-methoxy)-6-fluorobenzamide (1 equiv) in DMF (0.5 M) was added KHMDS (2 equiv, 1 M in THF) dropwise at 0° C. The reaction mixture was stirred at 100° C. for 2 h and then cooled to RT and acidified with 2 N HCl to approximately pH 1. The white precipitates were filtered, washed with water, and dried to afford the title compound as a yellow solid. m/z [M+H]⁺ 379.3.

Reference 18

Synthesis of 1-(2-chlorophenyl)-7-cyclopropyl-5-methoxyquinazoline-2,4(1H,3H)-dione

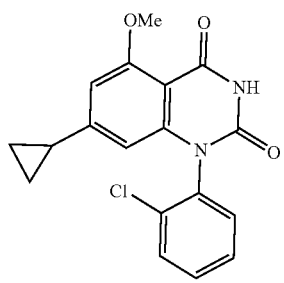 [SMILES: COc1cc(C2CC2)cc2c1c(=O)[nH]c(=O)n2-c1ccccc1Cl]

Step 1: Synthesis of 4-bromo-2-fluoro-6-methoxybenzamide

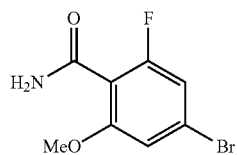

To a stirred solution of 4-bromo-2,6-difluorobenamide (1 equiv) in MeOH (200 ml) was added NaOMe (2.5 equiv) and the reaction mixture was stirred at 70° C. for 16 h. The reaction mixture was concentrated under reduced pressure and the residue was diluted with water and extracted with EtOAc. The combined organic layers were separated, washed with brine, dried over anhydrous sodium sulfate. The solution was filtered and concentrated under reduced pressure to afford crude product. The crude was purified by column chromatography (40% EtOAc/Hexane) and concentrated under reduced pressure to afford the title compound as a white solid.

Step 2: Synthesis of 4-cyclopropyl-2-fluoro-6-methoxybenzamide

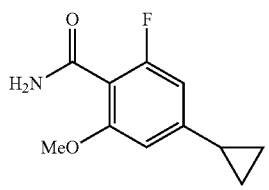 [SMILES: COc1cc(C2CC2)cc(F)c1C(N)=O]

To a stirred solution of 4-bromo-2-fluoro-6-methoxybenzamide (1 equiv) in toluene/water (4:1, 0.3 M) were added cyclopropylboronic acid (1.5 equiv), K₂CO₃ (3 equiv), tributylphosphine (20 mol %), Pd₂(dba)₃ (10 mol %) and the reaction mixture was stirred at 115° C. for 16 h. The reaction mixture was diluted with water and extracted with EtOAc and the combined organic layers were separated, washed with brine, and dried over anhydrous sodium sulfate. The solution was then filtered and concentrated under reduced pressure to afford crude product which was purified by column chromatography (30% EtOAc/Hexane) and concentrated under reduced pressure to afford the title compound as an off white solid.

Step 3: Synthesis of N-((2-chlorophenyl)carbamoyl)-4-cyclopropyl-2-fluoro-6-methoxy-benzamide

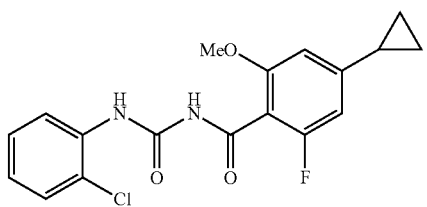 [SMILES: COc1cc(C2CC2)cc(F)c1C(=O)NC(=O)Nc1ccccc1Cl]

To a stirred solution of 4-cyclopropyl-2-fluoro-6-methoxybenzamide (1 equiv) in DCE (0.25 M) was added oxalyl chloride (1.3 equiv) at 0° C. and the reaction mixture was stirred at 55° C. for 1 h and then refluxed for 20 h. The crude 4-cyclopropyl-2-fluoro-6-methoxybenzoyl isocyanate in DCE (1.4 M) was added to a solution of 2-chloroaniline (1 equiv) in DCE (0.7 M) at 0° C. under nitrogen atmosphere and stirred at RT for 2 h. The solids were filtered and washed with diethyl ether and dried under vacuum to afford the title compound as a brown solid.

Step 4: Synthesis of 1-(2-chlorophenyl)-7-cyclopropyl-4-hydroxy-5-methoxyquinazolin-2(1H)-one

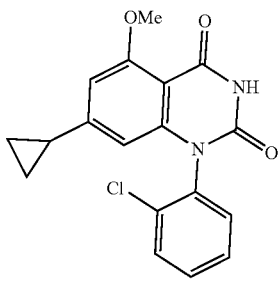 [SMILES: COc1cc(C2CC2)cc2c1c(=O)[nH]c(=O)n2-c1ccccc1Cl]

To a stirred solution of N-((2-chlorophenyl)carbamoyl)-4-cyclopropyl-2-fluoro-6-methoxybenzamide (1 equiv) in DMF (0.05 M) was added KHMDS (1M in THF, 2.5 equiv) dropwise at 0° C. and the reaction mixture was stirred at 100° C. for 4 h. The reaction mixture was diluted with water and acidified to approximately pH 1 with 2 N HCl. The solids were filtered and dried under vacuum to afford the title compound as an off white solid. m/z [M+H]+ 343.34.

Reference 19

Synthesis of (1-((2-(Trimethylsilyl)ethoxy)methyl)-1H-imidazol-4yl)methanamine

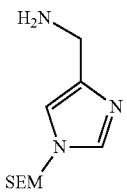 [SMILES: C[Si](C)(C)CCOCn1cnc(CN)c1]

A vial was charged under nitrogen with 1-((2-(trimethylsilyl)ethoxy)methyl)-1H-imidazole-4-carbonitrile (1.0 equiv) and THF (0.5 M). LAH (2.0 equiv) was added and the reaction mixture was stirred at 70° C. for 2 h. The reaction mixture was cooled to 0° C. and quenched with wet Na$_2$SO$_4$. The reaction mixture was filtered on a pad of Celite by washing with EtOAc. The filtrate was dried over Na$_2$SO$_4$, filtered and concentrated to give the title compound; m/z [M+H]+ 228.28.

Reference 20

Synthesis of 1-(1-((2-(Trimethylsilyl)ethoxy)methyl)-1H-imidazol-4-yl)ethan-1-amine

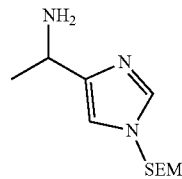 [SMILES: CC(N)c1cn(COCC[Si](C)(C)C)cn1]

Step 1: 1-(1-((2-(Trimethylsilyl)ethoxy)methyl)-1H-imidazol-4-yl)ethan-1-one

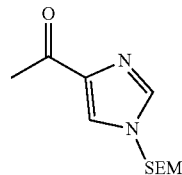 [SMILES: CC(=O)c1cn(COCC[Si](C)(C)C)cn1]

A vial was charged under nitrogen with 1-(H-imidazol-4-yl)ethan-1-one (1.0 equiv) and THF (0.5 M). Sodium hydride (2.0 equiv) was added at 0° C. and the reaction mixture was stirred at room temperature for 1 h. (2-(chloromethoxy)ethyl)trimethylsilane (1.6 equiv) was added at 0° C. and the mixture was stirred at room temperature for 2 h. The reaction mixture was quenched with ice-cold water and diluted with EtOAc. The organic layer was dried over Na$_2$SO$_4$, filtered and concentrated. Purification by silica gel chromatography (20-25% EtOAc/Hexane) afforded the title product; m/z [M+H]+ 241.4.

Step 2: Synthesis of 1-(1-((2-(Trimethylsilyl)ethoxy)methyl)-1H-imidazol-4-yl)ethan-1-one oxime

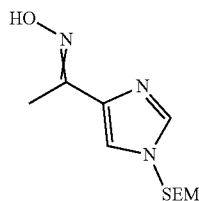 [SMILES: CC(=NO)c1cn(COCC[Si](C)(C)C)cn1]

A vial was charged under nitrogen with 1-(1-((2-(trimethylsilyl)ethoxy)methyl)-1H-imidazol-4-yl)ethan-1-one (1 equiv) and methanol (0.5 M). Hydroxylamine hydrochloride (1.2 equiv) and K$_2$CO$_3$ (3 equiv) were added and the mixture was stirred at room temperature for 2 h. The reaction mixture was passed through a pad of Celite by washing with methanol. The filtrate was dried over Na$_2$SO$_4$, filtered and concentrated to give the title product; m/z [M+H]$^+$ 256.39.

Step 3: 1-(1-((2-(Trimethylsilyl)ethoxy)methyl)-1H-imidazol-4-yl)ethan-1-amine

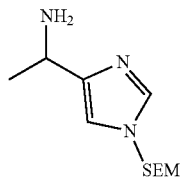 [SMILES: CC(N)c1cn(COCC[Si](C)(C)C)cn1]

A vial was charged under nitrogen with 1-(1-((2-(trimethylsilyl)ethoxy)methyl)-1H-imidazol-4-yl)ethan-1-one oxime (1 equiv) and EtOH. Zinc (15 equiv) and ammonium chloride (10 equiv) were added at room temperature and the reaction mixture was stirred at 80° C. for 48 h. The reaction mixture was filtered through a pad of Celite by washing with ethanol. The filtrate was dried over Na$_2$SO$_4$, filtered and concentrated. Purification by reverse phase chromatography (30% ACN/water) afforded the title compound; m/z [M+H]$^+$ 242.38.

Reference 21

Synthesis of 5-cyano-4-cyclopropyl-2-fluorobenzamide

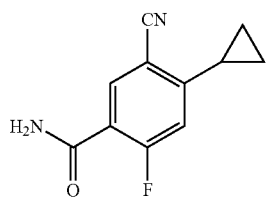 [SMILES: N#Cc1cc(C(N)=O)c(F)cc1C1CC1]

A vial was charged with 5-bromo-4-cyclopropyl-2-fluorobenzamide (1 equiv) and copper cyanide (2 equiv). Dimethylformamide was added (0.5 M) and the reaction mixture was heated to 120° C. for 18 h and then cooled. The crude reaction mixture was filtered and purified by reverse phase purification (30-60% MeCN/water, 0.1% formic acid) to give the title compound. m/z [M+H]$^+$ 205.0.

Reference 22

Synthesis of 2-Chloro-4-methoxy-6-(trifluoromethyl)nicotinic acid

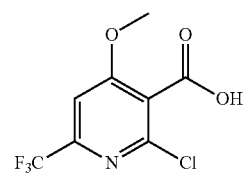

Step 1: ethyl 2-chloro-4-methoxy-6-(trifluoromethyl)nicotinate

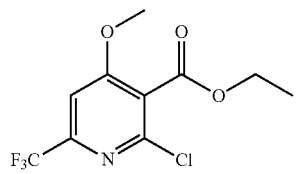 [SMILES: CCOC(=O)c1c(OC)cc(C(F)(F)F)nc1Cl]

To a vial charged under nitrogen with ethyl 2,4-dichloro-6-(trifluoromethyl)nicotinate (1.0 equiv) in DMF (0.9 M) was added MeOH (1.0 equiv) at room temperature. Then the reaction mixture was cooled to 0° C. and slowly added portion wise NaH (60%) (1.0 equiv). The reaction mixture was stirred at same temperature for 1 h, then quenched with cold water and extracted with EtOAc. The combined organic layers were separated and washed with brine solution, dried over anhydrous Na$_2$SO$_4$, filtered and concentrated under reduced pressure to afford the title compound; m/z [M+H]$^+$ 284.23.

Step 2: 2-Chloro-4-methoxy-6-(trifluoromethyl)nicotinic acid

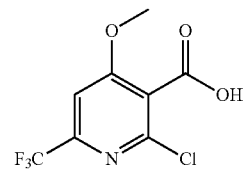

To a stirred solution of ethyl 2-chloro-4-methoxy-6-(trifluoromethyl)nicotinate (1.0 equiv) in MeOH:THF:H$_2$O (2:7:1, 0.5 M) was added LiOH (5.0 equiv) at room temperature. The reaction mixture was heated at 80° C. and stirred for 16 h. The reaction mixture was diluted with water and adjusted to pH 4 with 1 N HCl, extracted with EtOAc. The combined organic layers were separated and washed with brine solution, dried over anhydrous Na$_2$SO$_4$, filtered and concentrated under reduced pressure to afford the title compound; m/z [M+H]+ 256.11.

Reference 23

Synthesis of 6-bromo-1-(2-chlorophenyl)-7-(1,1-difluoroethyl)quinazoline-2,4(1H,3H)-dione

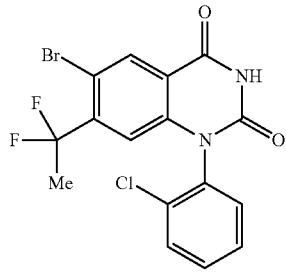 [SMILES: CC(F)(F)c1cc2c(cc1Br)c(=O)[nH]c(=O)n2-c1ccccc1Cl]

To a solution of 1-(2-chlorophenyl)-7-(1,1-difluoroethyl)quinazoline-2,4(1H,3H)-dione (1 equiv.) in trifluoroacetic acid (0.3 M) was added N-bromosuccinimide (1.2 equiv.) and sulfuric acid (18 M, 0.1 equiv.). The reaction mixture was heated to 40° C. for 4 h and then cooled. The crude mixture was poured into water and the precipitate formed was collected by filtration and dried under vacuum to afford the title compound as a white solid. m/z [M+H]+ 415.0/416.9.

Proceeding analogously as described above, 6-bromo-1-(2-chlorophenyl)-7-cyclopropylpyrido[2,3-d]pyrimidine-2,4(1H,3H)-dione was prepared using 1-(2-chlorophenyl)-7-cyclopropylpyrido[2,3-d]pyrimidine-2,4(1H,3H)-dione.

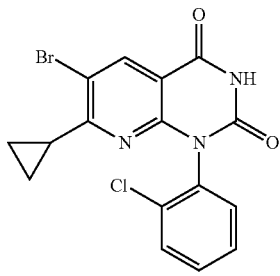

m/z [M + H]+ 391.9/393.9.

Reference 24

Synthesis of 7-ethyl-1-phenylpyrido[2,3-d]pyrimidine-2,4(1H,3H)-dione

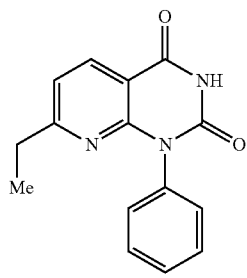 [SMILES: CCc1ccc2c(=O)[nH]c(=O)n(-c3ccccc3)c2n1]

A vial was charged with 7-chloro-1-phenylpyrido[2,3-d]pyrimidine-2,4(1H,3H)-dione (1 equiv), potassium ethyltrifluoroborate (3 equiv), potassium tert-butoxide (3 equiv) and chloro(crotyl)(2-dicyclohexylphosphino-2',6'-diisopropoxy-1,1'-biphenyl)palladium(II) (0.1 equiv). A 9:1 mixture of toluene:water (0.1 M) was added. The reaction mixture was heated to 100° C. for 2 h and then cooled. The crude reaction mixture was diluted with ethyl acetate, filtered and concentrated under reduced pressure. The residue was purified by preparatory HPLC (40-65% MeCN/water, 0.1% formic acid) to give the title compound. m/z [M+H]+ 374.05

Proceeding analogously as described in Reference 24 above, the following compounds were prepared by substituting for 7-chloro-1-phenylpyrido[2,3-d]pyrimidine-2,4(1H,3H)-dione.

7-Ethyl-1-(o-tolyl)pyrido[2,3-d]pyrimidine-2,4(1H,3H)-dione was prepared by using 7-chloro-1-(o-tolyl)pyrido[2,3-d]pyrimidine-2,4(1H,3H)-dione

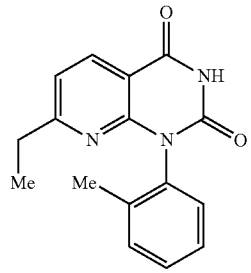

m/z [M + H]+ 282.1

1-(2-Chlorophenyl)-7-ethylpyrido[2,3-d]pyrimidine-2,4(1H,3H)-dione was prepared by using 7-chloro-1-(2-chlorophenyl)pyrido[2,3-d]pyrimidine-2,4(1H,3H)-dione

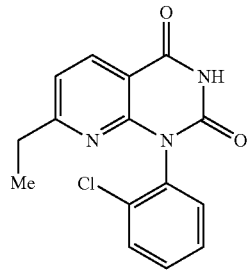

m/z [M + H]+ 302.1

7-Ethyl-1-(2-fluorophenyl)pyrido[2,3-d]pyrimidine-2,4(1H,3H)-dione was prepared by using 7-chloro-1-(2-fluorophenyl)pyrido[2,3-d]pyrimidine-2,4(1H,3H)-dione

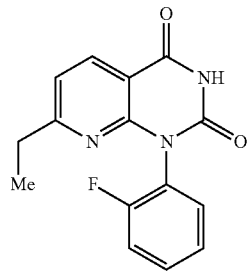

m/z [M + H]+ 286.1

7-Ethyl-1-(pyridin-3-yl)pyrido[2,3-d]pyrimidine-2,4(1H,3H)-dione was prepared by using 7-chloro-1-(pyridin-3-yl)pyrido[2,3-d]pyrimidine-2,4(1H,3H)-dione

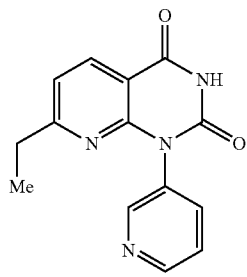

m/z [M + H]+ 269.1.

Reference 25

Synthesis of 1-(2-Chlorophenyl)-7-(trifluoromethyl)-6-vinylquinazoline-2,4(1H,3H)-dione

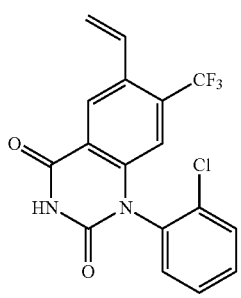 [SMILES: C=Cc1cc2c(=O)[nH]c(=O)n(-c3ccccc3Cl)c2cc1C(F)(F)F]

A vial was purged with nitrogen and then charged with 6-bromo-1-(2-chlorophenyl)-7-(trifluoromethyl)quinazoline-2,4(1H,3H)-dione (1.0 equiv), vinyl boronic acid pinacol ester (4 equiv) and K$_2$CO$_3$ (5 equiv). To the reaction vessel was added toluene:H$_2$O (4:1, 0.4 M) followed by addition of Pd(dppf)Cl$_2$ DCM complex (0.1 equiv). The reaction mixture was heated at 100° C. for 16 h. The reaction mixture was then diluted with water and extracted with EtOAc. The combined organic layers were separated, washed with brine solution, dried over anhydrous Na$_2$SO$_4$, filtered and concentrated under reduced pressure to afford crude product. The crude reaction mixture was directly purified by column chromatography using silica gel (10-20% EtOAC/Hexane). The fractions were combined to provide the title compound as a yellow solid. m/z [M+H]+ 367.12

Proceeding analogously as described in Reference 25 above, the following compounds were prepared by substituting for 6-bromo-1-(2-chlorophenyl)-7-(trifluoromethyl)quinazoline-2,4(1H,3H)-dione and vinyl boronic acid pinacol ester:

1-(2-Chlorophenyl)-7-cyclopropyl-6-vinylquinazoline-2,4(1H,3H)-dione was prepared by using 6-bromo-1-(2-chlorophenyl)-7-(trifluoromethyl)quinazoline-2,4(1H,3H)-dione.

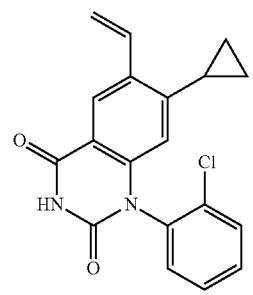

m/z [M + H]+ 339.15.

6-Chloro-1-(2-chlorophenyl)-7-cyclopropylquinazoline-2,4(1H,3H)-dione was prepared by using 7-bromo-6-chloro-1-(2-chlorophenyl)quinazoline-2,4(1H,3H)-dione and cyclopropylboronic acid.

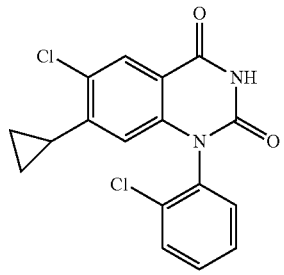

m/z [M + H]+ 347.0.

1-(2-Chlorophenyl)-6-methyl-7-(trifluoromethyl)quinazoline-2,4(1H,3H)-dione was prepared by using 6-bromo-1-(2-chlorophenyl)-7-(trifluoromethyl)quinazoline-2,4(1H,3H)-dione and methylboronic acid.

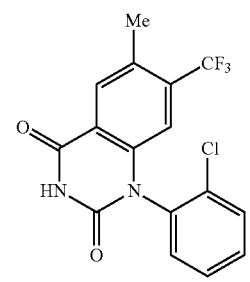

m/z [M + H]+ 355.3.

1-(2-Chlorophenyl)-7-cyclopropyl-6-methylquinazoline-2,4(1H,3H)-dione was prepared by using 6-bromo-1-(2-chlorophenyl)-7-cyclopropylquinazoline-2,4(1H,3H)-dione and methylboronic acid.

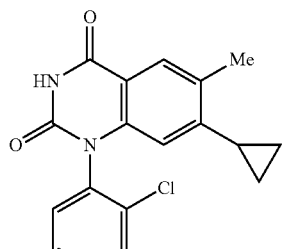

m/z [M + H]+ 327.2.

Reference 26

Synthesis of 1-(2-chlorophenyl)-2,4-dioxo-7-(trifluoromethyl)-1,2,3,4-tetrahydroquinazoline-6-carbaldehyde

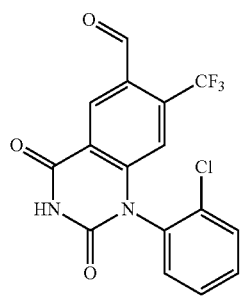 [SMILES: O=Cc1cc2c(=O)[nH]c(=O)n(-c3ccccc3Cl)c2cc1C(F)(F)F]

A vial was charged under nitrogen with 1-(2-chlorophenyl)-7-(trifluoromethyl)-6-vinylquinazoline-2,4(1H,3H)-dione (1.0 equiv) in THF:H$_2$O (10:3, 0.5 M) was added OsO$_4$ (0.1 M in H$_2$O) (2.0 equiv) followed by addition of NaIO$_4$ (4.0 equiv) and the reaction mixture was stirred at room temperature for 1 h. The reaction mixture was filtered under celite bed, the filtrate was diluted with water and extracted with EtOAc. The combined organic layers were separated, washed with brine solution, dried over anhydrous Na$_2$SO$_4$, filtered and concentrated under reduced pressure to give the title compound. m/z [M+H]+ 369.04.

Proceeding analogously as described in Reference 26 above, 1-(2-chlorophenyl)-7-cyclopropyl-2,4-dioxo-1,2,3,4-tetrahydroquinazoline-6-carbaldehyde was prepared by substituting 1-(2-chlorophenyl)-7-(trifluoromethyl)-6-vinylquinazoline-2,4(1H,3H)-dione with 1-(2-chlorophenyl)-7-cyclopropyl-6-vinylquinazoline-2,4(1H,3H)-dione.

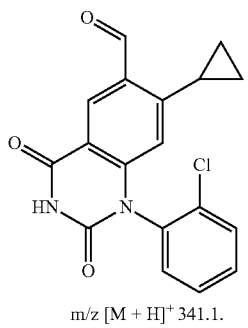 [SMILES: O=Cc1cc2c(=O)[nH]c(=O)n(-c3ccccc3Cl)c2cc1C1CC1]

m/z [M + H]+ 341.1.

Reference 27

Synthesis of 1-(2-Chlorophenyl)-6-(difluoromethyl)-7-(trifluoromethyl) quinazoline-2,4(1H,3H)-dione

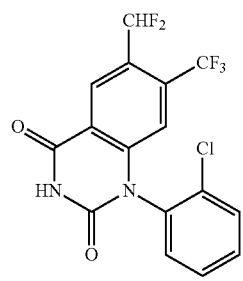 [SMILES: O=c1[nH]c(=O)n(-c2ccccc2Cl)c2cc(C(F)(F)F)c(C(F)F)cc12]

A vial was charged under nitrogen with 1-(2-chlorophenyl)-2,4-dioxo-7-(trifluoromethyl)-1,2,3,4-tetrahydroquinazoline-6-carbaldehyde (1.0 equiv) in DCM (0.7 M) was added DAST (10 equiv) at 0° C. followed by addition of ethanol (catalytic) and heated at 60° C. for 16 h. The reaction mixture was quenched with saturated NaHCO$_3$ solution and extracted with EtOAc. The combined organic layers were separated, washed with brine solution, dried over anhydrous Na$_2$SO$_4$, filtered and concentrated under reduced pressure to afford crude product. The crude was purified by column chromatography (10-20% EtOAC/Hexane). The pure fractions were collected and concentrated under reduced pressure to give the title compound. m/z [M+H]+ 391.11.

Proceeding analogously as described in Reference 27 above, 1-(2-chlorophenyl)-7-cyclopropyl-6-(difluoromethyl)quinazoline-2,4(1H,3H)-dione was prepared by substituting 1-(2-chlorophenyl)-2,4-dioxo-7-(trifluoromethyl)-1,2,3,4-tetrahydroquinazoline-6-carbaldehyde with 1-(2-chlorophenyl)-7-cyclopropyl-2,4-dioxo-1,2,3,4-tetrahydroquinazoline-6-carbaldehyde.

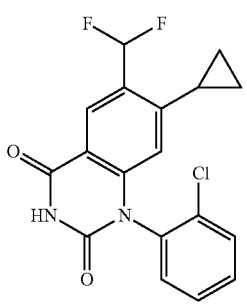

m/z [M + H]+ 363.5.

Reference 28

Synthesis of 5-methoxy-1-phenyl-7-(trifluoromethyl)pyrido[2,3-d]pyrimidine-2,4(1H,3H)-dione

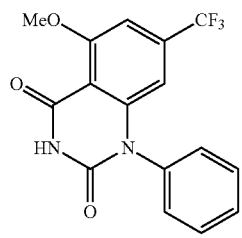 [SMILES: COc1cc(C(F)(F)F)cc2c1c(=O)[nH]c(=O)n2-c1ccccc1]

A 20 mL vial under nitrogen was added 5-fluoro-1-phenyl-7-(trifluoromethyl)quinazoline-2,4(1H,3H)-dione (1.0 equiv), MeOH (0.6 M) and MeONa (5.4 N in MeOH, 10 equiv). The reaction mixture was stirred for 60 minutes at room temperature. The reaction vessel was acidified by adding AcOH. The crude solution was purified by reverse phase chromatography (20-60% MeCN/water, with 0.1% Formic acid). m/z [M+H]+ 337.0

Example 1

Synthesis of 4,7-dichloro-1-phenylquinazolin-2(1H)-one

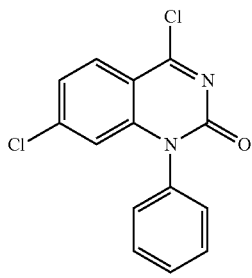

To a stirred solution of 7-chloro-4-hydroxy-1-phenylquinazolin-2(1H)-one (1 equiv) in ACN (0.1 M) were added DIPEA (5 equiv) and POCl3 (2 equiv) at 0° C. The reaction was stirred at 100° C. for 4 h, then poured in ice water and extracted with EtOAc. The combined organics were washed with NaHCO3 solution, dried with sodium sulfate, filtered and concentrated under reduced pressure below 10° C. to afford the title compound as a brown solid.

Example 2

Synthesis of 7-chloro-4-(methylamino)-1-phenylquinazolin-2(1H)-one

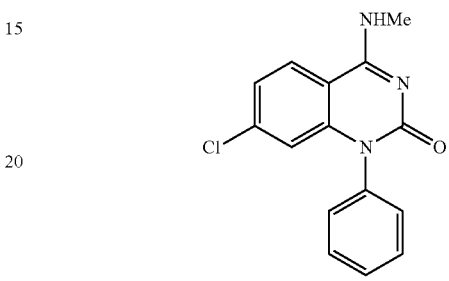

To a stirred solution of 4,7-dichloro-1-phenylquinazolin-2(1H)-one (0.3 g, 1.03 mmol) in DMF (10 ml) were added TEA (2 equiv) and methylamine (5 equiv) and the reaction mixture was stirred at 70° C. for 2 h. The crude compound was purified by column chromatography (50-90% EtOAc/Hexanes). The pure fractions were concentrated to afford 7 the title compound as an off-white solid. $^1$H NMR (400 MHz, DMSO-$d_6$): δ=8.64-8.53 (m, 1H), 8.10 (d, J=8.8 Hz, 1H), 7.62-7.56 (m, 2H), 7.54-7.48 (m, 1H), 7.33-7.22 (m, 3H), 6.32-6.27 (m, 1H), 2.98 (d, J=4.2 Hz, 3H). m/z [M+H]+ 286.23.

Proceeding analogously as described above, the following compounds were prepared by substituting for 7-chloro-4-hydroxy-1-phenylquinazolin-2(1H)-one and methylamine as needed:

7-Bromo-4-(methylamino)-1-phenylquinazolin-2(1H)-one by using 7-bromo-1-phenylquinazoline-2,4(1H,3H)-dione

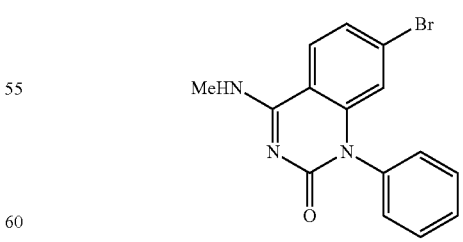

$^1$H NMR (400 MHz, CD3OH) δ 7.90 (d, J=8.7 Hz, 1H), 7.65 (t, J=7.5 Hz, 2H), 7.58 (t, J=7.4 Hz, 1H), 7.40 (d, J=8.6 Hz, 1H), 7.32 (d, J=7.6 Hz, 2H), 6.68 (s, 1H), 3.13 (s, 3H). m/z [M+H]+ 330.0

551

7-Fluoro-4-(methylamino)-1-phenylquinazolin-2(1H)-one was prepared by using 7-fluoro-1-phenylquinazoline-2,4(1H,3H)-dione

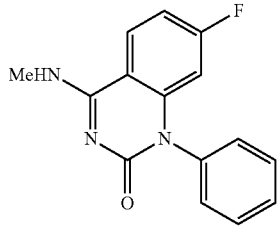 [SMILES: CNc1nc(=O)n(-c2ccccc2)c2cc(F)ccc12]

$^1$H NMR (400 MHz, CD$_3$OH) δ 8.06 (dd, J=8.7, 5.9 Hz, 1H), 7.64 (t, J=7.5 Hz, 2H), 7.58 (d, J=7.2 Hz, 1H), 7.32 (d, J=7.7 Hz, 2H), 7.02 (t, J=8.4 Hz, 1H), 6.21 (d, J=10.7 Hz, 1H), 3.13 (s, 3H). m/z [M+H]$^+$ 270.0

7-chloro-1-(3-fluoro-5-hydroxyphenyl)-4-(methylamino)quinazolin-2(1H)-one was prepared by using 7-chloro-1-(3-fluoro-5-hydroxyphenyl)quinazoline-2,4(1H,3H)-dione

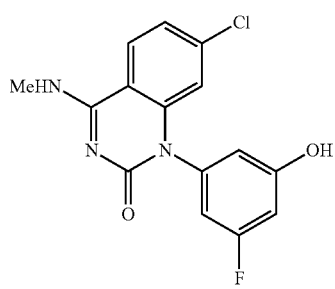 [SMILES: CNc1nc(=O)n(-c2cc(O)cc(F)c2)c2cc(Cl)ccc12]

$^1$H NMR (400 MHz, DMSO-d$_6$) (510.42 (s, 1H), 8.64 (d, J=4.1 Hz, 1H), 8.10 (d, J=8.6 Hz, 1H), 7.29 (d, J=8.5 Hz, 1H), 6.73 (d, J=10.7 Hz, 1H), 6.65 (d, J=9.1 Hz, 1H), 6.52 (s, 1H), 6.44 (s, 1H), 2.96 (s, 4H). m/z [M+H]$^+$ 320.0

7-Chloro-6-fluoro-4-(methylamino)-1-phenylquinazolin-2(1H)-one was prepared by using 7-chloro-6-fluoro-1-phenylquinazoline-2,4(1H,3H)-dione

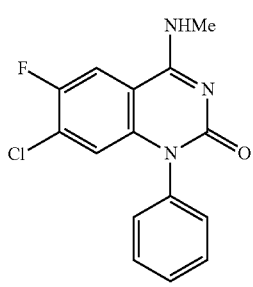

$^1$H NMR (400 MHz, DMSO-d$_6$) δ ppm 8.62-8.57 (m, 1H), 8.21 (d, J=9.9 Hz, 1H), 7.62-7.57 (m, 2H), 7.56-7.50 (m, 1H), 7.36-7.30 (m, 2H), 6.40 (d, J=6.0 Hz, 1H), 3.33 (s, 3H). m/z [M+H]$^+$ 304.08

552

7-Chloro-5-fluoro-4-(methylamino)-1-phenylquinazolin-2(1H)-one was prepared by using 7-chloro-5-fluoro-1-phenylquinazoline-2,4(1H,3H)-dione

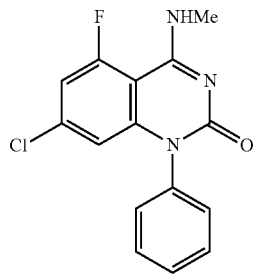 [SMILES: CNc1nc(=O)n(-c2ccccc2)c2cc(Cl)cc(F)c12]

$^1$H NMR (300 MHz, DMSO-d$_6$) δ ppm 8.08-7.96 (m, 1H), 7.64-7.49 (m, 31f), 7.35-7.24 (m, 3H), 6.11 (s, 1H), 3.03-2.93 (m, 3H). m/z [M+H]$^+$ 304.1

7-Chloro-4-(methylamino)-1-(pyridin-4-yl)quinazolin-2(1H)-one was prepared by using 7-chloro-1-(pyridin-4-yl)quinazoline-2,4(1H,3H)-dione.

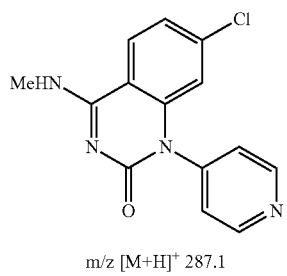 [SMILES: CNc1nc(=O)n(-c2ccncc2)c2cc(Cl)ccc12]

m/z [M+H]$^+$ 287.1

7-Chloro-4-(methylamino)-1-(pyridin-3-yl)quinazolin-2(1H)-one was prepared by using 7-chloro-1-(pyridin-3-yl)quinazoline-2,4(1H,3H)-dione

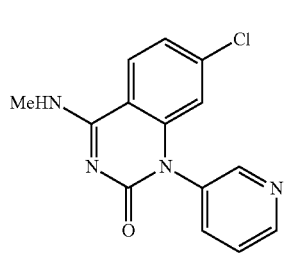

m/z [M+H]$^+$ 287.1

7-Chloro-4-(methylamino)-1-(pyridin-2-yl)quinazolin-2(1H)-one was prepared by using 7-chloro-1-(pyridin-2-yl)quinazoline-2,4(1H,3H)-dione

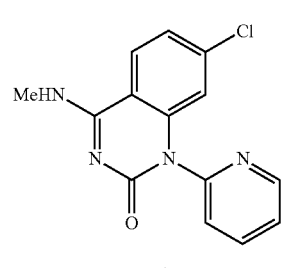

m/z [M+H]$^+$ 287.1

553

7-Chloro-4-(methylamino)-1-(pyrimidin-2-yl)quinazolin-2(1H)-one was prepared by using 7-chloro-1-(pyrimidin-2-yl)quinazoline-2,4(1H,3H)-dione

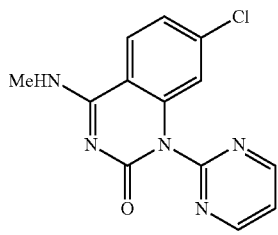

m/z [M+H]$^+$ 288.1

7-Chloro-4-(methylamino)-1-(pyrazin-2-yl)quinazolin-2(1H)-one was prepared by using 7-chloro-1-(pyrazin-2-yl)quinazoline-2,4(1H,3H)-dione

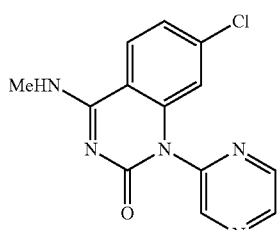

m/z [M+H]$^+$ 288.1

7-Chloro-4-(methylamino)-1-(pyridazin-3-yl)quinazolin-2(1H)-one was prepared by using 7-chloro-1-(pyridazin-3-yl)quinazoline-2,4(1H,3H)-dione

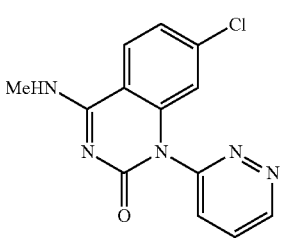

m/z [M+H]$^+$ 288.1

7-Chloro-4-(methylamino)-1-(pyrimidin-5-yl)quinazolin-2(1H)-one was prepared by using 7-chloro-1-(pyrimidin-5-yl)quinazoline-2,4(1H,3H)-dione

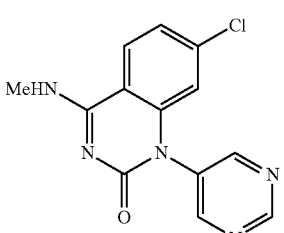

m/z [M+H]$^+$ 288.1

554

7-Chloro-4-(methylamino)-1-(1H-pyrazol-4-yl)quinazolin-2(1H)-one was prepared by using 7-chloro-1-(1H-pyrazol-4-yl)quinazoline-2,4(1H,3H)-dione

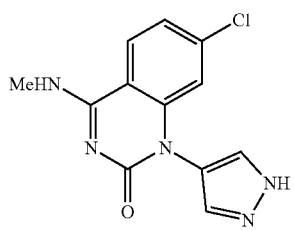

m/z [M+H]$^+$ 276.1

7-Chloro-1-(1H-imidazol-2-yl)-4-(methylamino)quinazolin-2(1H)-one was prepared by using 7-chloro-1-(1H-imidazol-2-yl)quinazoline-2,4(1H,3H)-dione

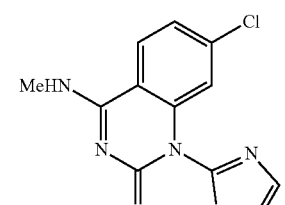

m/z [M+H]$^+$ 276.1

7-Chloro-4-(methylamino)-1-(thiazol-2-yl)quinazolin-2(1H)-one was prepared by using 7-chloro-1-(thiazol-2-yl)quinazoline-2,4(1H,3H)-dione

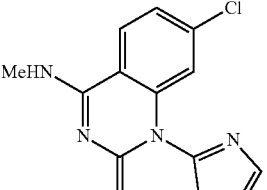

m/z [M+H]$^+$ 293.1

7-Chloro-4-(methylamino)-1-(thiazol-5-yl)quinazolin-2(1H)-one was prepared by using 7-chloro-1-(thiazol-5-yl)quinazoline-2,4(1H,3H)-dione

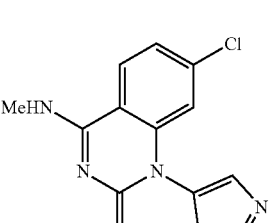

m/z [M+H]$^+$ 293.1

7-Chloro-4-(methylamino)-1-(1H-pyrazol-5-yl)quinazolin-2(1H)-one was prepared by using 7-chloro-1-(1H-pyrazol-5-yl)quinazoline-2,4(1H,3H)-dione

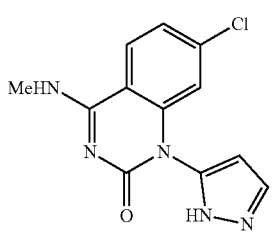

m/z [M+H]$^+$ 276.1

7-Chloro-4-(cyclopropylamino)-1-phenylquinazolin-2(1H)-one was prepared by using cyclopropyl amine

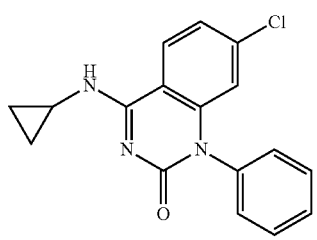 [SMILES: O=c1nc(NC2CC2)c2ccc(Cl)cc2n1-c1ccccc1]

$^1$H NMR (400 MHz, DMSO-d$_6$): δ=8.46 (d, J=3.9 Hz, 1H), 8.17 (d, J=8.8 Hz, 1H), 7.63-7.57 (m, 2H), 7.55-7.49 (m, 1H), 7.33-7.30 (m, 2H), 7.28-7.25 (m, 1H), 6.29 (d, J=2.0 Hz, 1H), 3.11-3.04 (m, 1H), 0.84-0.77 (m, 2H), 0.73-0.67 (m, 2H). m/z [M+H]$^+$ 312.20.

7-Chloro-4-(oxetan-3-ylamino)-1-phenylquinazolin-2(1H)-one was prepared by using oxetan-3-amine.

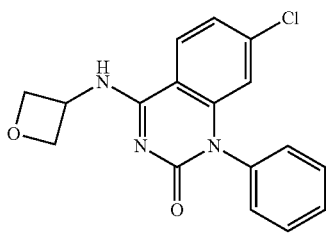 [SMILES: O=c1nc(NC2COC2)c2ccc(Cl)cc2n1-c1ccccc1]

$^1$H NMR (400 MHz, DMSO-d$_6$) δ=9.02 (d, J=5.0 Hz, 1H), 8.30 (d, J=8.8 Hz, 1H), 7.63-7.57 (m, 2H), 7.55-7.49 (m, 1H), 7.35-7.26 (m, 3H), 6.30 (d, J=1.8 Hz, 1H), 5.18-5.08 (m, 1H), 4.88-4.84 (m, 2H), 4.70-4.65 (m, 2H). m/z [M+H]$^+$ 328.19.

7-Chloro-1-phenyl-4-((tetrahydrofuran-3-yl)amino)quinazolin-2(1H)-one was prepared by using tetrahydrofuran-3-amine

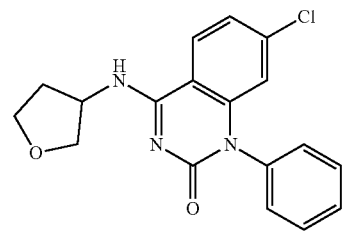 [SMILES: O=c1nc(NC2CCOC2)c2ccc(Cl)cc2n1-c1ccccc1]

$^1$H NMR (400 MHz, DMSO-d$_6$): δ=8.44 (d, J=6.1 Hz, 1H), 8.33 (d, J=8.6 Hz, 1H), 7.57-7.63 (m, 2H), 7.54-7.50 (m, 1H), 7.33-7.27 (m, 3H), 6.29 (d, J=1.8 Hz, 1H), 4.71-4.79 (m, 1H), 3.96-3.90 (m, 2H), 3.79-3.70 (m, 2H), 2.30-2.21 (m, 1H), 2.06 (td, J=12.2, 6.2 Hz, 1H). m/z [M+H]$^+$ 342.12

4-(Benzylamino)-7-chloro-1-phenylquinazolin-2(1H)-one prepared by using benzylamine

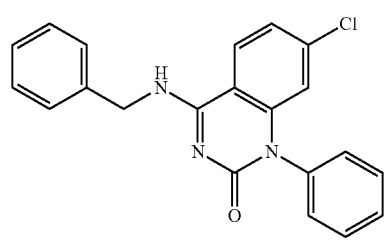 [SMILES: O=c1nc(NCc2ccccc2)c2ccc(Cl)cc2n1-c1ccccc1]

$^1$H NMR (400 MHz, DMSO-d$_6$): δ=9.13 (t, J=5.7 Hz, 1H), 8.25 (d, J=8.6 Hz, 1H), 7.63-7.57 (m, 2H), 7.54-7.47 (m, 1H), 7.27-7.42 (m, 8H), 6.31 (d, J=1.8 Hz, 1H), 4.76 (d, J=5.7 Hz, 2H). m/z [M+H]$^+$ 362.12

7-Chloro-4-(dimethylamino)-1-phenylquinazolin-2(1H)-one was prepared by using dimethylamine

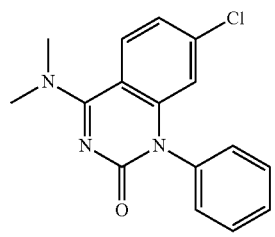 [SMILES: CN(C)c1nc(=O)n(-c2ccccc2)c2cc(Cl)ccc12]

$^1$H NMR (CDCl$_3$, 400 MHz): δ (ppm) 7.76 (d, J=8.8 Hz, 1H), 7.55-7.59 (m, 2H), 7.47-7.51 (m, 1H), 7.26-7.29 (m, 2H), 7.06 (dd, J=8.7, 2.1 Hz, 1H), 6.56 (d, J=2.0 Hz, 1H), 3.38 (s, 6H). m/z [M+H]$^+$ 300.21

4-(Azetidin-1-yl)-7-chloro-1-phenylquinazolin-2(1H)-one was prepared by using azetidine

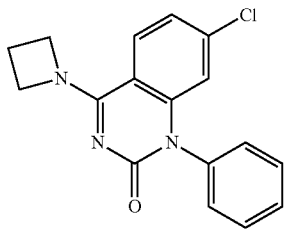 [SMILES: O=c1nc(N2CCC2)c2ccc(Cl)cc2n1-c1ccccc1]

¹H NMR (400 MHz, DMSO-d₆): δ=7.82 (d, J=8.8 Hz, 1H), 7.62-7.57 (m, 2H), 7.54-7.49 (m, 1H), 7.28 (d, J=7.2 Hz, 2H), 7.19 (dd, J=8.7, 2.1 Hz, 1H), 6.30 (d, J=2.0 Hz, 1H), 4.53-4.02 (m, 4H), 2.45-2.41 (m, 2H). m/z [M+H]⁺ 312.20

7-Chloro-4-(3-hydroxypyrrolidin-1-yl)-1-phenylquinazolin-2(1H)-one was prepared by using pyrrolidin-3-ol

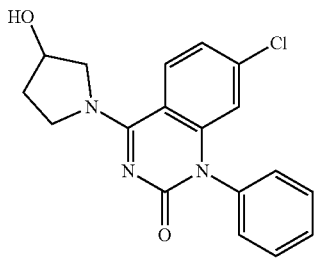 [SMILES: O=c1nc(N2CCC(O)C2)c2ccc(Cl)cc2n1-c1ccccc1]

¹H NMR (400 MHz, DMSO-d₆): δ=8.16 (d, J=8.8 Hz, 1H), 7.62.7.58 (m, 2H), 7.49-7.54 (m, 1H), 7.32-7.29 (m, 2H), 7.20 (dd, J=8.8, 2.1 Hz, 1H), 6.32 (d, J=2.1 Hz, 1H), 5.12 (d, J=3.1 Hz, 1H), 4.41 (br s, 1H), 3.84-4.02 (m, 3H), 3.69-3.64 (m, 1H), 1.92-2.08 (m, 2H). m/z [M+H]⁺ 342.12

7-Chloro-4-(4-methylpiperazin-1-yl)-1-phenylquinazolin-2(1H)-one was prepared by using 1-methylpiperazine

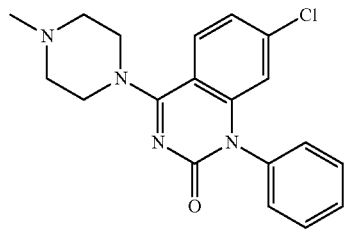 [SMILES: CN1CCN(c2nc(=O)n(-c3ccccc3)c3cc(Cl)ccc23)CC1]

¹H NMR (400 MHz, CDCl₃): δ=8.25 (d, J=1.8 Hz, 1H), 7.57-7.65 (m, 3H), 7.54-7.50 (m, 1H), 7.30-7.27 (m, 2H), 7.10 (dd, J=8.6, 2.0 Hz, 1H), 6.60 (d, J=2.0 Hz, 1H), 4.08-3.85 (m, 8H), 2.84-2.79 (m, 4H), 2.48 (s, 3H). m/z [M+H]⁺ 355.18

7-Chloro-4-morpholino-1-phenylquinazolin-2(1H)-one was prepared by using morpholine.

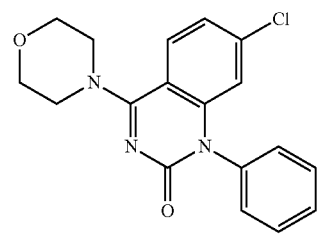 [SMILES: O=c1nc(N2CCOCC2)c2ccc(Cl)cc2n1-c1ccccc1]

¹H NMR (400 MHz, CDCl₃): δ=7.64-7.57 (m, 3H), 7.53-749 (m, 1H), 7.29 (d, J=7.2 Hz, 2H), 7.08 (dd, J=8.7, 1.9 Hz, 1H), 6.59 (d, J=1.8 Hz, 1H), 3.88 (s, 8H). m/z [M+H]⁺ 342.12

7-Chloro-1-phenyl-4-(1H-pyrazol-1-yl)quinazolin-2(1H)-one was prepared by using pyrazole

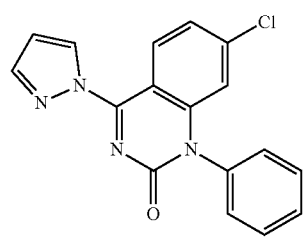 [SMILES: O=c1nc(-n2cccn2)c2ccc(Cl)cc2n1-c1ccccc1]

¹H NMR (400 MHz, CDCl₃); δ=9.49 (d, J=9.0 Hz, 1H), 8.87 (d, J=2.6 Hz, 1H), 7.94 (d, J=0.9 Hz, 1H), 7.67-7.62 (m, 2H), 7.61-7.55 (m, 1H), 7.36-7.32 (m, 2H), 7.25 (d, J=2.0 Hz, 1H), 6.69 (d, J=2.0 Hz, 1H), 6.58-6.56 (m, 1H). m/z [M+H]⁺ 323.13

7-Chloro-4-(ethylamino)-1-phenylquinazolin-2(1H)-one was prepared by using ethylamine

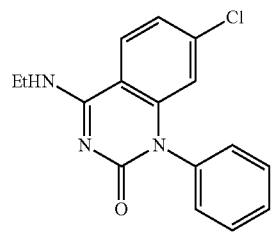

¹H NMR (400 MHz, DMSO-d₆): δ=8.57 (t, J=5.3 Hz, 1H), 8.17 (d, J=8.8 Hz, 1H), 7.62-7.57 (m, 2H), 7.55-7.48 (m, 1H), 7.33-7.26 (m, 3H), 6.29 (d, J=2.0 Hz, 1H), 3.57-3.49 (m, 2H), 1.25-1.21 (m, 3H). m/z [M+H]⁺ 300.21

7-Chloro-4-((2,2-difluoroethyl)amino)-1-phenylquinazolin-2(1H)-one was prepared by using 2,2-difluoroethan-1-amine

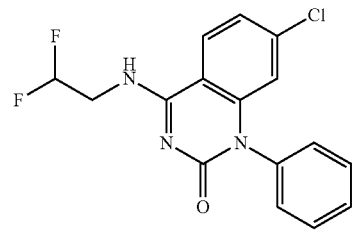 [SMILES: O=c1nc(NCC(F)F)c2ccc(Cl)cc2n1-c1ccccc1]

¹H NMR (400 MHz, DMSO-d₆): δ=8.90 (br s, 1H), 8.21 (d, J=8.8 Hz, 1H), 7.63-7.58 (m, 2H), 7.55-7.50 (m, 1H), 7.34-7.29 (m, 3H), 6.42-6.25 (m, 2H), 3.98-3.89 (m, 2H). m/z [M+H]⁺ 336.13

7-Chloro-1-phenyl-4-(pyridin-2-ylamino)quinazolin-2 (1H)-one by using pyridin-2-amine

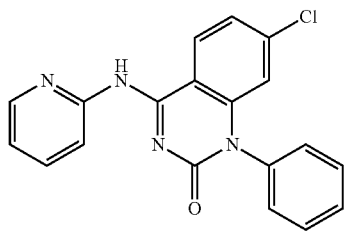 [SMILES: O=c1nc(Nc2ccccn2)c2ccc(Cl)cc2n1-c1ccccc1]

¹H NMR (400 MHz, DMSO-d₆): δ=13.84 (br s, 1H), 8.51 (br d, J=3.3 Hz, 1H), 8.42 (d, J=8.3 Hz, 1H), 7.94-7.89 (m, 1H), 7.66-7.48 (m, 5H), 7.39-7.33 (m, 2H), 7.22 (dd, J=5.5, 6.8 Hz, 1H), 6.31 (br s, 1H). m/z [M+H]⁺ 349.12

7-Chloro-1-phenyl-4-(pyridin-4-ylamino)quinazolin-2 (1H)-one by using pyridin-4-amine

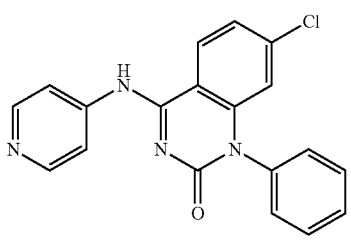 [SMILES: O=c1nc(Nc2ccncc2)c2ccc(Cl)cc2n1-c1ccccc1]

¹H NMR (400 MHz, DMSO-d₆): δ=10.16 (d, J=9.4 Hz, 1H), 8.54-8.44 (m, 3H), 7.97 (dd, J=3.5, 16.9 Hz, 2H), 7.65-7.60 (m, 2H), 7.58-7.52 (m, 1H), 7.42-7.35 (m, 3H), 6.37 (br s, 1H). m/z [M+H]⁺ 349.12

7-Bromo-4-(dimethylamino)-1-phenylquinazolin-2(1H)-one was prepared by using 7-bromo-1-phenylquinazoline-2,4(1H,3H)-dione and dimethylamine

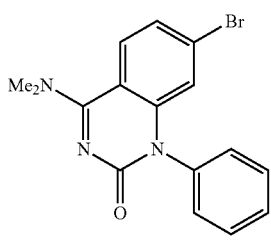 [SMILES: CN(C)c1nc(=O)n(-c2ccccc2)c2cc(F)ccc12]

¹H NMR (400 MHz, Chloroform-d) δ 7.68 (d, J=8.7 Hz, 1H), 7.57 (t, J=7.6 Hz, 2H), 7.49 (t, J=7.3 Hz, 1H), 7.28 (s, 2H), 7.21 (d, J=8.7 Hz, 1H), 6.72 (s, 1H), 3.38 (s, 6H). m/z [M+H]⁺ 344.0

4-(Dimethylamino)-7-fluoro-1-phenylquinazolin-2(1H)-one was prepared by using 7-fluoro-1-phenylquinazoline-2,4(1H,3H)-dione and dimethylamine

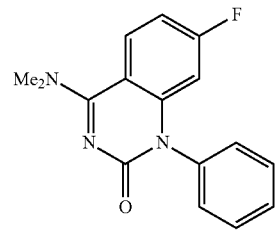

¹H NMR (400 MHz, Chloroform-d) δ 7.89-7.82 (m, 1H), 7.55 (t, J=7.4 Hz, 2H), 7.47 (t, J=7.3 Hz, 1H), 7.28 (s, 2H), 6.81 (t, J=8.3 Hz, 1H), 6.23 (d, J=10.6 Hz, 1H), 3.39 (s, 6H). m/z [M+H]⁺ 284.1

7-chloro-4-(dimethylamino)-1-(4-fluorophenyl)quinazolin-2(1H)-one was prepared by using 7-chloro-1-(4-fluorophenyl)quinazoline-2,4(1H,3H)-dione and dimethylamine

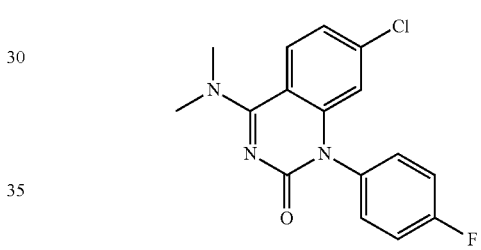

¹H NMR (400 MHz, DMSO-d₆) δ 8.05 (d, J=8.7 Hz, 1H), 7.41 (dt, J=17.4, 8.5 Hz, 4H), 7.21 (d, J=8.7 Hz, 1H), 6.38 (s, 1H), 3.31 (s, 8H). m/z [M+H]⁺ 318.0.

4-(Dimethylamino)-7-chloro-1-(5-fluoro-3-hydroxyphenyl)hydroquinazolin-2-one was prepared by using 7-chloro-1-(3-fluoro-5-hydroxyphenyl)quinazoline-2,4(1H,3H)-dione and dimethylamine

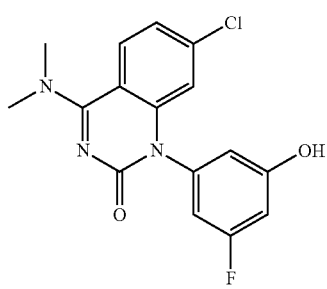 [SMILES: CN(C)c1nc(=O)n(-c2cc(O)cc(F)c2)c2cc(Cl)ccc12]

¹H NMR (400 MHz, DMSO-d₆) (510.40 (s, 1H), 8.04 (d, J=8.8 Hz, 1H), 7.22 (d, J=8.8 Hz, 1H), 6.73 (d, J=10.9 Hz, 1H), 6.66 (d, J=8.9 Hz, 1H), 6.53 (s, 1H), 6.48 (s, 1H), 3.30 (s, 6H). m/z [M+H]⁺ 334.0

4-(azetidin-1-yl)-7-chloro-1-(3-fluoro-5-hydroxyphenyl)quinazolin-2(1H)-one was prepared by using 7-chloro-1-(3-fluoro-5-hydroxyphenyl)quinazoline-2,4(1H,3H)-dione and azetidine

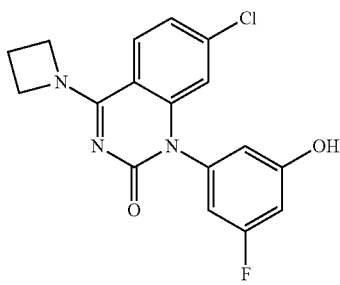 [SMILES: O=c1nc(N2CCC2)c2ccc(Cl)cc2n1-c1cc(O)cc(F)c1]

$^1$H NMR (400 MHz, DMSO-d$_6$) δ 7.82 (d, J=8.6 Hz, 1H), 7.21 (d, J=8.6 Hz, 1H), 6.73 (d, J=10.7 Hz, 1H), 6.63 (d, J=9.3 Hz, 1H), 6.50 (s, 1H), 6.45 (s, 1H), 4.96-4.53 (m, 3H), 4.53-4.12 (m, 3H), 3.83 (s, 1H), 2.46-2.39 (m, 2H). m/z [M+H]$^+$ 346.0

7-chloro-4-(cyclopropyl(methyl)amino)-1-(3-fluorophenyl)quinazolin-2(1H)-one was prepared by using 7-chloro-1-(3-fluorophenyl)quinazoline-2,4(1H,3H)-dione and N-methylcyclopropanamine

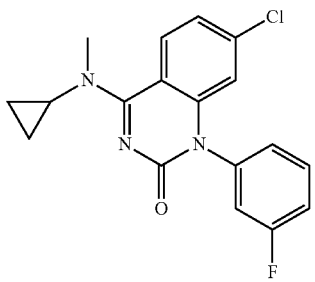 [SMILES: CN(c1nc(=O)n(-c2cccc(F)c2)c2cc(Cl)ccc12)C1CC1]

$^1$H NMR (400 MHz, DMSO-d$_6$) (8.44 (d, J=8.8 Hz, 1H), 7.64 (q, J=7.7 Hz, 1H), 7.39 (t, J=8.4 Hz, 1H), 7.30 (d, J=9.7 Hz, 1H), 7.20 (d, J=7.9 Hz, 2H), 6.37 (s, 1H), 3.52 (s, 1H), 3.22 (s, 3H), 0.91 (d, J=6.3 Hz, 2H), 0.68 (s, 2H). m/z [M+H]$^+$ 344.0

4-Amino-7-chloro-1-(5-fluoro-3-hydroxyphenyl)hydroquinazolin-2-one was prepared by using 7-chloro-1-(3-fluoro-5-hydroxyphenyl)quinazoline-2,4(1H,3H)-dione and ammonia (7 M in MeOH).

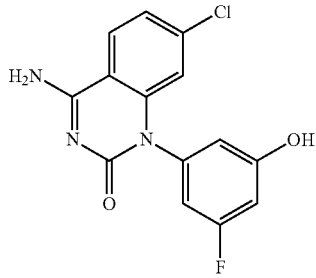 [SMILES: Nc1nc(=O)n(-c2cc(O)cc(F)c2)c2cc(Cl)ccc12]

$^1$H NMR (400 MHz, DMSO-d$_6$) (8.17 (s, 1H), 8.14 (d, J=8.7 Hz, 1H), 8.07 (s, 1H), 7.27 (d, J=8.5 Hz, 1H), 6.73 (d, J=10.9 Hz, 1H), 6.66 (d, J=9.2 Hz, 1H), 6.52 (s, 1H), 6.44 (s, 1H). m/z [M+H]$^+$ 306.0

4-Amino-7-chloro-1-(4-fluorophenyl)hydroquinazolin-2-one was prepared by using 7-chloro-1-(4-fluorophenyl)quinazoline-2,4(1H,3H)-dione and ammonia (7 M in MeOH).

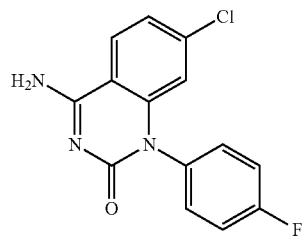 [SMILES: Nc1nc(=O)n(-c2ccc(F)cc2)c2cc(Cl)ccc12]

$^1$H NMR (400 MHz, DMSO-d$_6$), 8.16 (t, J=8.5 Hz, 2H), 8.08 (s, 1H), 7.40 (p, J=8.2, 7.7 Hz, 4H), 7.27 (d, J=8.4 Hz, 1H), 6.35 (s, 1H). m/z [M+H]$^+$ 290.0

7,8-Dichloro-4-(dimethylamino)-1-phenylquinazolin-2(1H)-one was prepared by using 7,8-dichloro-1-phenylquinazoline-2,4(1H,3H)-dione and dimethylamine

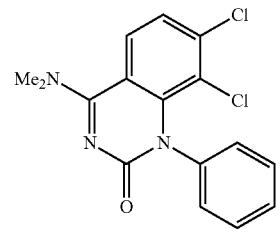 [SMILES: CN(C)c1nc(=O)n(-c2ccccc2)c2c(Cl)c(Cl)ccc12]

$^1$H NMR (400 MHz, Chloroform-d) δ 7.57 (dd, J=35.1, 8.6 Hz, 1H), 7.47-7.41 (m, 1H), 7.41-7.36 (m, 2H), 7.32 (q, J=8.9, 7.5 Hz, 3H), 3.36 (s, 6H). m/z [M+H]$^+$ 334.0

7-Chloro-4-(dimethylamino)-8-methyl-1-phenylquinazolin-2(1H)-one was prepared by using 7-chloro-8-methyl-1-phenylquinazoline-2,4(1H,3H)-dione and dimethylamine

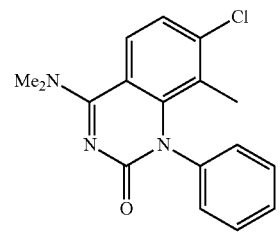 [SMILES: Cc1c(Cl)ccc2c(N(C)C)nc(=O)n(-c3ccccc3)c12]

$^1$H NMR (400 MHz, Chloroform-d) δ 7.55 (d, J=8.7 Hz, 1H), 7.44-7.37 (m, 2H), 7.33 (dd, J=15.5, 7.8 Hz, 3H), 7.20 (d, J=8.8 Hz, 1H), 3.35 (s, 6H), 1.71 (s, 3H). m/z [M+H]$^+$ 314.0

7-Chloro-4-(dimethylamino)-1-(o-tolyl)quinazolin-2(1H)-one was prepared by using 7-chloro-1-(o-tolyl)quinazoline-2,4(1H,3H)-dione and dimethylamine

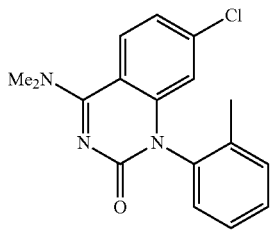

$^1$H NMR (400 MHz, DMSO-d$_6$) δ 8.75 (brs, 1H), 8.15 (d, J=12 Hz 1H), 7.44 (m, 3H), 7.31 (d, J=8 Hz, 1H), 7.21 (d, J=8 Hz, 1H), 6.21 (s, 1H), 3.01 (s, 3H).

7-Chloro-4-(dimethylamino)-1-(2-fluorophenyl)quinazolin-2(1H)-one was prepared by using 7-chloro-1-(2-fluorophenyl)quinazoline-2,4(1H,3H)-dione and dimethylamine

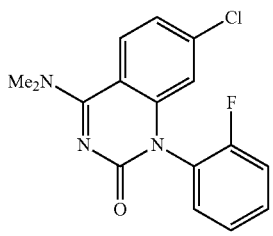 [SMILES: CN(C)c1nc(=O)n(-c2ccccc2F)c2cc(Cl)ccc12]

$^1$H NMR (400 MHz, DMSO-d$_6$) δ 8.75 (brs, 1H), 8.15 (d, J=8 Hz 1H), 7.63-7.40 (m, 4H), 7.34 (d, J=8 Hz, 1H), 6.38 (s, 1H), 2.99 (s, 3H).

3-(7-chloro-4-(dimethylamino)-2-oxoquinazolin-1(2H)-yl)benzonitrile was prepared by using 3-(7-chloro-2,4-dioxo-3,4-dihydroquinazolin-1(2H)-yl)benzonitrile and dimethylamine

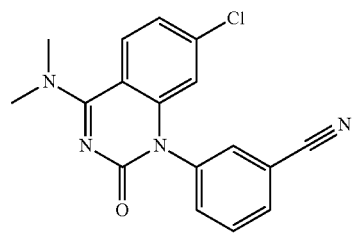 [SMILES: CN(C)c1nc(=O)n(-c2cccc(C#N)c2)c2cc(Cl)ccc12]

$^1$H NMR (400 MHz, DMSO-d$_6$) δ 8.06 (d, J=8.7 Hz, 1H), 8.00 (d, J=7.6 Hz, 1H), 7.93 (s, 1H), 7.80 (t, J=7.8 Hz, 1H), 7.72 (d, J=8.0 Hz, 1H), 7.24 (d, J=8.7 Hz, 1H), 6.40 (s, 1H), 3.32 (s, 6H). m/z [M+H]$^+$ 325.1

4-(Dimethylamino)-7-chloro-1-(3-methoxyphenyl)hydroquinazolin-2-one was prepared by using 7-chloro-1-(3-methoxyphenyl)quinazoline-2,4(1H,3H)-dione and dimethylamine

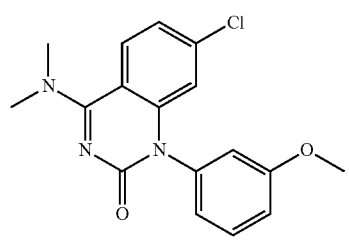

$^1$H NMR (400 MHz, DMSO-d$_6$) δ 8.04 (d, J=8.7 Hz, 1H), 7.51 (t, J=8.1 Hz, 1H), 7.21 (d, J=8.8 Hz, 1H), 7.10 (d, J=8.2 Hz, 1H), 6.90 (s, 1H), 6.87 (d, J=7.7 Hz, 1H), 6.39 (s, 1H), 3.79 (s, 3H), 3.30 (s, 8H). m/z [M+H]$^+$ 330.0

7-Chloro-1-(3-methoxyphenyl)-4-(methylamino)hydroquinazolin-2-one was prepared by using 7-chloro-1-(3-methoxyphenyl)quinazoline-2,4(1H,3H)-dione

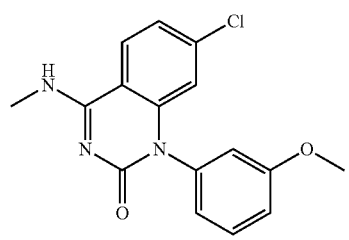

$^1$H NMR (400 MHz, DMSO-d$_6$), 8.65 (s, 1H), 8.11 (d, J=8.7 Hz, 1H), 7.50 (t, J=8.0 Hz, 1H), 7.28 (d, J=8.3 Hz, 1H), 7.09 (d, J=8.4 Hz, 1H), 6.90 (s, 4H), 6.36 (s, 1H), 3.79 (s, 3H), 2.98 (d, J=4.4 Hz, 3H). m/z [M+H]$^+$ 316.1

7-Chloro-1-(3-fluorophenyl)-4-(methylamino)hydroquinazolin-2-one was prepared by using 7-chloro-1-(3-fluorophenyl)quinazoline-2,4(1H,3H)-dione

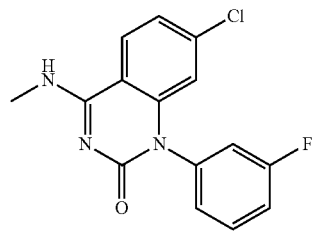 [SMILES: CNc1nc(=O)n(-c2cccc(F)c2)c2cc(Cl)ccc12]

$^1$H NMR (400 MHz, DMSO-d$_6$) δ 8.70 (d, J=4.8 Hz, 1H), 8.13 (d, J=8.6 Hz, 1H), 7.64 (q, J=7.7 Hz, 1H), 7.39 (t, J=8.7 Hz, 1H), 7.30 (d, J=8.9 Hz, 2H), 7.19 (d, J=7.9 Hz, 1H), 6.36 (d, J=2.0 Hz, 1H), 2.98 (d, J=4.2 Hz, 3H). m/z [M+H]$^+$ 304.1

7-Chloro-4-(methylamino)-1-(3-methylphenyl)hydroquinazolin-2-one was prepared by substituting 7-chloro-1-(m-tolyl)quinazoline-2,4(1H,3H)-dione

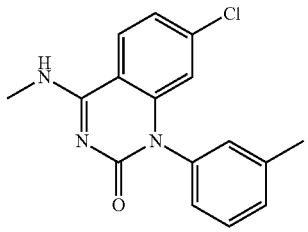

$^1$H NMR (400 MHz, DMSO-d$_6$) δ 8.61 (d, J=5.0 Hz, 1H), 8.11 (d, J=8.6 Hz, 1H), 7.48 (t, J=7.7 Hz, 1H), 7.34 (d, J=7.7 Hz, 1H), 7.31-7.24 (m, 1H), 7.11 (s, 1H), 7.08 (d, J=7.8 Hz, 1H), 6.32 (d, J=1.9 Hz, 1H), 2.98 (d, J=4.3 Hz, 3H). m/z [M+H]$^+$ 300.1

7-Chloro-1-(3-chlorophenyl)-4-(methylamino)hydroquinazolin-2-one was prepared by using 7-chloro-1-(3-chlorophenyl)quinazoline-2,4(1H,3H)-dione

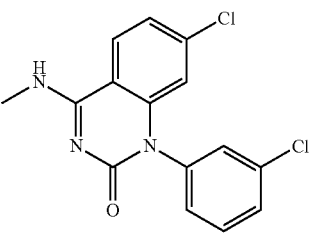 [SMILES: CNc1nc(=O)n(-c2cccc(Cl)c2)c2cc(Cl)ccc12]

$^1$H NMR (400 MHz, DMSO-d$_6$) δ 8.67 (d, J=4.9 Hz, 1H), 8.16-8.07 (m, 1H), 7.66-7.57 (m, 2H), 7.51 (t, J=1.8 Hz, 1H), 7.31 (tt, J=8.7, 1.8 Hz, 2H), 6.35 (t, J=1.7 Hz, 1H), 2.98 (dd, J=4.3, 1.7 Hz, 3H). m/z [M+H]$^+$ 320.0

1-[7-Chloro-1-(3-fluorophenyl)-2-oxohydroquinazolin-4-yl]azetidine-3-carbonitrile was prepared by using 7-chloro-1-(3-fluorophenyl)quinazoline-2,4(1H,3H)-dione and azetidine-3-carbonitrile

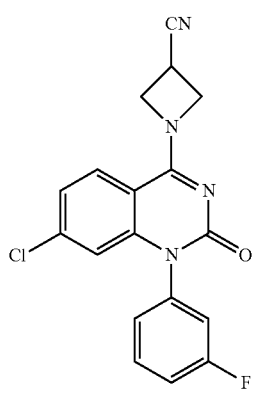

$^1$H NMR (400 MHz, MeCN-d$_3$) δ 7.70 (d, J=8.7 Hz, 1H), 7.63 (q, J=7.7 Hz, 1H), 7.32 (t, J=8.7 Hz, 1H), 7.19 (d, J=8.7 Hz, 1H), 7.14 (t, J=7.6 Hz, 2H), 6.57 (s, 1H), 4.77 (d, J=34.8 Hz, 4H), 3.91-3.79 (m, 1H). m/z [M+H]$^+$ 355.10

1-(3-Bromophenyl)-7-chloro-4-(dimethylamino)quinazolin-2(1H)-one was prepared by using 1-(3-bromophenyl)-7-chloroquinazoline-2,4(1H,3H)-dione

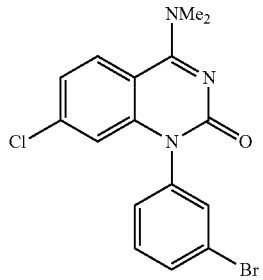

$^1$H NMR (400 MHz, DMSO-d$_6$) δ 8.04 (d, J=8.7 Hz, 1H), 7.73 (d, J=8.1 Hz, 1H), 7.61 (s, 1H), 7.56 (t, J=8.0 Hz, 1H), 7.35 (d, J=7.9 Hz, 1H), 7.22 (d, J=8.8 Hz, 1H), 6.37 (s, 1H), 3.31 (s, 6H). m/z [M+H]$^+$ 378.0

7-Chloro-4-((2-(dimethylamino)ethyl)amino)-1-phenylquinazolin-2(1H)-one was prepared by using N',N-dimethylethane-1,2-diamine

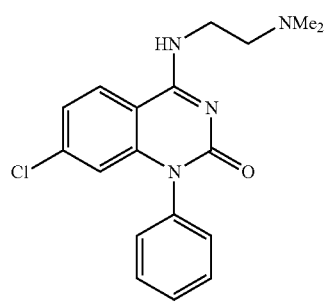 [SMILES: CN(C)CCNc1nc(=O)n(-c2ccccc2)c2cc(Cl)ccc12]

$^1$H NMR (400 MHz, DMSO-d$_6$) δ 8.50 (br s, 1H), 8.23-8.08 (m, 2H), 7.62-7.40 (m, 3H), 7.29-7.18 (m, 3H), 6.26 (d, J=1.8 Hz, 1H), 3.57 (br s, 2H), 2.56 (br t, J=6.6 Hz, 2H), 2.23 (s, 6H). m/z [M+H]$^+$ 343.1

7-Chloro-4-((2-(dimethylamino)ethyl)(methyl)amino)-1-phenylquinazolin-2(1H)-one with was prepared by using N$^1$,N$^1$,N$^2$-trimethylethane-1,2-diamine

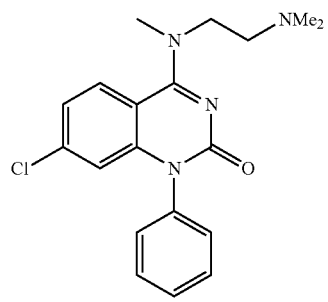 [SMILES: CN(C)CCN(C)c1nc(=O)n(-c2ccccc2)c2cc(Cl)ccc12]

$^1$H NMR (400 MHz, DMSO-d$_6$) δ 8.23 (br s, 1H), 8.06 (d, J=8.8 Hz, 1H), 7.61-7.50 (m, 3H), 7.31 (d, J=7.2 Hz, 2H), 7.20 (dd, J=2.0, 8.8 Hz, 1H), 6.33 (d, J=2.0 Hz, 1H), 3.80 (br t, J=6.5 Hz, 2H), 3.35 (s, 3H), 2.64 (t, J=6.5 Hz, 2H), 2.21 (s, 6H). m/z [M+H]$^+$ 357.1

567

7-Methyl-4-(methylamino)-1-phenylpyrido[4,3-d]pyrimidin-2(1H)-one was prepared by using 7-methyl-1-phenylpyrido[4,3-d]pyrimidine-2,4(1H,3H)-dione

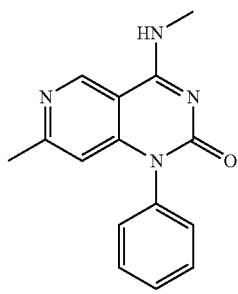

¹H NMR (400 MHz, DMSO-d₆) δ 9.10 (s, 1H), 8.82-8.75 (m, 1H), 7.60-7.55 (m, 2H), 7.54-7.50 (m, 1H), 7.28 (d, J=7.2 Hz, 2H), 6.13 (s, 1H), 2.99 (d, J=4.5 Hz, 3H), 2.35-2.32 (m, 3H). m/z [M+H]⁺ 267.3

7-Methyl-4-(methylamino)-1-phenylpyrido[2,3-d]pyrimidin-2(1H)-one was prepared by using 7-methyl-1-phenylpyrido[2,3-d]pyrimidine-2,4(1H,3H)-dione

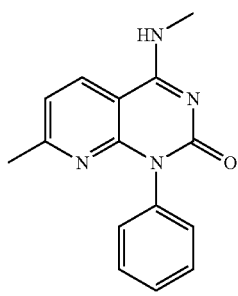

¹H NMR (400 MHz, DMSO-d₆) δ 8.59-8.56 (m, 1H), 8.34 (d, J=8.1 Hz, 1H), 7.49-7.44 (m, 2H), 7.40-7.35 (m, 1H), 7.21-7.17 (m, 2H), 7.11 (d, J=8.1 Hz, 1H), 2.98 (d, J=4.5 Hz, 3H), 2.29 (s, 3H). m/z [M+H]⁺ 267.3

7-Chloro-1-phenyl-4-(pyrrolidin-1-yl)quinazolin-2(1H)-one was prepared by using pyrrolidine

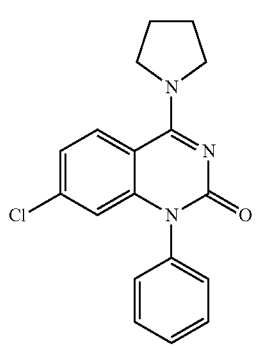 [SMILES: O=c1nc(N2CCCC2)c2ccc(Cl)cc2n1-c1ccccc1]

¹H NMR (400 MHz, Chloroform-d) δ 7.92 (d, J=8.8 Hz, 1H), 7.59-7.54 (m, 2H), 7.50-7.46 (m, 1H), 7.29-7.27 (m, 2H), 7.05 (dd, J=2.0, 8.8 Hz, 1H), 6.54 (d, J=2.0 Hz, 1H), 3.97 (br t, J=6.7 Hz, 4H), 2.07-2.02 (m, 4H). m/z [M+H]⁺ 326.2

568

7-Chloro-1-phenyl-4-(piperidin-1-yl)quinazolin-2(1H)-one was prepared by using piperidine

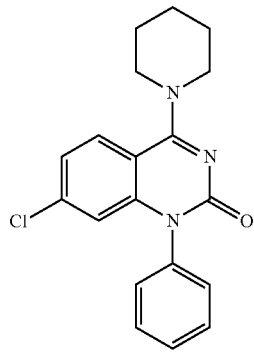 [SMILES: O=c1nc(N2CCCCC2)c2ccc(Cl)cc2n1-c1ccccc1]

¹H NMR (400 MHz, Chloroform-d) δ 7.64-7.54 (m, 3H), 7.52-7.46 (m, 1H), 7.31-7.27 (m, 2H), 7.06 (dd, J=2.0, 8.7 Hz, 1H), 6.55 (d, J=2.0 Hz, 1H), 3.79 (br s, 4H), 1.79 (br s, 6H). m/z [M+H]⁺ 340.2

4-Amino-7-chloro-1-phenylquinazolin-2(1H)-one was prepared by using ammonia (7 M in MeOH)

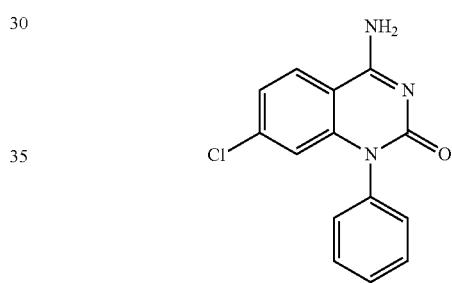

¹H NMR (400 MHz, DMSO-d₆) δ 8.17-8.02 (m, 3H), 7.60-7.47 (m, 3H), 7.33-7.18 (m, 3H), 6.29 (d, J=1.8 Hz, 1H). m/z [M+H]⁺ 272.1

7-Chloro-4-methoxy-1-phenylquinazolin-2(1H)-one was prepared by using methanol

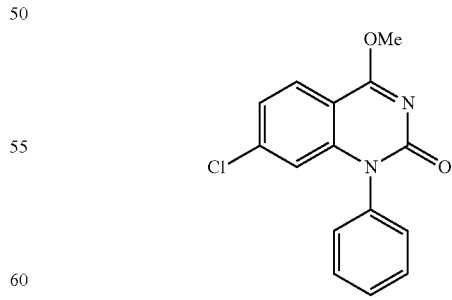

¹H NMR (400 MHz, Chloroform-d): δ 7.94 (d, J=8.6 Hz, 1H), 7.63-7.57 (m, 2H), 7.56-7.50 (m, 1H), 7.31-7.27 (m, 2H), 7.18-7.14 (m, 1H), 6.58 (d, J=1.8 Hz, 1H), 4.21 (s, 3H). m/z [M+H]⁺ 287.2

7-Chloro-4-(3-hydroxyazetidin-1-yl)-1-phenylquinazolin-2(1H)-one was prepared by using azetidin-3-ol

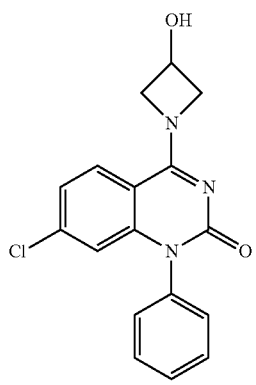

$^1$H NMR (400 MHz, DMSO-d$_6$) δ 7.84 (d, J=8.8 Hz, 1H), 7.62-7.57 (m, 2H), 7.54-7.49 (m, 1H), 7.28 (d, J=7.3 Hz, 2H), 7.19 (dd, J=2.0, 8.7 Hz, 1H), 6.30 (d, J=2.0 Hz, 1H), 5.91 (d, J=6.0 Hz, 1H), 5.01-3.69 (m, 5H). m/z [M+H]$^+$ 328.1

(R)-7-Chloro-4-(3-fluoropyrrolidin-1-yl)-1-phenylquinazolin-2(1H)-one was prepared by using (R)-3-fluoropyrrolidine

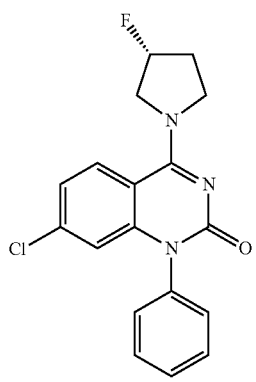

$^1$H NMR (400 MHz, Chloroform-d) δ 8.14 (s, 1H), 7.93 (d, J=8.8 Hz, 1H), 7.59 (t, J=7.6 Hz, 2H), 7.51 (t, J=7.3 Hz, 1H), 7.28 (s, 1H), 7.12 (d, J=8.8 Hz, 1H), 6.59 (s, 1H), 5.39 (d, J=52.3 Hz, 1H), 4.31-4.19 (m, 2H), 4.19-4.09 (m, 2H), 2.48 (td, J=14.4, 5.4 Hz, 1H), 2.26-2.04 (m, 1H). m/z [M+H]$^+$ 344.0

7-Chloro-1-(3-fluorophenyl)-4-((3-hydroxypropyl)(methyl)amino)quinazolin-2(1H)-one was prepared by using 3-(methylamino)propan-1-ol

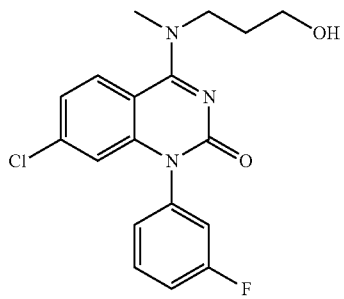 [SMILES: CN(CCCO)c1nc(=O)n(-c2cccc(F)c2)c2cc(Cl)ccc12]

$^1$H NMR (400 MHz, DMSO-d$_6$) (8.04 (d, J=8.8 Hz, 1H), 7.64 (q, J=7.7 Hz, 1H), 7.39 (t, J=8.0 Hz, 1H), 7.31 (d, J=9.6 Hz, 1H), 7.21 (t, J=8.5 Hz, 2H), 6.39 (s, 1H), 3.79-3.72 (m, 2H), 3.33 (s, 4H), 1.98-1.87 (m, 2H). m/z [M+H]$^+$ 362.0

7-Chloro-1-(2-chlorophenyl)-4-(methylamino)quinazolin-2(1H)-one was prepared by using 7-chloro-1-(2-chlorophenyl)quinazoline-2,4 (1H,3H)-dione

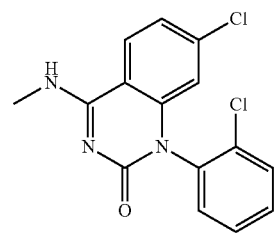 [SMILES: CNc1nc(=O)n(-c2ccccc2Br)c2cc(Cl)ccc12]

$^1$H NMR (400 MHz, DMSO-d$_6$) δ 8.74 (d, J=5.0 Hz, 1H), 8.16 (d, J=8.6 Hz, 1H), 7.84-7.68 (m, 1H), 7.65-7.44 (m, 3H), 7.33 (d, J=8.6 Hz, 1H), 6.22 (d, J=2.3 Hz, 1H), 3.00 (d, J=4.3 Hz, 3H). m/z [M+H]$^+$ 322.00

1-(2-Bromophenyl)-7-chloro-4-(methylamino)quinazolin-2(1H)-one was prepared by using 7-chloro-1-(2-bromophenyl)quinazoline-2,4(1H,3H)-dione

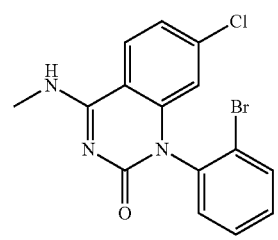

$^1$H NMR (400 MHz, DMSO-d$_6$) δ 8.65 (d, J=5.0 Hz, 1H), 8.09 (d, J=8.6 Hz, 1H), 7.82 (d, J=8.1 Hz, 1H), 7.62-7.36 (m, 3H), 7.25 (d, J=8.5 Hz, 1H), 6.12 (t, J=1.7 Hz, 1H), 2.99-2.82 (m, 3H). m/z [M+H]$^+$ 366.00

(R)-7-chloro-4-(3-hydroxypyrrolidin-1-yl)-1-phenylquinazolin-2(1H)-one was prepared by using (R)-3-hydroxypyrrolidine

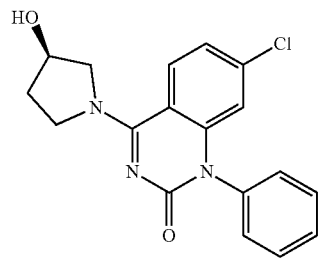 [SMILES: O=c1nc(N2CC[C@@H](O)C2)c2ccc(Cl)cc2n1-c1ccccc1]

$^1$H NMR (400 MHz, DMSO-d$_6$) δ=8.16 (d, J=8.4 Hz, 1H), 7.61-7.58 (m, 2H), 7.54-7.53 (m, 1H), 7.52-7.51 (m, 2H), 7.19 (dd, J=2.0, 8.8 Hz, 1H), 6.31 (d, J=2.0 Hz, 1H), 5.11 (br s, 2H), 4.41 (s, 1H), 4.01-3.85 (m, 3H), 3.66 (d, J=12 Hz, 1H), 2.03-1.96 (m, 2H). m/z [M+H]$^+$ 342.19.

571

1-(2-chlorophenyl)-4-(methylamino)-7-(trifluoromethyl) pyrido[2,3-d]pyrimidin-2(1H)-one was prepared by using 1-(2-chlorophenyl)-7-(trifluoromethyl)pyrido[2,3-d]pyrimidine-2,4(1H,3H)-dione

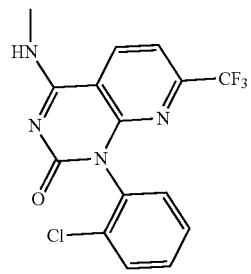 [SMILES: CNc1nc(=O)n(-c2ccccc2Cl)c2nc(C(F)(F)F)ccc12]

$^1$H NMR (400 MHz, DMSO-d$_6$) δ 9.12 (br s, 1H), 8.80 (d, J=8.1 Hz, 1H), 7.81 (dd, J=8.1, 1.8 Hz, 1H), 7.71-7.58 (m, 1H), 7.47 (m, 3H), 3.04 (s, 3H).

4-(Methylamino)-1-phenyl-7-(trifluoromethyl)pyrido[2,3-d]pyrimidin-2(1H)-one was prepared by using 1-phenyl-7-(trifluoromethyl)pyrido[2,3-d]pyrimidine-2,4(1H,3H)-dione

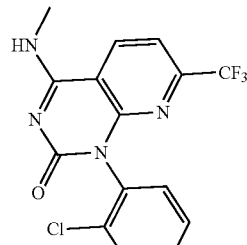

m/z[M+H]$^+$ 321.1

4-((2,2-Difluoroethyl)amino)-1-(o-tolyl)-7-(trifluoromethyl)quinazolin-2(1H)-one was prepared by using 2,2-difluoroethan-1-amine

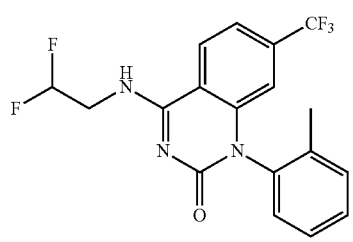 [SMILES: Cc1ccccc1-n1c(=O)nc(NCC(F)F)c2ccc(C(F)(F)F)cc21]

$^1$H NMR (400 MHz, DMSO-d$_6$) δ 9.14 (s, 1H), 8.46 (d, J=8.6 Hz, 1H), 7.64 (d, J=8.6 Hz, 1H), 7.57-7.34 (m, 3H), 7.27 (d, J=7.7 Hz, 1H), 6.60-6.07 (m, 2H), 3.97 (q, J=16.3 Hz, 2H), 1.96 (d, J=2.0 Hz, 3H). m/z [M+H]$^+$ 384.00

572

7-Cyclopropyl-4-(methylamino)-1-(o-tolyl)quinazolin-2(1H)-one was prepared by using 7-cyclopropyl-1-(o-tolyl)quinazoline-2,4(1H,3H)-dione

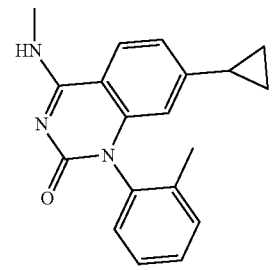 [SMILES: CNc1nc(=O)n(-c2ccccc2C)c2cc(C3CC3)ccc12]

$^1$H NMR (400 MHz, DMSO-d$_6$) δ=8.4 (d, J=3.6 Hz, 1H), 7.96 (d, J=6.8 Hz, 1H), 7.45-7.36 (m, 3H), 7.14 (d, J=6.8 Hz, 1H), 6.80 (dd, J=1.2, 6.8 Hz, 1H), 5.99 (d, J=1.2 Hz, 1H), 2.96 (d, J=3.6 Hz, 3H), 1.93 (d, J=8.0 Hz, 3H), 0.91 (dd, J=1.2, 6.4 Hz, 2H), 0.95-0.93 (m, 2H); LCMS: m/z [M+H]$^+$ 306.33.

6-Bromo-4-(methylamino)-1-phenyl-7-(trifluoromethyl)quinazolin-2(1H)-one was prepared by using 6-bromo-1-phenyl-7-(trifluoromethyl)quinazoline-2,4(1H,3H)-dione

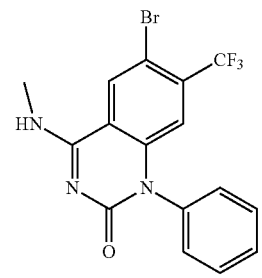 [SMILES: CNc1nc(=O)n(-c2ccccc2)c2cc(C(F)(F)F)c(Br)cc12]

$^1$H NMR (400 MHz, DMSO-d$_6$) δ 8.85 (s, 1H), 8.64 (s, 1H), 7.60 (t, J=7.4 Hz, 2H), 7.55-7.50 (m, 1H), 7.33 (d, J=7.5 Hz, 2H), 6.65 (s, 1H), 2.98 (s, 3H). m/z [M+H]$^+$ 398.0.

6-Bromo-1-(2-chlorophenyl)-4-(methylamino)-7-(trifluoromethyl)quinazolin-2(1H)-one was prepared by using 6-bromo-1-(2-chlorophenyl)-7-(trifluoromethyl)quinazoline-2,4(1H,3H)-dione

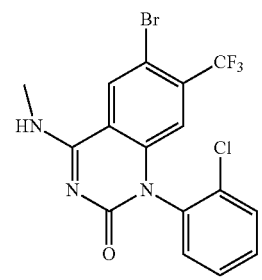 [SMILES: CNc1nc(=O)n(-c2ccccc2Cl)c2cc(C(F)(F)F)c(Br)cc12]

$^1$H NMR (400 MHz, DMSO-d$_6$) δ 8.99 (s, 1H), 8.71 (s, 1H), 7.76 (d, J=9.4 Hz, 1H), 7.62-7.52 (m, 3H), 6.52 (s, 1H), 3.00 (s, 3H). m/z [M+H]$^+$ 432.0.

7-Cyclopropyl-4-((2,2-difluoroethyl)amino)-1-phenylquinazolin-2(1H)-one was prepared by using 7-cyclopropyl-1-phenylquinazoline-2,4(1H,3H)-dione and 2,2-difluoroethan-1-amine

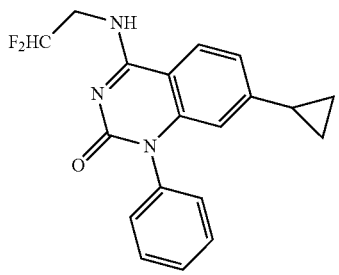 [SMILES: O=c1nc(NCC(F)F)c2ccc(C3CC3)cc2n1-c1ccccc1]

$^1$H NMR (400 MHz, DMSO-d$_6$) δ=8.71 (t, J=4.0 Hz, 1H), 8.03 (d, J=6.8 Hz, 1H), 7.60-7.57 (m, 2H), 7.52-7.49 (m, 1H), 7.27 (d, J=6.0 Hz, 2H), 6.84 (d, J=6.0 Hz, 1H), 6.37-6.11 (m, 2H), 3.93-3.86 (m, 2H), 1.80-1.77 (m, 1H), 0.95-0.91 (m, 2H), 0.58 (dd, J=4.0, 4.8 Hz, 2H). m/z [M+H]$^+$ 342.35.

1-(3-Chloropyridin-2-yl)-4-(methylamino)-7-(trifluoromethyl)pyrido[2,3-d]pyrimidin-2(1H)-one was prepared by using 1-(3-chloropyridin-2-yl)-7-(trifluoromethyl)pyrido[2,3-d]pyrimidine-2,4(1H,3H)-dione

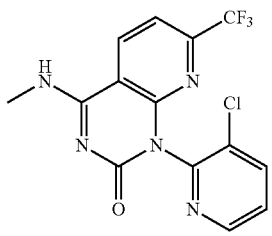 [SMILES: CNc1nc(=O)n(-c2ncccc2Cl)c2nc(C(F)(F)F)ccc12]

$^1$H NMR (400 MHz, DMSO-d$_6$) δ=9.22 (d, J=3.2 Hz, 1H), 8.83 (d, J=6.4 Hz, 1H), 8.59 (dd, J=1.2, 3.6 Hz, 1H), 8.20 (dd, J=1.2, 6.4 Hz, 1H), 7.84 (d, J=6.4 Hz, 1H), 7.59 (dd, J=3.6, 6.4 Hz, 1H), 3.04 (d, J=3.6 Hz, 3H). m/z [M+H]$^+$ 356.36

4-(Methylamino)-1-(3-methylpyridin-2-yl)-7-(trifluoromethyl)pyrido[2,3-d]pyrimidin-2(1H)-one was prepared by using 1-(3-methylpyridin-2-yl)-7-(trifluoromethyl)pyrido[2,3-d]pyrimidine-2,4(1H,3H)-dione

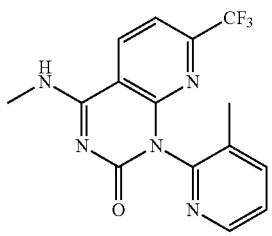 [SMILES: CNc1nc(=O)n(-c2ncccc2C)c2nc(C(F)(F)F)ccc12]

$^1$H NMR (400 MHz, DMSO-d$_6$) δ=8.50 (d, J=4.0 Hz, 1H), 8.14 (d, J=6.4 Hz, 1H), 7.77 (d, J=5.2 Hz, 1H), 7.52 (br s, 1H), 7.40-7.38 (m, 1H), 7.28 (s, 1H), 3.14 (d, J=4.0 Hz, 3H), 2.16 (s, 3H). m/z [M+H]$^+$ 336.37.

7-Isopropyl-4-(methylamino)-1-phenylpyrido[2,3-d]pyrimidin-2(1H)-one was prepared by using 7-isopropyl-1-phenylpyrido[2,3-d]pyrimidine-2,4(1H,3H)-dione

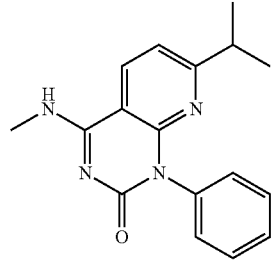 [SMILES: CNc1nc(=O)n(-c2ccccc2)c2nc(C(C)C)ccc12]

$^1$H NMR (400 MHz, DMSO-d$_6$) δ 8.63 (d, J=4.8 Hz, 1H), 8.37 (dd, J=8.2, 2.3 Hz, 1H), 7.47 (t, J=7.6 Hz, 2H), 7.41-7.30 (m, 1H), 7.20 (d, J=8.1 Hz, 1H), 7.15 (d, J=8.1, 1H), 2.98 (dd, J=4.5, 2.3 Hz, 4H), 2.81 (p, J=7.2 Hz, 1H), 1.00 (dd, J=7.0, 2.3 Hz, 7H). m/z [M+H]$^+$ 295.1

5-Fluoro-4-(methylamino)-1-phenyl-7-(trifluoromethyl)quinazolin-2(1H)-one was prepared by using 5-fluoro-1-phenyl-7-(trifluoromethyl)quinazoline-2,4(1H,3H)-dione

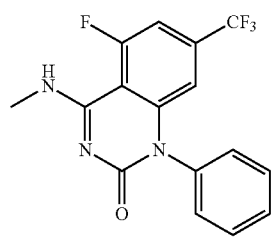 [SMILES: CNc1nc(=O)n(-c2ccccc2)c2cc(C(F)(F)F)cc(F)c12]

$^1$H NMR (400 MHz, DMSO-d$_6$) δ 8.20 (dd, J=12.4, 5.5 Hz, 1H), 7.62 (t, J=7.5 Hz, 2H), 7.58-7.50 (m, 2H), 7.35 (d, J=7.6 Hz, 2H), 6.36 (s, 1H), 3.02 (s, 3H). m/z [M+H]$^+$ 338.1.

6-bromo-1-(2-chlorophenyl)-7-cyclopropyl-4-(methylamino)quinazolin-2(1H)-one was prepared by using 6-bromo-1-(2-chlorophenyl)-7-cyclopropylquinazoline-2,4(1H,3H)-dione

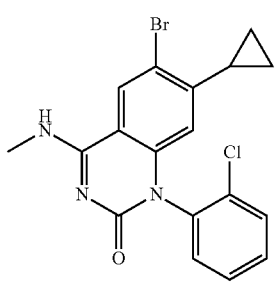 [SMILES: CNc1nc(=O)n(-c2ccccc2Cl)c2cc(C3CC3)c(Br)cc12]

$^1$H NMR (400 MHz, DMSO-d$_6$) δ 8.67 (s, 1H), 8.43 (s, 1H), 7.77-7.67 (m, 1H), 7.56 (dt, J=7.1, 2.1 Hz, 2H), 7.45 (dt, J=6.6, 2.6 Hz, 1H), 5.75 (s, 1H), 2.05 (d, J=8.0 Hz, 1H), 0.97 (d, J=8.2 Hz, 2H), 0.26 (s, 2H). m/z [M+H]$^+$ 404.0.

1-(2-chlorophenyl)-7-cyclopropyl-4-((cyclopropylmethyl)amino)-2-oxo-1,2-dihydro-quinazoline-6-carbonitrile was prepared by substituting 1-(2-chlorophenyl)-7-cyclopropyl-2,4-dioxo-1,2,3,4-tetrahydroquinazoline-6-carbonitrile and cyclopropylmethanamine

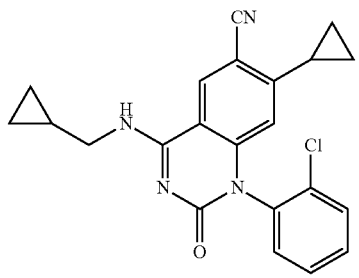 [SMILES: N#Cc1cc2c(NCC3CC3)nc(=O)n(-c3ccccc3Cl)c2cc1C1CC1]

$^{1}$H NMR (400 MHz, DMSO-d$_{6}$) δ 8.83 (t, J=5.1 Hz, 1H), 8.76 (s, 1H), 7.74 (d, J=7.3 Hz, 1H), 7.57 (d, J=7.0 Hz, 2H), 7.49 (d, J=7.5 Hz, 1H), 5.73 (s, 1H), 2.18-2.10 (m, 1H), 1.22-1.15 (m, 1H), 1.08 (d, J=7.4 Hz, 2H), 0.52 (d, J=6.8 Hz, 2H), 0.44-0.37 (m, 2H), 0.31 (d, J=3.9 Hz, 2H). m/z [M+H]$^{+}$ 391.0.

1-(2-chlorophenyl)-7-cyclopropyl-4-((oxetan-2-ylmethyl)amino)-2-oxo-1,2-dihydro-quinazoline-6-carbonitrile was prepared by substituting 1-(2-chlorophenyl)-7-cyclopropyl-2,4-dioxo-1,2,3,4-tetrahydroquinazoline-6-carbonitrile and oxetan-2-ylmethanamine

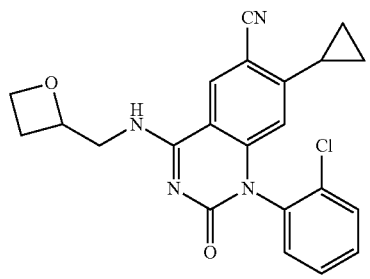 [SMILES: N#Cc1cc2c(NCC3CCO3)nc(=O)n(-c3ccccc3Cl)c2cc1C1CC1]

$^{1}$H NMR (400 MHz, DMSO-d$_{6}$) δ 8.93 (s, 1H), 8.78 (s, 1H), 7.79-7.74 (m, 1H), 7.60 (d, J=8.4 Hz, 2H), 7.52-7.46 (m, 1H), 5.74 (s, 1H), 5.01-4.92 (m, 1H), 4.60-4.44 (m, 3H), 3.84 (d, J=15.7 Hz, 1H), 3.77-3.66 (m, 1H), 3.50 (s, 1H), 2.14 (s, 1H), 1.07 (s, 2H), 0.40 (d, J=7.1 Hz, 2H). m/z [M+H]$^{+}$ 407.0.

1-(2-chlorophenyl)-7-cyclopropyl-4-((2-(methylsulfonyl)ethyl)amino)-2-oxo-1,2-dihydro-quinazoline-6-carbonitrile was prepared by substituting 1-(2-chlorophenyl)-7-cyclopropyl-2,4-dioxo-1,2,3,4-tetrahydroquinazoline-6-carbonitrile and 2-(methylsulfonyl)ethan-1-amine

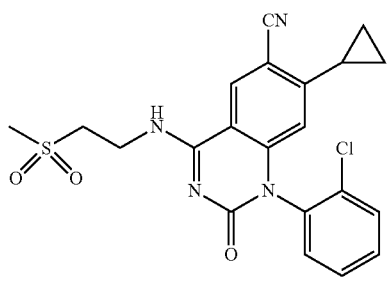 [SMILES: CS(=O)(=O)CCNc1nc(=O)n(-c2ccccc2Cl)c2cc(C3CC3)c(C#N)cc12]

$^{1}$H NMR (400 MHz, DMSO-d$_{6}$) δ 9.00 (d, J=5.9 Hz, 1H), 8.66 (s, 1H), 7.75 (dd, J=6.6, 3.2 Hz, 1H), 7.63-7.54 (m, 2H), 7.52-7.46 (m, 1H), 5.76 (s, 1H), 3.91 (p, J=7.3 Hz, 2H), 3.59-3.49 (m, 2H), 3.09 (s, 3H), 2.20-2.09 (m, 1H), 1.09 (d, J=8.4 Hz, 2H), 0.42 (d, J=6.4 Hz, 2H). m/z [M+H]$^{+}$ 443.1.

1-(2-chlorophenyl)-7-cyclopropyl-4-(((1R,2S)-2-fluorocyclopropyl)amino)quinazolin-2(1H)-one was prepared by substituting 1-(2-chlorophenyl)-7-cyclopropylquinazoline-2,4(1H,3H)-dione and (1R,2S)-2-fluorocyclopropan-1-amine

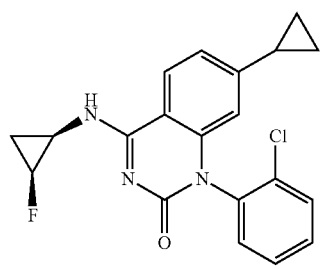 [SMILES: O=c1nc(N[C@@H]2C[C@@H]2F)c2ccc(C3CC3)cc2n1-c1ccccc1Cl]

$^{1}$H NMR (400 MHz, Methanol-d$_{4}$) δ 8.02 (dd, J=8.6, 1.9 Hz, 1H), 7.59 (tdt, J=49.6, 6.1, 2.9 Hz, 4H), 6.95 (d, J=8.5 Hz, 1H), 6.17 (s, 1H), 4.80-4.55 (m, 1H), 3.10 (dt, J=9.1, 6.3 Hz, 1H), 1.91-1.75 (m, 1H), 1.40-1.23 (m, 2H), 1.02 (d, J=8.2 Hz, 2H), 0.62 (dp, J=4.8, 2.3 Hz, 2H). m/z [M+H]$^{+}$ 370.0.

1-(2-Chlorophenyl)-7-cyclopropyl-4-(((1-fluorocyclopropyl)methyl)amino)-5-methoxyquinazolin-2(1H)-one was prepared by substituting 1-(2-chlorophenyl)-7-cyclopropyl-5-methoxyquinazoline-2,4(1H,3H)-dione and (1-fluorocyclopropyl)methanamine

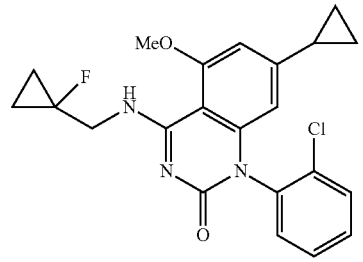 [SMILES: COc1cc(C2CC2)cc2c1c(NCC1(F)CC1)nc(=O)n2-c1ccccc1Cl]

$^{1}$H NMR (500 MHz, DMSO-d$_{6}$) δ 8.58 (t, 1H), 7.71-7.69 (m, 1H), 7.55-7.53 (m, 2H), 7.52-7.42 (m, 1H), 6.44 (d, J=1.5 Hz, 1H), 5.61 (d, J=1.5 Hz, 1H), 4.02-3.94 (m, 5H), 1.81-1.77 (m, 1H), 1.10-1.03 (m, 2H), 0.94-0.92 (m, 4H), 0.62-0.60 (m, 2H). m/z [M+H]$^{+}$ 414.39.

4-Methoxy-1-(2-methylpyridin-3-yl)-7-(trifluoromethyl)quinazolin-2(1H)-one was prepared by substituting 1-(2-methylpyridin-3-yl)-7-(trifluoromethyl)quinazoline-2,4(1H,3H)-dione and methanol

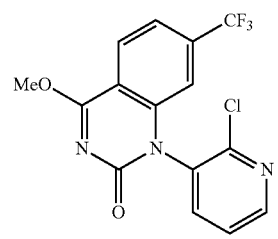 [SMILES: COc1nc(=O)n(-c2cccnc2Cl)c2cc(C(F)(F)F)ccc12]

$^{1}$H NMR (500 MHz, DMSO-d$_{6}$): δ 8.66 (dd, J=1.5 Hz, 1H), 8.25 (d, J=8 Hz, 1H), 7.84 (dd, J=1.5 Hz, 1H), 7.66 (dd,

J=1.0 Hz, 1H), 7.53-7.50 (m, 1H), 6.58 (s, 1H), 4.15 (s, 3H), 2.20 (s, 3H); LCMS. m/z [M+H]$^+$ 336.40.

1-(2-Chlorophenyl)-4-cyclopropoxy-7-(trifluoromethyl)pyrido[2,3-d]pyrimidin-2(1H)-one was prepared by using 1-(2-chlorophenyl)-7-(trifluoromethyl)pyrido[2,3-d]pyrimidine-2,4(1H,3H)-dione and cycloproanol

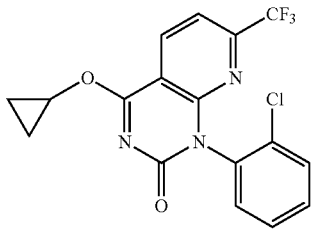 [SMILES: O=c1nc(OC2CC2)c2ccc(C(F)(F)F)nc2n1-c1ccccc1Cl]

$^1$H NMR (500 MHz, DMSO-d$_6$) δ 8.58 (d, J=8.0 Hz, 1H), 7.79 (d, J=8.0 Hz, 1H), 7.71-7.68 (m, 1H), 7.55-7.52 (m, 3H), 4.67-4.64 (m, 1H), 1.02-0.94 (m, 4H). m/z [M+H]$^+$ 382.33.

1-(2-Chlorophenyl)-4-(((S, S)-2-fluorocyclopropyl)amino)-7-(trifluoromethoxy)quinazolin-2(1H)-one was prepared by using 1-(2-chlorophenyl)-7-(trifluoromethoxy)-quinazoline-2,4(1H,3H)-dione and trans-2-fluorocyclopropan-1-amine

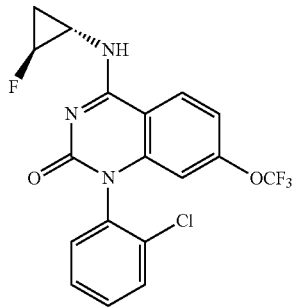

$^1$H NMR (500 MHz, DMSO-d$_6$) δ 8.59 (s, 1H), 8.26 (d, J=9.0 Hz, 1H), 7.77-7.73 (m, 1H), 7.64-7.50 (m, 3H), 7.26 (d, J=10.0 Hz, 1H), 6.10 (s, 1H), 4.96-4.82 (m, 1H), 3.48-3.42 (m, 1H), 1.55-1.47 (m, 1H), 1.24-1.19 (m, 1H). m/z [M+H]$^+$ 414.39.

1-(2-chlorophenyl)-7-cyclopropyl-5-(difluoromethoxy)-4-(methylamino)quinazolin-2(1H)-one was prepared by using 1-(2-chlorophenyl)-7-cyclopropyl-5-(difluoromethoxy)quinazoline-2,4(1H,3H)-dione

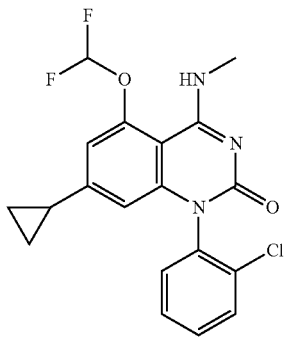 [SMILES: CNc1nc(=O)n(-c2ccccc2Cl)c2cc(C3CC3)cc(OC(F)F)c12]

$^1$H NMR (500 MHz, DMSO-d$_6$) δ ppm 7.74-7.72 (m, 1H), 7.59-7.55 (m, 3H), 7.45-7.28 (m, 1H), 6.56 (s, 1H), 5.87 (s, 1H), 3.01 (d, J=4.5 Hz, 3H), 1.86-1.82 (m, 1H), 0.97-0.95 (m, 2H), 0.61-0.59 (m, 2H). m/z [M+H]$^+$ 392.3.

7-Cyclopropyl-5-ethyl-4-(methylamino)-1-(o-tolyl)quinazolin-2(1H)-one was prepared by using 7-cyclopropyl-5-ethyl-1-(o-tolyl)quinazoline-2,4(1H,3H)-dione

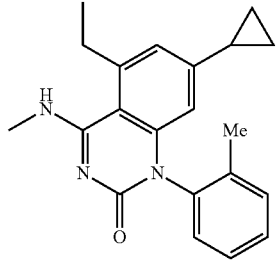 [SMILES: CCc1cc(C2CC2)cc2c1c(NC)nc(=O)n2-c1ccccc1C]

$^1$H NMR (500 MHz, DMSO-d$_6$) δ ppm 7.45-7.35 (m, 3H), 7.19 (s, 1H), 7.13-7.11 (m, 1H), 6.67 (s, 1H), 5.83 (d, J=1.5 Hz, 1H), 3.13 (q, J=7.5 Hz, 2H), 3.00 (s, 3H), 1.91 (s, 3H), 1.74-1.70 (m, 1H), 1.23 (t, J=7.5 Hz, 3H), 0.90-0.88 (m, 2H), 0.52-0.50 (m, 2H). m/z [M+H]$^+$ 334.37.

1-(2-Chlorophenyl)-7-cyclopropyl-4-methoxyquinazolin-2(1H)-one was prepared by using 1-(2-chlorophenyl)-7-cyclopropylquinazoline-2,4(1H,3H)-dione and methanol

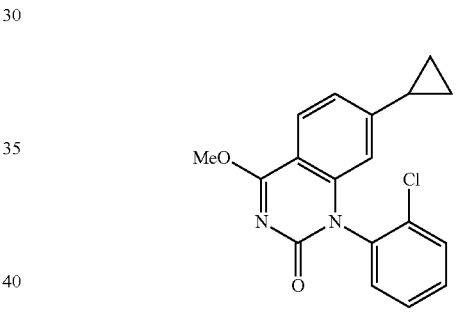

$^1$H NMR (400 MHz, DMSO-d$_6$) δ 7.87 (d, J=8.5 Hz 1H), 7.78-7.75 (m, 1H), 7.62-7.54 (m, 3H), 6.9 (dd, J=8.5, 1.5 Hz, 1H), 6.15 (d, J=1.5 Hz, 1H), 4.08 (s, 3H), 1.92-1.87 (m, 1H), 0.99-0.96 (m, 2H), 0.66-0.64 (m, 2H). m/z [M+H]$^+$ 327.16.

7-chloro-4-(methylamino)-1-(3-vinylphenyl)quinazolin-2(1H)-one was prepared by using 7-chloro-1-(3-vinylphenyl)quinazoline-2,4(1H,3H)-dione.

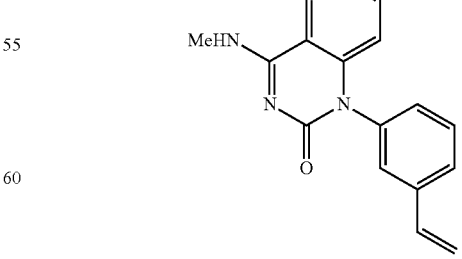

m/z [M + H]$^+$ 312.26.

1-(2-Chlorophenyl)-4-(pyridin-4-ylamino)-7-(trifluoromethyl)pyrido[2,3-d]pyrimidin-2(1H)-one was prepared by using 1-(2-chlorophenyl)-7-(trifluoromethyl)pyrido[2,3-d]pyrimidine-2,4(1H,3H)-dione and pyridin-4-amine

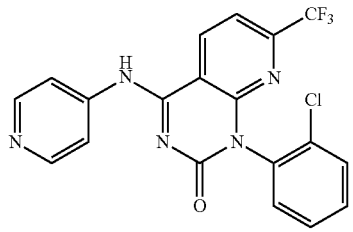 [SMILES: O=c1nc(Nc2ccncc2)c2ccc(C(F)(F)F)nc2n1-c1ccccc1Cl]

$^1$H NMR (400 MHz, DMSO-d$_6$) δ 9.14 (br s, 1H), 8.57 (d, J=5.3 Hz, 2H), 8.07-7.77 (m, 3H), 7.68 (m, 1H), 7.52 (m, 3H). m/z [M+H]$^+$ 418.00.

7-Bromo-6-chloro-1-(2-chlorophenyl)-4-(isoxazol-4-ylamino)quinazolin-2(1H)-one was prepared by using 7-bromo-6-chloro-1-(2-chlorophenyl)quinazoline-2,4(1H,3H)-dione and isoxazol-4-amine

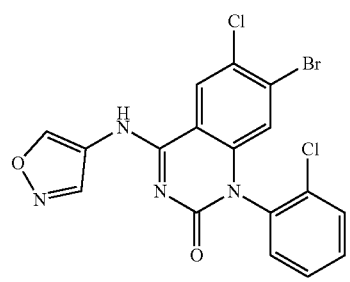 [SMILES: O=c1nc(Nc2cnoc2)c2cc(Cl)c(Br)cc2n1-c1ccccc1Cl]

$^1$H NMR (400 MHz, DMSO-d$_6$) δ 10.71 (s, 1H), 9.46 (s, 1H), 8.89 (s, 1H), 8.66 (s, 2H), 7.85-7.73 (m, 1H), 7.69-7.51 (m, 3H), 6.63 (s, 1H). m/z [M+H]$^+$ 452.9 (major).

7-Cyclopropyl-4-((cyclopropylmethyl)amino)-1-(2-(trifluoromethyl)pyridin-3-yl)-quinazolin-2(1H)-one was prepared by using 7-cyclopropyl-1-(2-(trifluoromethyl)pyridin-3-yl)quinazoline-2,4(1H,3H)-dione and cylcopropylmethanamine

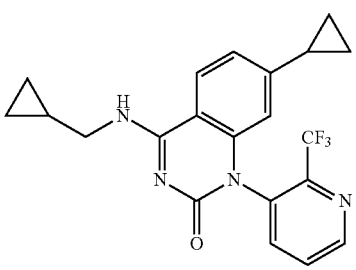

$^1$H NMR (400 MHz, DMSO-d$_6$) δ 8.77 (d, J=2.1 Hz, 1H), 8.53 (s, 1H), 8.07-7.88 (m, 2H), 7.84 (d, J=6.7 Hz, 1H), 6.70 (d, J=8.5 Hz, 1H), 5.91 (s, 1H), 1.73 (s, 1H), 1.05 (s, 1H), 0.81 (d, J=8.7 Hz, 2H), 0.47 (m, 2H), 0.35 (d, J=7.8 Hz, 2H), 0.16 (s, 2H). m/z [M+H]$^+$ 399.1.

7-Cyclopropyl-4-((cyclopropylmethyl)amino)-1-(2-(difluoromethoxy)pyridin-3-yl)-quinazolin-2(1H)-one was prepared by using 7-cyclopropyl-1-(2-(difluoromethoxy)pyridin-3-yl)quinazoline-2,4(1H,3H)-dione and cylcopropylmethanamine

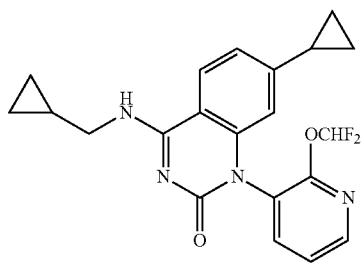 [SMILES: O=c1nc(NCC2CC2)c2ccc(C3CC3)cc2n1-c1cccnc1OC(F)F]

$^1$H NMR (400 MHz, DMSO-d$_6$) δ 8.64 (s, 1H), 8.41 (d, J=4.8 Hz, 1H), 8.09 (d, J=8.3 Hz, 1H), 7.99 (d, J=7.9 Hz, 1H), 7.74 (t, J=73.3, Hz, 1H), 7.50 (m, 1H), 6.86 (d, J=8.2 Hz, 1H), 6.15 (s, 1H), 1.88 (s, 1H), 1.20 (s, 1H), 0.96 (d, J=8.6 Hz, 2H), 0.63 (d, J=14.2 Hz, 2H), 0.49 (d, J=7.8 Hz, 2H), 0.30 (d, J=4.5 Hz, 2H). m/z [M+H]$^+$ 401.1

1-(2-chlorophenyl)-4-(((trans)-2-fluorocyclopropyl)amino)-7-(trifluoromethoxy)quinazolin-2(1H)-one was prepared by using 1-(2-chlorophenyl)-7-(trifluoromethoxy)quinazoline-2,4(1H,3H)-dione and trans-2-fluorocyclopropan-1-amine

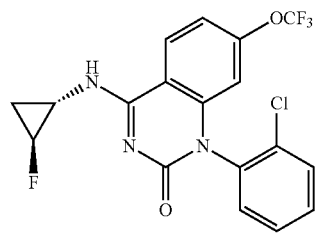 [SMILES: O=c1nc(N[C@H]2C[C@@H]2F)c2ccc(OC(F)(F)F)cc2n1-c1ccccc1Cl]

$^1$H NMR (400 MHz, DMSO-d$_6$) δ 8.64 (s, 1H), 8.23 (d, J=9.1 Hz, 1H), 7.75 (s, 1H), 7.58 (s, 2H), 7.51 (s, 1H), 7.24 (d, J=9.0 Hz, 1H), 6.10 (s, 1H), 1.52 (m, 1H), 1.22 (m, 1H), two missing protons under DMSO peak. m/z [M+H]$^+$ 414.0.

1-(2-Chlorophenyl)-4-((cyclopropylmethyl)amino)-7-(1,1-difluoroethyl)quinazolin-2(1H)-one was prepared by using 1-(2-chlorophenyl)-7-(1,1-difluoroethyl)quinazoline-2,4(1H,3H)-dione and cylcopropylmethanamine

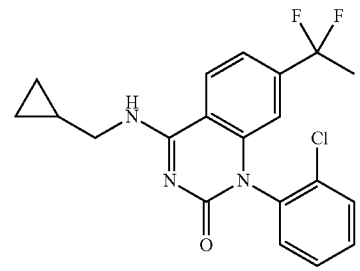 [SMILES: CC(F)(F)c1ccc2c(NCC3CC3)nc(=O)n(-c3ccccc3Cl)c2c1]

$^1$H NMR (400 MHz, Methanol-d$_4$) δ 8.06 (d, J=8.4 Hz, 1H), 7.60-7.48 (m, 1H), 7.40 (dt, J=6.2, 2.3 Hz, 2H), 7.26 (dd, J=16.4, 7.1 Hz, 2H), 6.36 (s, 1H), 3.42-3.23 (m, 2H), 1.63 (t, J=18.4 Hz, 3H), 1.12 (m, 1H), 0.40 (d, J=7.7 Hz, 2H), 0.19 (d, J=5.3 Hz, 2H). m/z [M+H]$^+$ 390.1.

581

4-(((1S,2R)-2-Fluorocyclopropyl)amino)-1-phenyl-7-(trifluoromethyl)quinazolin-2(1H)-one was prepared by using 1-phenyl-7-(trifluoromethyl)quinazoline-2,4(1H,3H)-dione and (1S,2R)-2-fluorocyclopropan-1-amine

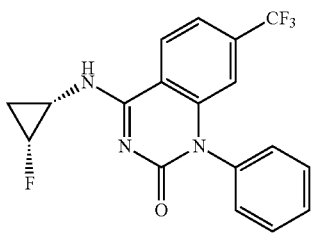 [SMILES: O=c1nc(N[C@H]2C[C@H]2F)c2ccc(C(F)(F)F)cc2n1-c1ccccc1]

$^1$H NMR (400 MHz, DMSO-d$_6$) δ 8.79 (s, 1H), 8.46 (d, J=8.5 Hz, 1H), 7.69-7.49 (m, 4H), 7.37 (d, J=7.2 Hz, 2H), 6.57 (s, 1H), 5.01-4.73 (m, 1H), 1.45-1.17 (m, 2H). m/z [M+H]$^+$ 364.1.

1-(2-Chlorophenyl)-7-cyclopropyl-4-(methylamino)quinazolin-2(1H)-one was prepared by substituting 1-(2-chlorophenyl)-7-cyclopropylquinazoline-2,4(1H,3H)-dione

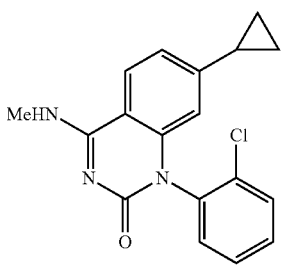 [SMILES: CNc1nc(=O)n(-c2ccccc2Cl)c2cc(C3CC3)ccc12]

$^1$H NMR (400 MHz, DMSO-d$_6$) δ 8.51 (s, 1H), 8.07-7.93 (m, 1H), 7.73 (dt, J=5.9, 2.8 Hz, 1H), 7.62-7.39 (m, 3H), 6.82 (d, J=8.5 Hz, 1H), 6.02 (s, 1H), 2.97 (t, J=3.1 Hz, 3H), 1.81 (s, 1H), 0.94 (d, J=8.4 Hz, 2H), 0.60 (s, 2H). m/z [M+H]$^+$ 326.0.

(R)-4-(2-(Hydroxymethyl)azetidin-1-yl)-1-(o-tolyl)-7-(trifluoromethyl)pyrido[2,3-d]pyrimidin-2(1H)-one was prepared by substituting (R)-azetidin-2-ylmethanol and 1-(o-tolyl)-7-(trifluoromethyl)pyrido[2,3-d]pyrimidine-2,4(1H,3H)-dione.

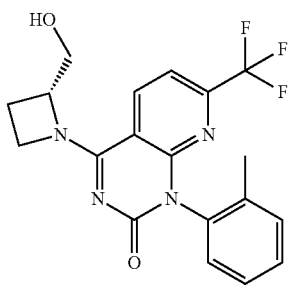 [SMILES: Cc1ccccc1-n1c(=O)nc(N2CC[C@@H]2CO)c2ccc(C(F)(F)F)nc21]

$^1$H NMR (400 MHz, DMSO-d$_6$) δ 8.49 (d, J=8.1 Hz, 1H), 7.61 (dd, J=8.2, 2.4 Hz, 1H), 7.40-7.25 (m, 3H), 7.12 (d, J=7.5 Hz, 1H), 5.26 (s, 1H), 4.94-4.50 (m, 3H), 3.96 (d, J=11.5 Hz, 1H), 3.70 (dd, J=11.9, 3.3 Hz, 2H), 2.57-2.46 (s, 1H), 2.43-2.31 (s, 1H), 1.92 (d, J=16.3 Hz, 3H). m/z [M+H]$^+$ 391.1

582

N-Methyl-2-((2-oxo-1-(o-tolyl)-7-(trifluoromethyl)-1,2-dihydropyrido[2,3-d]pyrimidin-4-yl)amino)ethane-1-sulfonamide was prepared by substituting 2-amino-N-methylethane-1-sulfonamide and 1-(o-tolyl)-7-(trifluoromethyl)pyrido[2,3-d]pyrimidine-2,4(1H,3H)-dione.

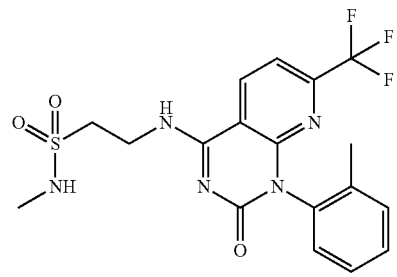 [SMILES: CNS(=O)(=O)CCNc1nc(=O)n(-c2ccccc2C)c2nc(C(F)(F)F)ccc12]

$^1$H NMR (400 MHz, DMSO-d$_6$) δ 9.23 (s, 1H), 8.79 (d, J=8.2 Hz, 1H), 7.80 (d, J=8.1 Hz, 1H), 7.38-7.24 (m, 3H), 7.17 (s, 1H), 7.16 (d, J=7.7 Hz, 1H), 3.86 (d, J=20.3 Hz, 2H), 3.52-3.26 (m, 2H), 2.64 (s, 3H), 1.93 (s, 3H). m/z [M+H]$^+$ 442.1

N-Methyl-3-((2-oxo-1-(o-tolyl)-7-(trifluoromethyl)-1,2-dihydropyrido[2,3-d]pyrimidin-4-yl)amino)propane-1-sulfonamide was prepared by substituting 3-amino-N-methylpropane-1-sulfonamide and 1-(o-tolyl)-7-(trifluoromethyl)pyrido[2,3-d]pyrimidine-2,4(1H,3H)-dione.

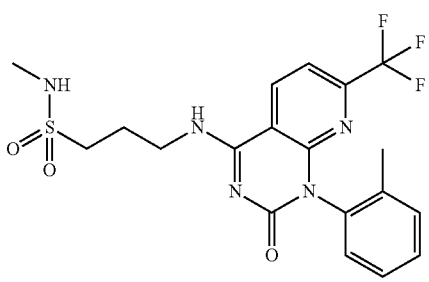 [SMILES: CNS(=O)(=O)CCCNc1nc(=O)n(-c2ccccc2C)c2nc(C(F)(F)F)ccc12]

$^1$H NMR (400 MHz, DMSO-d$_6$) δ 9.04 (s, 1H), 8.85 (d, J=7.2 Hz, 1H), 7.78 (d, J=8.2 Hz, 1H), 7.35-7.27 (m, 3H), 7.16 (d, J=7.5 Hz, 1H), 6.98 (s, 1H), 3.74-3.58 (m, 2H), 3.20-3.12 (m, 2H), 2.59 (d, J=2.5 Hz, 3H), 2.11-2.0 (m, 2H), 1.93 (d, J=2.5 Hz, 3H). m/z [M+H]$^+$ 456.1

N-Cyclopropyl-2-((2-oxo-1-(o-tolyl)-7-(trifluoromethyl)-1,2-dihydropyrido[2,3-d]pyrimidin-4-yl)amino)ethane-1-sulfonamide was prepared by substituting 2-amino-N-cyclopropylethane-1-sulfonamide and 1-(o-tolyl)-7-(trifluoromethyl)pyrido[2,3-d]pyrimidine-2,4(1H,3H)-dione.

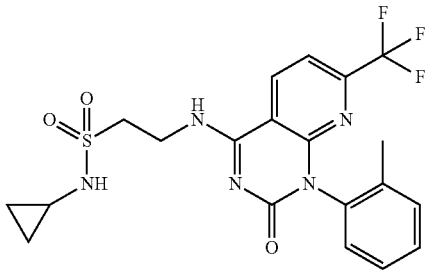 [SMILES: Cc1ccccc1-n1c(=O)nc(NCCS(=O)(=O)NC2CC2)c2ccc(C(F)(F)F)nc21]

583

¹H NMR (400 MHz, DMSO-d₆) δ 9.24 (s, 1H), 8.78 (d, J=7.3 Hz, 1H), 7.81 (d, J=8.1 Hz, 1H), 7.67 (s, 1H), 7.40-7.25 (m, 3H), 7.16 (d, J=7.6 Hz, 1H), 3.93-3.81 (m, 2H), 3.55-2.45 (m, 2H), 2.59-2.51 (m, 1H), 1.93 (d, J=2.6 Hz, 3H), 0.60 (t, J=3.3 Hz, 4H). m/z [M+H]⁺ 468.1

4-(((1S,2R)-2-Fluorocyclopropyl)amino)-1-(o-tolyl)-7-(trifluoromethyl)pyrido[2,3-d]pyrimidin-2(1H)-one was prepared by substituting (1S,2R)-2-fluorocyclopropan-1-amine HCl and 1-(o-tolyl)-7-(trifluoromethyl)pyrido[2,3-d]pyrimidine-2,4(1H,3H)-dione.

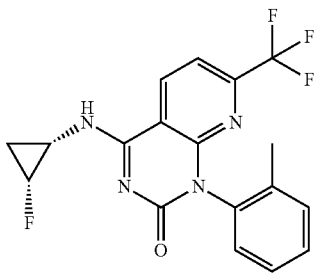 [SMILES: Cc1ccccc1-n1c(=O)nc(N[C@H]2C[C@H]2F)c2ccc(C(F)(F)F)nc21]

¹H NMR (400 MHz, DMSO-d₆) δ 8.99 (s, 1H), 8.91 (d, J=7.1 Hz, 1H), 7.79 (d, J=8.6 Hz, 1H), 7.39-7.27 (m, 3H), 7.18 (t, J=7.9 Hz, 1H), 4.91 (d, J=64.8 Hz, 1H), 3.15-3.09 (m, 1H), 1.93 (s, 3H), 1.42-1.22 (m, 2H). m/z [M+H]⁺ 379.1

4-(((1R,2S)-2-Fluorocyclopropyl)amino)-1-(o-tolyl)-7-(trifluoromethyl)pyrido[2,3-d]pyrimidin-2(1H)-one was prepared by substituting (1R,2S)-2-fluorocyclopropan-1-amine HCl and 1-(o-tolyl)-7-(trifluoromethyl)pyrido[2,3-d]pyrimidine-2,4(1H,3H)-dione.

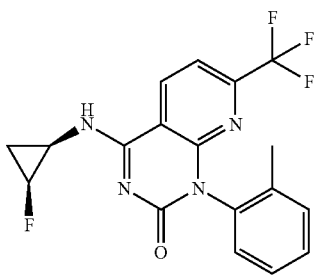 [SMILES: Cc1ccccc1-n1c(=O)nc(N[C@@H]2C[C@@H]2F)c2ccc(C(F)(F)F)nc21]

¹H NMR (400 MHz, DMSO-d₆) δ 8.99 (s, 1H), 8.91 (d, J=7.1 Hz, 1H), 7.79 (d, J=8.6 Hz, 1H), 7.39-7.27 (m, 3H), 7.18 (t, J=7.9 Hz, 1H), 4.91 (d, J=64.8 Hz, 1H), 3.15-3.09 (m, 1H), 1.93 (s, 3H), 1.42-1.22 (m, 2H). m/z [M+H]⁺ 379.1

N,N-Dimethyl-3-((2-oxo-1-(o-tolyl)-7-(trifluoromethyl)-1,2-dihydroquinazolin-4-yl)amino)propane-1-sulfonamide was prepared by substituting 3-amino-N,N-dimethylpropane-1-sulfonamide and 1-(o-tolyl)-7-(trifluoromethyl)quinazoline-2,4(1H,3H)-dione.

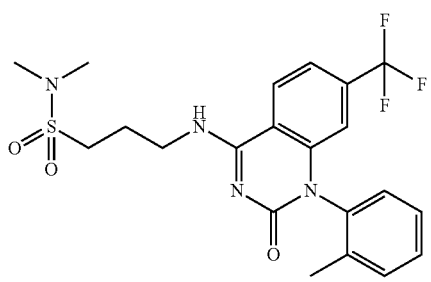 [SMILES: Cc1ccccc1-n1c(=O)nc(NCCCS(=O)(=O)N(C)C)c2ccc(C(F)(F)F)cc21]

584

¹H NMR (400 MHz, DMSO-d₆) (8.87 (s, 1H), 8.44 (d, J=7.7 Hz, 1H), 7.60 (d, J=8.4 Hz, 1H), 7.53-7.36 (m, 3H), 7.26 (d, J=7.4 Hz, 1H), 6.45 (s, 1H), 3.75-3.56 (m, 2H), 3.21 (t, J=7.1 Hz, 2H), 2.80 (d, J=2.5 Hz, 6H), 2.15-2.03 (m, 2H), 1.95 (d, J=2.5 Hz, 3H). m/z [M+H]⁺ 469.1

N,N-Dimethyl-2-((2-oxo-1-(o-tolyl)-7-(trifluoromethyl)-1,2-dihydroquinazolin-4-yl)amino)ethane-1-sulfonamide was prepared by substituting 2-amino-N,N-dimethylethane-1-sulfonamide and 1-(o-tolyl)-7-(trifluoromethyl)quinazoline-2,4(1H,3H)-dione.

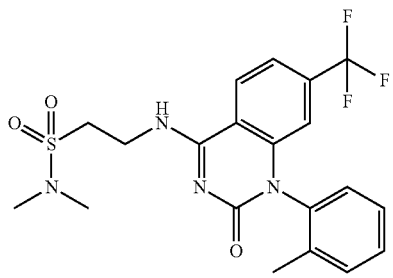 [SMILES: Cc1ccccc1-n1c(=O)nc(NCCS(=O)(=O)N(C)C)c2ccc(C(F)(F)F)cc21]

¹H NMR (400 MHz, DMSO-d₆) δ 9.05 (s, 1H), 8.37 (d, J=8.5 Hz, 1H), 7.63 (d, J=8.4 Hz, 1H), 7.50-7.40 (m, 3H), 7.26 (d, J=7.5 Hz, 1H), 6.46 (s, 1H), 4.01-3.84 (m, 2H), 3.49-3.42 (m, 2H), 2.83 (s, 6H), 1.96 (d, J=2.6 Hz, 3H). m/z [M+H]⁺ 455.1 tert-Butyl (R)-3-((2-oxo-1-(o-tolyl)-7-(trifluoromethyl)-1,2-dihydroquinazolin-4-yl)amino)pyrrolidine-1-carboxylate was prepared by substituting tert-butyl (R)-3-aminopyrrolidine-1-carboxylate and 1-(o-tolyl)-7-(trifluoromethyl)quinazoline-2,4(1H,3H)-dione.

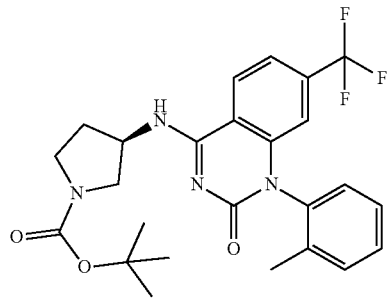

m/z [M + H]⁺ 389.2.

4-((2-(Morpholinosulfonyl)ethyl)amino)-1-(o-tolyl)-7-(trifluoromethyl)quinazolin-2(1H)-one was prepared by substituting 2-(morpholinosulfonyl)ethan-1-amine and 1-(o-tolyl)-7-(trifluoromethyl)quinazoline-2,4(1H,3H)-dione.

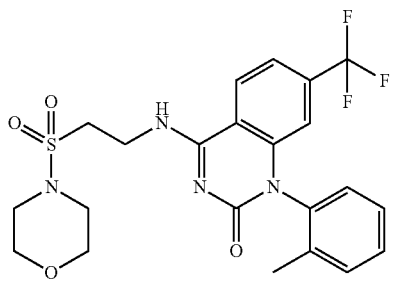 [SMILES: Cc1ccccc1-n1c(=O)nc(NCCS(=O)(=O)N2CCOCC2)c2ccc(C(F)(F)F)cc21]

¹H NMR (400 MHz, DMSO-d₆) δ 9.06 (s, 1H), 8.37 (d, J=8.5 Hz, 1H), 7.63 (d, J=8.3 Hz, 1H), 7.52-7.38 (m, 3H), 7.25 (d, J=7.5 Hz, 1H), 6.46 (s, 1H), 4-3.84 (m, 2H), 3.65 (s, 4H), 3.55-3.46 (m, 2H), 3.25-3.14 (m, 4H), 1.96 (s, 3H). m/z [M+H]⁺ 497.1

N-cyclopropyl-2-((2-oxo-1-(o-tolyl)-7-(trifluoromethyl)-1,2-dihydroquinazolin-4-yl)amino)ethane-1-sulfonamide was prepared by substituting 2-amino-N-cyclopropylethane-1-sulfonamide and 1-(o-tolyl)-7-(trifluoromethyl)quinazoline-2,4(1H,3H)-dione.

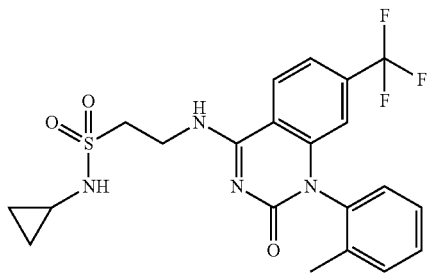 [SMILES: Cc1ccccc1-n1c(=O)nc(NCCS(=O)(=O)NC2CC2)c2ccc(C(F)(F)F)cc21]

¹H NMR (400 MHz, DMSO-d₆) δ 9.02 (s, 1H), 8.35 (d, J=8.7 Hz, 1H), 7.65 (s, 1H), 7.63 (d, J=8.5 Hz, 1H), 7.52-7.38 (m, 3H), 7.25 (d, J=7.5 Hz, 1H), 6.46 (s, 1H), 3.95-3.78 (m, 2H), 3.60-3.43 (m, 3H), 2.57 (d, J=6.4 Hz, 1H), 1.96 (d, J=2.7 Hz, 3H), 0.60 (t, J=3.9 Hz, 4H). m/z [M+H]⁺ 467.1

(R)-4-(2-(Hydroxymethyl)azetidin-1-yl)-1-(o-tolyl)-7-(trifluoromethyl)quinazolin-2(1H)-one was prepared by substituting (R)-azetidin-2-ylmethanol and 1-(o-tolyl)-7-(trifluoromethyl)quinazoline-2,4(1H,3H)-dione.

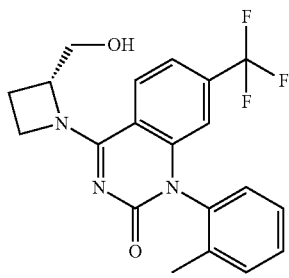

¹H NMR (400 MHz, DMSO-d₆) δ 8.15-8.06 (m, 1H), 7.54-7.37 (m, 4H), 7.22 (d, J=7.3 Hz, 1H), 6.44 (d, J=7.1 Hz, 1H), 5.29 (s, 1H), 4.98-4.44 (m, 3H), 3.99-3.88 (m, 1H), 3.71 (d, J=11.8 Hz, 1H), 2.57-2.45 (m, 1H), 2.40-2.27 (m, 1H), 1.95 (dd, J=16.3, 2.6 Hz, 3H). m/z [M+H]⁺ 390.1

4-(3-(Hydroxymethyl)azetidin-1-yl)-1-(o-tolyl)-7-(trifluoromethyl)quinazolin-2(1H)-one was prepared by substituting azetidin-3-ylmethanol and 1-(o-tolyl)-7-(trifluoromethyl)quinazoline-2,4(1H,3H)-dione.

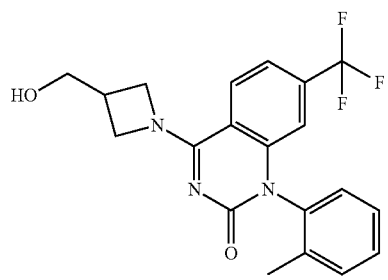 [SMILES: Cc1ccccc1-n1c(=O)nc(N2CC(CO)C2)c2ccc(C(F)(F)F)cc21]

¹H NMR (400 MHz, DMSO-d₆) δ 8.10 (d, J=8.5 Hz, 1H), 7.53-7.38 (m, 4H), 7.22 (d, J=7.3 Hz, 1H), 6.44 (s, 1H), 5.07-4.79 (m, 2H), 4.65-4.48 (m, 1H), 4.37-4.23 (m, 1H), 4.13-3.99 (m, 1H), 3.69-3.60 (m, 2H), 2.96-2.86 (m, 1H), 1.94 (s, 3H). m/z [M+H]⁺ 390.1

(R)-4-(2-(Methoxymethyl)azetidin-1-yl)-1-(o-tolyl)-7-(trifluoromethyl)quinazolin-2(1H)-one was prepared by substituting (R)-2-(methoxymethyl)azetidine and 1-(o-tolyl)-7-(trifluoromethyl)quinazoline-2,4(1H,3H)-dione.

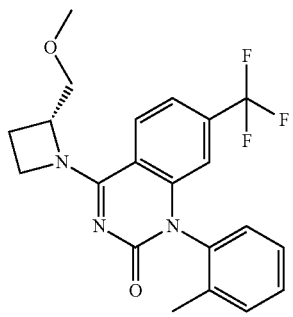 [SMILES: COC[C@H]1CCN1c1nc(=O)n(-c2ccccc2C)c2cc(C(F)(F)F)ccc12]

¹H NMR (400 MHz, DMSO-d₆) δ 8.08 (d, J=8.5 Hz, 1H), 7.56-7.38 (m, 4H), 7.23 (t, J=7.6 Hz, 1H), 6.45 (d, J=7.0 Hz, 1H), 5.03-4.68 (m, 2H), 4.64-4.40 (m, 1H), 3.96-3.86 (m, 1H), 3.71-3.62 (m, 2H), 2.61-2.50 (m, 1H), 2.45-2.30 (m, 1H), 1.95 (d, J=17.4 Hz, 3H). m/z [M+H]⁺ 404.1

4-((trans)-3,4-Dihydroxypyrrolidin-1-yl)-1-(o-tolyl)-7-(trifluoromethyl)quinazolin-2(1H)-one was prepared by substituting (3S,4S)-pyrrolidine-3,4-diol and 1-(o-tolyl)-7-(trifluoromethyl)quinazoline-2,4(1H,3H)-dione.

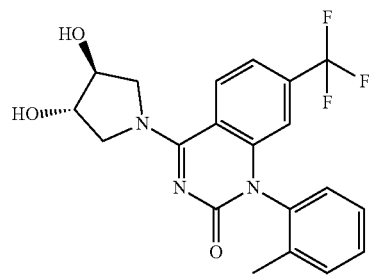 [SMILES: Cc1ccccc1-n1c(=O)nc(N2C[C@H](O)[C@@H](O)C2)c2ccc(C(F)(F)F)cc21]

¹H NMR (400 MHz, DMSO-d₆) δ 8.51-8.37 (m, 1H), 7.53-7.39 (m, 4H), 7.25 (dd, J=24.0, 7.5 Hz, 1H), 6.47 (d, J=16.7 Hz, 1H), 5.40 (s, 2H), 4.54-3.85 (m, 4H), 3.82-3.54 (m, 2H), 1.95 (d, J=34.0, 3H). m/z [M+H]⁺ 406.1

4-(((1R,2S)-2-fluorocyclopropyl)amino)-1-(o-tolyl)-7-(trifluoromethyl)quinazolin-2(1H)-one was prepared by substituting (1S,2R)-2-fluorocyclopropan-1-amine HCl and 1-(o-tolyl)-7-(trifluoromethyl)quinazoline-2,4(1H,3H)-dione.

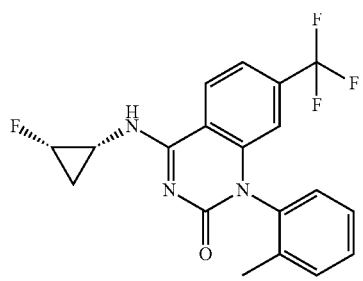

¹H NMR (400 MHz, DMSO-d₆) δ 8.83 (s, 1H), 8.51 (d, J=8.5 Hz, 1H), 7.61 (d, J=8.4 Hz, 1H), 7.53-7.38 (m, 3H), 7.28 (t, J=8.9 Hz, 1H), 6.47 (s, 1H), 4.90 (d, J=65.0 Hz, 1H), 3.15-3.05 (m, 1H), 1.96 (s, 3H), 1.49-1.18 (m, 2H). m/z [M+H]⁺ 378.1

4-(((1S,2R)-2-fluorocyclopropyl)amino)-1-(o-tolyl)-7-(trifluoromethyl)quinazolin-2(1H)-one was prepared by substituting (1R,2S)-2-fluorocyclopropan-1-amine HCl and 1-(o-tolyl)-7-(trifluoromethyl)quinazoline-2,4(1H,3H)-dione.

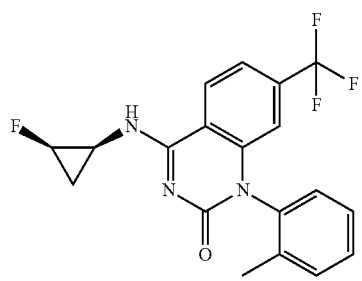

¹H NMR (400 MHz, DMSO-d₆) δ 8.83 (s, 1H), 8.51 (d, J=8.5 Hz, 1H), 7.61 (d, J=8.4 Hz, 1H), 7.53-7.38 (m, 3H), 7.28 (t, J=8.9 Hz, 1H), 6.47 (s, 1H), 4.90 (d, J=65.0 Hz, 1H), 3.15-3.05 (m, 1H), 1.96 (s, 3H), 1.49-1.18 (m, 2H). m/z [M+H]⁺ 378.1

3-((2-Oxo-1-(o-tolyl)-7-(trifluoromethyl)-1,2-dihydroquinazolin-4-yl)amino)propane-1-sulfonamide was prepared by substituting 3-aminopropane-1-sulfonamide and 1-(o-tolyl)-7-(trifluoromethyl)quinazoline-2,4(1H,3H)-dione.

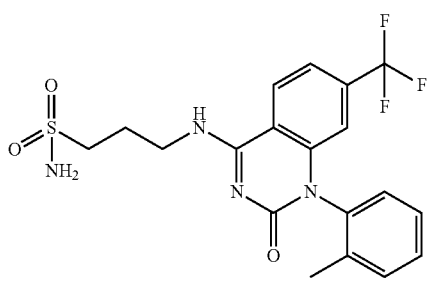 [SMILES: Cc1ccccc1-n1c(=O)nc(NCCCS(N)(=O)=O)c2ccc(C(F)(F)F)cc21]

¹H NMR (400 MHz, DMSO-d₆) δ 8.88 (bs, 1H), 8.34 (d, J=8.4 Hz, 1H), 7.56 (d, J=8.4 Hz, 1H), 7.50-7.37 (m, 3H), 7.21 (d, J=7.5 Hz, 1H), 6.66 (bs, 2H), 6.44 (s, 1H), 4.00-3.50 (m, 2H), 3.11 (t, J=8.0 Hz, 2H), 2.09 (t, J=8.0, 2H), 1.92 (s, 3H). m/z [M+H]⁺ 441.1

N-Methyl-3-((2-oxo-1-(o-tolyl)-7-(trifluoromethyl)-1,2-dihydroquinazolin-4-yl)amino)propane-1-sulfonamide was prepared by substituting 3-(methylamino)propane-1-sulfonamide and 1-(o-tolyl)-7-(trifluoromethyl)quinazoline-2,4(1H,3H)-dione.

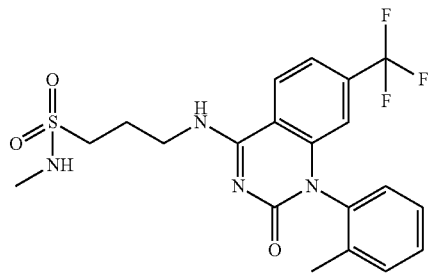 [SMILES: CNS(=O)(=O)CCCNc1nc(=O)n(-c2ccccc2C)c2cc(C(F)(F)F)ccc12]

¹H NMR (400 MHz, DMSO-d₆) δ 8.88 (bs, 1H), 8.34 (d, J=8.5 Hz, 1H), 7.56 (d, J=8.5 Hz, 1H), 7.49-7.37 (m, 3H), 7.21 (d, J=8.5 Hz, 1H), 6.68 (s, 1H), 6.44 (s, 1H), 4.0-3.5 (m, 2H), 3.13 (t, J=7.9 Hz, 1H), 2.57 (s, 3H), 2.03 (t, J=7.9 Hz, 1H), 1.92 (s, 3H). m/z [M+H]⁺ 455.1

2-((2-oxo-1-(o-tolyl)-7-(trifluoromethyl)-1,2-dihydroquinazolin-4-yl)amino)ethane-1-sulfonamide was prepared by substituting 2-aminoethane-1-sulfonamide and 1-(o-tolyl)-7-(trifluoromethyl)quinazoline-2,4(1H,3H)-dione.

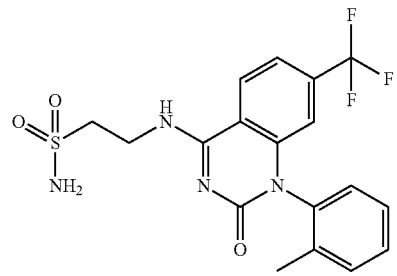 [SMILES: Cc1ccccc1-n1c(=O)nc(NCCS(N)(=O)=O)c2ccc(C(F)(F)F)cc21]

¹H NMR (400 MHz, DMSO-d₆) δ 8.95 (bs, 1H), 8.29 (d, J=8.2 Hz, 1H), 7.58 (d, J=8.3 Hz, 1H), 7.50-7.39 (m, 3H), 7.21 (d, J=7.4 Hz, 2H), 7.03 (bs, 1H), 6.67 (bs, 1H), 6.45 (s, 1H), 4.00-3.70 (m, 2H), 3.50-3.35 (m, 2H), 1.93 (s, 3H). m/z [M+H]⁺ 427.05

N-methyl-2-((2-oxo-1-(o-tolyl)-7-(trifluoromethyl)-1,2-dihydroquinazolin-4-yl)amino)ethane-1-sulfonamide was prepared by substituting 2-(methylamino)ethane-1-sulfonamide and 1-(o-tolyl)-7-(trifluoromethyl)quinazoline-2,4(1H,3H)-dione.

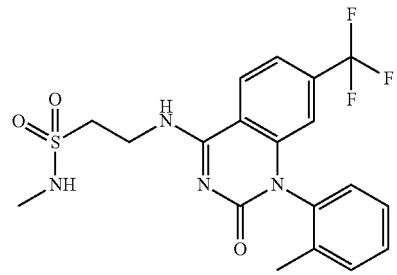 [SMILES: CNS(=O)(=O)CCNc1nc(=O)n(-c2ccccc2C)c2cc(C(F)(F)F)ccc12]

¹H NMR (400 MHz, DMSO-d₆) δ 8.96 (s, 1H), 8.29 (d, J=8.1 Hz, 1H), 7.58 (d, J=8.5 Hz, 1H), 7.52-7.38 (m, 3H), 7.21 (d, J=7.5 Hz, 1H), 6.67 (bs, 1H), 6.45 (s, 1H), 4.00-3.75 (m, 2H), 3.48-3.34 (m, 2H), 2.62 (s, 3H), 1.92 (s, 3H). m/z [M+H]⁺ 441.1

(S)-4-(2-(Hydroxymethyl)morpholino)-1-(o-tolyl)-7-(trifluoromethyl)quinazolin-2(1H)-one was prepared by substituting (S)-morpholin-2-ylmethanol and 1-(o-tolyl)-7-(trifluoromethyl)quinazoline-2,4(1H,3H)-dione.

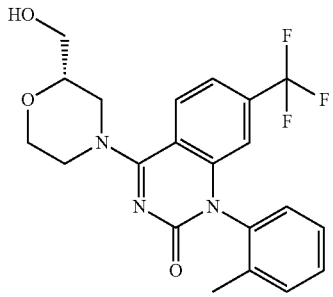 [SMILES: Cc1ccccc1-n1c(=O)nc(N2CCO[C@H](CO)C2)c2ccc(C(F)(F)F)cc21]

$^1$H NMR (400 MHz, DMSO-d$_6$) δ 8.14 (d, J=8.5 Hz, 1H), 7.54-7.38 (m, 4H), 7.31-7.24 (m, 1H), 6.51 (s, 1H), 4.91 (bs, 1H), 4.43-4.16 (m, 2H), 4.00-3.93 (m, 1H), 3.79-3.59 (m, 2H), 3.56-3.45 (m, 2H), 3.34-3.09 (m, 2H), 1.94 (s, 3H). m/z [M+H]$^+$ 420.1

4-(3-Methoxyazetidin-1-yl)-1-(o-tolyl)-7-(trifluoromethyl)quinazolin-2(1H)-one was prepared by substituting 3-methoxyazetidine and 1-(o-tolyl)-7-(trifluoromethyl)quinazoline-2,4(1H,3H)-dione.

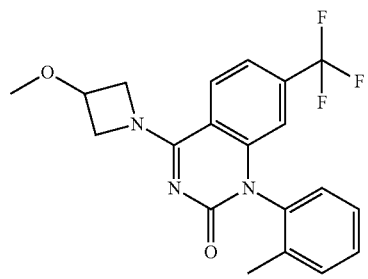 [SMILES: COC1CN(c2nc(=O)n(-c3ccccc3C)c3cc(C(F)(F)F)ccc23)C1]

$^1$H NMR (400 MHz, DMSO-d$_6$) δ 8.09 (d, J=8.5 Hz, 1H), 7.52-7.39 (m, 3H), 7.22 (d, J=7.4 Hz, 1H), 6.45 (s, 1H), 5.14-4.46 (m, 3H), 4.42-4.36 (m, 1H), 4.28-3.98 (m, 1H), 3.32 (s, 3H), 1.94 (s, 3H). m/z [M+H]$^+$ 390.1

4-(4-methyl-3-oxopiperazin-1-yl)-1-(o-tolyl)-7-(trifluoromethyl)quinazolin-2(1H)-one was prepared by substituting 1-methylpiperazin-2-one and 1-(o-tolyl)-7-(trifluoromethyl)quinazoline-2,4(1H,3H)-dione.

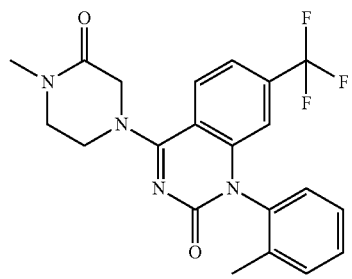 [SMILES: Cc1ccccc1-n1c(=O)nc(N2CCN(C)C(=O)C2)c2ccc(C(F)(F)F)cc21]

$^1$H NMR (400 MHz, DMSO-d$_6$) δ 8.17 (d, J=8.4 Hz, 1H), 7.56-7.40 (m, 4H), 7.26 (d, J=7.6 Hz, 1H), 6.50 (s, 1H), 4.49-4.35 (m, 2H), 4.21-4.09 (m, 1H), 4.08-3.99 (m, 2H), 2.93 (s, 3H), 1.95 (s, 3H). m/z [M+H]$^+$ 417.1

4-(3-Hydroxyazetidin-1-yl)-1-(o-tolyl)-7-(trifluoromethyl)quinazolin-2(1H)-one was prepared by substituting azetidin-3-ol and 1-(o-tolyl)-7-(trifluoromethyl)quinazoline-2,4(1H,3H)-dione.

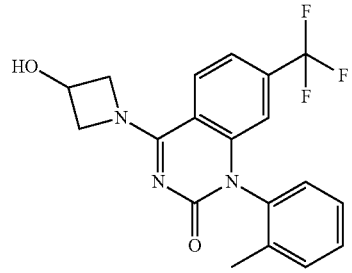

$^1$H NMR (400 MHz, DMSO-d$_6$) δ 8.08 (d, J=8.7 Hz, 1H), 7.52-7.37 (m, 4H), 7.22 (d, J=7.3 Hz, 1H), 6.45 (s, 1H), 6.01 (bs, 1H), 5.15-4.85 (m, 1H), 4.69-4.39 (m, 3H), 4.22-3.90 (m, 1H), 1.94 (s, 3H). m/z [M+H]$^+$ 376.1

1-(2-Oxo-1-(o-tolyl)-7-(trifluoromethyl)-1,2-dihydroquinazolin-4-yl)azetidine-3-carbonitrile was prepared by substituting azetidine-3-carbonitrile and 1-(o-tolyl)-7-(trifluoromethyl)quinazoline-2,4(1H,3H)-dione.

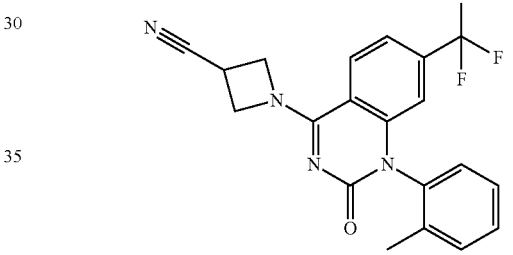

$^1$H NMR (400 MHz, DMSO-d$_6$) δ 8.02 (d, J=8.3 Hz, 1H), 7.55-7.37 (m, 4H), 7.22 (d, J=7.4 Hz, 1H), 6.47 (s, 1H), 5.31-4.45 (m, 4H), 4.09-3.98 (m, 1H), 1.94 (s, 3H). m/z [M+H]$^+$ 385.1

(3-((2-oxo-1-(o-tolyl)-7-(trifluoromethyl)-1,2-dihydroquinazolin-4-yl)amino)propyl)sulfamide was prepared by substituting 1-(o-tolyl)-7-(trifluoromethyl)quinazoline-2,4(1H,3H)-dione.

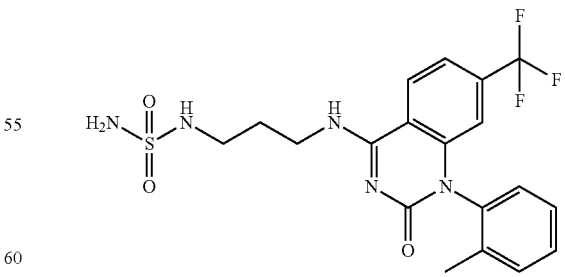

$^1$H NMR (400 MHz, DMSO-d$_6$) δ 8.79 (s, 1H), 8.42 (d, J=8.2 Hz, 1H), 7.59 (d, J=8.4 Hz, 1H), 7.52-7.37 (m, 3H), 7.25 (d, J=7.5 Hz, 1H), 6.61 (bs, 1H), 6.54 (bs, 2H), 6.44 (s, 1H), 3.67-3.49 (m, 2H), 3.02-2.97 (m, 2H), 1.95 (s, 3H), 1.89 (t, J=7.3 Hz, 2H). m/z [M+H]$^+$ 456.1

(2-((2-oxo-1-(o-tolyl)-7-(trifluoromethyl)-1,2-dihydro-quinazolin-4-yl)amino)ethyl)sulfamide was prepared by substituting 1-(o-tolyl)-7-(trifluoromethyl)quinazoline-2,4(1H,3H)-dione.

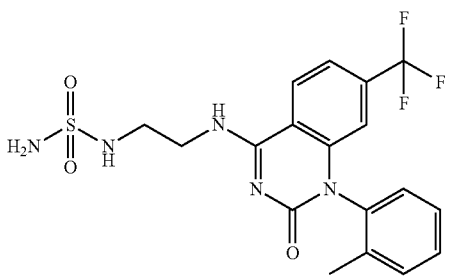 [SMILES: Cc1ccccc1-n1c(=O)nc(NCCNS(N)(=O)=O)c2ccc(C(F)(F)F)cc21]

$^1$H NMR (400 MHz, DMSO-d$_6$) δ 8.82 (bs, 1H), 8.40 (d, J=8.4 Hz, 1H), 7.60 (d, J=8.4 Hz, 1H), 7.52-7.38 (m, 3H), 7.24 (d, J=7.5 Hz, 1H), 6.74 (bs, 1H), 6.62 (bs, 2H), 6.45 (s, 1H), 3.76-3.60 (m, 2H), 3.27-3.13 (m, 2H), 1.95 (s, 3H). m/z [M+H]$^+$ 442.1

3-((1-(2-chlorophenyl)-7-cyclopropyl-2-oxo-1,2-dihydroquinazolin-4-yl)amino)propane-1-sulfonamide was prepared 3-aminopropane-1-sulfonamide and 1-(2-chlorophenyl)-7-cyclopropylquinazoline-2,4(1H,3H)-dione by substituting.

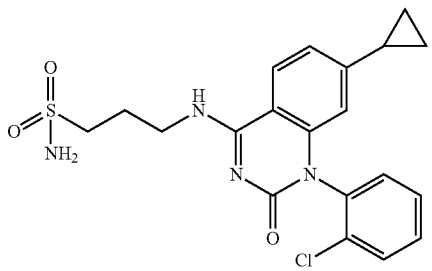 [SMILES: NS(=O)(=O)CCCNc1nc(=O)n(-c2ccccc2Cl)c2cc(C3CC3)ccc12]

$^1$H NMR (400 MHz, DMSO-d$_6$) δ 8.56 (s, 1H), 8.04 (d, J=8.6 Hz, 1H), 7.73 (dd, J=6.0, 3.2 Hz, 1H), 7.56 (dt, J=5.9, 3.0 Hz, 2H), 7.46 (d, J=7.7 Hz, 1H), 6.83 (d, J=5.7 Hz, 3H), 6.03 (s, 1H), 3.72-3.50 (m, 2H), 3.09 (t, J=8.2 Hz, 2H), 2.07 (t, J=7.9 Hz, 2H), 1.87-1.76 (m, 1H), 0.95 (d, J=8.4 Hz, 2H), 0.65-0.53 (m, 2H). m/z [M+H]$^+$ 433.1

3-((1-(2-chlorophenyl)-7-cyclopropyl-2-oxo-1,2-dihydroquinazolin-4-yl)amino)-N-methylpropane-1-sulfonamide was prepared by substituting 3-amino-N-methylpropane-1-sulfonamide and 1-(2-chlorophenyl)-7-cyclopropylquinazoline-2,4(1H,3H)-dione.

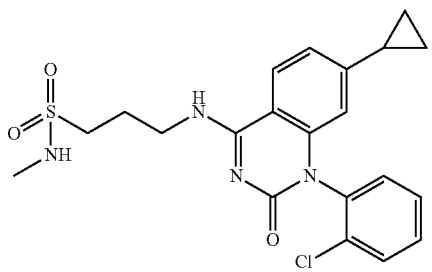 [SMILES: CNS(=O)(=O)CCCNc1nc(=O)n(-c2ccccc2Cl)c2cc(C3CC3)ccc12]

$^1$H NMR (400 MHz, DMSO-d$_6$) δ 8.54 (d, J=5.4 Hz, 1H), 8.08-7.98 (m, 1H), 7.73 (dt, J=6.2, 3.0 Hz, 1H), 7.56 (dt, J=6.2, 3.1 Hz, 2H), 7.47 (dt, J=5.8, 3.1 Hz, 1H), 6.96 (d, J=4.7 Hz, 1H), 6.83 (d, J=8.5 Hz, 1H), 6.03 (s, 1H), 3.71-3.50 (m, 2H), 3.17-3.08 (m, 2H), 2.58 (t, J=3.8 Hz, 3H), 2.03 (q, J=7.5 Hz, 2H), 1.88-1.75 (m, 1H), 0.94 (d, J=8.4 Hz, 2H), 0.66-0.52 (m, 2H). m/z [M+H]$^+$ 447.0.

2-((1-(2-Chlorophenyl)-7-cyclopropyl-2-oxo-1,2-dihydroquinazolin-4-yl)amino)ethane-1-sulfonamide was prepared by substituting 2-aminoethane-1-sulfonamide and 1-(2-chlorophenyl)-7-cyclopropylquinazoline-2,4(1H,3H)-dione.

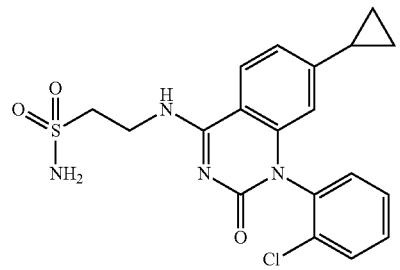 [SMILES: NS(=O)(=O)CCNc1nc(=O)n(-c2ccccc2Cl)c2cc(C3CC3)ccc12]

$^1$H NMR (400 MHz, DMSO-d$_6$) δ 8.61 (s, 1H), 8.01-7.91 (m, 1H), 7.73 (d, J=5.9 Hz, 1H), 7.56 (dd, J=6.3, 3.3 Hz, 2H), 7.47 (s, 1H), 7.01 (s, 2H), 6.84 (d, J=8.2 Hz, 1H), 6.04 (s, 1H), 3.96-3.81 (m, 2H), 3.40 (s, 2H), 1.90-1.76 (m, 1H), 0.95 (d, J=8.3 Hz, 2H), 0.65-0.53 (m, 2H). m/z [M+H]$^+$ 419.0.

2-((1-(2-Chlorophenyl)-7-cyclopropyl-2-oxo-1,2-dihydroquinazolin-4-yl)amino)-N-methylethane-1-sulfonamide was prepared by substituting 2-amino-N-methylethane-1-sulfonamide and 1-(2-chlorophenyl)-7-cyclopropylquinazoline-2,4(1H,3H)-dione.

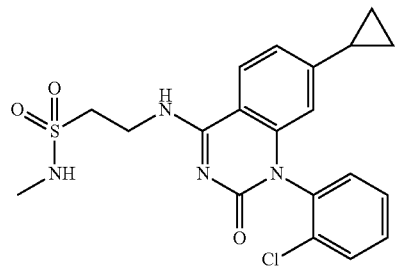 [SMILES: CNS(=O)(=O)CCNc1nc(=O)n(-c2ccccc2Cl)c2cc(C3CC3)ccc12]

$^1$H NMR (400 MHz, DMSO-d$_6$) δ 8.62 (d, J=7.0 Hz, 1H), 8.00-7.91 (m, 1H), 7.74 (dt, J=6.4, 3.0 Hz, 1H), 7.56 (dq, J=7.0, 3.5 Hz, 2H), 7.47 (dt, J=6.1, 3.2 Hz, 1H), 7.10 (d, J=5.0 Hz, 1H), 6.85 (d, J=8.4 Hz, 1H), 6.04 (s, 1H), 3.90-3.72 (m, 2H), 3.42 (t, J=6.5 Hz, 2H), 2.63 (t, J=3.8 Hz, 3H), 1.87-1.76 (m, 1H), 0.95 (d, J=8.4 Hz, 2H), 0.68-0.53 (m, 2H). m/z [M+H]$^+$ 433.1

1-(2-Chlorophenyl)-7-cyclopropyl-4-(4-(hydroxymethyl)piperidin-1-yl)quinazolin-2(1H)-one was prepared by substituting piperidin-4-ylmethanol and 1-(2-chlorophenyl)-7-cyclopropylquinazoline-2,4(1H,3H)-dione.

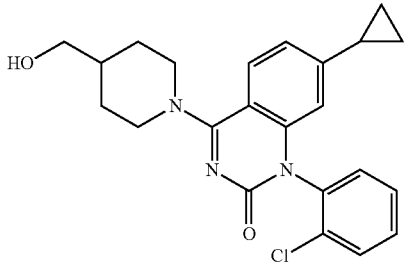 [SMILES: O=c1nc(N2CCC(CO)CC2)c2ccc(C3CC3)cc2n1-c1ccccc1Cl]

¹H NMR (400 MHz, DMSO-d₆) δ 7.76-7.65 (m 2H), 7.57 (dt, J=5.9, 2.5 Hz, 2H), 7.47 (dt, J=5.8, 2.6 Hz, 1H), 6.81 (d, J=8.4 Hz, 1H), 6.06 (s, 1H), 4.63 (s, 1H), 4.39-4.28 (m, 2H), 3.34 (s, 2H), 3.15 (d, J=15.0 Hz, 2H), 1.87-1.78 (m, 1H), 1.82 (d, J=13.0 Hz, 3H), 1.75 (s, 1H), 1.36 (q, J=12.7, 12.3 Hz, 2H), 0.96 (d, J=8.5 Hz, 2H), 0.65-0.50 (m, 2H). m/z [M+H]⁺ 410.1

1-(2-Chlorophenyl)-7-cyclopropyl-4-(3-hydroxypiperidin-1-yl)quinazolin-2(1H)-one was prepared by substituting piperidin-3-ol and 1-(2-chlorophenyl)-7-cyclopropylquinazoline-2,4(1H,3H)-dione.

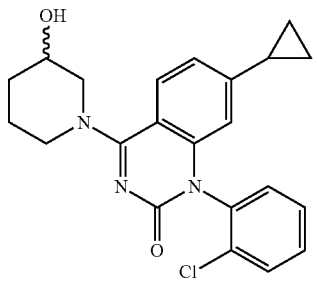 [SMILES: O=c1nc(N2CCCC(O)C2)c2ccc(C3CC3)cc2n1-c1ccccc1Cl]

¹H NMR (400 MHz, DMSO-d₆) δ 7.80 (t, J=9.4 Hz, 1H), 7.73 (dt, J=5.9, 2.6 Hz, 1H), 7.65-7.53 (m, 2H), 7.50-7.43 (m, 1H), 6.81 (d, J=8.5 Hz, 1H), 6.06 (s, 1H), 4.04 (t, J=10.8 Hz, 1H), 3.90-3.68 (m, 2H), 3.37-3.23 (m, 2H), 2.00-1.78 (m, 3H), 1.56 (dq, J=19.3, 9.5 Hz, 2H), 0.96 (d, J=8.6 Hz, 2H), 0.69-0.51 (m, 2H). m/z [M+H]⁺ 396.1

1-(2-Chlorophenyl)-7-cyclopropyl-4-(3-hydroxyazetidin-1-yl)quinazolin-2(1H)-one was prepared by substituting azetidin-3-ol and 1-(2-chlorophenyl)-7-cyclopropylquinazoline-2,4(1H,3H)-dione.

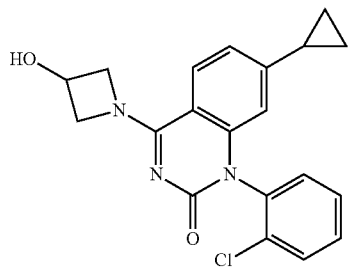 [SMILES: O=c1nc(N2CC(O)C2)c2ccc(C3CC3)cc2n1-c1ccccc1Cl]

¹H NMR (400 MHz, DMSO-d₆) δ 7.72 (dd, J=6.9, 3.1 Hz, 2H), 7.56 (dt, J=5.6, 2.5 Hz, 2H), 7.42 (d, J=2.5 Hz, 1H), 6.78 (d, J=8.4 Hz, 1H), 6.03 (s, 1H), 5.96 (bs, 1H), 5.09-4.72 (m, 1H), 4.74-3.88 (m, 3H), 4.68-4.57 (m, 1H), 1.88-1.73 (m, 1H), 0.95 (d, J=8.4 Hz, 2H), 0.64-0.46 (m, 2H). m/z [M+H]⁺ 368.1.

(3-((1-(2-chlorophenyl)-7-cyclopropyl-2-oxo-1,2-dihydroquinazolin-4-yl)amino)propyl)sulfamide was prepared by substituting 1-(2-chlorophenyl)-7-cyclopropylquinazoline-2,4(1H,3H)-dione.

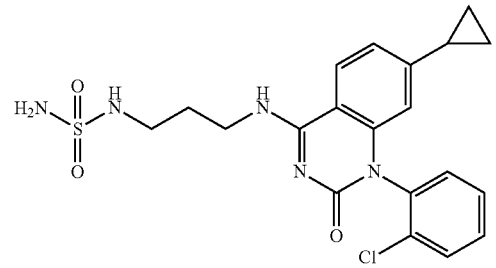 [SMILES: NS(=O)(=O)NCCCNc1nc(=O)n(-c2ccccc2Cl)c2cc(C3CC3)ccc12]

¹H NMR (400 MHz, DMSO-d₆) δ 8.48 (d, J=5.9 Hz, 1H), 8.02 (d, J=8.8 Hz, 1H), 7.72 (dt, J=6.1, 2.8 Hz, 1H), 7.56 (dt, J=5.9, 2.8 Hz, 2H), 7.45 (dt, J=6.0, 2.8 Hz, 1H), 6.82 (d, J=8.4 Hz, 1H), 6.58 (d, J=6.3 Hz, 1H), 6.52 (s, 2H), 6.02 (s, 1H), 3.47-3.27 (m, 2H), 2.98 (d, J=6.8 Hz, 2H), 1.91-1.76 (m, 3H), 0.94 (d, J=8.4 Hz, 2H), 0.65-0.52 (m, 2H). m/z [M+H]⁺ 448.1

(3-((1-(2-chlorophenyl)-7-cyclopropyl-2-oxo-1,2-dihydroquinazolin-4-yl)amino)propyl)sulfamide was prepared by substituting 1-(2-chlorophenyl)-7-cyclopropylquinazoline-2,4(1H,3H)-dione.

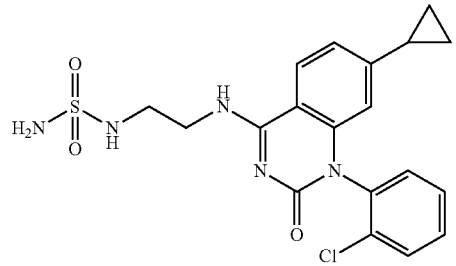 [SMILES: NS(=O)(=O)NCCNc1nc(=O)n(-c2ccccc2Cl)c2cc(C3CC3)ccc12]

¹H NMR (400 MHz, DMSO-d₆) δ 8.49 (s, 1H), 8.02 (d, J=8.4 Hz, 1H), 7.73 (dt, J=6.1, 2.8 Hz, 1H), 7.56 (dt, J=6.0, 2.8 Hz, 2H), 7.50-7.43 (m, 1H), 6.83 (d, J=8.6 Hz, 2H), 6.76 (t, J=6.3 Hz, 1H), 6.62 (s, 2H), 6.02 (s, 1H), 3.75-3.54 (m, 2H), 3.18 (d, J=6.5 Hz, 2H), 1.84-1.75 (m, 1H), 0.95 (d, J=8.3 Hz, 2H), 0.64-0.53 (m, 2H). m/z [M+H]⁺ 434.0

1-(2-chlorophenyl)-7-cyclopropyl-4-((2-(difluoromethyl)pyridin-4-yl)amino)quinazolin-2(1H)-one was prepared by substituting 2-(difluoromethyl)pyridin-4-amine and 1-(2-chlorophenyl)-7-cyclopropylquinazoline-2,4(1H,3H)-dione.

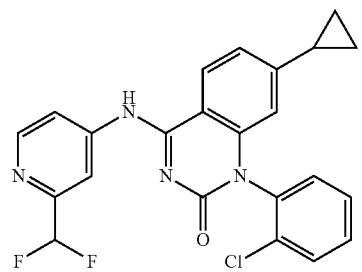 [SMILES: O=c1nc(Nc2ccnc(C(F)F)c2)c2ccc(C3CC3)cc2n1-c1ccccc1Cl]

¹H NMR (400 MHz, DMSO-d₆) δ 8.61 (t, J=4.2 Hz, 1H), 8.39 (d, J=8.6 Hz, 1H), 8.21 (s, 2H), 7.78 (dt, J=6.1, 3.2 Hz, 1H), 7.64-7.52 (m, 3H), 6.96 (s, 2H), 6.95 (d, J=112 Hz, 1H), 6.13 (s, 1H), 1.94-1.83 (m, 1H), 1.00 (d, J=8.4 Hz, 2H), 0.71-0.59 (m, 2H). m/z [M+H]⁺ 439.1

1-(2-Chlorophenyl)-7-cyclopropyl-4-((2-cyclopropylpyridin-4-yl)amino)quinazolin-2(1H)-one was prepared by substituting 2-(cyclopropyl)pyridin-4-amine and 1-(2-chlorophenyl)-7-cyclopropylquinazoline-2,4(1H,3H)-dione.

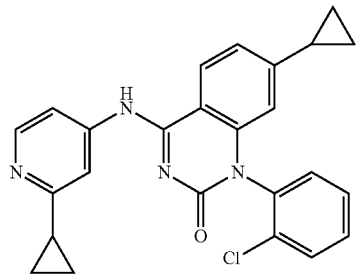

¹H NMR (400 MHz, DMSO-d₆) δ 9.99 (s, 1H), 8.45-8.29 (m, 2H), 7.95-7.71 (m, 3H), 7.66-7.49 (m, 3H), 6.95 (d, J=8.4 Hz, 1H), 6.12 (s, 1H), 2.10-1.99 (m, 1H), 1.94-1.82 (m, 1H), 1.06-0.83 (m, 6H), 0.70-0.57 (m, 2H). m/z [M+H]⁺ 429.1

1-(2-Chlorophenyl)-7-cyclopropyl-4-((2-(difluoromethoxy)pyridin-4-yl)amino)quinazolin-2(1H)-one was prepared by substituting 2-(difluoromethoxy)pyridin-4-amine and 1-(2-chlorophenyl)-7-cyclopropylquinazoline-2,4(1H,3H)-dione.

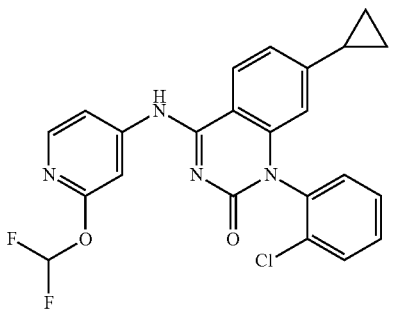 [SMILES: O=c1nc(Nc2ccnc(OC(F)F)c2)c2ccc(C3CC3)cc2n1-c1ccccc1Cl]

¹H NMR (400 MHz, DMSO-d₆) δ 10.25 (bs, 1H), 8.37 (d, J=8.4 Hz, 1H), 8.19 (d, J=5.7 Hz, 1H), 8.17 (d, J=212 Hz, 1H), 7.81-7.70 (m, 2H), 7.64-7.48 (m, 3H), 6.96 (d, J=8.5 Hz, 1H), 6.13 (s, 1H), 1.97-1.82 (m, 1H), 1.00 (d, J=8.4 Hz, 2H), 0.72-0.54 (m, 2H). m/z [M+H]⁺ 455.1

1-(2-Chlorophenyl)-7-cyclopropyl-4-((3-methyl-1,2,4-oxadiazol-5-yl)amino)quinazolin-2(1H)-one was prepared by substituting 3-methyl-1,2,4-oxadiazol-5-amine and 1-(2-chlorophenyl)-7-cyclopropylquinazoline-2,4(1H,3H)-dione.

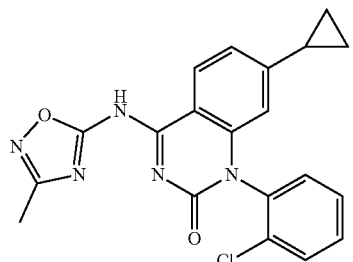

¹H NMR (400 MHz, DMSO-d₆) δ 12.14 (bs, 1H), 8.26 (dd, J=8.3, 2.6 Hz, 1H), 7.82 (d, J=7.0 Hz, 1H), 7.71-7.62 (m, 3H), 6.98 (d, J=8.4 Hz, 1H), 6.16 (s, 1H), 2.36 (d, J=2.7 Hz, 3H), 1.97-1.84 (m, 1H), 1.02 (d, J=8.1 Hz, 2H), 0.73-0.54 (m, 2H). m/z [M+H]⁺ 394.1.

1-(2-Chlorophenyl)-7-cyclopropyl-4-((oxazol-5-ylmethyl)amino)quinazolin-2(1H)-one was prepared by substituting oxazol-5-ylmethanamine and 1-(2-chlorophenyl)-7-cyclopropylquinazoline-2,4(1H,3H)-dione.

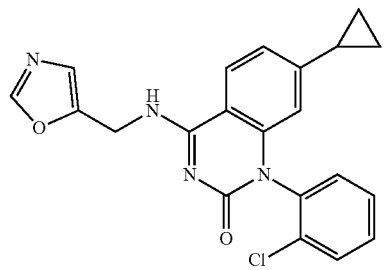 [SMILES: O=c1nc(NCc2cnco2)c2ccc(C3CC3)cc2n1-c1ccccc1Cl]

¹H NMR (400 MHz, DMSO-d₆) δ 8.97 (bs, 1H), 8.34 (s, 1H), 8.08 (d, J=8.5 Hz, 1H), 7.74 (bs, 1H), 7.56 (bs, 2H), 7.48 (bs, 1H), 7.13 (bs, 1H), 6.84 (d, J=8.5 Hz, 1H), 6.04 (s, 1H), 4.90-4.63 (m, 2H), 1.89-1.77 (m, 1H), 0.95 (d, J=8.3 Hz, 2H), 0.67-0.54 (m, 2H). m/z [M+H]⁺ 393.1

1-(2-Chlorophenyl)-7-cyclopropyl-4-((isoxazol-3-ylmethyl)amino)quinazolin-2(1H)-one was prepared by substituting isoxazol-3-ylmethanamine and 1-(2-chlorophenyl)-7-cyclopropylquinazoline-2,4(1H,3H)-dione.

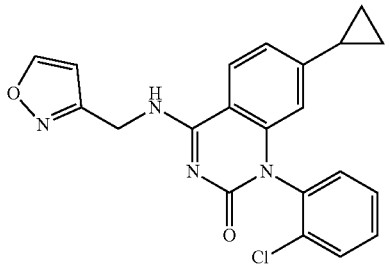 [SMILES: O=c1nc(NCc2ccon2)c2ccc(C3CC3)cc2n1-c1ccccc1Cl]

¹H NMR (400 MHz, DMSO-d₆) δ 9.08 (bs, 1H), 8.88 (s, 1H), 8.08 (dd, J=8.5, 2.6 Hz, 1H), 7.72 (bs, 1H), 7.60-7.53 (m, 2H), 7.48 (bs, 1H), 6.85 (d, J=8.5 Hz, 1H), 6.60 (s, 1H), 6.06 (s, 1H), 4.95-4.70 (m, 2H), 1.87-1.78 (m, 1H), 0.95 (d, J=8.3 Hz, 2H), 0.69-0.52 (m, 2H). m/z [M+H]⁺ 393.1

1-(2-Chlorophenyl)-7-cyclopropyl-4-((5-methylisoxazol-3-yl)amino)quinazolin-2(1H)-one was prepared by substituting 5-methylisoxazol-3-amine and 1-(2-chlorophenyl)-7-cyclopropylquinazoline-2,4(1H,3H)-dione.

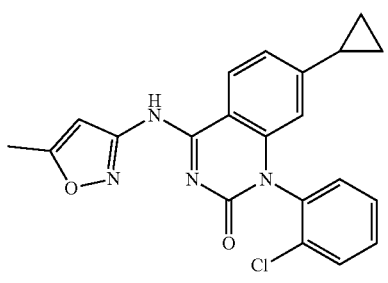 [SMILES: Cc1cc(Nc2nc(=O)n(-c3ccccc3Cl)c3cc(C4CC4)ccc23)no1]

¹H NMR (400 MHz, DMSO-d₆) δ 10.97 (bs, 1H), 8.32 (bs, 1H), 7.77 (bs, 1H), 7.70-7.51 (m, 3H), 6.90 (d, J=8.5 Hz,

1H), 6.68 (bs, 1H), 6.09 (s, 1H), 2.44 (s, 3H), 1.93-1.81 (m, 1H), 0.98 (d, J=8.4 Hz, 2H), 0.73-0.55 (m, 2H). m/z [M+H]+ 393.1

1-(2-Chlorophenyl)-7-cyclopropyl-4-(((1-methyl-1H-pyrazol-4-yl)methyl)amino)quinazolin-2(1H)-one was prepared by substituting (1-methyl-1H-pyrazol-4-yl)methanamine and 1-(2-chlorophenyl)-7-cyclopropylquinazoline-2,4(1H,3H)-dione.

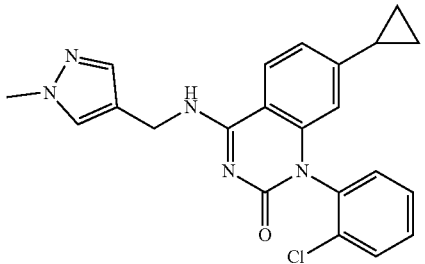 [SMILES: Cn1cc(CNc2nc(=O)n(-c3ccccc3Cl)c3cc(C4CC4)ccc23)cn1]

$^1$H NMR (400 MHz, DMSO-d$_6$) δ 8.79 (bs, 1H), 8.06 (dd, J=8.6, 2.5 Hz, 1H), 7.73 (bs, 1H), 7.67 (d, J=2.6 Hz, 1H), 7.60-7.51 (m, 2H), 7.49-7.38 (m, 2H), 6.81 (d, J=8.4 Hz, 1H), 6.02 (s, 1H), 4.66-4.41 (m, 2H), 3.80 (s, 3H), 1.85-1.75 (m, 1H), 0.94 (d, J=8.0 Hz, 2H), 0.64-0.52 (m, 2H). m/z [M+H]+ 406.1

1-(2-chlorophenyl)-7-cyclopropyl-4-(isoxazol-3-ylamino)quinazolin-2(1H)-one was prepared by substituting isoxazol-3-amine and 1-(2-chlorophenyl)-7-cyclopropylquinazoline-2,4(1H,3H)-dione.

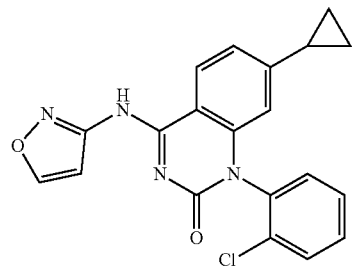

$^1$H NMR (400 MHz, DMSO-d$_6$) δ 8.86 (s, 1H), 8.32 (d, J=8.0 Hz, 1H), 7.77 (bs, 1H), 7.66-7.53 (m, 3H), 6.90 (bs, 1H), 6.89 (d, J=8.6 Hz, 1H), 6.08 (s, 1H), 1.91-1.81 (t, J=6.7 Hz, 1H), 0.97 (d, J=8.4 Hz, 2H), 0.69-0.56 (m, 2H). m/z [M+H]+ 379.05

1-(2-Chlorophenyl)-7-cyclopropyl-4-((5-methoxypyridin-3-yl)amino)quinazolin-2(1H)-one was prepared by substituting 5-methoxypyridin-3-amine and 1-(2-chlorophenyl)-7-cyclopropylquinazoline-2,4(1H,3H)-dione.

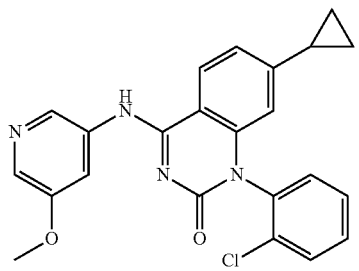 [SMILES: COc1cncc(Nc2nc(=O)n(-c3ccccc3Cl)c3cc(C4CC4)ccc23)c1]

$^1$H NMR (400 MHz, DMSO-d$_6$) δ 10.07 (bs, 1H), 8.68 (bs, 1H), 8.36 (d, J=8.4 Hz, 1H), 8.13 (s, 1H), 7.98 (bs, 1H), 7.76 (bs, 1H), 7.65-7.51 (m, 3H), 6.94 (d, J=8.4 Hz, 1H), 6.11 (s, 1H), 3.87 (s, 3H), 1.93-1.81 (m, 1H), 0.99 (d, J=8.4 Hz, 2H), 0.70-0.57 (m, 2H). m/z [M+H]+ 419.1

1-(2-Chlorophenyl)-7-cyclopropyl-4-((6-methylpyridin-3-yl)amino)quinazolin-2(1H)-one was prepared by substituting 6-methylpyridin-3-amine and 1-(2-chlorophenyl)-7-cyclopropylquinazoline-2,4(1H,3H)-dione.

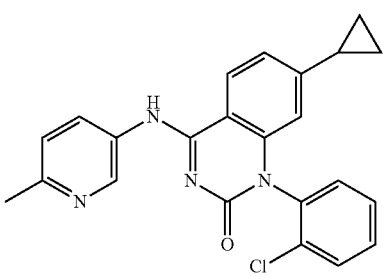 [SMILES: Cc1ccc(Nc2nc(=O)n(-c3ccccc3Cl)c3cc(C4CC4)ccc23)cn1]

$^1$H NMR (400 MHz, DMSO-d$_6$) δ 10.03 (s, 1H), 8.79 (s, 1H), 8.34 (d, J=8.5 Hz, 1H), 8.14 (d, J=8.1 Hz, 1H), 7.75 (s, 1H), 7.64-7.46 (m, 3H), 7.31 (d, J=8.4 Hz, 1H), 6.93 (d, J=8.5 Hz, 1H), 6.10 (s, 1H), 2.48 (s, 3H), 1.91-1.81 (m, 1H), 0.98 (d, J=8.3 Hz, 2H), 0.71-0.56 (m, 2H). m/z [M+H]+ 403.1.

1-(2-Chlorophenyl)-7-cyclopropyl-4-((6-methoxypyridin-3-yl)amino)quinazolin-2(1H)-one was prepared by substituting 6-methoxypyridin-3-amine and 1-(2-chlorophenyl)-7-cyclopropylquinazoline-2,4(1H,3H)-dione.

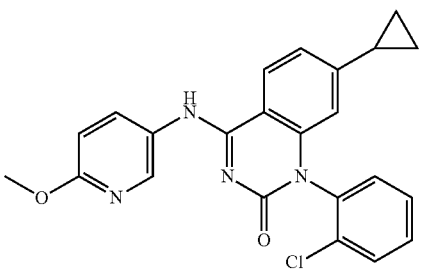 [SMILES: COc1ccc(Nc2nc(=O)n(-c3ccccc3Cl)c3cc(C4CC4)ccc23)cn1]

$^1$H NMR (400 MHz, DMSO-d$_6$) δ 9.98 (s, 1H), 8.47 (s, 1H), 8.30 (d, J=8.5 Hz, 1H), 8.07 (d, J=8.9 Hz, 1H), 7.75 (dd, J=6.3, 3.2 Hz, 1H), 7.62-7.46 (m, 3H), 6.92 (t, J=7.6 Hz, 2H), 6.10 (s, 1H), 3.88 (s, 3H), 1.92-1.81 (m, 1H), 0.98 (d, J=8.2 Hz, 2H), 0.70-0.55 (m, 2H). m/z [M+H]+ 419.1

1-(2-Chlorophenyl)-7-cyclopropyl-4-((pyridin-4-ylmethyl)amino)quinazolin-2(1H)-one was prepared by substituting pyridin-4-ylmethanamine and 1-(2-chlorophenyl)-7-cyclopropylquinazoline-2,4(1H,3H)-dione.

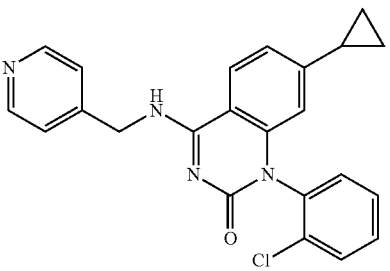 [SMILES: O=c1nc(NCc2ccncc2)c2ccc(C3CC3)cc2n1-c1ccccc1Cl]

¹H NMR (400 MHz, DMSO-d₆) δ 9.13 (s, 1H), 8.54 (s, 2H), 8.13 (dd, J=8.6, 2.6 Hz, 1H), 7.76-7.68 (m, 1H), 7.55 (d, J=3.2 Hz, 2H), 7.52-7.43 (m, 1H), 7.36 (s, 2H), 6.87 (d, J=8.3 Hz, 1H), 6.06 (s, 1H), 4.91-4.65 (m, 2H), 1.88-1.78 (m, 1H), 0.96 (d, J=8.3 Hz, 2H), 0.69-0.52 (m, 2H). m/z [M+H]⁺ 403.1

1-(2-Chlorophenyl)-7-cyclopropyl-4-((pyridin-3-ylmethyl)amino)quinazolin-2(1H)-one was prepared by substituting pyridin-3-ylmethanamine and 1-(2-chlorophenyl)-7-cyclopropylquinazoline-2,4(1H,3H)-dione.

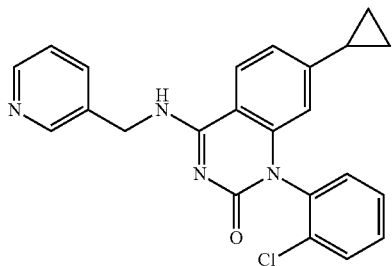 [SMILES: O=c1nc(NCc2cccnc2)c2ccc(C3CC3)cc2n1-c1ccccc1Cl]

¹H NMR (400 MHz, DMSO-d₆) δ 9.08 (s, 1H), 8.63 (s, 1H), 8.49 (s, 1H), 8.09 (dd, J=8.5, 2.5 Hz, 1H), 7.80 (d, J=8.0 Hz, 1H), 7.73 (d, J=3.2 Hz, 1H), 7.61-7.51 (m, 2H), 7.48 (d, J=3.2 Hz, 1H), 7.42-7.36 (m, 1H), 6.85 (d, J=8.4 Hz, 1H), 6.04 (s, 1H), 4.89-4.65 (m, 2H), 1.87-1.76 (m, 1H), 0.95 (d, J=8.3 Hz, 2H), 0.66-0.54 (m, 2H). m/z [M+H]⁺ 403.1

1-(2-Chlorophenyl)-7-cyclopropyl-4-((pyridin-2-ylmethyl)amino)quinazolin-2(1H)-one was prepared by substituting pyridin-2-ylmethanamine and 1-(2-chlorophenyl)-7-cyclopropylquinazoline-2,4(1H,3H)-dione.

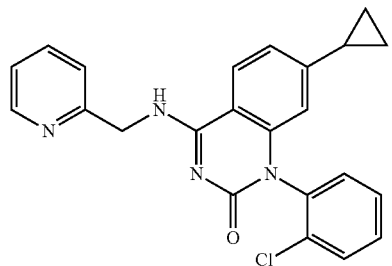 [SMILES: O=c1nc(NCc2ccccn2)c2ccc(C3CC3)cc2n1-c1ccccc1Cl]

¹H NMR (400 MHz, DMSO-d₆) δ 9.12 (s, 1H), 8.54 (d, J=3.6 Hz, 1H), 8.15 (dd, J=8.6, 2.6 Hz, 1H), 7.84-7.68 (m, 2H), 7.58-7.52 (m, 2H), 7.46 (s, 1H), 7.38 (d, J=8.0 Hz, 1H), 7.30 (s, 1H), 6.86 (d, J=8.5 Hz, 1H), 6.05 (s, 1H), 4.95-4.72 (m, 2H), 1.89-1.77 (m, 1H), 0.96 (d, J=8.3 Hz, 2H), 0.66-0.54 (m, 2H). m/z [M+H]⁺ 403.1.

1-(2-Chlorophenyl)-7-cyclopropyl-4-(pyrimidin-5-ylamino)quinazolin-2(1H)-one was prepared by substituting pyrimidin-5-amine and 1-(2-chlorophenyl)-7-cyclopropylquinazoline-2,4(1H,3H)-dione.

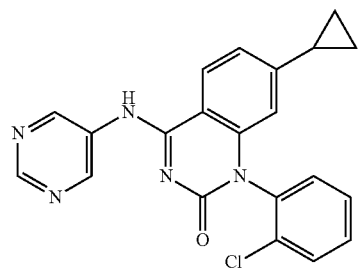 [SMILES: O=c1nc(Nc2cncnc2)c2ccc(C3CC3)cc2n1-c1ccccc1Cl]

¹H NMR (400 MHz, DMSO-d₆) δ 9.12 (s, 2H), 8.94 (s, 1H), 8.29 (d, J=8.5 Hz, 1H), 7.81-7.69 (m, 1H), 7.62-7.55 (m, 2H), 7.56-7.48 (m, 1H), 6.94 (d, J=8.4 Hz, 1H), 6.76 (s, 2H), 6.09 (s, 1H), 1.91-1.82 (m, 1H), 0.99 (d, J=8.3 Hz, 2H), 0.69-0.58 (m, 2H). m/z [M+H]⁺ 390.05

1-(2-Chlorophenyl)-7-isopropyl-4-(methylamino)pyrido[2,3-d]pyrimidin-2(1H)-one was prepared by substituting 1-(2-chlorophenyl)-7-isopropylpyrido[2,3-d]pyrimidine-2,4(1H,3H)-dione.

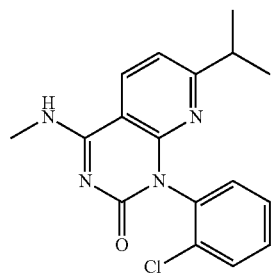 [SMILES: CNc1nc(=O)n(-c2ccccc2Cl)c2nc(C(C)C)ccc12]

¹H NMR (400 MHz, DMSO-d₆) δ 8.72 (s, 1H), 8.40 (dd, J=8.1, 2.2 Hz, 1H), 7.65-7.55 (m, 1H), 7.50-7.40 (m, 2H), 7.41-7.33 (m, 1H), 7.17 (dd, J=8.1, 2.3 Hz, 1H), 2.99 (s, 3H), 2.86-2.77 (m, 1H), 1.02-0.99 (m, 6H). m/z [M+H]⁺ 329.1

1-(2-Chlorophenyl)-7-(difluoromethyl)-4-(methylamino)quinazolin-2(1H)-one was prepared by substituting 1-(2-chlorophenyl)-7-(difluoromethyl)quinazoline-2,4(1H,3H)-dione.

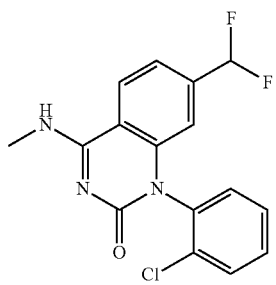 [SMILES: CNc1nc(=O)n(-c2ccccc2Cl)c2cc(C(F)F)ccc12]

¹H NMR (400 MHz, DMSO-d₆) δ 8.81 (s, 1H), 8.26 (d, J=8.3 Hz, 1H), 7.79-7.71 (m, 1H), 7.61-7.54 (m, 2H), 7.54-7.48 (m, 1H), 7.41 (d, J=8.3 Hz, 1H), 7.00 (td, J=55.3, 2.2 Hz, 1H), 6.46 (s, 1H), 3.01 (s, 3H). m/z [M+H]⁺ 336.0

1-(2-Chlorophenyl)-7-isopropyl-4-(methylamino)quinazolin-2(1H)-one was prepared by substituting 1-(2-chlorophenyl)-7-isopropylquinazoline-2,4(1H,3H)-dione.

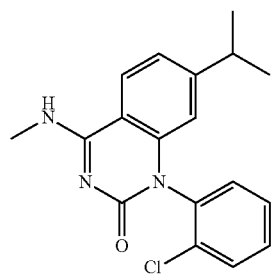

¹H NMR (400 MHz, DMSO-d₆) δ 8.56 (s, 1H), 8.03 (d, J=7.0 Hz, 1H), 7.78-7.66 (m, 1H), 7.60-7.51 (m, 2H), 7.48-7.41 (m, 1H), 7.15 (d, J=8.3 Hz, 1H), 6.09 (s, 1H), 2.98 (s, 3H), 2.76 (p, J=6.6 Hz, 1H), 1.05 (d, J=6.7 Hz, 6H). m/z [M+H]⁺ 328.1

1-(2-Chlorophenyl)-7-cyclopropyl-4-(pyridin-3-ylamino)quinazolin-2(1H)-one was prepared by substituting 3-amino pyridine and 1-(2-chlorophenyl)-7-cyclopropylquinazoline-2,4(1H,3H)-dione.

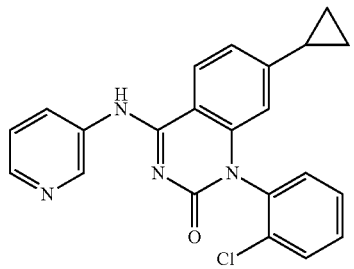 [SMILES: O=c1nc(Nc2cccnc2)c2ccc(C3CC3)cc2n1-c1ccccc1Cl]

¹H NMR (400 MHz, DMSO-d₆) δ 10.08 (s, 1H), 8.96 (s, 1H), 8.43-8.19 (m, 3H), 7.80-7.71 (m, 1H), 7.64-7.40 (m, 4H), 6.94 (d, J=8.4 Hz, 1H), 6.11 (s, 1H), 1.91-1.81 (m, 1H), 0.99 (d, J=8.3 Hz, 2H), 0.69-0.58 (m, 2H). m/z [M+H]⁺ 389.05

1-(2-Chlorophenyl)-7-cyclopropyl-4-(pyridin-4-ylamino)quinazolin-2(1H)-one was prepared by substituting 4-amino pyridine and 1-(2-chlorophenyl)-7-cyclopropylquinazoline-2,4(1H,3H)-dione.

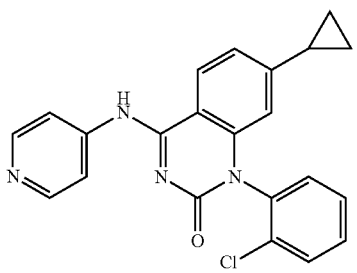 [SMILES: O=c1nc(Nc2ccncc2)c2ccc(C3CC3)cc2n1-c1ccccc1Cl]

¹H NMR (400 MHz, DMSO-d₆) δ 10.09 (s, 1H), 8.53 (s, 2H), 8.39 (d, J=8.5 Hz, 1H), 8.03 (bs, 2H), 7.83-7.73 (m, 1H), 7.64-7.49 (m, 3H), 6.96 (d, J=8.4 Hz, 1H), 6.13 (s, 1H), 1.92-1.83 (m, 1H), 1.00 (d, J=8.3 Hz, 2H), 0.69-0.60 (m, 2H). m/z [M+H]⁺ 389.05.

4-((1-(2-Chlorophenyl)-7-cyclopropyl-2-oxo-1,2-dihydroquinazolin-4-yl)amino)picolinonitrile was prepared by substituting 4-aminopicolinonitrile and 1-(2-chlorophenyl)-7-cyclopropylquinazoline-2,4(1H,3H)-dione.

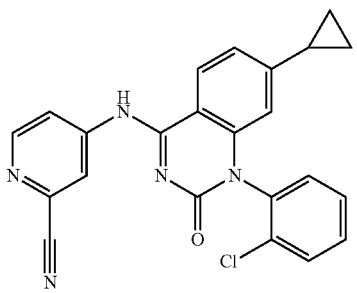 [SMILES: N#Cc1cc(Nc2nc(=O)n(-c3ccccc3Cl)c3cc(C4CC4)ccc23)ccn1]

¹H NMR (400 MHz, DMSO-d₆) δ 8.64 (d, J=5.7 Hz, 1H), 8.44 (s, 1H), 8.31 (d, J=8.5 Hz, 1H), 8.07 (s, 1H), 7.81-7.74 (m, 1H), 7.66-7.50 (m, 3H), 6.95 (d, J=8.5 Hz, 1H), 6.12 (s, 1H), 1.92-1.83 (m, 1H), 0.99 (d, J=8.4 Hz, 2H), 0.69-0.58 (m, 2H). m/z [M+H]⁺ 414.1

1-(2-Chlorophenyl)-7-cyclopropyl-4-((2-methoxypyridin-4-yl)amino)quinazolin-2(1H)-one was prepared by substituting 2-methoxypyridin-4-amine and 1-(2-chlorophenyl)-7-cyclopropylquinazoline-2,4(1H,3H)-dione.

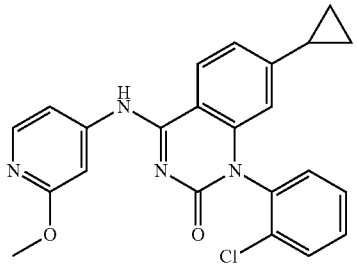

¹H NMR (400 MHz, DMSO-d₆) δ 10.00 (s, 1H), 8.36 (bs, 1H), 8.16-8.01 (m, 1H), 7.84-7.73 (m, 1H), 7.67-7.49 (m, 5H), 6.95 (d, J=8.3 Hz, 1H), 6.12 (s, 1H), 3.86, 4H), 1.93-1.82 (m, 1H), 0.99 (d, J=8.5 Hz, 2H), 0.70-0.52 (m, 2H). m/z [M+H]⁺ 419.1.

1-(2-Chlorophenyl)-7-cyclopropyl-4-((2-morpholinopyridin-4-yl)amino)quinazolin-2(1H)-one was prepared by substituting 2-morpholinopyridin-4-amine and 1-(2-chlorophenyl)-7-cyclopropylquinazoline-2,4(1H,3H)-dione.

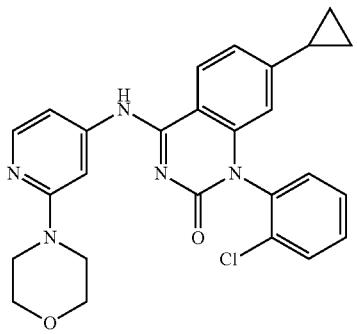

¹H NMR (400 MHz, DMSO-d₆) δ 9.86 (s, 1H), 8.36 (d, J=8.5 Hz, 1H), 8.10 (d, J=5.6 Hz, 1H), 7.82-7.69 (m, 1H), 7.62-7.41 (m, 5H), 6.94 (d, J=8.5 Hz, 1H), 6.12 (s, 1H), 3.73 (s, 5H), 1.93-1.80 (m, 1H), 0.99 (d, J=8.4 Hz, 2H), 0.68-0.56 (m, 2H). m/z [M+H]⁺ 474.1

1-(2-Chlorophenyl)-7-cyclopropyl-4-((2-fluoropyridin-4-yl)amino)quinazolin-2(1H)-one was prepared by substituting 2-fluoropyridin-4-amine and 1-(2-chlorophenyl)-7-cyclopropylquinazoline-2,4(1H,3H)-dione.

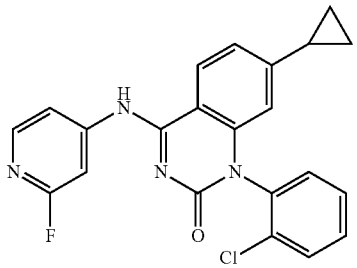

603

¹H NMR (400 MHz, DMSO-d₆) δ 10.32 (bs, 1H), 8.35 (d, J=8.5 Hz, 1H), 8.17 (d, J=5.1 Hz, 1H), 7.83-7.73 (m, 2H), 7.82 (bs, 1H), 7.66-7.49 (m, 3H), 6.96 (d, J=8.5 Hz, 1H), 6.13 (s, 1H), 1.92-1.82 (m, 1H), 1.00 (d, J=8.3 Hz, 2H), 0.70-0.58 (m, 2H). m/z [M+H]⁺ 407.0

1-(2-Chlorophenyl)-4-((2-chloropyridin-4-yl)amino)-7-cyclopropylquinazolin-2(1H)-one was prepared by substituting 2-chloropyridin-4-amine and 1-(2-chlorophenyl)-7-cyclopropylquinazoline-2,4(1H,3H)-dione.

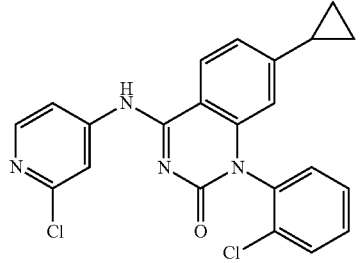

¹H NMR (400 MHz, DMSO-d₆) δ 10.21 (bs, 1H), 8.33 (d, J=6.1 Hz, 2H), 8.16 (bs, 1H), 7.91 (bs, 1H), 7.81-7.70 (m, 1H), 7.66-7.41 (m, 3H), 6.95 (d, J=8.5 Hz, 1H), 6.12 (s, 1H), 1.93-1.80 (m, 1H), 0.99 (d, J=8.3 Hz, 2H), 0.72-0.54 (m, 2H). m/z [M+H]⁺ 423.0

1-(2-Chlorophenyl)-5-methoxy-4-(methylamino)-7-(trifluoromethyl)quinazolin-2(1H)-one was prepared by substituting 1-(2-chlorophenyl)-5-methoxy-7-(trifluoromethyl)quinazoline-2,4(1H,3H)-dione.

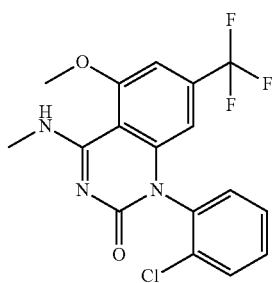 [SMILES: CNc1nc(=O)n(-c2ccccc2Cl)c2cc(C(F)(F)F)cc(OC)c12]

1-(2-chlorophenyl)-4-((cyclopropylmethyl)amino)-7-(trifluoromethyl)quinazolin-2(1H)-one was prepared by substituting cyclopropylmethanamine and 1-(2-chlorophenyl)-7-(trifluoromethyl)quinazoline-2,4(1H,3H)-dione.

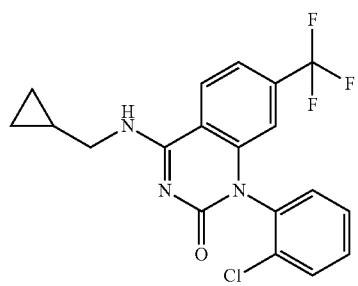 [SMILES: O=c1nc(NCC2CC2)c2ccc(C(F)(F)F)cc2n1-c1ccccc1Cl]

¹H NMR (400 MHz, DMSO-d₆) δ 9.01 (s, 1H), 8.49 (d, J=8.5 Hz, 1H), 7.81-7.70 (m, 1H), 7.67-7.54 (m, 4H), 6.44 (s, 1H), 3.50-3.25 (m, 1H), 1.28-1.15 (m, 1H), 0.52 (d, J=7.8 Hz, 2H), 0.38-0.29 (m, 2H). m/z [M+H]⁺ 394.1

604

(R)-1-(2-Chlorophenyl)-7-(trifluoromethyl)-4-((1,1,1-trifluoropropan-2-yl)amino)quinazolin-2(1H)-one was prepared by substituting (R)-1,1,1-trifluoropropan-2-amine and 1-(2-chlorophenyl)-7-(trifluoromethyl)quinazoline-2,4(1H,3H)-dione.

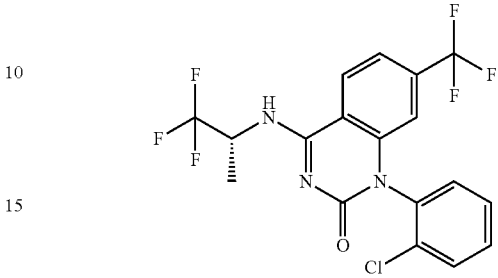

¹H NMR (400 MHz, DMSO-d₆) δ 9.03-8.92 (m, 1H), 8.66 (t, J=7.3 Hz, 1H), 7.83-7.74 (m, 1H), 7.70 (d, J=8.5 Hz, 1H), 7.67-7.53 (m, 3H), 6.49 (s, 1H), 5.43 (h, J=7.6 Hz, 1H), 1.53-1.47 (m, 3H), 1.34-1.15 (m, 1H). m/z [M+H]⁺ 436.0

(trans)-3-((1-(2-chlorophenyl)-2-oxo-7-(trifluoromethyl)-1,2-dihydroquinazolin-4-yl)amino)cyclobutane-1-carbonitrile was prepared by substituting trans-3-aminocyclobutane-1-carbonitrile and 1-(2-chlorophenyl)-7-(trifluoromethyl)quinazoline-2,4(1H,3H)-dione.

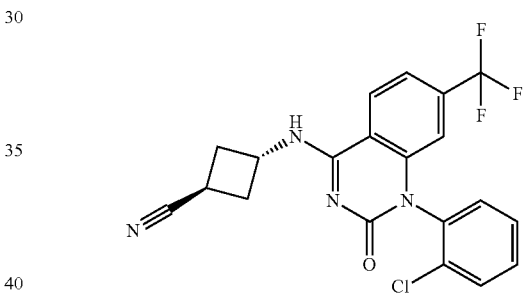

¹H NMR (400 MHz, DMSO-d₆) δ 9.06 (d, J=6.3 Hz, 1H), 8.50 (d, J=8.5 Hz, 1H), 7.81-7.74 (m, 1H), 7.70-7.53 (m, 4H), 6.44 (s, 1H), 4.93 (p, J=7.6 Hz, 1H), 3.40-3.25 (m, 1H), 2.76-2.58 (m, 4H). m/z [M+H]⁺ 419.05

4-(isopropylamino)-1-phenyl-7-(trifluoromethyl)quinazolin-2(1H)-one was prepared by substituting isopropylamine 1-phenyl-7-(trifluoromethyl)quinazoline-2,4(1H,3H)-dione.

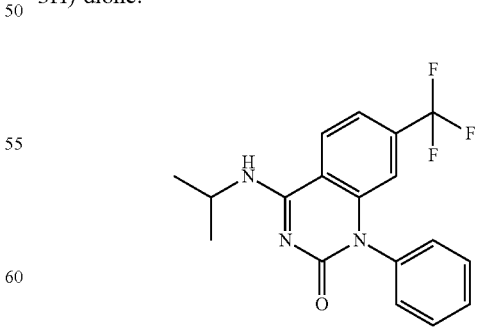

¹H NMR (400 MHz, DMSO-d₆) δ 8.49 (d, J=5.8 Hz, 1H), 8.43 (d, J=7.8 Hz, 1H), 7.68-7.49 (m, 4H), 7.35 (d, J=7.6 Hz, 2H), 6.54 (s, 1H), 4.55-4.45 (m, 1H), 1.29 (d, J=6.2 Hz, 6H). m/z [M+H]⁺ 348.1

605

1-(2-Chlorophenyl)-4-(isopropylamino)-7-(trifluoromethyl)quinazolin-2(1H)-one was prepared by substituting isopropylamine and 1-(2-chlorophenyl)-7-(trifluoromethyl)quinazoline-2,4(1H,3H)-dione.

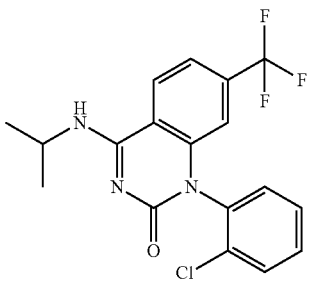 [SMILES: CC(C)Nc1nc(=O)n(-c2ccccc2Cl)c2cc(C(F)(F)F)ccc12]

¹H NMR (400 MHz, DMSO-d₆) δ 8.54 (d, J=8.2 Hz, 2H), 7.81-7.73 (m, 1H), 7.66-7.53 (m, 4H), 6.43 (s, 1H), 4.52 (h, J=7.0 Hz, 1H), 1.35-1.25 (m, 6H). m/z [M+H]⁺ 382.0

1-(2-Chlorophenyl)-4-(cyclopropylamino)-7-(trifluoromethyl)quinazolin-2(1H)-one was prepared by substituting cyclopropylamine and 1-(2-chlorophenyl)-7-(trifluoromethyl)quinazoline-2,4(1H,3H)-dione.

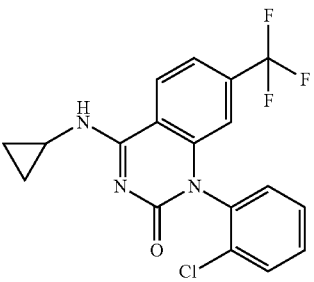 [SMILES: O=c1nc(NC2CC2)c2ccc(C(F)(F)F)cc2n1-c1ccccc1Cl]

¹H NMR (400 MHz, DMSO-d₆) δ 8.78 (s, 1H), 8.44 (d, J=8.5 Hz, 1H), 7.81-7.74 (m, 1H), 7.65-7.51 (m, 3H), 6.68 (bs, 1H), 6.43 (s, 1H), 3.18-3.08 (m, 1H), 0.85 (d, J=7.4 Hz, 2H), 0.80-0.70 (m, 2H). m/z [M+H]⁺ 380.0.

1-(2-Chlorophenyl)-4-(isoxazol-4-ylamino)-7-(trifluoromethyl)quinazolin-2(1H)-one was prepared by substituting isoxazol-4-amine and 1-(2-chlorophenyl)-7-(trifluoromethyl)-quinazoline-2,4(1H,3H)-dione.

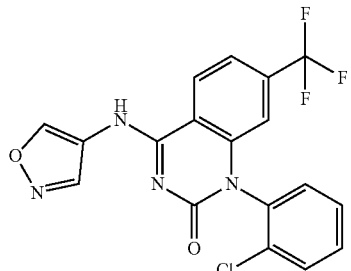

m/z [M+H]⁺ 406.75.

606

1-(2-Chlorophenyl)-4-((1,3-difluoropropan-2-yl)amino)-7-(trifluoromethyl)quinazolin-2(1H)-one was prepared by substituting 1,3-difluoropropan-2-amine and 1-(2-chlorophenyl)-7-(trifluoromethyl)quinazoline-2,4(1H,3H)-dione.

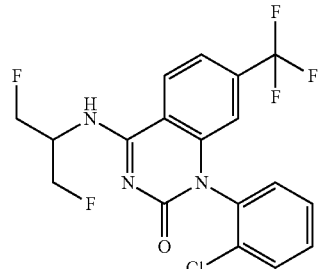

¹H NMR (400 MHz, DMSO-d₆) δ 8.94 (d, J=7.5 Hz, 1H), 8.62 (d, J=8.5 Hz, 1H), 7.81-7.76 (m, 1H), 7.69 (d, J=8.7 Hz, 1H), 7.65-7.56 (m, 3H), 6.47 (s, 1H), 5.06-4.89 (m, 1H), 4.89-4.62 (m, 4H). m/z [M+H]⁺ 418.1

1-(2-Chlorophenyl)-4-(((1R,2S)-2-fluorocyclopropyl)amino)-7-(trifluoromethyl)quinazolin-2(1H)-one was prepared by substituting (1R,2S)-2-fluorocyclopropan-1-amine HCl and 1-(2-chlorophenyl)-7-(trifluoromethyl)quinazoline-2,4(1H,3H)-dione.

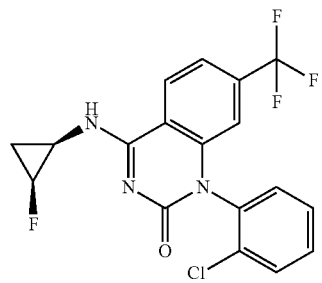 [SMILES: O=c1nc(N[C@@H]2C[C@@H]2F)c2ccc(C(F)(F)F)cc2n1-c1ccccc1Cl]

¹H NMR (400 MHz, DMSO-d₆) δ 8.91 (s, 1H), 8.53 (d, J=8.5 Hz, 1H), 7.84-7.5 (m, 1H), 7.69-7.53 (m, 4H), 6.46 (s, 1H), 4.90 (d, J=65.0 Hz, 1H), 3.15-3.05 (m, 1H), 1.48-1.17 (m, 2H). m/z [M+H]⁺ 398.05.

1-(2-Chlorophenyl)-4-(((1S,2R)-2-fluorocyclopropyl)amino)-7-(trifluoromethyl)quinazolin-2(1H)-one was prepared by substituting (1S,2R)-2-fluorocyclopropan-1-amine HCl and 1-(2-chlorophenyl)-7-(trifluoromethyl)quinazoline-2,4(1H,3H)-dione.

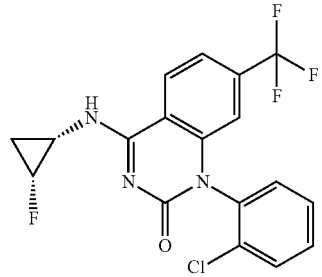 [SMILES: O=c1nc(N[C@H]2C[C@H]2F)c2ccc(C(F)(F)F)cc2n1-c1ccccc1Cl]

¹H NMR (400 MHz, DMSO-d₆) δ 8.91 (s, 1H), 8.53 (d, J=8.5 Hz, 1H), 7.84-7.75 (m, 1H), 7.69-7.53 (m, 4H), 6.46 (s, 1H), 4.90 (d, J=65.0 Hz, 1H), 3.15-3.05 (m, 1H), 1.48-1.17 (m, 2H). m/z [M+H]⁺ 398.1.

4-((Cyclopropylmethyl)amino)-1-phenyl-7-(trifluoromethyl)quinazolin-2(1H)-one was prepared by substituting cyclopropylmethanamine and 1-phenyl-7-(trifluoromethyl)quinazoline-2,4(1H,3H)-dione.

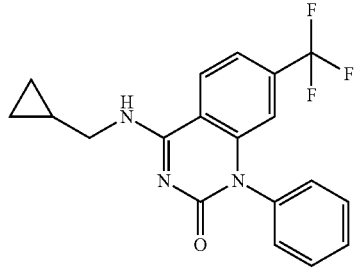

$^1$H NMR (400 MHz, DMSO-d$_6$) δ 8.91 (s, 1H), 8.44 (d, J=8.9 Hz, 1H), 7.66-7.49 (m, 3H), 7.35 (d, J=7.6 Hz, 2H), 6.90 (bs, 1H), 6.55 (s, 1H), 3.38-3.26 (m, 2H), 1.31-1.16 (m, 1H), 0.51 (d, J=7.7 Hz, 2H), 0.36-0.26 (m, 2H). m/z [M+H]$^+$ 360.1

7-isopropyl-4-(methylamino)-1-phenylquinazolin-2(1H)-one was prepared by substituting 7-isopropyl-1-phenylquinazoline-2,4(1H,3H)-dione.

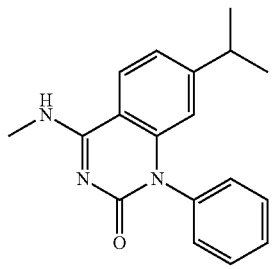 [SMILES: CNc1nc(=O)n(-c2ccccc2)c2cc(C(C)C)ccc12]

$^1$H NMR (400 MHz, DMSO-d$_6$) δ 8.46 (s, 1H), 8.00 (d, J=8.3 Hz, 1H), 7.58 (t, J=7.0 Hz, 2H), 7.51 (d, J=6.6 Hz, 1H), 7.26 (d, J=7.6 Hz, 2H), 7.11 (d, J=8.4 Hz, 1H), 6.20 (s, 1H), 2.97 (s, 3H), 2.73 (p, J=7.1 Hz, 1H), 1.04 (d, J=6.6 Hz, 6H). m/z [M+H]$^+$ 294.2.

4-((2,2-Difluorocyclopropyl)amino)-1-phenyl-7-(trifluoromethyl)quinazolin-2(1H)-one was prepared by substituting 2,2-difluorocyclopropan-1-amine and 1-phenyl-7-(trifluoromethyl)quinazoline-2,4(1H,3H)-dione.

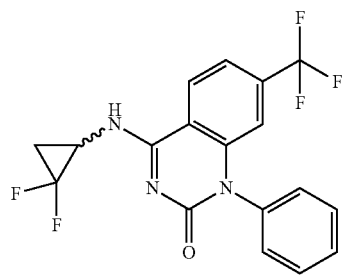 [SMILES: O=c1nc(NC2CC2(F)F)c2ccc(C(F)(F)F)cc2n1-c1ccccc1]

$^1$H NMR (400 MHz, DMSO-d$_6$) δ 8.41 (s, 1H), 7.65-7.59 (m, 3H), 7.56 (t, J=7.7 Hz, 2H), 7.35 (t, J=7.6 Hz, 2H), 6.57 (d, J=8.9 Hz, 1H), 6.18-5.87 (m, 1H), 3.78-3.65 (m, 1H), 2.15-2.06 (m, 1H), 1.94-1.82 (m, 1H). m/z [M+H]$^+$ 382.05.

4-((1,3-Difluoropropan-2-yl)amino)-1-phenyl-7-(trifluoromethyl)quinazolin-2(1H)-one was prepared by substituting 1,3-difluoropropan-2-amine and 1-phenyl-7-(trifluoromethyl)quinazoline-2,4(1H,3H)-dione.

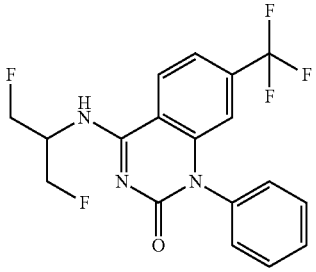 [SMILES: O=c1nc(NC(CF)CF)c2ccc(C(F)(F)F)cc2n1-c1ccccc1]

$^1$H NMR (400 MHz, DMSO-d$_6$) δ 8.83 (d, J=7.4 Hz, 1H), 8.56 (d, J=8.4 Hz, 1H), 7.62 (t, J=6.8 Hz, 3H), 7.56 (d, J=7.5 Hz, 1H), 7.37 (d, J=7.6 Hz, 2H), 6.58 (s, 1H), 5.03-4.87 (m, 1H), 4.86-4.75 (m, 2H), 4.76-4.62 (m, 2H). m/z [M+H]$^+$ 384.1.

(R)-4-((1-Cyclopropylethyl)amino)-1-phenyl-7-(trifluoromethyl)quinazolin-2(1H)-one was prepared by substituting (R)-1-cyclopropylethan-1-amine and 1-phenyl-7-(trifluoromethyl)quinazoline-2,4(1H,3H)-dione.

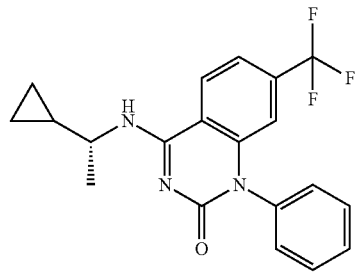 [SMILES: C[C@@H](Nc1nc(=O)n(-c2ccccc2)c2cc(C(F)(F)F)ccc12)C1CC1]

$^1$H NMR (400 MHz, DMSO-d$_6$) δ 8.43 (d, J=8.0 Hz, 1H), 8.32 (d, J=8.4 Hz, 1H), 7.45-7.28 (m, 4H), 7.16 (s, 2H), 6.35 (s, 1H), 3.67 (q, J=7.6 Hz, 1H), 2.34-2.27 9 m, 1H), 1.13 (d, J=6.4 Hz, 3H), 0.99-0.87 (m, 2H), 0.40-0.22 (m, 2H). m/z [M+H]$^+$ 374.1.

4-(((1-Fluorocyclopropyl)methyl)amino)-1-phenyl-7-(trifluoromethyl)quinazolin-2(1H)-one was prepared by substituting (1-fluorocyclopropyl)methanamine and 1-phenyl-7-(trifluoromethyl)quinazoline-2,4(1H,3H)-dione.

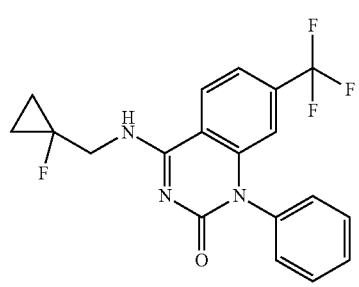

$^1$H NMR (400 MHz, DMSO-d$_6$) δ 9.06 (d, J=6.2 Hz, 1H), 8.53 (d, J=8.5 Hz, 1H), 7.66-7.49 (m, 4H), 7.36 (d, J=7.6 Hz, 2H), 6.57 (s, 1H), 4.02 (dd, J=21.5, 5.4 Hz, 2H), 1.07 (d, J=19.0 Hz, 2H), 0.95 (d, J=8.0 Hz, 2H). m/z [M+H]$^+$ 378.1.

4-((((trans)-2-(hydroxymethyl)cyclopropyl)methyl) amino)-1-phenyl-7-(trifluoromethyl)quinazolin-2(1H)-one was prepared by substituting (trans-2-(aminomethyl)cyclopropyl)methanol and 1-phenyl-7-(trifluoromethyl)quinazoline-2,4(1H,3H)-dione.

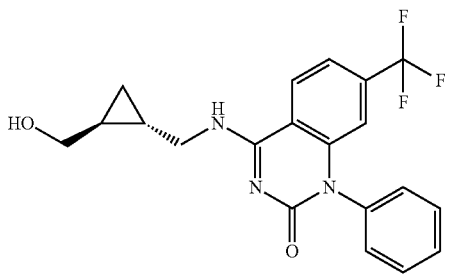 [SMILES: O=c1nc(NC[C@H]2C[C@@H]2CO)c2ccc(C(F)(F)F)cc2n1-c1ccccc1]

¹H NMR (400 MHz, DMSO-d₆) δ 8.85 (s, 1H), 8.43 (d, J=8.4 Hz, 1H), 7.66-7.48 (m, 4H), 7.35 (d, J=7.6 Hz, 2H), 6.55 (s, 1H), 4.53 (s, 1H), 3.55-3.41 (m, 2H), 3.36-3.19 (m, 2H), 1.16-1.06 (m, 1H), 1.02-0.92 (m, 1H), 0.52-0.35 (m, 2H). m/z [M+H]⁺ 390.1

1-(Imidazo[1,2-a]pyridin-5-yl)-4-(methylamino)-7-(trifluoromethyl)quinazolin-2(1H)-one was prepared by substituting (1-(imidazo[1,2-a]pyridin-5-yl)-7-(trifluoromethyl) quinazoline-2,4(1H,3H)-dione.

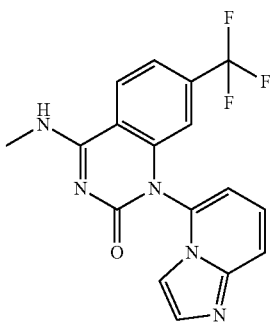 [SMILES: CNc1nc(=O)n(-c2cccc3nccn23)c2cc(C(F)(F)F)ccc12]

¹H NMR (400 MHz, DMSO-d₆) δ 9.12 (s, 1H), 8.41 (d, J=8.4 Hz, 1H), 7.80 (d, J=9.1 Hz, 1H), 7.71-7.65 (m, 2H), 7.60 (s, 1H), 7.46 (t, J=8.1 Hz, 1H), 7.18 (d, J=7.1 Hz, 1H), 6.50 (s, 1H), 3.09-3.02 (m, 3H). m/z [M+H]⁺ 360.1.

1-(2-Chlorophenyl)-7-cyclopropyl-4-(methylamino) pyrido[2,3-d]pyrimidin-2(1H)-one was prepared by substituting 1-(2-chlorophenyl)-7-cyclopropylpyrido[2,3-d]pyrimidine-2,4(1H,3H)-dione.

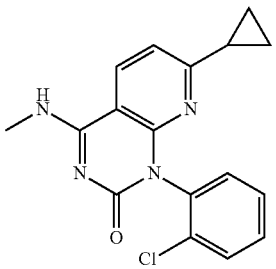 [SMILES: CNc1nc(=O)n(-c2ccccc2Cl)c2nc(C3CC3)ccc12]

¹H NMR (400 MHz, DMSO-d₆) δ 8.68 (s, 1H), 8.32 (d, J=8.2 Hz, 1H), 7.60 (d, J=5.4 Hz, 1H), 7.48-7.40 (m, 2H), 7.34 (d, J=5.7 Hz, 1H), 7.19 (d, J=8.1 Hz, 1H), 2.99 (d, J=4.3 Hz, 3H), 2.05-1.96 (m, 1H), 0.87-0.79 (m, 2H), 0.54-0.47 (m, 2H). m/z [M+H]⁺ 327.1

7-Cyclopropyl-1-(imidazo[1,2-a]pyridin-5-yl)-4-(methylamino)pyrido[2,3-d]pyrimidin-2(1H)-one was prepared by substituting 7-cyclopropyl-1-(imidazo[1,2-a]pyridin-5-yl)pyrido[2,3-d]pyrimidine-2,4(1H,3H)-dione.

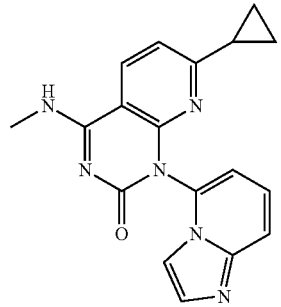 [SMILES: CNc1nc(=O)n(-c2cccc3nccn23)c2nc(C3CC3)ccc12]

¹H NMR (400 MHz, DMSO-d₆) δ 8.65 (d, J=4.9 Hz, 1H), 8.59 (d, J=7.4 Hz, 1H), 8.31 (d, J=8.4 Hz, 1H), 8.01 (s, 1H), 7.62 (s, 1H), 7.43 (s, 1H), 7.18 (d, J=8.4 Hz, 1H), 6.76 (d, J=7.3 Hz, 1H), 2.99 (s, 3H), 2.06-1.97 (m, 1H), 0.89-0.82 (m, 2H), 0.64-0.56 (m, 2H). m/z [M+H]⁺ 333.1

7-Methoxy-4-(methylamino)-1-phenylpyrido[2,3-d]pyrimidin-2(1H)-one was prepared by substituting 7-methoxy-1-phenylpyrido[2,3-d]pyrimidine-2,4(1H,3H)-dione.

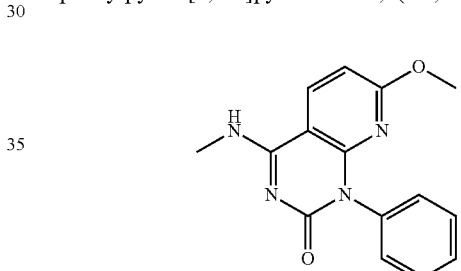

¹H NMR (400 MHz, DMSO-d₆) δ 8.46 (d, J=4.9 Hz, 1H), 8.35 (d, J=7.6 Hz, 1H), 7.48 (t, J=7.7 Hz, 2H), 7.39 (t, J=7.5 Hz, 1H), 7.24 (d, J=7.6 Hz, 2H), 6.64 (d, J=8.6 Hz, 1H), 3.48 (s, 3H), 2.97 (d, J=2.7 Hz, 3H). m/z [M+H]⁺ 283.1

1-(3-Chloropyridin-2-yl)-4-(methylamino)-7-(trifluoromethyl)quinazolin-2(1H)-one was prepared by substituting 1-(3-chloropyridin-2-yl)-7-(trifluoromethyl)quinazoline-2,4(1H,3H)-dione.

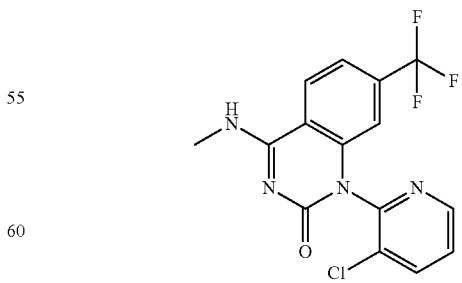

¹H NMR (400 MHz, DMSO-d₆) δ 9.04 (s, 1H), 8.68 (d, J=4.5 Hz, 1H), 8.40 (d, J=8.4 Hz, 1H), 8.30 (d, J=8.0 Hz, 1H), 7.72-7.62 (m, 2H), 6.47 (s, 1H), 3.03 (d, J=4.3 Hz, 3H). m/z [M+H]⁺ 355.0

611

4-(Methylamino)-7-(trifluoromethyl)-1-(2-(trifluoromethyl)pyridin-3-yl)quinazolin-2(1H)-one was prepared by substituting 7-(trifluoromethyl)-1-(2-(trifluoromethyl)pyridin-3-yl)quinazoline-2,4(1H,3H)-dione.

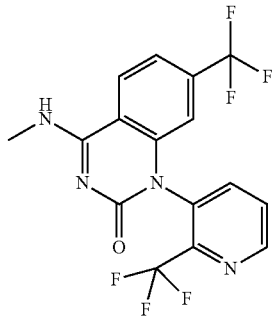 [SMILES: CNc1nc(=O)n(-c2cccnc2C(F)(F)F)c2cc(C(F)(F)F)ccc12]

$^1$H NMR (400 MHz, DMSO-d$_6$) δ 9.04 (s, 1H), 8.93 (d, J=4.7 Hz, 1H), 8.37 (d, J=8.3 Hz, 1H), 8.18 (d, J=8.1 Hz, 1H), 8.01 (t, J=6.3 Hz, 1H), 7.64 (d, J=8.3 Hz, 1H), 6.52 (s, 1H), 3.02 (s, 3H). m/z [M+H]$^+$ 389.1

4-(Methylamino)-1-(pyrimidin-5-yl)-7-(trifluoromethyl)quinazolin-2(1H)-one was prepared by substituting 1-(pyrimidin-5-yl)-7-(trifluoromethyl)quinazoline-2,4(1H,3H)-dione.

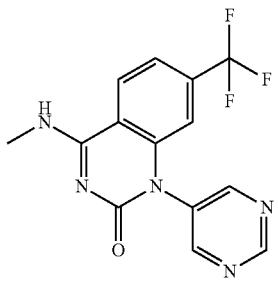 [SMILES: CNc1nc(=O)n(-c2cncnc2)c2cc(C(F)(F)F)ccc12]

$^1$H NMR (400 MHz, DMSO-d$_6$) δ 9.34 (s, 1H), 9.01 (s, 1H), 8.94 (s, 2H), 8.36 (d, J=8.4 Hz, 1H), 7.64 (d, J=8.4 Hz, 1H), 6.80 (s, 1H), 3.03 (s, 3H). m/z [M+H]$^+$ 322.1.

(S)-1-Phenyl-7-(trifluoromethyl)-4-((1,1,1-trifluoropropan-2-yl)amino)quinazolin-2(1H)-one was prepared by substituting (S)-1,1,1-trifluoropropan-2-amine and 1-phenyl-7-(trifluoromethyl)quinazoline-2,4(1H,3H)-dione.

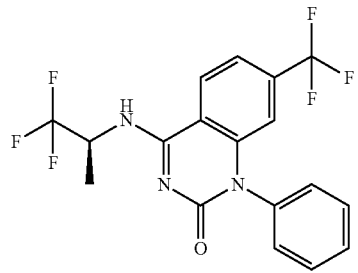

$^1$H NMR (400 MHz, DMSO-d$_6$) δ 8.88 (d, J=8.2 Hz, 1H), 8.59 (d, J=8.1 Hz, 1H), 7.68-7.52 (m, 4H), 7.44-7.33 (m, 2H), 6.59 (s, 1H), 5.42 (m, 1H), 1.48 (d, J=7.1 Hz, 3H). m/z [M+H]$^+$ 402.1.

612

4-((Oxetan-2-ylmethyl)amino)-1-phenyl-7-(trifluoromethyl)quinazolin-2(1H)-one was prepared by substituting oxetan-2-ylmethanamine and 1-phenyl-7-(trifluoromethyl)quinazoline-2,4(1H,3H)-dione.

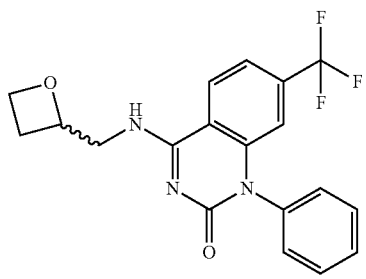 [SMILES: O=c1nc(NCC2CCO2)c2ccc(C(F)(F)F)cc2n1-c1ccccc1]

$^1$H NMR (400 MHz, DMSO-d$_6$) δ 8.96 (s, 1H), 8.46 (d, J=8.4 Hz, 1H), 7.67-7.50 (m, 4H), 7.35 (d, J=7.5 Hz, 2H), 6.56 (s, 1H), 5.01 (p, J=6.5 Hz, 1H), 4.61-4.44 (m, 2H), 3.92-3.71 (m, 2H), 2.69 (q, J=8.4, 6.8 Hz, 1H), 2.52-2.42 (m, 1H). m/z [M+H]$^+$ 376.1

4-(((1R,2S)-2-fluorocyclopropyl)amino)-1-phenyl-7-(trifluoromethyl)quinazolin-2(1H)-one was prepared by substituting (1R,2S)-2-fluorocyclopropan-1-amine HCl and 1-phenyl-7-(trifluoromethyl)quinazoline-2,4(1H,3H)-dione.

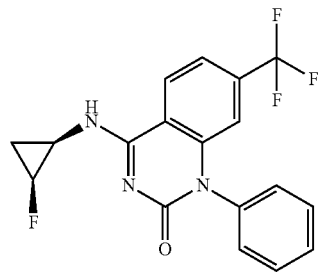

$^1$H NMR (400 MHz, DMSO-d$_6$) δ 8.79 (s, 1H), 8.47 (d, J=8.5 Hz, 1H), 7.67-7.49 (m, 4H), 7.37 (s, 2H), 6.57 (s, 1H), 4.89 (d, J=65.1 Hz, 1H), 3.13-3.02 (m, 1H), 1.45-1.18 (m, 2H). m/z[M+H]$^+$ 364.1

4-(((trans)-2-fluorocyclopropyl)amino)-1-phenyl-7-(trifluoromethyl)quinazolin-2(1H)-one was prepared by substituting (trans)-2-fluorocyclopropan-1-amine HCl and 1-phenyl-7-(trifluoromethyl)quinazoline-2,4(1H,3H)-dione.

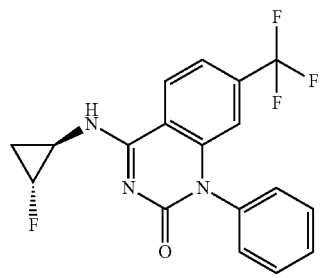 [SMILES: O=c1nc(N[C@@H]2C[C@H]2F)c2ccc(C(F)(F)F)cc2n1-c1ccccc1]

$^1$H NMR (400 MHz, DMSO-d$_6$) δ 8.66 (s, 1H), 8.31 (d, J=8.0 Hz, 1H), 7.69-7.51 (m, 4H), 7.35 (d, J=7.5 Hz, 2H), 6.56 (s, 1H), 4.88 (d, J=63.1 Hz, 1H), 3.35-3.23 (m, 1H), 1.61-1.45 (m, 1H), 1.30-1.17 (m, 1H). m/z [M+H]$^+$ 364.1.

613

4-(((2,2-Difluorocyclopropyl)methyl)amino)-1-phenyl-7-(trifluoromethyl)quinazolin-2(1H)-one was prepared by substituting (2,2-difluorocyclopropyl)methanamine and 1-phenyl-7-(trifluoromethyl)quinazoline-2,4(1H,3H)-dione.

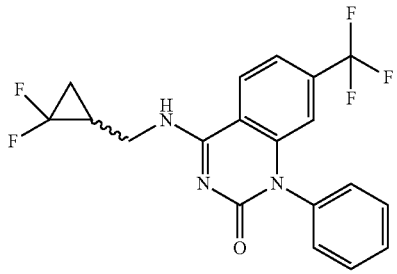 [SMILES: O=c1nc(NCC2CC2(F)F)c2ccc(C(F)(F)F)cc2n1-c1ccccc1]

$^1$H NMR (400 MHz, DMSO-d$_6$) δ 9.03 (s, 1H), 8.40 (d, J=8.4 Hz, 1H), 7.66-7.50 (m, 4H), 7.35 (d, J=7.6 Hz, 2H), 6.56 (s, 1H), 3.69-3.54 (m, 2H), 2.28-2.14 (m, 1H), 1.73-1.58 (m, 1H), 1.48-1.36 (m, 1H). m/z [M+H]$^+$ 396.1.

(R)-4-((1-Hydroxypropan-2-yl)amino)-1-phenyl-7-(trifluoromethyl)quinazolin-2(1H)-one was prepared by substituting (R)-2-aminopropan-1-ol and 1-phenyl-7-(trifluoromethyl)quinazoline-2,4(1H,3H)-dione.

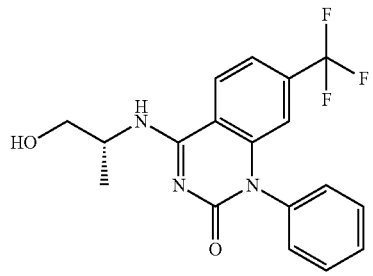

$^1$H NMR (400 MHz, DMSO-d$_6$) δ 8.50 (d, J=8.3 Hz, 1H), 8.34 (d, J=7.7 Hz, 1H), 7.64-7.52 (m, 4H), 7.34 (d, J=7.6 Hz, 2H), 6.55 (s, 1H), 4.90 (s, 1H), 4.45 (p, J=6.8 Hz, 1H), 3.55 (d, J=40 Hz, 1H), 1.24 (d, J=6.6 Hz, 3H). m/z [M+H]$^+$ 364.1.

4-(oxetan-3-ylamino)-1-phenyl-7-(trifluoromethyl)quinazolin-2(1H)-one was prepared by substituting oxetan-3-amine and 1-phenyl-7-(trifluoromethyl)quinazoline-2,4(1H,3H)-dione.

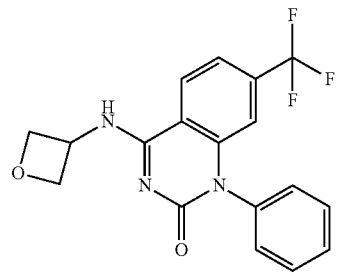 [SMILES: O=c1nc(NC2COC2)c2ccc(C(F)(F)F)cc2n1-c1ccccc1]

$^1$H NMR (400 MHz, DMSO-d$_6$) δ 9.24 (s, 1H), 8.50 (d, J=8.5 Hz, 1H), 7.61 (t, J=7.5 Hz, 4H), 7.33 (d, J=7.7 Hz, 2H), 6.56 (s, 1H), 5.16 (p, J=6.5 Hz, 1H), 4.88 (t, J=7.3 Hz, 2H), 4.70 (t, J=6.4 Hz, 2H). m/z [M+H]$^+$ 362.1.

614

4-(((trans)-3-methoxycyclobutyl)amino)-1-phenyl-7-(trifluoromethyl)quinazolin-2(1H)-one was prepared by substituting (trans)-3-methoxycyclobutan-1-amine and 1-phenyl-7-(trifluoromethyl)quinazoline-2,4(1H,3H)-dione.

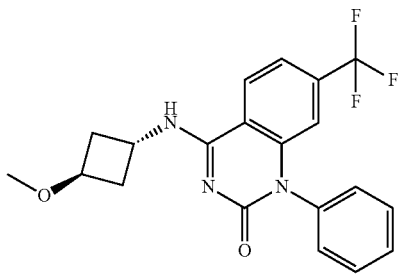 [SMILES: CO[C@H]1C[C@H](Nc2nc(=O)n(-c3ccccc3)c3cc(C(F)(F)F)ccc23)C1]

$^1$H NMR (400 MHz, DMSO-d$_6$) δ 8.80 (d, J=6.3 Hz, 1H), 8.49 (d, J=8.5 Hz, 1H), 7.64-7.53 (m, 4H), 7.34 (d, J=7.6 Hz, 2H), 6.54 (s, 1H), 4.77-4.62 (m, 1H), 4.12-4.00 (m, 1H), 3.20 (s, 3H), 2.44-2.31 (m, 4H). m/z [M+H]$^+$ 390.1.

4-((3-Methoxypropyl)amino)-1-phenyl-7-(trifluoromethyl)quinazolin-2(1H)-one was prepared by substituting 3-methoxypropan-1-amine and 1-phenyl-7-(trifluoromethyl)quinazoline-2,4(1H,3H)-dione.

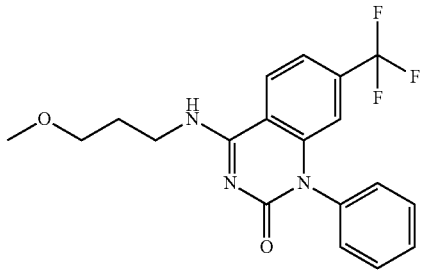 [SMILES: COCCCNc1nc(=O)n(-c2ccccc2)c2cc(C(F)(F)F)ccc12]

$^1$H NMR (400 MHz, DMSO-d$_6$) δ 8.76 (s, 1H), 8.39 (d, J=8.4 Hz, 1H), 7.64-7.51 (m, 4H), 7.35 (d, J=7.6 Hz, 2H), 6.55 (s, 1H), 3.57 (q, J=6.8 Hz, 2H), 3.45 (t, J=6.2 Hz, 2H), 3.28 (s, 3H), 1.91 (p, J=7.1 Hz, 2H). m/z [M+H]$^+$ 378.1.

4-((2-Methoxyethyl)amino)-1-phenyl-7-(trifluoromethyl)quinazolin-2(1H)-one was prepared by substituting 2-methoxyethan-1-amine and 1-phenyl-7-(trifluoromethyl)quinazoline-2,4(1H,3H)-dione.

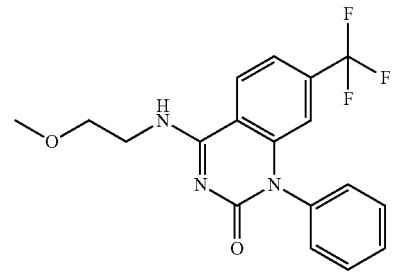 [SMILES: COCCNc1nc(=O)n(-c2ccccc2)c2cc(C(F)(F)F)ccc12]

$^1$H NMR (400 MHz, DMSO-d$_6$) δ 8.43 (d, J=8.5 Hz, 1H), 7.64-7.51 (m, 4H), 7.35 (d, J=7.6 Hz, 2H), 6.55 (s, 1H), 3.75-3.66 (m, 2H), 3.61 (t, J=5.9 Hz, 2H), 3.32 (s, 3H). m/z [M+H]$^+$ 364.1.

615

4-((2-(Difluoromethoxy)ethyl)amino)-1-phenyl-7-(trifluoromethyl)quinazolin-2(1H)-one was prepared by substituting 2-(difluoromethoxy)ethan-1-amine and 1-phenyl-7-(trifluoromethyl)quinazoline-2,4(1H,3H)-dione.

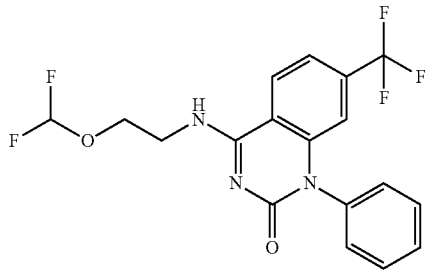 [SMILES: O=c1nc(NCCOC(F)F)c2ccc(C(F)(F)F)cc2n1-c1ccccc1]

$^1$H NMR (400 MHz, DMSO-d$_6$) δ 8.41 (d, J=8.5 Hz, 1H), 7.67-7.51 (m, 4H), 7.36 (d, J=7.6 Hz, 2H), 6.84 (d, J=75.8 Hz, 1H), 6.56 (s, 1H), 4.17-4.07 (m, 2H), 3.82-3.73 (m, 2H). m/z [M+H]$^+$ 400.1.

7-Cyclopropyl-4-(methylamino)-1-phenylpyrido[2,3-d]pyrimidin-2(1H)-one was prepared by substituting 7-cyclopropyl-1-phenylpyrido[2,3-d]pyrimidine-2,4(1H,3H)-dione.

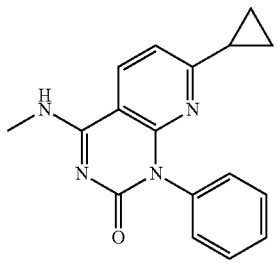 [SMILES: CNc1nc(=O)n(-c2ccccc2)c2nc(C3CC3)ccc12]

$^1$H NMR (400 MHz, DMSO-d$_6$) δ 8.56 (d, J=5.2 Hz, 1H), 8.29 (d, J=8.1 Hz, 1H), 7.49-7.35 (m, 3H), 7.16 (d, J=7.6 Hz, 3H), 2.97 (d, J=4.3 Hz, 3H), 1.98 (p, J=6.6 Hz, 1H), 0.82 (d, J=7.7 Hz, 2H), 0.54-0.46 (m, 2H). m/z [M+H]$^+$ 293.1

(R)-4-(3-Hydroxypyrrolidin-1-yl)-1-phenyl-7-(trifluoromethyl)pyrido[2,3-d]pyrimidin-2(1H)-one was prepared by using (R)-pyrrolidin-3-ol and 1-phenyl-7-(trifluoromethyl)pyrido[2,3-d]pyrimidine-2,4(1H,3H)-dione.

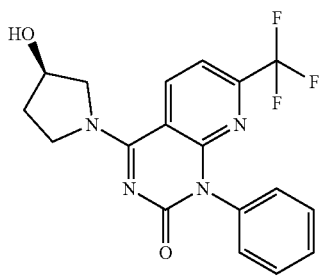 [SMILES: O=c1nc(N2CC[C@@H](O)C2)c2ccc(C(F)(F)F)nc2n1-c1ccccc1]

$^1$H NMR (400 MHz, DMSO-d$_6$) δ 8.79 (br s, 1H), 7.61 (d, J=8.1 Hz, 1H), 0.49 (m, 2H), 7.41 (m, 2H), 7.24 (d, J=7.6 Hz, 2H), 4.45 (s, 1H), 3.74 (m, 4H), 2.03 (t, J=11.5 Hz, 2H).

616

1-(2-Bromophenyl)-4-(methylamino)-7-(trifluoromethyl)pyrido[2,3-d]pyrimidin-2(1H)-one was prepared by using 1-(2-bromophenyl)-7-(trifluoromethyl)pyrido[2,3-d]pyrimidine-2,4(1H,3H)-dione.

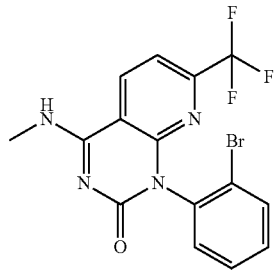

$^1$H NMR (400 MHz, DMSO) δ 9.13 (br s, 1H), 8.81 (d, J=8.1 Hz, 1H), 7.80 (t, J=7.4 Hz, 2H), 7.53 (t, J=7.7 Hz, 1H), 7.48-7.33 (m, 2H), 3.04 (s, 3H). m/z [M+H]$^+$ 401.0, 399.0.

1-(2-Fluorophenyl)-4-(methylamino)-7-(trifluoromethyl)pyrido[2,3-d]pyrimidin-2(1H)-one was prepared by using 1-(2-fluorophenyl)-7-(trifluoromethyl)pyrido[2,3-d]pyrimidine-2,4(1H,3H)-dione.

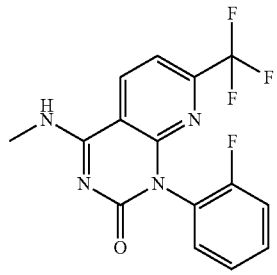

$^1$H NMR (400 MHz, DMSO) δ 9.13 (s, 1H), 8.79 (d, J=8.1 Hz, 1H), 7.82 (d, J=8.1 Hz, 1H), 7.49 (m, 1H), 7.46-7.27 (m, 3H), 3.03 (s, 3H). m/z [M+H]$^+$ 339.1

1-(2-chlorophenyl)-4-(pyridin-3-ylamino)-7-(trifluoromethyl)pyrido[2,3-d]pyrimidin-2(1H)-one was prepared by using pyridin-3-amine and 1-(2-chlorophenyl)-7-(trifluoromethyl)pyrido[2,3-d]pyrimidine-2,4(1H,3H)-dione.

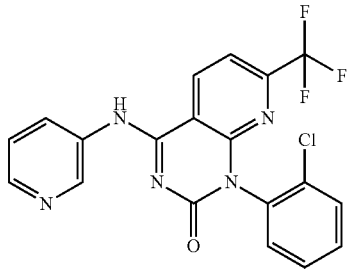

$^1$H NMR (400 MHz, DMSO) δ 10.62 (s, 1H), 9.19 (d, J=8.2 Hz, 1H), 9.03 (s, 1H), 8.45 (d, J=4.6 Hz, 1H), 8.34 (d, J=8.4 Hz, 1H), 7.95 (d, J=8.0 Hz, 1H), 7.73-7.62 (m, 1H), 7.52 (d, J=7.9 Hz, 4H). m/z [M+H]$^+$ 418.0.

1-(2-Chlorophenyl)-4-((1-methyl-1H-pyrazol-5-yl)amino)-7-(trifluoromethyl)pyrido[2,3-d]pyrimidin-2(1H)-one was prepared by using 1-methyl-1H-pyrazol-5-amine and 1-(2-chlorophenyl)-7-(trifluoromethyl)pyrido[2,3-d]pyrimidine-2,4(1H,3H)-dione.

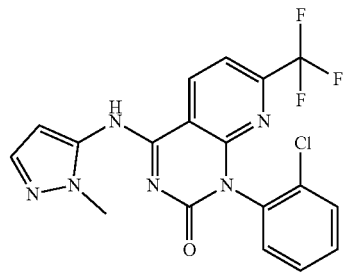 [SMILES: Cn1nccc1Nc1nc(=O)n(-c2ccccc2Cl)c2nc(C(F)(F)F)ccc12]

¹H NMR (400 MHz, DMSO) δ 10.80 (s, 1H), 9.05 (d, J=8.2 Hz, 1H), 8.33 (s, 1H), 7.88 (d, J=8.1 Hz, 1H), 7.79 (s, 1H), 7.66 (m, 1H), 7.50 (m, 3H), 3.90 (s, 3H). m/z [M+H]⁺ 421.0.

1-(2-chlorophenyl)-4-((1-methyl-1H-imidazol-4-yl)amino)-7-(trifluoromethyl)pyrido[2,3-d]pyrimidin-2(1H)-one was prepared by using 1-methyl-1H-imidazol-4-amine and 1-(2-chlorophenyl)-7-(trifluoromethyl)pyrido[2,3-d]pyrimidine-2,4(1H,3H)-dione.

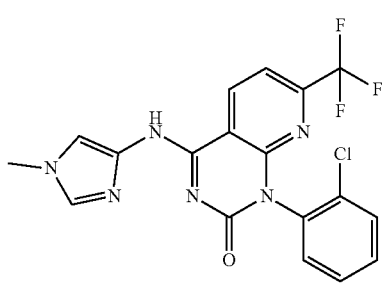 [SMILES: Cn1cnc(Nc2nc(=O)n(-c3ccccc3Cl)c3nc(C(F)(F)F)ccc23)c1]

¹H NMR (400 MHz, DMSO) δ 8.82 (d, J=7.7 Hz, 1H), 8.01 (s, 1H), 7.75 (d, J=8.0 Hz, 1H), 7.68 (d, J=6.4 Hz, 1H), 7.63-7.57 (m, 1H), 7.53 (dd, J=5.9, 3.2 Hz, 3H), 7.44 (s, 1H), 3.76 (s, 3H). m/z [M+H]⁺ 421.0.

1-(2-chlorophenyl)-4-((1-methyl-1H-pyrazol-3-yl)amino)-7-(trifluoromethyl)pyrido[2,3-d]pyrimidin-2(1H)-one was prepared by using 1-methyl-1H-pyrazol-3-amine and 1-(2-chlorophenyl)-7-(trifluoromethyl)pyrido[2,3-d]pyrimidine-2,4(1H,3H)-dione.

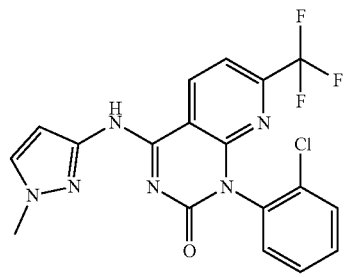 [SMILES: Cn1ccc(Nc2nc(=O)n(-c3ccccc3Cl)c3nc(C(F)(F)F)ccc23)n1]

¹H NMR (400 MHz, DMSO) δ 10.62 (s, 1H), 8.96 (s, 1H), 7.82 (s, 1H), 7.68 (s, 1H), 7.50 (d, J=27.4 Hz, 4H), 6.32 (s, 1H), 3.77 (s, 3H). m/z [M+H]⁺ 421.0.

1-(2-chlorophenyl)-4-((1-methyl-1H-pyrazol-4-yl)amino)-7-(trifluoromethyl)pyrido[2,3-d]pyrimidin-2(1H)-one was prepared by using 1-methyl-1H-pyrazol-4-amine and 1-(2-chlorophenyl)-7-(trifluoromethyl)pyrido[2,3-d]pyrimidine-2,4(1H,3H)-dione.

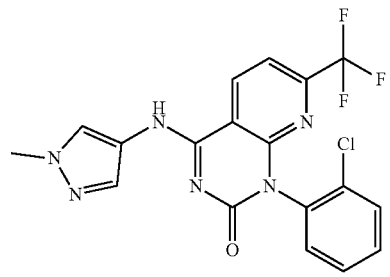 [SMILES: Cn1cc(Nc2nc(=O)n(-c3ccccc3Cl)c3nc(C(F)(F)F)ccc23)cn1]

¹H NMR (400 MHz, DMSO) δ 11.95 (s, 1H), 8.83 (d, J=8.0 Hz, 1H), 7.81 (s, 1H), 7.76 (d, J=8.2 Hz, 1H), 7.72-7.67 (m, 1H), 7.64-7.58 (m, 1H), 7.57-7.47 (m, 3H), 6.36 (s, 1H), 3.94 (s, 3H). m/z [M+H]⁺ 421.0.

1-(2-chlorophenyl)-4-(isoxazol-4-ylamino)-7-(trifluoromethyl)pyrido[2,3-d]pyrimidin-2(1H)-one was prepared by using isoxazol-4-amine and 1-(2-chlorophenyl)-7-(trifluoromethyl)pyrido[2,3-d]pyrimidine-2,4(1H,3H)-dione.

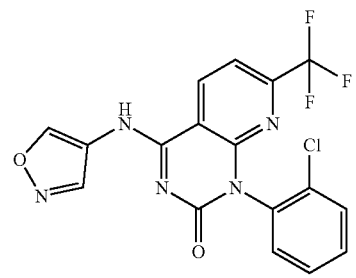 [SMILES: O=c1nc(Nc2cnoc2)c2ccc(C(F)(F)F)nc2n1-c1ccccc1Cl]

¹H NMR (400 MHz, DMSO) δ 11.09 (br s, 1H), 9.50 (s, 1H), 9.02 (d, J=8.2 Hz, 1H), 8.94 (s, 1H), 7.94 (d, J=8.1 Hz, 1H), 7.68 (d, J=6.1 Hz, 1H), 7.58-7.44 (m, 3H). m/z [M+H]⁺ 408.0

1-(2-Chlorophenyl)-4-((5-methylisoxazol-3-yl)amino)-7-(trifluoromethyl)pyrido[2,3-d]pyrimidin-2(1H)-one was prepared by using isoxazol-4-amine and 1-(2-chlorophenyl)-7-(trifluoromethyl)pyrido[2,3-d]pyrimidine-2,4(1H,3H)-dione.

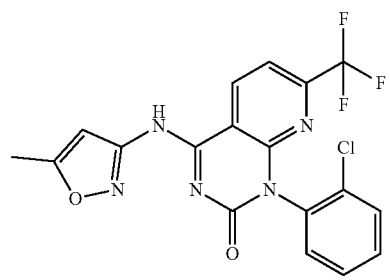 [SMILES: Cc1cc(Nc2nc(=O)n(-c3ccccc3Cl)c3nc(C(F)(F)F)ccc23)no1]

¹H NMR (400 MHz, MeOD) δ 8.98 (d, J=8.1 Hz, 1H), 7.72 (d, J=8.1 Hz, 1H), 7.68-7.58 (m, 1H), 7.53 (s, 4H), 6.25 (s, 1H), 2.48 (s, 3H). m/z [M+H]⁺ 422.05.

1-(2-Chlorophenyl)-4-((2-methylpyridin-4-yl)amino)-7-(trifluoromethyl)pyrido[2,3-d]pyrimidin-2(1H)-one was prepared by using 2-methylpyridin-4-amine and 1-(2-chlorophenyl)-7-(trifluoromethyl)pyrido[2,3-d]pyrimidine-2,4(1H,3H)-dione.

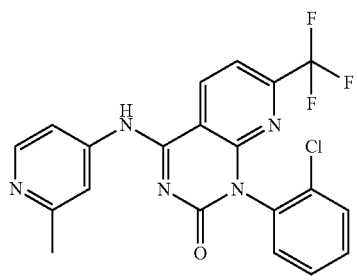 [SMILES: Cc1cc(Nc2nc(=O)n(-c3ccccc3Cl)c3nc(C(F)(F)F)ccc23)ccn1]

¹H NMR (400 MHz, MeOD) δ 8.73 (d, J=8.3 Hz, 1H), 7.91 (br s, 1H), 7.72 (d, J=8.1, 1H), 7.66 (d, J=7.3 Hz, 1H), 7.60-7.38 (m, 3H), 6.70 (br s, 1H), 6.65 (s, 1H), 2.47 (s, 3H).

1-(2-Chlorophenyl)-4-((2-methoxypyridin-4-yl)amino)-7-(trifluoromethyl)pyrido[2,3-d]pyrimidin-2(1H)-one was prepared by using 2-methoxypyridin-4-amine and 1-(2-chlorophenyl)-7-(trifluoromethyl)pyrido[2,3-d]pyrimidine-2,4(1H,3H)-dione.

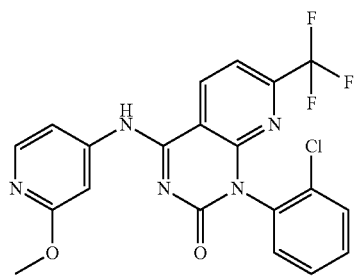

1-(2-Chlorophenyl)-7-(trifluoromethyl)-4-((2-(trifluoromethyl)pyridin-4-yl)amino)pyrido[2,3-d]pyrimidin-2(1H)-one was prepared by using 2-(trifluoromethyl)pyridin-4-amine and 1-(2-chlorophenyl)-7-(trifluoromethyl)pyrido[2,3-d]pyrimidine-2,4(1H,3H)-dione.

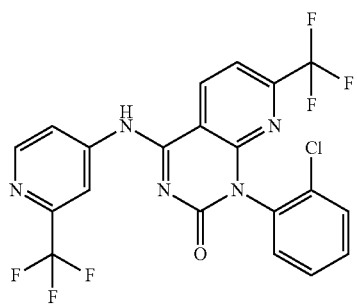 [SMILES: O=c1nc(Nc2ccnc(C(F)(F)F)c2)c2ccc(C(F)(F)F)nc2n1-c1ccccc1Cl]

¹H NMR (400 MHz, MeOD) δ 9.07 (br s, 1H), 8.72 (br s, 1H), 8.49 (br s, 1H), 7.82 (br s, 1H), 7.65 (br s, 1H), 7.59-7.42 (m, 4H). m/z [M+H]⁺ 486.05.

1-(2-chlorophenyl)-4-(isothiazol-4-ylamino)-7-(trifluoromethyl)pyrido[2,3-d]pyrimidin-2(1H)-one was prepared by using isothiazol-4-amine and 1-(2-chlorophenyl)-7-(trifluoromethyl)pyrido[2,3-d]pyrimidine-2,4(1H,3H)-dione.

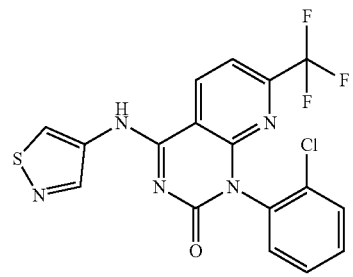

¹H NMR (400 MHz, MeOD) δ 9.63 (s, 1H), 9.00 (d, J=8.4 Hz, 1H), 8.93 (s, 1H), 7.79 (d, J=8.4 Hz, 1H), 7.72-7.61 (m, 1H), 7.59-7.38 (m, 3H). m/z [M+H]⁺ 424.0.

7-ethyl-4-(methylamino)-1-phenylpyrido[2,3-d]pyrimidin-2(1H)-one was prepared by using 7-ethyl-1-phenylpyrido[2,3-d]pyrimidine-2,4(1H,3H)-dione.

¹H NMR (400 MHz, DMSO) δ 8.61 (br, 1H), 8.37 (d, J=8.2, 1H), 7.52-7.42 (m, 2H), 7.41-7.33 (m, 1H), 7.20 (d, J=7.7 Hz, 2H), 7.13 (d, J=8.0, 1H), 2.98 (d, J=4.5, 3H), 2.56 (q, J=7.6 Hz, 2H), 1.00 (t, J=7.5 Hz, 3H). m/z [M+H]⁺ 281.2.

7-Ethyl-4-(methylamino)-1-(o-tolyl)pyrido[2,3-d]pyrimidin-2(1H)-one was prepared by using 7-ethyl-1-(o-tolyl)pyrido[2,3-d]pyrimidine-2,4(1H,3H)-dione.

¹H NMR (400 MHz, DMSO) δ 8.63 (br s, 1H), 8.39 (d, J=8.6 Hz, 1H), 7.30 (m, 3H), 7.11 (m, 2H), 3.04-2.94 (s, 3H), 2.55 (q, J=7.7 Hz, 2H), 1.90 (s, 3H), 0.98 (t, J=7.6, 3H). m/z [M+H]⁺ 295.15.

621

1-(2-Chlorophenyl)-7-ethyl-4-(methylamino)pyrido[2,3-d]pyrimidin-2(1H)-one was prepared by using 1-(2-chlorophenyl)-7-ethylpyrido[2,3-d]pyrimidine-2,4(1H,3H)-dione.

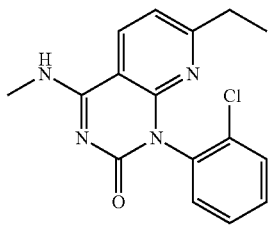

¹H NMR (400 MHz, DMSO) δ 8.72 (br s, 1H), 8.40 (d, J=8.2 Hz, 1H), 7.61 (br s, 1H), 7.50-7.41 (m, 2H), 7.37 (br s, 1H), 7.16 (d, J=8.2 Hz, 1H), 2.99 (s, 3H), 2.58 (q, J=7.6 Hz, 2H), 0.99 (t, J=7.6 Hz, 3H). m/z [M+H]⁺ 315.1.

7-ethyl-1-(2-fluorophenyl)-4-(methylamino)pyrido[2,3-d]pyrimidin-2(1H)-one was prepared by using 1-(2-fluorophenyl)-7-ethylpyrido[2,3-d]pyrimidine-2,4(1H,3H)-dione.

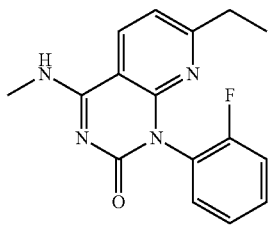

¹H NMR (400 MHz, MeOD) δ 8.28 (d, J=8.0, 1H), 7.50 (m, 1H), 7.32 (m, 8.3 Hz, 2H), 7.17 (d, J=8.3, 1H), 3.14 (s, 3H), 2.79-2.59 (q, J=7.6 Hz, 2H), 1.33 (d, J=6.6 Hz, 1H), 1.10 (t, J=7.6 Hz, 3H). m/z [M+H]⁺ 299.1.

7-Ethyl-4-(methylamino)-1-(pyridin-3-yl)pyrido[2,3-d]pyrimidin-2(1H)-one was prepared by using 7-ethyl-1-(pyridin-3-yl)pyrido[2,3-d]pyrimidine-2,4(1H,3H)-dione.

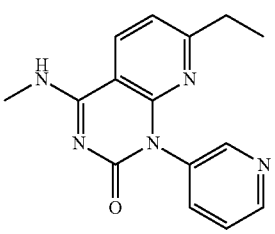 [SMILES: CCc1ccc2c(NC)nc(=O)n(-c3cccnc3)c2n1]

¹H NMR (400 MHz, MeOD) δ 8.60 (br s, 1H), 8.51 (s, 1H), 8.30 (d, J=8.2 Hz, 1H), 7.85 (d, J=8.3 Hz, 1H), 7.64 (m, 1H), 7.19 (d, J=8.2 Hz, 1H), 3.15 (s, 3H), 2.70 (q, J=7.3 Hz, 2H), 1.33 (d, J=6.6 Hz, 1H), 1.10 (dd, J=8.5, 6.7 Hz, 3H). m/z [M+H]⁺ 282.15.

622

1-(2-chlorophenyl)-4-(cyclopropylamino)-7-(trifluoromethoxy)quinazolin-2(1H)-one was prepared by using cyclopropylamine and 1-(2-chlorophenyl)-7-(trifluoromethoxy)quinazoline-2,4(1H,3H)-dione.

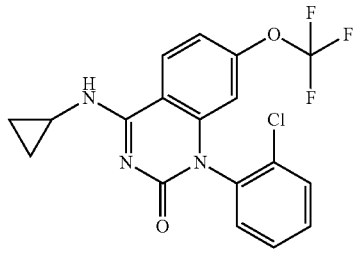 [SMILES: O=c1nc(NC2CC2)c2ccc(OC(F)(F)F)cc2n1-c1ccccc1Cl]

¹H NMR (400 MHz, MeOD) δ 8.21 (d, J=8.7 Hz, 1H), 7.75 (m, 1H), 7.61 (m, 2H), 7.55-7.36 (m, 1H), 7.17 (d, J=9.0 Hz, 1H), 6.24 (s, 1H), 3.17 (m, 1H), 0.95 (d, J=7.2 Hz, 2H), 0.80 (m, 2H). m/z [M+H]⁺ 396.0

1-(2-chlorophenyl)-4-((cyclopropylmethyl)amino)-7-(trifluoromethoxy)quinazolin-2(1H)-one was prepared by using cyclopropylmethanamine and 1-(2-chlorophenyl)-7-(trifluoromethoxy)quinazoline-2,4(1H,3H)-dione.

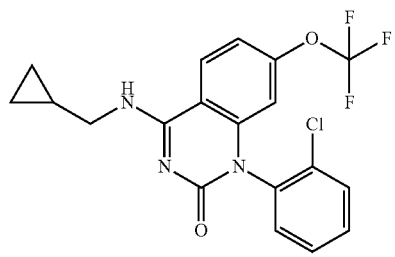 [SMILES: O=c1nc(NCC2CC2)c2ccc(OC(F)(F)F)cc2n1-c1ccccc1Cl]

¹H NMR (400 MHz, MeOD) δ 8.28 (d, J=8.8 Hz, 1H), 7.74 (m, 1H), 7.60 (m, 2H), 7.48 (m, 1H), 7.20 (d, J=9.0 Hz, 1H), 6.25 (s, 1H), 3.53 (m, 2H), 1.40-1.19 (m, 1H), 0.60 (d, J=7.7 Hz, 2H), 0.39 (m, 2H). m/z [M+H]⁺ 410.0

1-(2-chlorophenyl)-4-((2-methoxyethyl)amino)-7-(trifluoromethoxy)quinazolin-2(1H)-one was prepared by using 2-methoxyethan-1-amine and 1-(2-chlorophenyl)-7-(trifluoromethoxy)quinazoline-2,4(1H,3H)-dione.

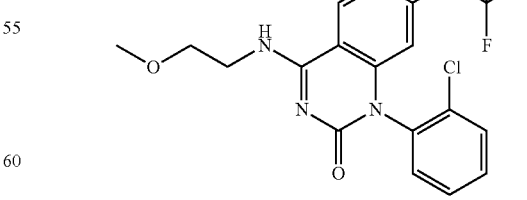

¹H NMR (400 MHz, MeOD) δ 8.25 (d, J=9.1 Hz, 1H), 7.74 (m, 1H), 7.67-7.57 (m, 2H), 7.49 (s, 1H), 7.20 (d, J=9.2 Hz, 1H), 6.25 (s, 1H), 3.85 (m, 2H), 3.72 (m, 2H), 3.43 (s, 2H). m/z [M+H]⁺ 414.0.

623

1-(2-Chlorophenyl)-4-(((trans)-3-hydroxycyclobutyl)amino)-7-(trifluoromethoxy)quinazolin-2(1H)-one was prepared by using trans-3-aminocyclobutan-1-ol and 1-(2-chlorophenyl)-7-(trifluoromethoxy)quinazoline-2,4(1H,3H)-dione.

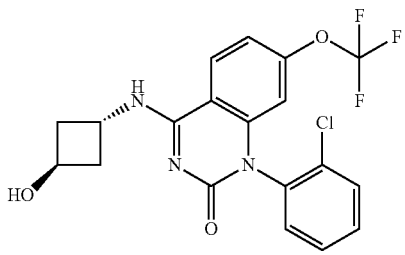 [SMILES: O=c1nc(N[C@H]2C[C@H](O)C2)c2ccc(OC(F)(F)F)cc2n1-c1ccccc1Cl]

$^1$H NMR (400 MHz, MeOD) δ 8.35 (d, J=8.8 Hz, 1H), 7.81-7.66 (m, 1H), 7.65-7.53 (m, 2H), 7.47 (m, 1H), 7.20 (d, J=9.0 Hz, 1H), 6.24 (s, 1H), 4.53 (m, 1H), 2.63-2.40 (m, 4H). m/z [M+H]$^+$ 426.1.

1-(2-Chlorophenyl)-4-((2-hydroxyethyl)amino)-7-(trifluoromethoxy)quinazolin-2(1H)-one was prepared by using 2-aminoethan-1-ol and 1-(2-chlorophenyl)-7-(trifluoromethoxy)quinazoline-2,4(1H,3H)-dione.

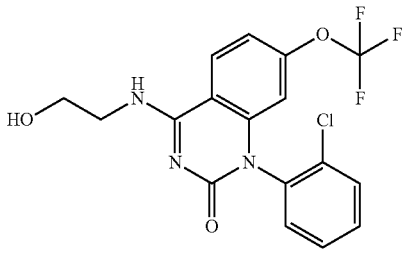

$^1$H NMR (400 MHz, MeOD) δ 8.30 (d, J=9.0, Hz, 1H), 7.75 (m, 1H), 7.69-7.58 (m, 2H), 7.51 (m, 1H), 7.25 (d, J=9.0 Hz, 1H), 6.28 (s, 1H), 3.92-3.86 (m, 2H), 3.86-3.76 (m, 2H). m/z [M+H]$^+$ 400.1.

1-(2-Chlorophenyl)-4-(((1R,2S)-2-fluorocyclopropyl)amino)-7-(trifluoromethoxy)quinazolin-2(1H)-one was prepared by using (1R,2S)-2-fluorocyclopropan-1-amine and 1-(2-chlorophenyl)-7-(trifluoromethoxy)quinazoline-2,4(1H,3H)-dione.

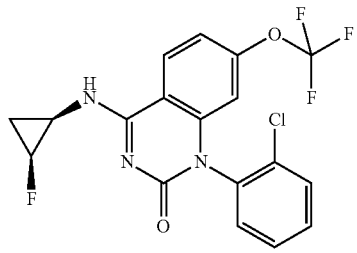 [SMILES: O=c1nc(N[C@@H]2C[C@@H]2F)c2ccc(OC(F)(F)F)cc2n1-c1ccccc1Cl]

$^1$H NMR (400 MHz, DMSO) δ 8.79 (s, 1H), 8.38 (d, J=9.0 Hz, 1H), 7.75 (m, 1H), 7.69-7.49 (m, 3H), 7.25 (d, J=8.8 Hz, 1H), 6.11 (s, 1H), 4.86 (d, J=64.6 Hz, 1H), 3.06 (br s, 1H), 1.38-1.24 (m, 1H), 1.19 (d, J=6.4 Hz, 1H). m/z [M+H]$^+$ 414.05

624

1-(2-Chlorophenyl)-4-(((1S,2R)-2-fluorocyclopropyl)amino)-7-(trifluoromethoxy)quinazolin-2(1H)-one was prepared by using (1S,2R)-2-fluorocyclopropan-1-amine and 1-(2-chlorophenyl)-7-(trifluoromethoxy)quinazoline-2,4(1H,3H)-dione.

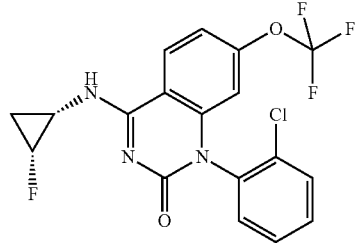 [SMILES: O=c1nc(N[C@H]2C[C@H]2F)c2ccc(OC(F)(F)F)cc2n1-c1ccccc1Cl]

$^1$H NMR (400 MHz, DMSO) δ 8.79 (s, 1H), 8.38 (d, J=9.0 Hz, 1H), 7.75 (m, 1H), 7.69-7.49 (m, 3H), 7.25 (d, J=8.8 Hz, 1H), 6.11 (s, 1H), 4.86 (d, J=64.6 Hz, 1H), 3.06 (br s, 1H), 1.38-1.24 (m, 1H), 1.19 (d, J=6.4 Hz, 1H). m/z [M+H]$^+$ 414.05.

1-(2-Chlorophenyl)-4-(isoxazol-4-ylamino)-7-(trifluoromethoxy)quinazolin-2(1H)-one was prepared by using isoxazol-4-amine and 1-(2-chlorophenyl)-7-(trifluoromethoxy)quinazoline-2,4(1H,3H)-dione.

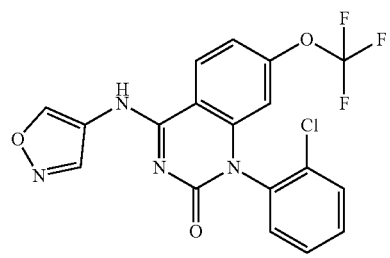 [SMILES: O=c1nc(Nc2cnoc2)c2ccc(OC(F)(F)F)cc2n1-c1ccccc1Cl]

$^1$H NMR (400 MHz, DMSO) δ 9.46 (s, 1H), 8.90 (s, 1H), 8.50 (d, J=8.5 Hz, 1H), 7.78 (m, 1H), 7.61 (m, 3H), 7.39 (d, J=8.9 Hz, 1H), 6.18 (s, 1H). m/z [M+H]$^+$ 423.0.

1-(2-Chlorophenyl)-4-(((trans)-2-hydroxycyclobutyl)amino)-7-(trifluoromethoxy)quinazolin-2(1H)-one was prepared by using trans-2-aminocyclobutan-1-ol and 1-(2-chlorophenyl)-7-(trifluoromethoxy)quinazoline-2,4(1H,3H)-dione.

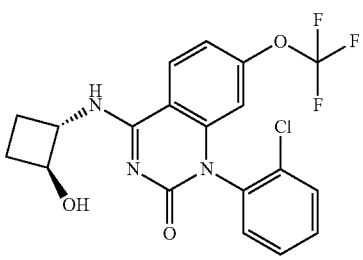 [SMILES: O=c1nc(N[C@H]2CC[C@@H]2O)c2ccc(OC(F)(F)F)cc2n1-c1ccccc1Cl]

$^1$H NMR (400 MHz, MeOD) δ 8.31 (d, J=9.0, 2.1 Hz, 1H), 7.74 (m, 1H), 7.67-7.54 (m, 2H), 7.48 (m, 1H), 7.21 (d, J=9.0 Hz, 1H), 6.25 (s, 1H), 4.23 (m, 1H), 2.24 (m, 2H), 1.68 (m, 2H). m/z [M+H]$^+$ 426.1.

4-Amino-1-(2-chlorophenyl)-7-(trifluoromethoxy)qui-nazolin-2(1H)-one was prepared by using ammonia in THF (2 M) and 1-(2-chlorophenyl)-7-(trifluoromethoxy)-qui-nazoline-2,4(1H,3H)-dione

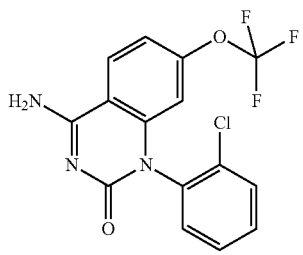

m/z [M + H]⁺ 356.0.

1-(2-Chlorophenyl)-4-(cyclopropylamino)-7-(1,1-difluo-roethyl)quinazolin-2(1H)-one was prepared by using cyclo-propanamine and 1-(2-chlorophenyl)-7-(1,1-difluoroethyl)quinazoline-2,4(1H,3H)-dione.

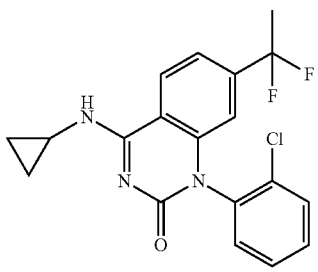 [SMILES: CC(F)(F)c1ccc2c(NC3CC3)nc(=O)n(-c3ccccc3Cl)c2c1]

¹H NMR (400 MHz, MeOD) δ 8.19 (d, J=8.5 Hz, 1H), 7.74 (m, 1H), 7.60 (m, 1H), 7.49 (m, 1H), 7.41 (d, J=8.5 Hz, 1H), 6.56 (s, 1H), 3.17 (br s, 1H), 1.82 (t, J=18.4 Hz, 2H), 1.31 (d, J=6.4 Hz, 1H), 0.95 (d, J=7.2 Hz, 1H), 0.81 (m, 1H). m/z [M+H]⁺ 376.1.

1-(2-Chlorophenyl)-7-(1,1-difluoroethyl)-4-((2-hydroxy-ethyl)amino)quinazolin-2(1H)-one was prepared by using 2-aminoethan-1-ol and 1-(2-chlorophenyl)-7-(1,1-difluoro-ethyl)quinazoline-2,4(1H,3H)-dione.

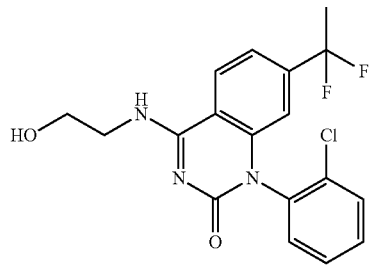

¹H NMR (400 MHz, MeOD) δ 8.22 (d, J=8.5 Hz, 1H), 7.73 (m, 1H), 7.60 (m, 2H), 7.46 (m, 2H), 6.56 (s, 1H), 3.97-3.72 (m, 4H), 1.83 (t, J=18.1, 3H). m/z [M+H]⁺ 380.05.

1-(2-Chlorophenyl)-7-(1,1-difluoroethyl)-4-((2-methoxy-ethyl)amino)quinazolin-2(1H)-one was prepared by using 2-methoxyethan-1-amine and 1-(2-chlorophenyl)-7-(1,1-di-fluoroethyl)quinazoline-2,4(1H,3H)-dione.

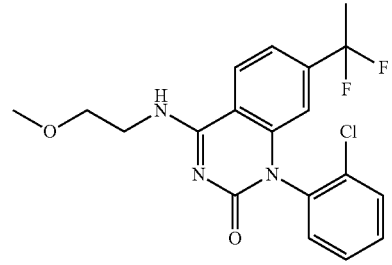 [SMILES: COCCNc1nc(=O)n(-c2ccccc2Cl)c2cc(C(C)(F)F)ccc12]

¹H NMR (400 MHz, MeOD) δ 8.22 (d, J=8.4 Hz, 1H), 7.84-7.69 (m, 1H), 7.60 (m, 2H), 7.46 (m, 2H), 6.56 (s, 1H), 3.94-3.80 (m, 2H), 3.73 (m, 2H), 3.43 (s, 3H), 1.83 (t, J=18.4, 3H). m/z [M+H]⁺ 394.05.

1-(2-Chlorophenyl)-7-(1,1-difluoroethyl)-4-(((trans)-3-hydroxycyclobutyl)amino)-quinazolin-2(1H)-one was pre-pared by using trans-3-aminocyclobutan-1-ol and 1-(2-chlo-rophenyl)-7-(1,1-difluoroethyl)quinazoline-2,4(1H,3H)-dione.

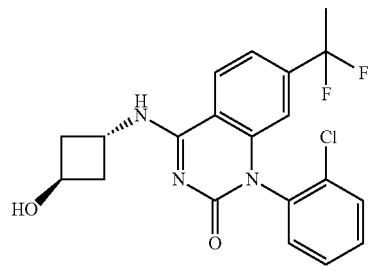 [SMILES: CC(F)(F)c1ccc2c(N[C@H]3C[C@H](O)C3)nc(=O)n(-c3ccccc3Cl)c2c1]

¹H NMR (400 MHz, MeOD) δ 8.32 (d, J=8.5 Hz, 1H), 7.73 (m, 1H), 7.60 (m, 2H), 7.46 (m, 2H), 6.56 (s, 1H), 4.59-4.45 (m, 1H), 2.63-2.44 (m, 4H), 1.83 (t, J=18.4, 3H). m/z [M+H]⁺ 406.1.

7-(1,1-Difluoroethyl)-1-(imidazo[1,2-a]pyridin-5-yl)-4-(methylamino)quinazolin-2(1H)-one was prepared by using 7-(1,1-difluoroethyl)-1-(imidazo[1,2-a]pyridin-5-yl)qui-nazoline-2,4(1H,3H)-dione.

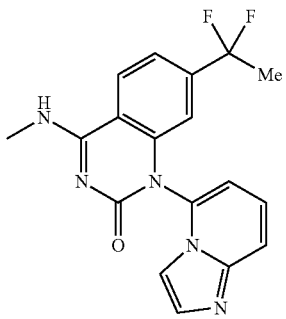 [SMILES: CNc1nc(=O)n(-c2cccc3nccn23)c2cc(C(C)(F)F)ccc12]

¹H NMR (400 MHz, MeOD) δ 8.20 (d, J=7.5 Hz, 1H), 7.84 (d, J=9.0 Hz, 1H), 7.70-7.56 (m, 3H), 7.50 (d, J=8.5 Hz, 1H), 7.23 (d, J=7.1 Hz, 1H), 6.58 (s, 1H), 3.20 (s, 3H), 1.78 (t, J=18.5, 3H). m/z [M+H]⁺ 356.1.

4-(Cyclopropylamino)-7-(1,1-difluoroethyl)-1-(imidazo[1,2-a]pyridin-5-yl)quinazolin-2(1H)-one was prepared by using cyclopropylamine and 7-(1,1-difluoroethyl)-1-(imidazo[1,2-a]pyridin-5-yl)quinazoline-2,4(1H,3H)-dione.

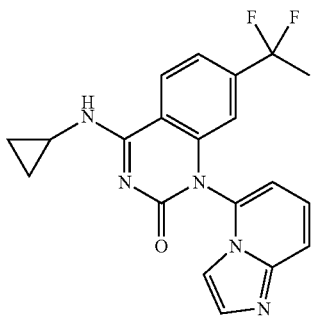 [SMILES: CC(F)(F)c1ccc2c(NC3CC3)nc(=O)n(-c3cccc4nccn34)c2c1]

¹H NMR (400 MHz, MeOD) δ 8.29 (d, J=8.5 Hz, 1H), 8.02 (d, J=9.3 Hz, 1H), 7.88 (m, 3H), 7.50 (t, J=8.5 Hz, 2H), 6.71 (s, 1H), 3.23 (m, 1H), 1.80 (t, J=18.5, 3H), 0.98 (d, J=7.4 Hz, 2H), 0.86 (m, 2H). m/z [M+H]⁺ 382.2.

4-((Cyclopropylmethyl)amino)-7-(1,1-difluoroethyl)-1-(imidazo[1,2-a]pyridin-5-yl)quinazolin-2(1H)-one was prepared by using cyclopropylmethylamine and 7-(1,1-difluoroethyl)-1-(imidazo[1,2-a]pyridin-5-yl)quinazoline-2,4(1H,3H)-dione.

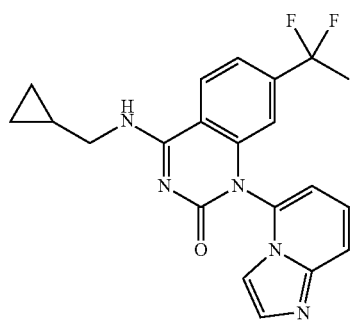 [SMILES: CC(F)(F)c1ccc2c(NCC3CC3)nc(=O)n(-c3cccc4nccn34)c2c1]

¹H NMR (400 MHz, MeOD) δ 8.35 (d, J=8.4 Hz, 1H), 8.00 (d, J=9.2 Hz, 1H), 7.92-7.79 (m, 3H), 7.54 (d, J=8.6 Hz, 1H), 7.48 (d, J=7.2 Hz, 1H), 6.71 (s, 1H), 3.68-3.48 (m, 2H), 1.81 (t, J=18.5, 3H), 1.33 (m, 1H), 0.62 (d, J=7.7 Hz, 2H), 0.42 (m, 2H). m/z [M+H]⁺ 396.2.

1-(2-Chlorophenyl)-7-cyclopropyl-4-(cyclopropylamino)quinazolin-2(1H)-one was prepared by using cyclopropylamine and 1-(2-chlorophenyl)-7-cyclopropylquinazoline-2,4(1H,3H)-dione.

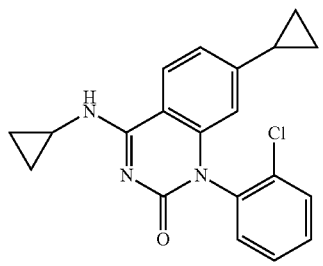 [SMILES: O=c1nc(NC2CC2)c2ccc(C3CC3)cc2n1-c1ccccc1Cl]

¹H NMR (400 MHz, MeOD) δ 7.95 (d, J=8.5 Hz, 1H), 7.72 (m, 1H), 7.58 (m, 2H), 7.44 (m, 1H), 6.92 (d, J=8.4 Hz, 1H), 6.15 (s, 1H), 3.12 (m, 1H), 1.83 (m, 1H), 1.01 (d, J=8.2 Hz, 2H), 0.93 (d, J=7.0 Hz, 2H), 0.78 (m, 2H), 0.61 (m, 2H). m/z [M+H]⁺ 352.1.

1-(2-Chlorophenyl)-7-cyclopropyl-4-((cyclopropylmethyl)amino)quinazolin-2(1H)-one was prepared by using cyclopropylmethylamine and 1-(2-chlorophenyl)-7-cyclopropylquinazoline-2,4(1H,3H)-dione.

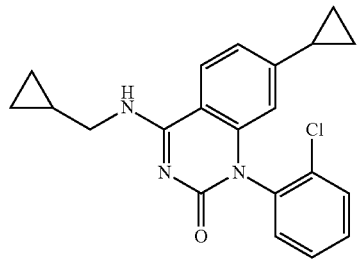

¹H NMR (400 MHz, MeOD) δ 7.80 (d, J=8.2 Hz, 1H), 7.50 (m, 1H), 7.37 (m, 2H), 7.22 (m, 1H), 6.74 (d, J=8.5 Hz, 1H), 5.94 (s, 1H), 3.30 (m, 2H), 2.61 (m, 2H), 1.63 (m, 1H), 1.16-0.98 (m, 2H), 0.80 (d, J=8.2 Hz, 2H), 0.43-0.32 (m, 2H), 0.17 (d, J=4.5 Hz, 2H). m/z [M+H]⁺ 366.1.

1-(2-chlorophenyl)-7-cyclopropyl-4-((2-hydroxyethyl)amino)quinazolin-2(1H)-one was prepared by using 2-aminoethan-1-ol and 1-(2-chlorophenyl)-7-cyclopropylquinazoline-2,4(1H,3H)-dione.

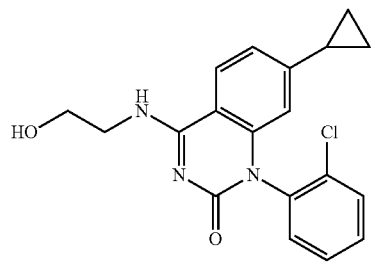 [SMILES: O=c1nc(NCCO)c2ccc(C3CC3)cc2n1-c1ccccc1Cl]

¹H NMR (400 MHz, MeOD) δ 7.97 (d, J=8.5 Hz, 1H), 7.71 (m, 1H), 7.58 (m, 2H), 7.51-7.36 (m, 1H), 6.95 (d, J=8.5 Hz, 1H), 6.15 (s, 1H), 3.84 (m, 2H), 3.78 (m, 2H), 1.83 (br s, 1H), 1.01 (d, J=8.2 Hz, 2H), 0.62 (br s, 2H). m/z [M+H]⁺ 356.1.

1-(2-Chlorophenyl)-7-cyclopropyl-4-((2-methoxyethyl)amino)quinazolin-2(1H)-one was prepared by using 2-methoxyethan-1-amine and 1-(2-chlorophenyl)-7-cyclopropylquinazoline-2,4(1H,3H)-dione.

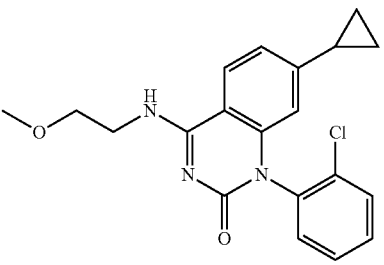 [SMILES: COCCNc1nc(=O)n(-c2ccccc2Cl)c2cc(C3CC3)ccc12]

¹H NMR (400 MHz, MeOD) δ 7.97 (d, J=8.7 Hz, 1H), 7.72 (m, 1H), 7.58 (m, 2H), 7.44 (m, 1H), 6.95 (d, J=8.4 Hz,

1H), 6.15 (s, 1H), 3.93-3.76 (m, 2H), 3.71 (m, 2H), 3.42 (s, 3H), 1.84 (m, 1H), 1.01 (d, J=7.9 Hz, 2H), 0.62 (br s, 2H). m/z [M+H]⁺ 370.1.

1-(2-Chlorophenyl)-7-cyclopropyl-4-(((trans)-2-hydroxycyclobutyl)amino)quinazolin-2(1H)-one was prepared by using trans-2-aminocyclobutan-1-ol and 1-(2-chlorophenyl)-7-cyclopropylquinazoline-2,4(1H,3H)-dione.

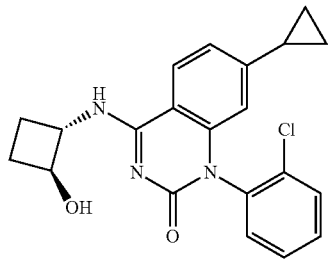 [SMILES: O=c1nc(N[C@H]2CC[C@@H]2O)c2ccc(C3CC3)cc2n1-c1ccccc1Cl]

$^1$H NMR (400 MHz, MeOD) δ 8.04 (d, J=8.5 Hz, 1H), 7.81-7.66 (m, 1H), 7.58 (m, 2H), 7.43 (m, 1H), 6.95 (d, J=8.5 Hz, 1H), 6.15 (s, 1H), 4.21 (s, 1H), 2.23 (m, 2H), 1.84 (m, 1H), 1.68 (m, 2H), 1.02 (d, J=8.3 Hz, 2H), 0.62 (d, J=4.8 Hz, 2H). m/z [M+H]⁺ 382.1.

1-(2-Chlorophenyl)-7-cyclopropyl-4-((1-methylcyclobutyl)amino)quinazolin-2(1H)-one was prepared by using 1-methylcyclobutan-1-amine and 1-(2-chlorophenyl)-7-cyclopropylquinazoline-2,4(1H,3H)-dione.

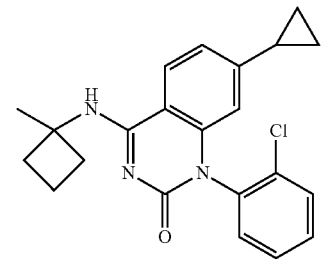 [SMILES: CC1(Nc2nc(=O)n(-c3ccccc3Cl)c3cc(C4CC4)ccc23)CCC1]

$^1$H NMR (400 MHz, MeOD) δ 7.99 (d, J=9.1 Hz, 1H), 7.71 (m, 1H), 7.57 (m, 2H), 7.48-7.26 (m, 1H), 6.92 (d, J=8.2 Hz, 1H), 6.12 (s, 1H), 2.46 (m, 2H), 2.31 (m, 2H), 1.94 (m, 2H), 1.83 (m, 1H), 1.72 (s, 3H), 1.00 (d, J=8.1 Hz, 2H), 0.67-0.45 (m, 2H). m/z [M+H]⁺ 380.15.

1-(2-Chlorophenyl)-7-cyclopropyl-4-(((R)-1-hydroxypropan-2-yl)amino)quinazolin-2(1H)-one was prepared by using (R)-2-aminopropan-1-ol and 1-(2-chlorophenyl)-7-cyclopropylquinazoline-2,4(1H,3H)-dione.

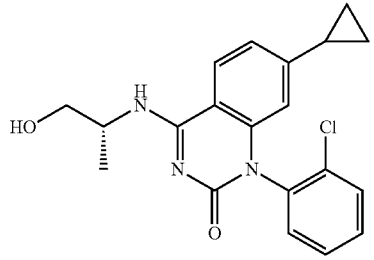 [SMILES: C[C@H](CO)Nc1nc(=O)n(-c2ccccc2Cl)c2cc(C3CC3)ccc12]

$^1$H NMR (400 MHz, MeOD) δ 8.05 (d, J=8.4, 1H), 7.72 (m, 1H), 7.57 (m, 2H), 7.43 (m, 1H), 6.94 (d, J=8.5 Hz, 1H), 6.14 (s, 1H), 4.77-4.53 (m, 1H), 3.71 (m, 2H), 1.82 (m, 1H), 1.35 (d, J=6.3 Hz, 3H), 1.01 (d, J=8.1 Hz, 2H), 0.62 (s, 2H). m/z [M+H]⁺ 370.1.

1-(2-Chlorophenyl)-7-cyclopropyl-4-(((S)-1-hydroxypropan-2-yl)amino)quinazolin-2(1H)-one was prepared by using (S)-2-aminopropan-1-ol and 1-(2-chlorophenyl)-7-cyclopropylquinazoline-2,4(1H,3H)-dione.

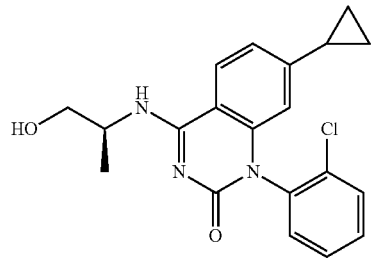 [SMILES: C[C@@H](CO)Nc1nc(=O)n(-c2ccccc2Cl)c2cc(C3CC3)ccc12]

$^1$H NMR (400 MHz, MeOD) δ 8.05 (d, J=8.4, 1H), 7.72 (m, 1H), 7.57 (m, 2H), 7.43 (m, 1H), 6.94 (d, J=8.5 Hz, 1H), 6.14 (s, 1H), 4.77-4.53 (m, 1H), 3.71 (m, 2H), 1.82 (m, 1H), 1.35 (d, J=6.3 Hz, 3H), 1.01 (d, J=8.1 Hz, 2H), 0.62 (s, 2H). m/z [M+H]⁺ 370.1.

1-(2-Chlorophenyl)-7-cyclopropyl-4-((3-hydroxypropyl)amino)quinazolin-2(1H)-one was prepared by using 3-aminopropan-1-ol and 1-(2-chlorophenyl)-7-cyclopropylquinazoline-2,4(1H,3H)-dione.

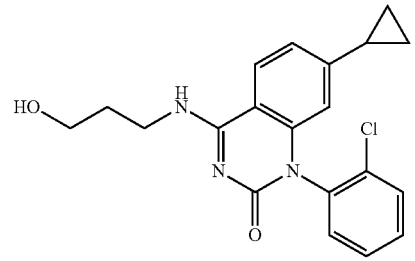 [SMILES: O=c1nc(NCCCO)c2ccc(C3CC3)cc2n1-c1ccccc1Cl]

$^1$H NMR (400 MHz, MeOD) δ 7.95 (d, J=5.9, 1H), 7.71 (m, 1H), 7.58 (m, 2H), 7.44 (m, 1H), 6.95 (d, J=8.5 Hz, 1H), 6.15 (s, 1H), 3.72 (m, 4H), 1.96 (t, J=6.7 Hz, 2H), 1.83 (s, 1H), 1.01 (d, J=8.2 Hz, 2H), 0.71-0.49 (m, 2H). m/z [M+H]⁺ 370.1.

1-(2-Chlorophenyl)-7-cyclopropyl-4-((3-methoxypropyl)amino)quinazolin-2(1H)-one was prepared by using 3-methoxypropan-1-amine and 1-(2-chlorophenyl)-7-cyclopropylquinazoline-2,4(1H,3H)-dione.

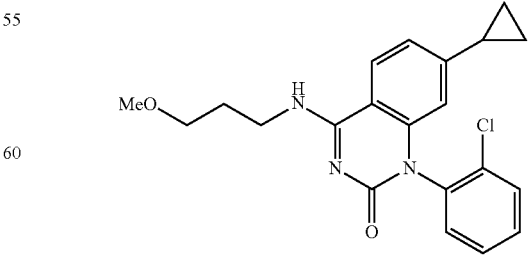

$^1$H NMR (400 MHz, MeOD) δ 7.91 (d, J=8.5 Hz, 1H), 7.71 (br s, 1H), 7.58 (br s, 2H), 7.43 (br s, 1H), 6.94 (d, J=8.5 Hz,

1H), 6.15 (s, 1H), 3.72 (t, J=7.2 Hz, 2H), 3.55 (t, J=6.1, 2H), 3.38 (s, 3H), 2.02 (quin, J=5.9 Hz, 2H), 1.84 (d, J=7.8 Hz, 1H), 1.01 (br s, 2H), 0.61 (dq, J=4.8, 2.5 Hz, 2H). m/z [M+H]⁺ 384.1.

1-(2-Chlorophenyl)-7-cyclopropyl-4-((cyclopropylmethyl)(methyl)amino)quinazolin-2(1H)-one was prepared by using 1-cyclopropyl-N-methylmethanamine and 1-(2-chlorophenyl)-7-cyclopropylquinazoline-2,4(1H,3H)-dione.

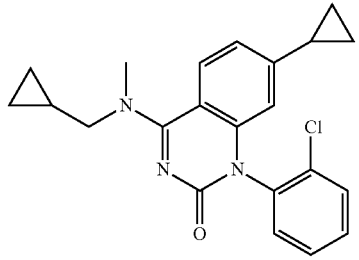 [SMILES: CN(CC1CC1)c1nc(=O)n(-c2ccccc2Cl)c2cc(C3CC3)ccc12]

¹H NMR (400 MHz, MeOD) δ 9.24 (s, 1H), 8.17 (d, J=6.1 Hz, 1H), 7.74 (m, 1H), 7.60 (m, 1H), 7.47 (m, 1H), 7.04 (d, J=8.6 Hz, 1H), 6.24 (s, 1H), 2.44 (s, 2H), 1.88 (m, 1H), 1.05 (d, J=8.4 Hz, 1H), 0.67 (m, 1H). m/z [M+H]⁺ 380.15.

1-(2-Chlorophenyl)-7-cyclopropyl-4-((5-methylisoxazol-4-yl)amino)quinazolin-2(1H)-one was prepared by using 5-methylisoxazol-4-amine and 1-(2-chlorophenyl)-7-cyclopropylquinazoline-2,4(1H,3H)-dione.

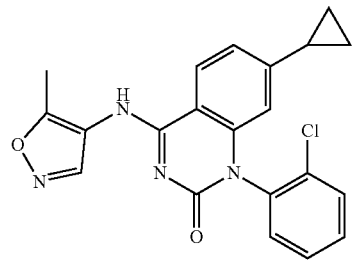

¹H NMR (400 MHz, MeOD) δ 9.24 (s, 1H), 8.29-8.09 (m, 1H), 7.74 (d, J=5.0 Hz, 1H), 7.70-7.57 (m, 2H), 7.47 (d, J=6.3 Hz, 1H), 7.04 (d, J=8.6 Hz, 1H), 6.24 (s, 1H), 2.44 (s, 3H), 1.88 (br s, 1H), 1.05 (d, J=8.4 Hz, 2H), 0.67 (br s, 2H). m/z [M+H]⁺ 393.1.

1-(2-Chlorophenyl)-7-cyclopropyl-4-((3-methylisoxazol-4-yl)amino)quinazolin-2(1H)-one was prepared by using 3-methylisoxazol-4-amine and 1-(2-chlorophenyl)-7-cyclopropylquinazoline-2,4(1H,3H)-dione.

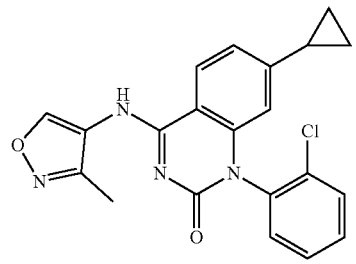 [SMILES: Cc1nocc1Nc1nc(=O)n(-c2ccccc2Cl)c2cc(C3CC3)ccc12]

¹H NMR (400 MHz, MeOD) δ 8.7 (s, 1H), 8.13 (d, J=8.8 Hz, 1H), 7.73 (d, J=7.5 Hz, 1H), 7.59 (d, J=6.5 Hz, 3H), 7.46 (br s, 1H), 7.03 (d, J=8.4 Hz, 1H), 6.22 (s, 1H), 2.50 (s, 3H), 1.87 (br s, 1H), 1.05 (d, J=8.8 Hz, 2H), 0.65 (br s, 2H). m/z [M+H]⁺ 393.1.

1-(2-Chlorophenyl)-7-cyclopropyl-4-((3,5-dimethylisoxazol-4-yl)amino)quinazolin-2(1H)-one was prepared by using 3,5-dimethylisoxazol-4-amine and 1-(2-chlorophenyl)-7-cyclopropylquinazoline-2,4(1H,3H)-dione.

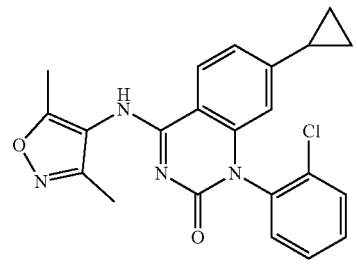 [SMILES: Cc1noc(C)c1Nc1nc(=O)n(-c2ccccc2Cl)c2cc(C3CC3)ccc12]

¹H NMR (400 MHz, MeOD) δ 8.12 (d, J=8.7 Hz, 1H), 7.72 (br s, 1H), 7.59 (m, 2H), 7.46 (br s, 1H), 7.04 (d, J=8.6 Hz, 1H), 6.23 (s, 1H), 2.41 (s, 3H), 2.26 (s, 3H), 1.88 (s, 1H), 1.05 (m, 2H), 0.75-0.50 (m, 2H). m/z [M+H]⁺ 407.1.

4-(Methylamino)-1-(pyrazin-2-yl)-7-(trifluoromethyl)quinazolin-2(1H)-one was prepared by using 1-(pyrazin-2-yl)-7-(trifluoromethyl)quinazoline-2,4(1H,3H)-dione.

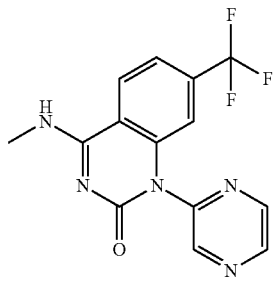 [SMILES: CNc1nc(=O)n(-c2cnccn2)c2cc(C(F)(F)F)ccc12]

¹H NMR (400 MHz, MeOD) δ 8.86 (s, 1H), 8.81 (d, J=7.2 Hz, 2H), 8.25 (d, J=8.5 Hz, 1H), 7.60 (d, J=8.5 Hz, 1H), 6.84 (s, 1H), 3.18 (d, J=1.9 Hz, 3H). m/z [M+H]⁺ 322.1.

7-Cyclopropyl-4-((cyclopropylmethyl)amino)-1-(imidazo[1,2-a]pyridin-5-yl)quinazolin-2(1H)-one was prepared by using cyclopropylmethanamine and 7-cyclopropyl-1-(imidazo[1,2-a]pyridin-5-yl)quinazoline-2,4(1H,3H)-dione.

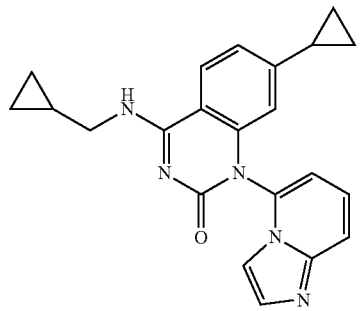 [SMILES: O=c1nc(NCC2CC2)c2ccc(C3CC3)cc2n1-c1cccc2nccn12]

¹H NMR (400 MHz, MeOD) δ 8.11 (m, 3H), 8.03 (s, 2H), 7.65 (d, J=5.6 Hz, 1H), 6.99 (d, J=8.5 Hz, 1H), 6.47 (s, 1H), 3.55 (m, 2H), 1.86 (s, 1H), 1.44-1.26 (m, 1H), 1.00 (d, J=8.1 Hz, 2H), 0.70 (d, J=5.9 Hz, 2H), 0.61 (d, J=7.9 Hz, 2H), 0.39 (m, 2H). m/z [M+H]⁺ 372.15.

4-(Methylamino)-1-(pyridazin-3-yl)-7-(trifluoromethyl) quinazolin-2(1H)-one was prepared by using 1-(pyridazin-3-yl)-7-(trifluoromethyl)quinazoline-2,4(1H,3H)-dione.

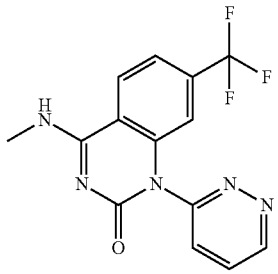 [SMILES: CNc1nc(=O)n(-c2cccnn2)c2cc(C(F)(F)F)ccc12]

¹H NMR (400 MHz, DMSO) δ 9.40 (s, 1H), 9.05 (br s, 1H), 8.38 (d, J=8.5 Hz, 1H), 8.02 (t, J=6.6 Hz, 1H), 7.95 (d, J=8.6 Hz, 1H), 7.65 (d, J=8.4 Hz, 1H), 6.64 (s, 1H), 3.04 (s, 3H). m/z [M+H]⁺ 322.1.

7-Cyclopropyl-4-(isoxazol-4-ylamino)-1-(o-tolyl)quinazolin-2(1H)-one was prepared by using isoxazol-4-amine and 7-cyclopropyl-1-(o-tolyl)quinazoline-2,4(1H,3H)-dione.

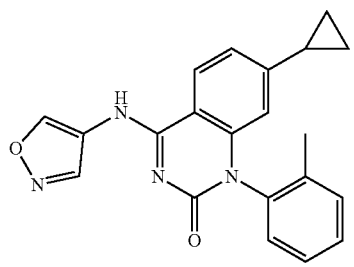

¹H NMR (400 MHz, DMSO) δ 10.42 (br s, 1H), 9.47 (s, 1H), 8.88 (s, 1H), 8.20 (d, J=8.4 Hz, 1H), 7.54-7.36 (m, 3H), 7.22 (d, J=7.2 Hz, 1H), 6.95 (d, J=8.5 Hz, 1H), 6.09 (s, 1H), 1.96 (s, 3H), 1.82 (br s, 1H), 0.97 (d, J=8.4 Hz, 2H), 0.61 (br s, 2H). m/z [M+H]⁺ 359.1.

7-Cyclopropyl-4-(isothiazol-4-ylamino)-1-(o-tolyl)quinazolin-2(1H)-one was prepared by using thioisoxazol-4-amine and 7-cyclopropyl-1-(o-tolyl)quinazoline-2,4(1H, 3H)-dione.

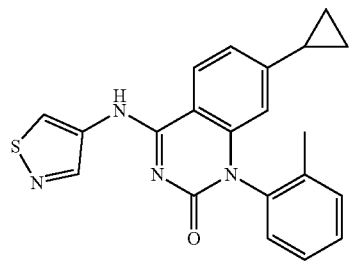 [SMILES: Cc1ccccc1-n1c(=O)nc(Nc2cnsc2)c2ccc(C3CC3)cc21]

¹H NMR (400 MHz, DMSO) δ 10.56 (s, 1H), 9.37 (s, 1H), 8.95 (s, 1H), 8.29 (s, 1H), 7.57-7.32 (m, 3H), 7.22 (d, J=7.3 Hz, 1H), 6.95 (d, J=8.4 Hz, 1H), 6.10 (s, 1H), 1.96 (s, 3H), 1.83 (br s, 1H), 0.97 (d, J=8.3 Hz, 2H), 0.62 (br s, 2H). m/z [M+H]⁺ 375.1.

1-(Imidazo[1,2-a]pyridin-5-yl)-4-(methylamino)-7-(trifluoromethoxy)quinazolin-2(1H)-one was prepared by using 1-(imidazo[1,2-a]pyridin-5-yl)-7-(trifluoromethoxy)quinazoline-2,4(1H,3H)-dione.

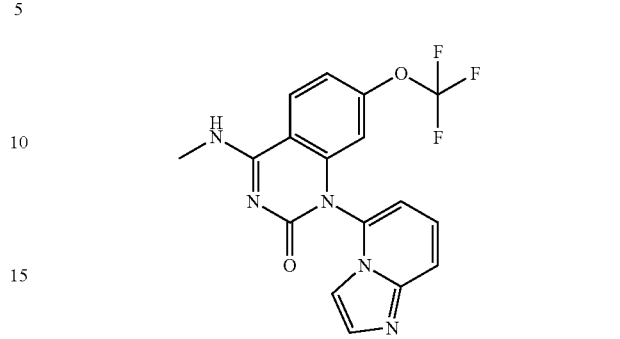

¹H NMR (400 MHz, DMSO) δ 8.99 (br s, 1H), 8.32 (d, J=9.5 Hz, 1H), 7.83 (d, J=9.1 Hz, 1H), 7.75 (s, 1H), 7.67 (s, 1H), 7.53 (t, J=8.2 Hz, 1H), 7.32 (d, J=8.9 Hz, 1H), 7.22 (d, J=7.2 Hz, 1H), 6.31 (s, 1H), 3.04 (m, 3H). m/z [M+H]⁺ 376.1.

4-((Cyclopropylmethyl)amino)-1-(imidazo[1,2-a]pyridin-5-yl)-7-(trifluoromethoxy)-quinazolin-2(1H)-one was prepared by using cyclopropylmethylamine and 1-(imidazo[1,2-a]pyridin-5-yl)-7-(trifluoromethoxy)quinazoline-2,4(1H,3H)-dione.

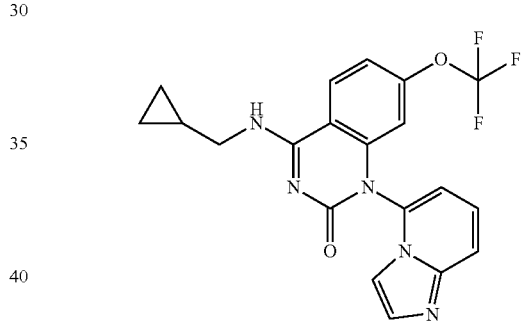

¹H NMR (400 MHz, DMSO) δ 9.03 (br s, 1H), 8.43 (d, J=9.0 Hz, 1H), 7.78 (d, J=9.0 Hz, 1H), 7.67 (s, 1H), 7.59 (s, 1H), 7.46 (t, J=9.0 Hz, 1H), 7.32 (d, J=8.9 Hz, 1H), 7.16 (d, J=7.1 Hz, 1H), 6.23 (s, 1H), 1.24 (quin, J=6.7 Hz, 1H), 0.53 (d, J=7.9 Hz, 2H), 0.34 (br s, 2H). m/z [M+H]⁺ 416.1.

7-Cyclopropyl-1-(2-(difluoromethoxy)pyridin-3-yl)-4-(methylamino)quinazolin-2(1H)-one was prepared by using 7-cyclopropyl-1-(2-(difluoromethoxy)pyridin-3-yl)quinazoline-2,4(1H,3H)-dione.

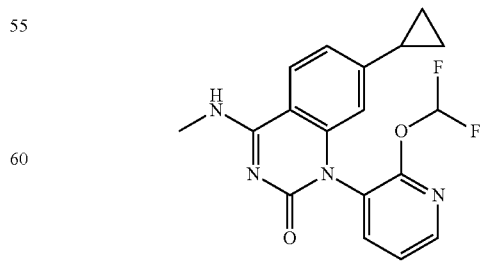

¹H NMR (400 MHz, DMSO) δ 8.57 (br s, 1H), 8.41 (s, 1H), 7.99 (d, J=8.2 Hz, 2H), 7.83 (s, 1H), 7.50 (m, 1H), 6.85

(d, J=8.4 Hz, 1H), 6.16 (s, 1H), 2.98 (s, 3H), 1.87 (m, 1H), 0.95 (d, J=8.7 Hz, 2H), 0.63 (m, 2H). m/z [M+H]$^+$ 359.1.

7-Cyclopropyl-4-(methylamino)-1-(2-(trifluoromethyl)pyridin-3-yl)quinazolin-2(1H)-one was prepared by using 7-cyclopropyl-1-(2-(trifluoromethyl)pyridin-3-yl)quinazoline-2,4(1H,3H)-dione.

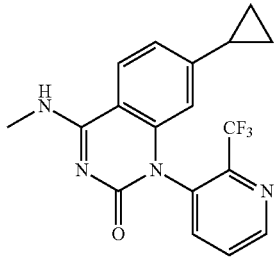

$^1$H NMR (400 MHz, DMSO) δ 8.90 (s, 1H), 8.60 (s, 1H), 8.08 (d, J=8.1 Hz, 1H), 7.99 (m, 2H), 6.83 (d, J=8.4 Hz, 1H), 6.06 (s, 1H), 3.04-2.93 (m, 3H), 1.87 (m, 1H), 0.94 (d, J=8.2 Hz, 2H), 0.61 (m, 2H). m/z [M+H]$^+$ 361.1.

4-Amino-7-cyclopropyl-1-(2-(trifluoromethyl)pyridin-3-yl)quinazolin-2(1H)-one was prepared by using ammonia in THF (2 M) and 7-cyclopropyl-1-(2-(trifluoromethyl)pyridin-3-yl)quinazoline-2,4(1H,3H)-dione.

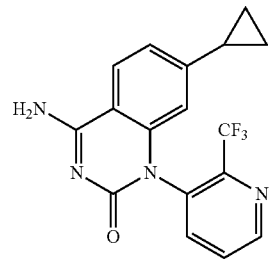 [SMILES: Nc1nc(=O)n(-c2cccnc2C(F)(F)F)c2cc(C3CC3)ccc12]

$^1$H NMR (400 MHz, MeOD) δ 8.90 (s 1H), 8.10-7.88 (m, 3H), 6.96 (d, J=8.5 Hz, 1H), 6.11 (s, 1H), 1.96-1.72 (m, 1H), 1.03 (dd, J=3.4 Hz, 2H), 0.65 (d, J=3.9 Hz, 2H). m/z [M+H]$^+$ 347.0.

7-Bromo-6-chloro-1-(2-chlorophenyl)-4-(methylamino)quinazolin-2(1H)-one was prepared by using 7-bromo-6-chloro-1-(2-chlorophenyl)quinazoline-2,4(1H,3H)-dione.

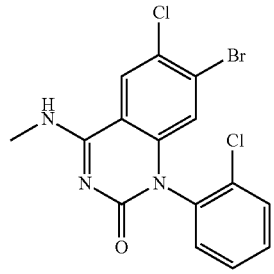 [SMILES: CNc1nc(=O)n(-c2ccccc2Cl)c2cc(Br)c(Cl)cc12]

$^1$H NMR (400 MHz, DMSO) δ 8.82 (br s, 1H), 8.47 (s, 1H), 7.75 (m, 1H), 7.58 (m, 2H), 7.52 (d, J=4.6 Hz, 1H), 6.53 (s, 1H), 3.06-2.90 (s, 3H). m/z [M+H]$^+$ 399.9.

7-Bromo-6-chloro-1-(2-chlorophenyl)-4-((cyclopropylmethyl)amino)quinazolin-2(1H)-one was prepared by using cyclopropylmethylamine and 7-bromo-6-chloro-1-(2-chlorophenyl)quinazoline-2,4(1H,3H)-dione.

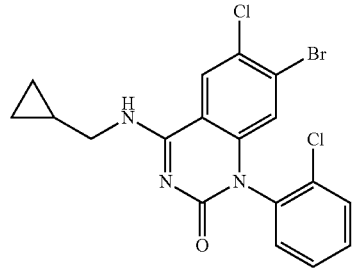 [SMILES: O=c1nc(NCC2CC2)c2cc(Cl)c(Br)cc2n1-c1ccccc1Cl]

$^1$H NMR (400 MHz, DMSO) δ 8.16 (s, 1H), 7.81 (d, J=7.2 Hz, 2H), 7.73-7.56 (m, 3H), 6.61 (s, 1H), 2.67 (br s, 1H), 1.26 (m, 4H). m/z [M+H]$^+$ 439.9.

6-Bromo-1-(2-chlorophenyl)-7-cyclopropyl-4-(isoxazol-4-ylamino)quinazolin-2(1H)-one was prepared by substituting with isoxazol-4-amine and 6-bromo-1-(2-chlorophenyl)-7-cyclopropylquinazoline-2,4(1H,3H)-dione.

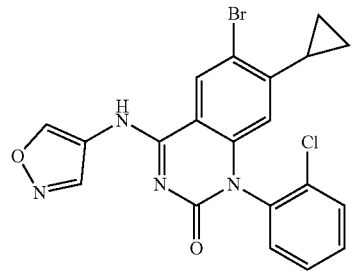 [SMILES: O=c1nc(Nc2cnoc2)c2cc(Br)c(C3CC3)cc2n1-c1ccccc1Cl]

$^1$H NMR (400 MHz, MeOD) δ 9.67 (s, 1H), 8.79 (s, 1H), 8.58 (s, 1H), 7.76 (m, 1H), 7.62 (m, 2H), 7.49 (m, 1H), 6.04 (s, 1H), 2.22 (br s, 1H), 1.06 (d, J=8.1 Hz, 2H), 0.39 (br s, 2H). m/z [M+H]$^+$ 458.0.

6-Bromo-1-(2-chlorophenyl)-7-cyclopropyl-4-((cyclopropylmethyl)amino)quinazolin-2(1H)-one was prepared by using cyclopropylmethylamine and 6-bromo-1-(2-chlorophenyl)-7-cyclopropylquinazoline-2,4(1H,3H)-dione.

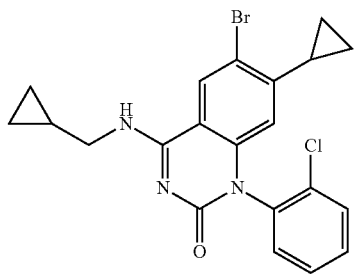 [SMILES: O=c1nc(NCC2CC2)c2cc(Br)c(C3CC3)cc2n1-c1ccccc1Cl]

$^1$H NMR (400 MHz, DMSO) δ 8.74 (br s, 1H), 8.56 (s, 1H), 7.81-7.67 (m, 1H), 7.66-7.54 (m, 2H), 7.53-7.34 (m, 1H), 5.75 (s, 1H), 2.08 (s, 1H), 1.19 (s, 1H), 0.98 (d, J=8.3 Hz, 2H), 0.51 (d, J=7.7 Hz, 2H), 0.35-0.22 (m, 4H). m/z [M+H]$^+$ 445.0.

4-Amino-6-chloro-1-(2-chlorophenyl)-7-cyclopropylquinazolin-2(1H)-one was prepared by using ammonia in THF (2 M) and 6-chloro-1-(2-chlorophenyl)-7-cyclopropylquinazoline-2,4(1H,3H)-dione.

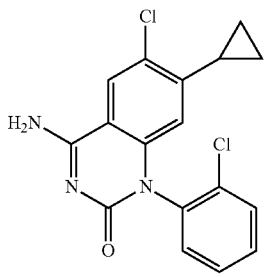 [SMILES: Nc1nc(=O)n(-c2ccccc2Cl)c2cc(C3CC3)c(Cl)cc12]

¹H NMR (400 MHz, MeOD) δ 8.21 (s, 1H), 7.72 (m, 1H), 7.65-7.53 (m, 2H), 7.44 (m, 1H), 5.97 (s, 1H), 2.23 (m, 1H), 1.13-0.96 (m, 2H), 0.39 (m, 2H). m/z [M+H]⁺ 347.0.

(R)-6-Chloro-1-(2-chlorophenyl)-7-cyclopropyl-4-((2-hydroxypropyl)amino)quinazolin-2(1H)-one was prepared by using (R)-2-aminopropan-1-ol and 6-chloro-1-(2-chlorophenyl)-7-cyclopropylquinazoline-2,4(1H,3H)-dione.

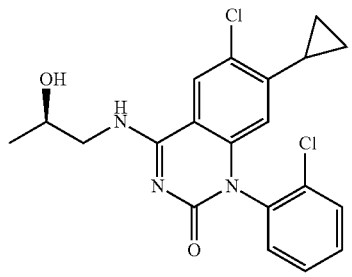

(S)-6-Chloro-1-(2-chlorophenyl)-7-cyclopropyl-4-((2-hydroxypropyl)amino)quinazolin-2(1H)-one was prepared by using (S)-2-aminopropan-1-ol and 6-chloro-1-(2-chlorophenyl)-7-cyclopropylquinazoline-2,4(1H,3H)-dione.

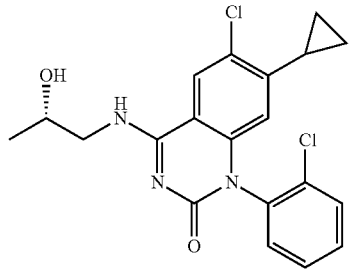 [SMILES: C[C@H](O)CNc1nc(=O)n(-c2ccccc2Cl)c2cc(C3CC3)c(Cl)cc12]

5-fluoro-4-(((trans)-2-fluorocyclopropyl)amino)-1-phenyl-7-(trifluoromethyl)quinazolin-2(1H)-one was prepared by using trans-2-fluorocyclopropan-1-amine and 5-fluoro-1-phenyl-7-(trifluoromethyl)quinazoline-2,4(1H,3H)-dione.

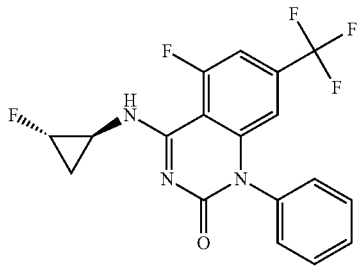

¹H NMR (400 MHz, DMSO) δ 7.86 (d, J=12.2 Hz, 1H), 7.70-7.53 (m, 3H), 7.38 (br s, 2H), 6.39 (s, 1H), 4.92 (d, J=64.9 Hz, 1H), 3.08 (br s, 1H), 1.40 (br d, J=25.4 Hz, 1H), 1.27 (m, 1H). m/z [M+H]⁺ 382.1.

4-((Cyclopropylmethyl)amino)-5-methoxy-1-phenyl-7-(trifluoromethyl)quinazolin-2(1H)-one was prepared by using cyclopropylmethylamine and 1-(2-chlorophenyl)-5-methoxy-7-(trifluoromethyl)quinazoline-2,4(1H,3H)-dione.

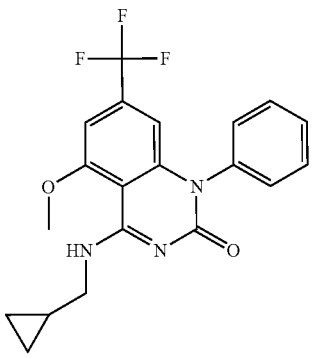 [SMILES: COc1cc(C(F)(F)F)cc2c1c(NCC1CC1)nc(=O)n2-c1ccccc1]

¹H NMR (400 MHz, DMSO) δ 8.70 (m, 1H), 7.56 (dt, J=30.6, 7.5 Hz, 3H), 7.31 (d, J=7.6 Hz, 2H), 7.09 (s, 1H), 6.81 (s, 1H), 6.14 (s, 1H), 4.13 (s, 3H), 1.26 (s, 1H), 0.50 (d, J=7.8 Hz, 2H), 0.35 (d, J=4.9 Hz, 2H). m/z [M+H]⁺ 390.1.

4-((2-Hydroxyethyl)amino)-5-methoxy-1-phenyl-7-(trifluoromethyl)quinazolin-2(1H)-one was prepared by using 2-aminoethan-1-ol and 1-(2-chlorophenyl)-5-methoxy-7-(trifluoromethyl)quinazoline-2,4(1H,3H)-dione.

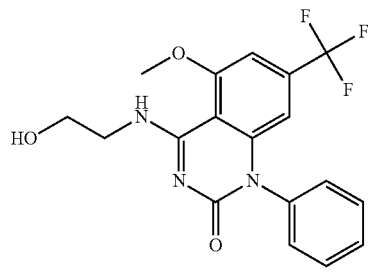 [SMILES: COc1cc(C(F)(F)F)cc2c1c(NCCO)nc(=O)n2-c1ccccc1]

¹H NMR (400 MHz, DMSO) δ 8.67 (s, 1H), 7.56 (m, 2H), 7.31 (d, J=7.5 Hz, 1H), 7.10 (s, 1H), 6.14 (s, 1H), 4.11 (d, J=2.2 Hz, 3H), 3.71 (t, J=6.2 Hz, 1H), 3.60 (t, J=6.1 Hz, 1H). m/z [M+H]⁺ 380.1.

5-Methoxy-4-((2-methoxyethyl)amino)-1-phenyl-7-(trifluoromethyl)quinazolin-2(1H)-one was prepared by using 2-methoxyethan-1-amine and 1-(2-chlorophenyl)-5-methoxy-7-(trifluoromethyl)quinazoline-2,4(1H,3H)-dione.

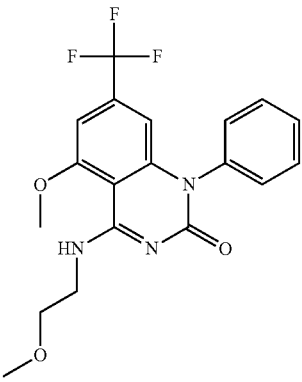 [SMILES: COCCNc1nc(=O)n(-c2ccccc2)c2cc(C(F)(F)F)cc(OC)c12]

(S)-4-((2-Hydroxypropyl)amino)-5-methoxy-1-phenyl-7-(trifluoromethyl)quinazolin-2(1H)-one was prepared by using (S)-2-aminopropan-1-ol and 1-(2-chlorophenyl)-5-methoxy-7-(trifluoromethyl)quinazoline-2,4(1H,3H)-dione.

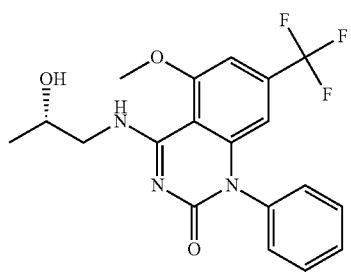 [SMILES: COc1cc(C(F)(F)F)cc2c1c(NC[C@H](C)O)nc(=O)n2-c1ccccc1]

$^1$H NMR (400 MHz, DMSO) δ 8.72 (m, 1H), 7.68-7.45 (m, 3H), 7.31 (d, J=7.5 Hz, 2H), 7.11 (s, 1H), 6.15 (s, 1H), 5.12 (br s, 1H), 4.11 (s, 3H), 4.03-3.90 (br s, 1H), 3.64 (dd, J=12.6, 6.0 Hz, 1H), 1.16 (d, J=6.3 Hz, 3H). m/z [M+H]$^+$ 394.1.

4-(((trans)-2-Hydroxycyclobutyl)amino)-5-methoxy-1-phenyl-7-(trifluoromethyl)quinazolin-2(1H)-one was prepared by using 1-(2-chlorophenyl)-7-cyclopropylpyrido[2,3-d]pyrimidine-2,4(1H,3H)-dione and 1-(2-chlorophenyl)-5-methoxy-7-(trifluoromethyl)quinazoline-2,4(1H,3H)-dione.

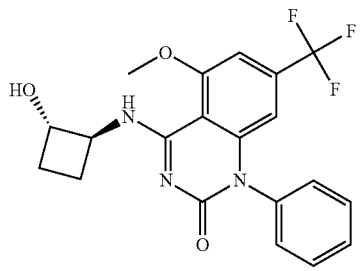

4-(((trans)-2-Fluorocyclopropyl)amino)-5-methoxy-1-phenyl-7-(trifluoromethyl)quinazolin-2(1H)-one was prepared by using trans-2-fluorocyclopropan-1-amine and 1-(2-chlorophenyl)-5-methoxy-7-(trifluoromethyl)quinazoline-2,4(1H,3H)-dione.

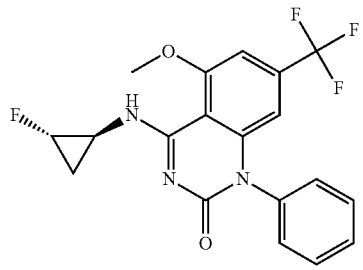

$^1$H NMR (400 MHz, MeOD) δ 8.57 (s, 1H), 7.76-7.51 (m, 3H), 7.33 (d, J=7.5 Hz, 2H), 7.10 (s, 1H), 6.37 (s, 1H), 4.62 (m, 1H), 4.14 (s, 3H), 3.53 (m, 1H), 1.55 (m, 1H), 1.22 (m, 1H). m/z [M+H]$^+$ 394.05.

4-Amino-5-methoxy-1-phenyl-7-(trifluoromethyl)quinazolin-2(1H)-one was prepared by using ammonia in THF (2 M) and 1-(2-chlorophenyl)-5-methoxy-7-(trifluoromethyl)quinazoline-2,4(1H,3H)-dione.

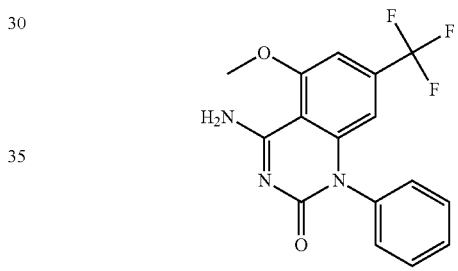

$^1$H NMR (400 MHz, MeOD) δ 7.61 (m, 4H), 7.33 (d, J=7.6 Hz, 2H), 7.11 (s, 1H), 6.36 (s, 1H), 4.62 (br s, 1H), 4.16 (s, 3H). m/z [M+H]$^+$ 336.0.

4-(((1S,2R)-2-Fluorocyclopropyl)amino)-5-methoxy-1-phenyl-7-(trifluoromethyl)quinazolin-2(1H)-one was prepared by using (1S,2R)-2-fluorocyclopropan-1-amine and 1-(2-chlorophenyl)-5-methoxy-7-(trifluoromethyl)quinazoline-2,4(1H,3H)-dione.

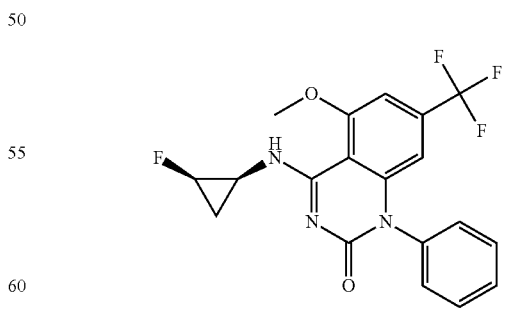

$^1$H NMR (400 MHz, MeOD) δ 7.71-7.54 (m, 3H), 7.35 (d, J=7.4 Hz, 2H), 7.13 (s, 1H), 6.39 (s, 1H), 4.28-4.18 (m, 1H), 4.15 (s, 3H), 4.06 (br s, 1H), 3.90 (appar q, J=6.5 Hz, 1H), 1.34 (m, 1H), 1.14 (br d, J=26.1 Hz, 1H). m/z [M+H]$^+$ 394.05.

641

4-(((1R,2S)-2-Fluorocyclopropyl)amino)-5-methoxy-1-phenyl-7-(trifluoromethyl)quinazolin-2(1H)-one was prepared by using (1R,2S)-2-fluorocyclopropan-1-amine and 1-(2-chlorophenyl)-5-methoxy-7-(trifluoromethyl)quinazoline-2,4(1H,3H)-dione.

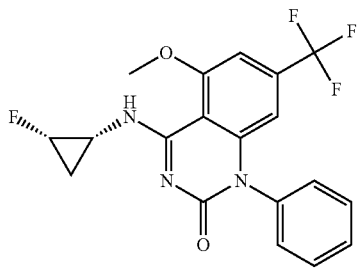 [SMILES: COc1cc(C(F)(F)F)cc2c1c(N[C@@H]1C[C@@H]1F)nc(=O)n2-c1ccccc1]

¹H NMR (400 MHz, MeOD) δ 7.71-7.54 (m, 3H), 7.35 (d, J=7.4 Hz, 2H), 7.13 (s, 1H), 6.39 (s, 1H), 4.28-4.18 (m, 1H), 4.15 (s, 3H), 4.06 (br s, 1H), 3.90 (appar q, J=6.5 Hz, 1H), 1.34 (m, 1H), 1.14 (br d, J=26.1 Hz, 1H). m/z [M+H]⁺ 394.05.

4-(Isobutylamino)-5-methoxy-1-phenyl-7-(trifluoromethyl)quinazolin-2(1H)-one was prepared by using sec-Butylamine and 1-(2-chlorophenyl)-5-methoxy-7-(trifluoromethyl)quinazoline-2,4(1H,3H)-dione.

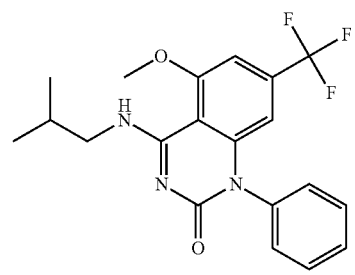 [SMILES: COc1cc(C(F)(F)F)cc2c1c(NCC(C)C)nc(=O)n2-c1ccccc1]

¹H NMR (400 MHz, MeOD) δ 7.72-7.53 (m, 3H), 7.32 (d, J=7.6 Hz, 2H), 7.12 (s, 1H), 6.36 (s, 1H), 4.18 (s, 3H), 3.53 (d, J=7.1, 2H), 2.13 (appar q, J=7.2 Hz, 1H), 1.06 (d, J=6.9, 8H). m/z [M+H]⁺ 392.15.

5-Methoxy-4-((oxazol-2-ylmethyl)amino)-1-phenyl-7-(trifluoromethyl)quinazolin-2(1H)-one was prepared by using oxazol-2-ylmethanamine and 1-(2-chlorophenyl)-5-methoxy-7-(trifluoromethyl)quinazoline-2,4(1H,3H)-dione.

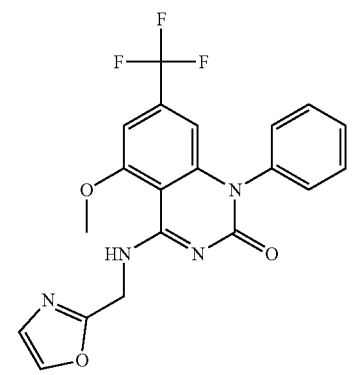 [SMILES: COc1cc(C(F)(F)F)cc2c1c(NCc1ncco1)nc(=O)n2-c1ccccc1]

¹H NMR (400 MHz, MeOD) δ 7.92 (s, 1H), 7.71-7.52 (m, 3H), 7.38-7.24 (d, J=7.8 Hz, 2H), 7.16 (d, J=8.6 Hz, 2H), 6.38 (s, 1H), 5.03 (s, 2H), 4.20 (s, 3H). m/z [M+H]⁺ 417.1.

642

4-((Isoxazol-4-ylmethyl)amino)-5-methoxy-1-phenyl-7-(trifluoromethyl)quinazolin-2(1H)-one was prepared by using isoxazol-4-ylmethanamine and 1-(2-chlorophenyl)-5-methoxy-7-(trifluoromethyl)quinazoline-2,4(1H,3H)-dione.

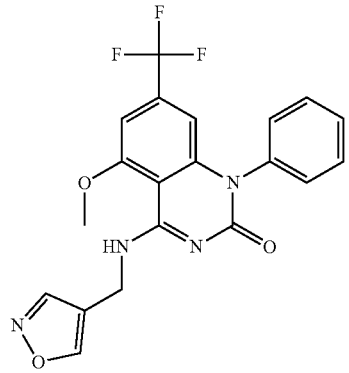 [SMILES: COc1cc(C(F)(F)F)cc2c1c(NCc1cnoc1)nc(=O)n2-c1ccccc1]

¹H NMR (400 MHz, MeOD) δ 8.82 (s, 1H), 8.62 (s, 1H), 7.76-7.52 (m, 3H), 7.34 (d, J=7.6 Hz, 2H), 7.11 (s, 1H), 6.36 (s, 1H), 4.74 (s, 2H), 4.17 (s, 3H). m/z [M+H]⁺ 417.1.

5-Methoxy-4-((oxazol-4-ylmethyl)amino)-1-phenyl-7-(trifluoromethyl)quinazolin-2(1H)-one was prepared by using oxazol-4-ylmethanamine and 1-(2-chlorophenyl)-5-methoxy-7-(trifluoromethyl)quinazoline-2,4(1H,3H)-dione.

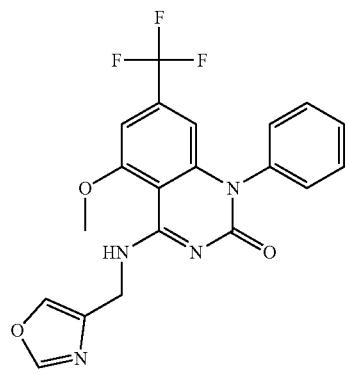 [SMILES: COc1cc(C(F)(F)F)cc2c1c(NCc1cocn1)nc(=O)n2-c1ccccc1]

¹H NMR (400 MHz, MeOD) δ 8.22 (s, 1H), 8.05 (s, 1H), 7.71-7.54 (m, 3H), 7.33 (d, J=7.6 Hz, 2H), 7.12 (s, 1H), 6.36 (s, 1H), 4.80 (s, 2H), 4.17 (1, 3H). m/z [M+H]⁺ 417.1.

5-Methoxy-4-(((3-methoxyisoxazol-5-yl)methyl)amino)-1-phenyl-7-(trifluoromethyl)quinazolin-2(1H)-one was prepared by using (3-methoxyisoxazol-5-yl)methanamine and 1-(2-chlorophenyl)-5-methoxy-7-(trifluoromethyl)quinazoline-2,4(1H,3H)-dione.

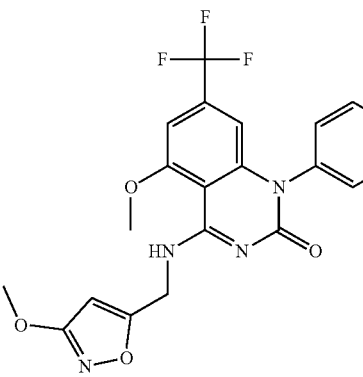

¹H NMR (400 MHz, MeOD) δ 7.74-7.51 (m, 3H), 7.33 (d, J=7.6 Hz, 2H), 7.13 (s, 1H), 6.37 (s, 1H), 6.13 (s, 1H), 4.93 (s, 3H), 4.19 (s, 3H), 3.93 (s, 3H). m/z [M+H]⁺ 447.1.

4-((isoxazol-3-ylmethyl)amino)-5-methoxy-1-phenyl-7-(trifluoromethyl)quinazolin-2(1H)-one was prepared by using isoxazol-3-ylmethanamine and 1-(2-chlorophenyl)-5-methoxy-7-(trifluoromethyl)quinazoline-2,4(1H,3H)-dione.

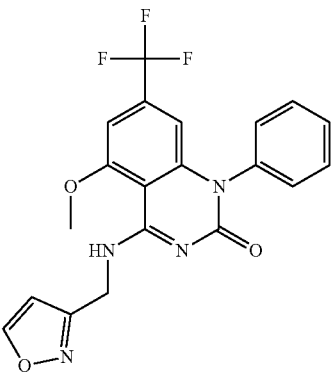 [SMILES: COc1cc(C(F)(F)F)cc2c1c(NCc1ccon1)nc(=O)n2-c1ccccc1]

¹H NMR (400 MHz, MeOD) δ 8.65 (s, 1H), 7.73-7.53 (m, 3H), 7.34 (d, J=7.6 Hz, 2H), 7.14 (s, 1H), 6.64 (s, 1H), 6.38 (s, 1H), 5.00 (s, 2H), 4.19 (d, J=2.5 Hz, 3H). m/z [M+H]⁺ 417.1.

7-cyclopropyl-4-((cyclopropylmethyl)amino)-1-(3-(trifluoromethyl)pyrazin-2-yl)quinazolin-2(1H)-one was prepared by using cyclopropylmethylamine and 7-cyclopropyl-1-(3-(trifluoromethyl)pyrazin-2-yl)quinazoline-2,4(1H,3H)-dione.

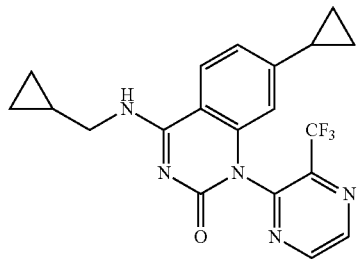

¹H NMR (400 MHz, MeOD) δ 8.85 (s, 1H), 8.78 (s, 1H), 7.83 (d, J=8.5, 1H), 6.75 (d, J=8.5 Hz, 1H), 5.97 (s, 1H), 3.31 (m, 2H), 1.68 (m, 1H), 1.08 (m, 1H), 0.82 (d, J=8.5 Hz, 3H), 0.48 (m, 3H), 0.38 (d, J=7.7 Hz, 2H), 0.18 (d, J=5.0 Hz, 2H). m/z [M+H]⁺ 402.1.

7-cyclopropyl-4-(methylamino)-1-(3-(trifluoromethyl)pyrazin-2-yl)quinazolin-2(1H)-one was prepared by using 7-cyclopropyl-1-(3-(trifluoromethyl)pyrazin-2-yl)quinazoline-2,4(1H,3H)-dione.

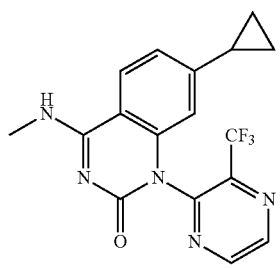 [SMILES: CNc1nc(=O)n(-c2nccnc2C(F)(F)F)c2cc(C3CC3)ccc12]

¹H NMR (400 MHz, MeOD) δ 8.87 (s, 1H), 8.81 (s, 1H), 7.73 (d, J=8.2 Hz, 1H), 6.75 (d, J=8.6 Hz, 1H), 5.98 (s, 1H), 2.95 (s, 3H), 1.69 (br s, 1H), 0.83 (d, J=8.5 Hz, 3H), 0.49 (br s, 2H). m/z [M+H]⁺ 362.1.

6-Bromo-4-((cyclopropylmethyl)amino)-1-phenyl-7-(trifluoromethoxy)quinazolin-2(1H)-one was prepared by using cyclopropylmethylamine and 6-bromo-1-phenyl-7-(trifluoromethoxy)quinazoline-2,4(1H,3H)-dione.

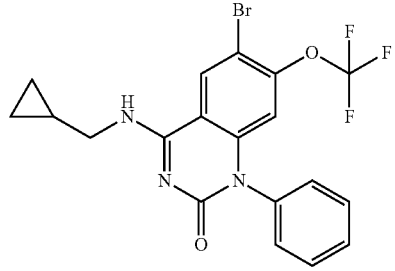 [SMILES: O=c1nc(NCC2CC2)c2cc(Br)c(OC(F)(F)F)cc2n1-c1ccccc1]

¹H NMR (400 MHz, MeOD) δ 8.62 (s, 1H), 7.62 (m, 3H), 7.35 (d, J=7.6 Hz, 2H), 6.49 (s, 1H), 3.51 (d, J=6.9, 2H), 1.30 (m, 1H), 0.60 (d, J=7.7 Hz, 2H), 0.38 (m, 2H). m/z [M+H]⁺ 456.1, 454.1.

6-Bromo-4-((cyclopropylmethyl)amino)-1-(o-tolyl)-7-(trifluoromethoxy)quinazolin-2(1H)-one was prepared by using cyclopropylmethylamine and 6-bromo-1-(o-tolyl)-7-(trifluoromethoxy)quinazoline-2,4(1H,3H)-dione.

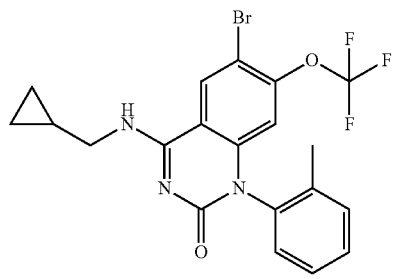 [SMILES: Cc1ccccc1-n1c(=O)nc(NCC2CC2)c2cc(Br)c(OC(F)(F)F)cc21]

¹H NMR (400 MHz, MeOD) δ 8.65 (s, 1H), 7.56-7.35 (m, 3H), 7.24 (d, J=7.6 Hz, 1H), 6.38 (s, 1H), 3.60-3.46 (m, 2H), 2.06 (d, J=2.1 Hz, 3H), 1.30 (d, J=6.7 Hz, 1H), 0.61 (d, J=7.7 Hz, 2H), 0.38 (d, J=5.0 Hz, 2H). m/z [M+H]⁺ 468.0, 470.0.

6-Bromo-4-(methylamino)-1-(o-tolyl)-7-(trifluoromethoxy)quinazolin-2(1H)-one was prepared by using 6-bromo-1-(o-tolyl)-7-(trifluoromethoxy)quinazoline-2,4(1H,3H)-dione.

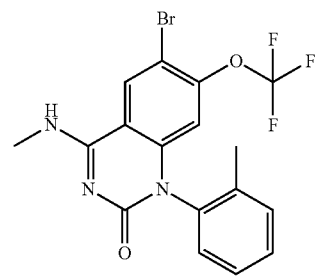 [SMILES: CNc1nc(=O)n(-c2ccccc2C)c2cc(OC(F)(F)F)c(Br)cc12]

¹H NMR (400 MHz, MeOD) δ 8.51 (s, 1H), 7.54-7.44 (m, 3H), 7.33 (d, J=7.6 Hz, 1H), 6.39 (s, 1H), 6.24 (s, 1H), 3.16 (s, 3H), 2.07 (s 3H). m/z [M+H]⁺ 430.0, 428.0.

4-(((3-Methoxyisoxazol-5-yl)methyl)amino)-1-(o-tolyl)-7-(trifluoromethyl)quinazolin-2(1H)-one was prepared by using (3-methoxyisoxazol-5-yl)methanamine and 1-(o-tolyl)-7-(trifluoromethyl)quinazoline-2,4(1H,3H)-dione.

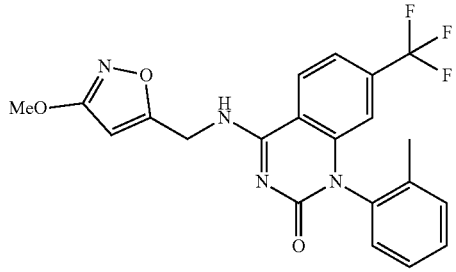 [SMILES: COc1cc(CNc2nc(=O)n(-c3ccccc3C)c3cc(C(F)(F)F)ccc23)on1]

$^1$H NMR (400 MHz, MeOD) δ 8.30 (d, J=8.2 Hz, 1H), 7.58 (d, J=8.6 Hz, 1H), 7.54-7.43 (m, 2H), 7.26 (d, J=7.6 Hz, 1H), 6.69 (s, 1H), 6.18 (s, 1H), 3.94 (d, J=2.6 Hz, 3H), 2.05 (d, J=2.6 Hz, 3H). m/z [M+H]$^+$ 431.1.

(R)-4-(2-(Hydroxymethyl)pyrrolidin-1-yl)-1-(o-tolyl)-7-(trifluoromethyl)quinazolin-2(1H)-one was prepared by using (R)-pyrrolidin-2-ylmethanol and 1-(o-tolyl)-7-(trifluoromethyl)quinazoline-2,4(1H,3H)-dione.

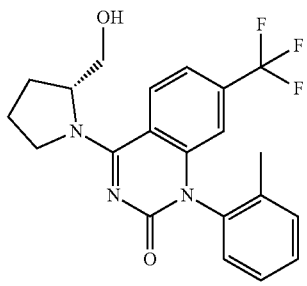 [SMILES: Cc1ccccc1-n1c(=O)nc(N2CCC[C@@H]2CO)c2ccc(C(F)(F)F)cc21]

$^1$H NMR (400 MHz, MeOD) δ 8.43 (t, J=10.3 Hz, 1H), 7.62-7.40 (m, 5H), 7.23 (dd, J=19.6, 7.7 Hz, 1H), 6.69 (d, J=14.6 Hz, 1H), 4.15 (s, 2H), 4.04 (s, 1H), 3.85 (s, 1H), 2.27-1.97 (m, 6H). m/z [M+H]$^+$ 404.1.

(S)-4-(3-(Hydroxymethyl)pyrrolidin-1-yl)-1-(o-tolyl)-7-(trifluoromethyl)quinazolin-2(1H)-one was prepared by using (S)-pyrrolidin-3-ylmethanol and 1-(o-tolyl)-7-(trifluoromethyl)quinazoline-2,4(1H,3H)-dione.

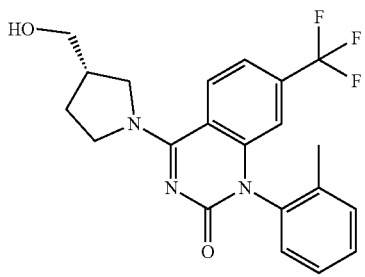

$^1$H NMR (400 MHz, MeOD) δ 8.48 (d, J=8.7 Hz, 1H), 7.51 (q, J=8.9, 7.9 Hz, 4H), 7.23 (s, 1H), 6.69 (d, J=5.8 Hz, 1H), 4.15 (s, 2H), 3.77-3.58 (m, 2H), 2.61 (s, 1H), 2.22 (s, 1H), 2.05 (dd, J=12.3, 2.5 Hz, 3H). m/z [M+H]$^+$ 404.1.

(R)-4-(3-(Hydroxymethyl)pyrrolidin-1-yl)-1-(o-tolyl)-7-(trifluoromethyl)quinazolin-2(1H)-one was prepared by using (R)-pyrrolidin-3-ylmethanol and 1-(o-tolyl)-7-(trifluoromethyl)quinazoline-2,4(1H,3H)-dione.

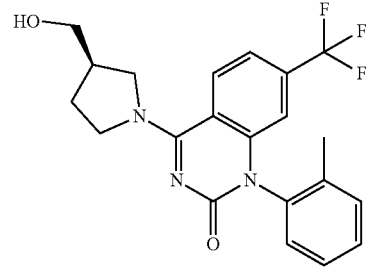 [SMILES: Cc1ccccc1-n1c(=O)nc(N2CC[C@@H](CO)C2)c2ccc(C(F)(F)F)cc21]

$^1$H NMR (400 MHz, MeOD) δ 8.48 (d, J=8.5 Hz, 1H), 7.66-7.38 (m, 4H), 7.23 (s, 1H), 6.68 (d, J=5.8 Hz, 1H), 4.15 (s, 2H), 3.69 (d, J=12.9 Hz, 2H), 2.60 (s, 1H), 2.22 (s, 1H), 2.15-1.99 (m, 3H), 1.93 (s, 1H). m/z [M+H]$^+$ 404.1.

(R)-4-(2-(methoxymethyl)pyrrolidin-1-yl)-1-(o-tolyl)-7-(trifluoromethyl)quinazolin-2(1H)-one was prepared by using (R)-2-(methoxymethyl)pyrrolidine and 1-(o-tolyl)-7-(trifluoromethyl)quinazoline-2,4(1H,3H)-dione.

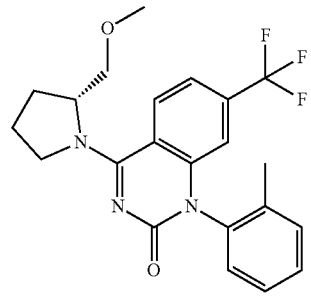 [SMILES: COC[C@H]1CCCN1c1nc(=O)n(-c2ccccc2C)c2cc(C(F)(F)F)ccc12]

$^1$H NMR (400 MHz, MeOD) δ 8.49-8.22 (m, 1H), 7.50 (dt, J=23.2, 7.9 Hz, 4H), 7.31-7.10 (m, 1H), 6.69 (d, J=14.9 Hz, 1H), 4.93 (s, 1H), 4.20-4.03 (m, 2H), 3.88 (d, J=8.8 Hz, 1H), 3.74 (d, J=10.1 Hz, 1H), 3.40 (s, 3H), 2.18 (d, J=7.1 Hz, 3H), 2.06 (dd, J=30.0, 2.3 Hz, 4H). m/z [M+H]$^+$ 418.1.

4-(3-(2-Hydroxyethyl)pyrrolidin-1-yl)-1-(o-tolyl)-7-(trifluoromethyl)quinazolin-2(1H)-one was prepared by using 2-(pyrrolidin-3-yl)ethan-1-ol and 1-(o-tolyl)-7-(trifluoromethyl)quinazoline-2,4(1H,3H)-dione.

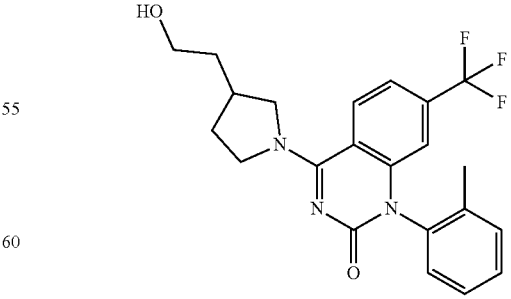

$^1$H NMR (400 MHz, MeOD) δ 8.48 (s, 1H), 7.61-7.37 (m, 4H), 7.23 (t, J=8.2 Hz, 1H), 6.68 (d, J=11.2 Hz, 1H), 3.71 (m, 2H), 2.49 (m, 1H), 2.30 (m, 1H), 2.05 (appar d, J=23.1 Hz, 3H), 1.79 (m, 3H). m/z [M+H]$^+$ 418.1.

4-(Pyrrolidin-1-yl)-1-(o-tolyl)-7-(trifluoromethyl)pyrido[2,3-d]pyrimidin-2(1H)-one was prepared by using pyrrolidine and 1-(o-tolyl)-7-(trifluoromethyl)pyrido[2,3-d]pyrimidine-2,4(1H,3H)-dione.

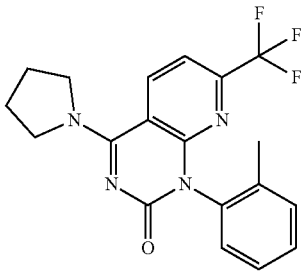 [SMILES: Cc1ccccc1-n1c(=O)nc(N2CCCC2)c2ccc(C(F)(F)F)nc21]

¹H NMR (400 MHz, MeOD) δ 8.96-8.75 (m, 1H), 7.63 (dd, J=8.2, 2.5 Hz, 1H), 7.48-7.26 (m, 3H), 7.14 (d, J=7.5 Hz, 1H), 4.04 (m, J=61.3 Hz, 4H), 2.13 (m, 4H), 2.02 (d, J=2.5 Hz, 3H). m/z [M+H]⁺ 375.2.

(R)-4-(2-(hydroxymethyl)pyrrolidin-1-yl)-1-(o-tolyl)-7-(trifluoromethyl)pyrido[2,3-d]pyrimidin-2(1H)-one was prepared by using (R)-pyrrolidin-2-ylmethanol and 1-(o-tolyl)-7-(trifluoromethyl)pyrido[2,3-d]pyrimidine-2,4(1H,3H)-dione.

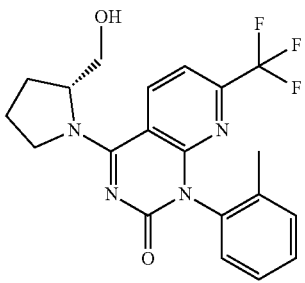 [SMILES: Cc1ccccc1-n1c(=O)nc(N2CCC[C@@H]2CO)c2ccc(C(F)(F)F)nc21]

¹H NMR (400 MHz, MeOD) δ 8.83 (t, J=10.0 Hz, 1H), 8.18 (s, 1H), 7.63 (dd, J=8.4, 2.4 Hz, 1H), 7.47-7.28 (m, 3H), 7.14 (dd, J=23.5, 7.7 Hz, 1H), 4.78 (s, 1H), 4.21-3.99 (m, 3H), 3.83 (ddt, J=11.4, 5.9, 2.8 Hz, 1H), 2.19 (dd, J=19.4, 10.9 Hz, 3H), 2.13-2.04 (m, 2H), 1.97 (d, J=2.5 Hz, 2H). m/z [M+H]⁺ 405.00.

(R)-4-(3-(hydroxymethyl)pyrrolidin-1-yl)-1-(o-tolyl)-7-(trifluoromethyl)pyrido[2,3-d]pyrimidin-2(1H)-one was prepared by using (R)-pyrrolidin-3-ylmethanol and 1-(o-tolyl)-7-(trifluoromethyl)pyrido[2,3-d]pyrimidine-2,4(1H,3H)-dione.

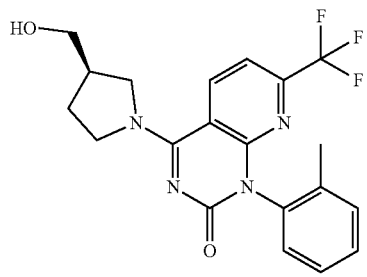

¹H NMR (400 MHz, MeOD) δ 8.86 (d, J=8.3 Hz, 1H), 8.40 (s, 1H), 7.63 (d, J=8.6 Hz, 1H), 7.46-7.25 (m, 3H), 7.14 (t, J=7.1 Hz, 1H), 4.07 (m, 4H), 3.70 (m, 2H), 2.62 (m, 1H), 2.21 (m, 1H), 2.08-1.86 (m, 4H). m/z [M+H]⁺ 405.00.

4-Amino-1-(2-chlorophenyl)-7-cyclopropylquinazolin-2(1H)-one was prepared by substituting was prepared by using ammonia (7 M solution in MeOH) and 1-(2-chlorophenyl)-7-cyclopropylquinazoline-2,4(1H,3H)-dione.

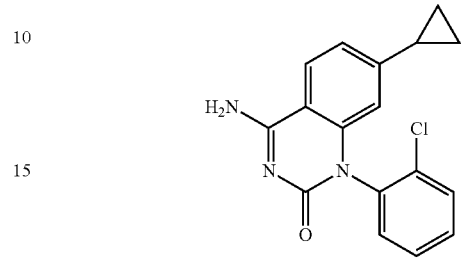

¹H NMR (400 MHz, DMSO-d₆) δ 8.15-7.84 (m, 3H), 7.73 (dt, J=6.1, 2.8 Hz, 1H), 7.62-7.39 (m, 3H), 6.80 (d, J=8.4 Hz, 1H), 6.02 (s, 1H), 1.91-1.73 (m, 1H), 0.94 (d, J=8.4 Hz, 2H), 0.61 (d, J=6.5 Hz, 2H). m/z [M+H]⁺ 312.00.

1-(2-chlorophenyl)-7-cyclopropyl-4-(isopropylamino)quinazolin-2(1H)-one was prepared by using isopropylamine and 1-(2-chlorophenyl)-7-cyclopropylquinazoline-2,4(1H,3H)-dione.

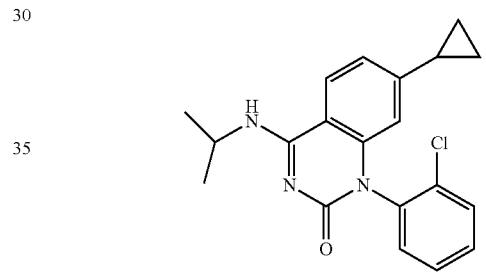

¹H NMR (400 MHz, DMSO-d₆) δ 8.12 (t, J=9.1 Hz, 2H), 7.72 (q, J=3.6, 2.2 Hz, 1H), 7.63-7.39 (m, 3H), 6.82 (d, J=8.4 Hz, 1H), 6.00 (s, 1H), 4.49 (q, J=6.8 Hz, 1H), 1.81 (s, 1H), 1.34-1.17 (m, 5H), 0.94 (d, J=8.3 Hz, 2H), 0.59 (s, 2H). m/z [M+H]⁺ 354.20.

1-(2-chlorophenyl)-7-cyclopropyl-4-(((1S,2R)-2-fluorocyclopropyl)amino)quinazolin-2(1H)-one was prepared by using (1S,2R)-2-fluorocyclopropan-1-amine and 1-(2-chlorophenyl)-7-cyclopropylquinazoline-2,4(1H,3H)-dione.

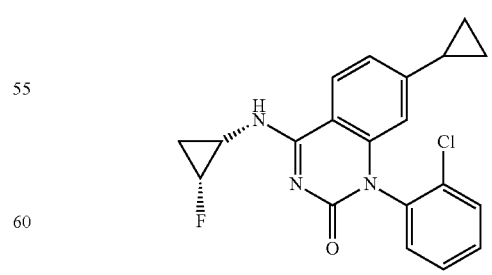

¹H NMR (400 MHz, DMSO-d₆) δ 8.49 (s, 1H), 8.13 (d, J=8.4 Hz, 1H), 7.74 (h, J=4.0, 3.2 Hz, 1H), 7.63-7.40 (m, 3H), 6.84 (d, J=8.4 Hz, 1H), 6.04 (s, 1H), 4.85 (d, J=65.2 Hz, 1H), 3.63 (dt, J=20.5, 6.8 Hz, 1H), 3.05 (d, J=6.8 Hz, 1H), 1.90-1.73 (m, 1H), 1.45-1.14 (m, 3H), 0.95 (d, J=8.3 Hz, 2H), 0.60 (d, J=6.5 Hz, 2H). m/z [M+H]+ 370.00.

1-(2-chlorophenyl)-7-cyclopropyl-4-(isoxazol-4-ylamino)quinazolin-2(1H)-one was prepared by using isoxazol-4-amine and 1-(2-chlorophenyl)-7-cyclopropylquinazoline-2,4(1H,3H)-dione.

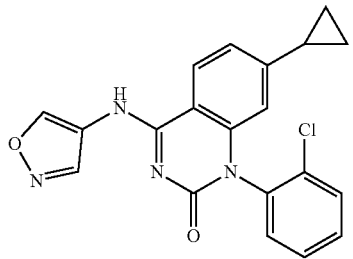

¹H NMR (400 MHz, DMSO-d₆) δ 10.48 (s, 1H), 9.43 (s, 1H), 8.89 (d, J=1.9 Hz, 1H), 8.22 (d, J=8.4 Hz, 1H), 7.85-7.42 (m, 4H), 6.95 (d, J=8.4 Hz, 1H), 6.68 (s, 1H), 6.12 (s, 1H), 1.86 (q, J=7.6, 7.1 Hz, 1H), 0.98 (d, J=8.3 Hz, 2H), 0.66 (q, J=8.0, 6.6 Hz, 2H). m/z [M+H]+ 379.00.

1-(2-Chlorophenyl)-7-cyclopropyl-4-(isothiazol-4-ylamino)quinazolin-2(1H)-one was prepared by using thioisoxazol-4-amine and 1-(2-chlorophenyl)-7-cyclopropylquinazoline-2,4(1H,3H)-dione.

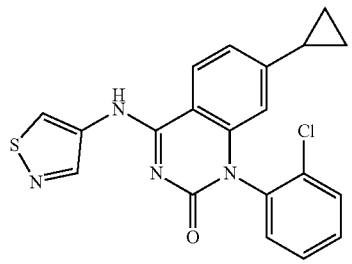 [SMILES: O=c1nc(Nc2cnsc2)c2ccc(C3CC3)cc2n1-c1ccccc1Cl]

¹H NMR (400 MHz, DMSO-d₆) δ 10.65 (s, 1H), 9.36 (s, 1H), 8.96 (s, 1H), 8.34 (d, J=8.5 Hz, 1H), 7.87-7.69 (m, 1H), 7.57 (ddt, J=23.9, 5.8, 2.4 Hz, 3H), 6.96 (d, J=8.3 Hz, 1H), 6.12 (s, 1H), 1.99-1.77 (m, 1H), 0.99 (d, J=8.3 Hz, 2H), 0.66 (d, J=6.8 Hz, 2H). m/z [M+H]+ 395.00.

1-(2-Chlorophenyl)-7-cyclopropyl-4-((2-(trifluoromethyl)pyridin-4-yl)amino)quinazolin-2(1H)-one was prepared by using 2-(trifluoromethyl)pyridin-4-amine and 1-(2-chlorophenyl)-7-cyclopropylquinazoline-2,4(1H,3H)-dione.

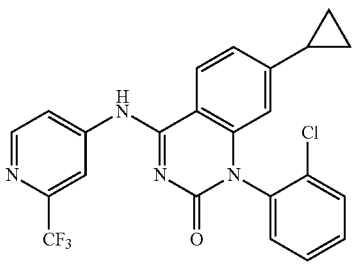 [SMILES: O=c1nc(Nc2ccnc(C(F)(F)F)c2)c2ccc(C3CC3)cc2n1-c1ccccc1Cl]

¹H NMR (400 MHz, DMSO-d₆) δ 10.33 (s, 1H), 8.73 (d, J=5.3 Hz, 1H), 8.56 (s, 1H), 8.41 (d, J=13.3 Hz, 2H), 7.79 (s, 1H), 7.59 (d, J=17.1 Hz, 3H), 7.00 (d, J=8.5 Hz, 1H), 6.17 (s, 1H), 1.91 (s, 1H), 1.01 (d, J=8.4 Hz, 2H), 0.68 (s, 2H). m/z [M+H]+ 457.00.

7-Cyclopropyl-1-(imidazo[1,2-a]pyridin-5-yl)-4-(methylamino)quinazolin-2(1H)-one was prepared by using 7-cyclopropyl-1-(imidazo[1,2-a]pyridin-5-yl)pyrido[2,3-d]pyrimidine-2,4(1H,3H)-dione.

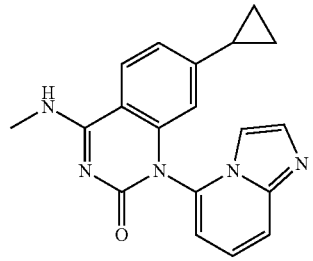 [SMILES: CNc1nc(=O)n(-c2cccc3nccn23)c2cc(C3CC3)ccc12]

¹H NMR (400 MHz, Methanol-d₄) δ 8.42 (d, J=2.0 Hz, 1H), 7.85 (dd, J=8.5, 2.1 Hz, 1H), 7.70 (d, J=9.2 Hz, 1H), 7.57-7.29 (m, 3H), 7.11-6.99 (m, 1H), 6.85 (d, J=8.5 Hz, 1H), 6.10 (s, 1H), 3.05 (d, J=2.1 Hz, 3H), 1.69 (t, J=6.8 Hz, 1H), 0.86 (d, J=8.7 Hz, 2H), 0.47 (d, J=15.0 Hz, 2H). m/z [M+H]+ 332.00.

7-Cyclopropyl-4-((cyclopropylmethyl)amino)-1-(pyrazin-2-yl)quinazolin-2(1H)-one was prepared by using cyclopropylmethylamine and 7-cyclopropyl-1-(pyrazin-2-yl)quinazoline-2,4(1H,3H)-dione.

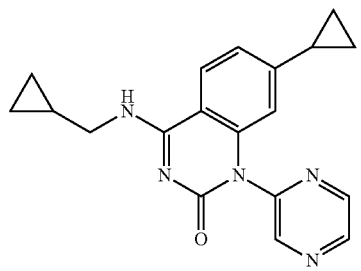 [SMILES: O=c1nc(NCC2CC2)c2ccc(C3CC3)cc2n1-c1cnccn1]

¹H NMR (400 MHz, DMSO-d₆) δ 8.79 (d, J=2.8 Hz, 2H), 8.69 (d, J=6.7 Hz, 1H), 8.09 (d, J=8.5 Hz, 1H), 6.85 (d, J=8.5 Hz, 1H), 6.21 (s, 1H), 3.39 (d, J=6.4 Hz, 3H), 1.87 (s, 1H), 1.20 (s, 2H), 0.95 (d, J=7.9 Hz, 2H), 0.65 (d, J=5.1 Hz, 2H), 0.49 (d, J=7.9 Hz, 2H), 0.31 (d, J=4.9 Hz, 2H). m/z [M+H]+ 334.20.

7-Cyclopropyl-4-(methylamino)-1-(3-methylpyrazin-2-yl)quinazolin-2(1H)-one was prepared by using 7-cyclopropyl-1-(3-methylpyrazin-2-yl)quinazoline-2,4(1H,3H)-dione.

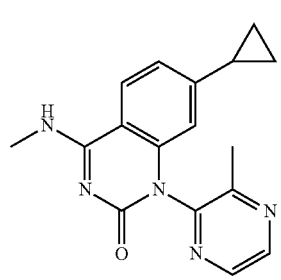 [SMILES: CNc1nc(=O)n(-c2nccnc2C)c2cc(C3CC3)ccc12]

651

¹H NMR (400 MHz, DMSO-d6) δ 8.78-8.53 (m, 3H), 8.02 (dd, J=8.4, 2.1 Hz, 1H), 6.84 (d, J=8.5 Hz, 1H), 6.09 (s, 1H), 3.06-2.92 (m, 3H), 2.29 (d, J=2.1 Hz, 3H), 1.87 (q, J=7.4 Hz, 1H), 0.94 (d, J=6.8 Hz, 2H), 0.65 (s, 2H). m/z [M+H]⁺ 308.20.

7-cyclopropyl-4-((cyclopropylmethyl)amino)-1-(3-methylpyrazin-2-yl)quinazolin-2(1H)-one was prepared by using cyclopropylmethylamine and 7-cyclopropyl-1-(3-methylpyrazin-2-yl)quinazoline-2,4(1H,3H)-dione.

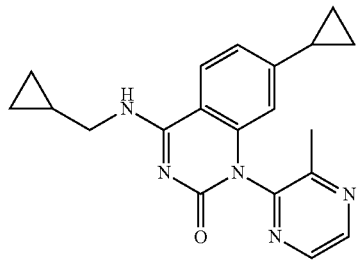 [SMILES: Cc1nccnc1-n1c(=O)nc(NCC2CC2)c2ccc(C3CC3)cc21]

¹H NMR (400 MHz, DMSO-d₆) δ 8.79-8.53 (m, 3H), 8.20-8.04 (m, 1H), 6.85 (d, J=8.4 Hz, 1H), 6.09 (s, 1H), 3.61 (dt, J=38.2, 6.6 Hz, 2H), 3.44 (d, J=7.8 Hz, 2H), 2.29 (d, J=2.2 Hz, 3H), 1.86 (d, J=7.3 Hz, 1H), 1.82-1.68 (m, 1H), 1.64-1.51 (m, 1H), 1.22 (d, J=8.0 Hz, 2H), 0.95 (t, J=6.1 Hz, 2H), 0.66 (s, 2H), 0.50 (d, J=7.9 Hz, 2H), 0.31 (d, J=4.8 Hz, 2H). m/z [M+H]⁺ 348.20.

7-Cyclopropyl-1-(imidazo[1,2-a]pyridin-7-yl)-4-(methylamino)quinazolin-2(1H)-one was prepared by using 7-cyclopropyl-1-(imidazo[1,2-a]pyridin-7-yl)quinazoline-2,4(1H,3H)-dione.

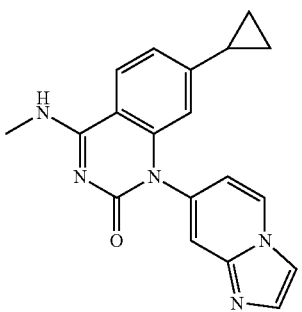 [SMILES: CNc1nc(=O)n(-c2ccn3ccnc3c2)c2cc(C3CC3)ccc12]

¹H NMR (400 MHz, DMSO-d₆) δ 9.00 (d, J=7.1 Hz, 1H), 8.76 (s, 1H), 8.40 (s, 1H), 8.17 (s, 1H), 8.13-7.95 (m, 1H), 7.96-7.81 (m, 1H), 7.36 (d, J=6.9 Hz, 1H), 6.84 (d, J=8.4 Hz, 1H), 6.56 (s, 1H), 5.72 (q, J=12.2, 11.5 Hz, 1H), 4.44-4.22 (m, 1H), 3.92 (t, J=6.8 Hz, 2H), 3.13-3.05 (m, 2H), 3.04-2.96 (m, 2H), 2.55 (d, J=2.0 Hz, 1H), 2.36 (d, J=12.5 Hz, 1H), 1.87 (s, 1H), 1.24 (t, J=7.0 Hz, 5H), 0.94 (d, J=8.0 Hz, 2H), 0.70 (d, J=5.1 Hz, 2H). m/z [M+H]⁺ 332.00.

652

4-((Cyclopropylmethyl)amino)-5-fluoro-7-(trifluoromethyl)-1-(2-(trifluoromethyl)pyridin-3-yl)quinazolin-2(1H)-one was prepared by using cyclopropylmethylamine and 5-fluoro-7-(trifluoromethyl)-1-(2-(trifluoromethyl)pyridin-3-yl)quinazoline-2,4(1H,3H)-dione.

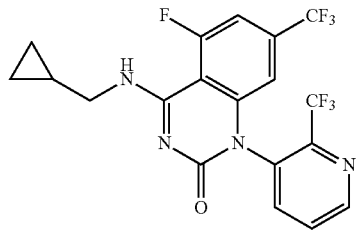 [SMILES: O=c1nc(NCC2CC2)c2c(F)cc(C(F)(F)F)cc2n1-c1cccnc1C(F)(F)F]

¹H NMR (400 MHz, DMSO-d₆) δ 8.94 (d, J=4.7 Hz, 1H), 8.45-8.28 (m, 1H), 8.20 (d, J=8.4 Hz, 1H), 8.02 (t, J=6.2 Hz, 1H), 7.66 (d, J=11.8 Hz, 1H), 6.41 (s, 1H), 3.59-3.37 (m, 2H), 1.27 (s, 1H), 0.59-0.25 (m, 4H). m/z [M+H]⁺ 447.00.

5-fluoro-4-(methylamino)-7-(trifluoromethyl)-1-(2-(trifluoromethyl)pyridin-3-yl)quinazolin-2(1H)-one was prepared by using 5-fluoro-7-(trifluoromethyl)-1-(2-(trifluoromethyl)pyridin-3-yl)quinazoline-2,4(1H,3H)-dione.

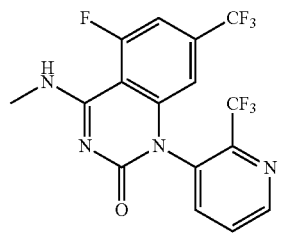 [SMILES: CNc1nc(=O)n(-c2cccnc2C(F)(F)F)c2cc(C(F)(F)F)cc(F)c12]

1-(2-chlorophenyl)-7-cyclopropyl-4-(((1S,2R)-2-fluorocyclopropyl)amino)-2-oxo-1,2-dihydropyrido[2,3-d]pyrimidine-6-carbonitrile was prepared by substituting (1S,2R)-2-fluorocyclopropan-1-amine for methyl amine and using 1-(2-chlorophenyl)-7-cyclopropyl-2,4-dioxo-1,2,3,4-tetrahydropyrido[2,3-d]pyrimidine-6-carbonitrile.

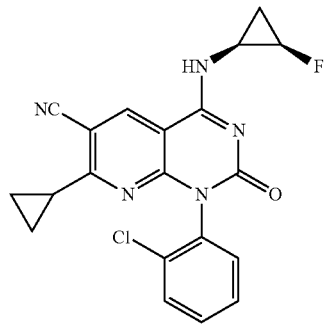 [SMILES: N#Cc1cc2c(N[C@H]3C[C@H]3F)nc(=O)n(-c3ccccc3Cl)c2nc1C1CC1]

¹H NMR (400 MHz, Chloroform-d) δ 8.87 (s, 1H), 7.53 (d, J=5.7 Hz, 1H), 7.46-7.35 (m, 2H), 7.29 (d, J=6.2 Hz, 1H), 4.77 (d, J=63.1 Hz, 1H), 2.37 (d, J=4.4 Hz, 2H), 1.41-1.22 (m, 2H), 1.12-0.96 (m, 3H), 0.75 (d, J=23.4 Hz, 2H). m/z [M+H]⁺ 396.0.

1-(2-chlorophenyl)-7-cyclopropyl-4-((cyclopropylmethyl)amino)-2-oxo-1,2-dihydropyrido[2,3-d]pyrimidine-6-carbonitrile was prepared by substituting cyclopropylmethanamine for methyl amine and using 1-(2-chlorophenyl)-7-cyclopropyl-2,4-dioxo-1,2,3,4-tetrahydropyrido[2,3-d]pyrimidine-6-carbonitrile.

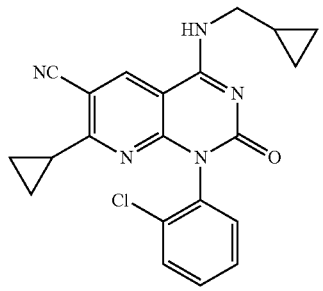 [SMILES: N#Cc1cc2c(NCC3CC3)nc(=O)n(-c3ccccc3Cl)c2nc1C1CC1]

¹H NMR (400 MHz, Chloroform-d) δ 8.35 (s, 1H), 7.50 (dd, J=5.1, 1.8 Hz, 1H), 7.41-7.33 (m, 2H), 6.89 (s, 1H), 3.56-3.39 (m, 2H), 2.42-2.32 (m, 1H), 1.18-1.09 (m, 1H), 1.09-0.95 (m, 2H), 0.75 (d, J=23.2 Hz, 2H), 0.56 (d, J=7.0 Hz, 2H), 0.32-0.23 (m, 2H). m/z [M+H]⁺ 392.1.

6-bromo-4-((cyclopropylmethyl)(methyl)amino)-1-phenyl-7-(trifluoromethyl)quinazolin-2(1H)-one was prepared by substituting 1-cyclopropyl-N-methylmethanamine for methyl amine and using 6-bromo-1-phenyl-7-(trifluoromethyl)quinazoline-2,4(1H,3H)-dione.

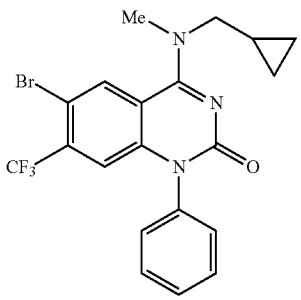 [SMILES: CN(CC1CC1)c1nc(=O)n(-c2ccccc2)c2cc(C(F)(F)F)c(Br)cc12]

¹H NMR (400 MHz, Chloroform-d) δ 8.16 (s, 1H), 7.56 (t, J=7.3 Hz, 2H), 7.53-7.46 (m, 1H), 7.24 (s, 2H), 6.87 (s, 1H), 3.65 (d, J=6.4 Hz, 2H), 3.45 (s, 3H), 1.26-1.14 (m, 1H), 0.68 (d, J=7.4 Hz, 2H), 0.35 (d, J=4.3 Hz, 2H). m/z [M+H]⁺ 452.0, 454.0.

6-bromo-4-((cyclopropylmethyl)amino)-1-phenyl-7-(trifluoromethyl)quinazolin-2(1H)-one was prepared substituting cyclopropylmethanamine for methyl amine and using 6-bromo-1-phenyl-7-(trifluoromethyl)quinazoline-2,4(1H,3H)-dione.

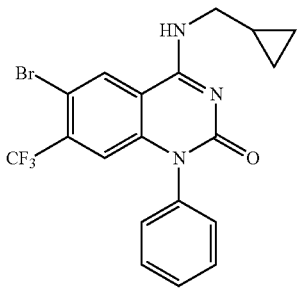 [SMILES: O=c1nc(NCC2CC2)c2cc(Br)c(C(F)(F)F)cc2n1-c1ccccc1]

¹H NMR (400 MHz, Chloroform-d) δ 8.22 (s, 1H), 7.55 (t, J=7.3 Hz, 2H), 7.51-7.45 (m, 1H), 7.25-7.22 (m, 3H),
6.85 (s, 1H), 3.51 (d, J=7.0 Hz, 2H), 1.22-1.11 (m, 1H), 0.57 (d, J=7.1 Hz, 2H), 0.31 (d, J=4.0 Hz, 2H). m/z [M+H]⁺ 438.0, 440.0.

7-cyclopropyl-4-((cyclopropylmethyl)amino)-2-oxo-1-(o-tolyl)-1,2-dihydroquinazoline-6-carbonitrile was prepared by substituting cyclopropylmethanamine for methyl amine and using 7-cyclopropyl-2,4-dioxo-1-(o-tolyl)-1,2,3,4-tetrahydroquinazoline-6-carbonitrile.

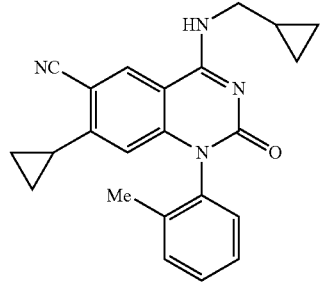 [SMILES: Cc1ccccc1-n1c(=O)nc(NCC2CC2)c2cc(C#N)c(C3CC3)cc21]

¹H NMR (400 MHz, Chloroform-d) δ 7.95 (s, 1H), 7.43-7.34 (m, 3H), 7.10 (d, J=7.3 Hz, 1H), 5.90 (s, 1H), 3.56 (t, J=7.9 Hz, 2H), 2.24-2.16 (m, 1H), 2.04 (s, 3H), 1.24-1.15 (m, 1H), 1.09 (d, J=8.2 Hz, 2H), 0.65 (d, J=7.5 Hz, 2H), 0.49 (d, J=4.5 Hz, 2H), 0.35 (d, J=4.5 Hz, 2H). m/z [M+H]⁺ 371.2.

7-cyclopropyl-4-(methylamino)-2-oxo-1-(o-tolyl)-1,2-dihydroquinazoline-6-carbonitrile was prepared using 7-cyclopropyl-2,4-dioxo-1-(o-tolyl)-1,2,3,4-tetrahydroquinazoline-6-carbonitrile.

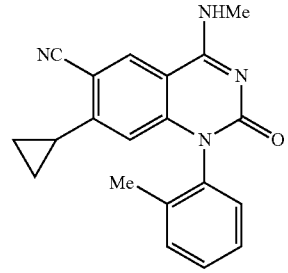 [SMILES: CNc1nc(=O)n(-c2ccccc2C)c2cc(C3CC3)c(C#N)cc12]

¹H NMR (400 MHz, Chloroform-d) δ 8.12 (s, 1H), 7.43-7.31 (m, 3H), 7.12 (d, J=6.9 Hz, 1H), 5.90 (s, 1H), 3.19 (s, 3H), 2.23-2.14 (m, 1H), 2.05 (s, 3H), 1.09 (d, J=7.8 Hz, 2H), 0.52-0.45 (m, 2H). m/z [M+H]⁺ 331.2.

1-(2-chlorophenyl)-4-((cyclopropylmethyl)amino)-7-(1,1-difluoroethyl)-2-oxo-1,2-dihydroquinazoline-6-carbonitrile was prepared by substituting cyclopropylmethanamine for methyl amine and using 1-(2-chlorophenyl)-7-(1,1-difluoroethyl)-2,4-dioxo-1,2,3,4-tetrahydroquinazoline-6-carbonitrile.

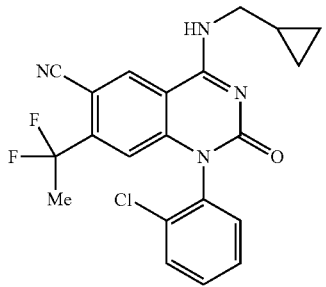

¹H NMR (400 MHz, DMSO-d₆) δ 9.08 (s, 1H), 9.01 (s, 1H), 7.76 (d, J=3.3 Hz, 1H), 7.59 (dd, J=8.6, 4.9 Hz, 3H), 6.45 (s, 1H), 3.49-3.40 (m, 2H), 1.96 (t, J=19.1 Hz, 3H), 1.24-1.16 (m, 1H), 0.53 (d, J=7.1 Hz, 2H), 0.36-0.30 (m, 2H). m/z [M+H]+ 415.0.

1-(2-chlorophenyl)-7-(1,1-difluoroethyl)-4-(methylamino)-2-oxo-1,2-dihydroquinazoline-6-carbonitrile was prepared using 1-(2-chlorophenyl)-7-(1,1-difluoroethyl)-2,4-dioxo-1,2,3,4-tetrahydroquinazoline-6-carbonitrile.

1-(2-chlorophenyl)-7-cyclopropyl-4-((2,2-difluoroethyl)amino)-2-oxo-1,2-dihydroquinazoline-6-carbonitrile was prepared by substituting 2,2-difluoroethan-1-amine for methylamine and using 1-(2-chlorophenyl)-7-cyclopropyl-2,4-dioxo-1,2,3,4-tetrahydroquinazoline-6-carbonitrile.

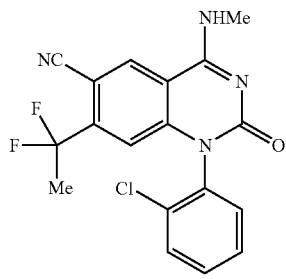 [SMILES: CNc1nc(=O)n(-c2ccccc2Cl)c2cc(C(C)(F)F)c(C#N)cc12]

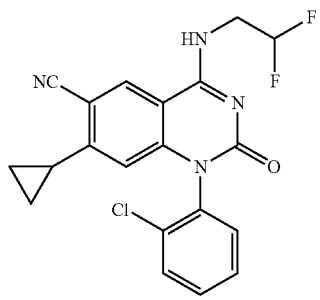

1H NMR (400 MHz, DMSO-d6) δ 9.08 (s, 1H), 8.86 (s, 1H), 7.76 (d, J=3.1 Hz, 1H), 7.63-7.57 (m, 2H), 7.57-7.50 (m, 1H), 6.45 (s, 1H), 3.01 (s, 3H), 1.95 (t, J=19.4 Hz, 3H). m/z [M+H]+ 375.0.

6-bromo-1-(2-chlorophenyl)-7-(1,1-difluoroethyl)-4-(((1S,2R)-2-fluorocyclopropyl)-amino)quinazolin-2(1H)-one was prepared by substituting (1S,2R)-2-fluorocyclopropan-1-amine for methylamine and using 6-bromo-1-(2-chlorophenyl)-7-(1,1-difluoroethyl)quinazoline-2,4(1H,3H)-dione.

1H NMR (400 MHz, DMSO-d6) δ 9.10 (s, 1H), 8.75 (s, 1H), 7.75 (d, J=6.5 Hz, 1H), 7.65-7.54 (m, 2H), 7.50 (d, J=6.6 Hz, 1H), 6.27 (t, J=56.7 Hz, 1H), 5.76 (s, 1H), 3.95 (dq, J=31.0, 15.5, 14.6 Hz, 2H), 2.16 (p, J=7.0, 6.5 Hz, 1H), 1.09 (d, J=7.3 Hz, 2H), 0.41 (s, 2H). m/z [M+H]+ 401.1.

1-(2-chlorophenyl)-4-((cyclopropylmethyl)amino)-2-oxo-7-(trifluoromethyl)-1,2-dihydroquinazoline-6-carbonitrile was prepared by substituting cyclopropylmethanamine for methylamine and using 1-(2-chlorophenyl)-2,4-dioxo-7-(trifluoromethyl)-1,2,3,4-tetrahydroquinazoline-6-carbonitrile.

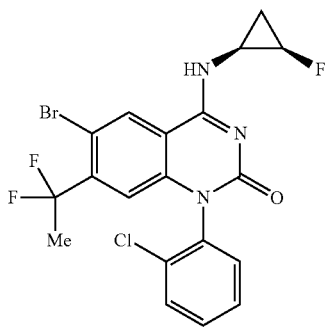 [SMILES: CC(F)(F)c1cc2c(cc1Br)c(N[C@H]1C[C@H]1F)nc(=O)n2-c1ccccc1Cl]

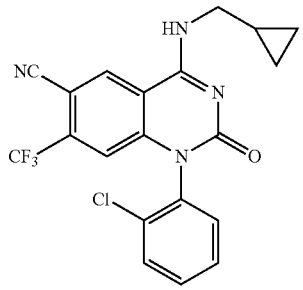

1H NMR (400 MHz, DMSO-d6) δ 8.88 (s, 1H), 8.76 (s, 1H), 7.76 (d, J=4.0 Hz, 1H), 7.58 (s, 2H), 7.08 (s, 1H), 6.47 (s, 1H), 4.89 (d, J=62.4 Hz, 1H), 3.10 (s, 1H), 1.96 (t, J=19.2 Hz, 3H), 1.42-1.21 (m, 2H). m/z [M+H]+ 472.0, 474.0.

6-bromo-1-(2-chlorophenyl)-7-(1,1-difluoroethyl)-4-(methylamino)quinazolin-2(1H)-one was prepared using 6-bromo-1-(2-chlorophenyl)-7-(1,1-difluoroethyl)quinazoline-2,4(1H,3H)-dione.

1H NMR (400 MHz, DMSO-d6) δ 9.18 (s, 1H), 9.12 (s, 1H), 7.78 (d, J=4.2 Hz, 1H), 7.61 (d, J=8.6 Hz, 3H), 6.57 (s, 1H), 3.44 (d, J=14.3 Hz, 2H), 1.26-1.14 (m, 1H), 0.54 (d, J=7.3 Hz, 2H), 0.40-0.29 (m, 2H). m/z [M+H]+ 419.0.

1-(2-chlorophenyl)-4-(methylamino)-2-oxo-7-(trifluoromethyl)-1,2-dihydroquinazoline-6-carbonitrile was prepared by using 1-(2-chlorophenyl)-2,4-dioxo-7-(trifluoromethyl)-1,2,3,4-tetrahydroquinazoline-6-carbonitrile.

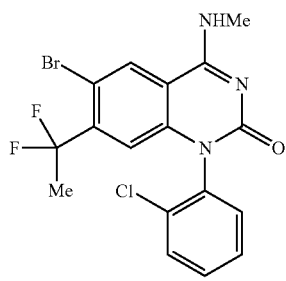 [SMILES: CNc1nc(=O)n(-c2ccccc2Cl)c2cc(C(C)(F)F)c(Br)cc12]

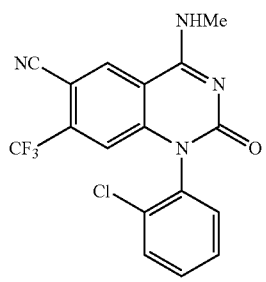 [SMILES: CNc1nc(=O)n(-c2ccccc2Cl)c2cc(C(F)(F)F)c(C#N)cc12]

1H NMR (400 MHz, DMSO-d6) δ 8.93 (s, 1H), 8.61 (s, 1H), 7.75 (dd, J=5.4, 2.3 Hz, 1H), 7.60-7.54 (m, 2H), 7.54-7.49 (m, 1H), 6.96 (s, 1H), 6.45 (s, 1H), 2.99 (s, 3H), 1.96 (t, J=19.0 Hz, 3H). m/z [M+H]+ 428.0, 430.0.

1H NMR (400 MHz, DMSO-d6) δ 9.16 (s, 1H), 8.97 (s, 1H), 7.78 (d, J=4.7 Hz, 1H), 7.65-7.54 (m, 3H), 6.57 (s, 1H), 3.03 (s, 3H). m/z [M+H]+ 379.0.

1-(2-Chlorophenyl)-7-cyclopropyl-4-((1-(hydroxymethyl)cyclopropyl)amino)-2-oxo-1,2-dihydroquinazoline-6-carbonitrile was prepared by substituting (1-aminocyclopropyl)methanol for methylamine and using 1-(2-chlorophenyl)-7-cyclopropyl-2,4-dioxo-1,2,3,4-tetrahydroquinazoline-6-carbonitrile.

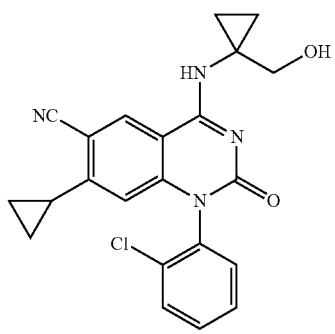 [SMILES: N#Cc1cc2c(NC3(CO)CC3)nc(=O)n(-c3ccccc3Cl)c2cc1C1CC1]

$^1$H NMR (400 MHz, DMSO-d$_6$) δ 8.90 (s, 1H), 8.49 (s, 1H), 7.74 (d, J=6.4 Hz, 1H), 7.57 (dd, J=6.3, 2.4 Hz, 2H), 7.46 (d, J=6.7 Hz, 1H), 5.71 (s, 1H), 4.98 (t, J=4.5 Hz, 1H), 3.90-3.76 (m, 2H), 2.31 (dd, J=20.7, 10.0 Hz, 4H), 2.19-2.09 (m, 1H), 1.90-1.74 (m, 2H), 1.08 (d, J=7.0 Hz, 2H), 0.39 (s, 2H).

4-Amino-1-(2-chlorophenyl)-7-cyclopropyl-2-oxo-1,2-dihydroquinazoline-6-carbonitrile was prepared by substituting ammonia for methylamine and using 1-(2-chlorophenyl)-7-cyclopropyl-2,4-dioxo-1,2,3,4-tetrahydroquinazoline-6-carbonitrile.

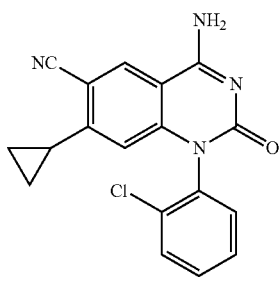 [SMILES: N#Cc1cc2c(N)nc(=O)n(-c3ccccc3Cl)c2cc1C1CC1]

$^1$H NMR (400 MHz, Chloroform-d) δ 8.46 (s, 1H), 7.68 (d, J=7.5 Hz, 1H), 7.55 (dt, J=15.5, 7.4 Hz, 2H), 7.37 (d, J=7.3 Hz, 1H), 5.88 (s, 1H), 2.32-2.23 (m, 1H), 1.15 (d, J=8.3 Hz, 2H), 0.59-0.49 (m, 2H). m/z [M+H]$^+$ 337.0.

1-(2-Chlorophenyl)-7-cyclopropyl-4-(((trans)-2-fluorocyclopropyl)amino)-2-oxo-1,2-dihydroquinazoline-6-carbonitrile was prepared by substituting (trans)-2-fluorocyclopropan-1-amine for methylamine and using 1-(2-chlorophenyl)-7-cyclopropyl-2,4-dioxo-1,2,3,4-tetrahydroquinazoline-6-carbonitrile.

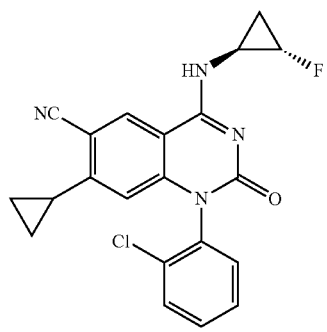 [SMILES: N#Cc1cc2c(N[C@H]3C[C@@H]3F)nc(=O)n(-c3ccccc3Cl)c2cc1C1CC1]

$^1$H NMR (400 MHz, Chloroform-d) δ 8.59 (d, J=12.0 Hz, 1H), 7.63 (d, J=3.9 Hz, 1H), 7.50 (s, 2H), 7.43-7.31 (m, 1H), 5.85 (s, 1H), 5.01-4.75 (m, 1H), 3.45 (d, J=16.0 Hz, 1H), 2.20 (s, 1H), 1.52 (d, J=25.1 Hz, 2H), 1.27 (s, 1H), 1.11 (d, J=7.2 Hz, 2H), 0.52 (s, 2H). m/z [M+H]$^+$ 395.0.

1-(2-Chlorophenyl)-7-cyclopropyl-4-(((1S,2R)-2-fluorocyclopropyl)amino)-2-oxo-1,2-dihydroquinazoline-6-carbonitrile was prepared by substituting (1S,2R)-2-fluorocyclopropan-1-amine for methyl amine and using 1-(2-chlorophenyl)-7-cyclopropyl-2,4-dioxo-1,2,3,4-tetrahydroquinazoline-6-carbonitrile.

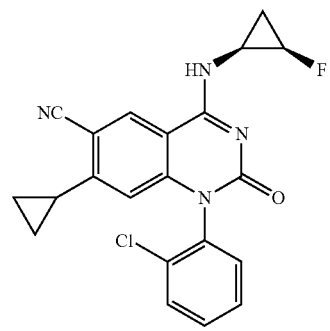

$^1$H NMR (400 MHz, DMSO-d$_6$) δ 8.75 (d, J=11.5 Hz, 2H), 7.75 (d, J=6.5 Hz, 1H), 7.58 (d, J=8.3 Hz, 2H), 7.56-7.45 (m, 1H), 5.76 (s, 1H), 4.88 (d, J=66.7 Hz, 1H), 3.09 (d, J=7.3 Hz, 1H), 2.20-2.09 (m, 1H), 1.40-1.20 (m, 2H), 1.09 (d, J=8.0 Hz, 2H), 0.41 (s, 2H). m/z [M+H]$^+$ 395.0.

6-Bromo-1-(2-chlorophenyl)-7-cyclopropyl-4-(((1S,2R)-2-fluorocyclopropyl)amino)-quinazolin-2(1H)-one was prepared by substituting (1S,2R)-2-fluorocyclopropan-1-amine for methylamine and using 6-bromo-1-(2-chlorophenyl)-7-cyclopropylquinazoline-2,4(1H,3H)-dione.

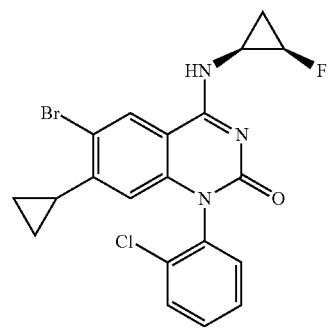 [SMILES: O=c1nc(N[C@H]2C[C@H]2F)c2cc(Br)c(C3CC3)cc2n1-c1ccccc1Cl]

$^1$H NMR (400 MHz, Chloroform-d) δ 7.77 (s, 1H), 7.64-7.58 (m, 1H), 7.50-7.42 (m, 2H), 7.34 (d, J=3.3 Hz, 1H), 6.16 (s, 1H), 5.93 (s, 1H), 4.85 (d, J=63.8 Hz, 1H), 3.35 (s, 1H), 2.11 (p, J=7.0 Hz, 1H), 1.33 (dd, J=16.0, 7.5 Hz, 1H), 1.20-1.04 (m, 1H), 0.98 (d, J=8.0 Hz, 2H), 0.46-0.36 (m, 2H). m/z [M+H]$^+$ 448.0/450.0.

7-(1,1-Difluoroethyl)-1-(imidazo[1,2-a]pyridin-7-yl)-4-(methylamino)quinazolin-2(1H)-one was prepared by using 7-(1,1-difluoroethyl)-1-(imidazo[1,2-a]pyridin-7-yl)quinazoline-2,4(1H,3H)-dione.

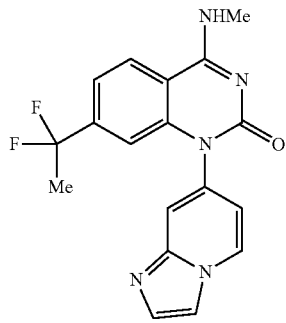 [SMILES: CNc1nc(=O)n(-c2ccn3ccnc3c2)c2cc(C(C)(F)F)ccc12]

¹H NMR (400 MHz, DMSO-d₆) δ 8.73 (d, J=7.4 Hz, 2H), 8.23 (d, J=8.6 Hz, 1H), 8.08 (s, 1H), 7.69 (s, 1H), 7.64 (s, 1H), 7.41 (d, J=7.9 Hz, 1H), 6.85 (d, J=7.1 Hz, 1H), 6.73 (s, 1H), 3.03-2.95 (m, 3H), 1.87 (t, J=19.0 Hz, 3H). m/z [M+H]⁺ 356.0.

4-Amino-7-(1,1-difluoroethyl)-1-(imidazo[1,2-a]pyridin-7-yl)quinazolin-2(1H)-one was prepared by substituting ammonia for methylamine and using 7-(1,1-difluoroethyl)-1-(imidazo[1,2-a]pyridin-7-yl)quinazoline-2,4(1H,3H)-dione.

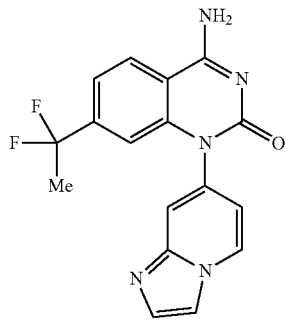 [SMILES: CC(F)(F)c1ccc2c(N)nc(=O)n(-c3ccn4ccnc4c3)c2c1]

¹H NMR (400 MHz, DMSO-d₆) δ 8.72 (d, J=7.4 Hz, 1H), 8.26 (d, J=8.6 Hz, 2H), 8.15 (s, 1H), 8.08 (s, 1H), 7.69 (s, 1H), 7.64 (s, 1H), 7.39 (d, J=7.9 Hz, 1H), 6.85 (d, J=7.4 Hz, 1H), 6.72 (s, 1H), 1.87 (t, J=19.1 Hz, 3H). m/z [M+H]⁺ 342.1.

1-(3-Chloropyridin-2-yl)-7-(1,1-difluoroethyl)-4-(methylamino)quinazolin-2(1H)-one was prepared by using 1-(3-chloropyridin-2-yl)-7-(1,1-difluoroethyl)quinazoline-2,4(1H,3H)-dione.

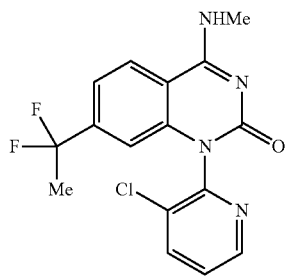 [SMILES: CNc1nc(=O)n(-c2ncccc2Cl)c2cc(C(C)(F)F)ccc12]

¹H NMR (400 MHz, DMSO-d₆) δ 8.93-8.84 (m, 1H), 8.67 (d, J=4.4 Hz, 1H), 8.28 (d, J=8.6 Hz, 2H), 7.70-7.63 (m, 1H), 7.46 (d, J=8.3 Hz, 1H), 6.32 (s, 1H), 3.02 (d, J=3.3 Hz, 3H), 1.88 (t, J=19.0 Hz, 3H). m/z [M+H]⁺ 351.0.

4-Amino-1-(3-chloropyridin-2-yl)-7-(1,1-difluoroethyl)quinazolin-2(1H)-one was prepared by substituting ammonia for methylamine and using 1-(3-chloropyridin-2-yl)-7-(1,1-difluoroethyl)quinazoline-2,4(1H,3H)-dione.

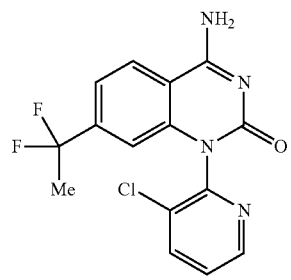 [SMILES: CC(F)(F)c1ccc2c(N)nc(=O)n(-c3ncccc3Cl)c2c1]

¹H NMR (400 MHz, DMSO-d₆) δ 8.67 (d, J=4.4 Hz, 1H), 8.41 (s, 1H), 8.30 (t, J=8.9 Hz, 3H), 7.70-7.64 (m, 1H), 7.44 (d, J=8.4 Hz, 1H), 6.32 (s, 1H), 1.88 (t, J=19.0 Hz, 3H). m/z [M+H]⁺ 337.0.

1-(3-Chloropyridin-2-yl)-7-ethyl-4-(methylamino)quinazolin-2(1H)-one was prepared by using 1-(3-chloropyridin-2-yl)-7-ethylquinazoline-2,4(1H,3H)-dione.

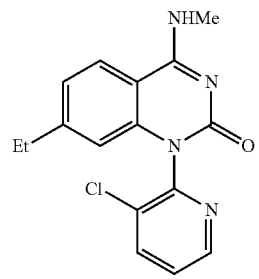 [SMILES: CCc1ccc2c(NC)nc(=O)n(-c3ncccc3Cl)c2c1]

¹H NMR (400 MHz, DMSO-d₆) δ 8.61 (t, J=5.8 Hz, 2H), 8.22 (d, J=8.1 Hz, 1H), 8.02 (d, J=8.6 Hz, 1H), 7.65-7.57 (m, 1H), 7.09 (d, J=7.8 Hz, 1H), 6.02 (s, 1H), 2.96 (d, J=3.9 Hz, 3H), 2.51 (s, 2H), 1.01 (t, J=7.4 Hz, 3H). m/z [M+H]⁺ 315.0.

1-(2-Chlorophenyl)-7-(1,1-difluoroethyl)-4-(methylamino)quinazolin-2(1H)-one was prepared using 1-(2-chlorophenyl)-7-(1,1-difluoroethyl)quinazoline-2,4(1H,3H)-dione.

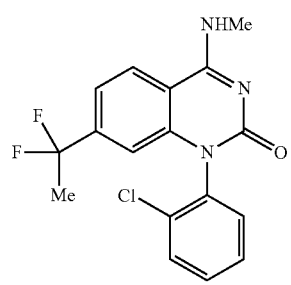 [SMILES: CNc1nc(=O)n(-c2ccccc2Cl)c2cc(C(C)(F)F)ccc12]

¹H NMR (400 MHz, DMSO-d₆) δ 8.80-8.74 (m, 1H), 8.23 (d, J=8.5 Hz, 1H), 7.76-7.70 (m, 1H), 7.59-7.53 (m,

2H), 7.49 (d, J=3.1 Hz, 1H), 7.41 (d, J=9.2 Hz, 1H), 6.35 (s, 1H), 2.99 (d, J=3.5 Hz, 3H), 1.85 (t, J=18.9 Hz, 3H). m/z [M+H]⁺ 350.1.

1-(2-Chlorophenyl)-7-(1,1-difluoroethyl)-4-(isoxazol-4-ylamino)quinazolin-2(1H)-one was prepared by substituting isoxazol-4-amine for methylamine and using 1-(2-chlorophenyl)-7-(1,1-difluoroethyl)quinazoline-2,4(1H,3H)-dione.

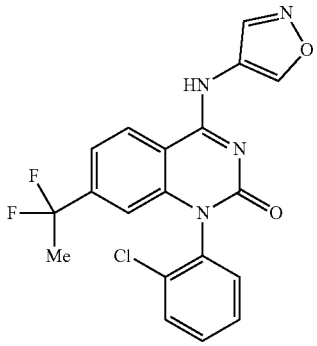 [SMILES: CC(F)(F)c1ccc2c(Nc3cnoc3)nc(=O)n(-c3ccccc3Cl)c2c1]

¹H NMR (400 MHz, DMSO-d₆) δ 9.44 (s, 1H), 8.88 (s, 1H), 8.44 (d, J=8.0 Hz, 1H), 7.79-7.74 (m, 1H), 7.62-7.50 (m, 4H), 6.41 (s, 1H), 1.87 (t, J=18.8 Hz, 3H). m/z [M+H]⁺ 403.0.

1-(2-Chlorophenyl)-7-(1,1-difluoroethyl)-4-(amino)quinazolin-2(1H)-one was prepared by substituting ammonia for methylamine and using 1-(2-chlorophenyl)-7-(1,1-difluoroethyl)quinazoline-2,4(1H,3H)-dione.

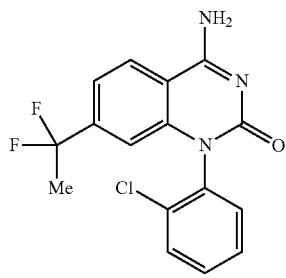 [SMILES: CC(F)(F)c1ccc2c(N)nc(=O)n(-c3ccccc3Cl)c2c1]

¹H NMR (400 MHz, DMSO-d₆) δ 8.34-8.24 (m, 2H), 8.18 (s, 1H), 7.76-7.70 (m, 1H), 7.59-7.53 (m, 2H), 7.53-7.47 (m, 1H), 7.39 (d, J=8.4 Hz, 1H), 6.34 (s, 1H), 1.85 (t, J=18.9 Hz, 3H). m/z [M+H]⁺ 336.1.

1-(2-Chlorophenyl)-4-(methylamino)-7-(trifluoromethoxy)quinazolin-2(1H)-one was prepared using 1-(2-chlorophenyl)-7-(trifluoromethoxy)quinazoline-2,4(1H,3H)-dione.

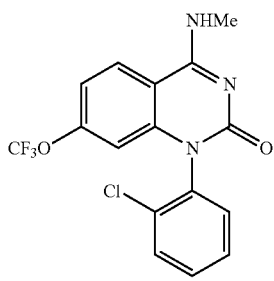

¹H NMR (400 MHz, DMSO-d₆) δ 8.78 (d, J=3.5 Hz, 1H), 8.25 (d, J=8.5 Hz, 1H), 7.76-7.70 (m, 1H), 7.60-7.52 (m, 2H), 7.52-7.46 (m, 1H), 7.24 (d, J=8.4 Hz, 1H), 6.07 (s, 1H), 2.98 (d, J=3.3 Hz, 3H). m/z [M+H]⁺ 370.1.

7-Chloro-1-(imidazo[1,2-a]pyridin-5-yl)-4-(methylamino)quinazolin-2(1H)-one was prepared using 7-chloro-1-(imidazo[1,2-a]pyridin-5-yl)quinazoline-2,4(1H,3H)-dione.

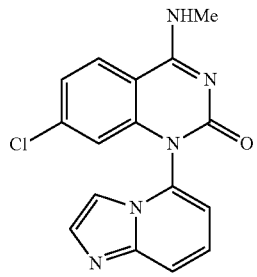 [SMILES: CNc1nc(=O)n(-c2cccc3nccn23)c2cc(Cl)ccc12]

¹H NMR (400 MHz, DMSO-d₆) δ 8.90 (s, 1H), 8.17 (d, J=8.3 Hz, 1H), 7.76 (d, J=8.3 Hz, 1H), 7.63 (s, 1H), 7.57 (s, 1H), 7.45-7.39 (m, 1H), 7.36 (d, J=8.5 Hz, 1H), 7.11 (d, J=6.9 Hz, 1H), 6.33 (s, 1H), 3.01 (d, J=3.5 Hz, 3H). m/z [M+H]⁺ 326.0.

7-chloro-4-((2,2-difluoroethyl)amino)-1-(imidazo[1,2-a]pyridin-7-yl)quinazolin-2(1H)-one was prepared by substituting 2,2-difluoroethan-1-amine for methylamine and using 7-chloro-1-(imidazo[1,2-a]pyridin-7-yl)quinazoline-2,4(1H,3H)-dione.

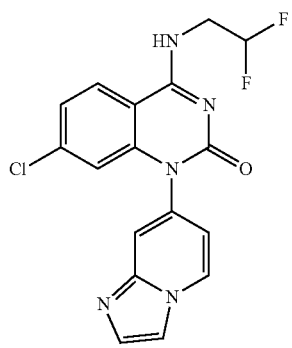 [SMILES: O=c1nc(NCC(F)F)c2ccc(Cl)cc2n1-c1ccn2ccnc2c1]

¹H NMR (400 MHz, DMSO-d₆) δ 8.97 (t, J=6.2 Hz, 1H), 8.71 (d, J=7.6 Hz, 1H), 8.21 (d, J=8.9 Hz, 1H), 8.07 (s, 1H), 7.68 (s, 1H), 7.64 (s, 1H), 7.34 (d, J=8.8 Hz, 1H), 6.84 (d, J=7.0 Hz, 1H), 6.70 (s, 1H), 6.43-6.09 (m, 1H), 3.92 (t, J=14.6 Hz, 2H). m/z [M+H]⁺ 376.0.

7-chloro-1-(imidazo[1,2-a]pyridin-7-yl)-4-(methylamino)quinazolin-2(1H)-one was prepared by using 7-chloro-1-(imidazo[1,2-a]pyridin-7-yl)quinazoline-2,4(1H,3H)-dione.

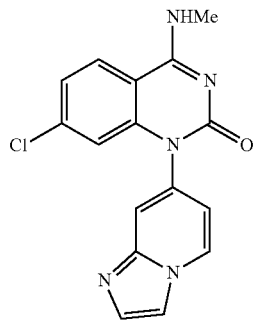 [SMILES: CNc1nc(=O)n(-c2ccn3ccnc3c2)c2cc(Cl)ccc12]

¹H NMR (400 MHz, DMSO-d₆) δ 8.70 (dd, J=11.0, 5.5 Hz, 2H), 8.13 (s, 1H), 8.07 (s, 1H), 7.68 (s, 1H), 7.62 (s, 1H), 7.30 (d, J=8.7 Hz, 1H), 6.83 (d, J=7.0 Hz, 1H), 6.66 (s, 1H), 2.98 (d, J=3.7 Hz, 3H). m/z [M+H]⁺ 326.0.

7-bromo-1-(2-chlorophenyl)-6-fluoro-4-(methylamino)quinazolin-2(1H)-one was prepared using 7-bromo-1-(2-chlorophenyl)-6-fluoroquinazoline-2,4(1H,3H)-dione.

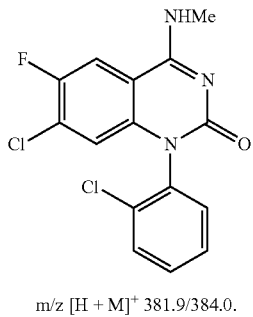 [SMILES: CNc1nc(=O)n(-c2ccccc2Cl)c2cc(Cl)c(F)cc12]

m/z [H + M]⁺ 381.9/384.0.

(R)-1-(2-Bromophenyl)-7-chloro-4-(3-hydroxypyrrolidin-1-yl)quinazolin-2(1H)-one was prepared by using (R)-pyrrolidin-3-ol and 1-(2-bromophenyl)-7-chloroquinazoline-2,4(1H,3H)-dione.

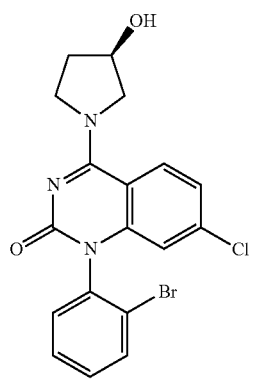 [SMILES: O=c1nc(N2CC[C@@H](O)C2)c2ccc(Cl)cc2n1-c1ccccc1Br]

¹H NMR (400 MHz, DMSO-d₆) δ 8.22 (br s, 1H), 7.90-7.88 (m, 1H), 7.63-7.59 (m, 1H), 7.51-7.46 (m, 2H), 7.26-7.23 (m, 1H), 6.21 (dd, J=4.4, 2.0 Hz, 1H), 5.13 (dd, J=11.6, 3.2 Hz, 1H), 4.42 (s, 1H), 4.02-3.90 (m, 3H), 3.71-3.68 (m, 1H), 3.05-2.98 (m, 2H). m/z [M+H]⁺ 420.0.

1-(2-Chlorophenyl)-4-(((trans)-2-fluorocyclopropyl)amino)-7-(trifluoromethyl)pyrido[2,3-d]pyrimidin-2(1H)-one—single enantiomer with unknown stereochemistry was prepared by using trans-2-fluorocyclopropan-1-amine and using 1-(2-chlorophenyl)-7-(trifluoromethyl)pyrido[2,3-d]pyrimidine-2,4(1H,3H)-dione. SFC purification (20% MeOH, R,R WHELK-01, peak 1)

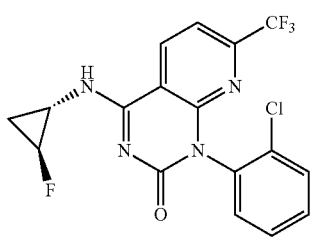 [SMILES: O=c1nc(N[C@H]2C[C@@H]2F)c2ccc(C(F)(F)F)nc2n1-c1ccccc1Cl]

¹H NMR (400 MHz, DMSO-d₆) δ 8.93 (d, J=10.8 Hz, 1H), 8.77 (d, J=8.0 Hz, 1H), 7.79 (d, J=8.0 Hz, 1H), 7.66-7.63 (m, 1H), 7.50-7.44 (m, 3H), 4.96-4.79 (m, 1H), 3.50-3.47 (m, 1H), 1.61-1.51 (m, 1H), 1.27-1.24 (m, 1H). m/z [M+H]⁺ 399.4.

1-(2-Chlorophenyl)-4-(((trans)-2-fluorocyclopropyl)amino)-7-(trifluoromethyl)pyrido[2,3-d]pyrimidin-2(1H)-one—single enantiomer with unknown stereochemistry was prepared by using trans-2-fluorocyclopropan-1-amine and 1-(2-chlorophenyl)-7-(trifluoromethyl)pyrido[2,3-d]pyrimidine-2,4(1H,3H)-dione. SFC purification (20% MeOH, R,R WHELK-01, peak 2)

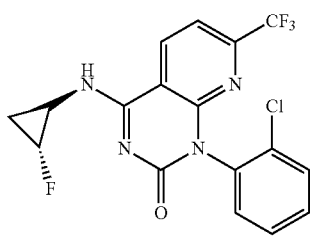

¹H NMR (400 MHz, DMSO-d₆) δ 8.93 (d, J=10.8 Hz, 1H), 8.77 (d, J=8.0 Hz, 1H), 7.79 (d, J=8.0 Hz, 1H), 7.66-7.63 (m, 1H), 7.50-7.44 (m, 3H), 4.96-4.79 (m, 1H), 3.50-3.47 (m, 1H), 1.61-1.51 (m, 1H), 1.27-1.24 (m, 1H). m/z [M+H]⁺ 399.4.

1-(2-Chloropyridin-3-yl)-4-(methylamino)-7-(trifluoromethyl)pyrido[2,3-d]pyrimidin-2(1H)-one was prepared by using 1-(2-chloropyridin-3-yl)-7-(trifluoromethyl)pyrido[2,3-d]pyrimidine-2,4(1H,3H)-dione.

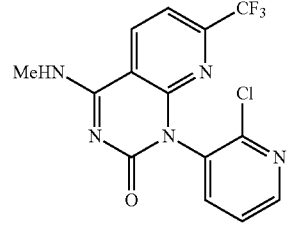 [SMILES: CNc1nc(=O)n(-c2cccnc2Cl)c2nc(C(F)(F)F)ccc12]

¹H NMR (400 MHz, DMSO-d₆) δ 9.19 (s, 1H), 8.81 (s, J=8.0 Hz, 1H), 8.50 (dd, J=4.5 Hz, J=1.5 Hz, 1H), 7.99 (dd, J=8.0 Hz, 2.0 Hz, 1H), 7.84 (d, J=8.5 Hz, 1H), 7.62 (m, 1H), 3.04 (s, 3H). m/z [M+H]⁺ 356.3

4-(Methylamino)-7-(trifluoromethyl)-1-(2-(trifluoromethyl)pyridin-3-yl)pyrido[2,3-d]pyrimidin-2(1H)-one was prepared by using 7-(trifluoromethyl)-1-(2-(trifluoromethyl)pyridin-3-yl)pyrido[2,3-d]pyrimidine-2,4(1H,3H)-dione.

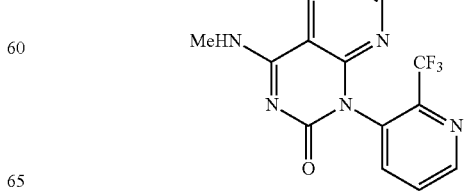

¹H NMR (500 MHz, DMSO-d₆) δ 9.20 (d, J=4.5 Hz, 1H), 8.85-8.81 (m, 2H), 8.08 (d, J=8.0 Hz, 1H), 7.93 (dd, J=8.0, 4.5 Hz, 1H), 7.83 (d, J=8.0 Hz, 1H), 3.04 (d, J=4.5 Hz, 3H). m/z [M+H]⁺ 390.4.

7-Cyclopropyl-1-(2-methylpyridin-3-yl)-4-((3-morpholinopropyl)amino)quinazolin-2(1H)-one was prepared by using 3-morpholinopropan-1-amine and 7-cyclopropyl-1-(2-methylpyridin-3-yl)quinazoline-2,4(1H,3H)-dione.

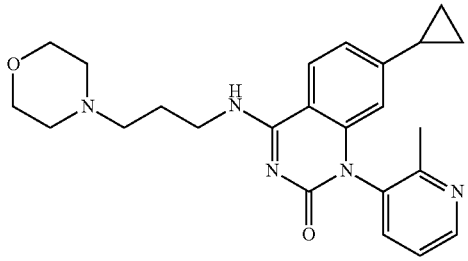 [SMILES: Cc1ncccc1-n1c(=O)nc(NCCCN2CCOCC2)c2ccc(C3CC3)cc21]

¹H NMR (500 MHz, DMSO-d₆) δ 8.57 (dd, J=5.0, 1.5 Hz, 1H), 8.46 (t, J=5.5 Hz, 1H), 8.03 (d, J=8.5 Hz 1H), 7.66 (dd, J=8.0, 1.5 Hz, 1H), 7.45-7.42 (m, 1H), 6.82 (dd, J=8.5, 1.5 Hz, 1H), 6.03 (s, 1H), 3.58-3.49 (m, 6H), 2.39-2.36 (m, 6H), 2.13 (s, 3H), 1.84-1.80 (m, 3H), 0.94-0.92 (m, 2H), 0.62-0.57 (m, 2H). m/z [M+H]⁺ 420.31.

3-((7-Cyclopropyl-1-(2-methylpyridin-3-yl)-2-oxo-1,2-dihydroquinazolin-4-yl)amino)-N-methylpropanamide was prepared by using 3-amino-N-methylpropanamide and 7-cyclopropyl-1-(2-methylpyridin-3-yl)quinazoline-2,4(1H,3H)-dione.

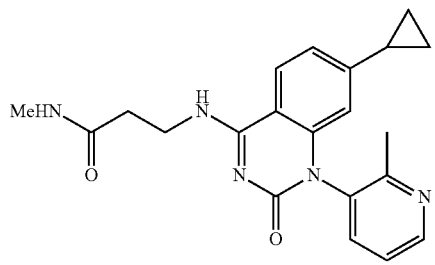 [SMILES: CNC(=O)CCNc1nc(=O)n(-c2cccnc2C)c2cc(C3CC3)ccc12]

¹H NMR (400 MHz, DMSO-d₆) δ 9.74 (br s, 1H), 8.75 (dd, 4.8, 1.2 Hz 1H), 8.00 (d, J=8.8 Hz, 1H), 7.66 (dd, J=8, 1.6 Hz, 1H), 7.47 (dd, 8.0, 5.2 Hz, 1H), 6.83 (dd, J=8.4, 1.2 Hz, 1H), 6.76 (br s, 1H), 6.13 (s, 1H), 4.01 (t, J=5.6 Hz, 2H), 2.83 (d, J=4.8 Hz, 3H), 2.79 (t, J=5.6 Hz, 2H), 2.40 (s, 3H), 1.79-1.75 (m, 1H), 1.07-1.02 (m, 2H), 0.69-0.65 (m, 2H). m/z [M+H]⁺ 378.47.

2-((7-Cyclopropyl-1-(2-methylpyridin-3-yl)-2-oxo-1,2-dihydroquinazolin-4-yl)amino)-N,N-dimethylethane-1-sulfonamide was prepared by using 2-amino-N,N-dimethylethane-1-sulfonamide and 7-cyclopropyl-1-(2-methylpyridin-3-yl)quinazoline-2,4(1H,3H)-dione.

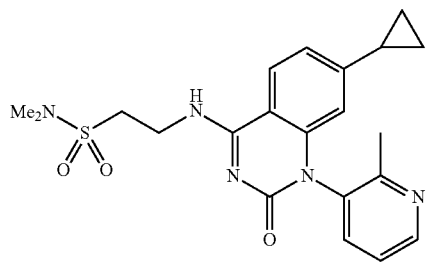 [SMILES: Cc1ncccc1-n1c(=O)nc(NCCS(=O)(=O)N(C)C)c2ccc(C3CC3)cc21]

¹H NMR (500 MHz, DMSO-d₆) δ 8.67 (t, J=5.5 Hz, 1H), 8.60-8.58 (dd, J=5, 1.5 Hz, 1H), 7.97 (d, J=8.58.5 Hz, 1H), 7.69-7.67 (dd, J=8, 1.5 Hz, 1H), 7.49-7.47 (m, 1H), 6.87-6.85 (dd, J=8.5, 1.5 Hz, 1H), 3.90-3.84 (m, 2H), 3.46-3.42 (m, 2H), 2.81 (s, 6H), 2.15 (s, 3H), 1.85-1.82 (m, 1H), 0.98-0.95 (m, 2H), 0.63-0.58 (m, 2H). m/z [M+H]⁺ 428.49.

7-Cyclopropyl-4-((2-(dimethylamino)ethyl)amino)-1-(2-methylpyridin-3-yl)quinazolin-2(1H)-one was prepared by using N1,N1-dimethylethane-1,2-diamine and 7-cyclopropyl-1-(2-methylpyridin-3-yl)quinazoline-2,4(1H,3H)-dione.

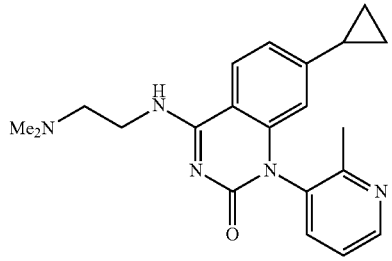 [SMILES: Cc1ncccc1-n1c(=O)nc(NCCN(C)C)c2ccc(C3CC3)cc21]

¹H NMR (500 MHz, DMSO-d₆) δ 8.57 (dd, J=4.5, 1.5 Hz, 1H), 8.38 (t, J=5 Hz, 1H), 8.03 (d, J=8.5 Hz 1H), 7.66 (dd, J=8.0, 1.5 Hz, 1H), 7.44 (dd, J=8.0, 5 Hz, 1H), 6.83 (dd, J=8.5, 1.5 Hz, 1H), 6.03 (s, 1H), 3.66-3.53 (m, 2H), 2.54-2.50 (m, 2H), 2.23 (s, 6H), 2.10 (s, 3H), 1.85-1.81 (m, 1H), 0.94-0.92 (m, 2H), 0.62-0.58 (m, 2H). m/z [M−H]⁺ 362.52.

3-((1-(2-Chlorophenyl)-2-oxo-7-(trifluoromethyl)-1,2-dihydropyrido[2,3-d]pyrimidin-4-yl)amino)-N-methylpropanamide was prepared by using 3-amino-N-methylpropanamide and 1-(2-chlorophenyl)-7-(trifluoromethyl)pyrido[2,3-d]pyrimidine-2,4(1H,3H)-dione.

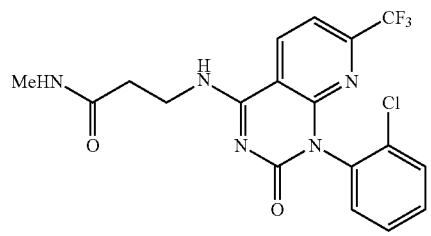 [SMILES: CNC(=O)CCNc1nc(=O)n(-c2ccccc2Cl)c2nc(C(F)(F)F)ccc12]

¹H NMR (500 MHz, DMSO-d₆), 9.13 (s, 1H), 8.85 (d, J=8.0 Hz, 1H), 7.91 (d, J=4.0 Hz, 1H), 7.79 (d, J=8.5 Hz, 1H), 7.65-7.63 (m, 1H), 7.49-7.43 (m, 3H), 3.72-3.72 (m, 2H), 2.60 (d, J=4.5 Hz, 3H), 2.54-2.52 (m, 2H). m/z [M+H]⁺ 426.4.

2-((1-(2-chlorophenyl)-2-oxo-7-(trifluoromethyl)-1,2-dihydropyrido[2,3-d]pyrimidin-4-yl)amino)-N,N-dimethylethanesulfonamide was prepared by using 2-amino-N,N-dimethylethane-1-sulfonamide and 1-(2-chlorophenyl)-7-(trifluoromethyl)pyrido[2,3-d]pyrimidine-2,4(1H,3H)-dione.

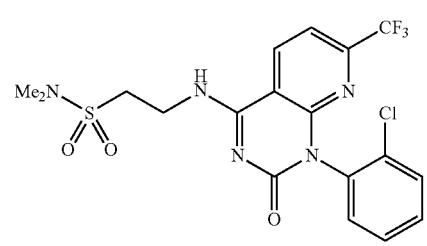 [SMILES: CN(C)S(=O)(=O)CCNc1nc(=O)n(-c2ccccc2Cl)c2nc(C(F)(F)F)ccc12]

¹H NMR (500 MHz, DMSO-d₆): δ 8.98 (br s, 1H), 8.85 (d, J=10 Hz, 1H), 7.80 (d, J=10 Hz, 1H), 7.64-7.61 (m, 1H), 7.49-7.43 (m, 3H), 3.69-3.65 (m, 2H), 3.58 (t, J=5.5 Hz, 4H), 2.62 (d, J=8.5 Hz, 2H), 2.5 (m, 4H).

4-(((trans)-2-fluorocyclopropyl)amino)-5-methoxy-1-phenyl-7-(trifluoromethyl)quinazolin-2(1H)-one, single unknown enantiomer was prepared by using trans-2-fluorocyclopropan-1-amine and 5-methoxy-1-phenyl-7-(trifluoromethyl)quinazoline-2,4(1H,3H)-dione. SFC purification (40% MeOH, Chiralpak IC, peak 1).

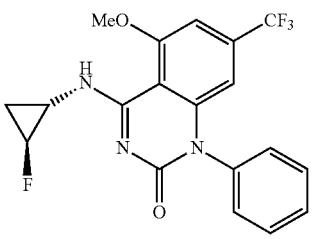

¹H NMR (500 MHz, DMSO-d₆), 8.27 (s, 1H), 7.62-7.59 (m, 2H), 7.55-7.51 (m, 1H), 7.33-7.31 (m, 2H), 7.07 (d, J=1.0 Hz, 1H), 6.14 (d, J=1.0 Hz, 1H), 5.01-4.86 (m, 1H), 4.08 (s, 3H), 3.43-3.41 (m, 1H), 1.54-1.47 (m, 1H), 1.30-1.23 (m, 1H). m/z [M+H]⁺ 394.4.

4-(((trans)-2-fluorocyclopropyl)amino)-5-methoxy-1-phenyl-7-(trifluoromethyl)quinazolin-2(1H)-one, single unknown enantiomer was prepared by using trans-2-fluorocyclopropan-1-amine and 5-methoxy-1-phenyl-7-(trifluoromethyl)quinazoline-2,4(1H,3H)-dione. SFC purification (40% MeOH, Chiralpak IC, peak 2).

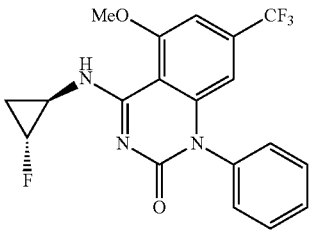 [SMILES: COc1cc(C(F)(F)F)cc2c1c(N[C@@H]1C[C@H]1F)nc(=O)n2-c1ccccc1]

¹H NMR (500 MHz, DMSO-d₆) δ 8.27 (s, 1H), 7.62-7.59 (m, 2H), 7.55-7.51 (m, 1H), 7.33-7.31 (m, 2H), 7.07 (d, J=1.0 Hz, 1H), 6.14 (d, J=1.0 Hz, 1H), 5.01-4.86 (m, 1H), 4.08 (s, 3H), 3.43-3.41 (m, 1H), 1.54-1.47 (m, 1H), 1.30-1.23 (m, 1H). m/z [M+H]⁺ 394.4.

7-Cyclopropyl-4-(methylamino)-2-oxo-1-(2-(trifluoromethyl)phenyl)-1,2-dihydroquinazoline-6-carbonitrile was prepared by using 7-cyclopropyl-2,4-dioxo-1-(2-(trifluoromethyl)phenyl)-1,2,3,4-tetrahydroquinazoline-6-carbonitrile.

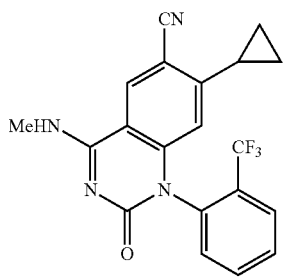 [SMILES: CNc1nc(=O)n(-c2ccccc2C(F)(F)F)c2cc(C3CC3)c(C#N)cc12]

¹H NMR (500 MHz, DMSO-d₆) δ 8.79 (d, J=4 Hz, 1H), 8.59 (s, 1H), 7.98 (d, J=7.5 Hz, 1H), 7.91 (t, J=7.5 Hz, 1H), 7.78 (t, J=8 Hz, 1H), 7.52 (d, J=8 Hz, 1H), 5.65 (s, 1H), 2.99 (s, 3H), 2.14-2.11 (m, 1H), 1.08-1.03 (m, 2H), 0.40-0.37 (dd, J=10.5, 2 Hz, 2H). m/z [M+H]⁺ 385.44.

7-Cyclopropyl-1-(2-cyclopropylphenyl)-4-(methylamino)-2-oxo-1,2-dihydroquinazoline-6-carbonitrile was prepared by using 7-cyclopropyl-1-(2-cyclopropylphenyl)-2,4-dioxo-1,2,3,4-tetrahydroquinazoline-6-carbonitrile.

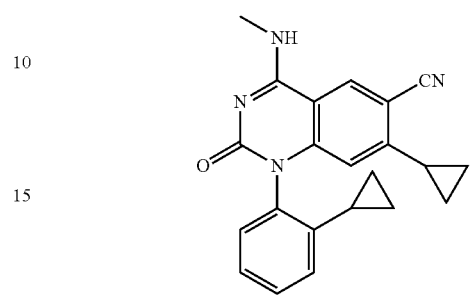

¹H NMR (500 MHz, DMSO-d₆), 8.69 (d, J=4.0 Hz, 1H), 8.58 (s, 1H), 7.44-7.41 (m, 1H), 7.36-7.33 (m, 1H), 7.16-7.11 (m, 2H), 5.76 (s, 1H), 2.98 (d, J=4.0 Hz, 3H), 2.13-2.11 (m, 1H), 1.40-1.39 (m, 1H), 1.09-1.04 (m, 2H), 0.79-0.71 (m, 2H), 0.59-0.57 (m, 1H), 0.36-0.31 (m, 3H). m/z [M+H]⁺ 357.40.

1-(2-Bromophenyl)-7-cyclopropyl-4-(methylamino)-2-oxo-1,2-dihydroquinazoline-6-carbonitrile, single unknown atropisomer was prepared by using 1-(2-bromophenyl)-7-cyclopropyl-2,4-dioxo-1,2,3,4-tetrahydroquinazoline-6-carbonitrile. SFC purification (30% MeOH, (R,R) WHELK-01, peak 1).

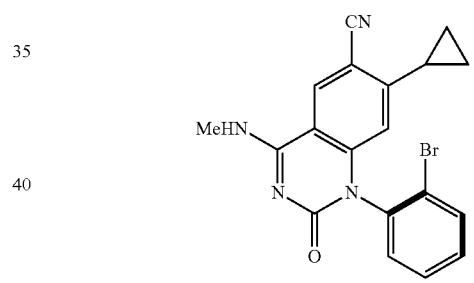

¹H NMR (500 MHz, DMSO-d₆) δ 8.79 (s, 1H), 8.60 (s, 1H), 7.88 (dd, 8.0, 1.0 Hz 1H), 7.62-7.59 (m, 1H), 7.51-7.45 (m, 2H), 5.71 (s, 1H), 2.98 (s, 3H), 2.16-2.11 (m, 1H), 1.09-1.05 (m, 2H), 0.42-0.39 (m, 2H). m/z [M+H]⁺ 395.41.

1-(2-Bromophenyl)-7-cyclopropyl-4-(methylamino)-2-oxo-1,2-dihydroquinazoline-6-carbonitrile, single unknown atropisomer was prepared by using 1-(2-bromophenyl)-7-cyclopropyl-2,4-dioxo-1,2,3,4-tetrahydroquinazoline-6-carbonitrile. SFC purification (30% MeOH, (R,R) WHELK-01, peak 2).

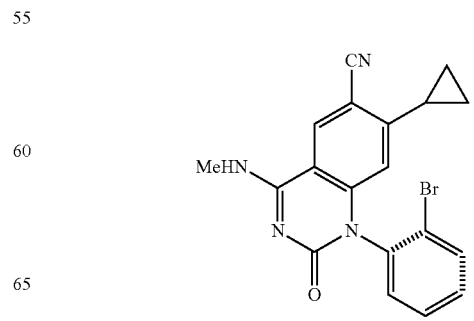

¹H NMR (500 MHz, DMSO-d₆) δ 8.79 (s, 1H), 8.60 (s, 1H), 7.88 (dd, 8.0, 1.0 Hz 1H), 7.62-7.59 (m, 1H), 7.51-7.45 (m, 2H), 5.71 (s, 1H), 2.98 (s, 3H), 2.16-2.11 (m, 1H), 1.09-1.05 (m, 2H), 0.42-0.39 (m, 2H). m/z [M+H]⁺ 395.41.

6-Bromo-7-cyclopropyl-4-(methylamino)-1-(2-(trifluoromethyl)pyridin-3-yl)quinazolin-2(1H)-one was prepared by using 6-bromo-7-cyclopropyl-1-(2-(trifluoromethyl)pyridin-3-yl)quinazoline-2,4(1H,3H)-dione.

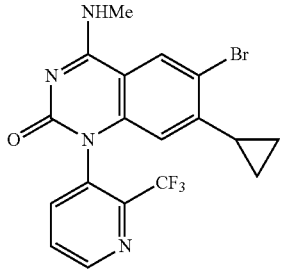 [SMILES: CNc1nc(=O)n(-c2cccnc2Cl)c2cc(C3CC3)c(Br)cc12]

¹H NMR (500 MHz, DMSO-d₆) δ 8.92-8.91 (m, 1H), 8.75 (d, J=4.0 Hz, 1H), 8.45 (s, 1H), 8.10-8.08 (m, 1H), 7.98 (dd, J=8.0, 5.0 Hz, 1H), 5.70 (s, 1H), 2.97 (d, J=4.5 Hz, 3H), 2.10-2.05 (m, 1H), 0.99-0.95 (m, 2H), 0.35-0.28 (m, 2H). m/z [M+H]⁺ 439.4.

6-Bromo-1-(2-chloropyridin-3-yl)-7-cyclopropyl-4-(methylamino)quinazolin-2(1H)-one was prepared by using 6-bromo-1-(2-chloropyridin-3-yl)-7-cyclopropylquinazoline-2,4(1H,3H)-dione.

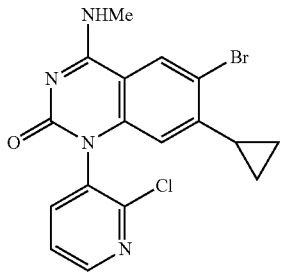

¹H NMR (500 MHz, DMSO-d₆) δ 8.75 (d, J=4.5 Hz, 1H), 8.58 (dd, J=5.0, 2.0 Hz, 1H), 8.46 (s, 1H), 8.02 (dd, J=8.0, 2.0 Hz, 1H), 7.67 (dd, J=8.0, 5.0 Hz, 1H), 5.78 (s, 1H), 2.97 (d, J=4.5 Hz, 3H), 2.11-2.06 (m, 1H), 1.00-0.96 (m, 2H), 0.37-0.34 (m, 2H). m/z [M+H]⁺ 405.2.

1-(2-Chlorophenyl)-6-(difluoromethyl)-4-(methylamino)-7-(trifluoromethyl)quinazolin-2(1H)-one was prepared by using 1-(2-Chlorophenyl)-6-(difluoromethyl)-7-(trifluoromethyl) quinazoline-2,4(1H,3H)-dione.

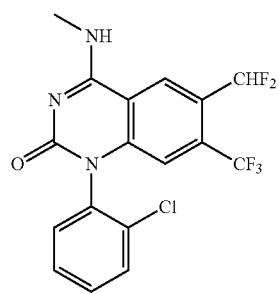 [SMILES: CNc1nc(=O)n(-c2ccccc2Cl)c2cc(C(F)(F)F)c(C(F)F)cc12]

¹H NMR (500 MHz, DMSO-d₆) δ 9.19 (d, J=4.5 Hz, 1H), 8.74 (s, 1H), 7.79-7.77 (m, 1H), 7.62-7.56 (m, 3H), 7.27 (t, J=53.5 Hz, 1H), 6.54 (s, 1H), 3.02 (d, J=4.4 Hz, 3H). m/z [M+H]⁺ 404.4.

1-(2-Chlorophenyl)-7-cyclopropyl-6-(difluoromethyl)-4-(methylamino)quinazolin-2(1H)-one was prepared by using 1-(2-Chlorophenyl)-7-cyclopropyl-6-(difluoromethyl)quinazoline-2,4(1H,3H)-dione.

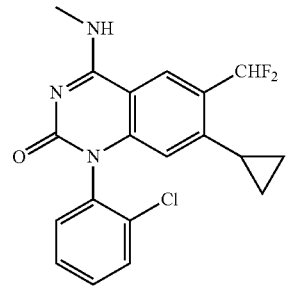

¹H NMR (400 MHz, DMSO-d₆) δ 8.81 (d, J=4.4 Hz, 1H), 8.36 (s, 1H), 7.75-7.73 (m, 1H), 7.58-7.54 (m, 2H), 7.49-7.21 (m, 2H), 5.82 (s, 1H), 2.98 (d, J=4.4 Hz, 3H), 2.09-2.07 (m, 1H), 0.95-0.92 (m, 2H), 0.32-0.31 (m, 2H). m/z [M+H]⁺ 376.4.

1-(2-Chlorophenyl)-6-methyl-4-(methylamino)-7-(trifluoromethyl)quinazolin-2(1H)-one was prepared by using 1-(2-Chlorophenyl)-6-methyl-7-(trifluoromethyl)quinazoline-2,4(1H,3H)-dione.

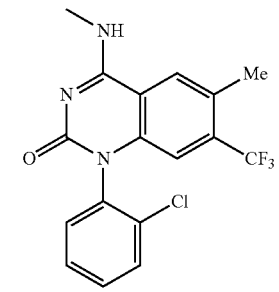 [SMILES: CNc1nc(=O)n(-c2ccccc2Cl)c2cc(C(F)(F)F)c(C)cc12]

¹H NMR (500 MHz, DMSO-d₆) δ 8.83 (d, J=4.5 Hz, 1H), 8.23 (s, 1H), 7.76-7.74 (m, 1H), 7.59-7.56 (m, 2H), 7.53-7.51 (m, 1H), 6.44 (s, 1H), 3.01 (d, J=4.5 Hz, 3H), 2.45 (s, 3H). m/z [M+H]⁺ 368.4

1-(2-Chlorophenyl)-7-cyclopropyl-6-methyl-4-(methylamino) quinazolin-2(1H)-one was prepared by using 1-(2-Chlorophenyl)-7-cyclopropyl-6-methylquinazoline-2,4(1H,3H)-dione.

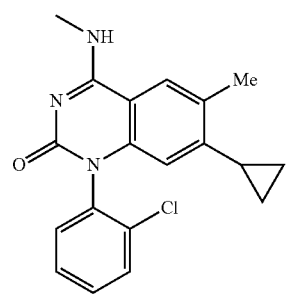 [SMILES: CNc1nc(=O)n(-c2ccccc2Cl)c2cc(C3CC3)c(C)cc12]

¹H NMR (500 MHz, DMSO-d₆) δ 8.45 (d, J=4 Hz, 1H), 7.89 (s, 1H), 7.72-7.70 (m, 1H), 7.56-7.52 (m, 2H), 7.41-7.39 (m, 1H), 5.76 (s, 1H), 2.97 (d, J=4 Hz, 3H), 2.39 (s, 3H), 1.92-1.88 (m, 1H), 0.88-0.85 (m, 2H), 0.23-0.20 (m, 2H). m/z [M+H]⁺ 340.34.

1-(2-Chlorophenyl)-7-cyclopropyl-4-(((1-methyl-1H-pyrazol-3-yl)methyl)amino)-2-oxo-1,2-dihydroquinazoline-6-carbonitrile was prepared by using (1-methyl-1H-pyrazol-3-yl)methanamine and 1-(2-Chlorophenyl)-7-cyclopropyl-2,4-dioxo-1,2,3,4-tetrahydroquinazoline-6-carbonitrile.

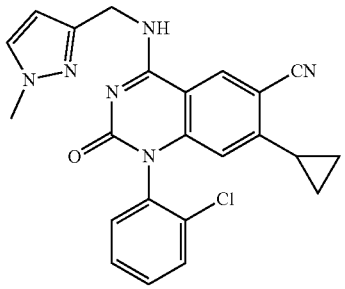 [SMILES: Cn1ccc(CNc2nc(=O)n(-c3ccccc3Cl)c3cc(C4CC4)c(C#N)cc23)n1]

¹H NMR (500 MHz, DMSO-d₆): δ 9.12 (s, 1H), 8.76 (s, 1H), 7.75-7.72 (m, 1H), 7.61 (d, J=2 Hz, 1H), 7.60-7.54 (m, 2H), 7.49-7.47 (m, 1H), 6.23 (s, 1H), 5.74 (s, 1H), 4.66 (dd, J=26, 15 Hz, 2H), 3.81 (s, 3H), 2.16-2.11 (m, 1H), 1.08-1.06 (m, 2H), 0.42-0.38 (m, 2H), m/z [M+H]⁺ 431.38.

1-(2-Chlorophenyl)-7-cyclopropyl-4-((isoxazol-3-ylmethyl)amino)-2-oxo-1,2-dihydroquinazoline-6-carbonitrile was prepared by using isoxazol-3-ylmethanamine and 1-(2-Chlorophenyl)-7-cyclopropyl-2,4-dioxo-1,2,3,4-tetrahydroquinazoline-6-carbonitrile.

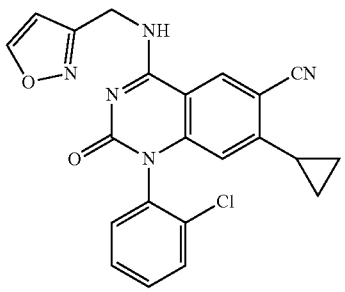 [SMILES: N#Cc1cc2c(NCc3ccon3)nc(=O)n(-c3ccccc3Cl)c2cc1C1CC1]

¹H NMR (500 MHz, DMSO-d₆) δ 9.29 (s, 1H), 8.88 (d, J=1.5 Hz, 1H), 8.71 (s, 1H), 7.76-7.74 (m, 1H), 7.60-7.56 (m, 2H), 7.50-7.48 (m, 1H), 6.63 (d, J=1.5 Hz, 1H), 5.77 (s, 1H), 4.83 (dd, J=40.0, 15.5 Hz, 2H), 2.15-2.14 (m, 1H), 1.10-1.08 (m, 2H), 0.43-0.42 (m, 2H). m/z [M+H]⁺ 418.3.

1-(2-Chlorophenyl)-7-cyclopropyl-4-((isoxazol-5-ylmethyl)amino)-2-oxo-1,2-dihydroquinazoline-6-carbonitrile was prepared by using isoxazol-5-ylmethanamine and 1-(2-Chlorophenyl)-7-cyclopropyl-2,4-dioxo-1,2,3,4-tetrahydroquinazoline-6-carbonitrile.

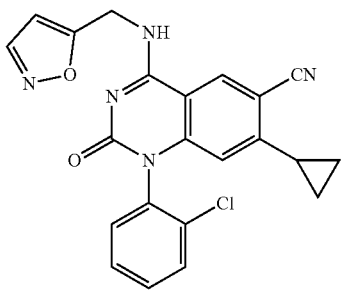 [SMILES: N#Cc1cc2c(NCc3ccno3)nc(=O)n(-c3ccccc3Cl)c2cc1C1CC1]

¹H NMR (500 MHz, DMSO-d₆): δ 9.34 (t, J=5.5 Hz, 1H), 8.72 (s, 1H), 8.54 (d, J=1.5 Hz, 1H), 7.76-7.74 (m, 1H), 7.60-7.55 (m, 2H), 7.51-7.49 (m, 1H), 6.49 (s, 1H), 4.95 (dd, J=16.5, 5.5 Hz, 2H), 4.87 (dd, J=16, 5.5 Hz, 1H), 2.17-2.13 (m, 1H), 1.23 (d, J=3.5 Hz, 1H), 1.11-1.07 (m, 2H), 0.42-0.41 (m, 2H). m/z [M+H]⁺ 418.35.

1-(2-Chlorophenyl)-7-cyclopropyl-4-((1-methyl-1H-pyrazol-5-yl)amino)-2-oxo-1,2-dihydroquinazoline-6-carbonitrile was prepared by using-methyl-H-pyrazol-5-amine and 1-(2-Chlorophenyl)-7-cyclopropyl-2,4-dioxo-1,2,3,4-tetrahydroquinazoline-6-carbonitrile.

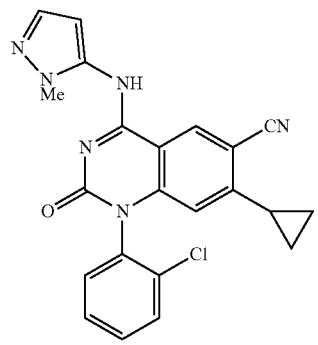 [SMILES: Cn1nccc1Nc1nc(=O)n(-c2ccccc2Cl)c2cc(C3CC3)c(C#N)cc12]

¹H NMR (500 MHz, DMSO-d₆) δ 10.30 (s, 1H), 8.87 (br s, 1H), 7.78 (d, J=7 Hz, 1H), 7.60-7.55 (m, 3H), 7.44 (br s, 1H), 6.27 (br s, 1H), 5.77 (t, J=15.5 Hz, 1H), 3.74 (br s, 3H), 2.21-2.16 (m, 1H), 1.13-1.09 (m, 2H), 0.5-0.4 (m, 2H). m/z [M+H]⁺ 417.36.

1-(2-Chlorophenyl)-7-cyclopropyl-2-oxo-4-(thiazol-5-ylamino)-1,2-dihydroquinazoline-6-carbonitrile was prepared by using thiazol-5-amine and 1-(2-Chlorophenyl)-7-cyclopropyl-2,4-dioxo-1,2,3,4-tetrahydroquinazoline-6-carbonitrile.

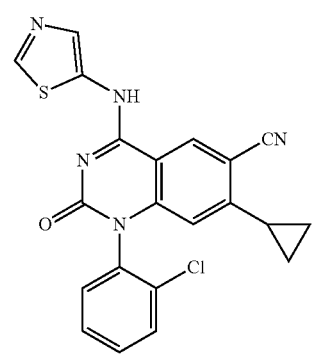 [SMILES: N#Cc1cc2c(Nc3cncs3)nc(=O)n(-c3ccccc3Cl)c2cc1C1CC1]

¹H NMR (500 MHz, DMSO-d₆): δ 11.9 (br s, 1H), 8.75 (s, 1H), 8.59 (s, 1H), 7.84 (s, 1H), 7.76-7.73 (m, 1H), 7.60-7.55 (m, 2H), 7.50-7.47 (m, 1H), 5.74 (s, 1H), 2.17-2.12 (m, 1H), 1.08-1.07 (m, 2H), 0.45-0.41 (m, 2H). m/z [M+H]⁺ 420.1.

1-(2-Chlorophenyl)-7-cyclopropyl-2-oxo-4-((2-(trifluoromethyl)pyridin-4-yl)amino)-1,2-dihydroquinazoline-6-carbonitrile was prepared by using 2-(trifluoromethyl)pyridin-4-amine and 1-(2-Chlorophenyl)-7-cyclopropyl-2,4-dioxo-1,2,3,4-tetrahydroquinazoline-6-carbonitrile.

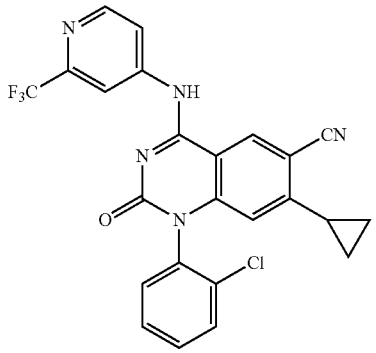 [SMILES: N#Cc1cc2c(Nc3ccnc(C(F)(F)F)c3)nc(=O)n(-c3ccccc3Cl)c2cc1C1CC1]

$^1$H NMR (500 MHz, DMSO-d$_6$) δ 10.54 (br s, 1H), 8.92-8.17 (m, 4H), 7.79-7.77 (m, 1H), 7.64-7.54 (m, 3H), 5.79 (d, J=13.5 Hz, 1H), 2.22-2.16 (m, 1H), 1.13-1.11 (m, 2H), 0.45-0.45 (m, 2H). m/z [M+H]$^+$ 482.5.

1-(2-Chlorophenyl)-7-cyclopropyl-4-(((1S,2S)-2-hydroxycyclobutyl)amino)-2-oxo-1,2-dihydroquinazoline-6-carbonitrile as a single, unknown enantiomer/atropisomer was prepared by using trans-2-aminocyclobutan-1-ol and 1-(2-Chlorophenyl)-7-cyclopropyl-2,4-dioxo-1,2,3,4-tetrahydroquinazoline-6-carbonitrile. SFC purification (20% MeOH, Chiralpak IC, peak 3).

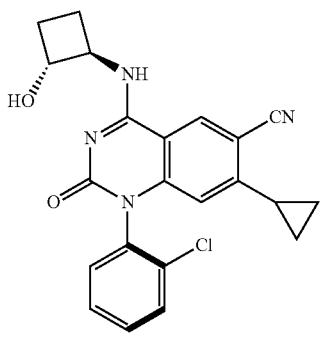

$^1$H NMR (500 MHz, DMSO-d$_6$): δ 8.86 (s, 1H), 8.73 (s, 1H), 7.74-7.72 (m, 1H), 7.59-7.54 (m, 2H), 7.47-7.46 (m, 1H), 5.71 (d, J=10 Hz, 1H), 4.44 (s, 1H), 4.11 (s, 1H), 2.14-2.12 (m, 1H), 2.08-2.02 (m, 2H), 1.56-1.48 (m, 1H), 1.43-1.37 (m, 1H), 1.23 (s, 1H), 1.06 (dd, J=8, 2 Hz, 2H), 0.40 (d, J=4.5 Hz, 2H), m/z [M+H]$^+$ 407.47.

1-(2-Chloropyridin-3-yl)-7-cyclopropyl-4-(methylamino)-2-oxo-1,2-dihydroquinazoline-6-carbonitrile was prepared by using 1-(2-chloropyridin-3-yl)-7-cyclopropyl-2,4-dioxo-1,2,3,4-tetrahydroquinazoline-6-carbonitrile.

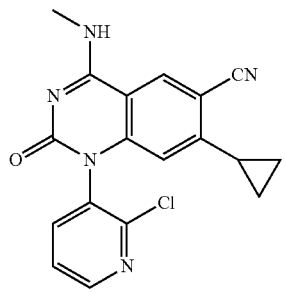 [SMILES: CNc1nc(=O)n(-c2cccnc2Cl)c2cc(C3CC3)c(C#N)cc12]

$^1$H NMR (500 MHz, DMSO-d$_6$) δ 8.88 (d, J=4.0 Hz, 1H), 8.63 (s, 1H), 8.59 (dd, J=5.0, 1.5 Hz, 1H), 8.04 (dd, J=8.0, 1.5 Hz, 1H), 7.68 (dd, J=7.5, 5.0 Hz, 1H), 5.82 (s, 1H), 2.99 (d, J=4.5 Hz, 3H), 2.18-2.13 (m, 1H), 1.09 (dd, J=8.0, 2.0 Hz, 2H), 1.54-1.53 (m, 2H). m/z [M+H]$^+$ 352.4.

1-(2-chlorophenyl)-4-((trans-2-fluorocyclopropyl)amino)-7-(trifluoromethoxy)quinazolin-2(1H)-one, single unknown enantiomer was prepared by using trans-2-fluorocyclopropan-1-amine and 1-(2-chlorophenyl)-7-(trifluoromethoxy)quinazoline-2,4(1H,3H)-dione. SFC purification (20% MeOH, R,R Whelk-01, peak 1).

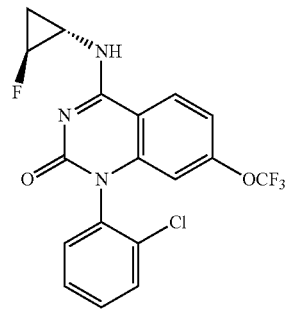 [SMILES: O=c1nc(N[C@H]2C[C@@H]2F)c2ccc(OC(F)(F)F)cc2n1-c1ccccc1Cl]

$^1$H NMR (500 MHz, DMSO-d$_6$) δ 8.59 (s, 1H), 8.26 (d, J=9.0 Hz, 1H), 7.77-7.75 (m, 1H), 7.60-7.52 (m, 3H), 7.27 (d, J=8.0 Hz, 1H), 6.11 (s, 1H), 4.92-4.78 (m, 1H), 3.49-3.43 (m, 1H), 1.57-1.48 (m, 1H), 1.35-1.26 (m, 1H). m/z [M+H]$^+$ 414.3.

1-(2-chlorophenyl)-4-((trans-2-fluorocyclopropyl)amino)-7-(trifluoromethoxy)quinazolin-2(1H)-one, single unknown enantiomer was prepared by using trans-2-fluorocyclopropan-1-amine and 1-(2-chlorophenyl)-7-(trifluoromethoxy)quinazoline-2,4(1H,3H)-dione. SFC purification (20% MeOH, R,R Whelk-01, peak 2).

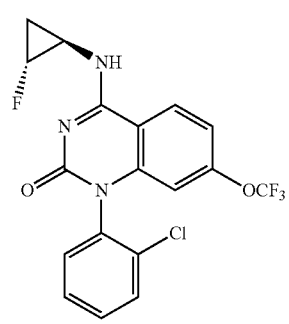 [SMILES: O=c1nc(N[C@@H]2C[C@H]2F)c2ccc(OC(F)(F)F)cc2n1-c1ccccc1Cl]

$^1$H NMR (500 MHz, DMSO-d$_6$) δ 8.59 (s, 1H), 8.26 (d, J=9.0 Hz, 1H), 7.77-7.75 (m, 1H), 7.60-7.52 (m, 3H), 7.27 (d, J=8.0 Hz, 1H), 6.11 (s, 1H), 4.92-4.78 (m, 1H), 3.49-3.43 (m, 1H), 1.57-1.48 (m, 1H), 1.35-1.26 (m, 1H). m/z [M+H]$^+$ 414.3.

1-(2-chlorophenyl)-7-(1,1-difluoroethyl)-4-(((trans)-2-hydroxycyclobutyl)amino)quinazolin-2(1H)-one, a single unknown enantiomer/atropisomer was prepared by using trans-2-aminocyclobutan-1-ol and 1-(2-chlorophenyl)-7-(1,1-difluoroethyl)quinazoline-2,4(1H,3H)-dione. SFC purification (15% MeOH, Chiralpak IC, peak 1).

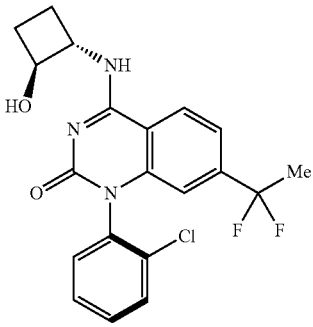

$^1$H NMR (500 MHz, DMSO-d$_6$) δ 8.82 (d, J=7 Hz, 1H), 8.38 (d, J=8.5 Hz, 1H), 7.76-7.73 (m, 1H), 7.59-7.55 (m, 2H), 7.52-7.45 (m, 1H), 7.43 (dd, J=8.5, 1.5 Hz, 1H), 6.36 (s, 1H), 5.43 (d, J=7 Hz, 1H), 4.55-4.49 (m, 1H), 4.20-4.14 (m, 1H), 2.09-2.02 (m, 2H), 1.83 (t, J=19 Hz, 3H), 1.57-1.49 (m, 1H), 1.46-1.39 (m, 1H). m/z [M+H]$^+$ 406.37.

1-(2-chlorophenyl)-7-(1,1-difluoroethyl)-4-(((trans)-2-hydroxycyclobutyl)amino)quinazolin-2(1H)-one, a single unknown enantiomer/atropisomer was prepared by using trans-2-aminocyclobutan-1-ol and 1-(2-chlorophenyl)-7-(1,1-difluoroethyl)quinazoline-2,4(1H,3H)-dione. SFC purification (15% MeOH, Chiralpak IC, peak 1).

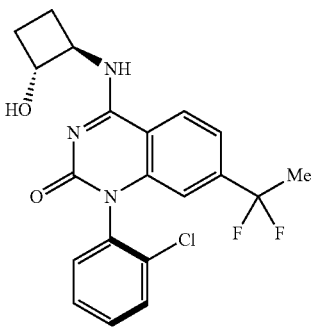

$^1$H NMR (500 MHz, DMSO-d$_6$) δ 8.82 (d, J=7 Hz, 1H), 8.38 (d, J=8.5 Hz, 1H), 7.76-7.73 (m, 1H), 7.59-7.55 (m, 2H), 7.52-7.45 (m, 1H), 7.43 (dd, J=8.5, 1.5 Hz, 1H), 6.36 (s, 1H), 5.43 (d, J=7 Hz, 1H), 4.55-4.49 (m, 1H), 4.20-4.14 (m, 1H), 2.09-2.02 (m, 2H), 1.83 (t, J=19 Hz, 3H), 1.57-1.49 (m, 1H), 1.46-1.39 (m, 1H). m/z [M+H]$^+$ 406.37.

1-(2-chlorophenyl)-7-(1,1-difluoroethyl)-4-(((trans)-2-hydroxycyclobutyl)amino)quinazolin-2(1H)-one, a single unknown enantiomer/atropisomer was prepared by using trans-2-aminocyclobutan-1-ol and 1-(2-chlorophenyl)-7-(1,1-difluoroethyl)quinazoline-2,4(1H,3H)-dione. SFC purification (15% MeOH, Chiralpak IC, peak 1).

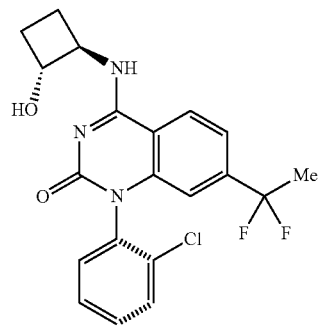

$^1$H NMR (500 MHz, DMSO-d$_6$) δ 8.82 (d, J=7 Hz, 1H), 8.38 (d, J=8.5 Hz, 1H), 7.76-7.73 (m, 1H), 7.59-7.55 (m, 2H), 7.52-7.45 (m, 1H), 7.43 (dd, J=8.5, 1.5 Hz, 1H), 6.36 (s, 1H), 5.43 (d, J=7 Hz, 1H), 4.55-4.49 (m, 1H), 4.20-4.14 (m, 1H), 2.09-2.02 (m, 2H), 1.83 (t, J=19 Hz, 3H), 1.57-1.49 (m, 1H), 1.46-1.39 (m, 1H). m/z [M+H]$^+$ 406.37.

1-(2-Chloropyridin-3-yl)-7-cyclopropyl-4-(((1S,2R)-2-fluorocyclopropyl) amino)quinazolin-2(1H)-one was prepared by using (1S,2R)-2-fluorocyclopropan-1-amine and 1-(2-chloropyridin-3-yl)-7-cyclopropylquinazoline-2,4(1H,3H)-dione.

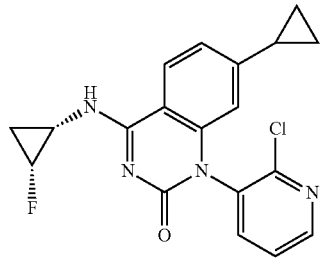 [SMILES: O=c1nc(N[C@H]2C[C@H]2F)c2ccc(C3CC3)cc2n1-c1cccnc1Cl]

$^1$H NMR (500 MHz, DMSO-d$_6$) δ 8.58-8.53 (m, 2H), 8.14 (d, J=8.5 Hz, 1H), 8.08-8.07 (m, 1H), 7.69-7.66 (m, 1H), 6.84 (dd, J=8.5, 1.5 Hz, 1H), 6.15 (d, J=1.5 Hz, 1H), 4.91-4.77 (m, 1H), 3.06-3.05 (m, 1H), 1.91-1.88 (m, 1H), 1.38-1.32 (m, 1H), 1.25-1.21 (m, 1H), 0.97-0.95 (m, 2H), 0.68-0.62 (m, 2H). m/z [M+H]$^+$ 371.3.

1-(2-Chloropyridin-3-yl)-7-cyclopropyl-4-((cyclopropylmethyl)amino) quinazolin-2(1H)-one was prepared by using cyclopropylmethanamine and 1-(2-chloropyridin-3-yl)-7-cyclopropylquinazoline-2,4(1H,3H)-dione.

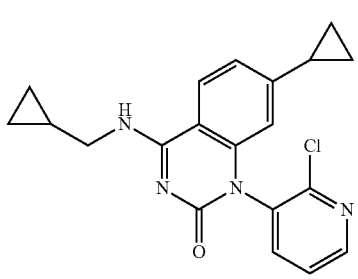 [SMILES: O=c1nc(NCC2CC2)c2ccc(C3CC3)cc2n1-c1cccnc1Cl]

¹H NMR (500 MHz, DMSO-d₆) δ 8.63 (t, J=5.0 Hz, 1H), 8.57-8.56 (m, 1H), 8.10 (d, J=8.5 Hz, 1H), 8.03 (dd, J=7.5, 2.0 Hz, 1H), 7.68-7.65 (m, 1H), 6.83 (dd, J=8.5, 1.5 Hz, 1H), 6.11 (d, J=1.5 Hz, 1H), 3.41-3.39 (m, 1H), 3.31-3.31 (m, 1H), 1.90-1.87 (m, 1H), 1.20-1.85 (m, 1H), 0.96-0.94 (m, 2H), 0.66-0.62 (m, 2H), 0.51-0.47 (m, 2H), 0.32-0.29 (m, 2H). m/z [M+H]⁺ 367.4.

1-(2-Chlorophenyl)-7-cyclopropyl-4-(((1S,2S)-2-fluorocyclopropyl)amino)quinazolin-2(1H)-one, a single unknown enantiomer/atropisomer was prepared by using trans-2-fluorocyclopropan-1-amine and 1-(2-chlorophenyl)-7-cyclopropylquinazoline-2,4(1H,3H)-dione. SFC purification (30% MeOH, R,R Whelk-01, peak 1).

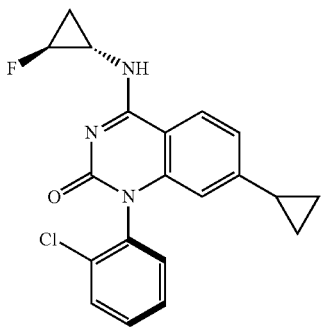

¹H NMR (500 MHz, DMSO-d₆) δ 8.32 (s, 1H), 7.96 (d, J=8.5 Hz, 1H), 7.74-7.71 (m, 1H), 7.58-7.55 (m, 2H), 7.45 (dd, J=6, 3.5 Hz, 1H), 6.81 (dd, J=8.5, 1.5 Hz, 1H), 6.02 (d, J=1 Hz, 1H), 4.90-4.70 (m, 1H), 3.45-3.41 (m, 1H), 1.83-1.79 (m, 1H), 1.50-1.45 (m, 1H), 1.22-1.18 (m, 1H), 0.94-0.92 (m, 2H), 0.60-0.56 (m, 2H). m/z [M+H]⁺ 370.34.

1-(2-Chlorophenyl)-7-cyclopropyl-4-(((1S,2S)-2-fluorocyclopropyl)amino)quinazolin-2(1H)-one, a single unknown enantiomer/atropisomer was prepared by using trans-2-fluorocyclopropan-1-amine and 1-(2-chlorophenyl)-7-cyclopropylquinazoline-2,4(1H,3H)-dione. SFC purification (30% MeOH, R,R Whelk-01, peak 2).

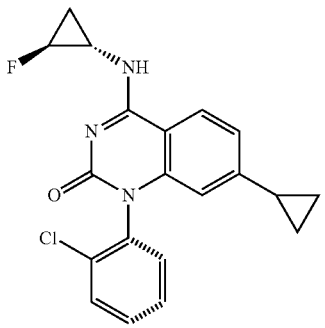

¹H NMR (500 MHz, DMSO-d₆) δ 8.32 (s, 1H), 7.96 (d, J=8.5 Hz, 1H), 7.74-7.71 (m, 1H), 7.58-7.55 (m, 2H), 7.45 (dd, J=6, 3.5 Hz, 1H), 6.81 (dd, J=8.5, 1.5 Hz, 1H), 6.02 (d, J=1 Hz, 1H), 4.90-4.70 (m, 1H), 3.45-3.41 (m, 1H), 1.83-1.79 (m, 1H), 1.50-1.45 (m, 1H), 1.22-1.18 (m, 1H), 0.94-0.92 (m, 2H), 0.60-0.56 (m, 2H). m/z [M+H]⁺ 370.34.

1-(2-Chlorophenyl)-7-cyclopropyl-4-(((1S,2S)-2-fluorocyclopropyl)amino)quinazolin-2(1H)-one, a single unknown enantiomer/atropisomer was prepared by using trans-2-fluorocyclopropan-1-amine and 1-(2-chlorophenyl)-7-cyclopropylquinazoline-2,4(1H,3H)-dione. SFC purification (30% MeOH, R,R Whelk-01, peak 3).

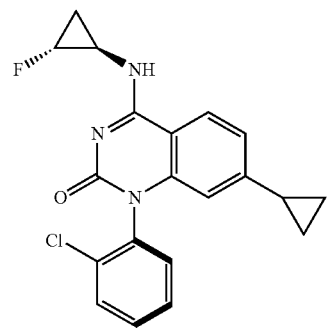

¹H NMR (500 MHz, DMSO-d₆) δ 8.32 (s, 1H), 7.96 (d, J=8.5 Hz, 1H), 7.74-7.71 (m, 1H), 7.58-7.55 (m, 2H), 7.45 (dd, J=6, 3.5 Hz, 1H), 6.81 (dd, J=8.5, 1.5 Hz, 1H), 6.02 (d, J=1 Hz, 1H), 4.90-4.70 (m, 1H), 3.45-3.41 (m, 1H), 1.83-1.79 (m, 1H), 1.50-1.45 (m, 1H), 1.22-1.18 (m, 1H), 0.94-0.92 (m, 2H), 0.60-0.56 (m, 2H). m/z [M+H]⁺ 370.34.

1-(2-Chlorophenyl)-4-(((1S,2S)-2-fluorocyclopropyl)amino)-7-(trifluoromethyl)quinazolin-2(1H)-one, a single unknown enantiomer/atropisomer was prepared by using trans-2-fluorocyclopropan-1-amine and 1-(2-chlorophenyl)-7-cyclopropylquinazoline-2,4(1H,3H)-dione. SFC purification (30% MeOH, R,R Whelk-01, peak 1).

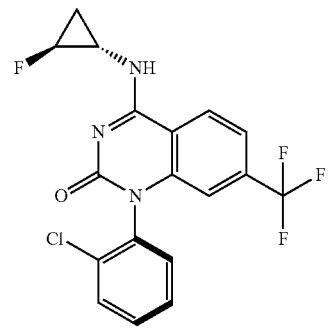

¹H NMR (500 MHz, DMSO-d₆) δ 8.74 (s, 1H), 8.36 (d, J=8.5 Hz, 1H), 7.79-7.76 (m, 1H), 7.64-7.55 (m, 4H), 6.45 (s, 1H), 4.95-4.80 (m, 1H), 3.52-3.45 (m, 1H), 1.58-1.49 (m, 1H), 1.29-1.22 (m, 1H). m/z [M+H]⁺ 398.3.

1-(2-Chlorophenyl)-4-(((1S,2S)-2-fluorocyclopropyl) amino)-7-(trifluoromethyl)quinazolin-2(1H)-one, a single unknown enantiomer/atropisomer was prepared by using trans-2-fluorocyclopropan-1-amine and 1-(2-chlorophenyl)-7-cyclopropylquinazoline-2,4(1H,3H)-dione. SFC purification (30% MeOH, R,R Whelk-01, peak 2).

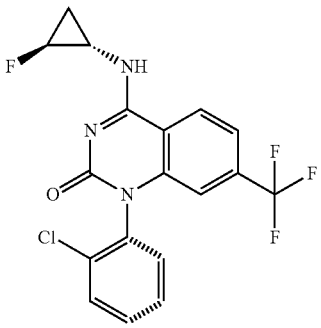

$^1$H NMR (500 MHz, DMSO-d$_6$) δ 8.74 (s, 1H), 8.36 (d, J=8.5 Hz, 1H), 7.79-7.76 (m, 1H), 7.64-7.55 (m, 4H), 6.45 (s, 1H), 4.95-4.80 (m, 1H), 3.52-3.45 (m, 1H), 1.58-1.49 (m, 1H), 1.29-1.22 (m, 1H). m/z [M+H]$^+$ 398.3.

1-(2-Chlorophenyl)-4-(((1S,2S)-2-fluorocyclopropyl) amino)-7-(trifluoromethyl)quinazolin-2(1H)-one, a single unknown enantiomer/atropisomer was prepared by using trans-2-fluorocyclopropan-1-amine and 1-(2-chlorophenyl)-7-cyclopropylquinazoline-2,4(1H,3H)-dione. SFC purification (30% MeOH, R,R Whelk-01, peak 3).

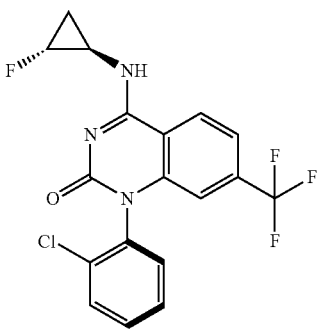

$^1$H NMR (500 MHz, DMSO-d$_6$) δ 8.74 (s, 1H), 8.36 (d, J=8.5 Hz, 1H), 7.79-7.76 (m, 1H), 7.64-7.55 (m, 4H), 6.45 (s, 1H), 4.95-4.80 (m, 1H), 3.52-3.45 (m, 1H), 1.58-1.49 (m, 1H), 1.29-1.22 (m, 1H). m/z [M+H]$^+$ 398.3.

1-(2-Chlorophenyl)-4-(((1S,2S)-2-fluorocyclopropyl) amino)-7-(trifluoromethyl)quinazolin-2(1H)-one, a single unknown enantiomer/atropisomer was prepared by using trans-2-fluorocyclopropan-1-amine and 1-(2-chlorophenyl)-7-cyclopropylquinazoline-2,4(1H,3H)-dione. SFC purification (30% MeOH, R,R Whelk-01, peak 4).

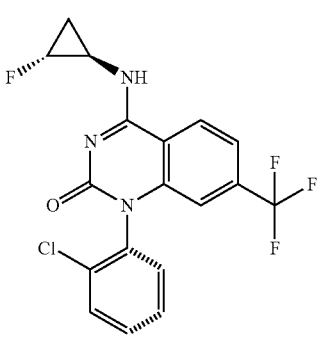

$^1$H NMR (500 MHz, DMSO-d$_6$) δ 8.74 (s, 1H), 8.36 (d, J=8.5 Hz, 1H), 7.79-7.76 (m, 1H), 7.64-7.55 (m, 4H), 6.45 (s, 1H), 4.95-4.80 (m, 1H), 3.52-3.45 (m, 1H), 1.58-1.49 (m, 1H), 1.29-1.22 (m, 1H). m/z [M+H]$^+$ 398.3.

5-Chloro-4-(methyl amino)-1-(o-tolyl)-7-(trifluoromethyl) quinazolin-2(1H)-one was prepared by using 5-chloro-1-(o-tolyl)-7-(trifluoromethyl)quinazoline-2,4(1H,3H)-dione.

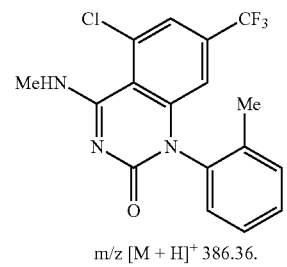 [SMILES: CNc1nc(=O)n(-c2ccccc2C)c2cc(C(F)(F)F)cc(Cl)c12]

m/z [M + H]$^+$ 386.36.

1-(2-Chloropyridin-3-yl)-7-cyclopropyl-5-methoxy-4-(methylamino)quinazolin-2(1H)-one was prepared by using trans-2-1-(2-chloropyridin-3-yl)-7-cyclopropyl-5-methoxy-quinazoline-2,4(1H,3H)-dione.

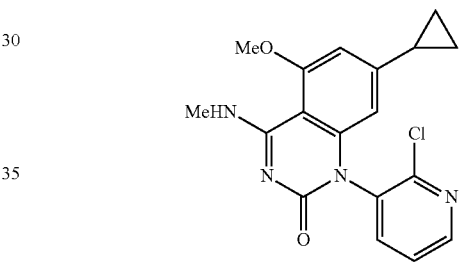

$^1$H NMR (500 MHz, DMSO-d$_6$) 8.56-8.51 (m, 2H), 7.98 (dd, J=1.5, 2 Hz, 1H), 7.67-7.64 (m, 1H), 6.39 (d, J=1.5 Hz, 1H), 3.99 (s, 3H), 2.99 (d, J=5 Hz, 3H), 1.84 (m, 1H), 0.94-0.92 (m, 2H), 0.67-0.64 (m, 2H). m/z [M+H]$^+$ 357.37

1-(2-Chloropyridin-3-yl)-7-cyclopropyl-4-methoxyquinazolin-2(1H)-one was prepared by using methanol and 1-(2-chloropyridin-3-yl)-7-cyclopropylquinazoline-2,4(1H,3H)-dione.

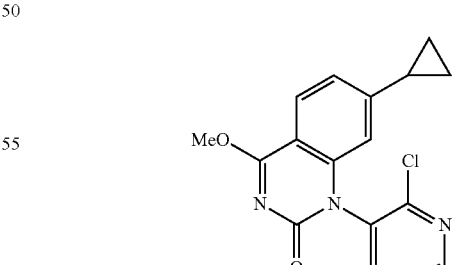

$^1$H NMR (500 MHz, DMSO-d$_6$) δ 8.63 (dd, J=5.0, 2.0 Hz, 1H), 8.13 (dd, J=7.5, 1.5 Hz, 1H), 7.89 (d, J=8.0 Hz, 1H), 7.73-7.71 (m, 1H), 6.90 (dd, J=8.5, 1.5 Hz, 1H), 6.30 (d, J=1.5 Hz, 1H), 4.09 (s, 3H), 1.99-1.94 (m, 1H), 1.01-0.97 (m, 2H), 0.73-0.71 (m, 2H). m/z [M+H]$^+$ 328.3.

681

1-(2-Chloropyridin-3-yl)-7-cyclopropyl-4-(methylamino)quinazolin-2(1H)-one was prepared by using 1-(2-chloropyridin-3-yl)-7-cyclopropylquinazoline-2,4(1H,3H)-dione.

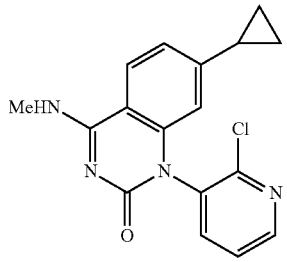 [SMILES: CNc1nc(=O)n(-c2cccnc2Cl)c2cc(C3CC3)ccc12]

$^1$H NMR (500 MHz, DMSO-d$_6$) δ 8.57 (dd, J=5.0, 2.0 Hz, 2H), 8.03-7.99 (m, 2H), 7.68-7.66 (m, 1H), 6.82 (dd, J=8.5, 1.5 Hz, 1H), 6.12 (d, J=1.5 Hz, 1H), 2.97 (d, J=4.5 Hz, 3H), 1.89-1.85 (m, 1H), 0.96-0.94 (m, 2H), 0.68-0.66 (m, 2H). m/z [M+H]$^+$ 327.3.

4-(Methylamino)-7-(trifluoromethyl)-1-(1-(1-((2-(trimethylsilyl)ethoxy)methyl)-1H-imidazol-4-yl)ethyl)quinazolin-2(1H)-one was prepared by using 17-(trifluoromethyl)-1-(1-(1-((2-(trimethylsilyl)ethoxy)methyl)-1H-imidazol-4-yl)ethyl)quinazoline-2,4(1H,3H)-dione.

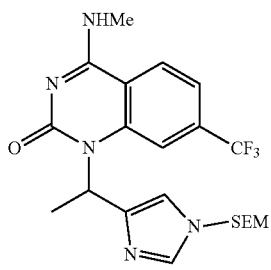

m/z [M + H]$^+$ 468.3.

1-(2-Chlorophenyl)-7-cyclopropyl-4-(((2,2-difluorocyclopropyl)methyl)amino)-5-methoxyquinazolin-2(1H)-one was prepared by using (2,2-difluorocyclopropyl)methanamine and 1-(2-chlorophenyl)-7-cyclopropyl-5-methoxyquinazoline-2,4(1H,3H)-dione.

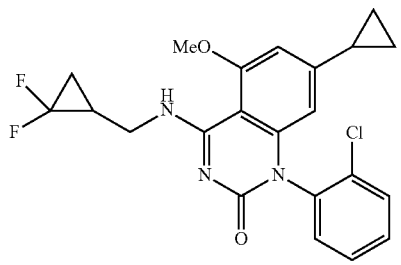 [SMILES: COc1cc(C2CC2)cc2c1c(NCC1CC1(F)F)nc(=O)n2-c1ccccc1Cl]

$^1$H NMR (500 MHz, DMSO-d$_6$) δ 8.59 (t, J=5.5 Hz, 1H), 7.73-7.69 (m, 1H), 7.56-7.52 (m, 2H), 7.45-7.42 (m, 1H), 6.42 (d, J=1.0 Hz, 1H), 5.59 (d, J=1.0 Hz, 1H), 4.01 (s, 3H), 3.73-3.66 (m, 2H), 2.26-2.23 (m, 1H), 1.80-1.77 (m, 1H), 1.65-1.61 (m, 1H), 1.49-1.45 (m, 1H), 0.94-0.91 (m, 2H), 0.62-0.58 (m, 2H). m/z [M+H]$^+$ 432.4.

682

1-(2-Chlorophenyl)-7-cyclopropyl-4-((cyclopropylmethyl)amino)-5-methoxyquinazolin-2(1H)-one was prepared by using cyclopropylmethanamine and 1-(2-chlorophenyl)-7-cyclopropyl-5-methoxyquinazoline-2,4(1H,3H)-dione.

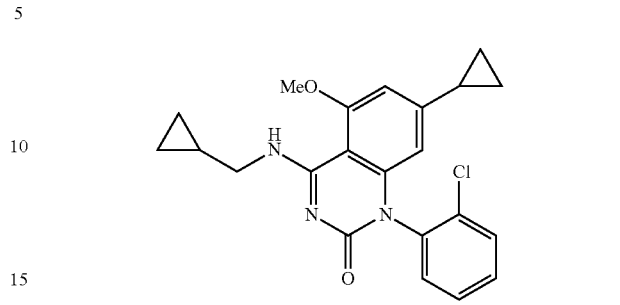

$^1$H NMR (500 MHz, DMSO-d$_6$) δ 8.48 (s, 1H), 7.71-7.69 (m, 1H), 7.54-7.52 (m, 2H), 7.43-7.41 (m, 1H), 6.42 (d, J=1.5 Hz, 1H), 5.58 (d, J=1.5 Hz, 1H), 4.01 (s, 3H), 3.31-3.31 (m, 2H), 1.79-1.76 (m, 1H), 1.23-1.20 (m, 1H), 0.92 (dd, J=8.0, 2.0 Hz, 2H), 0.61-0.59 (m, 2H), 0.51-0.47 (m, 2H), 0.33-0.32 (m, 2H). m/z [M+H]$^+$ 396.4.

1-(2-Chlorophenyl)-7-cyclopropyl-4-(((1S,2R)-2-fluorocyclopropyl)amino)-5-methoxyquinazolin-2(1H)-one was prepared by using (1S,2R)-2-fluorocyclopropan-1-amine and 1-(2-chlorophenyl)-7-cyclopropyl-5-methoxyquinazoline-2,4(1H,3H)-dione.

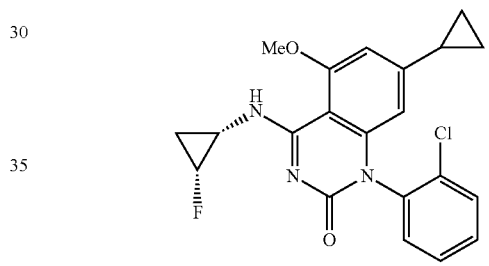

$^1$H NMR (500 MHz, DMSO-d$_6$) δ 8.32-8.29 (m, 1H), 7.74-7.70 (m, 1H), 7.57-7.53 (m, 2H), 7.47-7.43 (m, 1H), 6.43 (d, J=1.5 Hz, 1H), 5.62 (d, J=1 Hz, 1H), 4.88-4.86 (m, 1H), 3.99 (s, 3H), 3.15-3.12 (m, 1H), 1.81-1.78 (m, 1H), 1.27-1.16 (m, 2H), 0.94-0.93 (m, 2H), 0.63-0.60 (m, 2H). m/z [M+H]$^+$ 400.33.

1-(2-Chlorophenyl)-7-cyclopropyl-4-(cyclopropylamino)-5-methoxyquinazolin-2(1H)-one was prepared by using cyclopropylamine and 1-(2-chlorophenyl)-7-cyclopropyl-5-methoxyquinazoline-2,4(1H,3H)-dione.

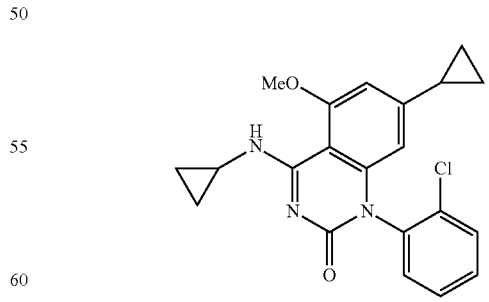

$^1$H NMR (500 MHz, DMSO-d$_6$) δ 8.17 (d, J=4.5 Hz, 1H), 7.73-7.69 (m, 1H), 7.56-7.52 (m, 2H), 7.44-7.41 (m, 1H), 6.39 (d, J=1 Hz, 1H), 5.58 (d, J=1.5 Hz, 1H), 3.98 (s, 3H), 3.06-3.05 (m, 1H), 1.77 (m, 1H), 0.92 (dd, J=2, 2 Hz, 2H), 0.82 (dd, J=1.5, 1 Hz, 2H), 0.70-0.69 (m, 2H), 0.68-0.59 (m, 2H). m/z [M+H]$^+$ 382.35.

1-(2-Chlorophenyl)-7-cyclopropyl-4-(isopropylamino)-5-methoxy quinazolin-2(1H)-one was prepared by using isopropylamine and 1-(2-chlorophenyl)-7-cyclopropyl-5-methoxyquinazoline-2,4(1H,3H)-dione.

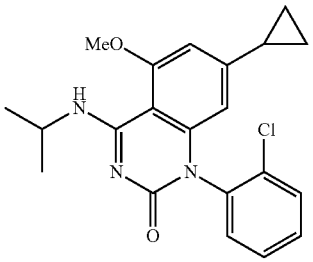 [SMILES: COc1cc(C2CC2)cc2c1c(NC(C)C)nc(=O)n2-c1ccccc1Cl]

$^1$H NMR (500 MHz, DMSO-d$_6$) δ 8.08 (d, J=7.5 Hz, 1H), 7.71-7.69 (m, 1H), 7.54-7.52 (m, 2H), 7.43-7.41 (m, 1H), 6.41 (s, 1H), 5.58 (s, 1H), 4.40-4.36 (m, 1H), 4.01 (s, 3H), 1.79-1.76 (m, 1H), 1.28-1.25 (m, 7H), 0.93-0.91 (m, 2H), 0.61-0.58 (m, 2H). m/z [M+H]$^+$ 384.4.

1-(2-Bromophenyl)-7-cyclopropyl-4-(methylamino)quinazolin-2(1H)-one as a single atropisomer was prepared by using isopropylamine and 1-(2-chlorophenyl)-7-cyclopropyl-5-methoxyquinazoline-2,4(1H,3H)-dione. SFC purification (30% MeOH, Chiralpak IG-3, peak 2).

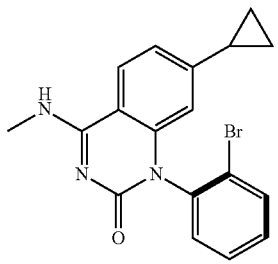

$^1$H NMR (500 MHz, DMSO-d6) δ 8.48-8.49 (br m, 1H), 7.97 (d, J=8.5 Hz, 1H), 7.87 (dd, J=8.0, 1.0 Hz, 1H), 7.59 (td, J=7.5, 1.0 Hz, 1H), 7.42-7.48 (m, 2H), 6.81 (dd, J=8.5, 1.5 Hz, 1H), 5.99 (d, J=1.5 Hz, 1H), 2.97 (d, J=4.5 Hz, 3H), 1.77-1.99 (m, 1H), 0.90-0.96 (m, 2H), 0.58-0.63 (m, 2H). m/z [M+H] 370.3.

4-((trans-2-Hydroxycyclobutyl) amino)-1-phenyl-7-(trifluoromethyl) quinazolin-2(1H)-one was prepared by using trans-2-aminocyclobutan-1-ol and 1-phenyl-7-(trifluoromethyl)quinazoline-2,4(1H,3H)-dione.

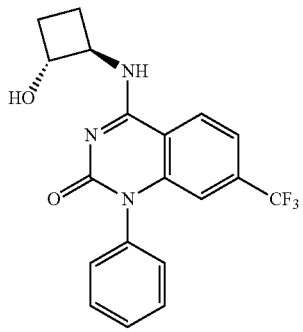 [SMILES: O=c1nc(N[C@@H]2CC[C@H]2O)c2ccc(C(F)(F)F)cc2n1-c1ccccc1]

$^1$H NMR (500 MHz, DMSO-d$_6$) δ 8.89-8.88 (m, 1H), 8.46 (d, J=8.5 Hz, 1H), 7.62-7.52 (m, 4H), 7.35-7.33 (m, 2H), 7.44-7.41 (m, 1H), 6.55 (s, 1H), 5.44 (d, J=7 Hz, 1H), 4.5-4.47 (m, 1H), 4.2-4.13 (m, 1H), 2.09-2.02 (m, 2H), 1.58-1.50 (m, 1H), 1.47-1.39 (m, 1H). m/z [M+H]$^+$ 376.36.

4-Amino-7-cyclopropyl-1-(pyrimidin-5-yl)quinazolin-2(1H)-one was prepared by using ammonia (7.4 M in THF) and 7-cyclopropyl-1-(pyrimidin-5-yl)quinazoline-2,4(1H,3H)-dione.

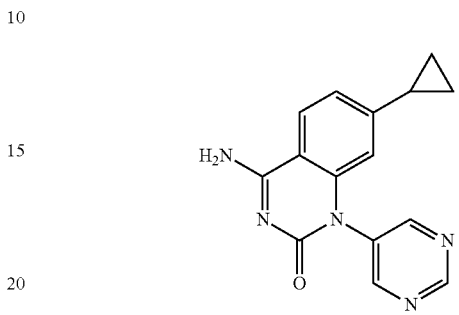

$^1$H NMR (500 MHz, DMSO-d$_6$) δ 9.30 (s, 1H), 8.87 (s, 2H), 8.13 (s, 1H), 8.02 (d, J=8.5 Hz, 2H), 6.83 (dd, J=8.5, 1.5 Hz, 1H), 6.30 (s, 1H), 1.92-1.88 (m, 1H), 0.97-0.93 (m, 2H), 0.68-0.65 (m, 2H). m/z [M+H]$^+$ 280.26.

4-Amino-7-cyclopropyl-1-(pyrazin-2-yl)quinazolin-2(1H)-one was prepared by using ammonia (0.4 M in THF) and 7-cyclopropyl-1-(pyrazin-2-yl)quinazoline-2,4(1H,3H)-dione.

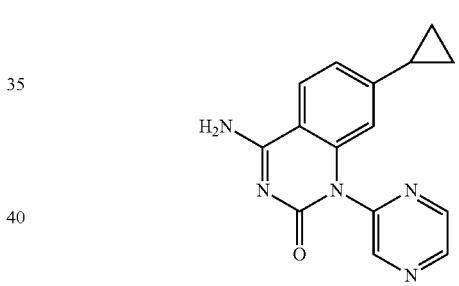

$^1$H NMR (500 MHz, DMSO-d$_6$) δ 8.78 (s, 3H), 8.15 (s, 1H), 8.02 (d, J=8.5 Hz, 2H), 6.82 (dd, J=8.5, 1.5 Hz, 1H), 6.21 (d, J=1.5 Hz, 1H), 1.89-1.84 (m, 1H), 0.96-0.92 (m, 2H), 0.66-0.65 (m, 2H). m/z [M+H]$^+$ 280.4.

4-Amino-1-(3-chloropyridin-2-yl)-7-cyclopropylquinazolin-2(1H)-one was prepared by using ammonia (0.4 M in THF) and 1-(3-chloropyridin-2-yl)-7-cyclopropylquinazoline-2,4(1H,3H)-dione.

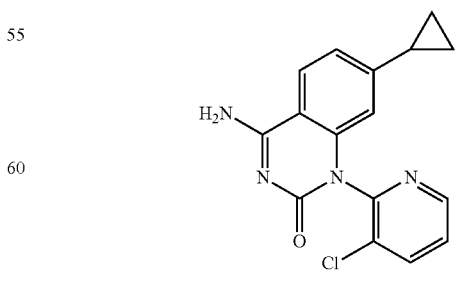

$^1$H NMR (500 MHz, DMSO-d$_6$) δ 8.65 (dd, J=4.5, 1.2 Hz, 1H), 8.25 (dd, J=8.5, 2.0 Hz, 1H), 8.13 (s, 1H), 8.03 (d,

J=8.5 Hz, 1H), 7.98 (s, 1H), 7.65-7.63 (m, 1H), 6.81 (dd, J=8.5, 1.5 Hz, 1H), 6.00 (d, J=1.5 Hz, 1H), 1.87-1.82 (m, 1H), 0.96-0.93 (m, 2H), 0.66-0.62 (m, 2H). m/z [M+H]⁺ 313.3.

7-Cyclopropyl-4-(methylamino)-1-(pyrimidin-5-yl)quinazolin-2(1H)-one was prepared by using 7-cyclopropyl-1-(pyrimidin-5-yl)quinazoline-2,4(1H,3H)-dione.

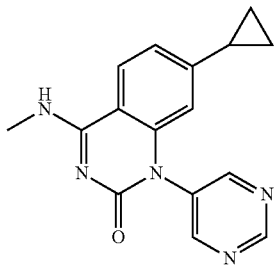 [SMILES: CNc1nc(=O)n(-c2cncnc2)c2cc(C3CC3)ccc12]

¹H NMR (500 MHz, DMSO-d₆) δ 9.30 (s, 1H), 8.86 (s, 1H), 8.57 (d, J=4.5, 1H), 7.98 (d, J=10, 1H), 6.83 (dd, J=8.5, 1.5 Hz, 1H), 6.30 (s, 1H), 2.97 (d, J=4.5, 3H), 1.92-1.87 (m, 1H), 0.96-0.92 (m, 2H), 0.68-0.65 (m, 2H). m/z [M+H]⁺ 294.33.

7-Cyclopropyl-4-(methylamino)-1-(pyrazin-2-yl)quinazolin-2(1H)-one was prepared by using 4-chloro-7-cyclopropyl-1-(pyrazin-2-yl)quinazolin-2(1H)-one.

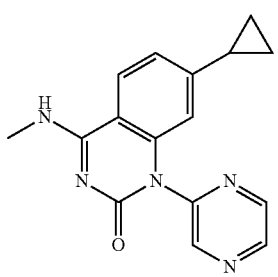 [SMILES: CNc1nc(=O)n(-c2cnccn2)c2cc(C3CC3)ccc12]

¹H NMR (500 MHz, DMSO-d₆) δ 8.79-8.78 (m, 3H), 8.60 (d, J=4.5 Hz, 1H), 7.99 (d, J=8.5 Hz, 1H), 6.84 (dd, J=8.5, 1.5 Hz, 1H), 6.21 (d, J=1.5 Hz, 1H), 2.98 (d, J=4.5 Hz, 3H), 1.89-1.83 (m, 1H), 0.95-0.92 (m, 2H), 0.66-0.63 (m, 2H). m/z [M+H]⁺ 294.4.

1-(2-Chlorophenyl)-4-(((1-methyl-1H-imidazol-4-yl)methyl)amino)-7-(trifluoromethyl)pyrido[2,3-d]pyrimidin-2(1H)-one was prepared by using (1-methyl-H-imidazol-4-yl)methanamine and 1-(2-chlorophenyl)-7-(trifluoromethyl)pyrido[2,3-d]pyrimidine-2,4(1H,3H)-dione.

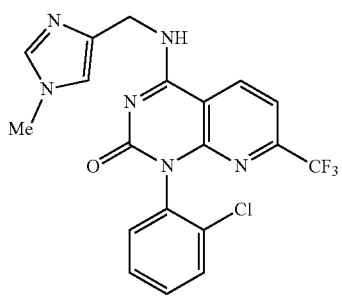 [SMILES: Cn1cnc(CNc2nc(=O)n(-c3ccccc3Cl)c3nc(C(F)(F)F)ccc23)c1]

¹H NMR (500 MHz, DMSO-d₆) δ 9.36 (t, J=5 Hz, 1H), 8.93 (d, J=8 Hz, 1H), 7.76 (d, J=8.5 Hz, 1H), 7.64-7.62 (m, 1H), 7.54 (s, 1H), 7.48-7.43 (m, 3H), 7.1 (s, 1H), 4.60 (t, J=5 Hz, 2H), 3.62 (s, 1H). m/z [M+H]⁺ 435.27.

1-(2-Chlorophenyl)-4-(((1-methyl-1H-pyrazol-5-yl)methyl)amino)-7-(trifluoromethyl)pyrido[2,3-d]pyrimidin-2(1H)-one was prepared by using (1-methyl-1H-pyrazol-5-yl)methanamine and 1-(2-chlorophenyl)-7-(trifluoromethyl)pyrido[2,3-d]pyrimidine-2,4(1H,3H)-dione.

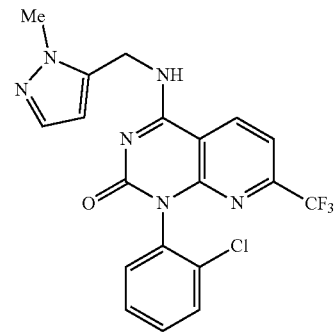 [SMILES: Cn1nccc1CNc1nc(=O)n(-c2ccccc2Cl)c2nc(C(F)(F)F)ccc12]

¹H NMR (500 MHz, DMSO-d₆): δ 9.43 (t, J=5 Hz, 1H), 8.91 (d, J=8 Hz, 1H), 7.80 (d, J=8 Hz, 1H), 7.63 (m, 1H), 7.50-7.44 (m, 3H), 7.36 (d, J=1.5 Hz, 1H), 6.29 (d, J=2 Hz, 1H), 4.87-4.74 (m, 2H), 3.90 (s, 3H). m/z [M+H]+: 435.27.

1-(2-Chlorophenyl)-4-((isoxazol-5-ylmethyl)amino)-7-(trifluoromethyl) pyrido[2,3-d]pyrimidin-2(1H)-one was prepared by using isoxazol-5-ylmethanamine and 1-(2-chlorophenyl)-7-(trifluoromethyl)pyrido[2,3-d]pyrimidine-2,4(1H,3H)-dione.

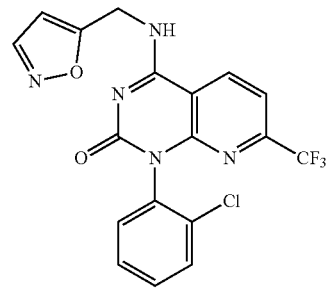 [SMILES: O=c1nc(NCc2ccno2)c2ccc(C(F)(F)F)nc2n1-c1ccccc1Cl]

¹H NMR (500 MHz, DMSO-d₆) δ 9.66 (t, J=5.5 Hz, 1H), 8.89 (d, J=3.0 Hz, 1H), 8.55 (d, J=1.5 Hz, 1H), 7.84 (d, J=8.0 Hz, 1H), 7.66-7.63 (m, 1H), 7.50-7.46 (m, 3H), 6.52 (d, J=2.0 Hz, 1H), 5.01-4.89 (m, 2H). m/z [M+H]⁺ 422.2.

1-(2-Chlorophenyl)-4-((isoxazol-3-ylmethyl)amino)-7-(trifluoromethyl) pyrido[2,3-d]pyrimidin-2(1H)-one was prepared by using isoxazol-3-ylmethanamine and 1-(2-chlorophenyl)-7-(trifluoromethyl)pyrido[2,3-d]pyrimidine-2,4(1H,3H)-dione.

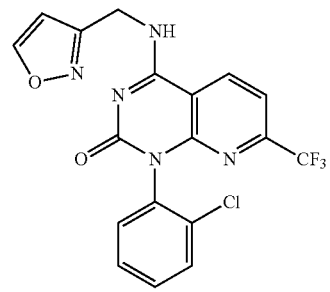 [SMILES: O=c1nc(NCc2ccon2)c2ccc(C(F)(F)F)nc2n1-c1ccccc1Cl]

¹H NMR (500 MHz, DMSO-d₆) δ 9.62 (t, J=5.5 Hz, 1H), 8.91-8.88 (m, 2H), 7.83 (d, J=8.5 Hz, 1H), 7.66-7.63 (m, 1H), 7.50-7.45 (m, 3H), 6.66 (d, J=2.0 Hz, 1H), 4.93-4.81 (m, 2H). m/z [M+H]⁺ 422.3.

1-(2-Chlorophenyl)-4-((isoxazol-4-ylmethyl)amino)-7-(trifluoromethyl) pyrido[2,3-d]pyrimidin-2(1H)-one was prepared by using isoxazol-4-ylmethanamine and 1-(2-chlorophenyl)-7-(trifluoromethyl)pyrido[2,3-d]pyrimidine-2,4(1H,3H)-dione.

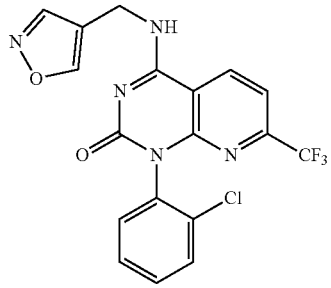 [SMILES: O=c1nc(NCc2cnoc2)c2ccc(C(F)(F)F)nc2n1-c1ccccc1Cl]

¹H NMR (500 MHz, DMSO-d₆) δ 9.41 (s, 1H), 8.98 (s, 1H), 8.86 (d, J=8.0 Hz, 1H), 8.68 (s, 1H), 7.82 (d, J=8.0 Hz, 1H), 7.65-7.63 (m, 1H), 7.50-7.44 (m, 3H), 4.65 (dd, J=40.0, 15.0 Hz, 2H). m/z [M+H]⁺ 422.3.

1-(2-Chlorophenyl)-4-(thiazol-4-ylamino)-7-(trifluoromethyl) pyrido[2,3-d]pyrimidin-2(1H)-one was prepared by using isoxazol-3-ylmethanamine and 1-(2-chlorophenyl)-7-(trifluoromethyl)pyrido[2,3-d]pyrimidine-2,4(1H,3H)-dione.

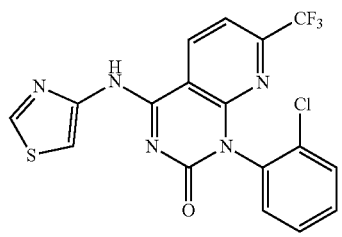 [SMILES: O=c1nc(Nc2cscn2)c2ccc(C(F)(F)F)nc2n1-c1ccccc1Cl]

¹H NMR (500 MHz, DMSO-d₆) δ 11.8 (s, 1H), 9.12 (s, 1H), 8.93 (d, J=8.0 Hz, 1H), 7.79 (s, 1H), 7.66 (d, J=8.0 Hz, 1H), 7.62-7.60 (m, 1H), 7.51-7.46 (m, 3H). m/z [M+H]⁺ 424.2.

7-Cyclopropyl-4-(pyridin-4-ylamino)-1-(o-tolyl)quinazolin-2(1H)-one was prepared by using pyridin-4-amine and 7-cyclopropyl-1-(o-tolyl)quinazoline-2,4(1H,3H)-dione.

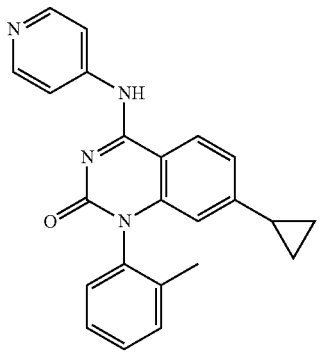 [SMILES: Cc1ccccc1-n1c(=O)nc(Nc2ccncc2)c2ccc(C3CC3)cc21]

¹H NMR (500 MHz, DMSO-d₆) δ 9.97 (s, 1H), 8.52 (d, J=6.5 Hz, 2H), 8.38 (d, 8.5 Hz, 1H), 8.04 (dd, 4.5 Hz, 1.5 Hz, 2H), 7.49-7.41 (m, 3H), 7.23 (dd, 7.5, 1.5 Hz, 1H), 6.95 (dd, 8.5, 1.5 Hz, 1H), 6.10 (s, 1H), 1.96 (s, 3H), 1.86-1.82 (m, 1H), 0.98-0.96 (m, 2H), 0.64-0.63 (m, 2H). m/z [M+H]⁺ 369.39.

4-(Methylamino)-7-(trifluoromethyl)-1-((1-((2-(trimethylsilyl)ethoxy)methyl)-1H-imidazol-4-yl)methyl)quinazolin-2(1H)-one was prepared by using 4-chloro-7-(trifluoromethyl)-1-((1-((2-(trimethylsilyl)ethoxy)methyl)-1H-imidazol-4-yl)methyl)quinazolin-2(1H)-one.

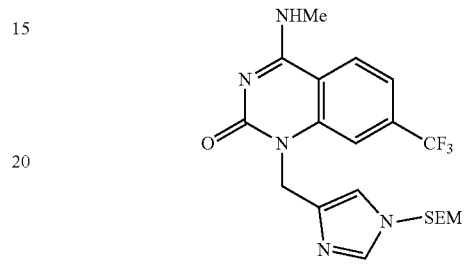

7-Cyclopropyl-4-(methylamino)-1-((1-((2-(trimethylsilyl)ethoxy)methyl)-1H-imidazol-4-yl)methyl)quinazolin-2(1H)-one was prepared by using 7-cyclopropyl-4-hydroxy-1-((1-((2-(trimethylsilyl)ethoxy)methyl)-1H-imidazol-4-yl)methyl)quinazolin-2(1H)-one.

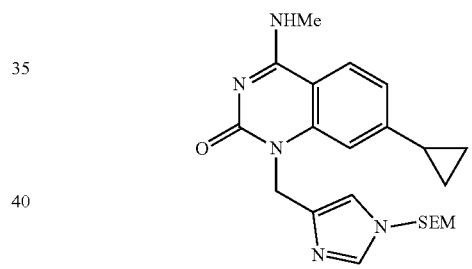

4-Amino-7-cyclopropyl-5-methoxy-1-(pyridin-3-yl) quinazolin-2(1H)-one was prepared by using ammonia (2 M in THF) and 4-chloro-1-(2-chloropyridin-3-yl)-7-cyclopropyl-5-methoxyquinazolin-2(1H)-one.

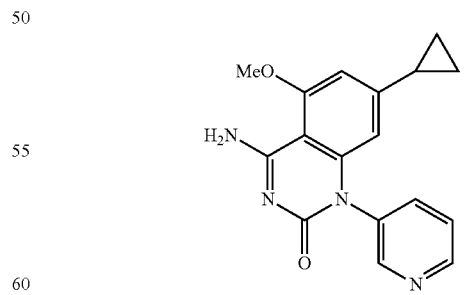

¹H NMR (500 MHz, DMSO-d₆) δ 8.66 (d, J=4 Hz, 1H), 8.46-8.45 (m, 1H), 8.03 (s, 1H), 7.88 (s, 1H), 7.77-7.75 (m, 1H), 7.62-7.59 (m, 1H), 6.38 (s, 1H), 5.67 (s, 1H), 3.97 (s, 3H), 1.83-1.78 (m, 1H), 0.95-0.90 (m, 2H), 0.64 (m, 2H). m/z [M+H]⁺ 309.36.

689

7-Cyclopropyl-5-methoxy-4-(methylamino)-1-(pyridin-3-yl)quinazolin-2(1H)-one was prepared by using 4-chloro-1-(2-chloropyridin-3-yl)-7-cyclopropyl-5-methoxyquinazolin-2(1H)-one.

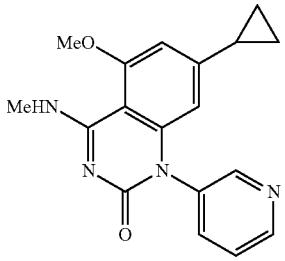 [SMILES: CNc1nc(=O)n(-c2cccnc2)c2cc(C3CC3)cc(OC)c12]

$^1$H NMR (500 MHz, DMSO-$d_6$) δ 8.68-8.67 (m, 1H), 8.47-8.45 (m, 2H), 7.77-7.75 (m, 1H), 7.62-7.59 (m, 1H), 6.40 (d, J=1.5 Hz, 1H), 5.67 (d, J=1 Hz, 1H), 3.98 (s, 3H), 2.98 (d, J=4.5 Hz, 3H), 1.81-1.78 (m, 1H), 0.93-0.90 (m, 2H), 0.62-0.61 (m, 2H). m/z [M+H]$^+$ 323.36.

4-Amino-7-cyclopropyl-5-methoxy-1-(o-tolyl)quinazolin-2(1H)-one was prepared by using ammonia (2 M in THF) and 4-chloro-7-cyclopropyl-5-methoxy-1-(o-tolyl)quinazolin-2(1H)-one.

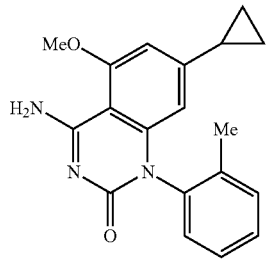 [SMILES: COc1cc(C2CC2)cc2c1c(N)nc(=O)n2-c1ccccc1C]

$^1$H NMR (400 MHz, DMSO-$d_6$) δ 8.54 (s, 1H), 7.90 (s, 1H), 7.80 (s, 1H), 7.43-7.34 (m, 3H), 7.12-7.10 (m, 1H), 6.36 (s, 1H), 5.56 (s, 1H), 3.96 (s, 3H), 1.92 (s, 3H), 1.76-1.71 (m, 1H), 0.91-0.89 (m, 2H), 0.57-0.56 (m, 2H). m/z [M+H]$^+$ 322.36.

7-Cyclopropyl-5-methoxy-4-(methylamino)-1-(o-tolyl)quinazolin-2(1H)-one was prepared by using 4-chloro-7-cyclopropyl-5-methoxy-1-(o-tolyl)quinazolin-2(1H)-one.

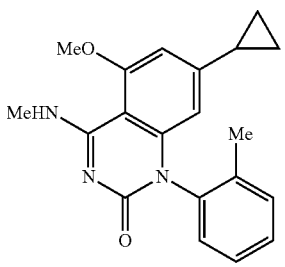 [SMILES: CNc1nc(=O)n(-c2ccccc2C)c2cc(C3CC3)cc(OC)c12]

$^1$H NMR (400 MHz, DMSO-$d_6$) δ 8.39 (d, J=4.4 Hz, 1H), 7.44-7.34 (m, 3H), 7.11-7.09 (m, 2H), 6.38 (s, 1H), 5.56 (d, J=0.8 Hz, 1H), 3.98 (s, 3H), 2.98 (d, J=4.8 Hz, 3H), 1.91 (s, 3H), 1.76-1.69 (m, 1H), 0.91-0.88 (m, 2H), 0.57-0.54 (m, 2H). m/z [M+H]$^+$ 336.44.

690

4-Amino-1-(2-chlorophenyl)-7-cyclopropyl-5-methoxyquinazolin-2(1H)-one was prepared by using ammonia (2 M in THF) and 1-(2-chlorophenyl)-7-cyclopropyl-4-hydroxy-5-methoxyquinazolin-2(1H)-one.

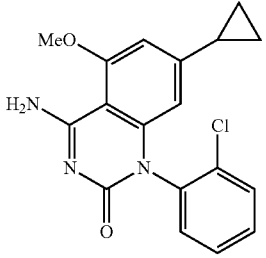 [SMILES: COc1cc(C2CC2)cc2c1c(N)nc(=O)n2-c1ccccc1Cl]

$^1$H NMR (400 MHz, DMSO-$d_6$) δ 8.0 (s, 1H), 7.86 (s, 1H), 7.71-7.68 (m, 1H), 7.55-7.51 (m, 2H), 7.43-7.40 (m, 1H), 6.37 (d, J=1.5 Hz, 1H), 5.57 (s, 1H), 3.97 (s, 3H), 1.80-1.75 (m, 1H), 0.93-0.90 (m, 2H), 0.64-0.63 (m, 1H). m/z [M+H]$^+$ 342.31.

1-(2-Chlorophenyl)-7-cyclopropyl-5-methoxy-4-(methylamino)quinazolin-2(1H)-one was prepared by using 1-(2-chlorophenyl)-7-cyclopropyl-4-hydroxy-5-methoxyquinazolin-2(1H)-one.

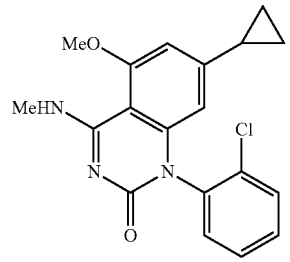 [SMILES: CNc1nc(=O)n(-c2ccccc2Cl)c2cc(C3CC3)cc(OC)c12]

$^1$H NMR (500 MHz, DMSO-$d_6$) δ 8.45 (d, 1H), 7.71-7.69 (m, 1H), 7.54-7.52 (m, 2H), 7.41-7.39 (m, 1H), 6.39 (s, 1H), 5.57 (d, J=1 Hz, 1H), 3.98 (s, 3H), 2.98 (d, J=4.5 Hz, 3H), 1.78-1.74 (m, 1H), 0.92-0.90 (m, 2H), 0.59 (m, 2H). m/z [M+H]$^+$ 356.35.

4-Amino-1-(2-Bromophenyl)-7-cyclopropylquinazolin-2(1H)-one was prepared by using ammonia (2 M in THF) and 1-(2-Bromophenyl)-7-cyclopropyl-4-hydroxyquinazolin-2(1H)-one.

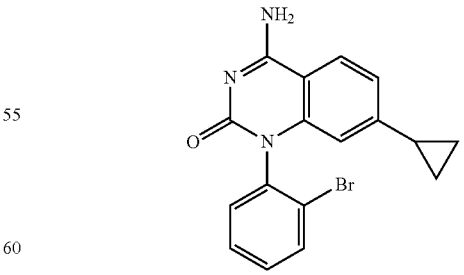

$^1$H NMR (500 MHz, DMSO-$d_6$) δ 8.01-7.99 (m, 2H), 7.89-7.85 (m, 2H), 7.60-7.58 (m, 1H), 7.47-7.42 (m, 2H), 6.79 (dd, J=8.5, 1.5 Hz, 1H), 5.98 (d, J=1.5 Hz, 1H), 1.82-1.78 (m, 1H), 0.94-0.90 (m, 2H), 0.62-0.57 (m, 2H). m/z [M+H]$^+$ 356.1.

1-(2-Chlorophenyl)-4-(((trans)-2-hydroxycyclobutyl)amino)-7-(trifluoromethyl)pyrido[2,3-d]pyrimidin-2(1H)-one a single unknown enantiomer/atropisomer was prepared by using trans-2-aminocyclobutan-1-ol and 1-(2-chlorophenyl)-7-(trifluoromethyl)pyrido[2,3-d]pyrimidine-2,4(1H,3H)-dione. SFC purification (20% MeOH, Chiralpak IC, peak 1).

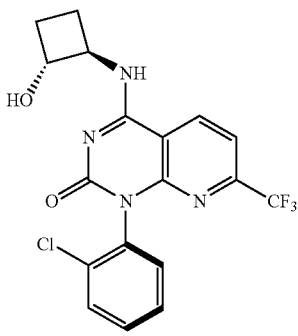

$^1$H NMR (400 MHz, DMSO-d$_6$) δ 9.15 (s, 1H), 8.83 (s, 1H), 7.72-7.71 (m, 1H), 7.67-7.60 (m, 1H), 7.46-7.41 (m, 3H), 5.67 (s, 1H), 4.37 (d, J=5.0 Hz, 1H), 4.07 (s, 1H), 2.06 (dd, J=17.0, 8.5 Hz, 2H), 1.56-1.42 (m, 2H). m/z [M+H]$^+$ 411.3.

1-(2-Chlorophenyl)-4-(((trans)-2-hydroxycyclobutyl)amino)-7-(trifluoromethyl)pyrido[2,3-d]pyrimidin-2(1H)-one a single unknown enantiomer/atropisomer was prepared by using trans-2-aminocyclobutan-1-ol and 1-(2-chlorophenyl)-7-(trifluoromethyl)pyrido[2,3-d]pyrimidine-2,4(1H,3H)-dione. SFC purification (20% MeOH, Chiralpak IC, peak 2).

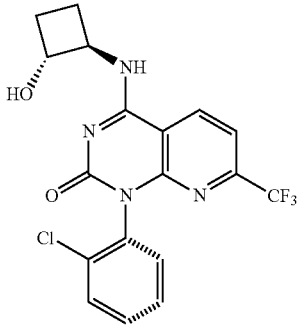

$^1$H NMR (400 MHz, DMSO-d$_6$) δ 9.15 (s, 1H), 8.83 (s, 1H), 7.72-7.71 (m, 1H), 7.67-7.60 (m, 1H), 7.46-7.41 (m, 3H), 5.67 (s, 1H), 4.37 (d, J=5.0 Hz, 1H), 4.07 (s, 1H), 2.06 (dd, J=17.0, 8.5 Hz, 2H), 1.56-1.42 (m, 2H). m/z [M+H]$^+$ 411.3.

7-Chloro-1-(2-chlorophenyl)-5-fluoro-4-(methylamino)quinazolin-2(1H)-one was prepared by using 4,7-dichloro-1-(2-chlorophenyl)-5-fluoroquinazolin-2(1H)-one.

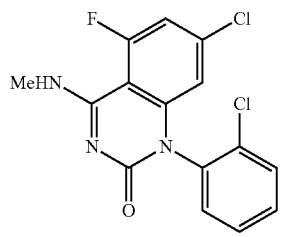 [SMILES: CNc1nc(=O)n(-c2ccccc2Cl)c2cc(Cl)cc(F)c12]

7-Chloro-5-fluoro-4-(((trans)-3-methoxycyclobutyl)amino)-1-(o-tolyl)quinazolin-2(1H)-one was prepared by using (trans)-3-methoxycyclobutan-1-amine and 7-chloro-5-fluoro-4-hydroxy-1-(o-tolyl)quinazolin-2(1H)-one.

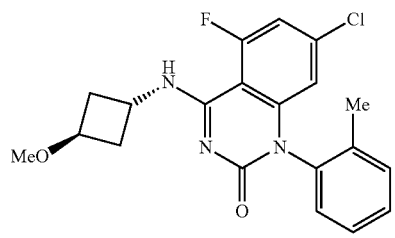

7-Chloro-4-((2,2-difluoroethyl)amino)-5-fluoro-1-(o-tolyl)quinazolin-2(1H)one was prepared by using 2,2-difluoroethan-1-amine and 7-chloro-5-fluoro-4-hydroxy-1-(o-tolyl)quinazolin-2(1H)-one.

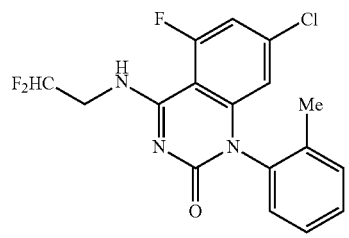 [SMILES: Cc1ccccc1-n1c(=O)nc(NCC(F)F)c2c(F)cc(Cl)cc21]

4-Amino-7-chloro-5-fluoro-1-(o-tolyl)quinazolin-2(1H)-one was prepared by using ammonia (0.4 M in THF) and 7-chloro-5-fluoro-4-hydroxy-1-(o-tolyl)quinazolin-2(1H)-one.

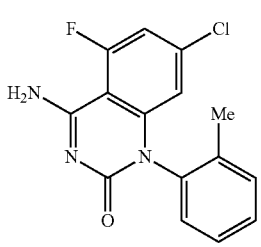

m/z [M + H]$^+$ 304.29.

1-Benzyl-4-(methylamino)-7-(trifluoromethyl)pyrido[2,3-d]pyrimidin-2(1H)-one was prepared by using 1-benzyl-4-hydroxy-7-(trifluoromethyl)pyrido[2,3-d]pyrimidin-2(1H)-one.

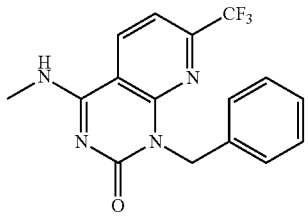 [SMILES: CNc1nc(=O)n(Cc2ccccc2)c2nc(C(F)(F)F)ccc12]

$^1$H NMR (500 MHz, DMSO-$d_6$), 8.89 (d, J=4.5 Hz, 1H), 8.71 (d, J=8.0 Hz, 1H), 7.76 (d, J=8.5 Hz, 1H), 7.35-7.33 (m, 2H), 7.28-7.25 (m, 1H), 7.22-7.19 (m, 1H), 5.35 (s, 2H), 2.97 (d, J=4.5 Hz, 3H). m/z [M+H]$^+$ 335.3.

1-(2-Chlorophenyl)-4-(3-hydroxy-3-methylpyrrolidin-1-yl)-7-(trifluoromethyl) pyrido[2,3-d]pyrimidin-2(1H)-one a single unknown enantiomer was prepared by using 3-methylpyrrolidin-3-ol and 1-(2-chlorophenyl)-7-(1,1-difluoroethyl)quinazoline-2,4(1H,3H)-dione. SFC purification (25% MeOH, Chiralpak IC, peak 1).

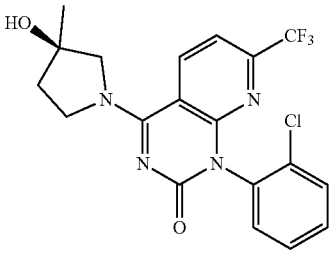 [SMILES: C[C@@]1(O)CCN(c2nc(=O)n(-c3ccccc3Cl)c3nc(C(F)(F)F)ccc23)C1]

$^1$H NMR (400 MHz, DMSO-$d_6$) (8.88-8.76 (m, 1H), 7.64-7.63 (m, 2H), 7.48-7.45 (m, 2H), 7.42-7.39 (m, 1H), 5.03 (s, 1H), 4.30-3.64 (m, 4H), 2.07-1.94 (m, 2H), 1.40 (s, 3H). m/z [M+H]$^+$ 425.1.

7-Cyclopropyl-4-(methylamino)-1-(2-methylpyridin-3-yl)quinazolin-2(1H)-one was prepared by using 7-Cyclopropyl-4-hydroxy-1-(2-methylpyridin-3-yl)quinazolin-2(1H)-one.

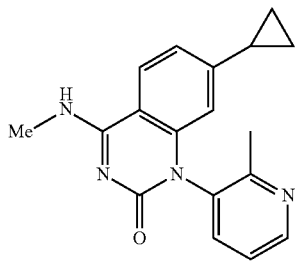

$^1$H NMR (500 MHz, DMSO-$d_6$) δ 8.58-8.57 (dd, J=4.5, 1.5 Hz, 1H), 8.51 (d, J=4 Hz, 1H), 8.0 (d, J=8.5 Hz, 1H), 7.66-7.65 (dd, J=8, 1.5 Hz, 1H), 7.45-7.43 (dd, J=7.5, 4.7 Hz, 1H), 6.83-6.81 (dd, J=8.5, 1.5 Hz, 1H), 6.03 (s, 1H), 2.97 (d, J=4.5 Hz, 3H), 2.13 (s, 3H), 1.85-1.80 (m, 1H), 0.94-0.90 (m, 2H), 0.64-0.59 (m, 2H). m/z [M+H]$^+$ 307.22.

1-(2-Chloro-6-fluorophenyl)-4-(methylamino)-7-(trifluoromethyl)pyrido [2,3-d]pyrimidin-2(1H)-one was prepared by using 4-chloro-1-(2-chloro-6-fluorophenyl)-7-(trifluoromethyl)pyrido[2,3-d]pyrimidin-2(1H)-one.

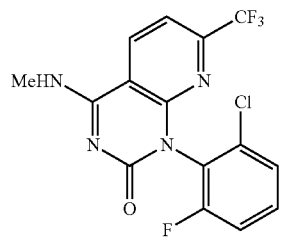

$^1$H NMR (500 MHz, DMSO-$d_6$), 9.26 (d, J=4.5 Hz, 1H), 8.84 (d, J=8.0 Hz, 1H), 7.87 (d, J=8.0 Hz, 1H), 7.59-7.52 (m, 2H), 7.46-7.43 (m, 1H), 3.04 (d, J=4.5 Hz, 3H). m/z [M+H]$^+$ 373.2.

5-Methoxy-4-(methylamino)-1-phenyl-7-(trifluoromethyl) pyrido[2,3-d]pyrimidin-2(1H)-one was prepared by using 5-methoxy-1-phenyl-7-(trifluoromethyl)pyrido[2,3-d]pyrimidine-2,4(1H,3H)-dione.

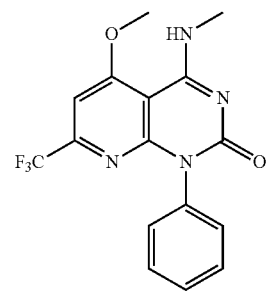 [SMILES: CNc1nc(=O)n(-c2ccccc2)c2nc(C(F)(F)F)cc(OC)c12]

$^1$H NMR (500 MHz, DMSO-$d_6$) δ 8.56 (d, J=5.0 Hz, 1H), 7.62-7.59 (m, 2H), 7.55-7.52 (m, 1H), 7.35-7.33 (m, 2H), 6.22 (s, 1H), 4.11 (s, 3H), 3.03 (d, J=5.0 Hz, 3H). m/z [M+H]$^+$ 351.3.

Example 3

Synthesis of 7-methyl-4-(methylamino)-1-phenylquinazolin-2(1H)-one

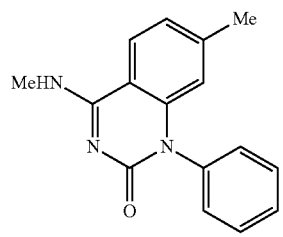 [SMILES: CNc1nc(=O)n(-c2ccccc2)c2cc(C)ccc12]

A vial was charged with 7-bromo-4-(methylamino)-1-phenylquinazolin-2(1H)-one (1 equiv), methylboronic acid (3 equiv) and 1,1'-bis(diphenylphosphino)ferrocene dichloropalladium (II) (0.1 equiv). A 1:1 mixture of toluene:t-butanol (0.1 M) was added followed by aqueous potassium carbonate (2 M, 4 equiv). The reaction mixture was heated to 100° C. for 2 h and then cooled. The crude reaction mixture was diluted with ethyl acetate, filtered and concentrated under reduced pressure. The residue was purified by preparatory HPLC (20-40% MeCN/water, 0.1% formic acid) to give the title compound. $^1$H NMR (400 MHz, CDCl$_3$) δ 7.81 (d, J=8.3 Hz, 1H), 7.52 (t, J=7.5 Hz, 2H), 7.45 (t, J=7.2 Hz, 1H), 7.24 (s, 3H), 6.95 (d, J=8.2 Hz, 1H), 6.30 (s, 1H), 3.18 (s, 3H), 2.23 (s, 3H). m/z [M+H]$^+$ 266.1

Proceeding analogously as described above the following compounds were prepared:

7-Cyclopropyl-4-(methylamino)-1-phenylquinazolin-2 (1H)-one was prepared by substituting cyclopropyl boronic acid for methylboronic acid

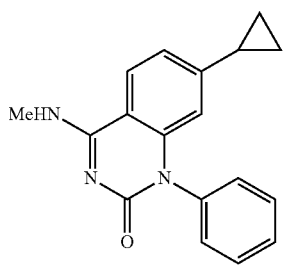 [SMILES: CNc1nc(=O)n(-c2ccccc2)c2cc(C3CC3)ccc12]

$^1$H NMR (400 MHz, CDCl$_3$) δ 7.92 (d, J=8.4 Hz, 1H), 7.52 (t, J=7.4 Hz, 2H), 7.48-7.40 (m, 1H), 7.24 (s, 2H), 6.71 (d, J=8.3 Hz, 1H), 6.23 (s, 1H), 3.15 (s, 3H), 1.77-1.66 (m, 1H), 0.94 (d, J=7.8 Hz, 2H), 0.58 (d, J=4.9 Hz, 2H). m/z [M+H]$^+$ 292.2

4-(Dimethylamino)-7-(oxetan-3-yl)-1-phenylquinazolin-2(1H)-one was prepared by substituting potassium trifluoro (oxetan-3-yl) borate for methyl boronic acid and 7-bromo-4-(dimethylamino)-1-phenylquinazolin-2(1H)-one for 7-bromo-4-(methylamino)-1-phenylquinazolin-2(1H)-one.

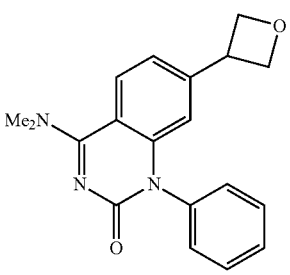 [SMILES: CN(C)c1nc(=O)n(-c2ccccc2)c2cc(C3COC3)ccc12]

$^1$H NMR (400 MHz, Chloroform-d) δ 7.80 (d, J=8.5 Hz, 1H), 7.56 (t, J=7.4 Hz, 2H), 7.51-7.44 (m, 1H), 7.28 (d, J=7.7 Hz, 3H), 7.17 (d, J=8.5 Hz, 1H), 6.46 (d, J=11.3 Hz, 2H), 6.30 (dt, J=15.4, 4.8 Hz, 1H), 4.28 (d, J=4.8 Hz, 2H), 3.41 (s, 6H). m/z [M+H]$^+$ 322.0

4-(Dimethylamino)-1-phenyl-7-(tetrahydrofuran-3-yl) quinazolin-2(1H)-one was prepared by substituting potassium tetrahydrofuran-3-trifluoroborate for methyl boronic acid and 7-bromo-4-(dimethylamino)-1-phenylquinazolin-2 (1H)-one for 7-bromo-4-(methylamino)-1-phenylquinazolin-2(1H)-one.

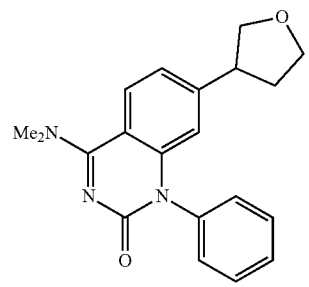 [SMILES: CN(C)c1nc(=O)n(-c2ccccc2)c2cc(C3CCOC3)ccc12]

$^1$H NMR (400 MHz, Chloroform-d) δ 7.79 (d, J=8.6 Hz, 1H), 7.56 (t, J=7.4 Hz, 2H), 7.49 (q, J=7.1, 6.2 Hz, 1H), 7.29 (d, J=7.9 Hz, 3H), 7.18 (d, J=8.4 Hz, 1H), 6.43 (s, 1H), 6.33 (d, J=17.6 Hz, 1H), 6.22 (dt, J=15.6, 6.9 Hz, 1H), 3.73 (t, J=6.0 Hz, 2H), 3.43 (s, 6H), 2.44 (q, J=6.6, 6.1 Hz, 2H). m/z [M+H]$^+$ 336.0

7-Ethyl-4-(methylamino)-1-phenylquinazolin-2(1H)-one was prepared by substituting ethyl boronic acid for methyl boronic acid.

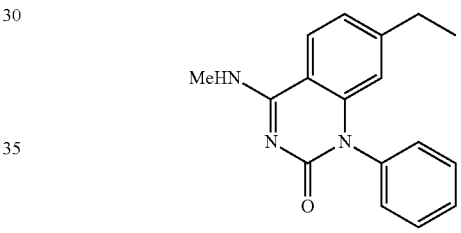

$^1$H NMR (400 MHz, Chloroform-d) δ 7.77 (d, J=8.3 Hz, 1H), 7.56 (t, J=7.7 Hz, 2H), 7.49 (t, J=7.5 Hz, 1H), 7.29 (d, J=8.0 Hz, 2H), 7.04 (d, J=8.3 Hz, 1H), 6.35 (s, 1H), 3.24 (s, 3H), 2.54 (q, J=7.7 Hz, 2H), 1.11 (t, J=7.6 Hz, 3H). m/z [M+H]$^+$ 280.1.

6-Chloro-1-(2-chlorophenyl)-7-cyclopropyl-4-((cyclopropylmethyl)amino)quinazolin-2(1H)-one was prepared by using cyclopropylboronic acid for methyl bornonic acid and 7-bromo-6-chloro-1-(2-chlorophenyl)-4-((cyclopropylmethyl)amino)quinazolin-2(1H)-one for 7-bromo-4-(methylamino)-1-phenylquinazolin-2(1H)-one.

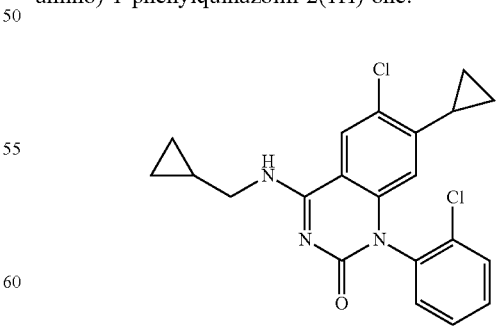

$^1$H NMR (400 MHz, DMSO-d$_6$) δ 8.72 (s, 1H), 8.41 (s, 1H), 7.73 (d, J=6.6 Hz, 1H), 7.65-7.53 (m, 2H), 7.53-7.41 (m, 1H), 5.75 (d, J=2.0 Hz, 1H), 2.12 (br s, 1H), 1.19 (s, 1H), 0.99 (d, J=8.3 Hz, 2H), 0.51 (d, J=7.8 Hz, 2H), 0.40-0.21 (m, 4H). m/z [M+H]$^+$ 400.1

697

6-Chloro-1-(2-chlorophenyl)-7-cyclopropyl-4-(methylamino)quinazolin-2(1H)-one was prepared by using cyclopropylboronic acid and 7-bromo-6-chloro-1-(2-chlorophenyl)-4-(methylamino)quinazolin-2(1H)-one.

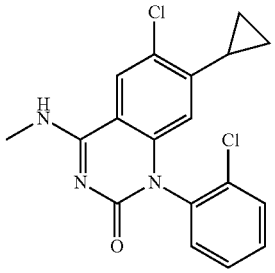 [SMILES: CNc1nc(=O)n(-c2ccccc2Cl)c2cc(C3CC3)c(Cl)cc12]

$^1$H NMR (400 MHz, DMSO) δ 8.67 (br s, 1H), 8.28 (s, 1H), 7.75 (m, 1H), 7.65-7.55 (m, 2H), 7.46 (m, 1H), 5.76 (s, 1H), 2.98 (s, 3H), 2.12 (s, 1H), 0.98 (d, J=8.2 Hz, 2H), 0.28 (s, 2H). m/z [M+H]$^+$ 360.0.

4-((Cyclopropylmethyl)amino)-6-methyl-1-phenyl-7-(trifluoromethoxy)quinazolin-2(1H)-one was prepared by using 6-bromo-4-((cyclopropylmethyl)amino)-1-phenyl-7-(trifluoromethoxy)quinazolin-2(1H)-one.

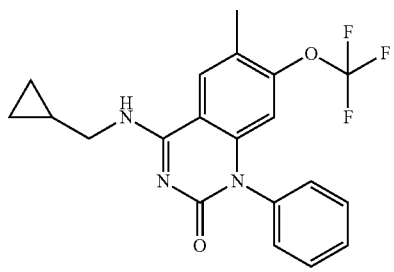 [SMILES: Cc1cc2c(NCC3CC3)nc(=O)n(-c3ccccc3)c2cc1OC(F)(F)F]

$^1$H NMR (400 MHz, MeOD) δ 8.15 (s, 1H), 7.61 (m, 3H), 7.33 (d, J=7.8 Hz, 2H), 6.38 (s, 1H), 3.52 (d, J=8.3 Hz, 2H), 2.37 (s, 3H), 1.30 (m, 2H), 0.59 (d, J=7.8 Hz, 2H), 0.39 (br s, 2H). m/z [M+H]$^+$ 390.1.

6-Methyl-4-(methylamino)-1-(o-tolyl)-7-(trifluoromethoxy)quinazolin-2(1H)-one was prepared by using 6-bromo-4-(methylamino)-1-(o-tolyl)-7-(trifluoromethoxy)quinazolin-2(1H)-one.

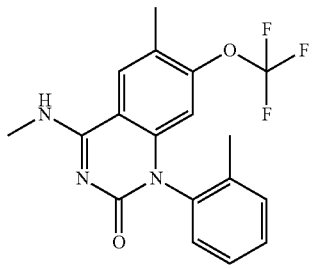 [SMILES: CNc1nc(=O)n(-c2ccccc2C)c2cc(OC(F)(F)F)c(C)cc12]

$^1$H NMR (400 MHz, MeOD) δ 8.04 (s, 1H), 7.58-7.37 (m, 3H), 7.22 (d, J=7.5 Hz, 1H), 6.27 (s, 1H), 3.15 (s, 3H), 2.37 (s, 3H), 2.05 (s, 3H). m/z [M+H]$^+$ 364.1.

698

4-((Cyclopropylmethyl)amino)-6-methyl-1-(o-tolyl)-7-(trifluoromethoxy)quinazolin-2(1H)-one was prepared by using 6-bromo-4-((cyclopropylmethyl)amino)-1-(o-tolyl)-7-(trifluoromethoxy)quinazolin-2(1H)-one.

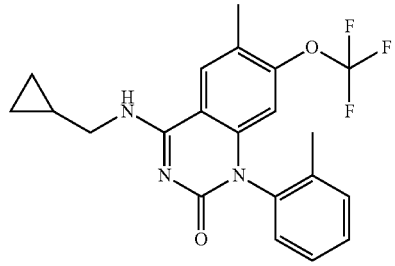 [SMILES: Cc1cc2c(NCC3CC3)nc(=O)n(-c3ccccc3C)c2cc1OC(F)(F)F]

$^1$H NMR (400 MHz, MeOD) δ 8.18 (s, 1H), 7.59-7.39 (m, 3H), 7.22 (d, J=7.5 Hz, 1H), 6.27 (s, 1H), 3.52 (appar t, J=6.9 Hz, 2H), 2.38 (s, 3H), 2.05 (s, 3H), 1.31 (s, 1H), 0.60 (d, J=7.8 Hz, 2H), 0.39 (br s, 2H). m/z [M+H]$^+$ 404.1

1-(2-chlorophenyl)-7-cyclopropyl-4-((cyclopropylmethyl)amino)-6-fluoroquinazolin-2(1H)-one was prepared by using cyclopropylboronic acid and 7-bromo-1-(2-chlorophenyl)-4-((cyclopropylmethyl)amino)-6-fluoroquinazolin-2(1H)-one.

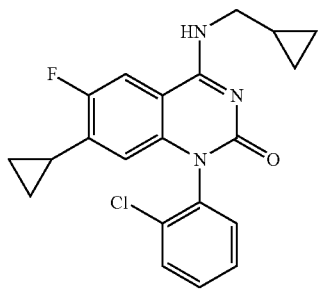

m/z [M + H]$^+$ 384.0.

1-(2-chlorophenyl)-7-cyclopropyl-6-fluoro-4-(methylamino)quinazolin-2(1H)-one was prepared by substituting cyclopropyl boronic acid and using 7-bromo-1-(2-chlorophenyl)-6-fluoro-4-(methylamino)quinazolin-2(1H)-one.

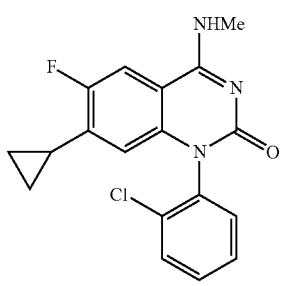 [SMILES: CNc1nc(=O)n(-c2ccccc2Cl)c2cc(C3CC3)c(F)cc12]

$^1$H NMR (400 MHz, DMSO-d$_6$) δ 8.56 (s, 1H), 7.97 (d, J=11.0 Hz, 1H), 7.76-7.69 (m, 1H), 7.55 (d, J=6.7 Hz, 2H), 7.44 (d, J=3.0 Hz, 1H), 5.75 (d, J=5.4 Hz, 1H), 2.97 (s, 3H), 2.05-1.93 (m, 1H), 0.95 (d, J=8.4 Hz, 2H), 0.40 (t, J=5.2 Hz, 2H). m/z [M+H]$^+$ 344.0.

Example 4

Synthesis of 7-chloro-1-(3-hydroxyphenyl)-4-(methylamino)-3,4-dihydroquinazolin-2(1H)-one

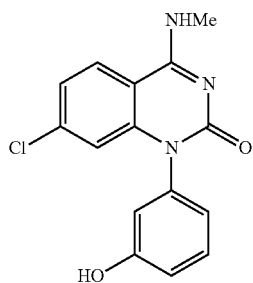

Step 1: 3-(7-chloro-2,4-dioxo-3,4-dihydroquinazolin-1(2H)-yl)phenyl acetate

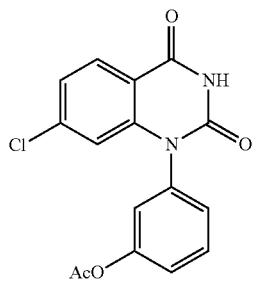 [SMILES: CC(=O)Oc1cccc(-n2c(=O)[nH]c(=O)c3ccc(Cl)cc32)c1]

A vial was charged with 7-chloro-1-(3-hydroxyphenyl)quinazoline-2,4(1H,3H)-dione (1.0 equiv) and Pyridine (0.6 M). To the reaction vessel was added acetic anhydride (1.2 equiv) and the reaction mixture was stirred to reflux for 60 minutes. The reaction was concentrated under vacuum, and the crude reaction mixture was purified by normal phase purification (0-20% MeOH/DCM) to give the title compound. m/z [M+H]$^+$ 331.1

3-(7-Chloro-2,4-dioxo-3,4-dihydroquinazolin-1(2H)-yl)phenyl acetate was converted to 3-(7-chloro-4-(methylamino)-2-oxoquinazolin-1(2H)-yl)phenyl acetate by following the procedure in Examples 1 and 2.

Step 2: 7-chloro-1-(3-hydroxyphenyl)-4-(methylamino)-3,4-dihydroquinazolin-2(1H)-one

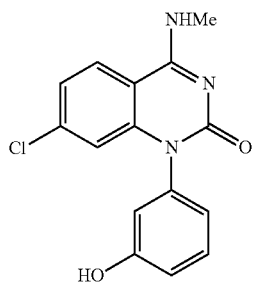

A vial was charged with crude 3-(7-chloro-4-(methylamino)-2-oxoquinazolin-1(2H)-yl)phenyl acetate (1.0 equiv) THF:MeOH (3:2 ratio 0.6 M) was added followed by addition of 2N aqueous solution of LiOH (10 equiv). The reaction vessel was stirred at room temperature for 30 min. The reaction was concentrated under vacuum, and the crude reaction mixture was purified by reverse phase purification (20-55% MeCN/water, 0.1% formic acid) to give the title compound. $^1$H NMR (400 MHz, DMSO-d$_6$) δ 10.2 (bs, 1H), 8.63 (d, J=5.1 Hz, 1H), 8.10 (d, J=8.7 Hz, 1H), 7.37 (t, J=8.0 Hz, 1H), 7.27 (d, J=8.5 Hz, 1H), 6.91 (d, J=8.4 Hz, 1H), 6.68 (d, J=7.9 Hz, 1H), 6.64 (s, 1H), 6.38 (s, 1H), 2.97 (d, J=4.2 Hz, 4H). m/z [M+H]$^+$ 302.1.

Proceeding analogously as described above, following compounds were prepared by substituting for 7-chloro-1-(3-hydroxyphenyl)quinazoline-2,4(1H,3H)-dione and methylamine as needed:

7-Chloro-1-[3-(2-hydroxyethyl)phenyl]-4-(methylamino)hydroquinazolin-2-one was prepared by using 3-(7-chloro-2,4-dioxo-3,4-dihydroquinazolin-1(2H)-yl)phenethyl acetate $^1$H NMR (400 MHz, DMSO-d$_6$) δ 8.61 (d, J=5.0 Hz, 1H), 8.10 (d, J=8.6 Hz, 1H), 7.49 (t, J=7.6 Hz, 1H), 7.37 (d, J=7.7 Hz, 1H), 7.27 (d, J=8.6 Hz, 1H), 7.11 (d, J=7.9 Hz, 2H), 6.34 (d, J=2.0 Hz, 1H), 4.69 (t, J=5.3 Hz, 1H), 3.66 (d, J=6.7 Hz, 2H), 2.98 (d, J=4.3 Hz, 3H), 2.81 (t, J=6.9 Hz, 2H). m/z [M+H]$^+$ 330.1

7-Chloro-1-[3-(3-hydroxypropyl)phenyl]-4-(methylamino)hydroquinazolin-2-one was prepared by using 3-(7-chloro-2,4-dioxo-3,4-dihydroquinazolin-1(2H)-yl)phenpropyl acetate $^1$H NMR (400 MHz, DMSO-d$_6$) δ 8.61 (d, J=5.2 Hz, 1H), 8.11 (d, J=8.6 Hz, 1H), 7.50 (t, J=7.7 Hz, 1H), 7.35 (d, J=7.9 Hz, 1H), 7.28 (d, J=8.7 Hz, 1H), 7.12 (s, 2H), 6.31 (s, 1H), 4.49 (t, J=5.2 Hz, 1H), 3.45 (d, J=6.1 Hz, 3H), 2.98 (d, J=4.3 Hz, 3H), 2.70 (t, J=7.8 Hz, 2H), 1.76 (p, J=6.9 Hz, 3H). 11.81 (s, 1H), 8.04 (d, J=8.5 Hz, 1H), 7.52 (t, J=7.6 Hz, 1H), 7.39 (d, J=7.8 Hz, 1H), 7.31 (dd, J=8.4, 1.8 Hz, 1H), 7.29-7.22 (m, 2H), 2.40 (s, 3H). m/z [M+H]$^+$ 344.1

4-(dimethylamino)-7-chloro-1-(3-hydroxyphenyl)hydroquinazolin-2-one was prepared by using 3-(7-chloro-2,4-dioxo-3,4-dihydroquinazolin-1(2H)-yl)phenyl acetate and dimethylamine

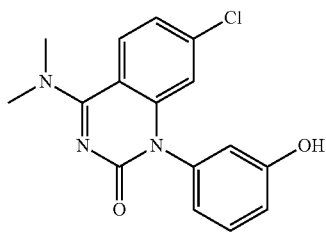 [SMILES: CN(C)c1nc(=O)n(-c2cccc(O)c2)c2cc(Cl)ccc12]

$^1$H NMR (400 MHz, DMSO-d$_6$) δ 9.87 (s, 1H), 8.03 (dd, J=8.7, 1.4 Hz, 1H), 7.38 (t, J=8.0 Hz, 1H), 7.23-7.14 (m, 1H), 6.92 (d, J=8.3 Hz, 1H), 6.69 (d, J=7.8 Hz, 1H), 6.65 (d, J=2.0 Hz, 1H), 6.41 (d, J=2.4 Hz, 1H), 3.32-3.27 (m, 7H). m/z [M+H]$^+$ 316.1

4-(dimethylamino)-7-chloro-1-[3-(hydroxymethyl)phenyl]hydroquinazolin-2-one was prepared by using 3-(7-chloro-2,4-dioxo-3,4-dihydroquinazolin-1(2H)-yl)phenmethyl acetate and dimethylamine

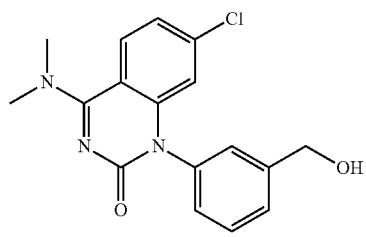 [SMILES: CN(C)c1nc(=O)n(-c2cccc(CO)c2)c2cc(Cl)ccc12]

$^1$H NMR (400 MHz, DMSO-d$_6$) δ 8.05 (d, J=8.8 Hz, 1H), 7.55 (t, J=7.6 Hz, 1H), 7.46 (d, J=7.9 Hz, 1H), 7.22 (s, 1H), 7.20-7.14 (m, 2H), 6.35 (s, 1H), 5.35 (s, 1H), 4.59 (s, 2H), 3.31 (s, 11H). m/z [M+H]$^+$ 330.0

Example 5

Synthesis of 7-methoxy-4-(methylamino)-1-phenylquinazolin-2(1H)-one

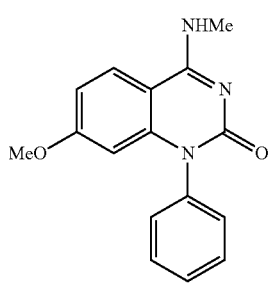

To a vial charged with 7-bromo-4-(methylamino)-1-phenylquinazolin-2(1H)-one (1 equiv) and copper iodide (2 equiv). DMF (0.1 M) was added sodium methoxide (10 equiv). The reaction mixture was heated to 100° C. for 2 hours and then cooled. The crude reaction mixture was diluted with ethyl acetate, filtered and concentrated under reduced pressure. The residue was purified by preparatory HPLC (10-30% MeCN/water, 0.1% formic acid) to give the title compound. $^1$H NMR (400 MHz, CDCl$_3$) δ 7.99 (d, J=9.0 Hz, 1H), 7.54 (t, J=7.6 Hz, 2H), 7.51-7.43 (m, 1H), 7.28 (d, J=7.7 Hz, 2H), 6.74 (d, J=9.0 Hz, 1H), 5.95 (s, 1H), 3.66 (s, 3H), 3.20 (s, 3H). m/z [M+H]$^+$ 282.1

Proceeding analogously as described above 1-(2-chlorophenyl)-7-cyclopropyl-4-((cyclopropylmethyl)amino)-6-methoxyquinazolin-2(1H)-one was prepared by using 6-bromo-1-(2-chlorophenyl)-7-cyclopropyl-4-((cyclopropylmethyl)amino)quinazolin-2(1H)-one.

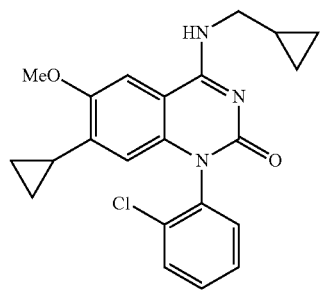 [SMILES: COc1cc2c(NCC3CC3)nc(=O)n(-c3ccccc3Cl)c2cc1C1CC1]

$^1$H NMR (400 MHz, DMSO-d$_6$) δ 8.59 (s, 1H), 7.71 (s, 1H), 7.65 (s, 1H), 7.53 (d, J=3.7 Hz, 2H), 7.41 (d, J=6.7 Hz, 1H), 5.64 (s, 1H), 3.90 (s, 3H), 3.42 (dd, J=12.8, 6.9 Hz, 2H), 2.12-2.05 (m, 1H), 1.26-1.19 (m, 1H), 0.88 (d, J=8.4 Hz, 2H), 0.51 (d, J=9.1 Hz, 2H), 0.32 (d, J=4.0 Hz, 2H), 0.27-0.20 (m, 2H). m/z [M+H]$^+$ 396.2.

Example 6

Synthesis of 4-(methylamino)-2-oxo-1-phenyl-1,2-dihydroquinazoline-7-carbonitrile

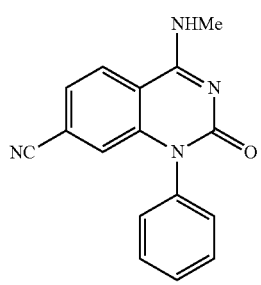 [SMILES: CNc1nc(=O)n(-c2ccccc2)c2cc(C#N)ccc12]

A vial was charged with 7-bromo-4-(methylamino)-1-phenylquinazolin-2(1H)-one (1 equiv), tetrakis(triphenylphosphine)palladium (0.1 equiv) and zinc cyanide (0.5 equiv). DMF (0.1 M) was added and the reaction mixture was heated to 100° C. for 12 h. Additional zinc cyanide (0.5 equiv) was added and the reaction mixture was heated to 100° C. for additional 24 h. The reaction mixture was cooled and diluted with saturated sodium bicarbonate solution, and extracted with dichloromethane. The organic layer was dried over sodium sulfate, filtered and concentrated under reduced pressure. The residue was purified by preparatory HPLC (10-30% MeCN/water, 0.1% formic acid) to give the title compound. $^1$H NMR (400 MHz, CD$_3$OD) δ 8.15 (d, J=8.4 Hz, 1H), 7.67 (t, J=7.7 Hz, 2H), 7.61 (d, J=7.0 Hz, 1H), 7.55 (d, J=8.2 Hz, 1H), 7.35 (d, J=7.7 Hz, 2H), 6.82 (s, 1H), 3.15 (s, 3H). m/z [M+H]$^+$ 277.0

703

Proceeding analogously as described above 4-((cyclopropylmethyl)amino)-2-oxo-1-(o-tolyl)-7-(trifluoromethoxy)-1,2-dihydroquinazoline-6-carbonitrile was prepared by using 6-Bromo-4-((cyclopropylmethyl)amino)-1-(o-tolyl)-7-(trifluoromethoxy)quinazolin-2(1H)-one.

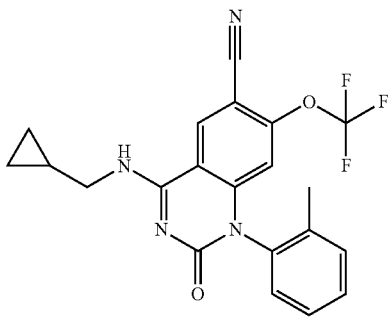 [SMILES: Cc1ccccc1-n1c(=O)nc(NCC2CC2)c2cc(C#N)c(OC(F)(F)F)cc21]

$^1$H NMR (400 MHz, MeOD) δ 8.78 (s, 1H), 7.58-7.40 (m, 3H), 7.25 (d, J=7.7 Hz, 1H), 6.40 (s, 1H), 3.52 (m, 2H), 2.07 (s, 3H), 1.29 (br s, 1H), 0.62 (d, J=7.7 Hz, 2H), 0.40 (br s, 2H). m/z [M+H]$^+$ 415.1.

Example 7

Synthesis of 4-(methylamino)-1-phenyl-7-(trifluoromethyl)quinazolin-2(1H)-one

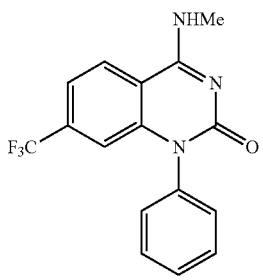 [SMILES: CNc1nc(=O)n(-c2ccccc2)c2cc(C(F)(F)F)ccc12]

A vial was charged with 7-bromo-4-(methylamino)-1-phenylquinazolin-2(1H)-one (1 equiv), methyl 2,2-difluoro-2-(fluorosulfonyl)acetate (2 equiv). Copper iodide (2 equiv). DMF (0.1 M) was added and the reaction mixture was heated to 100° C. for 12 h. Additional methyl 2,2-difluoro-2-(fluorosulfonyl)acetate (2 equiv) and copper iodide (2 equiv) were added and the reaction mixture was heated to 100° C. for additional 24 h. The reaction mixture was cooled, diluted with ethyl acetate, filtered and concentrated under reduced pressure. The residue was purified by preparatory HPLC (10-30% MeCN/water, 0.1% formic acid) to give the title compound. $^1$H NMR (400 MHz, CDCl$_3$) δ 7.76 (d, J=8.7 Hz, 1H), 7.59 (t, J=7.4 Hz, 2H), 7.52 (d, J=7.0 Hz, 1H), 7.36 (d, J=9.0 Hz, 1H), 7.29 (d, J=7.6 Hz, 2H), 6.81 (s, 1H), 3.27 (s, 3H). m/z [M+H]$^+$ 320.0

704

Proceeding analogously as described above the following compounds were prepared by substituting for 7-bromo-4-(methylamino)-1-phenylquinazolin-2(1H)-one as needed:

6-chloro-1-(2-chlorophenyl)-4-(methylamino)-7-(trifluoromethyl)quinazolin-2(1H)-one was prepared by using 7-bromo-6-chloro-1-(2-chlorophenyl)-4-(methylamino)quinazolin-2(1H)-one

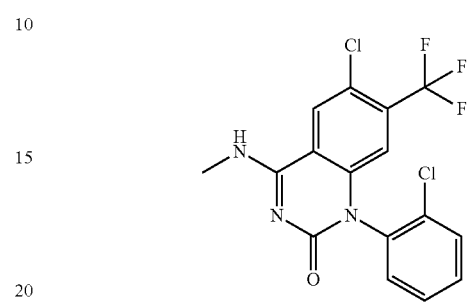

$^1$H NMR (400 MHz, DMSO) δ 8.99 (br s, 1H), 8.58 (s, 1H), 7.77 (br s, 1H), 7.67-7.52 (m, 3H), 6.54 (s, 1H), 3.02 (s, 3H). m/z [M+H]$^+$ 388.0

6-chloro-1-(2-chlorophenyl)-4-((cyclopropylmethyl)amino)-7-(trifluoromethyl)quinazolin-2(1H)-one was prepared by using 7-bromo-6-chloro-1-(2-chlorophenyl)-4-((cyclopropylmethyl)amino)quinazolin-2(1H)-one.

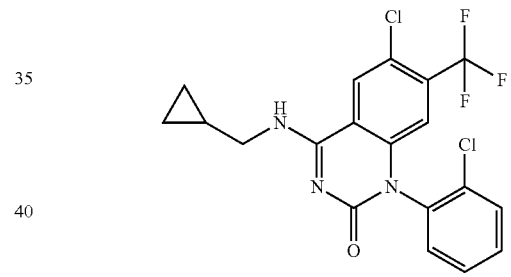

$^1$H NMR (400 MHz, DMSO) δ 9.03 (br, 1H), 8.71 (s, 1H), 7.76 (br, 1H), 7.59 (br, 3H), 6.53 (s, 1H), 3.43 (d, J=5.8 Hz, 2H), 1.21 (br s, 1H), 0.54 (d, J=7.8 Hz, 2H), 0.33 (br s, 2H). m/z [M+H]$^+$ 428.0 Example 8

Synthesis of 4-amino-7-chloro-1-cyclohexylquinazolin-2(1H)-one

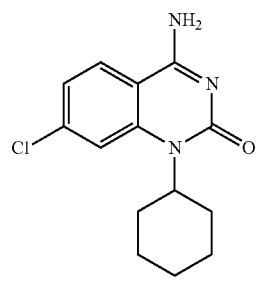 [SMILES: Nc1nc(=O)n(C2CCCCC2)c2cc(Cl)ccc12]

Step 1: Synthesis of 4-chloro-2-(cyclohexylamino)benzonitrile

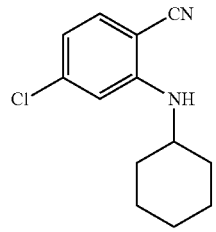 [SMILES: N#Cc1ccc(Cl)cc1NC1CCCCC1]

A microwave vial was charged under nitrogen with 2-bromo-4-chlorobenzonitrile (1.0 equiv), Pd(OAc)$_2$ (0.05 equiv), DPPF (0.1 equiv), cyclohexylamine (2.8 equiv) and toluene (0.4 M). The reaction vessel was sealed, purged with nitrogen for 10 min and submitted to microwave irradiation for 30 minutes at 120° C. The reaction vessel was diluted with 15 mL EtOAc and 5 mL of water. The layers were extracted twice with ethyl acetate (2×5 mL). The combined organic fractions were dried, and the crude mixture was purified by normal phase purification (0-70% EtOAc/Hex). m/z [M+H]$^+$ 235.1

Step 2: Synthesis of 2,2,2-trichloro-N-((5-chloro-2-cyanophenyl)(cyclohexyl)carbamoyl)-acetamide

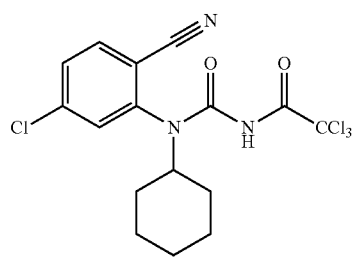

A vial was charged under nitrogen with 4-chloro-2-(cyclohexylamino)benzonitrile (1.0 equiv) and dry DCM (0.2 M). The reaction vessel was cooled to 0° C. and 2,2,2-trichloroacetyl isocyanate (1.0 equiv) was added. The reaction vessel was stirred for 1 h at room temperature. The reaction mixture was cooled to 0° C. and water 3 mL was added. The layers were extracted twice with DCM (2×5 mL). The combined organic fractions were dried, and the crude was used without purification. m/z [M+H]$^+$ 422.0

Step 3: Synthesis of 4-amino-7-chloro-1-cyclohexylquinazolin-2(1H)-one

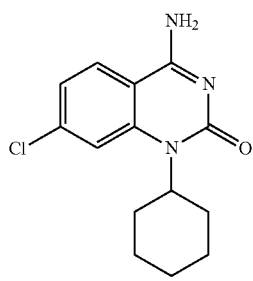

A vial at −10° C. was charged under nitrogen with 2,2,2-trichloro-N-((5-chloro-2-cyanophenyl)(cyclohexyl)carbamoyl)acetamide (1.0 equiv) followed by 7N NH$_3$ in methanol (20.0 equiv). The reaction vessel was stirred for 18 h at room temperature. The reaction mixture was concentrated under vacuum and directly purified by reverse phase purification (20-45% MeCN/water, 0.1% formic acid). $^1$H NMR (400 MHz, DMSO-d$_6$) δ 7.74 (d, J=8.5 Hz, 1H), 7.58 (s, 1H), 7.19 (d, J=8.7 Hz, 1H), 4.35 (s, 1H), 2.63-2.44 (m, 2H), 1.88 (d, J=13.7 Hz, 3H), 1.72 (d, J=12.6 Hz, 3H), 1.51 (dt, J=17.0, 11.5 Hz, 2H), 1.30 (q, J=13.3, 12.7 Hz, 1H). m/z [M+H]$^+$ 278.1

Example 9

Synthesis of N-(3-(7-chloro-4-(dimethylamino)-2-oxoquinazolin-1(2H)-yl)phenyl)-methanesulfonamide

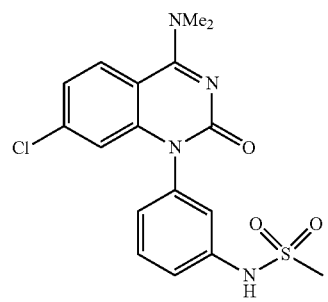 [SMILES: CN(C)c1nc(=O)n(-c2cccc(NS(C)(=O)=O)c2)c2cc(Cl)ccc12]

A vial was charged with 1-(3-bromophenyl)-7-chloro-4-(dimethylamino)quinazolin-2(1H)-one (1 equiv), tBuX-PhosPd(allyl)OTf (johnson Matthey C4277, 0.1 equiv), methanesulfonamide (1.6 equiv), potassium carbonate (2.2 equiv) and acetonitrile (0.075 M). The vial was flushed with nitrogen, and then heated to 80° C. for 18 h. The mixture was cooled to room temperature, diluted with DMSO, filtered and purified by reverse-phase prep HPLC (15-100% MeCN/water, 0.1% formic acid) to provide the title compound. $^1$H NMR (400 MHz, DMSO-d$_6$) δ 8.04 (d, J=8.6 Hz, 1H), 7.56 (t, J=8.0 Hz, 1H), 7.33 (d, J=8.3 Hz, 1H), 7.21 (d, J=8.7 Hz, 1H), 7.07 (s, 1H), 7.03 (d, J=8.0 Hz, 1H), 6.41 (s, 1H), 3.30 (s, 6H), 3.06 (s, 3H). m/z [M+H]$^+$ 393.0.

Example 10

Synthesis of 7-chloro-4-(dimethylamino)-1-(3-(2-phenoxyethyl)phenyl)quinazolin-2(1H)-one

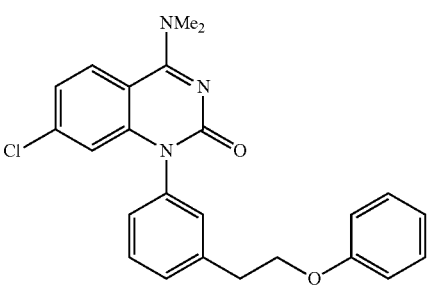 [SMILES: CN(C)c1nc(=O)n(-c2cccc(CCOc3ccccc3)c2)c2cc(Cl)ccc12]

A vial was charged with 1-(3-bromophenyl)-7-chloro-4-(dimethylamino)quinazolin-2(1H)-one (75 mg, 0.178 mmol), AmPhos Pd(crotyl)Cl pre-catalyst (Johnson Mathey, Pd-161, 0.1 equiv), potassium (2-phenyloxy)ethyltrifluoroborate (1.2 equiv), potassium carbonate (3 equiv) and toluene/water (5:10.1 M). The vial was flushed with nitrogen and then heated to 100° C. for 1.3 hr. The mixture was cooled to room temperature, filtered and purified by reverse-phase prep HPLC (20-80% MeCN/water, 0.1% formic acid) to provide the title compound. $^1$H NMR (400 MHz, DMSO-$d_6$) δ 8.03 (d, J=8.7 Hz, 1H), 7.59-7.42 (m, 2H), 7.23 (p, J=8.6, 8.2 Hz, 4H), 7.14 (d, J=7.7 Hz, 1H), 6.96-6.80 (m, 3H), 6.35 (s, 1H), 4.23 (t, J=6.6 Hz, 2H), 3.30 (s, 6H), 3.11 (t, J=6.5 Hz, 2H). m/z [M+H]$^+$ 420.0

Example 11

Synthesis of 2-(3-(7-Chloro-4-(methylamino)-2-oxoquinazolin-1(2H)-yl)phenyl)acetic acid

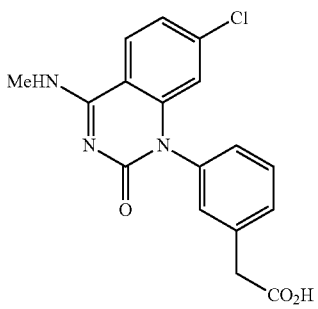 [SMILES: CNc1nc(=O)n(-c2cccc(CC(=O)O)c2)c2cc(Cl)ccc12]

To stirred solution of iodine (0.1 equiv) in acetonitrile (0.3 M) and water (0.15 M) was added 7-chloro-4-(methylamino)-1-(3-vinylphenyl)quinazolin-2(1H)-one (1 equiv). After 5 min, Oxone® (2 equiv) was added portion wise and the resulting reaction mixture was stirred at room temperature for 16 h. The reaction mixture was diluted with water and extracted with EtOAc and the combined organic layer was washed with water, brine and dried over anhydrous sodium sulfate. The dried organics were filtered and concentrated under reduced pressure to obtain crude compound which was purified by Prep-HPLC (MeCN/H$_2$O 60-100%, 0.1% Formic Acid) to afford the title compound as an off-white solid. $^1$H NMR (400 MHz, DMSO-$d_6$) δ 8.62 (d, J=4.5 1H), 8.10 (d, J=8.5, 1H), 7.48 (t, J=8.0, 1H), 7.38 (d, J=7.5, 1H), 7.25 (dd, J=11.0, 2.0 Hz, 1H), 7.15-7.11 (m, 2H), 6.33 (s, 1H), 3.51 (s, 2H), 2.98 (d, J=4.5 3H). m/z [M+H]$^+$ 344.30.

Example 12

Synthesis of 5-methoxy-4-(methylamino)-1-phenyl-7-(trifluoromethyl)quinazolin-2(1H)-one

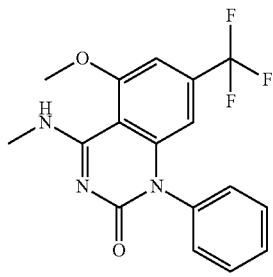 [SMILES: CNc1nc(=O)n(-c2ccccc2)c2cc(C(F)(F)F)cc(OC)c12]

A 20 mL vial under nitrogen was added 5-fluoro-4-(methylamino)-1-phenyl-7-(trifluoromethyl)quinazolin-2(1H)-one (1.0 equiv), MeOH (0.6 M) and MeONa (5.4 N in MeOH, 10 equiv). The reaction mixture was stirred for 60 minutes at 45° C. The reaction vessel was acidified by adding AcOH. The crude solution was purified by reverse phase chromatography (20-60% MeCN/water, with 0.1% Formic acid). $^1$H NMR (400 MHz, DMSO-$d_6$) δ 8.65 (bs, 1H), 7.60 (t, J=7.6 Hz, 2H), 7.53 (d, J=6.6 Hz, 1H), 7.30 (d, J=7.6 Hz, 2H), 7.07 (s, 1H), 6.13 (s, 1H), 4.10 (s, 3H), 3.02 (d, J=3.9 Hz, 3H). m/z [M+H]$^+$ 350.1.

Proceeding analogously as described above, following compound(s) were prepared by substituting for 5-fluoro-4-(methylamino)-1-phenyl-7-(trifluoromethyl)quinazolin-2(1H)-one as needed:

5-methoxy-4-(methylamino)-7-(trifluoromethyl)-1-(2-(trifluoromethyl)pyridin-3-yl)quinazolin-2(1H)-one was prepared by using 4-chloro-5-fluoro-7-(trifluoromethyl)-1-(2-(trifluoromethyl)pyridin-3-yl)quinazolin-2(1H)-one.

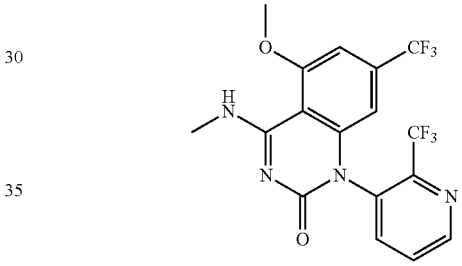

$^1$H NMR (400 MHz, DMSO-$d_6$) δ 8.94 (d, J=4.9 Hz, 1H), 8.39 (s, 1H), 8.18 (d, J=8.1 Hz, 1H), 8.02 (t, J=6.5 Hz, 1H), 7.81-7.57 (m, 4H), 6.41 (s, 1H), 3.04 (s, 3H), 2.36 (d, J=2.1 Hz, 3H).

5-Methoxy-4-(methyl amino)-1-(o-tolyl)-7-(trifluoromethyl) quinazolin-2(1H)-one was prepared by using 5-chloro-4-(methyl amino)-1-(o-tolyl)-7-(trifluoromethyl)quinazolin-2(1H)-one.

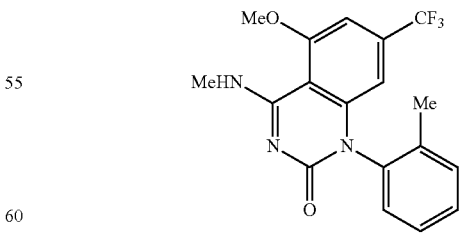

$^1$H NMR (500 MHz, DMSO-$d_6$) δ 8.67-8.66 (m, 1H), 7.47-7.38 (m, 3H), 7.14 (dd, J=1.5, 1.5 Hz, 1H), 7.08 (s, 1H), 6.02 (d, J=1 Hz, 1H), 4.1 (s, 3H), 3.02 (d, J=4.5 Hz, 3H), 1.94 (s, 3H). m/z [M+H]$^+$ 364.19.

7-Chloro-1-(2-chlorophenyl)-5-methoxy-4-(methylamino)quinazolin-2(1H)-one was prepared by using 7-chloro-1-(2-chlorophenyl)-5-fluoro-4-(methylamino)quinazolin-2(1H)-one.

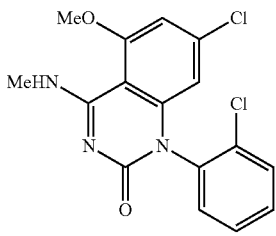 [SMILES: CNc1nc(=O)n(-c2ccccc2Cl)c2cc(Cl)cc(OC)c12]

¹H NMR (500 MHz, DMSO-d₆) δ 8.57 (d, J=4.5 Hz, 1H), 7.73-7.72 (m, 1H), 7.57-7.54 (m, 2H), 7.47-7.46 (m, 1H), 6.95 (d, J=2.0 Hz, 1H), 5.78 (d, J=2.0 Hz, 1H), 4.04 (s, 3H), 3.00 (d, J=4.5 Hz, 3H). m/z [M+H]⁺ 350.2.

7-Chloro-5-methoxy4-((trans-3-methoxycyclobutyl)amino)-1-(o-tolyl)quinazolin-2(1H)-one was prepared by using 7-Chloro-5-fluoro-4-((trans-3-methoxycyclobutyl)amino)-1-(o-tolyl)quinazolin-2(1H)-one.

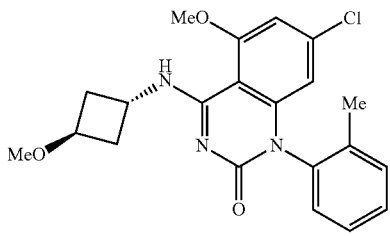 [SMILES: COc1cc(Cl)cc2c1c(N[C@H]1C[C@H](OC)C1)nc(=O)n2-c1ccccc1C]

¹H NMR (500 MHz, DMSO-d₆) δ 8.36 (d, J=6.5 Hz, 1H), 7.45-7.36 (m, 3H), 7.17 (d, J=7.0 Hz, 1H), 6.95 (d, J=2.0 Hz, 1H), 5.78 (d, J=2.0 Hz, H), 4.70-4.63 (m, 1H), 4.07 (s, 3H), 4.04-4.02 (m, 1H), 3.19 (m, 3H), 2.37-2.33 (m, 4H), 1.93 (s, 3H). m/z [M+H]⁺ 400.33.

7-Chloro-4-((2,2-difluoroethyl)amino)-5-methoxy-1-(o-tolyl)quinazolin-2(1H)-one was prepared by using 7-Chloro-4-((2,2-difluoroethyl)amino)-5-fluoro-1-(o-tolyl)quinazolin-2(1H)one.

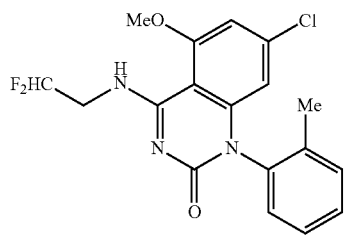 [SMILES: COc1cc(Cl)cc2c1c(NCC(F)F)nc(=O)n2-c1ccccc1C]

¹H NMR (500 MHz, DMSO-d₆) δ 8.65 (t, J=5.5 Hz, 1H), 7.46-7.37 (m, 3H), 7.19 (dd, J=7.5, 1.5 Hz, 1H), 6.97 (d, J=1.5 Hz, 1H), 6.43-6.18 (m, 1H), 5.80 (d, J=1.5 Hz, 1H), 4.05 (s, 3H), 4.03-3.91 (m, 2H), 1.94 (s, 3H). m/z [M+H]⁺ 380.35.

Example 13

Synthesis of (S)-4-(pyrrolidin-3-ylamino)-1-(o-tolyl)-7-(trifluoromethyl)quinazolin-2(1H)-one

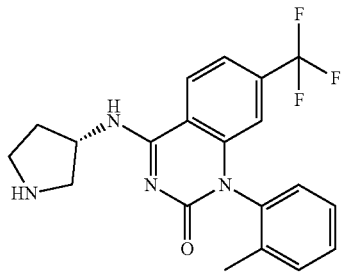 [SMILES: Cc1ccccc1-n1c(=O)nc(N[C@H]2CCNC2)c2ccc(C(F)(F)F)cc21]

A 20 mL vial was added tert-butyl (S)-3-((2-oxo-1-(o-tolyl)-7-(trifluoromethyl)-1,2-dihydroquinazolin-4-yl)amino)pyrrolidine-1-carboxylate (1.0 equiv), MeCN (0.6 M) and HCl (4N in Doxane, 25 equiv). The reaction mixture was stirred for 30 minutes 45° C. The reaction vessel was concentrated using the genevac. The crude was purified by reverse phase chromatography (10-40% ACN/water, with 0.1% Formic acid). ¹H NMR (400 MHz, MeCN-d₃) δ 8.87 (s, 1H), 8.58 (d, J=8.4 Hz, 1H), 8.38 (s, 1H), 7.60 (d, J=8.4 Hz, 1H), 7.54-7.38 (m, 3H) 7.25 (d, J=7.6 Hz, 1H), 6.44 (s, 1H), 4.85-4.72 (m, 1H), 3.80-2.94 (m, 4H), 2.24-2.11 (m, 1H), 2.03-1.88 (m, 1H), 1.95 (s, 3H). m/z [M+H]⁺ 389.15.

Proceeding analogously as described above, (S)-4-(3-(methylamino)pyrrolidin-1-yl)-1-(o-tolyl)-7-(trifluoromethyl)quinazolin-2(1H)-one was prepared by using tert-butyl (S)-methyl(1-(2-oxo-1-(o-tolyl)-7-(trifluoromethyl)-1,2-dihydroquinazolin-4-yl)pyrrolidin-3-yl)carbamate.

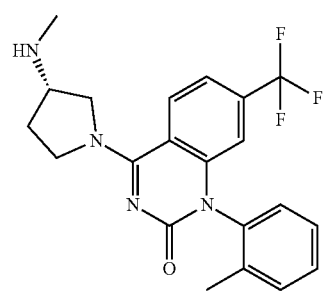 [SMILES: CN[C@H]1CCN(c2nc(=O)n(-c3ccccc3C)c3cc(C(F)(F)F)ccc23)C1]

¹H NMR (400 MHz, Methanol-d₄) δ 8.35 (d, J=8.6 Hz, 1H), 7.49-7.31 (m, 4H), 7.11 (d, J=7.6 Hz, 1H), 6.60 (s, 1H), 4.20-4.00 (m, 3H), 3.97-3.89 (m, 1H), 3.64-3.56 (m, 1H), 2.54 (s, 3H), 2.40-2.26 (m, 1H), 2.16-2.02 (m, 1H), 1.94 (s, 3H). m/z [M+H]⁺ 403.1 Example 14

Synthesis of 1-(2-chlorophenyl)-7-cyclopropyl-4-(methylamino)-6-(methylthio)quinazolin-2(1H)-one

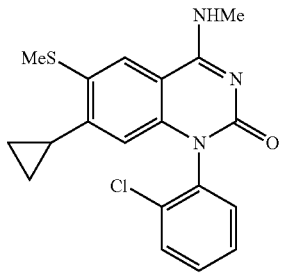 [SMILES: CNc1nc(=O)n(-c2ccccc2Cl)c2cc(C3CC3)c(SC)cc12]

To a solution of 6-bromo-1-(2-chlorophenyl)-7-cyclopropyl-4-(methylamino)quinazolin-2(1H)-one (1 equiv.) in dimethyl sulfoxide (0.05 M) was added copper (I) iodide (2 equiv.) and dimethyl amine in THF (2 M, 4 equiv.). The reaction mixture was heated to 90° C. for 18 h and then cooled. The crude reaction mixture was filtered and purified via reverse phase column chromatography (20-60% MeCN/water, 0.1% formic acid) to give the title compound. $^1$H NMR (400 MHz, DMSO-d$_6$) δ 8.69-8.62 (m, 1H), 7.85 (s, 1H), 7.71 (d, J=4.3 Hz, 1H), 7.58-7.51 (m, 2H), 7.46-7.39 (m, 1H), 5.77 (s, 1H), 3.02-2.97 (m, 3H), 2.55 (s, 3H), 1.99 (p, J=6.5 Hz, 1H), 0.91 (d, J=8.1 Hz, 2H), 0.24 (d, J=4.9 Hz, 2H). m/z [M+H]$^+$ 372.0.

Proceeding analogously as described above, 1-(2-chlorophenyl)-7-cyclopropyl-4-((cyclopropylmethyl)amino)-6-(methylthio)quinazolin-2(1H)-one was prepared by using 1-(2-chlorophenyl)-7-cyclopropyl-4-((cyclopropylmethyl)amino)-6-(methylthio)quinazolin-2(1H)-one.

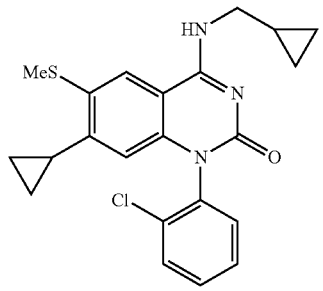

$^1$H NMR (400 MHz, DMSO-d$_6$) δ 8.80-8.73 (m, 1H), 7.96 (s, 1H), 7.75-7.69 (m, 1H), 7.59-7.51 (m, 2H), 7.47-7.41 (m, 1H), 5.76 (s, 1H), 3.43 (dt, J=12.0, 5.8 Hz, 2H), 2.57 (s, 3H), 2.08-2.00 (m, 1H), 1.23 (dt, J=13.0, 7.1 Hz, 1H), 0.92 (d, J=7.8 Hz, 2H), 0.50 (d, J=7.4 Hz, 2H), 0.35-0.29 (m, 2H), 0.23 (d, J=4.6 Hz, 2H). m/z [M+H]$^+$ 412.0.

Example 15

1-((1H-imidazol-4-yl)methyl)-4-(methylamino)-7-(trifluoromethyl)quinazolin-2(1H)-one

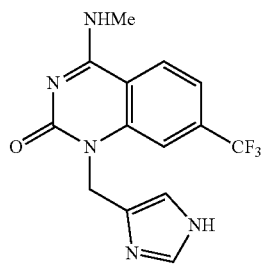

A vial was charged with 4-(methylamino)-7-(trifluoromethyl)-1-((1-((2-(trimethylsilyl)-ethoxy)methyl)-1H-imidazol-4-yl)methyl)quinazolin-2(1H)-one (1.0 equiv) and DCM (0.5 M). TFA (6 equiv) was added at 0° C. and the reaction mixture was stirred allowing to warm to room temperature for 16 h. Purification by preparative HPLC afforded the title product as a mixture of enaniomers. SFC purification (30% MeOH, Lux Cellulose-2, peak 1) $^1$H NMR (500 MHz, DMSO-d$_6$) δ 11.96 (s, 1H), 8.59 (d, J=4 Hz, 1H), 8.21 (d, J=8.5 Hz, 1H), 7.98 (s, 1H), 7.54-7.46 (m, 2H), 6.94 (s, 1H), 5.20 (s, 2H), 2.97-2.94 (m, 3H). m/z [M+H]$^+$ 324.35.

Proceeding analogously as described above, the following compounds were prepared:

(R)-1-(1-(1H-imidazol-4-yl)ethyl)-4-(methylamino)-7-(trifluoromethyl)quinazolin-2(1H)-one was prepared by substituting for 4-(methylamino)-7-(trifluoromethyl)-1-(1-(1-((2-(trimethylsilyl)ethoxy)methyl)-1H-imidazol-4-yl)ethyl)quinazolin-2(1H)-one. SFC purification (30% MeOH, Lux Cellulose-2, peak 1).

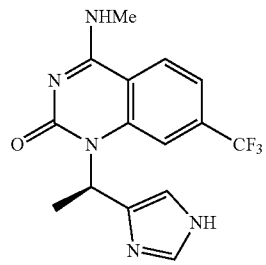 [SMILES: CNc1nc(=O)n([C@H](C)c2c[nH]cn2)c2cc(C(F)(F)F)ccc12]

$^1$H NMR (500 MHz, DMSO-d6) δ 8.58-8.57 (m, 1H), 8.17 (d, J=8.5 Hz, 1H), 7.66 (s, 1H), 7.55 (s, 1H), 7.45-7.40 (m, 1H), 7.07 (s, 1H), 6.50 (q, J=7 Hz, 1H), 2.95 (d, J=8.5 Hz, 3H), 1.72 (d, J=7.0 Hz, 3H). m/z [M+H] 338.3.

(S)-1-(1-(1H-imidazol-4-yl)ethyl)-4-(methylamino)-7-(trifluoromethyl)quinazolin-2(1H)-one was prepared by substituting for 4-(methylamino)-7-(trifluoromethyl)-1-(1-(1-((2-(trimethylsilyl)ethoxy)methyl)-1H-imidazol-4-yl)ethyl)quinazolin-2(1H)-one. SFC purification (30% MeOH, Lux Cellulose-2, peak 2).

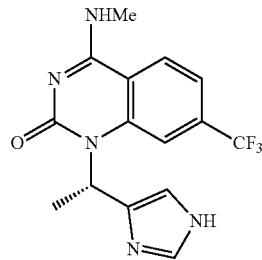

$^1$H NMR (500 MHz, DMSO-d6) δ 8.58-8.57 (m, 1H), 8.17 (d, J=8.5 Hz, 1H), 7.66 (s, 1H), 7.55 (s, 1H), 7.45-7.40 (m, 1H), 7.07 (s, 1H), 6.50 (q, J=7 Hz, 1H), 2.95 (d, J=8.5 Hz, 3H), 1.72 (d, J=7.0 Hz, 3H). m/z [M+H] 338.3.

1-((1H-imidazol-4-yl)methyl)-7-cyclopropyl-4-(methylamino) quinazolin-2(1H)-one was prepared by substituting with 7-cyclopropyl-4-(methylamino)-1-((1-((2-(trimethylsilyl)ethoxy)methyl)-1H-imidazol-4-yl)methyl)quinazolin-2(1H)-one.

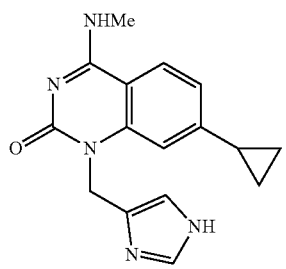 [SMILES: CNc1nc(=O)n(Cc2c[nH]cn2)c2cc(C3CC3)ccc12]

$^1$H NMR (500 MHz, DMSO-d$_6$) δ 8.18-8.20 (m, 1H), 7.84 (d, J=8.5 Hz, 1H), 7.53 (s, 1H), 7.25 (d, J=1 Hz, 1H), 6.85-6.81 (m, 2H), 5.14 (s, 1H), 2.91 (d, J=4.5 Hz, 3H), 1.94-1.92 (m, 1H), 1.04-1.00 (m, 2H), 0.98-0.97 (m, 2H). m/z [M+H]$^+$ 294.4.

Biological Examples

Example 1

Biochemical Assays

The ability of the compound of present disclosure to inhibit MAT2A enzyme was determined using the Malachite Green or Phosphate Sensor Fluorescence Assay described below.

A. Malachite Green Assay
Materials:
 Enzyme: MAT2A
 hMAT2A: 50 nM, Cepter, 10 mg/mL (234 μM), amino acids 1-395
 Substrates: 500 uM each
 Reaction time: 1 hour
 L-methionine Substrate: Alfa Aesar catalog #J61904
 ATP Substrate: Alfa Aesar cat #J60336
 Malachite Green Detection Reagent: Millipore Sigma catalog #MAK307-1KT
 Assay buffer: 50 mM Tris, pH 7.5/50 mM KCl/10 mM MgCl$_2$/0.01% Brij-35/1 mM DTT/0.1% BGG
 Temperature: 23° C.
 Total volume: 20 μL
Controls:
 0% inhibition control: DMSO
 100% inhibition control: No enzyme
Procedure:
 5 μL of 3×final concentration test compounds in DMSO or DMSO were transferred to the appropriate wells of a microtiter plate and the plate was centrifuged at 1000 rpm for 1 minute. 5 μL of 3×final concentration MAT2A enzyme in assay buffer or assay buffer alone was transferred to the appropriate wells and the plate was centrifuged at 1000 rpm for 1 minute. The plate was incubated at room temperature for 15 minutes and then 5 μL of 3×the L-methionine and ATP substrate mixture in assay buffer was transferred to all the test wells. The plate was centrifuged at 1000 rpm for 1 minute and then incubated at room temperature for 1 hour. 5 μL of malachite green detection reagent was added to all the test wells and the plate was centrifuged at 1000 rpm for 1 minute and then incubated at room temperature for 30 minutes. The plate was read for absorbance at 620 nm on a plate reader (e.g., Infinite M1000). The high control (DMSO) with high absorbance represents no inhibition of enzymatic reaction while the low control (no enzyme) with low absorbance represents full inhibition of enzymatic reaction.

The IC$_{50}$ of a representative number of compounds in Table 1 above are disclosed in Table 3 below:

(+) IC$_{50}$=10 uM-1 uM; (++) IC$_{50}$=1 uM-500 nM; (+++) IC$_{50}$=500 nM-200 nM; (++++) IC$_{50}$<200 nM; (+++++)<10 nm

TABLE 3

| Cpd. No. (Table 1) | IC$_{50}$ um | Cpd. No. (Table 1) | IC$_{50}$ um | Cpd. No. (Table 1) | IC$_{50}$ um |
| --- | --- | --- | --- | --- | --- |
| 2 | ++++ | 36 | ++++ | 70 | ++++ |
| 3 | ++++ | 37 | ++++ | 73 | ++++ |
| 4 | +++ | 38 | ++++ | 74 | ++++ |
| 5 | ++++ | 39 | ++++ | 75 | ++++ |
| 6 | ++++ | 42 | +++ | 76 | ++++ |
| 7 | ++++ | 43 | + | 77 | ++++ |
| 8 | + | 44 | ++++ | 80 | ++++ |
| 10 | +++ | 45 | ++++ | 81 | ++++ |
| 11 | ++++ | 46 | ++++ | 82 | ++++ |
| 12 | +++ | 47 | ++++ | | |
| 14 | ++++ | 48 | ++++ | | |
| 15 | ++++ | 49 | ++++ | | |
| 17 | ++++ | 50 | ++++ | | |
| 18 | ++++ | 51 | ++++ | | |
| 21 | +++ | 52 | ++++ | | |
| 22 | +++ | 54 | ++++ | | |
| 23 | +++ | 55 | ++++ | | |
| 24 | ++++ | 56 | ++++ | | |
| 25 | ++++ | 57 | ++++ | | |
| 26 | ++++ | 59 | ++++ | | |
| 27 | + | 60 | ++++ | | |
| 28 | +++ | 61 | ++++ | | |
| 29 | + | 62 | +++ | | |
| 31 | ++ | 63 | + | | |
| 32 | +++ | 64 | + | | |
| 34 | ++++ | 66 | ++++ | | |
| 35 | ++++ | 67 | ++++ | | |

B. Phosphate Sensor Fluorescence Assay

MAT2A enzyme is incubated with a test compound in DMSO or DMSO and its substrates (L-methionine and ATP) in a microtiter plate. The enzymatic reaction is stopped by the addition of Working Phosphate Sensor Mixture. The plate is analyzed for fluorescence at 450 nm. The high control (DMSO with enzyme and its substrates) gives high fluorescence which represents no inhibition of enzymatic activity while the low control (DMSO with MAT2A substrates and no enzyme) gives low fluorescence which represents full inhibition of enzymatic activity.

Materials:
 Human MAT2A: Cepter, amino acids 1-395
 Tris, pH 7.5: Invitrogen cat #15567-027
 KCl: Ambion cat #AM9640G
 MgCl$_2$: Ambion cat #AM9530G
 Brij-35: Sigma cat B4184-10ML
 DTT: Goldbio cat #DTT100
 BGG: Sigma cat #G5009-25G
 PNP: Novus Biologicals cat #NBP1-50872
 7-MEG: Cayman Chemical cat #15988
 L-Methionine: Alfa Aesar cat #J61904
 ATP: Alfa Aesar cat #J60336
 Phosphate Sensor: Thermo Fisher cat #PV4407
 EDTA: Life Tech cat #15575-038
 Assay plate: 384-well black polypropylene plate: Thomas Scientific cat #1149Q35

Final Assay Conditions:

Assay Buffer: 50 mM Tris, pH 7.5/50 mM KCl/10 mM MgCl$_2$/0.01% Brij-35/1 mM DTT/0.1% BGG/40 nM PNP/6 uM 7-MEG MAT2A: 10 nM for Cepter clone ID 329, lot 00023-123 before the addition of Working Phosphate Sensor Mixture 5 nM for Cepter clone ID 334, lot 00023-148 before the addition of Working Phosphate Sensor Mixture L-methionine: 500 uM before the addition of Working Phosphate Sensor Mixture ATP: 500 uM before the addition of Working Phosphate Sensor Mixture Procedure:

For the assay, a mixture of 1 mM L-methionine/1 mM ATP (2× final pre-stopped concentration) in assay buffer; MAT2A (2× final pre-stopped concentration) in Assay Buffer and Working Phosphate Sensor Mixture (1.5 uM Phosphate Sensor/30 mM EDTA in Assay Buffer, which is 3× final concentrations) were prepared. Test compounds or DMSO were added to the appropriate well suing D300e digital dispenser. 5 μl/well of Assay Buffer was added to the wells corresponding to the negative control and 5 μl/well of MAT2A was added to all the wells except for those corresponding to the negative control. After incubating the plate at room temperature for 15 minutes, 5 μl/well of the 1 mM L-methionine/1 mM ATP mixture was added to all wells. The plate was centrifuged at 1000 rpm for 1 minute and then incubated at room temperature for 1 hour. 5 μl of the Working Phosphate Sensor Mixture was added to all wells and the plate was centrifuged at 1000 rpm for 1 minute. The plate was read for fluorescence at 450 nm after exciting at 430 nm.

Data Analysis:

Percent inhibition was calculated in Chemical and Biological Information System (CBIS), (ChemInnovation Software Inc.). Curves were fitted by CBIS as % inhibition vs. log [compound concentration] using a 4-parameter inhibition model.

Fit=$(A+((B-A)/(1+((C/x)\hat{\,}D))))$

Res=$(y-\text{fit})$

The IC$_{50}$ of a representative number of compounds in Table 1 above are disclosed in Table 4 below:
(+) IC$_{50}$=10 uM-1 uM; (++) IC$_{50}$=1 uM-500 nM; (+++) IC$_{50}$=500 nM-200 nM; (++++) IC$_0$<200 nM

TABLE 4

| Cpd No (Table 1) | IC$_{50}$ um |
| --- | --- |
| 85 | >10 |
| 86 | +++ |
| 87 | ++++ |
| 88 | ++++ |
| 80 | ++++ |
| 90 | +++ |
| 91 | ++++ |
| 92 | +++ |
| 93 | >10 |
| 94 | ++ |
| 94 | + |
| 96 | ++++ |
| 97 | ++++ |
| 98 | ++++ |
| 99 | ++++ |
| 100 | ++++ |
| 101 | ++++ |
| 102 | ++++ |
| 103 | ++++ |

TABLE 4-continued

| Cpd No (Table 1) | IC$_{50}$ um |
| --- | --- |
| 104 | >10 |
| 105 | +++ |
| 106 | + |
| 107 | ++++ |
| 108 | >10 |
| 109 | ++++ |
| 110 | ++++ |
| 112 | >10 |
| 113 | >10 |
| 114 | ++++ |
| 115 | ++++ |
| 116 | >10 |
| 117 | + |
| 118 | ++++ |
| 119 | ++++ |
| 120 | + |
| 121 | +++ |
| 122 | ++++ |
| 123 | +++ |
| 124 | ++ |
| 125 | ++++ |
| 126 | ++++ |
| 127 | ++++ |
| 128 | ++++ |
| 129 | ++++ |
| 130 | ++ |
| 132 | >10 |
| 133 | ++++ |
| 134 | ++++ |
| 135 | ++++ |
| 136 | ++++ |
| 137 | ++++ |
| 138 | ++++ |
| 139 | ++++ |
| 140 | ++++ |
| 141 | ++++ |
| 142 | ++++ |
| 143 | ++++ |
| 144 | +++ |
| 145 | ++++ |
| 146 | ++++ |
| 147 | ++++ |
| 148 | ++++ |
| 149 | ++++ |
| 150 | ++++ |
| 151 | ++++ |
| 152 | ++++ |
| 153 | ++++ |
| 154 | ++++ |
| 155 | +++ |
| 156 | + |
| 157 | ++++ |
| 159 | ++++ |
| 160 | ++++ |
| 161 | ++++ |
| 162 | ++++ |
| 163 | ++++ |
| 164 | ++++ |
| 165 | ++++ |
| 166 | +++ |
| 167 | ++++ |
| 168 | ++++ |
| 169 | ++++ |
| 170 | ++++ |
| 171 | ++++ |
| 172 | ++++ |
| 173 | ++++ |
| 174 | >10 |
| 175 | ++++ |
| 176 | ++++ |
| 177 | ++++ |
| 178 | ++++ |
| 179 | ++++ |
| 180 | ++++ |
| 181 | ++++ |
| 182 | ++++ |
| 183 | ++++ |

TABLE 4-continued

| Cpd No (Table 1) | IC$_{50}$ um |
|---|---|
| 184 | ++++ |
| 185 | ++++ |
| 186 | ++++ |
| 187 | +++ |
| 188 | +++ |
| 189 | ++++ |
| 190 | + |
| 191 | >10 |
| 192 | >10 |
| 193 | >10 |
| 194 | >10 |
| 195 | >10 |
| 196 | ++++ |
| 197 | ++++ |
| 188 | ++ |
| 199 | ++++ |
| 200 | + |
| 201 | ++++ |
| 202 | >10 |
| 203 | +++ |
| 204 | ++++ |
| 205 | ++++ |
| 206 | >10 |
| 207 | ++++ |
| 208 | >10 |
| 209 | >10 |
| 210 | >10 |
| 211 | ++ |
| 212 | >10 |
| 213 | + |
| 214 | ++++ |
| 215 | >10 |
| 216 | ++++ |
| 217 | +++ |
| 218 | ++++ |
| 219 | +++ |
| 220 | + |
| 221 | + |
| 222 | ++++ |
| 223 | ++++ |
| 224 | >10 |
| 225 | ++++ |
| 226 | ++++ |
| 227 | ++++ |
| 228 | >10 |
| 229 | >10 |
| 230 | ++++ |
| 231 | + |
| 232 | ++++ |
| 233 | ++++ |
| 234 | ++++ |
| 235 | ++++ |
| 236 | >10 |
| 237 | ++++ |
| 238 | ++++ |
| 239 | ++++ |
| 240 | + |
| 241 | + |
| 242 | ++ |
| 243 | >10 |
| 244 | ++++ |
| 245 | ++++ |
| 246 | ++++ |
| 247 | ++++ |
| 248 | ++++ |
| 249 | >10 |
| 250 | ++ |
| 251 | + |
| 252 | >10 |
| 253 | >10 |
| 254 | ++++ |
| 255 | ++++ |
| 256 | ++++ |
| 257 | ++++ |
| 258 | ++++ |
| 259 | ++++ |
| 260 | ++++ |

TABLE 4-continued

| Cpd No (Table 1) | IC$_{50}$ um |
|---|---|
| 261 | ++++ |
| 262 | ++++ |
| 263 | ++++ |
| 264 | ++++ |
| 265 | ++++ |
| 266 | + |
| 267 | + |
| 268 | ++++ |
| 269 | ++++ |
| 270 | ++++ |
| 271 | ++++ |
| 272 | + |
| one of 273 and 292 is and the other of 273 and 292 is | ++++ |
| 274 | ++++ |
| 275 | ++ |
| 276 | + |
| 277 | ++++ |
| 278 | ++++ |
| 279 | ++++ |
| 280 | ++++ |
| 281 | ++++ |
| 282 | ++++ |
| 283 | ++++ |
| 284 | ++++ |
| 285 | ++++ |
| 286 | ++++ |
| 287 | ++++ |
| 288 | >10 |
| 289 | >10 |
| 290 | >10 |
| 291 | >10 |
| 293 | ++++ |
| 294 | ++++ |
| 295 | ++++ |
| 296 | ++++ |
| 297 | ++++ |
| 288 | ++++ |
| 299 | +++ |
| 300 | ++++ |
| 301 | ++++ |
| 302 | ++++ |
| 303 | ++++ |
| 304 | ++++ |
| 305 | >10 |
| 306 | ++++ |
| 307 | ++++ |
| 308 | ++++ |
| 309 | + |
| 310 | ++++ |
| 311 | >10 |
| 312 | ++++ |
| 313 | ++ |
| 314 | ++++ |
| 315 | ++++ |
| 316 | +++ |
| 317 | ++++ |
| 318 | ++++ |
| 319 | ++++ |
| 320 | ++++ |
| 321 | ++++ |
| 322 | ++++ |
| 323 | ++++ |
| 324 | ++++ |
| 325 | ++++ |
| 326 | ++++ |
| 327 | ++++ |
| 328 | ++++ |
| 329 | ++++ |
| 330 | >10 |
| 331 | ++++ |
| 332 | >10 |
| 333 | ++++ |

TABLE 4-continued

| Cpd No (Table 1) | IC$_{50}$ um |
|---|---|
| 334 | ++++ |
| 335 | ++++ |
| 336 | ++++ |
| 337 | ++++ |
| 338 | ++++ |
| 339 | ++++ |
| 340 | +++ |
| 341 | ++++ |
| 342 | >10 |
| 343 | >10 |
| 344 | ++++ |
| 345 | ++++ |
| 346 | ++++ |
| 347 | ++++ |
| 348 | ++++ |
| 349 | >10 |
| 350 | ++++ |
| 351 | ++++ |
| 352 | ++++ |
| 353 | ++++ |
| 354 | >10 |
| 355 | ++++ |
| 356 | >10 |
| 357 | + |
| 358 | ++++ |
| 359 | ++++ |
| 360 | >10 |
| 361 | >10 |
| 362 | ++++ |
| 363 | ++++ |
| 364 | ++++ |
| 365 | ++++ |
| 366 | ++++ |
| 367 | ++++ |
| 368 | ++++ |
| 369 | ++++ |
| 370 | ++++ |
| 371 | ++++ |
| 372 | ++++ |
| 373 | ++++ |
| 374 | ++++ |
| 375 | >10 |
| 376 | ++++ |
| 377 | ++++ |
| 378 | ++++ |
| 379 | ++++ |
| 380 | ++++ |
| 381 | ++++ |
| 382 | >10 |
| 383 | ++ |
| 384 | ++++ |
| 385 | ++++ |
| 386 | ++++ |
| 387 | + |
| 388 | ++++ |
| 389 | ++++ |
| 390 | ++++ |
| 391 | ++++ |
| 392 | >10 |
| 393 | >10 |
| 394 | ++++ |
| 395 | ++++ |
| 396 | +++ |
| 397 | ++++ |
| 398 | ++++ |
| 399 | ++++ |
| 400 | ++++ |
| 401 | +++ |
| 402 | ++ |
| 403 | + |
| 404 | ++++ |
| 405 | ++++ |
| 406 | +++ |
| 407 | ++++ |
| 408 | ++ |
| 409 | ++++ |
| 410 | ++++ |

TABLE 4-continued

| Cpd No (Table 1) | IC$_{50}$ um |
|---|---|
| 411 | ++++ |
| 412 | ++++ |
| 413 | ++++ |
| 414 | ++++ |
| 415 | ++++ |
| 416 | ++++ |
| 417 | ++++ |
| 418 | ++++ |
| 419 | ++++ |
| 420 | ++++ |
| 421 | ++++ |
| 422 | ++++ |
| 423 | ++++ |
| 424 | ++++ |
| 425 | ++++ |
| 426 | ++++ |
| 427 to 776 | ++++ |

What is claimed:

1. A compound of Formula (IIIa):

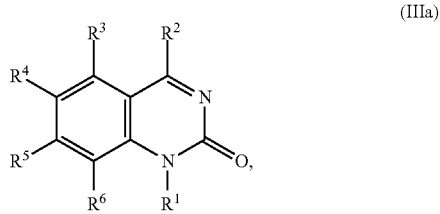

(IIIa)

or a pharmaceutically acceptable salt thereof, wherein $R^3$ is hydrogen;

$R^5$ is C3-6 cycloalkyl;

$R^4$ is hydrogen or cyano;

$R^6$ is hydrogen;

$R^1$ is $R^7$ wherein $R^7$ is phenyl or 5- to 6-membered heteroaryl, wherein phenyl or heteroaryl, is unsubstituted or substituted with $R^d$, $R^e$, and/or $R^f$;

$R^2$ is —NR$^9$R$^{10}$;

$R^9$ is hydrogen;

$R^{10}$ is hydrogen, $C_{1-6}$ alkyl, $C_{1-6}$ hydroxyalkyl, or $C_{3-6}$ cycloalkyl, wherein $C_{3-6}$ cycloalkyl is unsubstituted or substituted with halo;

$R^d$ and $R^e$ are independently selected from $C_{1-6}$ alkyl, halo, $C_{1-6}$ haloalkoxy, and $C_{1-6}$ haloalkyl; and $R^f$ is selected from $C_{1-6}$ alkyl, halo, $C_{1-6}$ haloalkoxy, and $C_{1-6}$ haloalkyl.

2. The compound of claim 1, or a pharmaceutically acceptable salt thereof, wherein $R^7$ is phenyl, wherein phenyl is unsubstituted or substituted with $R^d$, $R^e$, and/or $R^f$, wherein $R^d$ and $R^e$ are independently selected from $C_{1-6}$ alkyl and halo, and $R^f$ is selected from $C_{1-6}$ alkyl and halo.

3. The compound of claim 1, or a pharmaceutically acceptable salt thereof, wherein $R^7$ is pyridinyl or pyrazinyl, wherein pyridinyl or pyrazinyl, are independently unsubstituted or substituted with $R^d$, $R^e$, and/or $R^f$, wherein $R^d$ and $R^e$ are independently selected from $C_{1-6}$ alkyl, halo, $C_{1-6}$ haloalkoxy, and $C_{1-6}$ haloalkyl, and $R^f$ is selected from $C_{1-6}$ alkyl, halo, $C_{1-6}$ haloalkoxy, and $C_{1-6}$ haloalkyl.

4. A compound that is selected from:
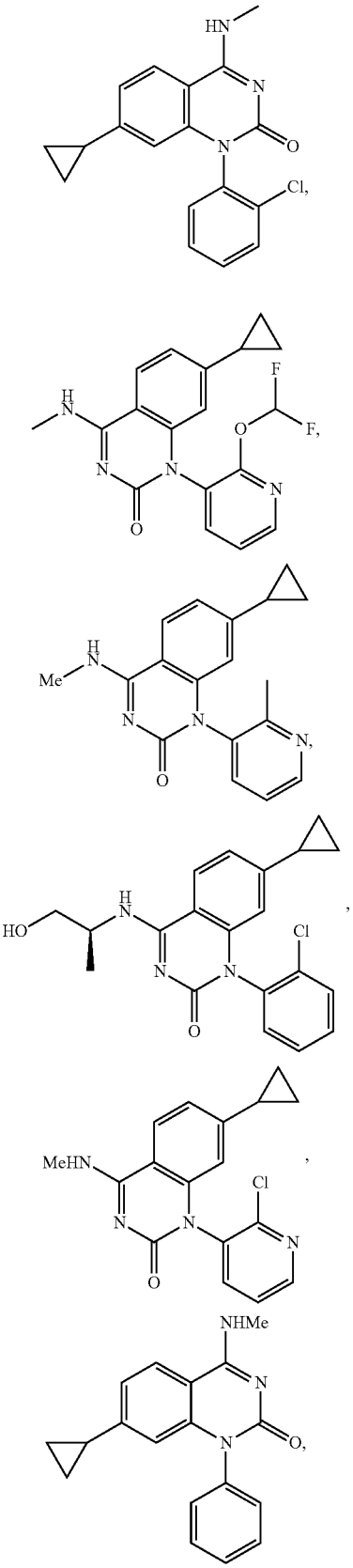
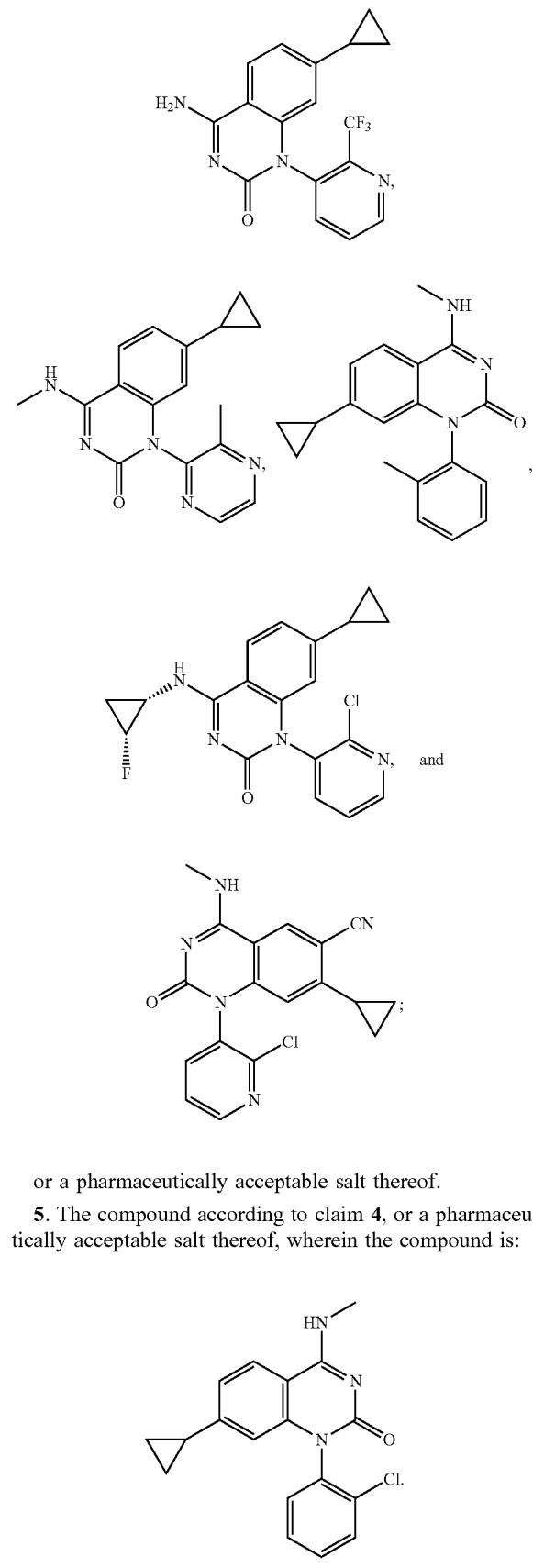
or a pharmaceutically acceptable salt thereof.
5. The compound according to claim 4, or a pharmaceutically acceptable salt thereof, wherein the compound is:
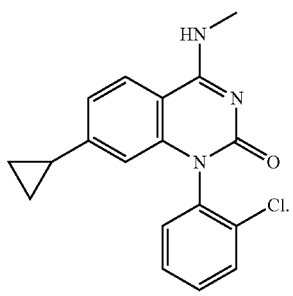 [SMILES: CNc1nc(=O)n(-c2ccccc2Cl)c2cc(C3CC3)ccc12]

6. The compound according to claim 4, or a pharmaceutically acceptable salt thereof, wherein the compound is:

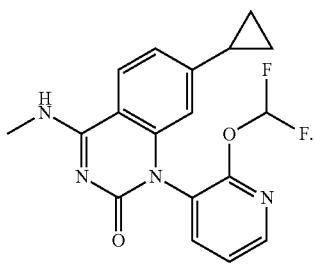 [SMILES: CNc1nc(=O)n(-c2cccnc2OC(F)F)c2cc(C3CC3)ccc12]

7. The compound according to claim 4, or a pharmaceutically acceptable salt thereof, wherein the compound is:

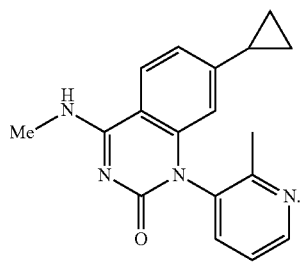 [SMILES: CNc1nc(=O)n(-c2cccnc2C)c2cc(C3CC3)ccc12]

8. The compound according to claim 4, or a pharmaceutically acceptable salt thereof, wherein the compound is:

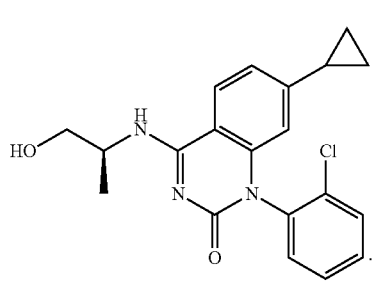 [SMILES: C[C@@H](CO)Nc1nc(=O)n(-c2ccccc2Cl)c2cc(C3CC3)ccc12]

9. The compound according to claim 4, or a pharmaceutically acceptable salt thereof, wherein the compound is:

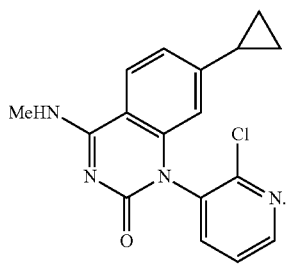 [SMILES: CNc1nc(=O)n(-c2cccnc2Cl)c2cc(C3CC3)ccc12]

10. The compound according to claim 4, or a pharmaceutically acceptable salt thereof, wherein the compound is:

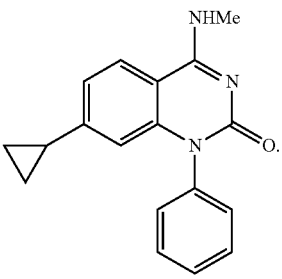 [SMILES: CNc1nc(=O)n(-c2ccccc2)c2cc(C3CC3)ccc12]

11. The compound according to claim 4, or a pharmaceutically acceptable salt thereof, wherein the compound is:

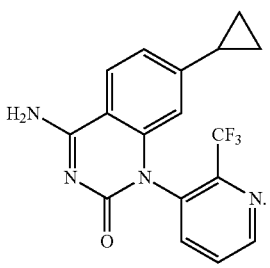 [SMILES: Nc1nc(=O)n(-c2cccnc2C(F)(F)F)c2cc(C3CC3)ccc12]

12. The compound according to claim 4, or a pharmaceutically acceptable salt thereof, wherein the compound is:

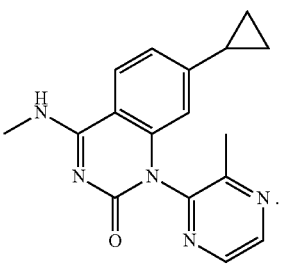 [SMILES: CNc1nc(=O)n(-c2nccnc2C)c2cc(C3CC3)ccc12]

13. The compound according to claim 4, or a pharmaceutically acceptable salt thereof, wherein the compound is:

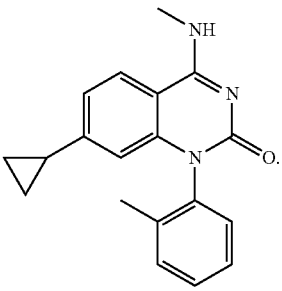 [SMILES: CNc1nc(=O)n(-c2ccccc2C)c2cc(C3CC3)ccc12]

14. The compound according to claim 4, or a pharmaceutically acceptable salt thereof, wherein the compound is:

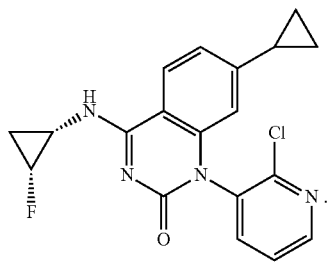 [SMILES: O=c1nc(N[C@H]2C[C@H]2F)c2ccc(C3CC3)cc2n1-c1cccnc1Cl]

15. The compound according to claim 4, or a pharmaceutically acceptable salt thereof, wherein the compound is:

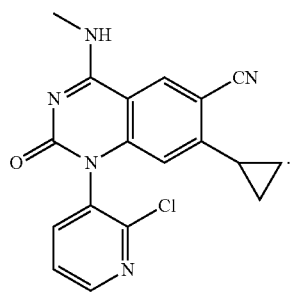 [SMILES: CNc1nc(=O)n(-c2cccnc2Cl)c2cc(C3CC3)c(C#N)cc12]

16. The compound according to claim 4, wherein the compound is:

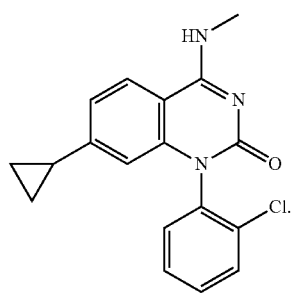 [SMILES: CNc1nc(=O)n(-c2ccccc2Cl)c2cc(C3CC3)ccc12]

17. The compound according to claim 4, wherein the compound is:

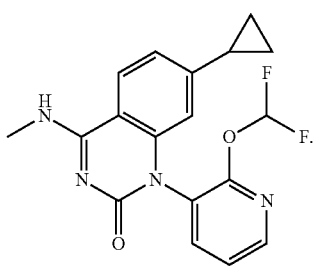 [SMILES: CNc1nc(=O)n(-c2cccnc2OC(F)F)c2cc(C3CC3)ccc12]

18. The compound according to claim 4, wherein the compound is:

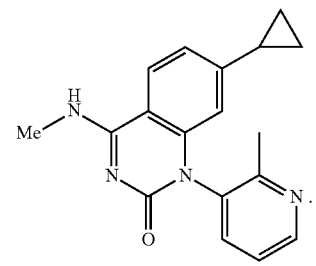 [SMILES: CNc1nc(=O)n(-c2cccnc2C)c2cc(C3CC3)ccc12]

19. The compound according to claim 4, wherein the compound is:

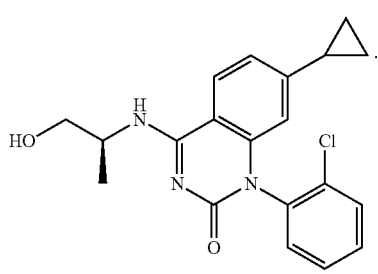 [SMILES: C[C@@H](CO)Nc1nc(=O)n(-c2ccccc2Cl)c2cc(C3CC3)ccc12]

20. The compound according to claim 4, wherein the compound is:

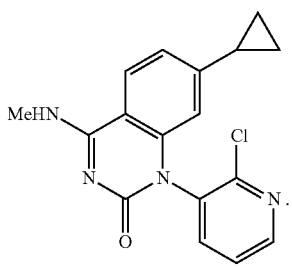 [SMILES: CNc1nc(=O)n(-c2cccnc2Cl)c2cc(C3CC3)ccc12]

21. The compound according to claim 4, wherein the compound is:

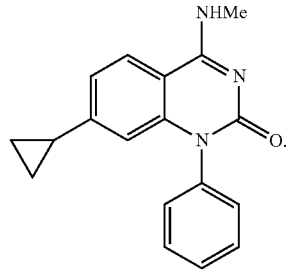 [SMILES: CNc1nc(=O)n(-c2ccccc2)c2cc(C3CC3)ccc12]

22. The compound according to claim 4, wherein the compound is:
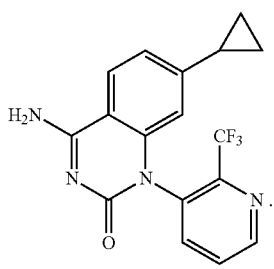 [SMILES: Nc1nc(=O)n(-c2cccnc2C(F)(F)F)c2cc(C3CC3)ccc12]
23. The compound according to claim 4, wherein the compound is:
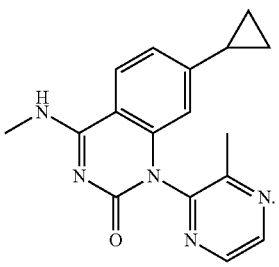 [SMILES: CNc1nc(=O)n(-c2nccnc2C)c2cc(C3CC3)ccc12]
24. The compound according to claim 4, wherein the compound is:
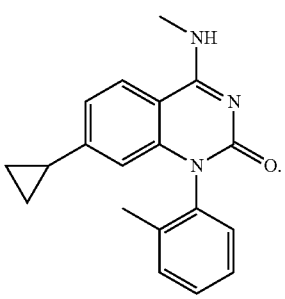 [SMILES: CNc1nc(=O)n(-c2ccccc2C)c2cc(C3CC3)ccc12]
25. The compound according to claim 4, wherein the compound is:
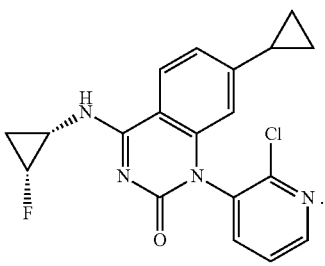 [SMILES: O=c1nc(N[C@H]2C[C@H]2F)c2ccc(C3CC3)cc2n1-c1cccnc1Cl]
26. The compound according to claim 4, wherein the compound is:
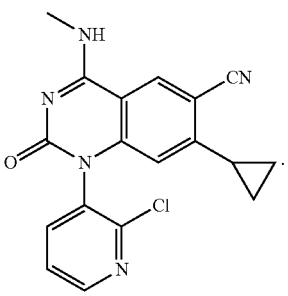 [SMILES: CNc1nc(=O)n(-c2cccnc2Cl)c2cc(C3CC3)c(C#N)cc12]
* * * * *